US012234292B2

(12) United States Patent
Song et al.

(10) Patent No.: US 12,234,292 B2
(45) Date of Patent: Feb. 25, 2025

(54) FN14 ANTIBODIES AND USES THEREOF

(71) Applicant: KYOWA KIRIN CO., LTD., Tokyo (JP)

(72) Inventors: Aihua Song, San Diego, CA (US); Andrew John McKnight, San Diego, CA (US); Rachel Soloff Nugent, San Diego, CA (US); John Lorca Laudenslager, La Mesa, CA (US); Giuseppe Destito, Encinitas, CA (US); Sarah Sunrise Bubeck, Livingston, TX (US); Shinya Ogawa, Tokyo (JP); Yuji Yamazaki, Tokyo (JP); David Mills, Seattle, WA (US); Aruna Bitra, La Jolla, CA (US); Dirk Michael Zajonc, La Jolla, CA (US)

(73) Assignee: KYOWA KIRIN CO., LTD., Tokyo (JP)

( * ) Notice: Subject to any disclaimer, the term of this patent is extended or adjusted under 35 U.S.C. 154(b) by 876 days.

(21) Appl. No.: 17/416,148

(22) PCT Filed: Dec. 19, 2019

(86) PCT No.: PCT/IB2019/061058
§ 371 (c)(1),
(2) Date: Jun. 18, 2021

(87) PCT Pub. No.: WO2020/128927
PCT Pub. Date: Jun. 25, 2020

(65) Prior Publication Data
US 2022/0289857 A1  Sep. 15, 2022

Related U.S. Application Data

(60) Provisional application No. 62/782,912, filed on Dec. 20, 2018.

(51) Int. Cl.
*C07K 16/28* (2006.01)
*A61P 35/00* (2006.01)
*A61P 37/00* (2006.01)

(52) U.S. Cl.
CPC .......... *C07K 16/2878* (2013.01); *A61P 35/00* (2018.01); *A61P 37/00* (2018.01); *C07K 2317/24* (2013.01); *C07K 2317/524* (2013.01); *C07K 2317/55* (2013.01); *C07K 2317/565* (2013.01); *C07K 2317/567* (2013.01); *C07K 2317/76* (2013.01)

(58) Field of Classification Search
CPC .......... C07K 16/2878; C07K 2317/24; C07K 2317/524; C07K 2317/55; C07K 2317/565; C07K 2317/567; C07K 2317/76; C07K 2317/33; C07K 2317/71; C07K 2317/92; A61P 35/00; A61P 37/00
See application file for complete search history.

(56) References Cited

U.S. PATENT DOCUMENTS

2019/0328677 A1 * 10/2019 Kim .................. C07K 16/2875
2021/0388096 A1    12/2021 Ito et al.

FOREIGN PATENT DOCUMENTS

| JP | 2014529597 A | 11/2014 | |
|---|---|---|---|
| WO | WO 2009140177 A2 | 11/2009 | |
| WO | WO 2009140177 A3 | 11/2009 | |
| WO | WO-2010113117 A2 * | 10/2010 | ............... A23C 9/20 |
| WO | WO 2013026099 A1 | 8/2012 | |

OTHER PUBLICATIONS

Almagro JC & Fransson J, Humanization of antibodies. Frontiers in Bioscience 2008; 13:1619-33 (Year: 2008).*
Michaelson JS et al. Development of an Fn14 agonistic antibody as an anti-tumor agent. MAbs. Jul.-Aug 2011; 3(4): 362-375 (Year: 2011).*
Gershoni et al., Epitope Mapping, Biodrugs 2007; 21 (3): 145-156 (Year: 2007).*
Blythe et al., Benchmarking B cell epitope prediction: Underperformance of existing methods, Protein Science (2005), 14:246-248 (Year: 2005).*
Schreiber et al. 3D-Epitope-Explorer (3DEX): Localization of Conformational Epitopes within Three-Dimensional Structures of Proteins, Journal of Computational Chemistry 2005 26(9) 879-887 (Year: 2005).*
Zhou H et al. The TWEAK Receptor Fn14 Is a Therapeutic Target in Melanoma: Immunotoxins Targeting Fn14 Receptor for Malignant Melanoma Treatment. (J Invest Dermatol. Apr. 2013; 133(4): 1052-1062). (Year: 2013).*
Campbell et al., 2004, "The role of TWEAK/Fn14 in the pathogenesis of inflammation and systemic autoimmunity," Front Biosci., 9:2273-2284.
Chen et al., 2012, "TWEAK/Fn14 promotes the proliferation and collagen synthesis of rat cardiac fibroblasts via the NF-κB pathway," Mol. Biol. Rep., 39(8):8231-8241.
Chicheportiche et al., 1997, "TWEAK, a new secreted ligand in the tumor necrosis factor family that weakly induces apoptosis," J. Biol. Chem., 272(51):32401-32410.
Claus et al., 2018, "The TWEAK/Fn14 pathway is required for calcineurin inhibitor toxicity of the kidneys," Am. J. Transplant, 18(7):1636-1645.
Doerner et al., 2015, "TWEAK/Fn14 Signaling Involvement in the Pathogenesis of Cutaneous Disease in the MRL/lpr Model of Spontaneous Lupus," J. Invest. Dermatol., 135(8):1986-1995.
Dogra et al., 2006, "Tumor necrosis factor-like weak inducer of apoptosis inhibits skeletal myogenesis through sustained activation of nuclear factor-kappaB and degradation of MyoD protein," J. Biol. Chem., 281(15):10327-10336.
Dogra et al., 2007, "TNF-related weak inducer of apoptosis (TWEAK) is a potent skeletal muscle-wasting cytokine," FASEB J., 21(8):1857-1869.

(Continued)

*Primary Examiner* — Karen A. Canella
*Assistant Examiner* — John J Skoko, III
(74) *Attorney, Agent, or Firm* — JONES DAY

(57) ABSTRACT

An antibody or antigen binding fragment thereof that binds to a Fn14, wherein the antibody or antigen binding fragment thereof is an antagonist and non-agonist of Fn14.

16 Claims, 43 Drawing Sheets

Specification includes a Sequence Listing.

(56) References Cited

OTHER PUBLICATIONS

Dohi et al., 2009, "TWEAK/Fn14 pathway: a nonredundant role in intestinal damage in mice through a TWEAK/intestinal epithelial cell axis," Gastroenterology, 136(3):912-923 and Supplementary Methods (Epub 2008) (20 pages).

Feng et al., 2000, "The Fn14 immediate-early response gene is induced during liver regeneration and highly expressed in both human and murine hepatocellular carcinomas," Am. J. Pathol., 156(4): 1253-1261.

Gomez et al., 2016, "TWEAK-Fn14 Signaling Activates Myofibroblasts to Drive Progression of Fibrotic Kidney Disease," J. Am. Soc. Nephrol., 27(12):3639-3652 and Supplemental Materials (41 pages).

Ho et al., 2004, "Soluble tumor necrosis factor-like weak inducer of apoptosis overexpression in HEK293 cells promotes tumor growth and angiogenesis in athymic nude mice," Cancer Res., 64(24):8968-8972.

International Preliminary Report on Patentability (Chapter I) for International Patent Application No. PCT/IB2019/061058 (Pub No. WO 2020128927) issued Jun. 16, 2021 (10 pages).

International Search Report and Written Opinion for International Patent Application No. PCT/IB2019/061058 (Pub No. WO 2020128927) mailed Apr. 22, 2020 (17 pages).

Johnston et al., 2015, "Targeting of Fn14 Prevents Cancer-Induced Cachexia and Prolongs Survival," Cell, 162(6):1365-1378.

Li et al., 2013, "Tumor necrosis factor-like weak inducer of apoptosis and its receptor fibroblast growth factor-inducible 14 are expressed in urticarial vasculitis," J. Dermatol., 40(11):891-895.

Liu et al., 2017, "TWEAK/Fn14 Activation Participates in Ro52-Mediated Photosensitization in Cutaneous Lupus Erythematosus," Front Immunol., 8:651 (14 pages).

Lynch et al., 1999, "TWEAK induces angiogenesis and proliferation of endothelial cells," J. Biol. Chem., 274(13):8455-8459.

Meighan-Mantha et al., 1999, "The mitogen-inducible Fn14 gene encodes a type I transmembrane protein that modulates fibroblast adhesion and migration," J. Biol. Chem., 274(46):33166-33176.

Mittal et al., 2010, "Genetic ablation of TWEAK augments regeneration and post-injury growth of skeletal muscle in mice," Am. J. Pathol., 177(4):1732-1742.

Nakayama et al., 2002, "Multiple pathways of TWEAK-induced cell death," J. Immunol., 168(2):734-743.

Nakayama et al., 2003, "Fibroblast growth factor-inducible 14 mediates multiple pathways of TWEAK-induced cell death," J. Immunol., 170(1):341-348.

Park et al., 2017, "Inhibition of the TWEAK/Fn14 pathway attenuates autoimmune arthritis in a SKG mouse model," Histol. Histopathol., 32(5):481-490 (Epub 2016).

Perper et al., 2006, "TWEAK is a novel arthritogenic mediator," J. Immunol., 177(4):2610-2620.

Salzmann et al., 2013, "Fibroblast growth factor inducible (Fn14)-specific antibodies concomitantly display signaling pathway-specific agonistic and antagonistic activity," J. Biol. Chem., 288(19):13455-13466.

Sanchez-Nino et al., 2013, "Fn14 in podocytes and proteinuric kidney disease," Biochim. Biophys. Acta., 1832(12):2232-2243.

Sasaki et al., 2015, "TWEAK/Fn14 system and crescent formation in IgA nephropathy" BMC Nephrol., 16:27 (10 pages).

Sidler et al., 2017, "TWEAK mediates inflammation in experimental atopic dermatitis and psoriasis," Nat. Commun., 8:15395 (11 pages).

Son et al., 2013, "TWEAK/Fn14 pathway promotes a T helper 2-type chronic colitis with fibrosis in mice," Mucosal. Immunol., 6(6):1131-1142.

Sydow et al., 2014, "Structure-based prediction of asparagine and aspartate degradation sites in antibody variable regions," PLoS One, 9(6):e100736 (13 pages).

Trebing et al., 2014, "A novel llama antibody targeting Fn14 exhibits anti-metastatic activity in vivo," Mabs, 6(1):297-308.

Van Kuijk et al., 2010, "TWEAK and its receptor Fn14 in the synovium of patients with rheumatoid arthritis compared to psoriatic arthritis and its response to tumour necrosis factor blockade," Ann. Rheum. Dis., 69(1):301-304.

Wiley et al., 1995, "Identification and characterization of a new member of the TNF family that induces apoptosis," Immunity, 3(6):673-682.

Wiley et al., 2001, "A novel TNF receptor family member binds TWEAK and is implicated in angiogenesis," Immunity, 15(5):837-846.

Wilhelm et al., 2016, "Interaction of TWEAK with Fn14 leads to the progression of fibrotic liver disease by directly modulating hepatic stellate cell proliferation," J. Pathol., 239(1):109-121.

Xia et al., 2012, "Inhibition of the TWEAK/Fn14 pathway attenuates renal disease in nephrotoxic serum nephritis," Clin. Immunol., 145(2):108-121.

Xia et al., 2015, "Deficiency of fibroblast growth factor-inducible 14 (Fn14) preserves the filtration barrier and ameliorates lupus nephritis," J. Am. Soc. Nephrol., 26(5):1053-1070 and Supplemental Materials (Epub 2014) (21 pages).

Yadava et al., 2015, "TWEAK/Fn14, a pathway and novel therapeutic target in myotonic dystrophy," Hum. Mol. Genet., 24(7):2035-2048 (Epub 2014).

Yadava et al., 2016, "TWEAK Regulates Muscle Functions in a Mouse Model of RNA Toxicity," PLoS One, 11(2):e0150192 (13 pages).

Zhao et al., 2007, "TWEAK/Fn14 interactions are instrumental in the pathogenesis of nephritis in the chronic graft-versus-host model of systemic lupus erythematosus," J. Immunol., 179(11):7949-7958.

Zheng et al., 2017, "Fn14 hepatic progenitor cells are associated with liver fibrosis in biliary atresia" Pediatr. Surg. Int., 33(5):593-599.

European Patent Office, Communication pursuant to Article 94(3) EPC dated Feb. 28, 2024 issued in counterpart European Patent Application No. 19835810.3 (4 pages).

Japanese Patent Office, Office Action mailed Mar. 5, 2024 issued in counterpart Japanese Patent Application No. 2021-535978, in Japanese with machine English translation (8 pages).

Japanese Patent Office, Office Action mailed Nov. 7, 2023 issued in counterpart Japanese Patent Application No. 2021-535978, in Japanese with machine English translation (5 pages).

* cited by examiner

Mouse VH and VL amino acid sequences of exemplary Fn14 antagonist monoclonal antibodies with corresponding SEQ ID NOs

FIG. 20

VL CDR and Framework Sequences

| Species | Light Vector ID | Name | LFR1 | SEQ ID NO | LCDR1 (Kabat) | SEQ ID NO | LFR2 | SEQ ID NO |
|---|---|---|---|---|---|---|---|---|
| Mouse | A290, A370 | 41c | DVVMTQTPLTLSVAIGQPASISC | 160 | KSSQSLLNSGNQKNYLTN | 127 | WLLQRPGQSPKRLIY | 163 |
| Mouse | A451, A452 | R35B9 | DVVMTQTPLSLPVTLGQPASISC | 160 | KSSQSLLNSGNQKNYLTN | 127 | WLLQRPGQSPKRLIY | 163 |
| Human Template | N/A | AAQ02700.1 | DVVMTQSPLSLPVTLGQPASISC | 161 | — | — | WFQQRPGQSPRRLIY | 164 |
| Humanized | A467 | hzR35B9-LV0 | DVVMTQSPLSLPVTLGQPASISC | 161 | KSSQSLLNSGNQKNYLTN | 127 | WFQQRPGQSPRRLIY | 164 |
| Humanized | A468 | hzR35B9-LV1a | DVVMTQSPLSLPVTLGQPASISC | 161 | KSSQSLLNSGNQKNYLTN | 127 | WLLQRPGQSPRRLIY | 165 |
| Humanized | A469 | hzR35B9-LV1b | DVVMTQSPLSLPVTLGQPASISC | 161 | KSSQSLLNSGNQKNYLTN | 127 | WLAQRPGQSPRRLIY | 166 |
| Humanized | A470 | hzR35B9-LV3a | DVVMTQSPLSLPVTLGQPASISC | 162 | KSSQSLLNSGNQKNYLTN | 127 | WFLQRPGQSPRRLIY | 167 |
| Humanized | A471 | hzR35B9-LV3b | DVVMTQSPLSLPVTLGQPASISC | 162 | KSSQSLLNSGNQKNYLTN | 127 | WLLQRPGQSPRRLIY | 168 |
| Humanized | A472 | hzR35B9-LV4 | DVVMTQSPLSLPVTLGQPASISC | 162 | KSSQSLLNSGNQKNYLTN | 127 | WLLQRPGQSPRRLIY | 163 |
| Humanized | A473 | hzR35B9-LV5 | DVVMTQSPLSLPVTLGQPASISC | 161 | KSSQSLLNSGNQKNYLTN | 127 | WLLQRPGQSPRRLIY | 163 |
| Humanized | A518 | hzR35B9(H98)-LV1a | DVVMTQSPLSLPVTLGQPASISC | 161 | KSSQSLLNSGNQKNYLTN | 127 | WLLQRPGQSPRRLIY | 165 |
| Humanized | A651 | hzR35B9(A56)-LV2a | DVVMTQSPLSLPVTLGQPASISC | 161 | KSSQSLLNSAGNQKNYLTN | 127 | WLLQRPGQSPRRGTY | 252 |
| Humanized | A652 | hzR35B9(A56)-LV2b | DVVMTQSPLSLPVTLGQPASISC | 161 | KSSQSLLNSAGNQKNYLTN | 127 | WLLQRPGQSPRRLAY | 253 |
| Humanized | A653 | hzR35B9(A56)-LV2c | DVVMTQSPLSLPVTLGQPASISC | 161 | KSSQSLLNSAGNQKNYLTN | 127 | WLLQRPGQSPRRLIY | 165 |
| Humanized | A654 | hzR35B9(A56)-LV2d | DVVMTQSPLSLPVTLGQPASISC | 161 | KSSQSLLNSAGNQKNYLTN | 127 | WLLQRPGQSPRRLIY | 165 |
| Humanized | A656 | hzR35B9(A56)-LV2f | DVVMTQSPLSLPVTLGQPASISC | 161 | KSSQSLLNSAGNQKNYLTN | 127 | WLLQRPGQSPRRLIY | 165 |

FIG. 21

| LCDR3 (Kabat) | SEQ ID NO | L-FR3 | SEQ ID NO | LCDR3 (Kabat) | SEQ ID NO | L-FR4 | SEQ ID NO | Complete Variable SEQ ID NO |
|---|---|---|---|---|---|---|---|---|
| LVSQLDS | 129 | GVPDRFSGSGSGTDFTLKISRVEAEDVGVYYC | 169 | WQGTHFPWT | 129 | FGGGTKLEIK | 171 | 40 |
| LVSQLDS | 129 | GVPDRFSGSGSGTDFTLKISRVEAEDLGVYYC | 169 | WQGTHFPWT | 130 | FGGGTKLEIK | 171 | 52 |
| --- | --- | GVPDRFSGSGSGTDFTLKISRVEAEDVGVYYC | 170 | --- | --- | FGGGTKVEIK | 172 | --- |
| LVSQLDS | 128 | GVPDRFSGSGSGTDFTLKISRVEAEDVGVYYC | 170 | WQGTHFPWT | 130 | FGGGTKVEIK | 172 | 92 |
| LVSQLDS | 128 | GVPDRFSGSGSGTDFTLKISRVEAEDVGVYYC | 170 | WQGTHFPWT | 130 | FGGGTKVEIK | 172 | 94 |
| LVSQLDS | 128 | GVPDRFSGSGSGTDFTLKISRVEAEDVGVYYC | 170 | WQGTHFPWT | 130 | FGGGTKVEIK | 172 | 96 |
| LVSQLDS | 128 | GVPDRFSGSGSGTDFTLKISRVEAEDVGVYYC | 170 | WQGTHFPWT | 130 | FGGGTKVEIK | 172 | 98 |
| LVSQLDS | 128 | GVPDRFSGSGSGTDFTLKISRVEAEDVGVYYC | 170 | WQGTHFPWT | 130 | FGGGTKVEIK | 172 | 100 |
| LVSQLDS | 128 | GVPDRFSGSGSGTDFTLKISRVEAEDVGVYYC | 170 | WQGTHFPWT | 131 | FGGGTKVEIK | 172 | 102 |
| LVSQLDS | 128 | GVPDRFSGSGSGTDFTLKISRVEAEDVGVYYC | 170 | WQGTHFPWT | 130 | FGGGTRLEIK | 171 | 104 |
| LVSQLDS | 128 | GVPDRFSGSGSGTDFTLKISRVEAEDVGVYYC | 170 | WQGTHFPWT | 130 | FGGGTKVEIK | 172 | 112 |
| LVSQLDS | 128 | GVPDRFSGSGSGTDFTLKISRVEAEDVGVYYC | 170 | WQGTHFPWT | 130 | FGGGTKVEIK | 172 | 229 |
| LVSQLDS | 255 | GVPDRFSGSGSGTDFTLKISRVEAEDVGVYYC | 170 | WQGTHFPWT | 130 | FGGGTKVEIK | 172 | 231 |
| LVSQLDS | 254 | GVPDRFSGSGSGTDFTLKISRVEAEDVGVYYC | 170 | WQGTHFPWT | 130 | FGGGTKVEIK | 172 | 233 |
| LVSQLDS | 256 | GVPDRFSGSGSGTDFTLKISRVEAEDVGVYYC | 170 | WQGTHFPWT | 130 | FGGGTKVEIK | 172 | 237 |

FIG. 21 (cont.)

VH amino acid sequences broken down into framework and CDR sequences with corresponding SEQ ID NOs

| Species | Heavy Vector ID | Name | H-FR1 | SEQ ID NO | HCDR1 (Chothia) | SEQ ID NO | H-FR2 | SEQ ID NO |
|---|---|---|---|---|---|---|---|---|
| Mouse | A293, A368 | 4h | [illegible] | 132 | [illegible] | 119 | [illegible] | 138 |
|  | A402, A451 | R3B89 | [illegible] | 132 | [illegible] | 122 | [illegible] | 138 |
|  | A427 | R3B89(Y58) | [illegible] | 132 | [illegible] | 122 | [illegible] | 138 |
|  | A448, A474 | R3B89(Y58G57) | [illegible] | 132 | [illegible] | 122 | [illegible] | 138 |
| Human template | N/A | hSGHG1 | [illegible] | 133 | — | — | [illegible] | 173 |
| Humanized | A709 | hzR3B89.HV0 | [illegible] | 133 | [illegible] | 122 | [illegible] | 173 |
|  | A454 | hzR3B89.HV5a | [illegible] | 133 | [illegible] | 122 | [illegible] | 139 |
|  | A453 | hzR3B89.HV5b | [illegible] | 134 | [illegible] | 122 | [illegible] | 140 |
|  | A456 | hzR3B89.HV6a | [illegible] | 134 | [illegible] | 122 | [illegible] | 141 |
|  | A457 | hzR3B89.HV6b | [illegible] | 133 | [illegible] | 122 | [illegible] | 142 |
|  | A458 | hzR3B89.HV6c | [illegible] | 133 | [illegible] | 122 | [illegible] | 142 |
|  | A459 | hzR3B89.HV7a | [illegible] | 134 | [illegible] | 122 | [illegible] | 141 |
|  | A460 | hzR3B89.HV7b | [illegible] | 134 | [illegible] | 122 | [illegible] | 140 |
|  | A461 | hzR3B89.HV7c | [illegible] | 133 | [illegible] | 122 | [illegible] | 143 |
|  | A462 | hzR3B89.HV9a | [illegible] | 135 | [illegible] | 122 | [illegible] | 139 |
|  | A463 | hzR3B89.HV9b | [illegible] | 133 | [illegible] | 122 | [illegible] | 144 |
|  | A464 | hzR3B89.HV10 | [illegible] | 133 | [illegible] | 122 | [illegible] | 142 |
|  | A465 | hzR3B89.HV11 | [illegible] | 136 | [illegible] | 122 | [illegible] | 141 |
|  | A469 | hzR3B89.HV18 | [illegible] | 137 | [illegible] | 122 | [illegible] | 144 |
|  | A512 | hzR3B89(A56).HV11 | [illegible] | 136 | [illegible] | 122 | [illegible] | 141 |
|  | A515 | hzR3B89(Y58A56G57).HV7b | [illegible] | 134 | [illegible] | 122 | [illegible] | 140 |
|  | A589 | hzR3B89(A56)_HV7c | [illegible] | 133 | [illegible] | 122 | [illegible] | 143 |
|  | A631 | hzR3B89(A56).HV12a | [illegible] | 136 | [illegible] | 122 | [illegible] | 240 |
|  | A632 | hzR3B89(A56).HV12b | [illegible] | 136 | [illegible] | 122 | [illegible] | 241 |
|  | A633 | hzR3B89(A56).HV13a | [illegible] | 136 | [illegible] | 122 | [illegible] | 242 |
|  | A634 | hzR3B89(A56).HV13b | [illegible] | 136 | [illegible] | 122 | [illegible] | 141 |
|  | A636 | hzR3B89(A56).HV13d | [illegible] | 136 | [illegible] | 122 | [illegible] | 243 |
|  | A638 | hzR3B89(A56).HV13f | [illegible] | 138 | [illegible] | 122 | [illegible] | 141 |
|  | A639 | hzR3B89(A56).HV13g | [illegible] | 136 | [illegible] | 122 | [illegible] | 244 |
|  | A641 | hzR3B89(A56).HV16 | [illegible] | 238 | [illegible] | 122 | [illegible] | 245 |
|  | A642 | hzR3B89(A56).HV17a | [illegible] | 238 | [illegible] | 122 | [illegible] | 246 |
|  | A643 | hzR3B89(A56).HV17b | [illegible] | 238 | [illegible] | 122 | [illegible] | 245 |
|  | A645 | hzR3B89(A56).HV17d | [illegible] | 238 | [illegible] | 122 | [illegible] | 245 |
|  | A648 | hzR3B89(A56).HV17g | [illegible] | 238 | [illegible] | 122 | [illegible] | 245 |
|  | A650 | hzR3B89(A56).HV17i | [illegible] | 239 | [illegible] | 122 | [illegible] | 245 |

FIG. 22

| HCDR2 (Kabat) | SEQ ID NO | R-F83 | SEQ ID NO | HCDR3 (Kabat) | SEQ ID NO | R-F84 | SEQ ID NO | Complete Variable SEQ ID NO |
|---|---|---|---|---|---|---|---|---|
| YINPRSGYTNYNQKFKG | 128 | RATLTVDKSSSTAYMEFRSLTSEDSAVYYCAR | 145 | SGWFTY | 121 | WGQGTLVTVSA | 158 | 35 |
| SINPRSGYTNYNQKFKG | 123 | RATLTVDKSSSTAYMEFRSLTSEDSAVYYCAS | 145 | SGWFTY | 121 | WGQGTLVTVSA | 158 | 50 |
| YINPRSGYTNYNQKFKG | 148 | RATLTVDKSSSTAYMEFRSLTSEDSAVYYCAR | 145 | SGWFTY | 121 | WGQGTLVTVSA | 158 | 181 |
| YINPRSGYTNYNQKFKG | 128 | RATLTVDKSSSTAYMEFRSLTSEDSAVYYCAS | 145 | SGWFTY | 121 | WGQGTLVTVSA | 158 | 54 |
| --- | --- | RVTISADTSKNTAYMELSSLRSEDTAVYYCAR | 174 | --- | --- | WGQGTLVTVSS | 159 | --- |
| SINPRSGYTNYNQKFKG | 123 | RVTISADTSKNTAYMELSSLRSEDTAVYYCAR | 178 | SGWFTY | 121 | WGQGTLVTVSS | 159 | 179 |
| SINPRSGYTNYNQKFKG | 123 | RATIKPDTSKNTAYMELSSLRSEDTAVYYCAS | 146 | SGWFTY | 121 | WGQGTLVTVSS | 159 | 66 |
| SINPRSGYTNYNQKFKG | 123 | RVTITADTSKNTAYMELSSLRSEDTAVYYCAR | 147 | SGWFTY | 121 | WGQGTLVTVSS | 159 | 68 |
| SINPRSGYTNYNQKFKG | 123 | RVTISADTSKNTAYMELSSLRSEDTAVYYCAR | 147 | SGWFTY | 121 | WGQGTLVTVSS | 159 | 70 |
| SINPRSGYTNYNQKFKG | 123 | RATIADTSTTAYMELSSLRSEDTAVYYCAR | 148 | SGWFTY | 121 | WGQGTLVTVSS | 159 | 72 |
| SINPRSGYTNYNQKFKG | 123 | RATIADSTYTAYMELSSLRSEDTAVYYCAS | 149 | SGWFTY | 121 | WGQGTLVTVSS | 159 | 74 |
| SINPRSGYTNYNQKFKG | 123 | RVTISANTSTAYMELSSLRSEDTAVYYCAR | 150 | SGWFTY | 121 | WGQGTLVTVSS | 159 | 76 |
| SINPRSGYTNYNQKFKG | 123 | RVTIADETRDTAYMELSSLRSEDTAVYYCAR | 151 | SGWFTY | 121 | WGQGTLVTVSS | 159 | 78 |
| SINPRSGYTNYNQKFKG | 123 | RATIADSTYTAYMELSSLRSEDTAVYYCAR | 152 | SGWFTY | 121 | WGQGTLVTVSS | 159 | 80 |
| SINPRSGYTNYNQKFKG | 123 | RATLTVRSTRDTAYMEFSSLRSEDTAVYYCAR | 153 | SGWFTY | 121 | WGQGTLVTVSS | 159 | 82 |
| SINPRSGYTNYNQKFKG | 123 | RATIADSTTAYMEFSSLRSEDTAVYYCAR | 154 | SGWFTY | 121 | WGQGTLVTVSS | 159 | 84 |
| SINPRSGYTNYNQKFKG | 123 | RATITADSTRDTAYMELSSLRSEDTAVYYCAR | 155 | SGWFTY | 121 | WGQGTLVTVSS | 159 | 86 |
| SINPRSGYTNYNQKFKG | 123 | RATIVRSTRDTAYMEFSSLRSEDTAVYYCAR | 156 | SGWFTY | 121 | WGQGTLVTVSS | 159 | 88 |
| SINPRSGYTNYNQKFKG | 123 | RATLTVRSTRDTAYMEFSSLRSEDTAVYYCAR | 157 | SGWFTY | 121 | WGQGTLVTVSS | 159 | 90 |
| SINPRAWTNYNQKFKG | 124 | RATITVRSTRDTAYMELSSLRSEDTAVYYCAR | 158 | SGWFTY | 121 | WGQGTLVTVSS | 159 | 188 |
| YINPRAGYTNYNQKFKG | 126 | RVTIADSTSTAYMELSSLRSEDTAVYYCAR | 151 | SGWFTY | 121 | WGQGTLVTVSS | 159 | 110 |
| SINPRAWTNYNQKFKG | 124 | RATIADSTYTAYMELSSLRSEDTAVYYCAS | 152 | SGWFTY | 121 | WGQGTLVTVSS | 159 | 106 |
| SINPRAWTNYNQKFKG | 124 | RATITVRSTRDTAYMELSSLRSEDTAVYYCAR | 158 | SGWFTY | 121 | WGQGTLVTVSS | 159 | 203 |
| SINPRAWTNYNQKFKG | 124 | RATIVRSTRDTAYMELSSLRSEDTAVYYCAR | 156 | SGWFTY | 121 | WGQGTLVTVSS | 159 | 205 |
| SINPRAWTNYNQKFKG | 124 | RATIVRSTRDTAYMELSSLRSEDTAVYYCAR | 156 | SGWFTY | 121 | WGQGTLVTVSS | 159 | 207 |
| SINPRAWTNYNQKFKG | 247 | RATIVRSTRDTAYMELSSLRSEDTAVYYCAR | 156 | SGWFTY | 121 | WGQGTLVTVSS | 159 | 209 |
| SINPRAWTNYNQKFKG | 124 | RATIVRSTRDTAYMELSSLRSEDTAVYYCAS | 156 | SGWFTY | 121 | WGQGTLVTVSS | 159 | 211 |
| SINPRAWTNYNQKFKG | 246 | RATIVRSTRDTAYMELSSLRSEDTAVYYCAR | 156 | SGWFTY | 121 | WGQGTLVTVSS | 159 | 213 |
| SINPRAWTNYNQKFKG | 124 | RATIVRSTRDTAYMELSSLRSEDTAVYYCAR | 156 | SGWFTY | 121 | WGQGTLVTVSS | 159 | 215 |
| SINPRAWTNYNQKFKG | 124 | RATLTVRSTRDTAYMELSSLRSEDTAVYYCAR | 251 | SGWFTY | 121 | WGQGTLVTVSS | 159 | 217 |
| SINPRAWTNYNQKFKG | 250 | RATLTVRSTRDTAYMELSSLRSEDTAVYYCAR | 251 | SGWFTY | 121 | WGQGTLVTVSS | 159 | 221 |
| SINPRAWTNYNQKFKG | 248 | RATLTVRSTRDTAYMELSSLRSEDTAVYYCAS | 251 | SGWFTY | 121 | WGQGTLVTVSS | 159 | 223 |
| SINPRAWTNYNQKFKG | 249 | RATLTVRSTRDTAYMELSSLRSEDTAVYYCAR | 251 | SGWFTY | 121 | WGQGTLVTVSS | 159 | 225 |
| SINPRAWTNYNQKFKG | 124 | RATLTVRSTRDTAYMELSSLRSEDTAVYYCAR | 251 | SGWFTY | 121 | WGQGTLVTVSS | 159 | 227 |

FIG. 22 (cont.)

List of exemplary humanized R35B9 antibodies and antibody variants produced

Humanized antibodies

| Antibody Name | Heavy Vector ID | Light Vector ID | VH Name | VL Name | Humanized framework VH | Humanized framework VL | HCDR1 | SEQ ID NO. |
|---|---|---|---|---|---|---|---|---|
| 41c (mouse) | A291 | A290 | 41c | 41c | 0 | 0 | GYTFTDYNMH | 119 |
| A466 / A467 | A466 | A467 | hzR35B9-HV18 | hzR35B9-LV0 | HV18 | LV0 | GYIFQDYNMH | 122 |
| A466 / A468 | A466 | A468 | hzR35B9-HV18 | hzR35B9-LV1a | HV18 | LV1a | GYIFQDYNMH | 122 |
| A466 / A469 | A466 | A469 | hzR35B9-HV18 | hzR35B9-LV1b | HV18 | LV1b | GYIFQDYNMH | 122 |
| A466 / A470 | A466 | A470 | hzR35B9-HV18 | hzR35B9-LV3a | HV18 | LV3a | GYIFQDYNMH | 122 |
| A466 / A471 | A466 | A471 | hzR35B9-HV18 | hzR35B9-LV3b | HV18 | LV3b | GYIFQDYNMH | 122 |
| A466 / A472 | A466 | A472 | hzR35B9-HV18 | hzR35B9-LV4 | HV18 | LV4 | GYIFQDYNMH | 122 |
| A466 / A473 | A466 | A473 | hzR35B9-HV18 | hzR35B9-LV5 | HV18 | LV5 | GYIFQDYNMH | 122 |
| A454 / A468 | A454 | A468 | hzR35B9-HV5a | hzR35B9-LV1a | HV5a | LV1a | GYIFQDYNMH | 122 |
| A455 / A468 | A455 | A468 | hzR35B9-HV5b | hzR35B9-LV1a | HV5b | LV1a | GYIFQDYNMH | 122 |
| A456 / A468 | A456 | A468 | hzR35B9-HV6a | hzR35B9-LV1a | HV6a | LV1a | GYIFQDYNMH | 122 |
| A457 / A468 | A457 | A468 | hzR35B9-HV6b | hzR35B9-LV1a | HV6b | LV1a | GYIFQDYNMH | 122 |
| A458 / A468 | A458 | A468 | hzR35B9-HV6c | hzR35B9-LV1a | HV6c | LV1a | GYIFQDYNMH | 122 |
| A459 / A468 | A459 | A468 | hzR35B9-HV7a | hzR35B9-LV1a | HV7a | LV1a | GYIFQDYNMH | 122 |
| A460 / A468 | A460 | A468 | hzR35B9-HV7b | hzR35B9-LV1a | HV7b | LV1a | GYIFQDYNMH | 122 |
| A461 / A468 | A461 | A468 | hzR35B9-HV7c | hzR35B9-LV1a | HV7c | LV1a | GYIFQDYNMH | 122 |
| A462 / A468 | A462 | A468 | hzR35B9-HV9a | hzR35B9-LV1a | HV9a | LV1a | GYIFQDYNMH | 122 |
| A463 / A468 | A463 | A468 | hzR35B9-HV9b | hzR35B9-LV1a | HV9b | LV1a | GYIFQDYNMH | 122 |
| A464 / A468 | A464 | A468 | hzR35B9-HV10 | hzR35B9-LV1a | HV10 | LV1a | GYIFQDYNMH | 122 |
| A465 / A468 | A465 | A468 | hzR35B9-HV11 | hzR35B9-LV1a | HV11 | LV1a | GYIFQDYNMH | 122 |
| A454 / A471 | A454 | A471 | hzR35B9-HV5a | hzR35B9-LV3b | HV5a | LV3b | GYIFQDYNMH | 122 |
| A455 / A471 | A455 | A471 | hzR35B9-HV5b | hzR35B9-LV3b | HV5b | LV3b | GYIFQDYNMH | 122 |
| A456 / A471 | A456 | A471 | hzR35B9-HV6a | hzR35B9-LV3b | HV6a | LV3b | GYIFQDYNMH | 122 |
| A457 / A471 | A457 | A471 | hzR35B9-HV6b | hzR35B9-LV3b | HV6b | LV3b | GYIFQDYNMH | 122 |
| A458 / A471 | A458 | A471 | hzR35B9-HV6c | hzR35B9-LV3b | HV6c | LV3b | GYIFQDYNMH | 122 |
| A459 / A471 | A459 | A471 | hzR35B9-HV7a | hzR35B9-LV3b | HV7a | LV3b | GYIFQDYNMH | 122 |
| A460 / A471 | A460 | A471 | hzR35B9-HV7b | hzR35B9-LV3b | HV7b | LV3b | GYIFQDYNMH | 122 |
| A461 / A471 | A461 | A471 | hzR35B9-HV7c | hzR35B9-LV3b | HV7c | LV3b | GYIFQDYNMH | 122 |
| A462 / A471 | A462 | A471 | hzR35B9-HV9a | hzR35B9-LV3b | HV9a | LV3b | GYIFQDYNMH | 122 |
| A463 / A471 | A463 | A471 | hzR35B9-HV9b | hzR35B9-LV3b | HV9b | LV3b | GYIFQDYNMH | 122 |
| A464 / A471 | A464 | A471 | hzR35B9-HV10 | hzR35B9-LV3b | HV10 | LV3b | GYIFQDYNMH | 122 |
| A465 / A471 | A465 | A471 | hzR35B9-HV11 | hzR35B9-LV3b | HV11 | LV3b | GYIFQDYNMH | 122 |
| A464 / A467 | A464 | A467 | hzR35B9-HV10 | hzR35B9-LV0 | HV10 | LV0 | GYIFQDYNMH | 122 |
| A461 / A472 | A461 | A472 | hzR35B9-HV7C | hzR35B9-LV4 | HV7C | LV4 | GYIFQDYNMH | 122 |

FIG. 23

Humanized antibodies

| Antibody Name | HCDR2 | SEQ ID NO. | HCDR3 | SEQ ID NO. | LCDR1 | SEQ ID NO. | LCDR2 | SEQ ID NO. | LCDR3 | SEQ ID NO. | Deamidation mutation | HC Isotype |
|---|---|---|---|---|---|---|---|---|---|---|---|---|
| 41c (mouse) | YINPNNGGTNYNQKFKG | 120 | SGWFTY | 123 | KSSQSLLNSAGKTYLN | 121 | LVSQLDS | 127 | WQGTHFPWT | 129 | N/A | N/A |
| A466 / A467 | SINPRNGWTNYNQKFKG | 123 | SGWFTY | 123 | KSSQSLLNSAGKTYLN | 121 | LVSQLDS | 127 | WQGTFYPWT | 130 | | |
| A466 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A466 / A469 | SINPRNGWTNYNQKFKG | 123 | SGWFTY | 123 | KSSQSLLNSAGKTYLN | 121 | LVSQLDS | 127 | WQGTFYPWT | 130 | | |
| A466 / A470 | SINPRNGWTNYNQKFKG | 123 | SGWFTY | 123 | KSSQSLLNSAGKTYLN | 121 | LVSQLDS | 127 | WQGTFYPWT | 130 | | |
| A466 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A466 / A472 | SINPRNGWTNYNQKFKG | 123 | SGWFTY | 123 | KSSQSLLNSAGKTYLN | 121 | LVSQLDS | 127 | WQGTFYPWT | 130 | | |
| A465 / A473 | SINPRNGWTNYNQKFKG | 123 | SGWFTY | 123 | KSSQSLLNSAGKTYLN | 121 | LVSQLDS | 127 | WQGTFYPWT | 130 | | |
| A454 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A455 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A456 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A457 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A458 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A459 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A460 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A461 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A462 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A463 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A464 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A465 / A468 | SINPRNGWTNYNQKFKG | 123 | SGWFTY | 123 | KSSQSLLNSAGKTYLN | 121 | LVSQLDS | 127 | WQGTFYPWT | 130 | | |
| A454 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A455 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A456 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A457 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A458 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A459 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A460 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A461 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A462 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A463 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A464 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A465 / A471 | SINPRNGWTNYNQKFKG | 123 | SGWFTY | 123 | KSSQSLLNSAGKTYLN | 121 | LVSQLDS | 127 | WQGTFYPWT | 130 | | |
| A464 / A471 | SINPRNGWTNYNQKFKG | 123 | SGWFTY | 123 | KSSQSLLNSAGKTYLN | 121 | LVSQLDS | 127 | WQGTFYPWT | 130 | | IgG4null |
| A461 / A467 | SINPRNGWTNYNQKFKG | 123 | SGWFTY | 123 | KSSQSLLNSAGKTYLN | 121 | LVSQLDS | 127 | WQGTFYPWT | 130 | | |
| A461 / A472 | SINPRNGWTNYNQKFKG | 123 | SGWFTY | 123 | KSSQSLLNSAGKTYLN | 121 | LVSQLDS | 127 | WQGTFYPWT | 130 | | |

FIG. 23 (cont.)

Humanized antibodies

| Antibody Name | Heavy Vector ID | Light Vector ID | VH Name | VL Name | Humanized framework VH | Humanized framework VL | HCDR1 | SEQ ID NO. |
|---|---|---|---|---|---|---|---|---|
| 41c (mouse) | A291 | A290 | 41c | 41c | 0 | 0 | GYTFTDYNMH | 119 |
| A512 / A468 | A512 | A468 | hzR35B9(A56)-HV11 | hzR35B9-LV1a | HV11 | LV1a | GYIFQDYNMH | 122 |
| A515 / A518 | A515 | A518 | hzR35B9(Y50A56G57)-HV7b | hzR35B9(H98)-LV1a | HV7b | LV1a | GYIFQDYNMH | 122 |
| A553 / A472 | A553 | A472 | hzR35B9(A56)_HV7c | hzR35B9-LV4 | HV7c | LV4 | GYIFQDYNMH | 122 |
| A512 / A654 | A512 | A654 | hzR35B9(A56)-HV11 | hzR35B9(A56)-LV2d | HV11 | LV2d | GYIFQDYNMH | 122 |
| A631 / A468 | A631 | A468 | hzR35B9(A56)-HV12a | hzR35B9(A56)-LV1a | HV12a | LV1a | GYIFQDYNMH | 122 |
| A512 / A651 | A512 | A651 | hzR35B9(A56)-HV11 | hzR35B9(A56)-LV2a | HV11 | LV2a | GYIFQDYNMH | 122 |
| A512 / A652 | A512 | A652 | hzR35B9(A56)-HV11 | hzR35B9(A56)-LV2b | HV11 | LV2b | GYIFQDYNMH | 122 |
| A634 / A468 | A634 | A468 | hzR35B9(A56)-HV13b | hzR35B9-LV1a | HV13b | LV1a | GYIFQDYNMH | 122 |
| A636 / A468 | A636 | A468 | hzR35B9(A56)-HV13d | hzR35B9-LV1a | HV13d | LV1a | GYIFQDYNMH | 122 |
| A643 / A468 | A643 | A468 | hzR35B9(A56)-HV17b | hzR35B9-LV1a | HV17b | LV1a | GYIFQDYNMH | 122 |
| A512 / A653 | A512 | A653 | hzR35B9(A56)-HV11 | hzR35B9(A56)-LV2c | HV11 | LV2c | GYIFQDYNMH | 122 |
| A632 / A468 | A632 | A468 | hzR35B9(A56)-HV12b | hzR35B9-LV1a | HV12b | LV1a | GYIFQDYNMH | 122 |
| A645 / A468 | A645 | A468 | hzR35B9(A56)-HV17d | hzR35B9-LV1a | HV17d | LV1a | GYIFQDYNMH | 122 |
| A648 / A468 | A648 | A468 | hzR35B9(A56)-HV17g | hzR35B9-LV1a | HV17g | LV1a | GYIFQDYNMH | 122 |
| A650 / A468 | A650 | A468 | hzR35B9(A56)-HV17i | hzR35B9-LV1a | HV17i | LV1a | GYIFQDYNMH | 122 |
| A639 / A468 | A639 | A468 | hzR35B9(A56)-HV13g | hzR35B9-LV1a | HV13g | LV1a | GYIFQDYNMH | 122 |
| A512 / A656 | A512 | A656 | hzR35B9(A56)-HV11 | hzR35B9(A56)-LV2f | HV11 | LV2f | GYIFQDYNMH | 122 |
| A633 / A468 | A633 | A468 | hzR35B9(A56)-HV13a | hzR35B9-LV1a | HV13a | LV1a | GYIFQDYNMH | 122 |
| A638 / A468 | A638 | A468 | hzR35B9(A56)-HV13f | hzR35B9-LV1a | HV13f | LV1a | GYIFQDYNMH | 122 |
| A641 / A468 | A641 | A468 | hzR35B9(A56)-HV16 | hzR35B9-LV1a | HV16 | LV1a | GYIFQDYNMH | 122 |
| A642 / A468 | A642 | A468 | hzR35B9(A56)-HV17a | hzR35B9-LV1a | HV17a | LV1a | GYIFQDYNMH | 122 |

FIG. 23 (cont.)

Humanized antibodies

| Antibody Name | HCDR2 | SEQ ID NO. | HCDR3 | SEQ ID NO. | LCDR1 | SEQ ID NO. | LCDR2 | SEQ ID NO. | LCDR3 | SEQ ID NO. | Deamidation mutation | HC Isotype |
|---|---|---|---|---|---|---|---|---|---|---|---|---|
| 41c (mouse) | YINPNNGGTNYNQKFKG | 120 | SGWFTY | | KSSQSLLNSAGKTYLN | 121 | LVSQLDS | 128 | WQGTHFPWT | 129 | N/A | N/A |
| A512 / A468 | SINPRNAWTNYNQKFKG | 124 | SGWFTY | | KSSQSLLNSAGKTYLN | 121 | LVSQLDS | 128 | WQGTFYPWT | 130 | A56 | |
| A515 / A518 | YINPRNAGTNYNQKFKG | 126 | SGWFTY | | KSSQSLLNSAGKTYLN | 121 | LVSQLDS | 128 | WQGTHYPWT | 131 | A56 | |
| A553 / A472 | SINPRNAWTNYNQKFKG | 124 | SGWFTY | | KSSQSLLNSAGKTYLN | 121 | LVSQLDS | 128 | WQGTFYPWT | 130 | A56 | |
| A512 / A654 | SINPRNAWTNYNQKFKG | 124 | SGWFTY | | KSSQSLLNSAGKTYLN | 121 | LVSQLDD | 254 | WQGTFYPWT | 130 | A56 | |
| A631 / A468 | SINPRNAWTNYNQKFKG | 124 | SGWFTY | | KSSQSLLNSAGKTYLN | 121 | LVSQLDS | 128 | WQGTFYPWT | 130 | A56 | IgG4null |
| A512 / A651 | SINPRNAWTNYNQKFKG | 124 | SGWFTY | | KSSQSLLNSAGKTYLN | 121 | LVSQLDS | 128 | WQGTFYPWT | 130 | A56 | |
| A512 / A652 | SINPRNAWTNYNQKFKG | 124 | SGWFTY | | KSSQSLLNSAGKTYLN | 121 | LVSQLDS | 128 | WQGTFYPWT | 130 | A56 | |
| A634 / A468 | SINPRNAWTNYNQKFGG | 247 | SGWFTY | | KSSQSLLNSAGKTYLN | 121 | LVSQLDS | 128 | WQGTFYPWT | 130 | A56 | |
| A636 / A468 | SINPRNAWTNYNQKFKG | 124 | SGWFTY | | KSSQSLLNSAGKTYLN | 121 | LVSQLDS | 128 | WQGTFYPWT | 130 | A56 | |
| A643 / A468 | SINPRNAWTNYNQKFHG | 250 | SGWFTY | | KSSQSLLNSAGKTYLN | 121 | LVSELDS | 255 | WQGTFYPWT | 130 | A56 | |
| A512 / A653 | SINPRNAWTNYNQKFKG | 124 | SGWFTY | | KSSQSLLNSAGKTYLN | 121 | LVSQLDS | 128 | WQGTFYPWT | 130 | A56 | |
| A632 / A468 | SINPRNAWTNYNQKFKG | 124 | SGWFTY | | KSSQSLLNSAGKTYLN | 121 | LVSQLDS | 128 | WQGTFYPWT | 130 | A56 | |
| A645 / A468 | SINPRNAWTNYNQKFDG | 248 | SGWFTY | | KSSQSLLNSAGKTYLN | 121 | LVSQLDS | 128 | WQGTFYPWT | 130 | A56 | |
| A648 / A468 | SINPRNAWTNYNDKFKG | 249 | SGWFTY | | KSSQSLLNSAGKTYLN | 121 | LVSQLDS | 128 | WQGTFYPWT | 130 | A56 | |
| A650 / A468 | SINPRNAWTNYNQKFKG | 124 | SGWFTY | | KSSQSLLNSAGKTYLN | 121 | LVSQLDS | 128 | WQGTFYPWT | 130 | A56 | |
| A639 / A468 | SINPRNAWTNYNQKFKG | 124 | SGWFTY | | KSSQSLLNSAGKTYLN | 121 | LVSQLDS | 128 | WQGTFYPWT | 130 | A56 | |
| A512 / A656 | SINPRNAWTNYNQKFKG | 124 | SGWFTY | | KSSQSLLNSAGKTYLN | 121 | LVAQLDS | 256 | WQGTFYPWT | 130 | A56 | |
| A633 / A468 | SINPRNAWTNYNQKFKG | 124 | SGWFTY | | KSSQSLLNSAGKTYLN | 121 | LVSQLDS | 128 | WQGTFYPWT | 130 | A56 | |
| A638 / A468 | SINPRNAWTNYNDKFKG | 249 | SGWFTY | | KSSQSLLNSAGKTYLN | 121 | LVSQLDS | 128 | WQGTFYPWT | 130 | A56 | |
| A641 / A468 | SINPRNAWTNYNQKFKG | 124 | SGWFTY | | KSSQSLLNSAGKTYLN | 121 | LVSQLDS | 128 | WQGTFYPWT | 130 | A56 | |
| A642 / A468 | SINPRNAWTNYNQKFKG | 124 | SGWFTY | | KSSQSLLNSAGKTYLN | 121 | LVSQLDS | 128 | WQGTFYPWT | 130 | A56 | |

FIG. 23 (cont.)

Exemplary humanized VH and VL amino acid sequences with corresponding SEQ ID NOs

| Heavy Vector ID | VH Name | Humanized framework | Variable sequence | SEQ ID NO |
|---|---|---|---|---|
| A700 | hzR35B9-HV0 | HV0 | QVQLVQSGAEVKKPGASVKVSCKASGYIFQDYRMHWVRQAPGQGLEWMGWINTNQKFKGRVTITADTSTSTAYMELSSLRSEDTAVYYCARSGMFTYWGQGTLVTVSS | 179 |
| A454 | hzR35B9-HV5a | HV5a | QVQLVQSGAEVKKPGASVKVSCKASGYIFQDYNMHWVRQAPGQGLEWIGSINPRNGWTNYNQKFKGRATITADTSTSTAYMELSSLRSEDTAVYYCASSGMFTYWGQGTLVTVSS | 66 |
| A455 | hzR35B9-HV5b | HV5b | QVQLVQSGAEVKKPGASVKVSCKASGYIFQDYNMHWVRQAPGQGLEWIGSINPRNGWTNYNQKFKGRATITADTSTSTAYMELSSLRSEDTAVYYCASSGMFTYWGQGTLVTVSS | 68 |
| A456 | hzR35B9-HV6a | HV6a | QVQLVQSGAEVKKPGASVKVSCKASGYIFQDYNMHWVRQAHGQGLEWIGSINPRNGWTNYNQKFKGRATITADTSTSTAYMELSSLRSEDTAVYYCARSGMFTYWGQGTLVTVSS | 70 |
| A457 | hzR35B9-HV6b | HV6b | QVQLVQSGAEVKKPGASVKVSCKASGYIFQDYNMHWVRQAHGQGLEWIGSINPRNGWTNYNQKFKGRATITADTSTSTAYMELSSLRSEDTAVYYCASSGMFTYWGQGTLVTVSS | 72 |
| A458 | hzR35B9-HV6c | HV6c | QVQLVQSGAEVKKPGASVKVSCKASGYIFQDYNMHWVRQAHGQGLEWIGSINPRNGWTNYNQKFKGRATITADKSTSTAYMELSSLRSEDTAVYYCASSGMFTYWGQGTLVTVSS | 74 |
| A459 | hzR35B9-HV7a | HV7a | QVQLVQSGAEVKKPGASVKVSCKASGYIFQDYNMHWVRQAHGQSLEWMGSINPRNGWTNYNQKFKGRVTITADTSTSTAYMELSSLRSEDTAVYYCASSGMFTYWGQGTLVTVSS | 76 |
| A460 | hzR35B9-HV7b | HV7b | QVQLVQSGAEVKKPGASVKVSCKASGYIFQDYNMHWVRQAHGQSLEWMGSINPRNGWTNYNQKFKGRVTITADKSTSTAYMELSSLRSEDTAVYYCASSGMFTYWGQGTLVTVSS | 78 |
| A461 | hzR35B9-HV7C | HV7C | QVQLVQSGAEVKKPGASVKVSCKASGYIFQDYNMHWVRQAPGQGLEWIGSINPRNGWTNYNQKFKGRVTITADTSTSTAYMELSSLRSEDTAVYYCASSGMFTYWGQGTLVTVSS | 80 |
| A462 | hzR35B9-HV9a | HV9a | QVQLVQSGAEVKKPGASVKVSCKASGYIFQDYNMHWVRQAPGQGLEWMGSINPRNGWTNYNQKFKGRATLTVDTSTSTAYMEFSSLRSEDTAVYYCASSGMFTYWGQGTLVTVSS | 82 |
| A463 | hzR35B9-HV9b | HV9b | QVQLVQSGAEVKKPGASVKVSCKASGYIFQDYNMHWVRQAPGQGLEWIGSINPRNGWTNYNQKFKGRATITADTSTSTAYMEFSSLRSEDTAVYYCASSGMFTYWGQGTLVTVSS | 84 |
| A464 | hzR35B9-HV10 | HV10 | QVQLVQSGAEVKKPGASVKVSCKASGYIFQDYNMHWVRQAHGQSLEWMGSINPRNGWTNYNQKFKGRATITADKSTSTAYMEFSSLRSEDTAVYYCASSGMFTYWGQGTLVTVSS | 86 |
| A465 | hzR35B9-HV11 | HV11 | QVQLVQSGAEVKKPGASVKVSCKASGYIFQDYNMHWVRQAHGQSLEWMGSINPRNGWTNYNQKFKGRATITVDKSTRTAYMELSSLRSEDTAVYYCASSGMFTYWGQGTLVTVSS | 88 |
| A466 | hzR35B9-HV18 | HV18 | EVQLVQSGAEVKKPGASVKVSCKASGYIFQDYNMHWVRQAHGQSLEWMGSINPRNGWTNYNQKFKGRATITVDKSTRTAYMELSSLRSEDTAVYYCASSGMFTYWGQGTLVTVSS | 93 |
| A512 | hzR35B9(A56)-HV11 | HV11 | QVQLVQSGAEVKKPGASVKVSCKASGYIFQDYNMHWVRQAHGQSLEWMGSINPRNGAWTNYNQKFKGRATITVDKSTRTAYMELSSLRSEDTAVYYCASSGMFTYWGQGTLVTVSS | 108 |
| A515 | hzR35B9(Y50A56G57)-HV7b | HV7b | QVQLVQSGAEVKKPGASVKVSCKASGYIFQDYNMHWVRQAHGQSLEWMGYINPRNAGWTNYNQKFKGRVTITADKSTSTAYMELSSLRSEDTAVYYCASSGMFTYWGQGTLVTVSS | 110 |
| A553 | hzR35B9(A56)-HV7c | HV7c | QVQLVQSGAEVKKPGASVKVSCKASGYIFQDYNMHWVRQAPGQGLEWIGSINPRNAWTNYNQKFKGRVTITADTSTSTAYMELSSLRSEDTAVYYCASSGMFTYWGQGTLVTVSS | 106 |
| A631 | hzR35B9(A56)-HV12a | HV12a | QVQLVQSGPEVVKPGASVKVSCKASGYIFQDYNMHWVRQADGQSLEWMGSINPRNAWTNYNQKFKGRATITVEAHSTRTAYMELSSLRSEDTAVYYCASSGMFTYWGQGTLVTVSS | 203 |
| A632 | hzR35B9(A56)-HV12b | HV12b | QVQLVQSGPEVVKPGASVKVSCKASGYIFQDYNMHWVRQAPGQSLEWMGSINPRNAWTNYNQKFKGRATITVEAHSTRTAYMELSSLRSEDTAVYYCASSGMFTYWGQGTLVTVSS | 205 |
| A633 | hzR35B9(A56)-HV13a | HV13a | QVQLVQSGPEVVKPGASVKVSCKASGYIFQDYNMHWVREAHGQSLEWMGSINPRNAWTNYNQKFKGRATITVEAHSTRTAYMELSSLRSEDTAVYYCASSGMFTYWGQGTLVTVSS | 207 |
| A634 | hzR35B9(A56)-HV13b | HV13b | QVQLVQSGPEVVKPGASVKVSCKASGYIFQDYNMHWVRQAHGQGLEWMGSINPRNAWTNYNQKFKGRGGRATITVEAHSTRTAYMELSSLRSEDTAVYYCASSGMFTYWGQGTLVTVSS | 209 |
| A635 | hzR35B9(A56)-HV13d | HV13d | QVQLVQSGPEVVKPGASVKVSCKASGYIFQDYNMHWVRQAHGQSLEWMGSINPRNAWTNYNDKFKGRATITVEAHSTRTAYMELSSLRSEDTAVYYCASSGMFTYWGQGTLVTVSS | 211 |
| A638 | hzR35B9(A56)-HV13f | HV13f | QVQLVQSGPEVVKPGASVKVSCKASGYIFQDYNMHWVRQAHGQSLEWMGSINPRNAWTNYNDKFKGRATITVEAHSTRTAYMELSSLRSEDTAVYYCASSGMFTYWGQGTLVTVSS | 213 |
| A639 | hzR35B9(A56)-HV13g | HV13g | QVQLVQSGPEVVKPGASVKVSCKASGYIFQDYNMHWVRQAHGDSLEWMGSINPRNAWTNYNDKFKGRATITVEAHSTRTAIMELSSLRSEDTAVYYCASSGMFTYWGQGTLVTVSS | 215 |
| A641 | hzR35B9(A56)-HV16 | HV16 | QVQLVQSGPEVVKPGASVKVSCKASGYIFQDYNMHWVRQAHGQSLEWMGSINPRNAWTNYNDKFKGRATITVEAHSTRTAIMELSSLRSEDTAVYYCASSGMFTYWGQGTLVTVSS | 217 |
| A642 | hzR35B9(A56)-HV17a | HV17a | QVQLQQSGPEVVKPGASVKVSCKASGYIFQDYNMHWVRQAHGQSLEWMGSINPRNAWTNYNKPDGKATLTVEDKSTRTAYMEFSSLRSEDTAVYYCASSGMFTYWGQGTLVTVSS | 219 |
| A643 | hzR35B9(A56)-HV17b | HV17b | QVQLQQSGPEVVKPGASVKVSCKASGYIFQDYNMHWVRQAHGQSLEWMGSINPRNAWTNYNKPDGKATLTVEDKSTRTAYMEFSSLRSEDTAVYYCASSGMFTYWGQGTLVTVSS | 221 |
| A645 | hzR35B9(A56)-HV17d | HV17d | QVQLQQSGPEVVKPGASVKVSCKASGYIFQDYNMHWVRQAHGQSLEWMGSINPRNAWTNYNKPDGKATLTVEDKSTRTAYMEFSSLRSEDTAVYYCASSGMFTYWGQGTLVTVSS | 223 |
| A648 | hzR35B9(A56)-HV17g | HV17g | QVQLQQSGPEVVKPGASVKVSCKASGYIFQDYNMHWVRQAHGQSLEWMGSINPRNAWTNYNKPDGKAFLTVEDKSTRTAYMEFSSLRSEDTAVYYCASSGMFTYWGQGTLVTVSS | 225 |
| A650 | hzR35B9(A56)-HV17i | HV17i | QVQLQQSGPEVAKPGASVKVSCKASGYIFQDYNMHWVRQAHGQSLEWMGSINPRNAWTNYNKPDGKAFLTVEDKSTRTAYMEFSSLRSEDTAVYYCASSGMFTYWGQGTLVTVSS | 227 |

FN14 ANTIBODIES AND USES THEREOF

CROSS-REFERENCE TO RELATED APPLICATIONS

This application is a U.S. National Stage Application under 35 U.S.C. § 371 of International Patent Application No. PCT/IB2019/061058, filed Dec. 19, 2019, which claims the benefit of U.S. Provisional Patent Application No. 62/782,912, filed Dec. 20, 2018, the disclosure of each of which is incorporated by reference herein in its entirety.

SEQUENCE LISTING

This application incorporates by reference a Sequence Listing submitted with this application as a text format, entitled 14233-010-228_SEQ_LISTING.txt, created on Dec. 4, 2019 having a size of 185,980 bytes.

1. FIELD

Provided herein are anti-Fn14 antibodies and pharmaceutical compositions, methods, and uses thereof.

2. BACKGROUND

Fn14 is a 15 kDa cell surface receptor that is a member of the TNF Receptor Superfamily (TNFRSF12A) and was initially identified as a protein with increased expression in cells stimulated with Fibroblast growth factor I or II (see Meighan-Mantha, R. L., et al., 1999, J. Biol. Chem. 274 (46):33166-76; Feng, S.L., et al., 2000, Am. J. Pathol. 156(4):1253-61; Wiley, S. R., et al., 2001 Immunity 15(5): 837-46). It was later discovered that TWEAK (TNFSF12) was a ligand for this receptor (Wiley, S. R., et al., 2001 Immunity 15(5):837-46) and is the only known ligand to date. TWEAK is able to induce multiple effects on cells expressing Fn14, including apoptosis (Wiley, S. R., et al., 1995 Immunity 3(6):673-82; Chicheportiche, Y., et al., 1997, J. Biol. Chem. 272(51):32401-10), angiogenesis (Lynch, C. N., et al., 1999, J. Biol. Chem. 274(13):8455-9; Ho, D. H., et al., 2004 Cancer Res. 64(24):8968-72), proliferation (Chen, H. N., et al., 2012, Mol. Biol. Rep. 39(8): 8231-41), inflammatory mediator release (reviewed in Campbell, S., et al., 2004, Front Biosci. 9:2273-84) and upregulation of fibrotic mediators (Chen, H. N., et al., 2012, Mol. Biol. Rep. 39(8):8231-41; Son, A., et al., 2013 Mucosal Immunol. 6(6):1131-42; Zheng, L., et al., 2017, Pediatr. Surg. Int. 33(5):593-599).

In normal tissues Fn14 is expressed at very low to negligible levels, however, upon tissue injury, Fn14 is upregulated. Fn14 expression can be induced in multiple cell types including epithelial cells, endothelial cells, myofibroblasts, keratinocytes, chondrocytes, adipocytes, mesangial cells, mesenchymal stem cells and stellate cells. TWEAK is expressed by a variety of cell types including macrophages and dendritic cells and can be present both in a soluble or membrane-bound form (Nakayama, M., et al., 2002, J. Immunol. 168(2):734-43). The normal function of the TWEAK-Fn14 interaction is to facilitate tissue and wound repair, however, in situations where constitutive inflammation or tissue injury occurs, the pathway may become dysregulated, resulting in increased inflammation and development of fibrosis.

In vivo studies using mouse models of inflammation or fibrosis have identified a role for the Fn14-TWEAK pathway including kidney function in lupus nephritis (Xia, Y., et al., 2015, J. Am. Soc. Nephrol. 26(5):1053-70), chronic kidney disease (Gomez, I. G., et al., 2016, J. Am. Soc. Nephrol. 27(12):3639-3652), inflammatory bowel disease (Dohi, T., et al., 2009, Gastroenterology 136(3):912-23), chronic liver fibrosis (Wilhelm, A., et al., 2016, J. Pathol. 239(1):109-21), cancer-induced cachexia (Johnston, A. J., et al., 2015, Cell 162(6):1365-78), and muscle atrophy (Dogra, C., et al., 2016, J. Biol. Chem. 281(15):10327-36; Dogra, C., et al., 2007, FASEB J. 21(8):1857-69; Mittal, A., et al., 2010, Am. J. Pathol. 177(4):1732-42; Yadava, R. S., et al., 2015, Hum. Mol. Genet. 24(7):2035-48; Yadava, R. S., et al., 2016, PLoS One, 11(2):e0150192).

In a nephrotoxic serum nephritis model of kidney disease, Fn14 knockout (KO) mice and wild-type (WT) mice treated with a neutralizing anti-TWEAK mAb (clone P5G9) had significantly reduced proteinuria and renal histopathology compared to isotype control treated WT mice (Xia, Y., et al., 2012, Clin. Immunol. 145(2):108-21). There have also been several reports demonstrating that TWEAK and Fn14 are increased in models of unilateral ureteral obstruction (UUO). TWEAK KO mice had reduced renal fibrosis in this model and overexpression of TWEAK in mice with no underlying kidney disease induced kidney inflammation and fibrosis (Sanchez-Nino, M. D., et al., 2013, Biochim. Biophys. Acta 1832(12):2232-43). Fn14 KO mice were protected from kidney fibrosis, inflammation and vascular instability as compared to WT mice in a UUO model (Gomez, I. G., et al., 2016, J. Am. Soc. Nephrol. 27(12):3639-3652). Additionally, delivery of neutralizing anti-TWEAK mAbs to mice prone to chronic kidney disease (Alport's mice) blocked progression of kidney disease and organ dysfunction compared to isotype control treated mice (Gomez, I. G., et al., 2016, J. Am. Soc. Nephrol. 27(12):3639-3652). Taken together, these results indicate a role for TWEAK-Fn14 in both acute and chronic kidney diseases.

This pathway is also reported to be important in a variety of autoimmune mouse models. In a model of chronic graft-versus-host disease modeling Lupus erythematosus, Fn14 KO mice or WT mice treated with neutralizing anti-TWEAK mAbs, had significantly less kidney disease, kidney IgG deposition, inflammatory mediators and inflammatory cell infiltration into the kidney versus untreated WT mice (Zhao, Z., et al., 2007, J. Immunol. 179(11):7949-58). In a collagen-induced arthritis (CIA) model of rheumatoid arthritis, neutralizing anti-TWEAK mAbs significantly ameliorated paw swelling, synovial hyperplasia and infiltration of inflammatory cell and pro-inflammatory cytokine induction (Perper, S. J., et al., 2006, J. Immunol. 177(4):2610-20). Fn14-Fc was able to reduce clinical and histological scores of arthritis in a spontaneous model of autoimmune arthritis (Park, J.S., et al., 2017, Histol. Histopathol. 32(5):481-490). Fn14 KO mice had significantly attenuated skin disease versus WT mice in an MRL/lpr spontaneous lupus model (Doerner, J. L., et al., 2015, J. Invest. Dermatol. 135(8):1986-95).

Additionally, there is evidence for involvement of the TWEAK-Fn14 pathway in numerous human diseases. Many instances of this are in the area of autoimmune diseases, and examples include positive staining for both Fn14 and TWEAK in synovial tissues of RA patients (van Kuijk, A. W., et al., 2010, Ann. Rheum. Dis. 69(1):301-4), high expression of TWEAK and Fn14 in dermal vessel walls of skin lesions of urticarial vasculitis patients (Li, M., et al., 2013, J. Dermatol. 40(11):891-5) and lesions of patients with discoid cutaneous lupus (Liu, Y., et al., 2017, Front Immunol. 8:651) versus non-lesioned or healthy donor skin biopsies. The TWEAK-Fn14 pathway is also involved in various fibrotic kidney diseases including IgA nephropathy (Sasaki, Y., et al., 2015, BMC Nephrol. 16:27) and proteinuric kidney disease (Sanchez-Nino, M. D., et al., 2013, Biochim. Biophys. Acta, 1832(12):2232-43) and muscle wasting diseases including myotonic dystrophy 1(Sidler D., et al., 2017, Nature Communications 8: 15395; Claus M., et al., 2018, Am. J. Transplant 18: 1636; Yadava, R. S., et al., 2015, Hum. Mol. Genet. 24(7):2035-48; Yadava, R.S., et al., 2016, PLoS One 11(2):e0150192; Sydow, J. F., et al., 2014, PLoS One, 9(6): el 00736).

Thus, there is a need in the art of an anti-Fn14 mAb with strong antagonist activity and no or minimal agonist activity, which would be beneficial in reducing inflammation and fibrosis in diseases where the TWEAK-Fn14 pathway is activated.

3. SUMMARY

In one aspect, provided herein is an antibody or antigen binding fragment thereof that binds to Fn14, wherein the antibody or antigen binding fragment thereof is an antagonist of Fn14, and wherein
 (a) the antibody or antigen binding fragment thereof is not an agonist of Fn14;
 (b) the antibody or antigen binding fragment thereof binds human, cynomolgus macaque, rat and mouse Fn14; and/or
 (c) the antibody or antigen binding fragment thereof binds subdomain 1 comprising amino acid 30-50 of human Fn14 having an amino acid sequence of SEQ ID NO: 2.

In some embodiments, the antibody or antigen binding fragment thereof attenuates TWEAK induced signaling pathway and/or attenuates the binding of TWEAK to Fn14.

In some embodiments, the antibody or antigen binding fragment thereof attenuates TWEAK induced chemokine expression, wherein the chemokine is optionally selected from a group consisting IL-8, CCL2, IL-1β, TGFβ, CCL21, TNFα, IL-6, CXCL1, CCL3, CCL4, CXCL12, CCLS, CXCL10, and CXCL16.

In some embodiments, the antibody or antigen binding fragment thereof reduces TWEAK induced IL-8 secretion.

In some embodiments, the antibody or antigen binding fragment thereof attenuates TWEAK induced ICAM-1 expression. In some embodiments, the antibody or antigen binding fragment thereof attenuates TWEAK induced apoptosis.

In some embodiments, the antibody or antigen binding fragment thereof is not an agonist of Fn14.

In some embodiments, the antibody or antigen binding fragment thereof does not induce IL-8 secretion in the absence of TWEAK.

In some embodiments, the antibody or antigen binding fragment thereof binds human, cynomolgus macaque, rat and mouse Fn14.

In some embodiments, the antibody or antigen binding fragment thereof binds subdomain 1 comprising amino acid 30-50 of human Fn14 having an amino acid sequence of SEQ ID NO: 2.

In some embodiments, the antibody or antigen binding fragment thereof interacts with one or more amino acid residues in the amino acid sequence of APGTAPCSRGSSWSADLDKCM (SEQ ID NO: 182).

In some embodiments, the antibody or antigen binding fragment thereof interacts with one or more amino acid residues of human Fn14 protein selected from a group consisting of Gly32, Thr33, Ala34, Pro35, Trp42, Ala44, Asp45, Leu46, Asp47, Lys48, Cys49, or a combination thereof. In a specific embodiment, the antibody or antigen binding fragment thereof interacts with all the amino acid residues Gly32, Thr33, Ala34, Pro35, Trp42, Ala44, Asp45, Leu46, Asp47, Lys48, and Cys49 of human Fn14 protein.

In some embodiments, the antibody or antigen binding fragment binds human Fn14 with a $K_D$ of less than 100 nM as determined by a surface plasmon resonance method, wherein the antibody or antigen binding fragment binds cynomolgus macaque Fn14 with a $K_D$ of less than 100 nM as determined by a surface plasmon resonance method, wherein the antibody or antigen binding fragment binds rat Fn14 with a $K_D$ of less than 100 nM as determined by a surface plasmon resonance method, and wherein the antibody or antigen binding fragment binds mouse Fn14 with a $K_D$ of less than 100 nM as determined by a surface plasmon resonance method.

In some embodiments, the antibody or antigen binding fragment binds human Fn14 with a $K_D$ of less than 10 nM as determined by a surface plasmon resonance method, wherein the antibody or antigen binding fragment binds cynomolgus macaque Fn14 with a $K_D$ of less than 10 nM as determined by a surface plasmon resonance method, wherein the antibody or antigen binding fragment binds rat Fn14 with a $K_D$ of less than 10 nM as determined by a surface plasmon resonance method, and wherein the antibody or antigen binding fragment binds mouse Fn14 with a $K_D$ of less than 10 nM as determined by a surface plasmon resonance method.

In some embodiments, the antibody or antigen binding fragment binds human Fn14 with a $K_D$ of less than 1 nM as determined by a surface plasmon resonance method, wherein the antibody or antigen binding fragment binds cynomolgus macaque Fn14 with a $K_D$ of less than 1 nM as determined by a surface plasmon resonance method, wherein the antibody or antigen binding fragment binds rat Fn14 with a $K_D$ of less than 1 nM as determined by a surface plasmon resonance method, and wherein the antibody or antigen binding fragment binds mouse Fn14 with a $K_D$ of less than 1 nM as determined by a surface plasmon resonance method.

In some embodiments, the antigen binding fragment is selected from a group consisting of a Fab, a Fab', a F(ab')2, a Fv, a scFv, a dsFv, a diabody, a triabody, a tetrabody, and a multispecific antibody formed from antibody fragments.

In some embodiments, the antibody is a mouse antibody. In some embodiments, the antibody is a chimeric antibody. In some embodiments, the antibody is a fully human antibody or antigen binding fragment thereof.

In some embodiments, the antibody or antigen binding fragment is a humanized antibody or antigen binding fragment thereof.

In some embodiments, the antibody or antigen binding fragment thereof is recombinantly produced.

In some embodiments, the antibody or antigen binding fragment thereof is produced by a hybridoma.

In some embodiments, the antibody or antigen binding fragment thereof comprises:
 (a) a heavy chain variable region (VH) comprising
  (i) VH complementarity determining region 1 (CDR H1) comprising an amino acid sequence of GYX$_1$FX$_2$DYNMEI (SEQ ID NO: 184), wherein X$_1$ is T, I or R, and X$_2$ is T or Q;
  (ii) VH complementarity determining region 2 (CDR H2) comprising an amino acid sequence of X$_3$INPX$_4$NX$_5$X$_6$TNYNX$_9$KFX$_{io}$G (SEQ ID NO:

257), wherein $X_3$ is Y or S, $X_4$ is N or R, $X_5$ is A or G, $X_6$ is G or W, $X_9$ is Q or D, and $X_{10}$ is K, G, H, or D; and
(iii) VH complementarity determining region 3 (CDR H3) comprising an amino acid sequence of SGWFTY (SEQ ID NO: 121); and
(b) a light chain variable region (VL) comprising
(i) VL complementarity determining region 1 (CDR L1) comprising an amino acid sequence of KSSQSLLN-SAGKTYLN (SEQ ID NO: 127);
(ii) VL complementarity determining region 2 (CDR L2) comprising an amino acid sequence of $LVX_{11}Xi2LDX_{13}$ (SEQ ID NO: 258), wherein $X_{11}$ is S or A, $X_{12}$ is Q or E, and $X_{13}$ is S or D; and
(iii) VL complementarity determining region 3 (CDR L3) comprising an amino acid sequence of $WQGTX_7X_8PWT$ (SEQ ID NO: 186), wherein $X_7$ is H or F, and $X_8$ is F or Y.

In some embodiments, the antibody or antigen binding fragment thereof comprises:
(a) a heavy chain variable region (VH) comprising
(i) VH complementarity determining region 1 (CDR H1) comprising an amino acid sequence selected from a group consisting of SEQ ID NO: 119 and SEQ ID NO: 122;
(ii) VH complementarity determining region 2 (CDR H2) comprising an amino acid sequence selected from a group consisting of SEQ ID NO: 120, SEQ ID NO: 123, SEQ ID NO: 124, SEQ ID NO: 125, SEQ ID NO: 126, SEQ ID NO: 149; SEQ ID NO: 247, SEQ ID NO: 248, SEQ ID NO: 249, and SEQ ID NO: 250; and
(iii) VH complementarity determining region 3 (CDR H3) comprising an amino acid sequence of SEQ ID NO: 121, and
(b) a light chain variable region (VL) comprising
(i) VL complementarity determining region 1 (CDR L1) comprising an amino acid sequence of SEQ ID NO: 127;
(ii) VL complementarity determining region 2 (CDR L2) comprising an amino acid sequence selected from a group consisting of SEQ ID NO: 128, SEQ ID NO: 254, SEQ ID NO: 255, and SEQ ID NO: 256; and
(iii) VL complementarity determining region 3 (CDR L3) comprising an amino acid sequence selected from a group consisting of SEQ ID NO: 129, SEQ ID NO: 130, and SEQ ID NO: 131.

In some embodiments, the antibody or antigen binding fragment thereof comprises:
(a) a heavy chain variable region (VH) comprising
(i) VH complementarity determining region 1 (CDR H1) comprising an amino acid sequence of $GYX_1FX_2DYNIVIII$ (SEQ ID NO: 184), wherein $X_1$ is T, I or R, and $X_2$ is T or Q;
(ii) VH complementarity determining region 2 (CDR H2) comprising an amino acid sequence of $X_3INPX_4NX_5X_6TNYNQKFKG$ (SEQ ID NO: 185), wherein $X_3$ is Y or S, $X_4$ is N or R; $X_5$ is A or G, and $X_6$ is G or W; and
(iii) VH complementarity determining region 3 (CDR H3) comprising an amino acid sequence of SGWFTY (SEQ ID NO: 121); and
(b) a light chain variable region (VL) comprising
(i) VL complementarity determining region 1 (CDR L1) comprising an amino acid sequence of KSSQSLLN-SAGKTYLN (SEQ ID NO: 127);
(ii) VL complementarity determining region 2 (CDR L2) comprising an amino acid sequence of LVSQLDS (SEQ ID NO: 128); and
(iii) VL complementarity determining region 3 (CDR L3) comprising an amino acid sequence of $WQGTX_7X_8PWT$ (SEQ ID NO: 186), wherein $X_7$ is H or F, and $X_8$ is F or Y.

In some embodiments, the antibody or antigen binding fragment thereof comprises:
(a) a heavy chain variable region (VH) comprising
(i) VH complementarity determining region 1 (CDR H1) comprising an amino acid sequence selected from a group consisting of SEQ ID NO: 119 and SEQ ID NO: 122;
(ii) VH complementarity determining region 2 (CDR H2) comprising an amino acid sequence selected from a group consisting of SEQ ID NO: 120, SEQ ID NO: 123, SEQ ID NO: 124, SEQ ID NO: 125, SEQ ID NO: 126, and SEQ ID NO: 149; and
(iii) VH complementarity determining region 3 (CDR H3) comprising an amino acid sequence of SEQ ID NO: 121, and
(b) a light chain variable region (VL) comprising
(i) VL complementarity determining region 1 (CDR L1) comprising an amino acid sequence of SEQ ID NO: 127;
(ii) VL complementarity determining region 2 (CDR L2) comprising an amino acid sequence of SEQ ID NO: 128; and
(iii) VL complementarity determining region 3 (CDR L3) comprising an amino acid sequence selected from a group consisting of SEQ ID NO: 129, SEQ ID NO: 130, and SEQ ID NO: 131.

In some embodiments, the antibody or antigen binding fragment thereof comprises a CDR H1 of SEQ ID NO: 119, a CDR H2 of SEQ ID NO: 120, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 119, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 119, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 119, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 119, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 119, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 119, a CDR H2 of SEQ ID NO: 120, a CDR H3 of SEQ ID NO:

121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 119, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 119, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 119, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 119, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 119, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 119, a CDR H2 of SEQ ID NO: 120, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 119, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 119, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 119, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 119, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 119, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 122, a CDR H2 of SEQ ID NO: 120, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 122, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 122, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 122, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 122, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 129.

In some embodiments, the antibody or antigen binding fragment thereof comprises a CDR H1 of SEQ ID NO: 122, a CDR H2 of SEQ ID NO: 120, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 122, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 122, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 122, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 122, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 122, a CDR H2 of SEQ ID NO: 249, a CDR H3 of SEQ ID NO: 121, a CDR L1 of SEQ ID NO: 127, a CDR L2 of SEQ ID NO: 128, and a CDR L3 of SEQ ID NO: 130.

In some embodiments, the antibody or antigen binding fragment thereof comprises a CDR H1 of SEQ ID NO: 122, a CDR H2 of SEQ ID NO: 120, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 122, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 122, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 122, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises a CDR H1 of SEQ ID NO: 122, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 131.

In some embodiments, the antibody or antigen binding fragment thereof comprises:
- (a) a heavy chain variable region (VH) comprising
  - (i) VH complementarity determining region 1 (CDR H1) comprising an amino acid sequence of GYIFQ-DYNMH (SEQ ID NO: 122);
  - (ii) VH complementarity determining region 2 (CDR H2) comprising an amino acid sequence of $X_3$INPRN$X_5X_6$TNYN$X_9$KF$X_{10}$G (SEQ ID NO: 259), wherein $X_3$ is Y or S, $X_5$ is A or G; $X_6$ is G or W, $X_9$ is Q or D, and $X_{10}$ is K, G, H, or D; and
  - (iii) VH complementarity determining region 3 (CDR H3) comprising an amino acid sequence of SGWFTY (SEQ ID NO: 121); and
- (b) a light chain variable region (VL) comprising
  - (i) VL complementarity determining region 1 (CDR L1) comprising an amino acid sequence of KSSQSLLN-SAGKTYLN (SEQ ID NO: 127);
  - (ii) VL complementarity determining region 2 (CDR L2) comprising an amino acid sequence of LV$X_{11}$i$X_{12}$LD$X_{13}$ (SEQ ID NO: 258), wherein $X_{11}$ is S or A, $X_{12}$ is Q or E, and $X_{13}$ is S or D; and
  - (iii) VL complementarity determining region 3 (CDR L3) comprising an amino acid sequence of WQGT$X_7$YPWT (SEQ ID NO: 188), wherein $X_7$ is H or F.

In some embodiments, the antibody or antigen binding fragment thereof comprises:
- (a) a heavy chain variable region (VH) comprising
  - (i) VH complementarity determining region 1 (CDR H1) comprising an amino acid sequence of SEQ ID NO: 122;
  - (ii) VH complementarity determining region 2 (CDR H2) comprising an amino acid sequence selected from a group consisting of SEQ ID NO: 123, SEQ ID NO: 124, SEQ ID NO: 126, SEQ ID NO: 247, SEQ ID NO: 248, SEQ ID NO: 249, SEQ ID NO: 250; and
  - (iii) VH complementarity determining region 3 (CDR H3) comprising an amino acid sequence of SEQ ID NO: 121; and
- (b) a light chain variable region (VL) comprising
  - (i) VL complementarity determining region 1 (CDR L1) comprising an amino acid sequence of SEQ ID NO: 127;
  - (ii) VL complementarity determining region 2 (CDR L2) comprising an amino acid sequence selected from a group consisting of SEQ ID NO: 128, SEQ ID NO: 254, SEQ ID NO: 255, and SEQ ID NO: 256; and
  - (iii) VL complementarity determining region 3 (CDR L3) comprising an amino acid sequence selected from a group consisting of SEQ ID NO: 130 and SEQ ID NO: 131.

In some embodiments, the antibody or antigen binding fragment thereof comprises:
- (a) a heavy chain variable region (VH) comprising
  - (i) VH complementarity determining region 1 (CDR H1) comprising an amino acid sequence of GYIFQ-DYNMH (SEQ ID NO: 122);
  - (ii) VH complementarity determining region 2 (CDR H2) comprising an amino acid sequence of $X_3$INPRN$X_5X_6$TNYNQKFKG (SEQ ID NO: 187), wherein $X_3$ is Y or S, $X_5$ is A or G; and $X_6$ is G or W; and
  - (iii) VH complementarity determining region 3 (CDR H3) comprising an amino acid sequence of SGWFTY (SEQ ID NO: 121); and
- (b) a light chain variable region (VL) comprising
  - (i) VL complementarity determining region 1 (CDR L1) comprising an amino acid sequence of KSSQSLLN-SAGKTYLN (SEQ ID NO: 127);
  - (ii) VL complementarity determining region 2 (CDR L2) comprising an amino acid sequence of LVSQLDS (SEQ ID NO: 128); and
  - (iii) VL complementarity determining region 3 (CDR L3) comprising an amino acid sequence of WQGT$X_7$YPWT (SEQ ID NO: 188), wherein $X_7$ is H or F.

In some embodiments, the antibody or antigen binding fragment thereof comprises:
- (a) a heavy chain variable region (VH) comprising
  - (i) VH complementarity determining region 1 (CDR H1) comprising an amino acid sequence of SEQ ID NO: 122;
  - (ii) VH complementarity determining region 2 (CDR H2) comprising an amino acid sequence selected from a group consisting of SEQ ID NO: 123, SEQ ID NO: 124, and SEQ ID NO: 126; and
  - (iii) VH complementarity determining region 3 (CDR H3) comprising an amino acid sequence of SEQ ID NO: 121, and
- (b) a light chain variable region (VL) comprising
  - (i) VL complementarity determining region 1 (CDR L1) comprising an amino acid sequence of SEQ ID NO: 127;
  - (ii) VL complementarity determining region 2 (CDR L2) comprising an amino acid sequence of SEQ ID NO: 128; and
  - (iii) VL complementarity determining region 3 (CDR L3) comprising an amino acid sequence selected from a group consisting of SEQ ID NO: 130 and SEQ ID NO: 131.

In some embodiments, the antibody or antigen binding fragment thereof comprises: a VH comprising CDR H1, CDR H2 and CDR H3 comprising amino acid sequences of the CDR H1, CDR H2 and CDR H3 contained in a VH amino acid sequence selected from a group consisting of SEQ ID NO: 35, SEQ ID NO: 50, SEQ ID NO: 54, SEQ ID NO: 60, SEQ ID NO: 56, and SEQ ID NO: 181; and a VL comprising CDR L1, CDR L2 and CDR L3 comprising amino acid sequences of the CDR L1, CDR L2 and CDR L3 contained in a VL amino acid sequence selected from a group consisting of SEQ ID NO: 40, SEQ ID NO: 52, and SEQ ID NO: 58.

In some embodiments, the antibody or antigen binding fragment thereof comprises: a VH comprising CDR H1, CDR H2 and CDR H3 comprising amino acid sequences of the CDR H1, CDR H2 and CDR H3 contained in a VH amino acid sequence selected from a group consisting of SEQ ID NO: 179, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 106, SEQ ID NO: 108, SEQ ID NO: 110, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, and SEQ ID NO: 227; and a VL comprising CDR L1, CDR L2 and CDR L3 comprising amino acid sequences of the CDR L1, CDR L2 and CDR L3 contained in a VL amino acid sequence selected from a group consisting of SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, SEQ ID NO: 229, SEQ ID NO: 231, SEQ ID NO: 233, SEQ ID NO: 235, and SEQ ID NO: 237.

In some embodiments, the CDR H1, CDR H2, CDR H3, CDR L1, CDR L2, and CDR L3 are determined according to Kabat numbering, AbM numbering, Chothia numbering, Contact numbering, or IMGT numbering, or a combination thereof.

In some embodiments, the CDR H1, CDR H2, CDR H3, CDR L1, CDR L2, and CDR L3 are determined according to Kabat numbering and Chothia numbering.

In some embodiments, the CDR H1, CDR H2, CDR H3, CDR L1, CDR L2, and CDR L3 are determined according to Kabat numbering.

In some embodiments, the CDR H1, CDR H2, CDR H3, CDR L1, CDR L2, and CDR L3 are determined according to AbM numbering.

In some embodiments, the CDR H1, CDR H2, CDR H3, CDR L1, CDR L2, and CDR L3 are determined according to Chothia numbering.

In some embodiments, the CDR H1, CDR H2, CDR H3, CDR L1, CDR L2, and CDR L3 are determined according to Contact numbering.

In some embodiments, the CDR H1, CDR H2, CDR H3, CDR L1, CDR L2, and CDR L3 are determined according to IMGT numbering.

In some embodiments, the antibody or antigen binding fragment thereof further comprises:
  (i) VH framework 1 (FR1) comprising an amino acid sequence of SEQ ID NO: 132;
  (ii) VH framework 2 (FR2) comprising an amino acid sequence of SEQ ID NO: 138;
  (iii) VH framework 3 (FR3) comprising an amino acid sequence of SEQ ID NO: 145;
  (iv) VH framework 4 (FR4) comprising an amino acid sequence of SEQ ID NO: 158;
  (v) VL FR1 comprising an amino acid sequence of SEQ ID NO: 160;
  (vi) VL FR2 comprising an amino acid sequence of SEQ ID NO: 163;
  (vii) VL FR3 comprising an amino acid sequence of SEQ ID NO: 169; and
  (viii) VL FR4 comprising an amino acid sequence of SEQ ID NO: 171.

In some embodiments, the antibody or antigen binding fragment thereof further comprises:
  (i) VH FR1 comprising an amino acid sequence selected from a group consisting of SEQ ID NO: 133, SEQ ID NO: 134, SEQ ID NO: 135, SEQ ID NO: 136, SEQ ID NO: 137, SEQ ID NO: 238, and SEQ ID NO: 239;
  (ii) VH FR2 comprising an amino acid sequence selected from a group consisting of SEQ ID NO: 139, SEQ ID NO: 140, SEQ ID NO: 141, SEQ ID NO: 142, SEQ ID NO: 143, SEQ ID NO: 144, SEQ ID NO: 173, SEQ ID NO: 240, SEQ ID NO: 241, SEQ ID NO: 242, SEQ ID NO: 243, SEQ ID NO: 244, SEQ ID NO: 245 and SEQ ID NO: 246;
  (iii) VH FR3 comprising an amino acid sequence selected from a group consisting SEQ ID NO: 146, SEQ ID NO: 147, SEQ ID NO: 148, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 174, and SEQ ID NO: 251;
  (iv) VH FR4 comprising an amino acid sequence of SEQ ID NO: 159; (v) VL FR1 comprising an amino acid sequence selected from a group consisting of SEQ ID NO: 161 and SEQ ID NO: 162;
  (vi) VL FR2 comprising an amino acid sequence selected from a group consisting of SEQ ID NO: 163, SEQ ID NO: 164, SEQ ID NO: 165, SEQ ID NO: 166, SEQ ID NO: 167, SEQ ID NO: 168, SEQ ID NO: 252, and SEQ ID NO: 253;
  (vii) VL FR3 comprising an amino acid sequence of SEQ ID NO: 170; and
  (viii) VL FR4 comprising an amino acid sequence selected from a group consisting of SEQ ID NO: 171 and SEQ ID NO: 172.

In some embodiments, the antibody or antigen binding fragment thereof comprises: a VH comprising an amino acid sequence selected from a group consisting of SEQ ID NO: 35, SEQ ID NO: 50, SEQ ID NO: 54, SEQ ID NO: 60, SEQ ID NO: 56, and SEQ ID NO: 181; and a VL comprising an amino acid sequence selected from a group consisting of SEQ ID NO: 40, SEQ ID NO: 52, and SEQ ID NO: 58.

In some embodiments, the antibody or antigen binding fragment thereof comprises: a VH comprising an amino acid sequence selected from a group consisting of SEQ ID NO: 179, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 106, SEQ ID NO: 108, and SEQ ID NO: 110, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, and SEQ ID NO: 227; and a VL comprising an amino acid sequence selected from a group consisting of SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, SEQ ID NO: 229, SEQ ID NO: 231, SEQ ID NO: 233, SEQ ID NO: 235, and SEQ ID NO: 237.

In some embodiments, the antibody or antigen binding fragment thereof is conjugated to an agent.

In some embodiments, the agent is selected from a group consisting of a cytotoxic agent, a radioisotope, a metal chelator, an enzyme, a fluorescent compound, a bioluminescent compound, a chemiluminescent compound, and a peptide.

In another aspect, provided herein is a pharmaceutical composition comprising the antibody or antigen binding fragment provided herein and a pharmaceutically acceptable excipient.

In yet another aspect, provided herein is a method of treating and/or preventing a disease or disorder comprising administering a therapeutically effective amount of the antibody or antigen binding fragment thereof provided herein to a subject.

In some embodiments, the disease or disorder is a disease or disorder mediated, induced and/or prolonged by Fn14 and/or TWEAK.

In some embodiments, the disease or disorder is selected from a group consisting of autoimmune and/or inflammatory diseases affecting joints, skin, kidney, liver, intestine, heart, lung, or muscle, wherein optionally the disease or disorder is selected from a group consisting of rheumatoid arthritis, bullous pemphigoid, discoid cutaneous lupus, urticarial vasculitis, Henoch-Schonlein Purpura, IgA nephrophathy, atopic dermatitis (atopic eczema), psoriasis (psoriasis vulgaris), seborrheic eczema, asthma, proteinuric kidney disease, liver disease, lupus nephritis, polymyositis, dermatomyositis, calcineurin inhibitor induced nephrotoxicity, myotonic dystrophy, cardiac dysfunction and failure, Alport syndrome, ulcerative colitis, Crohn's disease, cutaneous vasculitis, cachexia, and inflammatory bowel disease, and wherein optionally the disease or disorder is related to fibrosis and optionally selected from a group consisting tissue fibrosis, idiopathic pulmonary fibrosis, interstitial lung disease, scleroderma (systemic sclerosis), cancer, cancer-associated cachexia, muscle wasting, keloids, inclusion body myositis, and tissue remodeling.

In some embodiments, the subject is a human subject.

In another aspect, provided herein is a polynucleotide comprising nucleotide sequences encoding the antibody or antigen binding fragment thereof provided herein or a portion thereof.

In some embodiments, the polynucleotide comprises a polynucleotide sequence selected from a group consisting of the polynucleotide sequences listed in Table 36 and Table 37.

In another aspect, provided herein is a vector comprising the polynucleotide provided herein.

In another aspect, provided herein is a cell comprising the polynucleotide provided herein. In some embodiments, the cell provided herein comprises the vector provided herein.

In yet another aspect, provided herein is a method of making an antibody or antigen binding fragment thereof comprising culturing the cell provided herein to express the antibody or antigen binding fragment thereof.

4. BRIEF DESCRIPTION OF THE FIGURES

FIG. 1 depicts binding of anti-Fn14 hybridoma supernatants to human and mouse Fn14 transfected cells. A series of histograms obtained by flow cytometry demonstrate the reactivity of hybridoma supernatants (KO41c, KO42d and KO43b) to 293F cells transfected with a human (dark gray lines) or mouse (black lines) Fn14 expression vector or empty vector (light gray lines). Hybridoma supernatant binding was detected using anti-mouse IgG PE.

FIGS. 2A and 2B depict binding of purified anti-Fn14 monoclonal antibodies to endogenously expressed Fn14. Å series of histograms obtained by flow cytometry demonstrate the reactivity of purified anti-Fn14 antibodies to HK2 cells (FIG. 2A) and NRK-52E cells (FIG. 2B). Primary antibodies were used at a concentration of 1 μg/mL and binding was detected using anti-mouse IgG PE.

FIGS. 3A and 3B depict that Fn14 antagonist monoclonal antibodies neutralize TWEAK-induced CCL2 expression. HK2 (FIG. 3A) and NRK-52E (FIG. 3B) cells were incubated with the indicated purified anti-Fn14 mAbs (10 μg/mL) and then rhTWEAK was added to the cells (30 ng/mL). After 6 hours, RNA was collected from the cells and CCL2 expression was quantified by real-time PCR. Gene expression was normalized to GAPDH. The graphs show relative CCL2 expression level of experimental samples compared to control samples.

FIGS. 4A and 4B depict that Fn14 antagonist monoclonal antibodies neutralize TWEAK-induced NFκB activity. NRK52E-A1 5/Luc cells (NFκB-Luciferase reporter) were stimulated with hTWEAK or hTNFα (0-100 ng/mL) (FIG. 4A) or stimulated with hTWEAK (5 ng/mL) (FIG. 4B) in the presence of purified anti-Fn14 mAbs or control mouse IgG1 antibody (0-50 ng/mL). NFκB-Luciferase activity is reported as Luc [cps].

Figure 6A:
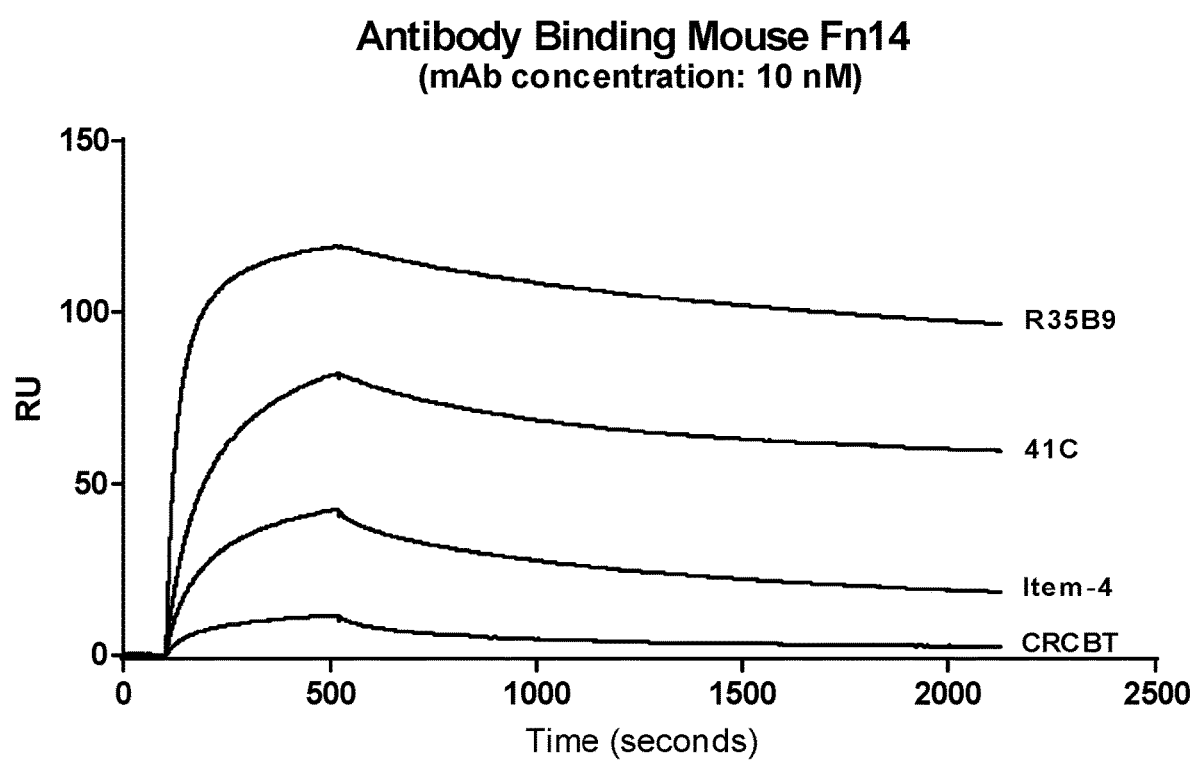
FIG. 6A depicts sensorgrams of individual anti-Fn14 Fab binding to mouse Fn14 by Biacore.
Figure 6B:
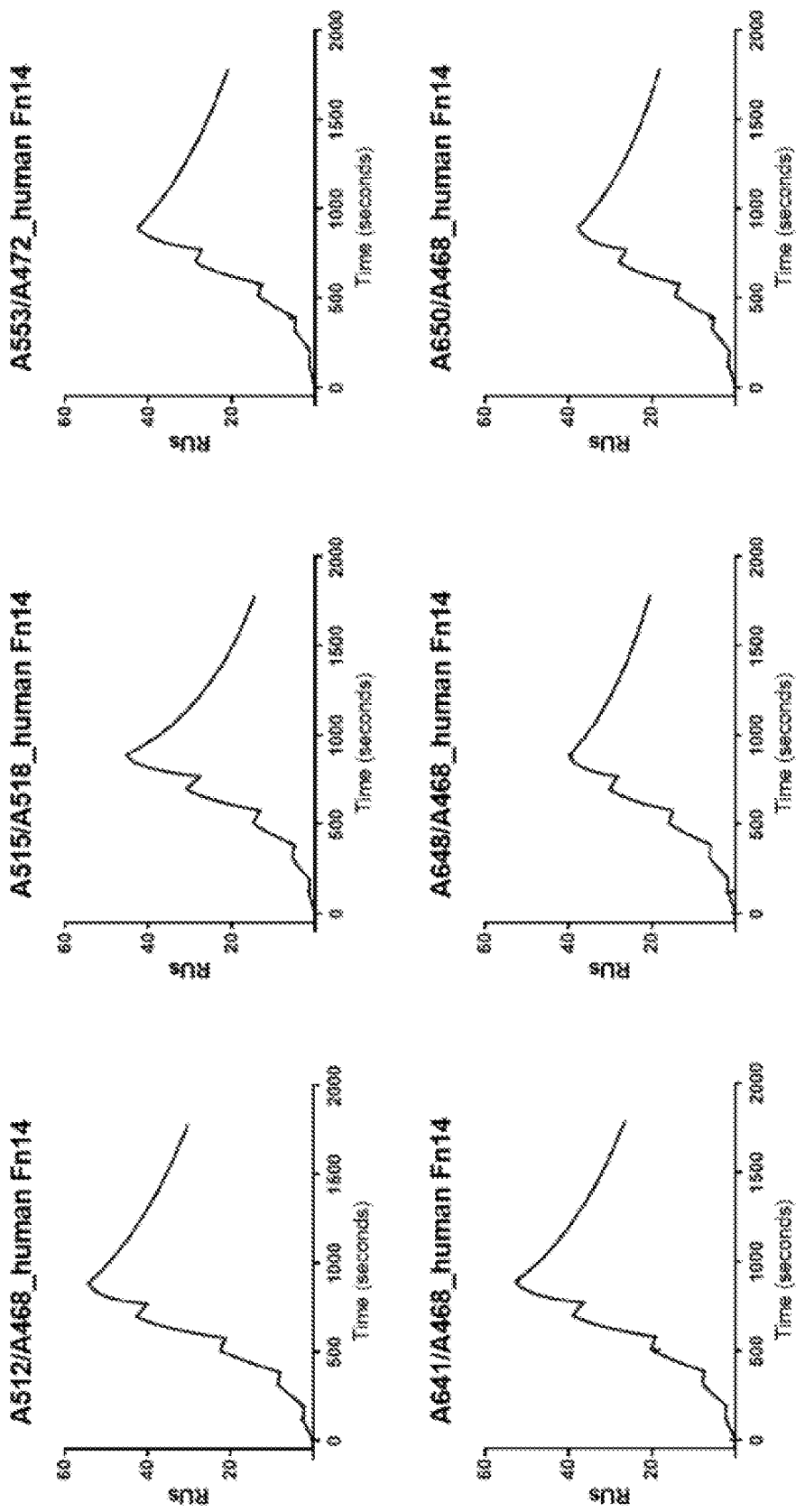

FIG. 6B depicts sensorgrams of six humanized mAbs binding to human Fn14 by Biacore. Recombinant human Fn14 was injected with increasing concentrations in a single cycle, the surface not being regenerated between injections. Anti-human Fc specific antibodies were immobilized on a CM5 sensor chip (cat# BR100012, GE Healthcare Life Sciences, Pittsburgh, Pennsylvania) by an amine coupling chemistry. Humanized anti-Fn14 antibodies were captured at approximately 200 RUs, followed by injections of increasing concentrations of recombinant human Fn14 protein. The association time was 120 seconds, and the final dissociation time was 900 seconds.

Figure 7:
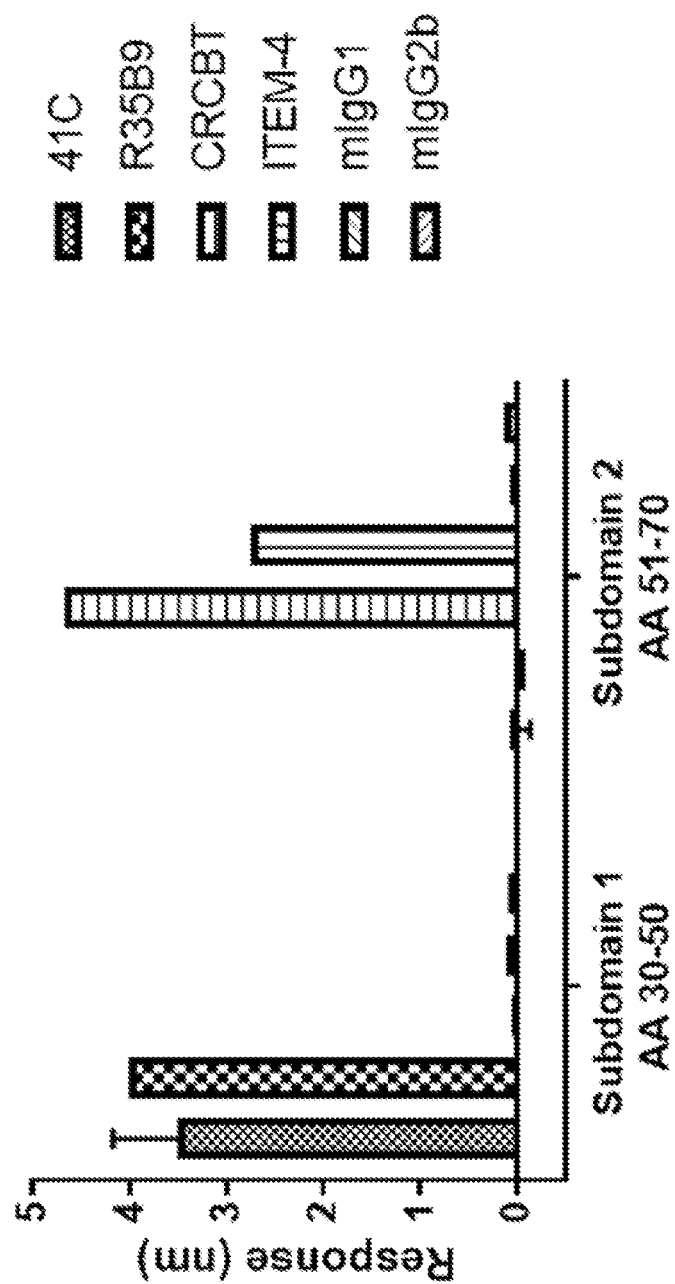

FIG. 7 depicts differential binding of anti-Fn14 monoclonal antibodies to subdomains of Fn14. All values were compared to a control sample (isotype antibodies, mIgG1 and mIgG2b).

Figure 8:
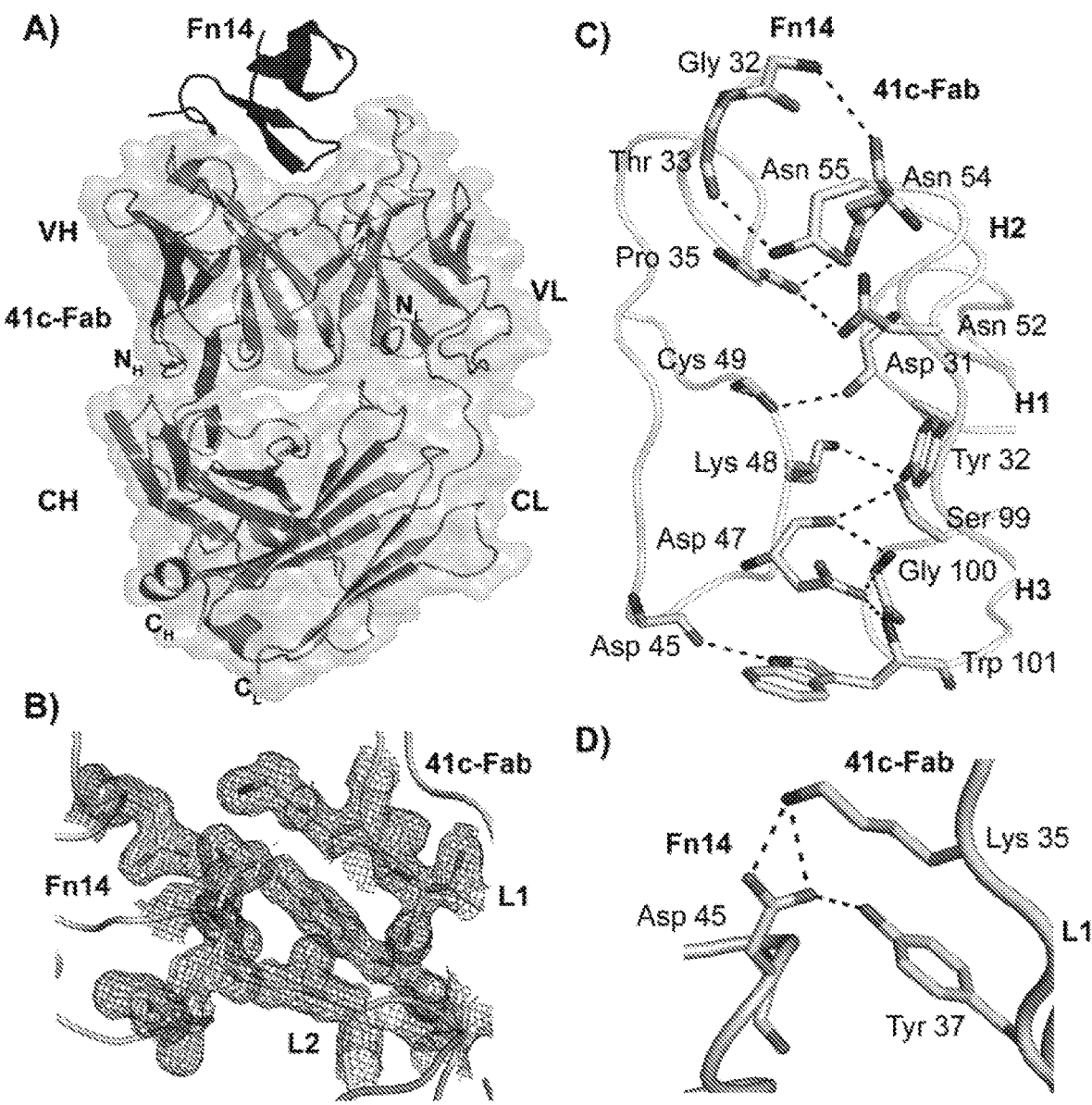

FIG. 8 depicts crystal structure of Fn14-41c-His Fab complex. Part A shows cartoon representation of Fn14-41c-His Fab complex with transparent molecular surface for 41c Fab molecule. VH (variable region of heavy chain), CH (constant region of heavy chain), VL (variable region of light chain), CL (constant region of light chain), and N-terminal and C-terminal ends of heavy chain and light chain are also indicated. Fn14 molecule is shown in black cartoon and 41 c-His Fab as gray cartoon with transparent molecular surface. Part B shows representative 2Fo-Fc electron density map contoured at 1σ, for residues from Fn14 that are in contact with light chain loops L1 and L2 of 41c Fab molecule. Part C shows specific interacting residues in the interface between Fn14 (left side) and the loops of 41c-His Fab molecule heavy chain region (right side). Part D shows interaction of Fn14 (left side) with the light chain region of 41c-His Fab (right side). All interacting residues from both Fn14 and 41c-His Fab are shown as sticks and the hydrogen bonds are shown as black dashed lines. All figures were made in PyMOL.

Figure 9:
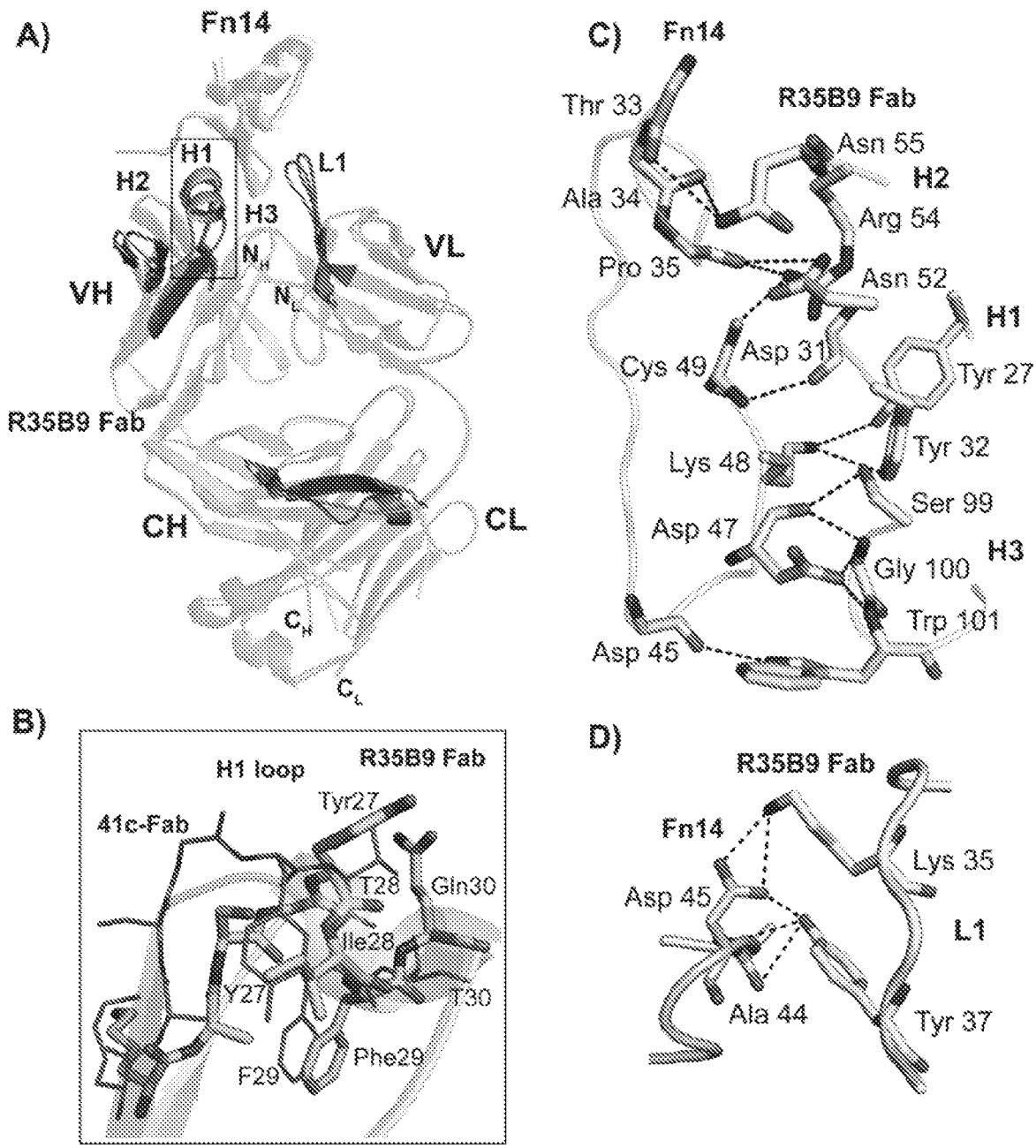

FIG. 9 depicts crystal structure of Fn14-R35B9-His Fab complex. Part A shows superposition of Fn14-41c-His Fab (parental) complex with Fn14-R35B9-His Fab complex. The regions that show conformational change between parental and R35B9 version of Fab are highlighted. The N-terminal, C-terminal ends and variable and constant regions of both heavy chain and light chain are marked. Part B shows structural changes in the H1 loop region of Fab. The residues of H1 loop region of 41c-His Fab are shown as lines and are labeled with single-letter amino acid code, while the residues of R35B9-His Fab are shown as sticks and marked with three-letter amino acid code. Part C shows interactions between CDRs of heavy chain region of R35B9-His Fab (right) and Fn14 (left). Part D shows specific interactions between the CDR1 region of light chain R35B9-His Fab (right) and Fn14 (left). All interacting residues are shown as sticks with transparent cartoon and black dashed lines indicate hydrogen bonds.

Figure 10:
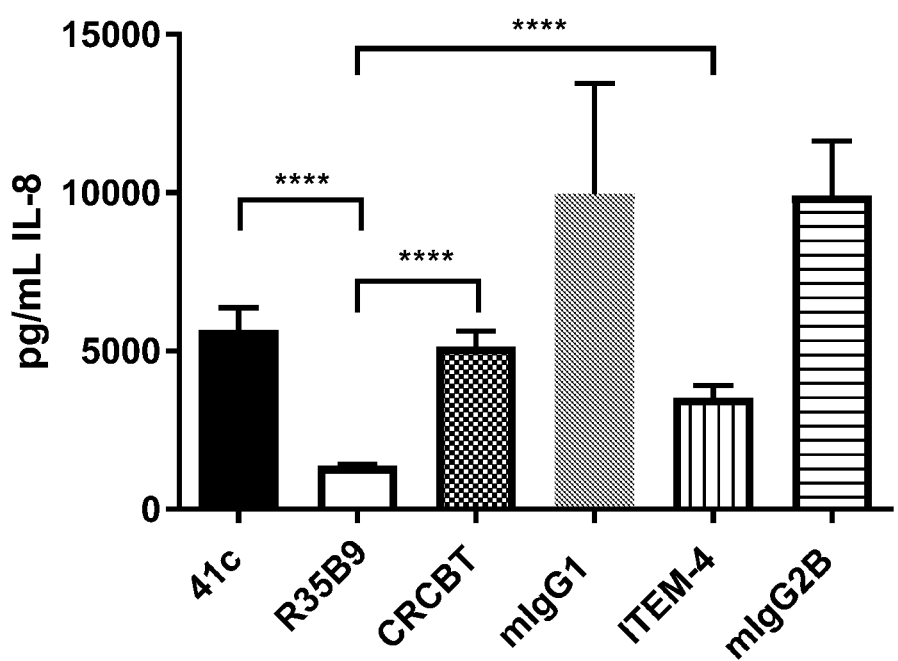

FIG. 10 depicts that Fn14 mAb R35B9 potently antagonizes TWEAK-induced IL-8 secretion from HRMC. HRMC were incubated with 1.04 nM anti-Fn14 or isotype control mAbs for 30 minutes at 37° C. and then rhTWEAK was added to the wells at 250 ng/mL for 24 h. Supernatants were harvested and tested for IL-8 using an IL-8 ELISA kit. Data were analyzed using Student's t-test, comparing IL-8 reduction by R35B9 to that of 41c, ITEM-4 and CRCBT-06-002. 41c vs. R35B9 $p<0.0001$, ITEM-4 vs. R35B9 $p<0.0001$, CRCBT-06-002 vs. R35B9 $p<0.0001$.

Figure 11A:
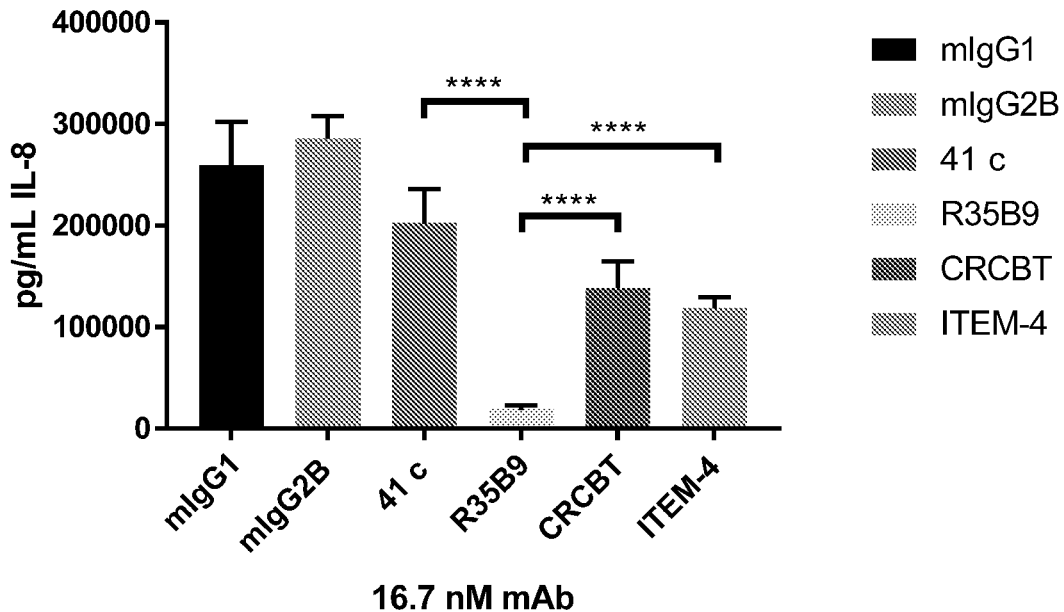
Figure 11B:
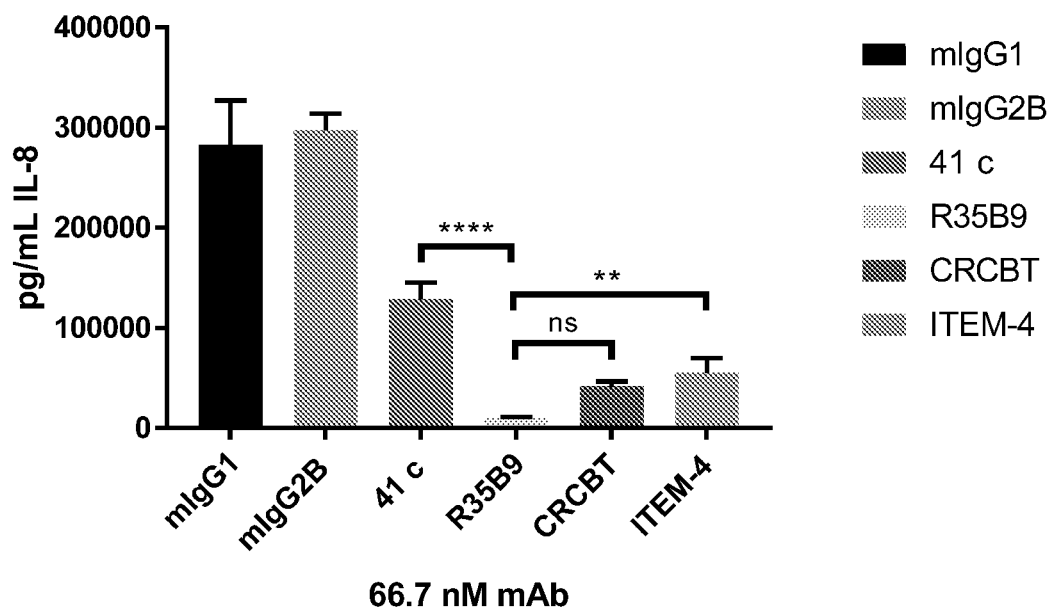
Figure 11C:
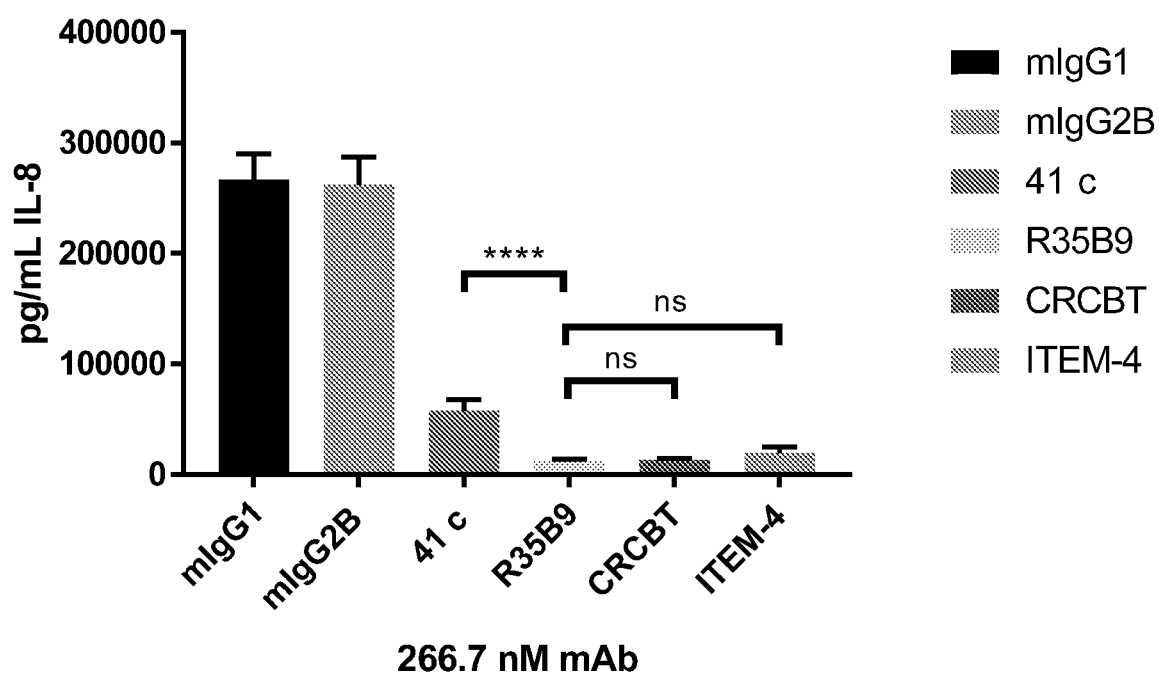

FIGS. 11A, 11B and 11C depict that Fn14 mAb R35B9 potently antagonizes TWEAK-induced IL-8 secretion from A375 cells. A375 cells were incubated with 16.7, 66.7, or 266.7 nM anti-Fn14 or isotype control mAbs for 30 minutes and then rhTWEAK was added to the wells at 300 ng/mL for 24 h. Supernatants were harvested and tested for IL-8 using an IL-8 ELISA kit. Data were analyzed using one-way ANOVA. The results for 16.7, 66.7, or 266.7 nM anti-Fn14 or isotype control mAbs are shown in FIG. 11A, FIG. 11B and FIG. 11C, respectively. Statistical results for IL-8 reduction by R35B9 compared to that of 41c, ITEM-4 and CRCBT-06-002 are as follows: mAb concentration at 16.7 nM: 41c vs. R35B9 $p<0.0001$, ITEM-4 vs. R35B9 $p<0.0001$, CRCBT-06-002 vs. R35B9 $p<0.0001$ (FIG. 11A); mAb concentration at 66.7 nM: 41c vs. R35B9 $p<0.0001$, ITEM-4 vs. R35B9 $p<0.01$, CRCBT-06-002 vs. R35B9 not significant (ns) (FIG. 11B), mAb concentration at 266.7 nM: 41c vs. R35B9 $p<0.0001$, others are not significant (ns) in this assay.

Figure 12:
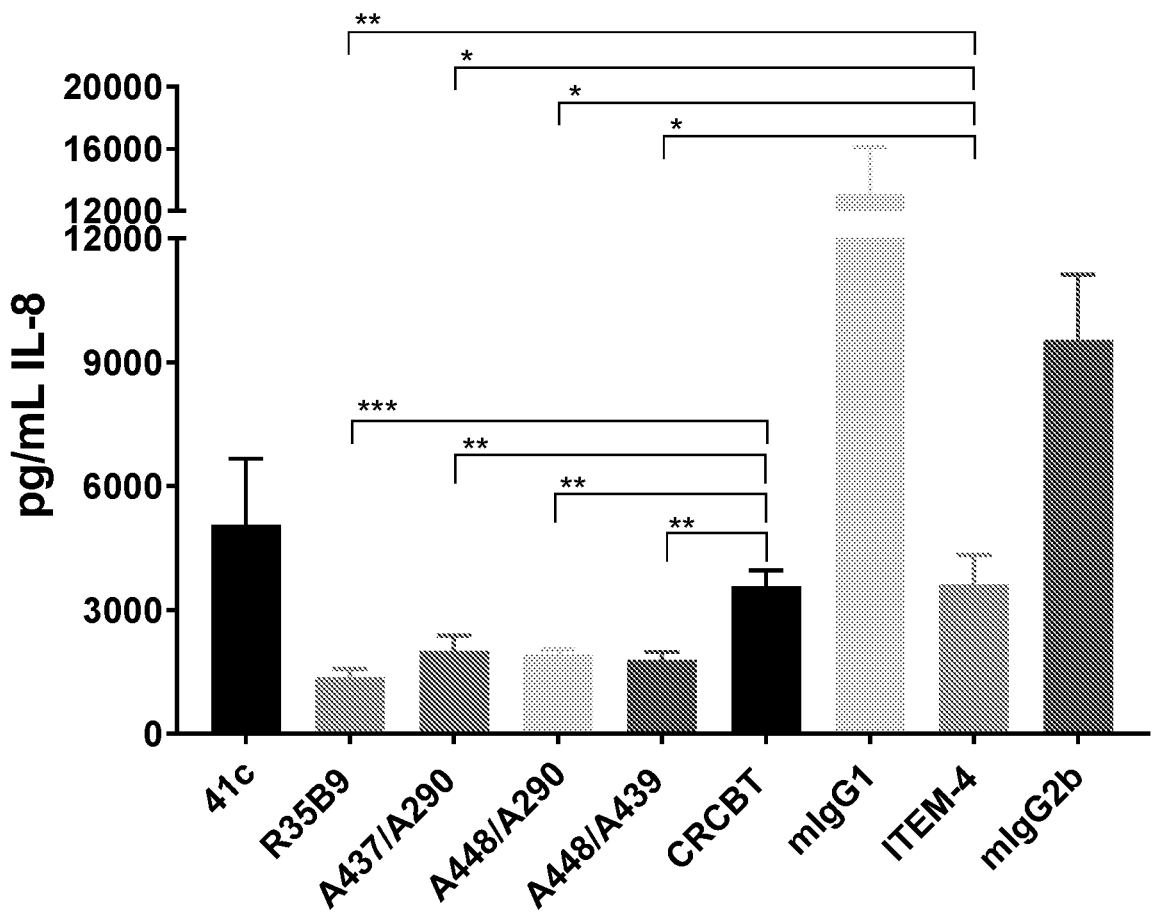

FIG. 12 depicts that Fn14 mAb R35B9 optimized clones potently antagonize TWEAK-induced IL-8 secretion from HRMC. HRMC were incubated with 0.8325 nM anti-Fn14 or isotype control mAbs for 30 minutes and then rhTWEAK was added to the wells at 250 ng/mL for 24 h. Supernatants were harvested and tested for IL-8 using an IL-8 ELISA kit. Data were analyzed using Student's t-test, comparing IL-8 reduction (ITEM-4 vs. R35B9 $p<0.01$, ITEM-4 vs. A437/A290 $p<0.05$, ITEM-4 vs. A448/A290 $p<0.05$, ITEM-4 vs. A448/A439 $p<0.05$, CRCBT-06-002 vs. R35B9 $p<0.001$, CRCBT-06-002 vs A437/A290 $p<0.01$, CRCBT-06-002 vs A448/A290 $p<0.01$, CRCBT-06-002 vs A448/A439 $p<0.01$).

Figure 13:
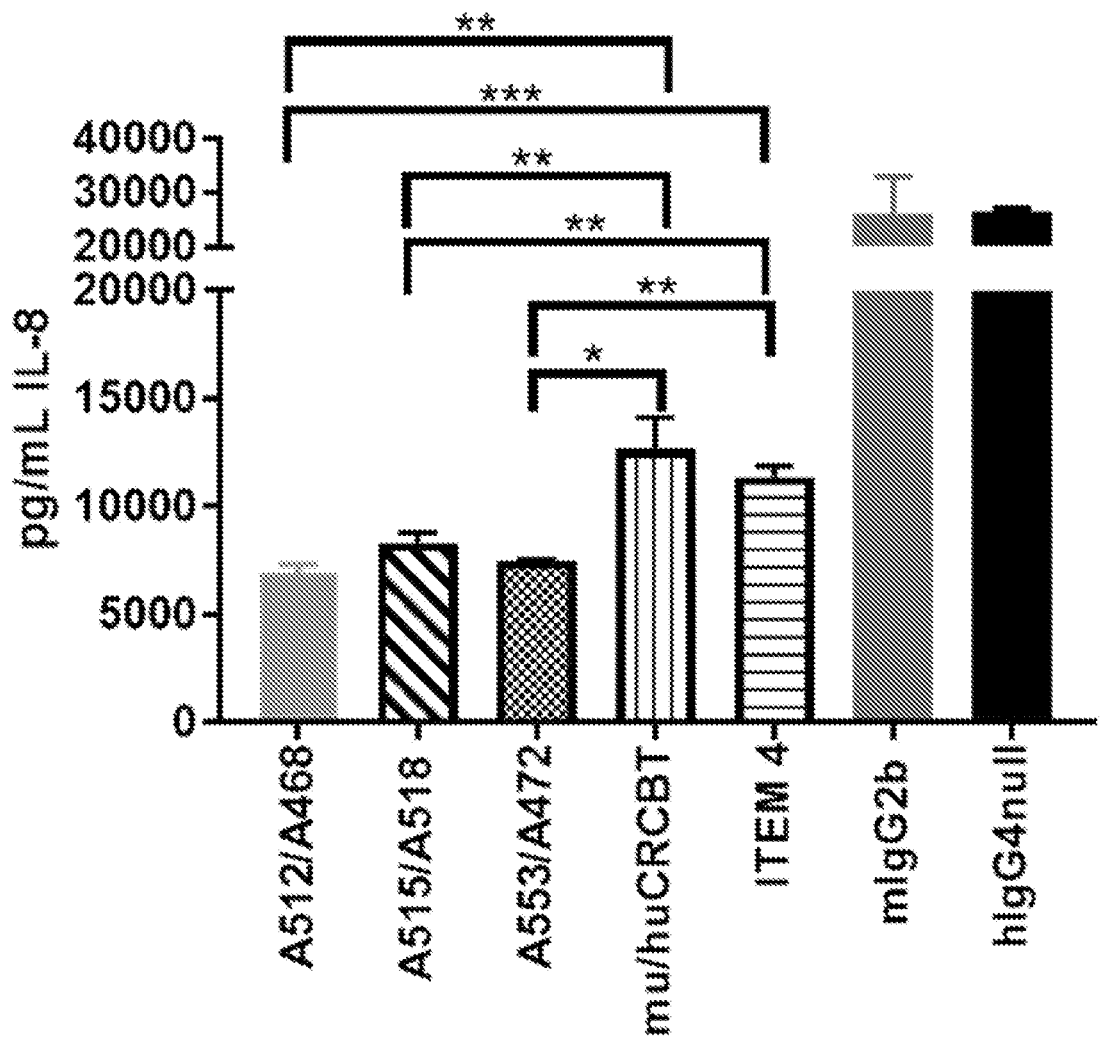

FIG. 13 depicts that humanized Fn14 mAbs potently antagonize TWEAK-induced IL-8 secretion from HRMC. HRMC were incubated with 0.833 nM humanized anti-Fn14 antibodies, mouse/human chimeric CRCBT-06-002 (mu/huCRCBT), ITEM-4 or isotype control mAbs for 30 minutes at 37° C. and then rhTWEAK was added to the wells at 250 ng/mL for 24 h. Supernatants were harvested and tested for IL-8 using an IL-8 ELISA kit. Each of the humanized anti-Fn14 clones was able to block TWEAK-induced IL-8 secretion significantly better than mu/huCRCBT-06-002 and ITEM-4. Data were analyzed using unpaired t test, comparing IL-8 reduction (ITEM-4 vs. A512/A468 $p<0.001$, ITEM-4 vs. A515/A518 $p<0.01$, ITEM-4 vs. A553/A472 $p<0.01$, mu/huCRCBT-06-002 vs A512/A468 $p<0.01$, mu/huCRCBT-06-002 vs A515/A518 $p<0.01$, mu/huCRCBT-06-002 vs A553/A472 $p<0.05$).

Figure 14:
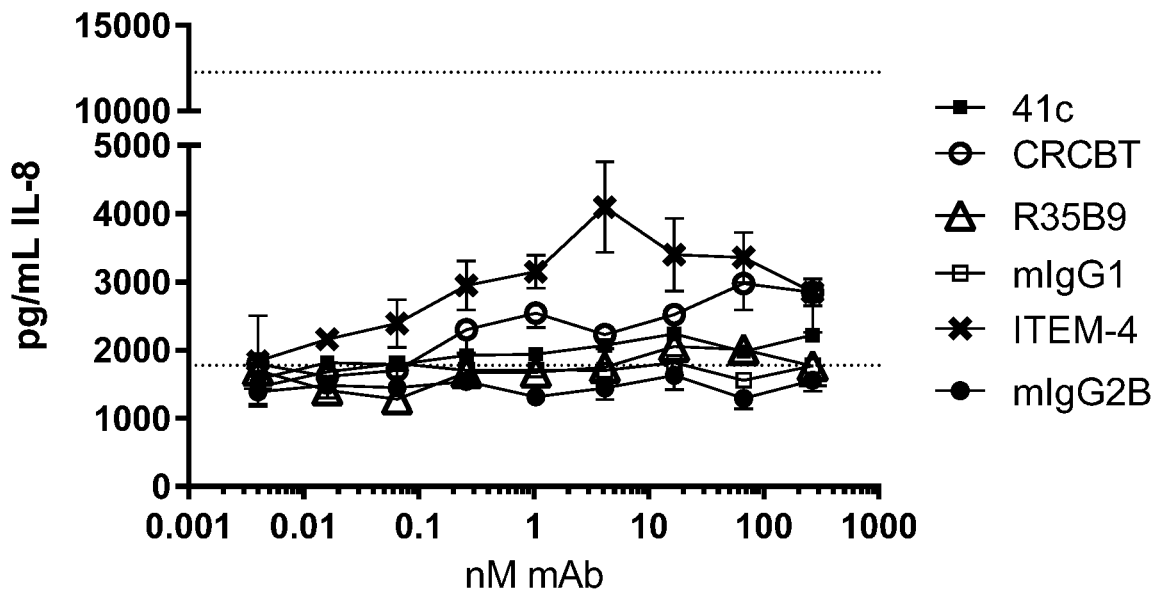

FIG. 14 depicts that Fn14 antagonist mAb R35B9 does not agonize Fn14. HRMC were incubated with 250 ng/mL rhTWEAK (positive control) or media alone (negative control) and anti-Fn14 or isotype control mAbs for 24 hours. Supernatants were harvested and tested for IL-8 using an IL-8 ELISA kit. Dotted lines represent average supernatant IL-8 levels from unstimulated cells (media alone) after 24 hours in culture (bottom line: 1,775 μg/mL) and cells stimulated with 250 ng/mL rhTWEAK for 24 hours (upper line: 12,271 μg/mL).

Figure 15:
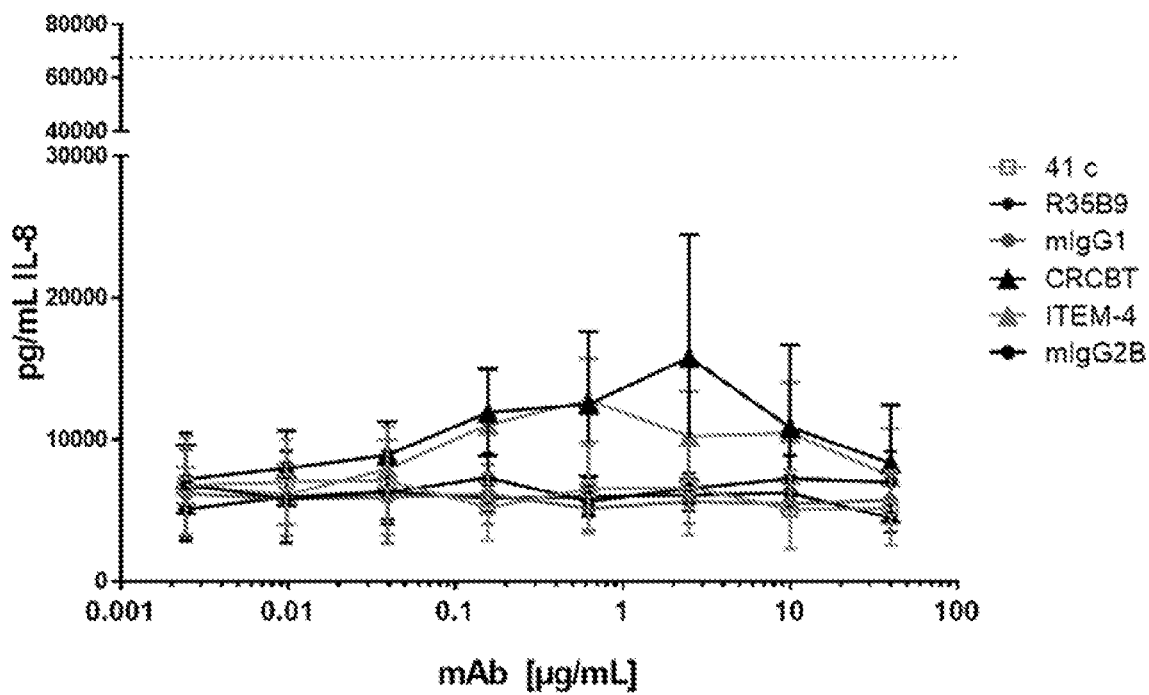

FIG. 15 depicts that Fn14 antagonist mAb R35B9 does not agonize Fn14. A375 cells were incubated with 300 ng/mL rhTWEAK, anti-Fn14 or isotype control mAbs for 24 h. Supernatants were harvested and tested for IL-8 using an IL-8 ELISA kit. Dotted line represents average supernatant IL-8 levels from cells stimulated with 300 ng/mL rhTWEAK for 24 hours (67,725 μg/mL).

Figure 16A:
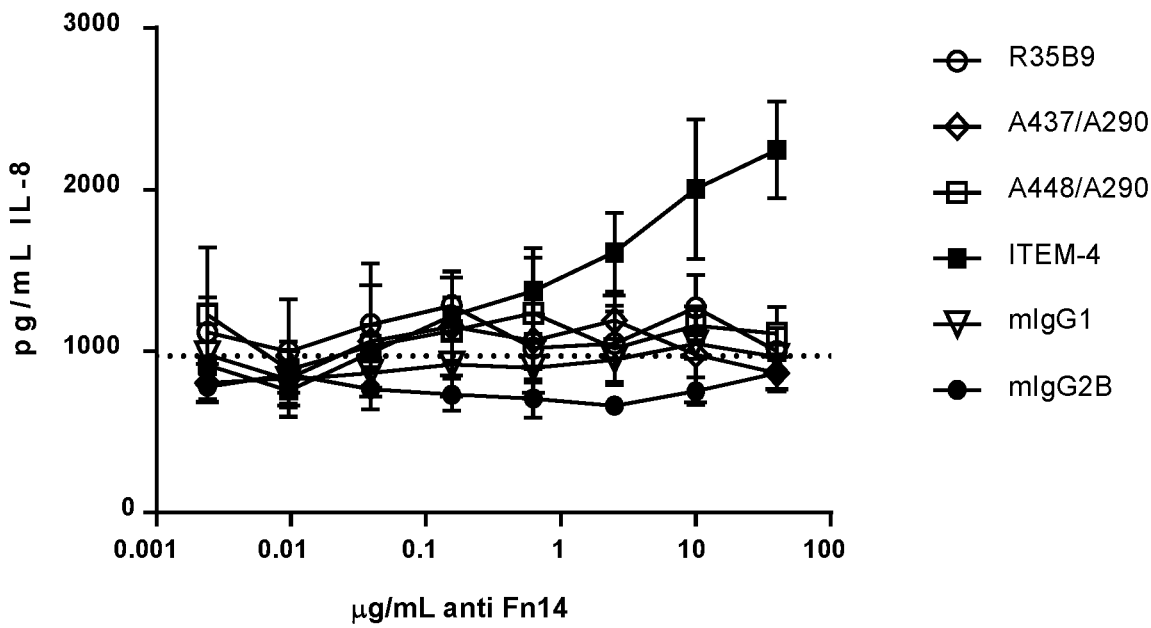
Figure 16B:
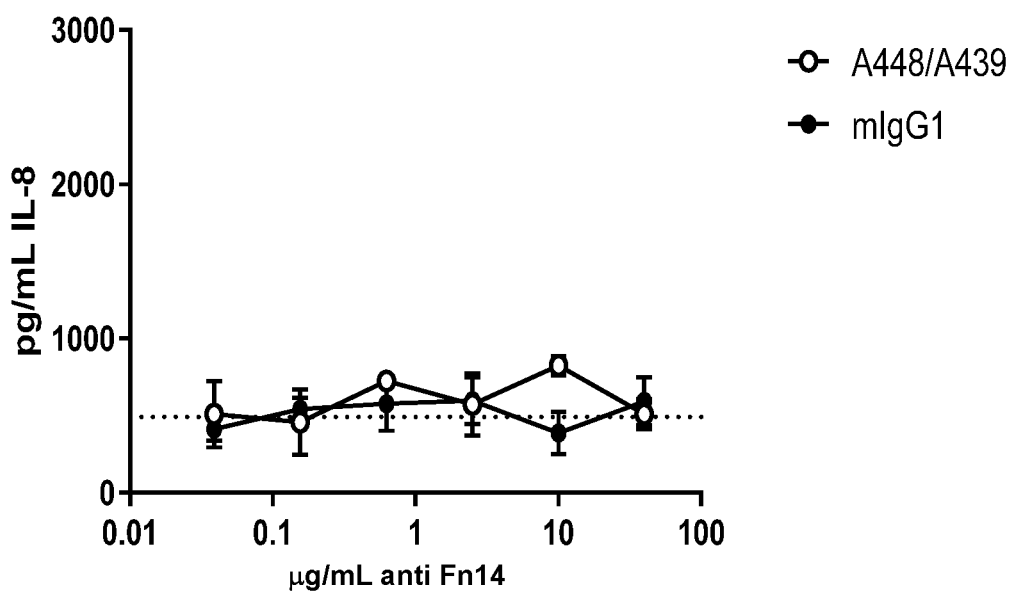

FIGS. 16A and 16B depict that Fn14 antagonist mAb R35B9 optimized clones do not agonize Fn14. HRMC were incubated with 250 ng/mL rhTWEAK (positive control), media alone (negative control), anti-Fn14 or isotype control mAbs for 24 hours. Supernatants were harvested and tested for IL-8 using an IL-8 ELISA kit. Dotted line represents average supernatant IL-8 levels from unstimulated cells (media alone) after 24 hours in culture (A: 972.4 μg/mL) or (B: 494 μg/mL).

Figure 17:
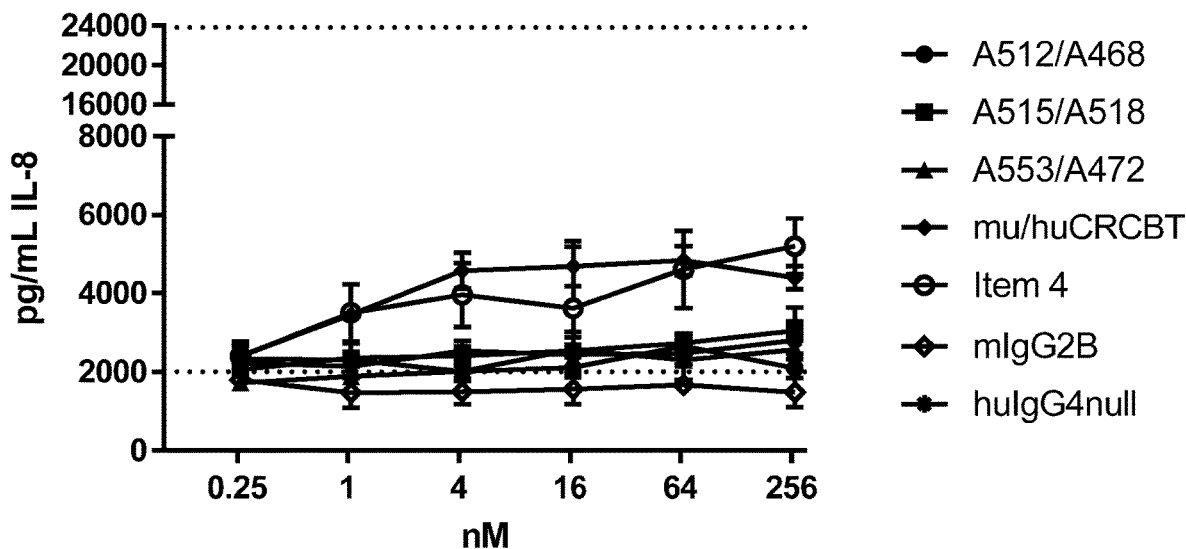

FIG. 17 depicts that humanized Fn14 antagonist mAbs do not agonize Fn14. HRMC were incubated with 250 ng/mL rhTWEAK (positive control) or media alone (negative control) and humanized anti-Fn14, mouse/human chimeric CRCBT-06-002 (mu/huCRCBT), ITEM-4 or isotype control mAbs for 24 h. Supernatants were harvested and tested for IL-8 using an IL-8 ELISA kit. Dotted lines represent average supernatant IL-8 levels from unstimulated cells (media alone) after 24 hours in culture (2,008 μg/mL) and cells stimulated with 250 ng/mL rhTWEAK for 24 hours (23,851 μg/mL).

Figure 18:
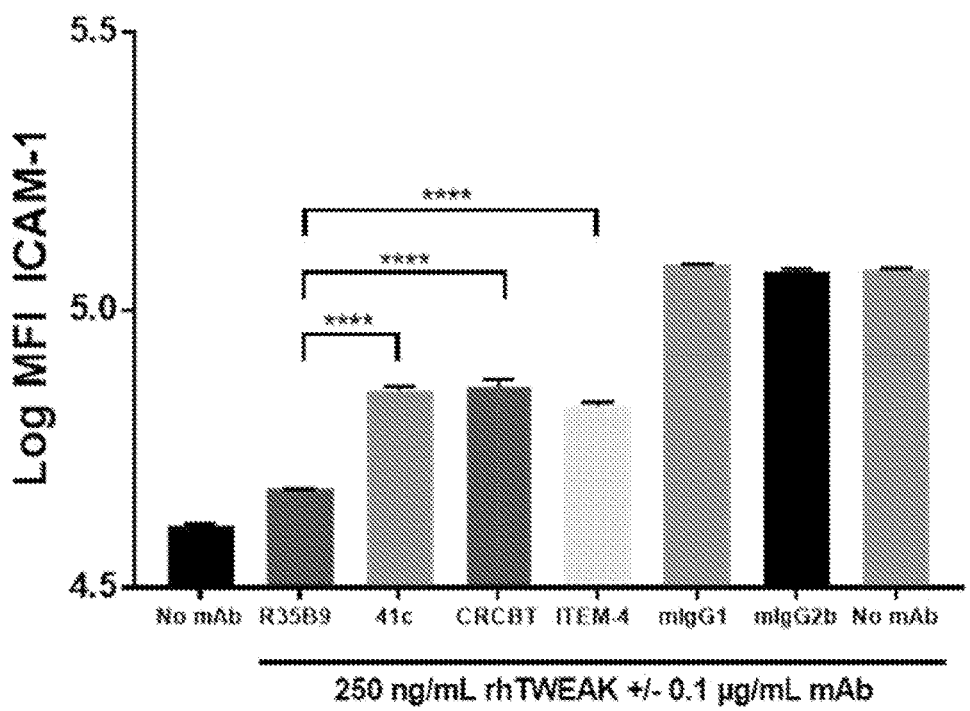

FIG. 18 depicts that Fn14 mAb R35B9 potently antagonizes TWEAK-induced ICAM expression. HRMC were incubated with media alone or with anti-Fn14 or isotype control mAbs (0.1 ng/mL) for 30 minutes and then media with or without rhTWEAK (250 ng/mL) was added to the cells for 24 hours. Cells were dissociated with trypsin and stained for surface ICAM-1 expression. Intensity of surface ICAM-1 expression was measured using a flow cytometer (BD Biosciences Fortessa), gated on live cells. Data were analyzed using one-way ANOVA with multiple comparisons, statistical results for R35B9 vs. 41c, CRCBT-06-002 and ITEM-4 are shown (0.1 ng/mL mAb: R35B9 vs. 41c $p \leq 0.0001$, R35B9 vs. CRCBT-06-002 $p \leq 0.0001$, R35B9 vs. ITEM-4 $p \leq 0.0001$).

Figure 19:
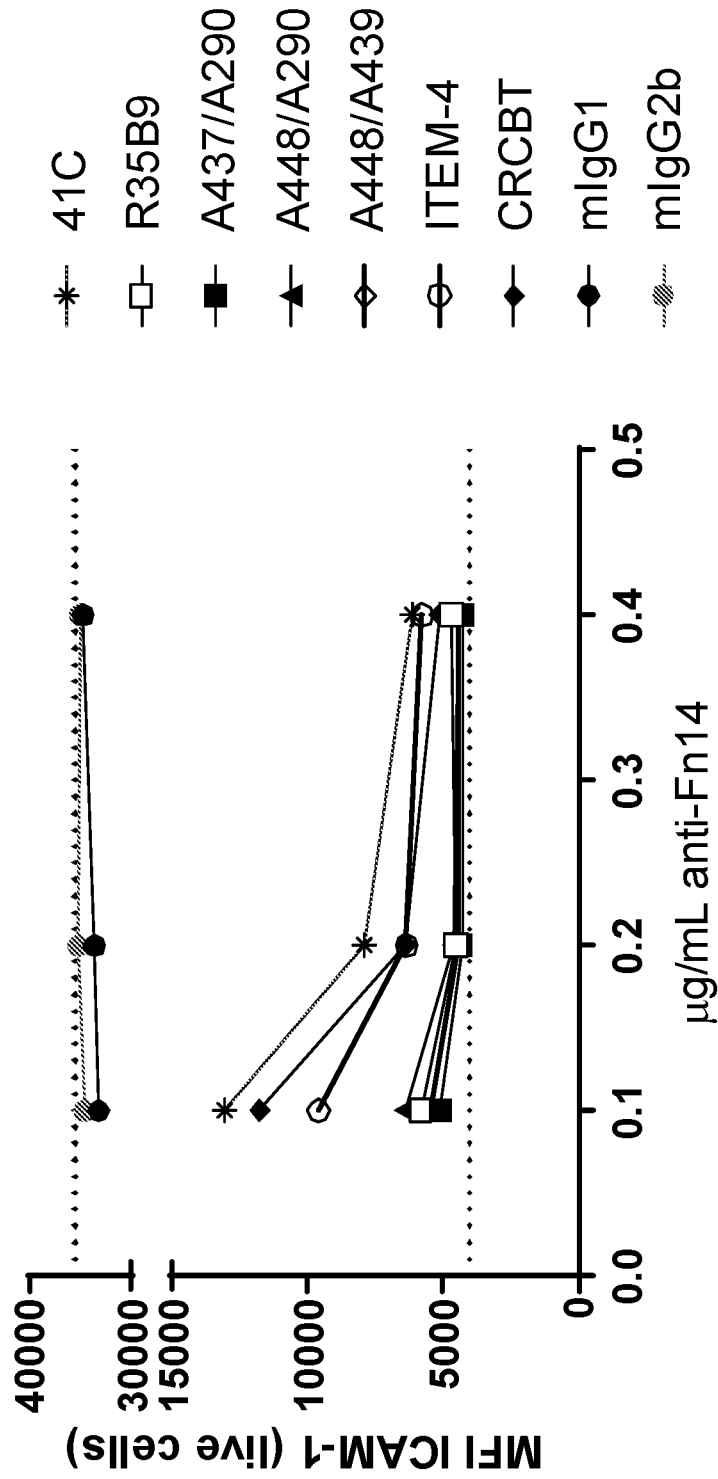

FIG. 19 depicts that anti-Fn14 mAb R35B9 optimized clones potently antagonize TWEAK-induced ICAM-1 expression. HRMC were incubated with media alone or with anti-Fn14 or isotype control mAbs at various concentrations for 30 minutes and then media with or without rhTWEAK (250 ng/mL) was added to the cells for 24 h. Cells were dissociated with trypsin and stained for surface ICAM-1 expression. Mean Fluorescence Intensity (MFI) of surface ICAM-1 expression was measured using a flow cytometer (BD Biosciences Fortessa), gated on live cells. Dotted lines represent the MFI of ICAM-1 on unstimulated cells (media alone) after 24 hours in culture (MFI 4,013) and cells stimulated with 250 ng/mL rhTWEAK for 24 hours (MFI 35,608).

FIG. 20 depicts VH and VL amino acid sequences of exemplary mouse Fn14 antagonist monoclonal antibodies.

FIG. 21 depicts VL amino acid sequences broken down into FR and CDR sequences of exemplary mouse and humanized antibodies provided herein.

FIG. 22 depicts VH amino acid sequences broken down into FR and CDR sequences of exemplary mouse and humanized antibodies provided herein.

FIG. 23 depicts CDRs of exemplary humanized R35B9 series antibodies.

Figure 24:
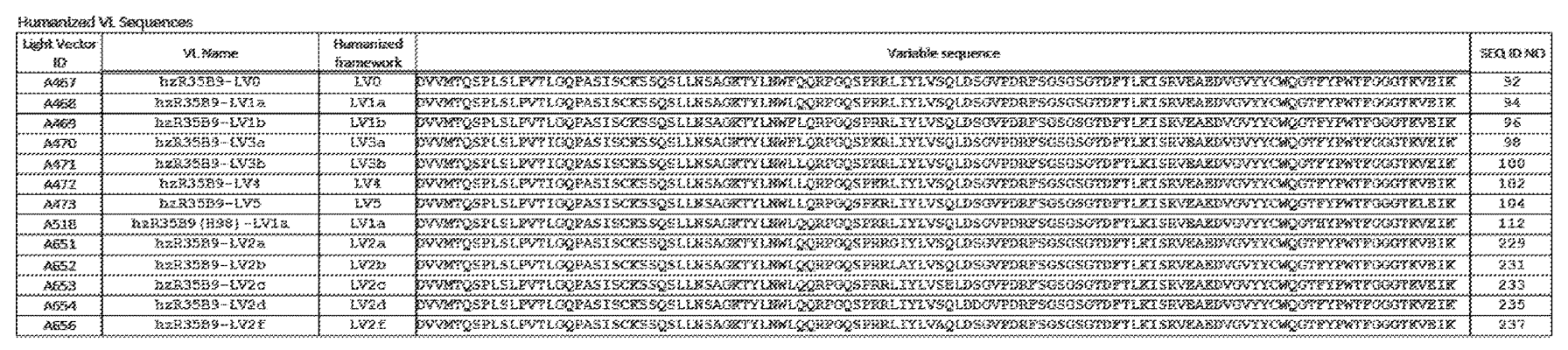

FIG. 24 depicts the VH and VL amino acid sequences of exemplary humanized antibodies provided herein.

Figure 25:
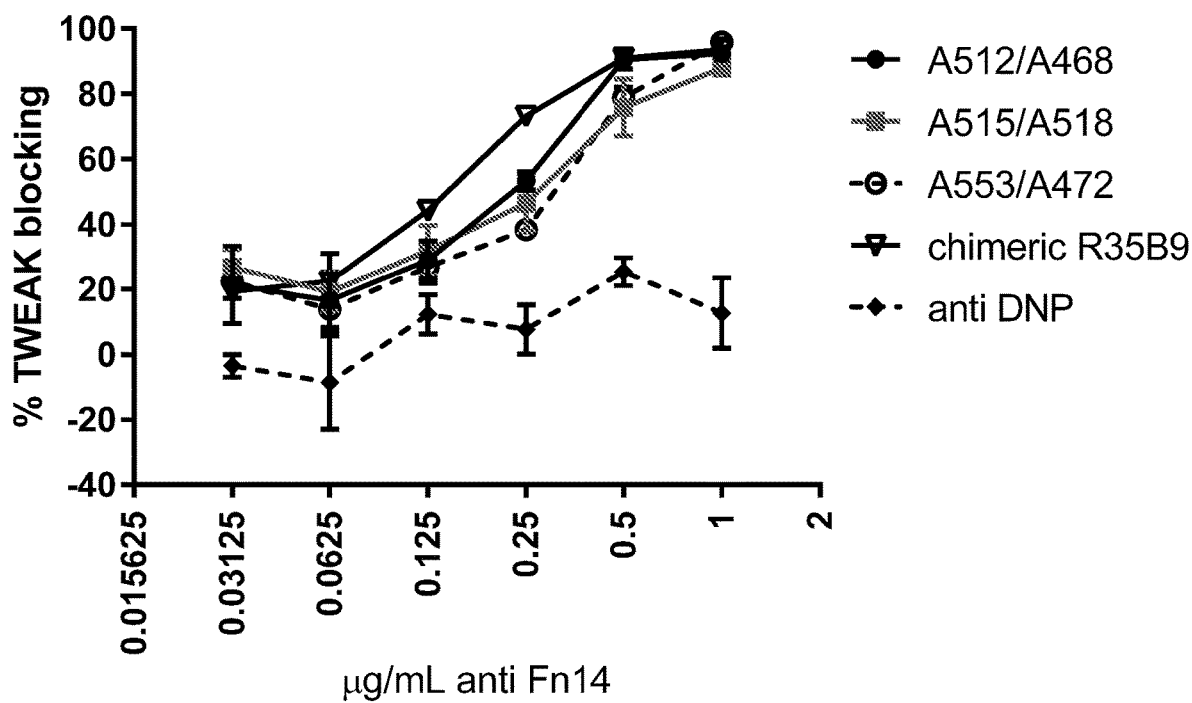

FIG. 25 depicts that humanized anti-Fn14 antibodies blocked TWEAK binding to Fn14 expressed on cells. HRMC were incubated with individual antibodies at various concentrations for 30 minutes followed by incubation with recombinant human TWEAK (250 ng/mL) for 45 minutes. Binding of TWEAK to HRMC cells was detected with biotinylated goat-anti-human TWEAK followed by streptavidin-PE. Stained cells were acquired on a Fortessa. % TWEAK blocking was calculated using the following formula: 100-(Geometric mean fluorescence intensity of sample—Geometric mean fluorescence intensity of cells without TWEAK)/(Geometric mean fluorescence intensity-TWEAK alone with no antibody—Geometric mean fluorescence intensity of cells without TWEAK)*100.

Figure 26A:
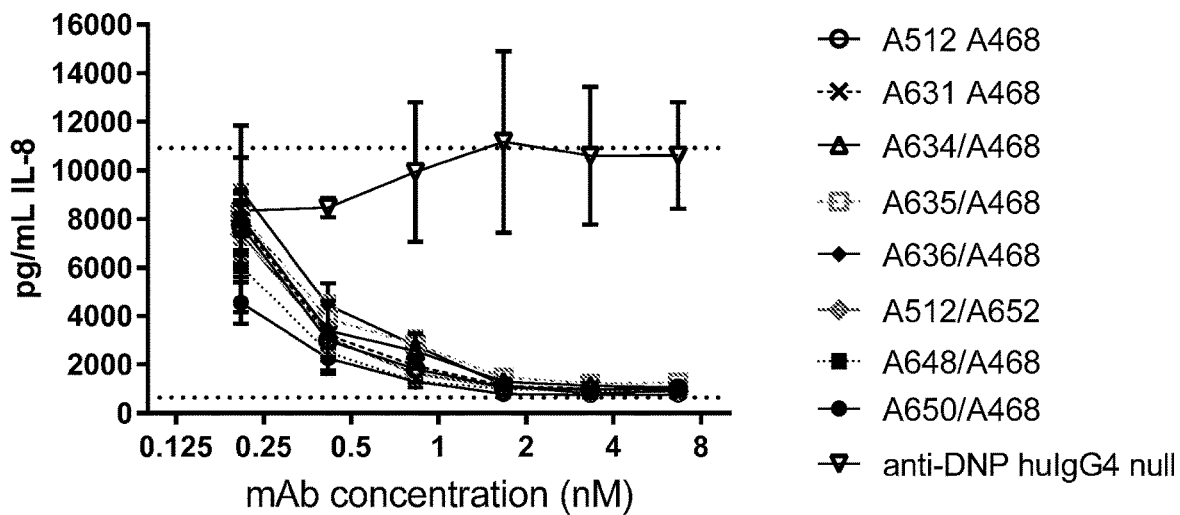
Figure 26B:
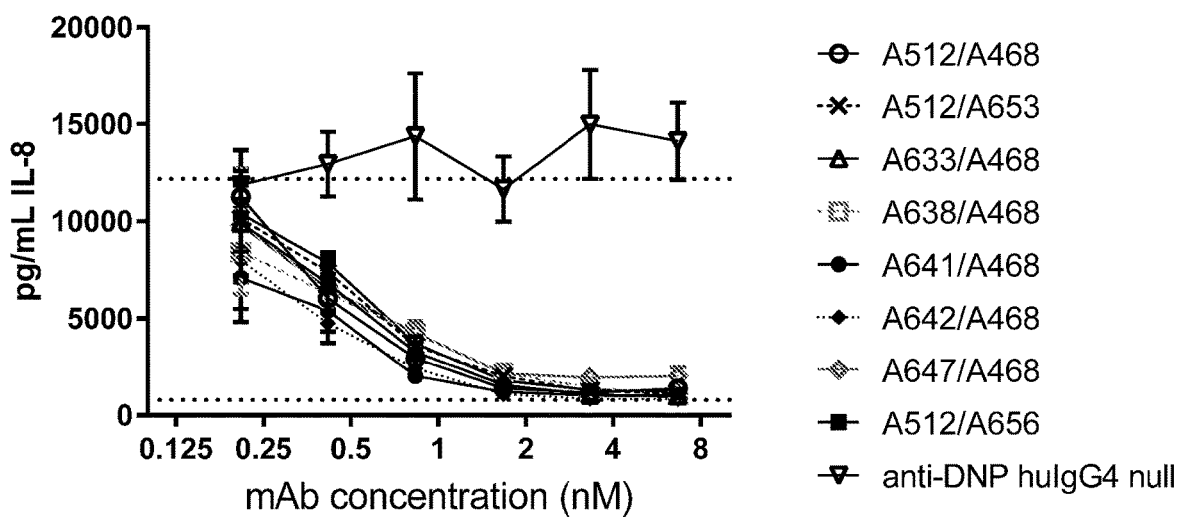
Figure 26C:
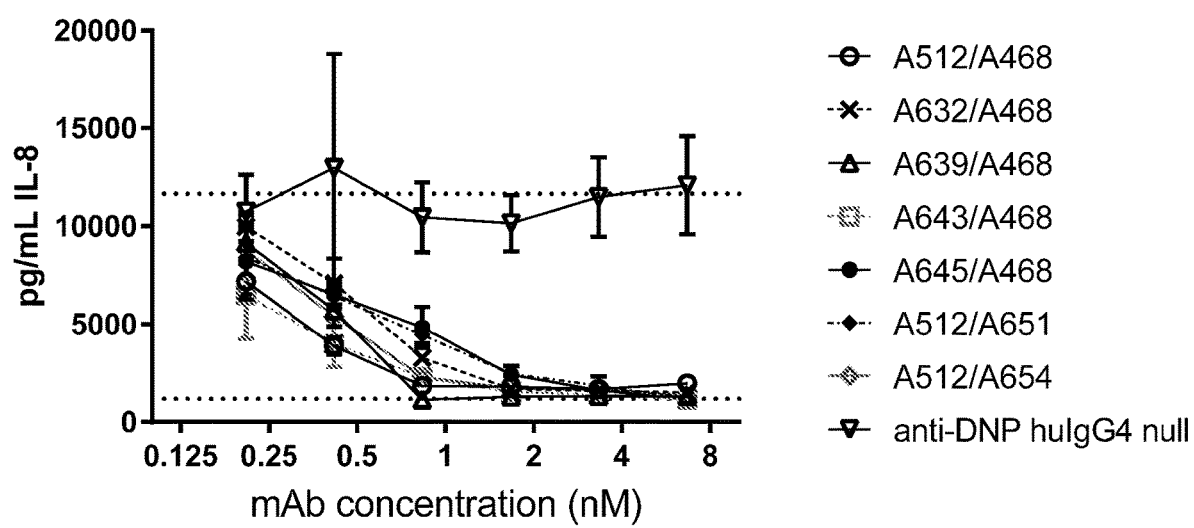

FIGS. 26A, 26B and 26C depict the results showing further engineered humanized Fn14 mAbs antagonize TWEAK-induced IL-8 secretion from HRMC. HRMC were incubated with anti-Fn14 or isotype control mAbs at various concentrations ranging from 6.67 to 0.2085 nM for 30 minutes at 37° C. and then TWEAK was added to the wells at 250 ng/mL for 24 hours. Supernatants were harvested and tested for IL-8 using an IL-8 ELISA kit. Data was plotted in Prism. A512/A468 is the original humanized antibody, and the rest are further engineered clones from A512/A468. Anti-DNP huIgG4 null is the isotype control for Fn14 mAbs. Top dotted line: IL-8 production from TWEAK stimulated cells. Bottom dotted line: IL-8 production from unstimulated cells.

Figure 27A:
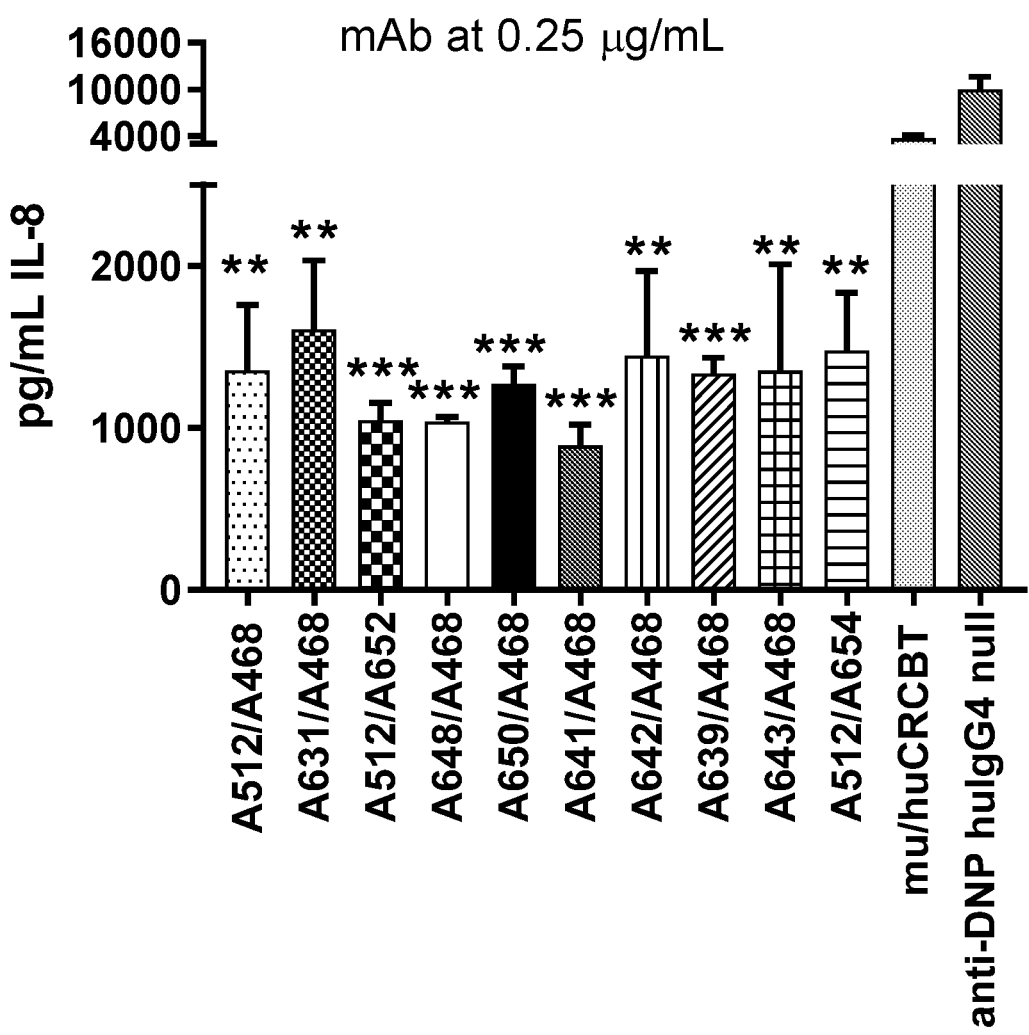
Figure 27B:
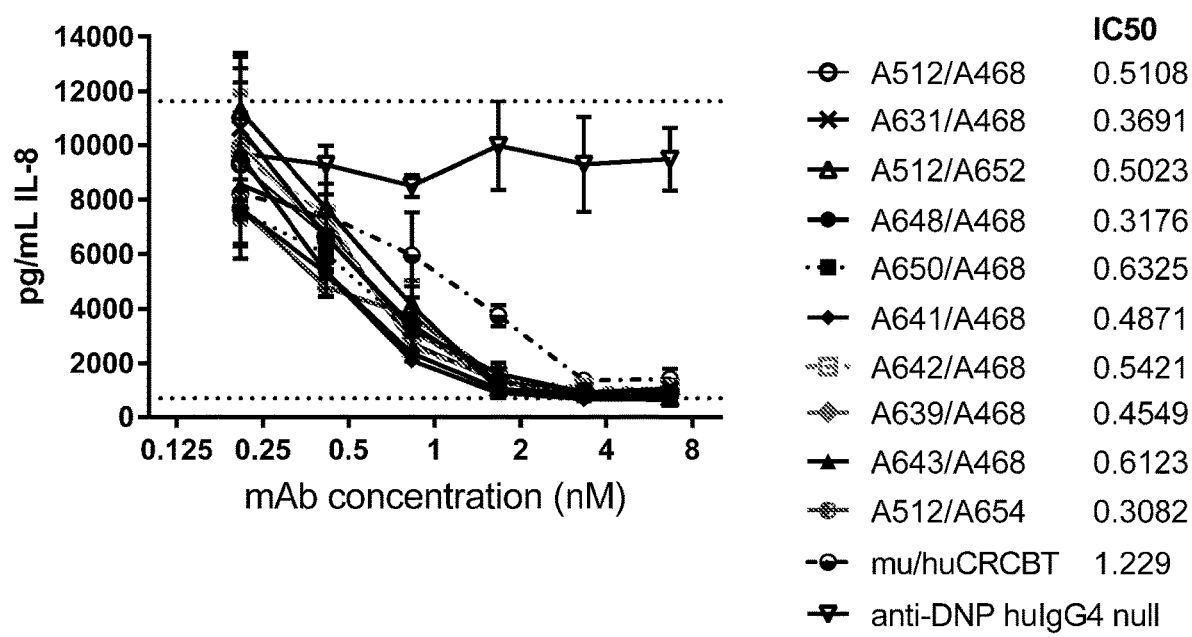

FIGS. 27A and 27B depict the results showing that further engineered humanized Fn14 mAbs are more potent antagonists of TWEAK-induced IL-8 secretion from HRMC than the CRCBT-06-002 Fn14 mAb. HRMC were incubated with various concentrations of anti-Fn14 antibodies, mouse/human chimeric CRCBT-06-002 (mu/huCRCBT), or isotype control mAb for 30 minutes at 37° C. and then TWEAK was added to the wells at 250 ng/mL for 24 hours. Supernatants were harvested and tested for IL-8 using an IL-8 ELISA kit. FIG. 27A shows data at the antibody concentration of 1.67 nM (0.25 µg/mL). FIG. 27B shows each of the anti-Fn14 clones was able to block TWEAK-induced IL-8 secretion more potently than mu/huCRCBT with lower IC50. Top dotted line: IL-8 production from TWEAK stimulated cells. Bottom dotted line: IL-8 production from unstimulated cells. Data were analyzed using unpaired t test, comparing IL-8 levels between individual anti-Fn14 mAb treated and mu/huCRCBT treated wells. *: p <0.001, : p <0.01. A512/A468: original humanized anti-Fn14 mAb, and the rest are further engineered clones of A512/A468. Anti-DNP huIgG4 null: isotype control.

Figure 28A:
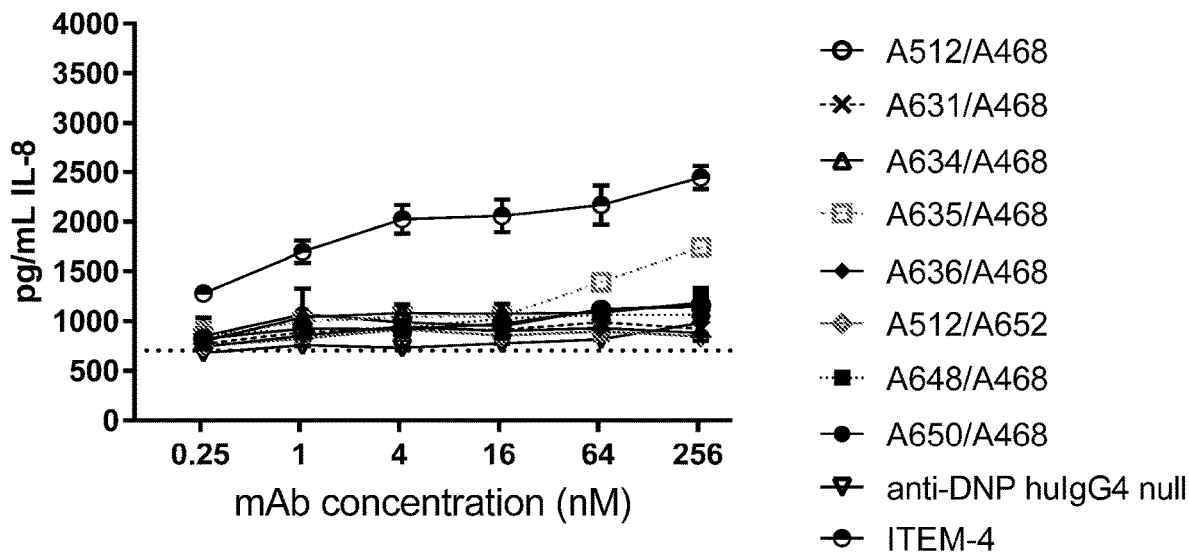
Figure 28B:
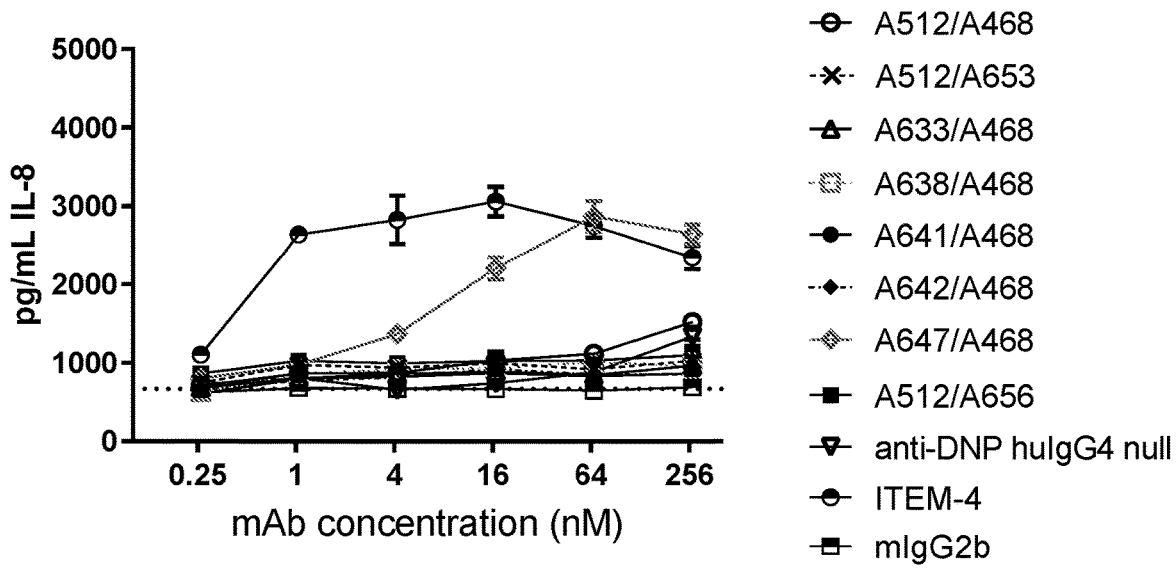
Figure 28C:
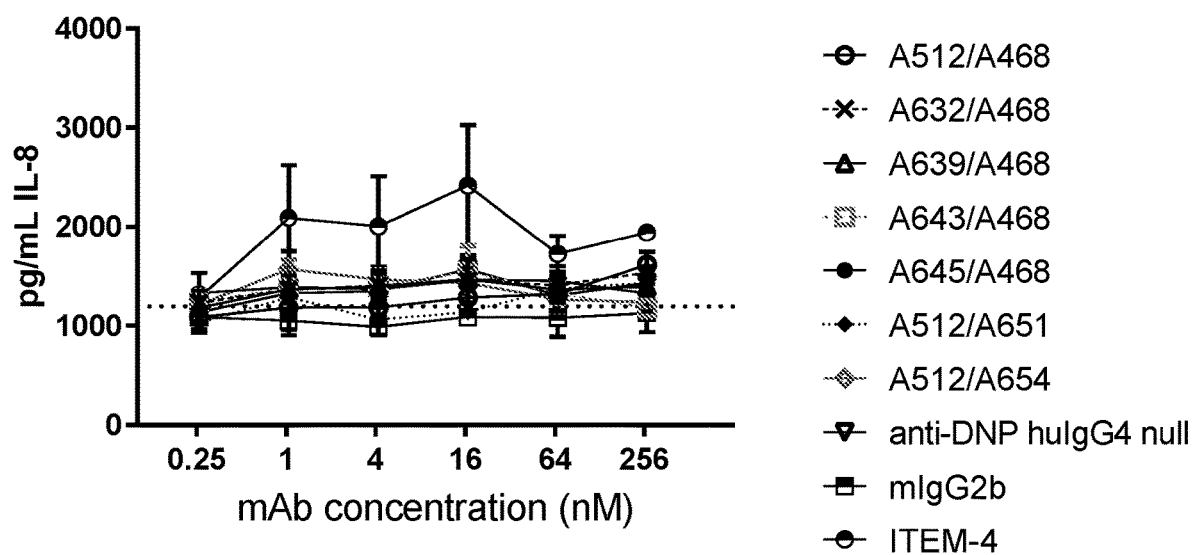

FIGS. 28A, 28B and 28C show that further engineered humanized mAbs do not agonize Fn14. HRMC were incubated with anti-Fn14 or isotype control mAbs at various concentrations ranging from 266.67 to 0.26 nM for 24 hours. Supernatants were harvested and tested for IL-8 using an IL-8 ELISA kit. Dotted line represents average supernatant IL-8 levels from unstimulated cells (media alone) after 24 hours. Anti-DNP huIgG4 null is the isotype control for Fn14 mAbs. ITEM-4 is a commercial mAb that exhibits agonist activity and used as a positive control. mIgG2b is the isotype control antibody for ITEM 4. Dotted line: IL-8 production from unstimulated cells.

Figure 29A:
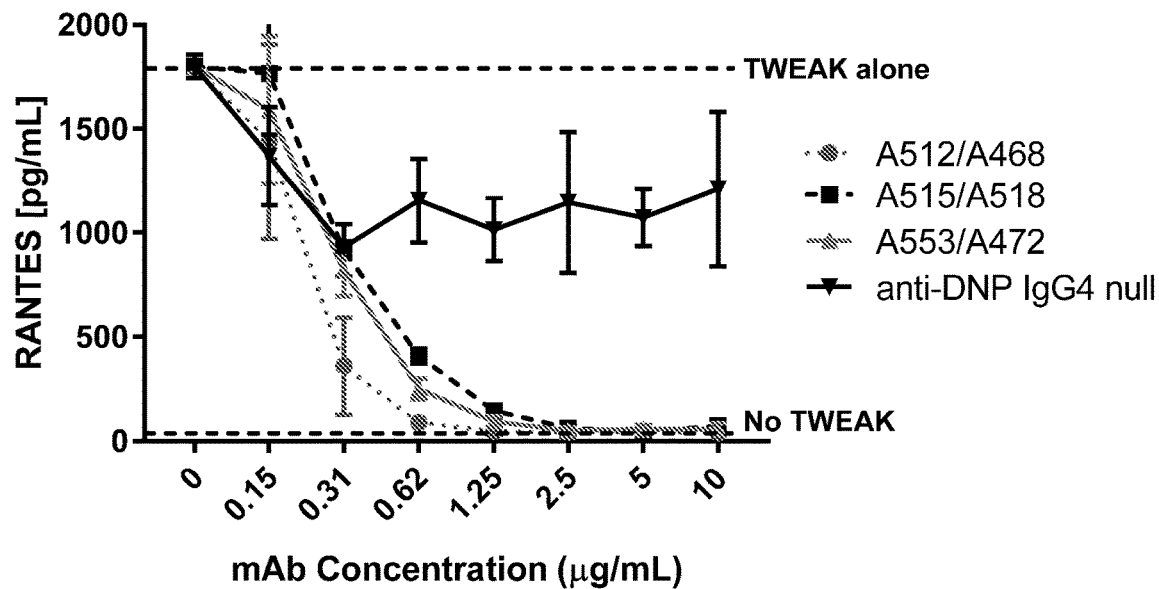

FIG. 29A shows that humanized Fn14 mAbs potently antagonize TWEAK-induced RANTES secretion from HaCaT cells. HaCaT cells were incubated with anti-Fn14 or isotype control mAbs at various concentrations ranging from 0.156 to 10 µg/mL for 30 minutes at 37° C. and then TWEAK was added to the wells at 100 ng/mL for 48 hours. Supernatants were harvested and tested for RANTES using a RANTES ELISA kit. Data was plotted in Prism. Anti-DNP huIgG4 null is the isotype control for Fn14 mAbs. Top dotted line: cells treated with TWEAK only with no antibody added. Bottom dotted line: cells not stimulated with TWEAK.

Figure 29B:
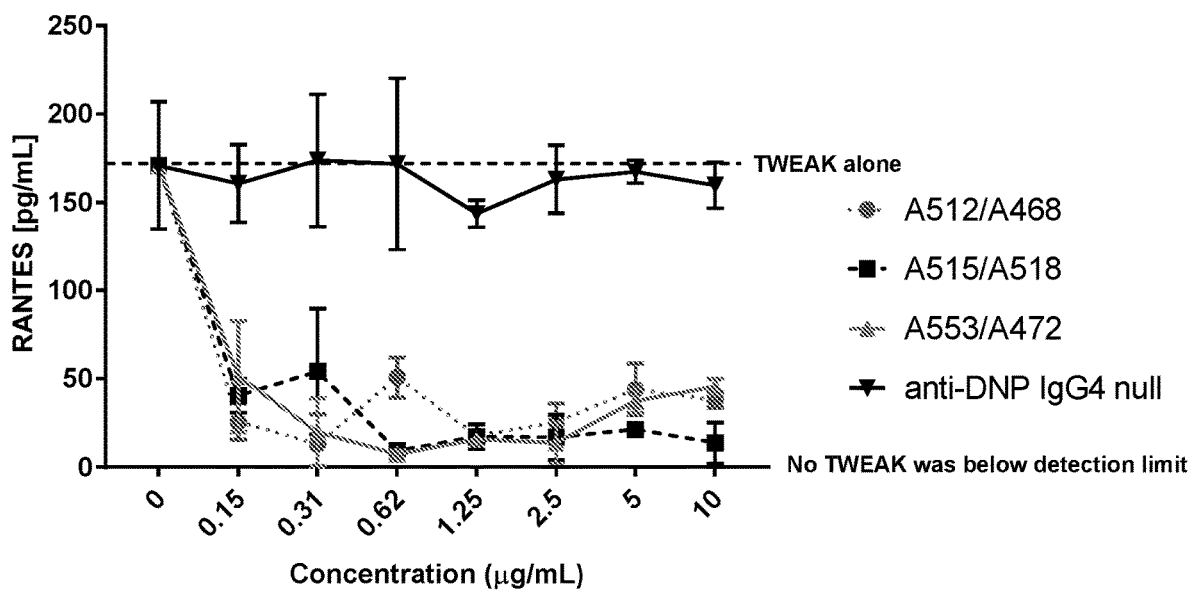

FIG. 29B shows that humanized Fn14 mAbs potently antagonize TWEAK-induced RANTES secretion from human primary adult keratinocytes. Primary keratinocytes were incubated with anti-Fn14 or isotype control mAbs at various concentrations ranging from 0.156 to 10 µg/mL for 30 minutes at 37° C. and then TWEAK was added to the wells at 100 ng/mL for 48 hours. Supernatants were harvested and tested for RANTES using a RANTES ELISA kit. Data was plotted in Prism. Anti-DNP huIgG4 null is the isotype control for Fn14 mAbs. Top dotted line: cells treated with TWEAK only with no antibody added. RANTES levels from cells that were not stimulated with TWEAK were below the limit of detection (no OD values obtained).

Figure 30:
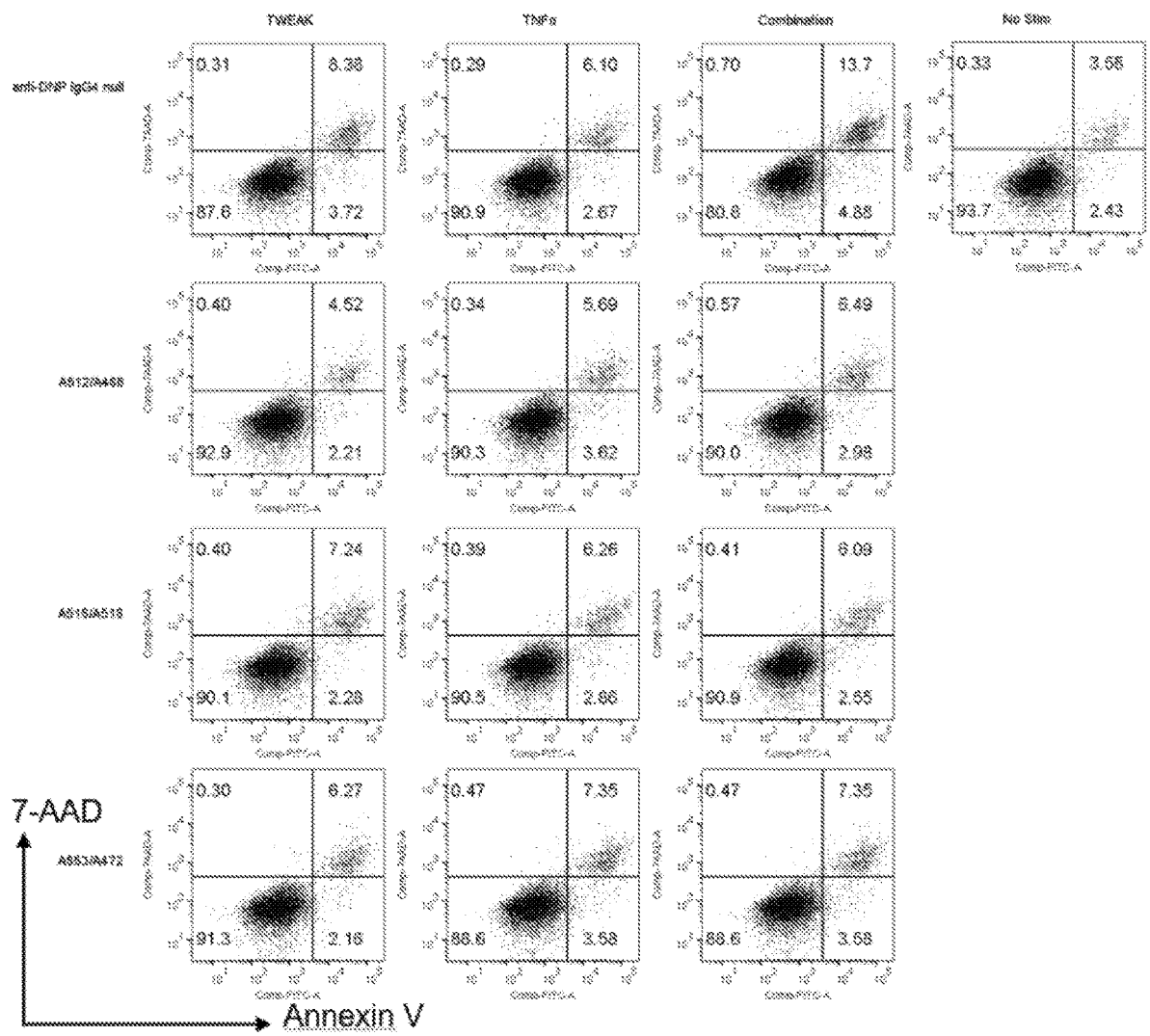

FIG. 30 shows humanized Fn14 mAbs potently antagonize TWEAK-induced apoptosis of human primary neonatal epidermal keratinocytes. Human primary epidermal keratinocytes were incubated with anti-Fn14 or isotype control mAbs (1.5 µg/mL), TWEAK (100 ng/mL), TNFα (10 ng/mL) or the combination of TWEAK and TNFα for 72 hours. Cells were collected, stained with Annexin V and 7-AAD, and analyzed on an LSR Fortessa. Annexin V+/7-AAD+cells: late apoptotic cells, Annexin V+/7-AAD- cells: early apoptotic cells.

Figure 31A:
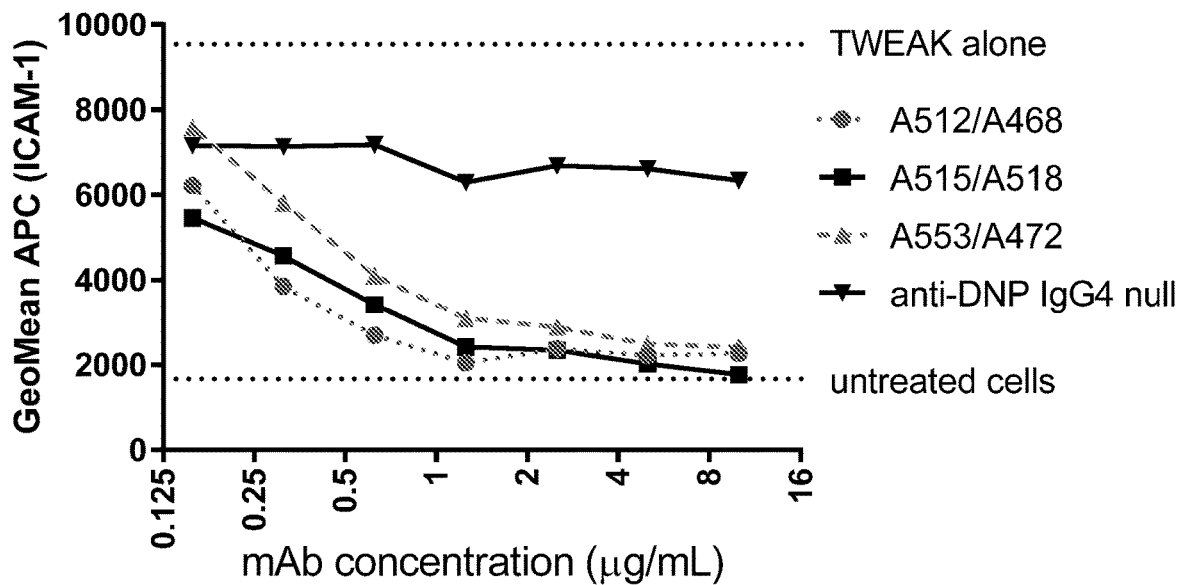

FIG. 31A shows humanized Fn14 mAbs potently antagonize TWEAK-induced ICAM-1 upregulation on HaCaT cells. HaCaT cells were incubated with anti-Fn14 or isotype control mAbs at various concentrations ranging from 0.156 to 10 µg/mL for 30 minutes at 37° C. and then TWEAK was added to the wells at 100 ng/mL for 48 hours. Cells were collected, stained with anti-ICAM-1, and analyzed on an LSR Fortessa. Anti-DNP huIgG4 null is the isotype control for Fn14 mAbs. Top dotted line: cells treated with TWEAK only with no antibody added. Bottom dotted line: cells not treated with TWEAK.

Figure 31B:
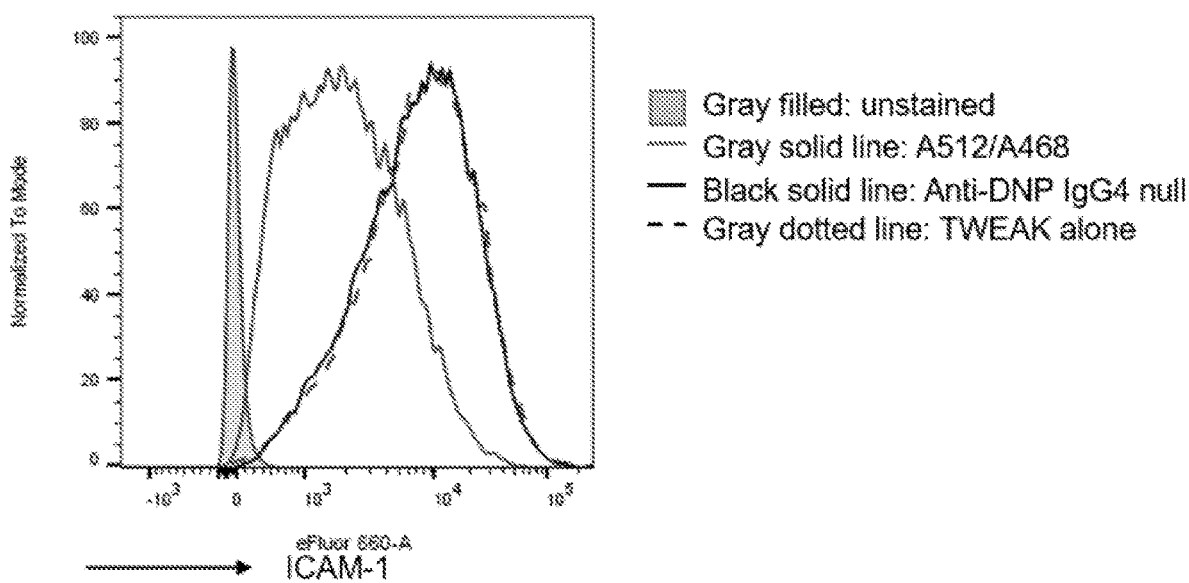

FIG. 31B shows humanized Fn14 mAb A512/A468 potently antagonizes TWEAK-induced ICAM-1 upregulation on human primary neonatal keratinocytes. Primary neonatal keratinocytes were incubated with anti-Fn14 or isotype control mAbs at 1 µg/mL for 30 minutes at 37° C. and then TWEAK was added to the wells at 100 ng/mL for 48 hours. Cells were collected, stained with anti-ICAM-1, and analyzed on an LSR Fortessa. Anti-DNP huIgG4 null is the isotype control for Fn14 mAbs.

Figure 32:
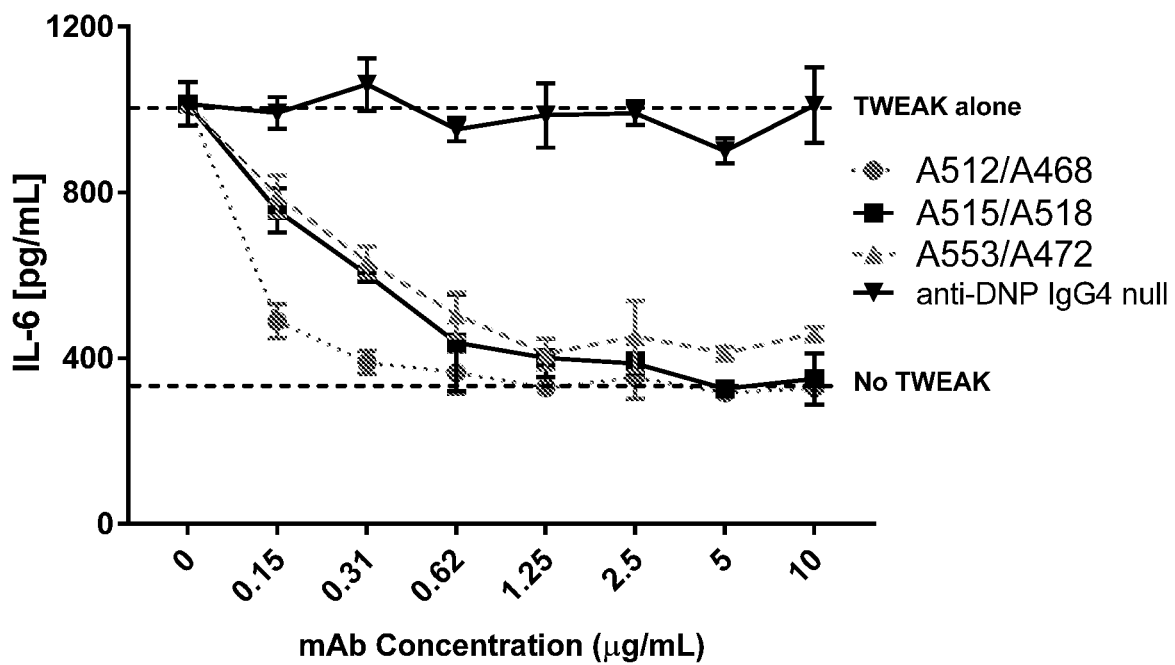

FIG. 32 shows humanized Fn14 mAbs potently antagonize TWEAK-induced IL-6 secretion from human primary dermal fibroblasts. Human primary dermal fibroblasts were incubated with anti-Fn14 or isotype control mAbs at various concentrations ranging from 0.156 to 10 µg/mL for 30 minutes at 37° C. and then TWEAK was added to the wells at 100 ng/mL for 48 hours. Supernatants were harvested and tested for IL-6 using an IL-6 ELISA kit. Data was plotted in Prism. Anti-DNP huIgG4 null is the isotype control for Fn14 mAbs. Top dotted line: cells treated with TWEAK only with no antibody added. Bottom dotted line: cells not stimulated with TWEAK.

5. DETAILED DESCRIPTION

The present disclosure provides novel Fn14 antibodies, pharmaceutical compositions comprising same, and uses thereof. More specifically, the present disclosure provides antibodies antagonizing Fn14, pharmaceutical compositions comprising these antibodies, and uses thereof.

Anti-Fn14 mAbs have been described (see, e.g., Johnston, A. J., et al., 2015 Cell 162(6):1365-78; Sanchez-Nino, M. D., et al., *Biochim Biophys Acta*, 2013, 1832(12):2232-43; Zhao, Z., et al., *J Immunol*, 2007, 179(11):7949-58). For example, Johnston et. al., generated several anti-Fn14 mAbs (001, 002 and 004) and characterized them both in vitro and in vivo (Johnston, A. J., et al., *Cell*, 2015, 162(6):1365-78; Johnston, A. J. et al., *Curr Opin Clin Nutr Metab Care*, 2016, 19(4):316-8). In vitro characterization of the monoclonal antibodies revealed that all three clones are antagonist/non-agonist in an NFκB reporter assay, but only 001 and 002 were able to block TWEAK-induced cell death in a cytotoxicity assay. However, 001 was shown to be an agonist, non-antagonist in an A375 cell—IL-8 secretion assay (US2013/0273036 A1). They identified that 001, 002 and 004 bind to an epitope termed Subdomain 2 (Fn14 AA 51-70) but not Subdomain 1 (Fn14 AA 31-50). Subdomains 1 and 2 comprise the majority of the extracellular domain of Fn14 (Johnston, A. J., et al., *Cell*, 2015, 162(6):1365-78).

Provided herein in certain embodiments are novel anti-Fn14 antagonist, non-agonist, monoclonal antibodies, which bind human, cynomolgus macaque, rat and mouse Fn14 with high affinities. As shown in Section 6 below, the antibodies provided herein robustly neutralize TWEAK-induced inflammatory and pro-fibrotic signaling through Fn14. This is demonstrated with in vitro functional assays utilizing an NF-κB reporter cell line, A375 melanoma cell line, a human kidney derived cell line and primary human renal mesangial cells to measure TWEAK binding, TWEAK-induced chemokine expression, IL-8 secretion and ICAM-1 expression. No agonist activity was induced by these antibodies in the absence of TWEAK in any of these assays. The binding epitope was mapped to Subdomain 1 of the extracellular region of Fn14 and further defined by co-crystallization studies of Fn14 with two anti-Fn14 Fabs.

The antibodies provided herein provide numerous advantages as demonstrated by the data shown in Section 6 below. For example, previously reported antagonist Fn14 antibody—clone ITEM-4 (Nakayama, M., et al., *J Immunol*, 2003, 170(1):341-8) demonstrates agonist activity (Nakayama, M., et al., *J Immunol*, 2003, 170(1):341-8; Potrovita, I., et al., *J Neurosci*, 2004, 24(38):8237-44) as well as antagonist properties (Nakayama, M., et al., *J Immunol*, 2003, 170(1):341-8; Potrovita, I., et al., *J Neurosci*, 2004, 24(38):8237-44; Justo, P., et al., *Kidney Int*, 2006, 70(10):1750-8).

5.1 Definitions

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: *Methods and Protocols* (Albitar ed. 2010); and *Antibody Engineering* Vols 1 and 2 (Kontermann and DUbel eds., 2d ed. 2010).

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "antibody," "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., Antibody Engineering (Borrebaeck ed., 2d ed. 1995); and Kuby, *Immunology* (3d ed. 1997). In specific embodiments, the specific molecular antigen can be bound by an antibody provided herein, including a polypeptide or an epitope. Antibodies also include, but are not limited to, synthetic antibodies, recombinantly produced antibodies, camelized antibodies or their humanized variants, intrabodies, anti-idiotypic (anti-Id) antibodies, and functional fragments (e.g., antigen-binding fragments) of any of the above, which refers to a portion of an antibody heavy or light chain polypeptide that retains some or all of the binding activity of the antibody from which the fragment was derived. Non-limiting examples of functional fragments (e.g., antigen binding fragments) include single-chain Fvs (scFv) (e.g., including monospecific, bispecific, etc.), Fab fragments, F(ab') fragments, F(ab)2 fragments, F(ab')2 fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, *Cell Biophysics* 22:189-224; Phickthun and Skerra, 1989, *Meth. Enzymol.* 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell.

An "antagonist" antibody is one, which inhibits or reduces biological activity of the antigen it binds. For example, antagonist antibodies may substantially or completely inhibit the biological activity of the antigen. As used herein, an "antagonist" or "inhibitor" of Fn14 refers to a molecule that is capable of inhibiting or otherwise decreasing one or more of the biological activities of Fn14. For example, in some embodiments, an antagonist of Fn14 (e.g., an antagonistic antibody provided herein) may act by inhibiting or otherwise decreasing the activation and/or cell signaling pathways of the cell expressing Fn14, thereby inhibiting or limiting an Fn14 mediated biological activity of the cell relative to the Fn14-mediated biological activity in the absence of antagonist.

An antagonist antibody as used herein is in contrast with an "agonist" antibody, which is an antibody that triggers a response, e.g., one that mimics at least one of the functional activities of a polypeptide of interest (e.g., Fn14). An agonist antibody includes an antibody that is a ligand mimetic, for example, wherein a ligand binds to a cell surface receptor and the binding induces cell signaling or activities via an intercellular cell signaling pathway and wherein the antibody induces a similar cell signaling or activation. An agonist of Fn14 refers to a molecule that is capable of activating or otherwise increasing one or more of the biological activities of Fn14, such as on a cell that is responsive to TWEAK through its expression of an Fn14. In some embodiments, an agonist of Fn14 may, for example, act by increasing the activity of Fn14, leading to an increase in the activation and/or cell signaling pathways of a cell expressing Fn14, thereby increasing an Fn14-mediated biological activity of the cell relative to the Fn14-mediated biological activity in the absence of agonist.

An "intact" antibody is one comprising an antigen binding site as well as a CL and at least heavy chain constant regions, CH1, CH2 and CH3. The constant regions may include human constant regions or amino acid sequence variants thereof. In certain embodiments, an intact antibody has one or more effector functions.

The terms "antigen binding fragment," "antigen binding domain," "antigen binding region," and similar terms refer to that portion of an antibody, which comprises the amino acid residues that interact with an antigen and confer on the binding agent its specificity and affinity for the antigen (e.g., the CDRs). "Antigen binding fragment" as used herein include "antibody fragment," which comprise a portion of an intact antibody, such as the antigen binding or variable region of the intact antibody. Examples of antibody fragments include, without limitation, Fab, Fab', F(ab')2, and Fv fragments; diabodies and di-diabodies (see, e.g., Holliger et al., *Proc Natl Acad Sci* 1993, 90:6444-48; Lu et al., *J Biol Chem,* 2005, 280:19665-72; Hudson et al., *Nat Med,* 2003, 9:129-34; WO 93/11161; and U.S. Pat. Nos. 5,837,242 and 6,492,123); single-chain antibody molecules (see, e.g., U.S. Pat. Nos. 4,946,778; 5,260,203; 5,482,858; and 5,476,786); dual variable domain antibodies (see, e.g., U.S. Pat. No. 7,612,181); single variable domain antibodies (sdAbs) (see, e.g., Woolven et al., *Immunogenetics,* 1999, 50: 98-101; and Streltsov et al., *Proc Natl Acad Sci USA.* 2004, 101:12444-49); and multispecific antibodies formed from antibody fragments.

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the antibody or antigen binding fragment described herein, the terms such as "bind to," "that specifically bind to," and analogous terms are also used interchangeably herein and refer to antibodies of antigen binding domains that specifically bind to an antigen, such as a polypeptide. An antibody or antigen binding domain that binds to or specifically binds to an antigen may be cross-reactive with related antigens. In certain embodiments, an antibody or antigen binding domain that binds to or specifically binds to an antigen does not cross-react with other antigens. An antibody or antigen binding domain that binds to or specifically binds to an antigen can be identified, for example, by immunoassays, Octet®, Biacore®, or other techniques known to those of skill in the art. In some embodiments, an antibody or antigen binding domain binds to or specifically binds to an antigen when it binds to an antigen with higher affinity than to any cross-reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., *Fundamental Immunology* 332-36 (Paul ed., 2d ed. 1989) for a discussion regarding binding specificity. In certain embodiments, the extent of binding of an antibody or antigen binding domain to a "non-target" protein is less than about 10% of the binding of the antibody or antigen binding domain to its particular target antigen, for example, as determined by fluorescence activated cell sorting (FACS) analysis or RIA. With regard to terms such as "specific binding," "specifically binds to," or "is specific for" means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. An antibody or antigen binding domain that binds to an antigen includes one that is capable of binding the antigen with sufficient affinity such that the antibody or antigen binding fragment is useful, for example, as a diagnostic or therapeutic agent in targeting the antigen. In certain embodiments, an antibody or antigen binding domain that binds to an antigen has a dissociation constant ($K_D$) of less than or equal to 1000 nM, 800 nM, 500 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, an antibody or antigen binding domain binds to an epitope of an antigen that is conserved among the antigen from different species (e.g., between human and cynomolgus macaque species).

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et a.l., *J. Mol Biol*, 1999, 293:865-81). The $K_D$ or $K_D$ value may also be measured by using biolayer interferometry (BLI) or surface plasmon resonance (SPR) assays by Octet®, using, for example, an Octet®Red96 system, or by Biacore®, using, for example, a Biacore® 2000 or a Biacore® 3000. An "on-rate" or "rate of association" or "association rate" or "$k_{on}$," may also be determined with the same biolayer interferometry (BLI) or surface plasmon resonance (SPR) techniques described above using, for example, the Octet®Red96, the Biacore® 2000, or the Biacore® 3000 system.

In certain embodiments, the antibodies or antigen binding fragments can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55).

In certain embodiments, the antibodies or antigen binding fragments can comprise portions of "humanized" forms of nonhuman (e.g., murine) antibodies that are chimeric antibodies that include human immunoglobulins (e.g., recipient antibody) in which the native CDR residues are replaced by residues from the corresponding CDR of a nonhuman species (e.g., donor antibody) such as mouse, rat, rabbit, or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., 1986, *Nature* 321:522-25; Riechmann et al., 1988, *Nature* 332:323-29; Presta, 1992, *Curr. Op. Struct. Biol.* 2:593-96; Carter et al., 1992, *Proc. Natl. Acad. Sci. USA* 89:4285-89; U.S. Pat. Nos. 6,800,738; 6,719,971; 6,639,055; 6,407,213; and 6,054,297.

In certain embodiments, the antibodies or antigen binding fragments can comprise portions of a "fully human antibody" or "human antibody," wherein the terms are used interchangeably herein and refer to an antibody that comprises a human variable region and, for example, a human constant region. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies having variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, 1991, J. Mol. Biol. 227:381; Marks et al., 1991, J. Mol. Biol. 222:581) and yeast display libraries (Chao et al., 2006, Nature Protocols 1: 755-68). Also available for the preparation of human monoclonal antibodies are methods described in Cole et al., *Monoclonal Antibodies and Cancer Therapy* 77 (1985); Boerner et al., 1991, J. Immunol. 147(1):86-95; and van Dijk and van de Winkel, 2001, Curr. Opin. Pharmacol. 5: 368-74. Human antibodies can be prepared by administering the antigen to a transgenic animal that has been modified to produce such antibodies in response to antigenic challenge, but whose endogenous loci have been disabled, e.g., mice (see, e.g., Jakobovits, 1995, Curr. Opin. Biotechnol. 6(5):561-66; Brtiggemann and Taussing, 1997, Curr. Opin. Biotechnol. 8(4):455-58; and U.S. Pat. Nos. 6,075,181 and 6,150,584 regarding XENO-MOUSE™ technology). See also, for example, Li et al., 2006, Proc. Natl. Acad. Sci. USA 103:3557-62 regarding human antibodies generated via a human B-cell hybridoma technology.

In certain embodiments, the antibodies or antigen binding fragments can comprise portions of a "recombinant human antibody," wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the antibodies or antigen binding fragments can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., 1975, Nature 256:495, or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., 1991, Nature 352:624-28 and Marks et al., 1991, J. Mol. Biol. 222:581-97, for example. Other methods for the preparation of clonal cell lines and of monoclonal antibodies expressed thereby are well known in the art. See, e.g., *Short Protocols in Molecular Biology* (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ. and isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994); and *Immunobiology* (Janeway et al. eds., $5^{th}$ ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region," "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL 0-sheet framework. Accordingly, CDRs are variable region sequences interspersed within the framework region sequences.

CDR regions are well known to those skilled in the art and have been defined by well-known numbering systems. For example, the Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35 Å and H35B; if neither 35 Å nor 35B is present, the loop ends at 32; if only 35 Å is present, the loop ends at 33; if both 35 Å and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and DUbel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., 2003, Dev. Comp. Immunol. 27(1):55-77). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Pluckthun, 2001, J. Mol. Biol. 309: 657-70. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). The residues from each of these hypervariable regions or CDRs are noted below.

TABLE 25

| Loop | Kabat | AbM | Chothia | Contact | IMGT |
| --- | --- | --- | --- | --- | --- |
| CDRL1 | L24--L34 | L24--L34 | L24--L34 | L30--L36 | L27--L38 |
| CDRL2 | L50--L56 | L50--L56 | L50--L56 | L46--L55 | L56--L65 |
| CDRL3 | L89--L97 | L89--L97 | L89--L97 | L89--L96 | L105-L117 |
| CDRH1 | H31--H35B (Kabat Numbering) | H26--H35B | H26-- H32 . . . 34 | H30--H35B | H27--H38 |

TABLE 25-continued

| Loop | Kabat | AbM | Chothia | Contact | IMGT |
|---|---|---|---|---|---|
| CDRH1 | H31--H35 (Chothia Numbering) | H26--H35 | H26--H32 | H30--H35 | |
| CDRH2 | H50--H65 | H50--H58 | H52--H56 | H47--H58 | H56--H65 |
| CDRH3 | H95--H102 | H95--H102 | H95--H102 | H93--H101 | H105-H117 |

The boundaries of a given CDR may vary depending on the scheme used for identification. Thus, unless otherwise specified, the terms "CDR" and "complementary determining region" of a given antibody or region thereof, such as a variable region, as well as individual CDRs (e.g., CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the Kabat, Chothia, or Contact method. In other cases, the particular amino acid sequence of a CDR is given.

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35 Å (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues. There are typically four FR regions in each of VH and VL regions. The FR regions in VH are VH FR1, VH FR2, VH FR3, and VH FR4 (or FR H1, FR H2, FR H3 and FR H4). The FR regions in VL are VL FR1, VL FR2, VL FR3 and VL FR4 (or FR L1, FR L2, FR L3 and FR L4).

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

The term "variant" when used in relation to an antigen or an antibody may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, an Fn14 variant may result from one or more (such as, for example, about 1 to about 25, about 1 to about 20, about 1 to about 15, about 1 to about 10, or about 1 to about 5) changes to an amino acid sequence of a native Fn14. Also by way of example, a variant of an anti-Fn14 antibody may result from one or more (such as, for example, about 1 to about 25, about 1 to about 20, about 1 to about 15, about 1 to about 10, or about 1 to about 5) changes to an amino acid sequence of a native or previously unmodified anti-Fn14 antibody. Variants may be naturally occurring, such as allelic or splice variants, or may be artificially constructed. Polypeptide variants may be prepared from the corresponding nucleic acid molecules encoding the variants. In specific embodiments, the Fn14 variant or anti-Fn14 antibody variant at least retains Fn14 or anti-Fn14 antibody functional activity, respectively. In specific embodiments, an anti-Fn14 antibody variant binds Fn14 and/or is antagonistic to Fn14 activity. In certain embodiments, the variant is encoded by a single nucleotide polymorphism (SNP) variant of a nucleic acid molecule that encodes Fn14 or anti-Fn14 antibody VH or VL regions or subregions, such as one or more CDRs.

The term "identity" refers to a relationship between the sequences of two or more polypeptide molecules or two or more nucleic acid molecules, as determined by aligning and comparing the sequences. "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN (DNAStar, Inc.) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/position. For example, typical modifications include substitution of the residue with another amino acid (e.g., a conservative or non-conservative substitution), insertion of one or more (e.g., generally fewer than 5, 4, or 3) amino acids adjacent to said residue/position, and/or deletion of said residue/position.

As used herein, an "epitope" is a term in the art and refers to a localized region of an antigen to which an antibody or antigen binding fragment can specifically bind. An epitope can be a linear epitope or a conformational, non-linear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, an antibody binds to a group of amino acids regardless of whether they are folded in a natural three dimensional protein structure. In other embodiments, an antibody requires amino acid residues making up the epitope to exhibit a particular conformation (e.g., bend, twist, turn or fold) in order to recognize and bind the epitope.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

The term "vector" refers to a substance that is used to carry or include a nucleic acid sequence, including for example, a nucleic acid sequence encoding an antibody or antigen binding fragment as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces an antibody or antigen binding fragment of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

The term "pharmaceutically acceptable" as used herein means being approved by a regulatory agency of the Federal or a state government, or listed in United States Pharmacopeia, European Pharmacopeia, or other generally recognized Pharmacopeia for use in animals, and more particularly in humans.

"Excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The term "excipient" can also refer to a diluent, adjuvant (e.g., Freunds' adjuvant (complete or incomplete) or vehicle.

In some embodiments, excipients are pharmaceutically acceptable excipients. Examples of pharmaceutically acceptable excipients include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; saltforming counterions, such as sodium; and/or nonionic surfactants, such as TWEEN™, polyethylene glycol (PEG), and PLURONICS™ Other examples of pharmaceutically acceptable excipients are described in Remington and Gennaro, *Remington's Pharmaceutical Sciences* (18th ed. 1990).

In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009. In some embodiments, pharmaceutically acceptable excipients are nontoxic to the cell or mammal being exposed thereto at the dosages and concentrations employed. In some embodiments, a pharmaceutically acceptable excipient is an aqueous pH buffered solution.

In some embodiments, excipients are sterile liquids, such as water and oils, including those of petroleum, animal, vegetable, or synthetic origin, such as peanut oil, soybean oil, mineral oil, sesame oil, and the like. Water is an exemplary excipient when a composition (e.g., a pharmaceutical composition) is administered intravenously. Saline solutions and aqueous dextrose and glycerol solutions can also be employed as liquid excipients, particularly for injectable solutions. An excipient can also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard excipients such as pharmaceutical grades of mannitol, lactose, starch, magnesium stearate, sodium saccharine, cellulose, magnesium carbonate, etc.

Compositions, including pharmaceutical compounds, may contain an antibody or antigen binding fragment, for example, in isolated or purified form, together with a suitable amount of excipients.

The term "effective amount" or "therapeutically effective amount" as used herein refers to the amount of an antibody or antigen binding fragment or pharmaceutical composition provided herein which is sufficient to result in the desired outcome.

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal, e.g., a human, diagnosed with a condition or disorder. In another embodiment, the subject is a mammal, e.g., a human, at risk of developing a condition or disorder.

"Administer" or "administration" refers to the act of injecting or otherwise physically delivering a substance as it exists outside the body into a patient, such as by mucosal, intradermal, intravenous, intramuscular, subcutaneous delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies. Treating may be determined by assessing whether there has been a decrease, alleviation and/or mitigation of one or more symptoms associated with the underlying disorder such that an improvement is observed with the patient, despite that the patient may still be afflicted with the underlying disorder. The term "treating" includes both managing and ameliorating the disease. The terms "manage," "managing," and "management" refer to the beneficial effects that a subject derives from a therapy which does not necessarily result in a cure of the disease.

The terms "prevent," "preventing," and "prevention" refer to reducing the likelihood of the onset (or recurrence) of a disease, disorder, condition, or associated symptom(s).

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "between" as used in a phrase as such "between A and B" or "between A-B" refers to a range including both A and B.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2 Anti-Fn14 Antibodies and Related Molecules
5.2.1 Anti-Fn14 Antibodies

The antibodies provided herein include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In particular, the antibodies provided herein include immunoglobulin molecules and immunologically active portions of immunoglobulin molecules, i.e., molecules that contain an antigen binding site that immunospecifically binds to an Fn14 antigen. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, such as an IgG1 antibody, IgG2 antibody or IgG4 antibody (e.g., IgG4 nullbody and variants of IgG4 antibodies).

Variants and derivatives of antibodies include antibody fragments that retain the ability to specifically bind to an epitope. Exemplary fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')2 (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a scFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific scFv (a scFv or a dsFv molecule having two antigen-binding domains, each of which may be directed to a different epitope); a diabody (a dimerized scFv formed when the VH domain of a first scFv assembles with the VL domain of a second scFv and the VL domain of the first scFv assembles with the VH domain of the second scFv; the two antigen-binding regions of the diabody may be directed towards the same or different epitopes); a triabody (a trimerized scFv, formed in a manner similar to a diabody, but in which three antigen-binding domains are created in a single complex; the three antigen binding domains may be directed towards the same or different epitopes); and a tetrabody (a tetramerized scFv, formed in a manner similar to a diabody, but in which four antigen-binding domains are created in a single complex; the four antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, an antibody provided herein comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in *The Pharmacology of Monoclonal Antibodies*, vol. 113, Rosenburg and Moore eds. Springer-Verlag, New York, pp. 269-315 (1994).

The antibodies provided herein may be from any animal origin including birds and mammals (e.g., human, monkey, murine, donkey, sheep, rabbit, goat, guinea pig, camel, horse, or chicken). In certain embodiments, the antibodies provided herein are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In certain embodiments, the antibodies are full mouse antibodies. In certain embodiments, the antibodies are mouse-human chimeric antibodies. In certain embodiments, the antibodies are humanized antibodies. In certain embodiments, the antibodies are fully human antibodies, such as fully human antibodies that immunospecifically bind an Fn14 polypeptide, an Fn14 polypeptide fragment, or an Fn14 epitope. In other embodiments, the antibodies provided herein are humanized antibodies (e.g., comprising human constant and framework regions) that bind Fn14, including an Fn14 polypeptide, an Fn14 polypeptide fragment, or an Fn14 epitope.

The antibodies provided herein may be monospecific, bispecific, trispecific or of greater multispecificity. For example, in certain embodiments, the bispecific antibodies have one specificity to one epitope of Fn14 polypeptide and a second specificity to a second epitope of the Fn14 polypeptide. In other embodiments, the bispecific antibodies have one specificity to an Fn14 polypeptide and a second specificity for a heterologous epitope, such as a heterologous polypeptide or solid support material.

In certain embodiments, the antibodies provided herein bind to human Fn14. In other embodiments, the antibodies provided herein bind to cynomolgus macaque Fn14. In yet other embodiments, the antibodies provided herein binds to rat Fn14. In yet other embodiments, the antibodies provided herein binds to mouse Fn14. In yet other embodiments, the antibodies provided herein binds to human, cynomolgus macaque, rat and mouse Fn14.

The terms "Fn14" and "Fn14 polypeptide" encompasses a polypeptide ("polypeptide" and "protein" are used interchangeably herein), including any native polypeptide, from any vertebrate source, including mammals such as primates (e.g., humans and cynomolgus monkeys (cynomolgus macaque)), dogs, and rodents (e.g., mice and rats), unless otherwise indicated. The term "Fn14" also encompasses "full-length," unprocessed Fn14 as well as any form of Fn14 that results from processing in the cell or extracellularly. "Related Fn14 polypeptides" include allelic variants (e.g., SNP variants); splice variants; fragments; derivatives; substitution, deletion, and insertion variants; fusion polypeptides; interspecies homologs; and interspecies chimeras, which can retain Fn14 activity. As those skilled in the art will appreciate, an anti-Fn14 antibody provided herein can bind to an Fn14 polypeptide, an Fn14 polypeptide fragment, an Fn14 antigen, and/or an Fn14 epitope. An "epitope" may be part of a larger Fn14 antigen, which may be part of a larger Fn14 polypeptide fragment, which, in turn, may be part of a larger Fn14 polypeptide. Fn14 may exist in a native or denatured form. Fn14 polypeptides described herein may be isolated from a variety of sources, such as from human tissue types or from another source, or prepared by recombinant or synthetic methods. Orthologs to the Fn14 polypeptide are also well known in the art.

Table 13 in Example 1 lists exemplary human, cynomolgus macaque, rat and mouse Fn14 amino acid and nucleotide sequences. In some embodiments, the antibody provided herein binds a peptide of SEQ ID NO: 2 or a fragment thereof. In some embodiments, the antibody provided herein binds a peptide of SEQ ID NO: 4 or a fragment thereof. In other embodiments, the antibody provided herein binds a peptide of SEQ ID NO: 6 or a fragment thereof. In other embodiments, the antibody provided herein binds a peptide of SEQ ID NO: 8 or a fragment thereof. In yet other embodiments, the antibody provided herein binds a peptide of SEQ ID NO: 10 or a fragment thereof.

In some embodiments, the antibody or antigen binding fragment provided herein bind to amino acid residues 30-50 of human Fn14 having an amino acid sequence of SEQ ID NO: 2. In some embodiments, the antibody or antigen binding fragment provided herein bind to the subdomain 1 comprises an amino acid sequence of APGTAPCSRGSS-WSADLDKCM (SEQ ID NO: 182). In some embodiments, the antibody or antigen binding fragment provided herein interacts with one or more amino acid residues of human Fn14 protein selected from a group consisting of Gly32, Thr33, Ala34, Pro35, Trp42, Ala44, Asp45, Leu46, Asp47, Lys48, Cys49, or a combination thereof.

In some embodiments, the antibody or antigen binding fragment provided herein binds Fn14 with a $K_D$ of less than 1000 nM. In some embodiments, the antibody or antigen binding fragment provided herein binds Fn14 with a $K_D$ of less than 100 nM. In some embodiments, the antibody or antigen binding fragment provided herein binds Fn14 with a $K_D$ of less than 50 nM. In some embodiments, the antibody or antigen binding fragment provided herein binds Fn14 with a $K_D$ of less than 40 nM. In some embodiments, the antibody or antigen binding fragment provided herein binds Fn14 with a $K_D$ of less than 30 nM. In some embodiments, the antibody or antigen binding fragment provided herein binds Fn14 with a $K_D$ of less than 20 nM. In some embodiments, the antibody or antigen binding fragment provided herein binds Fn14 with a $K_D$ of less than 10 nM. In some embodiments, the antibody or antigen binding fragment provided herein binds Fn14 with a $K_D$ of less than 9 nM. In some embodiments, the antibody or antigen binding fragment provided herein binds Fn14 with a $K_D$ of less than 8 nM. In some embodiments, the antibody or antigen binding fragment provided herein binds Fn14 with a $K_D$ of less than 7 nM. In some embodiments, the antibody or antigen binding fragment provided herein binds Fn14 with a $K_D$ of less than 6 nM. In some embodiments, the antibody or antigen binding fragment provided herein binds Fn14 with a $K_D$ of less than 5 nM. In some embodiments, the antibody or antigen binding fragment provided herein binds Fn14 with a $K_D$ of less than 4 nM. In some embodiments, the antibody or antigen binding fragment provided herein binds Fn14 with a $K_D$ of less than 3 nM. In some embodiments, the antibody or antigen binding fragment provided herein binds Fn14 with a $K_D$ of less than 2 nM. In some embodiments, the antibody or antigen binding fragment provided herein binds Fn14 with a $K_D$ of less than 1 nM. In some embodiments, the antibody or antigen binding fragment provided herein binds Fn14 with a $K_D$ of less than 0.1 nM. In some embodiments, the antibody or antigen binding fragment provided herein binds Fn14 with a $K_D$ of less than 0.01 nM. The $K_D$ or $K_D$ value may also be measured by any known methods in the art, for example, using biolayer interferometry (BLI) or surface plasmon resonance (SPR) assays by Octet®, using, for example, an Octet®Red96 system, or by Biacore®, using, for example, a Biacore®™-2000 or a Biacore®™-3000. An "on-rate" or "rate of association" or "association rate" or "kon" may also be determined with the same biolayer interferometry (BLI) or surface plasmon resonance (SPR) techniques described above using, for example, the Octet®Red96, the Biacore®TM-2000, or the Biacore®TM-3000 system. In a specific embodiment, the $K_D$ is determined by a Biacore® assay. In some embodiments, Fn14 is a human Fn14. In some embodiments, Fn14 is a cynomolgus macaque Fn14. In some embodiments, Fn14 is a rat Fn14. In other embodiments, Fn14 is mouse Fn14.

In some embodiments, the antibody or antigen binding fragment provided herein binds human Fn14 with a $K_D$ of less than 100 nM as determined by a surface plasmon resonance method (e.g. a Biacore® assay), the antibody or antigen binding fragment binds cynomolgus macaque Fn14 with a $K_D$ of less than 100 nM as determined by a surface plasmon resonance method (e.g. a Biacore® assay), the antibody or antigen binding fragment binds rat Fn14 with a $K_D$ of less than 100 nM as determined by a surface plasmon resonance method (e.g. a Biacore® assay), and the antibody or antigen binding fragment binds mouse Fn14 with a $K_D$ of less than 100 nM as determined by a surface plasmon resonance method (e.g. a Biacore® assay).

In some embodiments, the antibody or antigen binding fragment provided herein binds human Fn14 with a $K_D$ of less than 90 nM as determined by a surface plasmon resonance method (e.g. a Biacore® assay), the antibody or antigen binding fragment binds cynomolgus macaque Fn14 with a $K_D$ of less than 90 nM as determined by a surface plasmon resonance method (e.g. a Biacore® assay), the antibody or antigen binding fragment binds rat Fn14 with a $K_D$ of less than 90 nM as determined by a surface plasmon resonance method (e.g. a Biacore® assay), and the antibody or antigen binding fragment binds mouse Fn14 with a $K_D$ of less than 90 nM as determined by a surface plasmon resonance method (e.g. a Biacore® assay).

In some embodiments, the antibody or antigen binding fragment provided herein binds human Fn14 with a $K_D$ of less than 80 nM as determined by a surface plasmon resonance method (e.g. a Biacore® assay), the antibody or antigen binding fragment binds cynomolgus macaque Fn14 with a $K_D$ of less than 80 nM as determined by a surface plasmon resonance method (e.g. a Biacore® assay), the antibody or antigen binding fragment binds rat Fn14 with a $K_D$ of less than 80 nM as determined by a surface plasmon resonance method (e.g. a Biacore® assay), and the antibody or antigen binding fragment binds mouse Fn14 with a $K_D$ of less than 80 nM as determined by a surface plasmon resonance method (e.g. a Biacore® assay).

In some embodiments, the antibody or antigen binding fragment provided herein binds human Fn14 with a $K_D$ of less than 70 nM as determined by a surface plasmon resonance method (e.g. a Biacore® assay), the antibody or antigen binding fragment binds cynomolgus macaque Fn14 with a $K_D$ of less than 70 nM as determined by a surface plasmon resonance method (e.g. a Biacore® assay), the antibody or antigen binding fragment binds rat Fn14 with a $K_D$ of less than 70 nM as determined by a surface plasmon resonance method (e.g. a Biacore® assay), and the antibody or antigen binding fragment binds mouse Fn14 with a $K_D$ of less than 70 nM as determined by a surface plasmon resonance method (e.g. a Biacore® assay).

In some embodiments, the antibody or antigen binding fragment provided herein binds human Fn14 with a $K_D$ of less than 60 nM as determined by a surface plasmon resonance method (e.g. a Biacore® assay), the antibody or antigen binding fragment binds cynomolgus macaque Fn14 with a $K_D$ of less than 60 nM as determined by a surface plasmon resonance method (e.g. a Biacore® assay), the antibody or antigen binding fragment binds rat Fn14 with a $K_D$ of less than 60 nM as determined by a surface plasmon resonance method (e.g. a Biacore® assay), and the antibody or antigen binding fragment binds mouse Fn14 with a $K_D$ of less than 60 nM as determined by a surface plasmon resonance method (e.g. a Biacore® assay).

In some embodiments, the antibody or antigen binding fragment provided herein binds human Fn14 with a $K_D$ of less than 50 nM as determined by a surface plasmon resonance method (e.g. a Biacore® assay), the antibody or antigen binding fragment binds cynomolgus macaque Fn14 with a $K_D$ of less than 50 nM as determined by a surface plasmon resonance method (e.g. a Biacore® assay), the antibody or antigen binding fragment binds rat Fn14 with a $K_D$ of less than 50 nM as determined by a surface plasmon resonance method (e.g. a Biacore® assay), and the antibody or antigen binding fragment binds mouse Fn14 with a $K_D$ of less than 50 nM as determined by a surface plasmon resonance method (e.g. a Biacore® assay).

In some embodiments, the antibody or antigen binding fragment provided herein binds human Fn14 with a $K_D$ of less than 40 nM as determined by a surface plasmon resonance method (e.g. a Biacore® assay), the antibody or antigen binding fragment binds cynomolgus macaque Fn14 with a $K_D$ of less than 40 nM as determined by a surface plasmon resonance method (e.g. a Biacore® assay), the antibody or antigen binding fragment binds rat Fn14 with a $K_D$ of less than 40 nM as determined by a surface plasmon resonance method (e.g. a Biacore® assay), and the antibody or antigen binding fragment binds mouse Fn14 with a $K_D$ of less than 40 nM as determined by a surface plasmon resonance method (e.g. a Biacore® assay).

In some embodiments, the antibody or antigen binding fragment provided herein binds human Fn14 with a $K_D$ of less than 30 nM as determined by a surface plasmon resonance method (e.g. a Biacore® assay), the antibody or antigen binding fragment binds cynomolgus macaque Fn14 with a $K_D$ of less than 30 nM as determined by a surface plasmon resonance method (e.g. a Biacore® assay), the antibody or antigen binding fragment binds rat Fn14 with a $K_D$ of less than 30 nM as determined by a surface plasmon resonance method (e.g. a Biacore® assay), and the antibody or antigen binding fragment binds mouse Fn14 with a $K_D$ of less than 30 nM as determined by a surface plasmon resonance method (e.g. a Biacore® assay).

In some embodiments, the antibody or antigen binding fragment provided herein binds human Fn14 with a $K_D$ of less than 20 nM as determined by a surface plasmon resonance method (e.g. a Biacore® assay), the antibody or antigen binding fragment binds cynomolgus macaque Fn14 with a $K_D$ of less than 20 nM as determined by a surface plasmon resonance method (e.g. a Biacore® assay), the antibody or antigen binding fragment binds rat Fn14 with a $K_D$ of less than 20 nM as determined by a surface plasmon resonance method (e.g. a Biacore® assay), and the antibody or antigen binding fragment binds mouse Fn14 with a $K_D$ of less than 20 nM as determined by a surface plasmon resonance method (e.g. a Biacore® assay).

In some embodiments, the antibody or antigen binding fragment provided herein binds human Fn14 with a $K_D$ of less than 10 nM as determined by a surface plasmon resonance method (e.g. a Biacore® assay), the antibody or antigen binding fragment binds cynomolgus macaque Fn14 with a $K_D$ of less than 10 nM as determined by a surface plasmon resonance method (e.g. a Biacore® assay), the antibody or antigen binding fragment binds rat Fn14 with a $K_D$ of less than 10 nM as determined by a surface plasmon resonance method (e.g. a Biacore® assay), and the antibody or antigen binding fragment binds mouse Fn14 with a $K_D$ of less than 10 nM as determined by a surface plasmon resonance method (e.g. a Biacore® assay).

In some embodiments, the antibody or antigen binding fragment provided herein binds human Fn14 with a $K_D$ of less than 9 nM as determined by a surface plasmon resonance method (e.g. a Biacore® assay), the antibody or antigen binding fragment binds cynomolgus macaque Fn14 with a $K_D$ of less than 9 nM as determined by a surface plasmon resonance method (e.g. a Biacore® assay), the antibody or antigen binding fragment binds rat Fn14 with a $K_D$ of less than 9 nM as determined by a surface plasmon resonance method (e.g. a Biacore® assay), and the antibody or antigen binding fragment binds mouse Fn14 with a $K_D$ of less than 9 nM as determined by a surface plasmon resonance method (e.g. a Biacore® assay).

In some embodiments, the antibody or antigen binding fragment provided herein binds human Fn14 with a $K_D$ of less than 8 nM as determined by a surface plasmon resonance method (e.g. a Biacore® assay), the antibody or antigen binding fragment binds cynomolgus macaque Fn14 with a $K_D$ of less than 8 nM as determined by a surface plasmon resonance method (e.g. a Biacore® assay), the antibody or antigen binding fragment binds rat Fn14 with a $K_D$ of less than 8 nM as determined by a surface plasmon resonance method (e.g. a Biacore® assay), and the antibody or antigen binding fragment binds mouse Fn14 with a $K_D$ of less than 8 nM as determined by a surface plasmon resonance method (e.g. a Biacore® assay).

In some embodiments, the antibody or antigen binding fragment provided herein binds human Fn14 with a $K_D$ of less than 7 nM as determined by a surface plasmon resonance method (e.g. a Biacore® assay), the antibody or antigen binding fragment binds cynomolgus macaque Fn14 with a $K_D$ of less than 7 nM as determined by a surface plasmon resonance method (e.g. a Biacore® assay), the antibody or antigen binding fragment binds rat Fn14 with a $K_D$ of less than 7 nM as determined by a surface plasmon resonance method (e.g. a Biacore® assay), and the antibody or antigen binding fragment binds mouse Fn14 with a $K_D$ of less than 7 nM as determined by a surface plasmon resonance method (e.g. a Biacore® assay).

In some embodiments, the antibody or antigen binding fragment provided herein binds human Fn14 with a $K_D$ of less than 6 nM as determined by a surface plasmon resonance method (e.g. a Biacore® assay), the antibody or antigen binding fragment binds cynomolgus macaque Fn14 with a $K_D$ of less than 6 nM as determined by a surface plasmon resonance method (e.g. a Biacore® assay), the antibody or antigen binding fragment binds rat Fn14 with a $K_D$ of less than 6 nM as determined by a surface plasmon resonance method (e.g. a Biacore® assay), and the antibody or antigen binding fragment binds mouse Fn14 with a $K_D$ of less than 6 nM as determined by a surface plasmon resonance method (e.g. a Biacore® assay).

In some embodiments, the antibody or antigen binding fragment provided herein binds human Fn14 with a $K_D$ of less than 5 nM as determined by a surface plasmon resonance method (e.g. a Biacore® assay), the antibody or antigen binding fragment binds cynomolgus macaque Fn14 with a $K_D$ of less than 5 nM as determined by a surface plasmon resonance method (e.g. a Biacore® assay), the antibody or antigen binding fragment binds rat Fn14 with a $K_D$ of less than 5 nM as determined by a surface plasmon resonance method (e.g. a Biacore® assay), and the antibody or antigen binding fragment binds mouse Fn14 with a $K_D$ of less than 5 nM as determined by a surface plasmon resonance method (e.g. a Biacore® assay).

In some embodiments, the antibody or antigen binding fragment provided herein binds human Fn14 with a $K_D$ of less than 4 nM as determined by a surface plasmon resonance method (e.g. a Biacore® assay), the antibody or antigen binding fragment binds cynomolgus macaque Fn14 with a $K_D$ of less than 4 nM as determined by a surface plasmon resonance method (e.g. a Biacore® assay), the antibody or antigen binding fragment binds rat Fn14 with a $K_D$ of less than 4 nM as determined by a surface plasmon resonance method (e.g. a Biacore® assay), and the antibody or antigen binding fragment binds mouse Fn14 with a $K_D$ of less than 4 nM as determined by a surface plasmon resonance method (e.g. a Biacore® assay).

In some embodiments, the antibody or antigen binding fragment provided herein binds human Fn14 with a $K_D$ of less than 3 nM as determined by a surface plasmon resonance method (e.g. a Biacore® assay), the antibody or antigen binding fragment binds cynomolgus macaque Fn14 with a $K_D$ of less than 3 nM as determined by a surface plasmon resonance method (e.g. a Biacore® assay), the antibody or antigen binding fragment binds rat Fn14 with a $K_D$ of less than 3 nM as determined by a surface plasmon resonance method (e.g. a Biacore® assay), and the antibody or antigen binding fragment binds mouse Fn14 with a $K_D$ of less than 3 nM as determined by a surface plasmon resonance method (e.g. a Biacore® assay).

In some embodiments, the antibody or antigen binding fragment provided herein binds human Fn14 with a $K_D$ of less than 2 nM as determined by a surface plasmon resonance method (e.g. a Biacore® assay), the antibody or antigen binding fragment binds cynomolgus macaque Fn14 with a $K_D$ of less than 2 nM as determined by a surface plasmon resonance method (e.g. a Biacore® assay), the antibody or antigen binding fragment binds rat Fn14 with a $K_D$ of less than 2 nM as determined by a surface plasmon resonance method (e.g. a Biacore® assay), and the antibody or antigen binding fragment binds mouse Fn14 with a $K_D$ of less than 2 nM as determined by a surface plasmon resonance method (e.g. a Biacore® assay).

In some embodiments, the antibody or antigen binding fragment provided herein binds human Fn14 with a $K_D$ of less than 1 nM as determined by a surface plasmon resonance method (e.g. a Biacore® assay), the antibody or antigen binding fragment binds cynomolgus macaque Fn14 with a $K_D$ of less than 1 nM as determined by a surface plasmon resonance method (e.g. a Biacore® assay), the antibody or antigen binding fragment binds rat Fn14 with a $K_D$ of less than 1 nM as determined by a surface plasmon resonance method (e.g. a Biacore® assay), and the antibody or antigen binding fragment binds mouse Fn14 with a $K_D$ of less than 1 nM as determined by a surface plasmon resonance method (e.g. a Biacore® assay).

In some embodiments, the antibody or antigen binding fragment provided herein binds human Fn14 with a $K_D$ of less than 0.5 nM as determined by a surface plasmon resonance method (e.g. a Biacore® assay), the antibody or antigen binding fragment binds cynomolgus macaque Fn14 with a $K_D$ of less than 0.5 nM as determined by a surface plasmon resonance method (e.g. a Biacore® assay), the antibody or antigen binding fragment binds rat Fn14 with a $K_D$ of less than 0.5 nM as determined by a surface plasmon resonance method (e.g. a Biacore® assay), and the antibody or antigen binding fragment binds mouse Fn14 with a $K_D$ of less than 0.5 nM as determined by a surface plasmon resonance method (e.g. a Biacore® assay).

In some embodiments, the antibody or antigen binding fragment provided herein binds human Fn14 with a $K_D$ of less than 0.1 nM as determined by a surface plasmon resonance method (e.g. a Biacore® assay), the antibody or antigen binding fragment binds cynomolgus macaque Fn14 with a $K_D$ of less than 0.1 nM as determined by a surface plasmon resonance method (e.g. a Biacore® assay), the antibody or antigen binding fragment binds rat Fn14 with a $K_D$ of less than 0.1 nM as determined by a surface plasmon resonance method (e.g. a Biacore® assay), and the antibody or antigen binding fragment binds mouse Fn14 with a $K_D$ of less than 0.1 nM as determined by a surface plasmon resonance method (e.g. a Biacore® assay).

In some embodiments, the antibody or antigen binding fragment provided herein binds human Fn14 with a $K_D$ of less than 0.01 nM as determined by a surface plasmon resonance method (e.g. a Biacore® assay), the antibody or antigen binding fragment binds cynomolgus macaque Fn14 with a $K_D$ of less than 0.01 nM as determined by a surface plasmon resonance method (e.g. a Biacore® assay), the antibody or antigen binding fragment binds rat Fn14 with a $K_D$ of less than 0.01 nM as determined by a surface plasmon resonance method (e.g. a Biacore® assay), and the antibody or antigen binding fragment binds mouse Fn14 with a $K_D$ of less than 0.01 nM as determined by a surface plasmon resonance method (e.g. a Biacore® assay).

In some embodiments, the antibody or antigen binding fragment provided herein binds human Fn14 with a $K_D$ of 1 nM to 0.001 nM as determined by a surface plasmon resonance method (e.g. a Biacore® assay), the antibody or antigen binding fragment binds cynomolgus macaque Fn14 with a $K_D$ of 1 nM to 0.001 nM as determined by a surface plasmon resonance method (e.g. a Biacore® assay), the antibody or antigen binding fragment binds rat Fn14 with a $K_D$ of 1 nM to 0.001 nM as determined by a surface plasmon resonance method (e.g. a Biacore® assay), and the antibody or antigen binding fragment binds mouse Fn14 with a $K_D$ of 1 nM to 0.001 nM as determined by a surface plasmon resonance method (e.g. a Biacore® assay).

In one aspect, provided herein are antibodies that specifically bind to Fn14 and can modulate Fn14 activity and/or expression (e.g., inhibit Fn14 mediated signaling). In certain embodiments, an Fn14 antagonist is provided herein that is an antibody described herein that specifically binds to Fn14 and inhibits (including partially inhibits) at least one Fn14 activity. In some embodiments, the antibodies provided herein inhibit (including partially inhibit or reduce) the binding of Fn14 to its ligand.

An Fn14 activity can relate to any activity of Fn14 such as those known or described in the art. In certain embodiments, Fn14 activity and Fn14 signaling (or Fn14 mediated signaling) are used interchangeably herein. In certain aspects, Fn14 activity is induced by TWEAK (e.g., through Fn14 binding to TWEAK). In certain embodiments, provided herein are antibodies that specifically bind to Fn14 and inhibit (or reduce) chemokine and/or cytokine production. In some embodiments, the antibodies provided herein do not inhibit the binding of Fn14 to TWEAK, but nevertheless inhibit or reduce the Fn14 mediated or TWEAK mediated signaling.

In certain embodiments, the antibody described herein attenuates (e.g., partially attenuates) an Fn14 activity. In some embodiments, the antibody provided herein attenuates an Fn14 activity by at least about 10%. In some embodiments, the antibody provided herein attenuates an Fn14 activity by at least about 20%. In some embodiments, the antibody provided herein attenuates an Fn14 activity by at least about 30%. In some embodiments, the antibody provided herein attenuates an Fn14 activity by at least about 40%. In some embodiments, the antibody provided herein attenuates an Fn14 activity by at least about 50%. In some embodiments, the antibody provided herein attenuates an Fn14 activity by at least about 60%. In some embodiments, the antibody provided herein attenuates an Fn14 activity by at least about 70%. In some embodiments, the antibody provided herein attenuates an Fn14 activity by at least about 80%. In some embodiments, the antibody provided herein attenuates an Fn14 activity by at least about 90%. In some embodiments, the antibody provided herein attenuates an Fn14 activity by at least about 95%. In certain embodiments, the antibody described herein can attenuate (e.g., partially attenuate) an Fn14 activity by at least about 15% to about 65%. In certain embodiments, the antibody described herein can attenuate (e.g., partially attenuate) an Fn14 activity by at least about 20% to about 65%. In certain embodiments, the antibody described herein can attenuate (e.g., partially attenuate) an Fn14 activity by at least about 30% to about 65%.

In specific embodiments, the attenuation of an Fn14 activity is assessed by methods described herein. In specific embodiments, the attenuation of an Fn14 activity is assessed by methods known to one of skill in the art. In certain embodiments, the attenuation of an Fn14 activity is relative to the Fn14 activity in the presence of stimulation without any anti-Fn14 antibody. In certain embodiments, the attenuation of an Fn14 activity is relative to the Fn14 activity in the presence of stimulation with an unrelated antibody (e.g., an antibody that does not specifically bind to Fn14).

A non-limiting example of an Fn14 activity is Fn14 mediated signaling. Thus, in certain embodiments, the antibody described herein attenuates (e.g., partially attenuates) Fn14 mediated signaling. In some embodiments, the antibody provided herein attenuates Fn14 mediated signaling by at least about 10%. In some embodiments, the antibody provided herein attenuates Fn14 mediated signaling by at least about 20%. In some embodiments, the antibody provided herein attenuates Fn14 mediated signaling by at least about 30%. In some embodiments, the antibody provided herein attenuates Fn14 mediated signaling by at least about 40%. In some embodiments, the antibody provided herein attenuates Fn14 mediated signaling by at least about 50%. In some embodiments, the antibody provided herein attenuates Fn14 mediated signaling by at least about 60%. In some embodiments, the antibody provided herein attenuates Fn14 mediated signaling by at least about 70%. In some embodiments, the antibody provided herein attenuates Fn14 mediated signaling by at least about 80%. In some embodiments, the antibody provided herein attenuates Fn14 mediated signaling by at least about 90%. In some embodiments, the antibody provided herein attenuates Fn14 mediated signaling by at least about 95%. In certain embodiments, the antibody described herein can attenuate (e.g., partially attenuate) Fn14 mediated signaling by at least about 15% to about 65%. In certain embodiments, the antibody described herein can attenuate (e.g., partially attenuate) Fn14 mediated signaling by at least about 20% to about 65%. In certain embodiments, the antibody described herein can attenuate (e.g., partially attenuate) Fn14 mediated signaling by at least about 30% to about 65%.

Another non-limiting example of an Fn14 activity is binding to TWEAK. Thus, in certain embodiments, the antibody described herein attenuates (e.g., partially attenuates) the binding of Fn14 to TWEAK. In some embodiments, the antibody provided herein attenuates the binding of Fn14 to TWEAK by at least about 10%. In some embodiments, the antibody provided herein attenuates the binding of Fn14 to TWEAK by at least about 20%. In some embodiments, the antibody provided herein attenuates the binding of Fn14 to TWEAK by at least about 30%. In some embodiments, the antibody provided herein attenuates the binding of Fn14 to TWEAK by at least about 40%. In some embodiments, the antibody provided herein attenuates the binding of Fn14 to TWEAK by at least about 50%. In some embodiments, the antibody provided herein attenuates the binding of Fn14 to TWEAK by at least about 60%. In some embodiments, the antibody provided herein attenuates the binding of Fn14 to TWEAK by at least about 70%. In some embodiments, the antibody provided herein attenuates the binding of Fn14 to TWEAK by at least about 80%. In some embodiments, the antibody provided herein attenuates the binding of Fn14 to TWEAK by at least about 90%. In some embodiments, the antibody provided herein attenuates the binding of Fn14 to TWEAK by at least about 95%. In certain embodiments, the antibody described herein can attenuate (e.g., partially attenuate) the binding of Fn14 to TWEAK by at least about 15% to about 65%. In certain embodiments, the antibody described herein can attenuate (e.g., partially attenuate) the binding of Fn14 to TWEAK by at least about 20% to about 65%. In certain embodiments, the antibody described herein can attenuate (e.g., partially attenuate) the binding of Fn14 to TWEAK by at least about 30% to about 65%.

Another non-limiting example of an Fn14 activity is signaling mediated by TWEAK. Thus, in certain embodiments, the antibody described herein attenuates (e.g., partially attenuates) TWEAK mediated signaling. In some embodiments, the antibody provided herein attenuates TWEAK mediated signaling by at least about 10%. In some embodiments, the antibody provided herein attenuates TWEAK mediated signaling by at least about 20%. In some embodiments, the antibody provided herein attenuates TWEAK mediated signaling by at least about 30%. In some embodiments, the antibody provided herein attenuates TWEAK mediated signaling by at least about 40%. In some embodiments, the antibody provided herein attenuates TWEAK mediated signaling by at least about 50%. In some embodiments, the antibody provided herein attenuates TWEAK mediated signaling by at least about 60%. In some embodiments, the antibody provided herein attenuates TWEAK mediated signaling by at least about 70%. In some embodiments, the antibody provided herein attenuates TWEAK mediated signaling by at least about 80%. In some embodiments, the antibody provided herein attenuates TWEAK mediated signaling by at least about 90%. In some embodiments, the antibody provided herein attenuates TWEAK mediated signaling by at least about 95%. In certain embodiments, the antibody described herein can attenuate (e.g., partially attenuate) TWEAK mediated signaling by at least about 15% to about 65%. In certain embodiments, the antibody described herein can attenuate (e.g., partially attenuate) TWEAK mediated signaling by at least about 20% to about 65%. In certain embodiments, the antibody described herein can attenuate (e.g., partially attenuate) TWEAK mediated signaling by at least about 30% to about 65%.

In specific embodiments, antibodies provided herein specifically bind to Fn14 and inhibit the secretion of one or more cytokines and/or chemokines induced by TWEAK. In some embodiments, the one or more cytokines and/or chemokines are selected from a group consisting of IL-8, CCL2, IL-1β, TGFβ, CCL21, TNFα, IL-6, CXCL1, CCL3, CCL4, CXCL12, CCLS, CXCL10, and CXCL16.

For example, in one embodiment, an antibody provided herein specifically binds to Fn14 and inhibits IL-8 secretion by at least about 5%. In one embodiment, an antibody provided herein specifically binds to Fn14 and inhibits IL-8 secretion by at least about 10%. In one embodiment, an antibody provided herein specifically binds to Fn14 and inhibits IL-8 secretion by at least about 15%. In one embodiment, an antibody provided herein specifically binds to Fn14 and inhibits IL-8 secretion by at least about 20%. In one embodiment, an antibody provided herein specifically binds to Fn14 and inhibits IL-8 secretion by at least about 25%. In one embodiment, an antibody provided herein specifically binds to Fn14 and inhibits IL-8 secretion by at least about 30%. In one embodiment, an antibody provided herein specifically binds to Fn14 and inhibits IL-8 secretion by at least about 35%. In one embodiment, an antibody provided herein specifically binds to Fn14 and inhibits IL-8 secretion by at least about 40%. In one embodiment, an antibody provided herein specifically binds to Fn14 and inhibits IL-8 secretion by at least about 45%. In one embodiment, an antibody provided herein specifically binds to Fn14 and inhibits IL-8 secretion by at least about 50%. In one embodiment, an antibody provided herein specifically binds to Fn14 and inhibits IL-8 secretion by at least about 55%. In one embodiment, an antibody provided herein specifically binds to Fn14 and inhibits IL-8 secretion by at least about 60%. In one embodiment, an antibody provided herein specifically binds to Fn14 and inhibits IL-8 secretion by at least about 65%. In one embodiment, an antibody provided herein specifically binds to Fn14 and inhibits IL-8 secretion by at least about 70%. In one embodiment, an antibody provided herein specifically binds to Fn14 and inhibits IL-8 secretion by at least about 75%. In one embodiment, an antibody provided herein specifically binds to Fn14 and inhibits IL-8 secretion by at least about 80%. In one embodiment, an antibody provided herein specifically binds to Fn14 and inhibits IL-8 secretion by at least about 85%. In one embodiment, an antibody provided herein specifically binds to Fn14 and inhibits IL-8 secretion by at least about 90%. In one embodiment, an antibody provided herein specifically binds to Fn14 and inhibits IL-8 secretion by at least about 95%. In one embodiment, an antibody provided herein specifically binds to Fn14 and inhibits IL-8 secretion by at least about 96%. In one embodiment, an antibody provided herein specifically binds to Fn14 and inhibits IL-8 secretion by at least about 97%. In one embodiment, an antibody provided herein specifically binds to Fn14 and inhibits IL-8 secretion by at least about 98%. In one embodiment, an antibody provided herein specifically binds to Fn14 and inhibits IL-8 secretion by at least about 99%. In some embodiments, the inhibition of IL-8 secretion is assessed by methods described herein. In other embodiments, the inhibition of IL-8 secretion is assessed by methods known to one of skill in the art. In a specific embodiment, the IL-8 secretion is inhibited relative to IL-8 secretion in the absence of anti-Fn14 antibody. In other embodiments, the IL-8 secretion is inhibited relative to IL-8 secretion in the presence of an unrelated antibody (e.g., an antibody that does not specifically bind to Fn14).

In one embodiment, an antibody provided herein specifically binds to Fn14 and inhibits CCL2 expression by at least about 5%. In one embodiment, an antibody provided herein specifically binds to Fn14 and inhibits CCL2 expression by at least about 10%. In one embodiment, an antibody provided herein specifically binds to Fn14 and inhibits CCL2 expression by at least about 15%. In one embodiment, an antibody provided herein specifically binds to Fn14 and inhibits CCL2 expression by at least about 20%. In one embodiment, an antibody provided herein specifically binds to Fn14 and inhibits CCL2 expression by at least about 25%. In one embodiment, an antibody provided herein specifically binds to Fn14 and inhibits CCL2 expression by at least about 30%. In one embodiment, an antibody provided herein specifically binds to Fn14 and inhibits CCL2 expression by at least about 35%. In one embodiment, an antibody provided herein specifically binds to Fn14 and inhibits CCL2 expression by at least about 40%. In one embodiment, an antibody provided herein specifically binds to Fn14 and inhibits CCL2 expression by at least about 45%. In one embodiment, an antibody provided herein specifically binds to Fn14 and inhibits CCL2 expression by at least about 50%. In one embodiment, an antibody provided herein specifically binds to Fn14 and inhibits CCL2 expression by at least about 55%. In one embodiment, an antibody provided herein specifically binds to Fn14 and inhibits CCL2 expression by at least about 60%. In one embodiment, an antibody provided herein specifically binds to Fn14 and inhibits CCL2 expression by at least about 65%. In one embodiment, an antibody provided herein specifically binds to Fn14 and inhibits CCL2 expression by at least about 70%. In one embodiment, an antibody provided herein specifically binds to Fn14 and inhibits CCL2 expression by at least about 75%. In one embodiment, an antibody provided herein specifically binds to Fn14 and inhibits CCL2 expression by at least about 80%. In one embodiment, an antibody provided herein specifically binds to Fn14 and inhibits CCL2 expression by at least about 85%. In one embodiment, an antibody provided herein specifically binds to Fn14 and inhibits CCL2 expression by at least about 90%. In one embodiment, an antibody provided herein specifically binds to Fn14 and inhibits CCL2 expression by at least about 95%. In one embodiment, an antibody provided herein specifically binds to Fn14 and inhibits CCL2 expression by at least about 96%. In one embodiment, an antibody provided herein specifically binds to Fn14 and inhibits CCL2 expression by at least about 97%. In one embodiment, an antibody provided herein specifically binds to Fn14 and inhibits CCL2 expression by at least about 98%. In one embodiment, an antibody provided herein specifically binds to Fn14 and inhibits CCL2 expression by at least about 99%. In some embodiments, the inhibition of CCL2 expression is assessed by methods described herein. In other embodiments, the inhibition of CCL2 expression is assessed by methods known to one of skill in the art. In a specific embodiment, the CCL2 expression is inhibited relative to CCL2 expression in the absence of anti-Fn14 antibody. In other embodiments, the CCL2 expression is inhibited relative to CCL2 expression in the presence of an unrelated antibody (e.g., an antibody that does not specifically bind to Fn14).

In one embodiment, an antibody provided herein specifically binds to Fn14 and inhibits TWEAK induced ICAM-1 expression. In some embodiments, an antibody provided herein specifically binds to Fn14 and inhibits ICAM-1 expression by at least about 5%. In one embodiment, an antibody provided herein specifically binds to Fn14 and inhibits ICAM-1 expression by at least about 10%. In one embodiment, an antibody provided herein specifically binds to Fn14 and inhibits ICAM-1 expression by at least about 15%. In one embodiment, an antibody provided herein specifically binds to Fn14 and inhibits ICAM-1 expression by at least about 20%. In one embodiment, an antibody provided herein specifically binds to Fn14 and inhibits ICAM-1 expression by at least about 25%. In one embodiment, an antibody provided herein specifically binds to Fn14 and inhibits ICAM-1 expression by at least about 30%. In one embodiment, an antibody provided herein specifically binds to Fn14 and inhibits ICAM-1 expression by at least about 35%. In one embodiment, an antibody provided herein specifically binds to Fn14 and inhibits ICAM-1 expression by at least about 40%. In one embodiment, an antibody provided herein specifically binds to Fn14 and inhibits ICAM-1 expression by at least about 45%. In one embodiment, an antibody provided herein specifically binds to Fn14 and inhibits ICAM-1 expression by at least about 50%. In one embodiment, an antibody provided herein specifically binds to Fn14 and inhibits ICAM-1 expression by at least about 55%. In one embodiment, an antibody provided herein specifically binds to Fn14 and inhibits ICAM-1 expression by at least about 60%. In one embodiment, an antibody provided herein specifically binds to Fn14 and inhibits ICAM-1 expression by at least about 65%. In one embodiment, an antibody provided herein specifically binds to Fn14 and inhibits ICAM-1 expression by at least about 70%. In one embodiment, an antibody provided herein specifically binds to Fn14 and inhibits ICAM-1 expression by at least about 75%. In one embodiment, an antibody provided herein specifically binds to Fn14 and inhibits ICAM-1 expression by at least about 80%. In one embodiment, an antibody provided herein specifically binds to Fn14 and inhibits ICAM-1 expression by at least about 85%. In one embodiment, an antibody provided herein specifically binds to Fn14 and inhibits ICAM-1 expression by at least about 90%. In one embodiment, an antibody provided herein specifically binds to Fn14 and inhibits ICAM-1 expression by at least about 95%. In one embodiment, an antibody provided herein specifically binds to Fn14 and inhibits ICAM-1 expression by at least about 96%. In one embodiment, an antibody provided herein specifically binds to Fn14 and inhibits ICAM-1 expression by at least about 97%. In one embodiment, an antibody provided herein specifically binds to Fn14 and inhibits ICAM-1 expression by at least about 98%. In one embodiment, an antibody provided herein specifically binds to Fn14 and inhibits ICAM-1 expression by at least about 99%. In some embodiments, the inhibition of ICAM-1 expression is assessed by methods described herein. In other embodiments, the inhibition of ICAM-1 expression is assessed by methods known to one of skill in the art. In a specific embodiment, the ICAM-1 expression is inhibited relative to ICAM-1 expression in the absence of anti-Fn14 antibody. In other embodiments, the ICAM-1 expression is inhibited relative to ICAM-1 expression in the presence of an unrelated antibody (e.g., an antibody that does not specifically bind to Fn14).

Antibodies provided herein are not agonists of Fn14. In some embodiments, the antibody or antigen binding fragment provided herein does not stimulate an Fn14 activity. In some embodiments, the antibody or antigen binding fragment provided herein does not stimulate Fn14 mediated signaling. In some embodiments, the antibody or antigen binding fragment provided herein does not stimulate TWEAK mediated signaling.

In some embodiments, the antibody or antigen binding fragment thereof provided herein comprises one or more CDRs from the antibodies descrbied in Section 6 below including antibodies KO41c, KO42d, R35B9, and variants thereof.

In some embodiments, the antibody or antigen binding fragment thereof provided herein is antibody KO42d or variants thereof. In some embodiments, the antibody or antigen binding fragment thereof provided herein comprises CDR H1 comprising an amino acid sequence of SEQ ID NO: 113, CDR H2 comprising an amino acid sequence of SEQ ID NO: 114, CDR H3 comprising an amino acid sequence of SEQ ID NO: 115, CDR L1 comprising an amino acid sequence of SEQ ID NO: 116, CDR L2 comprising an amino acid sequence of SEQ ID NO: 117, CDR L3 comprising an amino acid sequence of SEQ ID NO: 118. In some embodiments, the antibody or antigen binding fragment thereof provided herein comprises a VH comprising an amino acid sequence of SEQ ID NO: 44 and a VL comprising an amino acid sequence of SEQ ID NO: 48.

In other embodiments, the antibody or antigen binding fragment thereof provided herein is KO41c, R35B9 or a variant thereof.

In some embodiments, the antibody or antigen binding fragment thereof provided herein comprises:
    (a) a heavy chain variable region (VH) comprising (i) VH complementarity determining region 1 (CDR H1) comprising an amino acid sequence of GYX$_1$FX$_2$DYNMH (SEQ ID NO: 184), wherein X$_1$ is T, I or R, and X$_2$ is T or Q; (ii) VH complementarity determining region 2 (CDR H2) comprising an amino acid sequence of X$_3$INPX$_4$NX$_5$X$_6$TNYNX$_9$KFXioG (SEQ ID NO: 257), wherein X$_3$ is Y or S, X$_4$ is N or R, X$_5$ is A or G, X$_6$ is G or W, X$_9$ is Q or D, and X$_{10}$ is K, G, H, or D; (iii) VH complementarity determining region 3 (CDR H3) comprising an amino acid sequence of SGWFTY (SEQ ID NO: 121);
(b) a light chain variable region (VL) comprising (i) VL complementarity determining region 1 (CDR L1) comprising an amino acid sequence of KSSQSLLN-SAGKTYLN (SEQ ID NO: 127); (ii) VL complementarity determining region 2 (CDR L2) comprising an amino acid sequence of LVXiiXi2LDXi3 (SEQ ID NO: 258), wherein X$_{11}$ is S or A, X$_{12}$ is Q or E, and X$_{13}$ is S or D; (iii) VL complementarity determining region 3 (CDR L3) comprising an amino acid sequence of WQGTX$_7$X$_8$PWT (SEQ ID NO: 186), wherein X$_7$ is H or F, and X$_8$ is F or Y.

In some embodiments, the antibody or antigen binding fragment thereof provided herein comprises:
(a) a heavy chain variable region (VH) comprising (i) VH complementarity determining region 1 (CDR H1) comprising an amino acid sequence of GYX$_1$FX$_2$DYNMH (SEQ ID NO: 184), wherein X$_1$ is T, I or R, and X$_2$ is T or Q; (ii) VH complementarity determining region 2 (CDR H2) comprising an amino acid sequence of X$_3$INPX$_4$NX$_5$X$_6$TNYNQKFKG (SEQ ID NO: 185), wherein X$_3$ is Y or S, X$_4$ is N or R; X$_5$ is A or G, and X$_6$ is G or W; (iii) VH complementarity determining region 3 (CDR H3) comprising an amino acid sequence of SGWFTY (SEQ ID NO: 121);
(b) a light chain variable region (VL) comprising (i) VL complementarity determining region 1 (CDR L1) comprising an amino acid sequence of KSSQSLLN-SAGKTYLN (SEQ ID NO: 127); (ii) VL complementarity determining region 2 (CDR L2) comprising an amino acid sequence of LVSQLDS (SEQ ID NO: 128); (iii) VL complementarity determining region 3 (CDR L3) comprising an amino acid sequence of WQGTX$_7$X$_8$PWT (SEQ ID NO: 186), wherein X$_7$ is H or F, and X$_8$ is F or Y.

In some embodiments, X$_1$ is T or I.

In some embodiments, the antibody provided herein comprises one or more CDRs listed in Table 26 below.

TABLE 26

CDRs of exemplary antibodies

| | CDR1 | CDR2 | CDR3 |
|---|---|---|---|
| VH | SEQ ID NO: 119<br>SEQ ID NO: 122 | SEQ ID NO: 120<br>SEQ ID NO: 123<br>SEQ ID NO: 124<br>SEQ ID NO: 125<br>SEQ ID NO: 126<br>SEQ ID NO: 149<br>SEQ ID NO: 247<br>SEQ ID NO: 248<br>SEQ ID NO: 249<br>SEQ ID NO: 250 | SEQ ID NO: 121 |
| VL | SEQ ID NO: 127 | SEQ ID NO: 128<br>SEQ ID NO: 254<br>SEQ ID NO: 255<br>SEQ ID NO: 256 | SEQ ID NO: 129<br>SEQ ID NO: 130<br>SEQ ID NO: 131 |

In some embodiments, the antibody or antigen binding fragment thereof comprises:
(a) a heavy chain variable region (VH) comprising (i) VH complementarity determining region 1 (CDR H1) comprising an amino acid sequence selected from a group consisting of SEQ ID NO: 119 and SEQ ID NO: 122; (ii)VH complementarity determining region 2 (CDR H2) comprising an amino acid sequence selected from a group consisting of SEQ ID NO: 120, SEQ ID NO: 123, SEQ ID NO: 124, SEQ ID NO: 125, SEQ ID NO: 126, SEQ ID NO: 149; SEQ ID NO: 247, SEQ ID NO: 248, SEQ ID NO: 249, and SEQ ID NO: 250; and (iii) VH complementarity determining region 3 (CDR H3) comprising an amino acid sequence of SEQ ID NO: 121, and
(b) a light chain variable region (VL) comprising (i) VL complementarity determining region 1 (CDR L1) comprising an amino acid sequence of SEQ ID NO: 127; (ii) VL complementarity determining region 2 (CDR L2) comprising an amino acid sequence selected from a group consisting of SEQ ID NO: 128, SEQ ID NO: 254, SEQ ID NO: 255, and SEQ ID NO: 256; and (iii) VL complementarity determining region 3 (CDR L3) comprising an amino acid sequence selected from a group consisting of SEQ ID NO: 129, SEQ ID NO: 130, and SEQ ID NO: 131.

In some embodiments, the antibody or antigen binding fragment thereof provided herein comprises:
(a) a heavy chain variable region (VH) comprising (i) VH complementarity determining region 1 (CDR H1) comprising an amino acid sequence selected from a group consisting of SEQ ID NO: 119 and SEQ ID NO: 122; (ii) VH complementarity determining region 2 (CDR H2) comprising an amino acid sequence selected from a group consisting of SEQ ID NO: 120, SEQ ID NO: 123, SEQ ID NO: 124, SEQ ID NO: 125, SEQ ID NO: 126, and SEQ ID NO: 149; and (iii) VH complementarity determining region 3 (CDR H3) comprising an amino acid sequence of SEQ ID NO: 121, and
(b) a light chain variable region (VL) comprising (i) VL complementarity determining region 1 (CDR L1) comprising an amino acid sequence of SEQ ID NO: 127; (ii) VL complementarity determining region 2 (CDR L2) comprising an amino acid sequence of SEQ ID NO: 128; and (iii) VL complementarity determining region 3 (CDR L3) comprising an amino acid sequence selected from a group consisting of SEQ ID NO: 129, SEQ ID NO: 130, and SEQ ID NO: 131.

In some embodiments, the antibody comprises a CDR H1 comprising an amino acid sequence selected from a group consisting of SEQ ID NO: 119 and SEQ ID NO: 122. In some embodiments, the antibody comprises a CDR H1 comprising an amino acid sequence of SEQ ID NO: 119. In some embodiments, the antibody comprises a CDR H1 comprising an amino acid sequence of SEQ ID NO: 122.

In some embodiments, the antibody comprises a CDR H2 comprising an amino acid sequence selected from a group consisting of SEQ ID NO: 120, SEQ ID NO: 123, SEQ ID NO: 124, SEQ ID NO: 125, SEQ ID NO: 126, SEQ ID NO: 149, SEQ ID NO: 247, SEQ ID NO: 248, SEQ ID NO: 249 and SEQ ID NO: 250. In some embodiments, the antibody comprises a CDR H2 comprising an amino acid sequence of SEQ ID NO: 120. In some embodiments, the antibody comprises a CDR H2 comprising an amino acid sequence of SEQ ID NO: 123. In some embodiments, the antibody comprises a CDR H2 comprising an amino acid sequence of SEQ ID NO: 124. In some embodiments, the antibody comprises a CDR H2 comprising an amino acid sequence of SEQ ID NO: 125. In some embodiments, the antibody comprises a CDR H2 comprising an amino acid of SEQ ID NO: 126. In some embodiments, the antibody comprises a CDR H2 comprising an amino acid sequence of SEQ ID NO: 149. In some embodiments, the antibody comprises a CDR H2 comprising an amino acid sequence of SEQ ID NO: 247. In some embodiments, the antibody comprises a CDR H2 comprising an amino acid sequence of SEQ ID NO: 248. In some embodiments, the antibody comprises a CDR H2 comprising an amino acid sequence of SEQ ID NO: 249. In some embodiments, the antibody comprises a CDR H2 comprising an amino acid sequence of SEQ ID NO: 250.

In some embodiments, the antibody comprises a CDR H3 comprising an amino acid sequence of SEQ ID NO: 121.

In some embodiments, the antibody comprises a CDR L1 comprising an amino acid sequence of SEQ ID NO: 127.

In some embodiments, the antibody comprises a CDR L2 comprising an amino acid sequence selected from a group consisting of SEQ ID NO: 128, SEQ ID NO: 254, SEQ ID NO: 255, and SEQ ID NO: 256. In some embodiments, the antibody comprises a CDR L2 comprising an amino acid sequence of SEQ ID NO: 128. In some embodiments, the antibody comprises a CDR L2 comprising an amino acid sequence of SEQ ID NO: 254. In some embodiments, the antibody comprises a CDR L2 comprising an amino acid sequence of SEQ ID NO: 255. In some embodiments, the antibody comprises a CDR L2 comprising an amino acid sequence of SEQ ID NO: 256.

In some embodiments, the antibody comprises a CDR L3 comprising an amino acid sequence selected from a group consisting of SEQ ID NO: 129, SEQ ID NO: 130 and SEQ ID NO: 131. In some embodiments, the antibody comprises a CDR L3 comprising an amino acid sequence of SEQ ID NO: 129. In some embodiments, the antibody comprises a CDR L3 comprising an amino acid sequence of SEQ ID NO: 130. In some embodiments, the antibody comprises a CDR L3 comprising an amino acid sequence of SEQ ID NO: 131.

In some embodiments, the antibody comprises a CDR H1 comprising an amino acid sequence selected from a group consisting of SEQ ID NO: 119 and SEQ ID NO: 122 and a CDR H2 comprising an amino acid sequence selected from a group consisting of SEQ ID NO: 120, SEQ ID NO: 123, SEQ ID NO: 124, SEQ ID NO: 125, SEQ ID NO: 126, SEQ ID NO: 149, SEQ ID NO: 247, SEQ ID NO: 248, SEQ ID NO: 249 and SEQ ID NO: 250.

In some embodiments, the antibody comprises a CDR H1 comprising an amino acid sequence of SEQ ID NO: 119 and a CDR H2 comprising an amino acid sequence of SEQ ID NO: 120. In some embodiments, the antibody comprises a CDR H1 comprising an amino acid sequence of SEQ ID NO: 119 and a CDR H2 comprising an amino acid sequence of SEQ ID NO: 123. In some embodiments, the antibody comprises a CDR H1 comprising an amino acid sequence of SEQ ID NO: 119 and a CDR H2 comprising an amino acid sequence of SEQ ID NO: 124. In some embodiments, the antibody comprises a CDR H1 comprising an amino acid sequence of SEQ ID NO: 119 and a CDR H2 comprising an amino acid sequence of SEQ ID NO: 125. In some embodiments, the antibody comprises a CDR H1 comprising an amino acid sequence of SEQ ID NO: 119 and a CDR H2 comprising an amino acid sequence of SEQ ID NO: 126. In some embodiments, the antibody comprises a CDR H1 comprising an amino acid sequence of SEQ ID NO: 119 and a CDR H2 comprising an amino acid sequence of SEQ ID NO: 149. In some embodiments, the antibody comprises a CDR H1 comprising an amino acid sequence of SEQ ID NO: 119 and a CDR H2 comprising an amino acid sequence of SEQ ID NO: 247. In some embodiments, the antibody comprises a CDR H1 comprising an amino acid sequence of SEQ ID NO: 119 and a CDR H2 comprising an amino acid sequence of SEQ ID NO: 248. In some embodiments, the antibody comprises a CDR H1 comprising an amino acid sequence of SEQ ID NO: 119 and a CDR H2 comprising an amino acid sequence of SEQ ID NO: 249. In some embodiments, the antibody comprises a CDR H1 comprising an amino acid sequence of SEQ ID NO: 119 and a CDR H2 comprising an amino acid sequence of SEQ ID NO: 250.

In some embodiments, the antibody comprises a CDR H1 comprising an amino acid sequence of SEQ ID NO: 122 and a CDR H2 comprising an amino acid sequence of SEQ ID NO: 120. In some embodiments, the antibody comprises a CDR H1 comprising an amino acid sequence of SEQ ID NO: 122 and a CDR H2 comprising an amino acid sequence of SEQ ID NO: 123. In some embodiments, the antibody comprises a CDR H1 comprising an amino acid sequence of SEQ ID NO: 122 and a CDR H2 comprising an amino acid sequence of SEQ ID NO: 124. In some embodiments, the antibody comprises a CDR H1 comprising an amino acid sequence of SEQ ID NO: 122 and a CDR H2 comprising an amino acid sequence of SEQ ID NO: 125. In some embodiments, the antibody comprises a CDR H1 comprising an amino acid sequence of SEQ ID NO: 122 and a CDR H2 comprising an amino acid sequence of SEQ ID NO: 126. In some embodiments, the antibody comprises a CDR H1 comprising an amino acid sequence of SEQ ID NO: 122 and a CDR H2 comprising an amino acid sequence of SEQ ID NO: 149. In some embodiments, the antibody comprises a CDR H1 comprising an amino acid sequence of SEQ ID NO: 122 and a CDR H2 comprising an amino acid sequence of SEQ ID NO: 247. In some embodiments, the antibody comprises a CDR H1 comprising an amino acid sequence of SEQ ID NO: 122 and a CDR H2 comprising an amino acid sequence of SEQ ID NO: 248. In some embodiments, the antibody comprises a CDR H1 comprising an amino acid sequence of SEQ ID NO: 122 and a CDR H2 comprising an amino acid sequence of SEQ ID NO: 249. In some embodiments, the antibody comprises a CDR H1 comprising an amino acid sequence of SEQ ID NO: 122 and a CDR H2 comprising an amino acid sequence of SEQ ID NO: 250.

In some embodiments, the antibody comprises a CDR H1 comprising an amino acid sequence selected from a group consisting of SEQ ID NO: 119 and SEQ ID NO: 122 and a CDR H3 comprising an amino acid of SEQ ID NO: 121.

In some embodiments, the antibody comprises a CDR H1 comprising an amino acid sequence of SEQ ID NO: 119 and a CDR H3 comprising an amino acid sequence of SEQ ID NO: 121.

In some embodiments, the antibody comprises a CDR H1 comprising an amino acid sequence of SEQ ID NO: 122 and a CDR H3 comprising an amino acid sequence of SEQ ID NO: 121.

In some embodiments, the antibody comprises a CDR H2 comprising an amino acid sequence selected from a group consisting of SEQ ID NO: 123, SEQ ID NO: 124, and SEQ ID NO: 126, SEQ ID NO: 247, SEQ ID NO: 248, SEQ ID NO: 249 and SEQ ID NO: 250 and a CDR H3 comprising an amino acid sequence of SEQ ID NO: 121. In some embodiments, the antibody comprises a CDR H2 comprising an amino acid sequence of SEQ ID NO: 123 and a CDR H3 comprising an amino acid sequence of SEQ ID NO: 121. In some embodiments, the antibody comprises a CDR H2 comprising an amino acid sequence of SEQ ID NO: 124 and a CDR H3 comprising an amino acid sequence of SEQ ID NO: 121. In some embodiments, the antibody comprises a CDR H2 comprising an amino acid sequence of SEQ ID NO: 126 and a CDR H3 comprising an amino acid sequence of SEQ ID NO: 121. In some embodiments, the antibody comprises a CDR H2 comprising an amino acid sequence of SEQ ID NO: 247 and a CDR H3 comprising an amino acid sequence of SEQ ID NO: 121. In some embodiments, the antibody comprises a CDR H2 comprising an amino acid sequence of SEQ ID NO: 248 and a CDR H3 comprising an amino acid sequence of SEQ ID NO: 121. In some embodiments, the antibody comprises a CDR H2 comprising an amino acid sequence of SEQ ID NO: 249 and a CDR H3 comprising an amino acid sequence of SEQ ID NO: 121. In some embodiments, the antibody comprises a CDR H2 comprising an amino acid sequence of SEQ ID NO: 250 and a CDR H3 comprising an amino acid sequence of SEQ ID NO: 121.

In some embodiments, the antibody comprises a CDR L1 comprising an amino acid sequence of SEQ ID NO: 127 and a CDR L2 comprising an amino acid sequence of SEQ ID NO: 128, SEQ ID NO: 254, SEQ ID NO: 255 or SEQ ID NO: 256. In some embodiments, the antibody comprises a CDR L1 comprising an amino acid sequence of SEQ ID NO: 127 and a CDR L2 comprising an amino acid sequence of SEQ ID NO: 128. In some embodiments, the antibody comprises a CDR L1 comprising an amino acid sequence of SEQ ID NO: 127 and a CDR L2 comprising an amino acid sequence of SEQ ID NO: 254. In some embodiments, the antibody comprises a CDR L1 comprising an amino acid sequence of SEQ ID NO: 127 and a CDR L2 comprising an amino acid sequence of SEQ ID NO: 255. In some embodiments, the antibody comprises a CDR L1 comprising an amino acid sequence of SEQ ID NO: 127 and a CDR L2 comprising an amino acid sequence of SEQ ID NO: 256.

In some embodiments, the antibody comprise a CDR L1 comprising an amino acid sequence of SEQ ID NO: 127 and a CDR L3 comprising an amino acid sequence selected from a group consisting of SEQ ID NO: 129, SEQ ID NO: 130 and SEQ ID NO: 131. In some embodiments, the antibody comprises a CDR L1 comprising an amino acid sequence of SEQ ID NO: 127 and a CDR L3 comprising an amino acid sequence of SEQ ID NO: 129. In some embodiments, the antibody comprises a CDR L1 comprising an amino acid sequence of SEQ ID NO: 127 and a CDR L3 comprising an amino acid sequence of SEQ ID NO: 130. In some embodiments, the antibody comprises a CDR L1 comprising an amino acid sequence of SEQ ID NO: 127 and a CDR L3 comprising an amino acid sequence of SEQ ID NO: 131.

In some embodiments, the antibody comprise a CDR L2 comprising an amino acid sequence of SEQ ID NO: 128, SEQ ID NO: 254, SEQ ID NO: 255, or SEQ ID NO: 256 and a CDR L3 comprising an amino acid sequence selected from a group consisting of SEQ ID NO: 129, SEQ ID NO: 130 and SEQ ID NO: 131. In some embodiments, the antibody comprises a CDR L2 comprising an amino acid sequence of SEQ ID NO: 128 and a CDR L3 comprising an amino acid sequence of SEQ ID NO: 129. In some embodiments, the antibody comprises a CDR L2 comprising an amino acid sequence of SEQ ID NO: 128 and a CDR L3 comprising an amino acid sequence of SEQ ID NO: 130. In some embodiments, the antibody comprises a CDR L2 comprising an amino acid sequence of SEQ ID NO: 128 and a CDR L3 comprising an amino acid sequence of SEQ ID NO: 131. In some embodiments, the antibody comprises a CDR L2 comprising an amino acid sequence of SEQ ID NO: 254 and a CDR L3 comprising an amino acid sequence of SEQ ID NO: 129. In some embodiments, the antibody comprises a CDR L2 comprising an amino acid sequence of SEQ ID NO: 254 and a CDR L3 comprising an amino acid sequence of SEQ ID NO: 130. In some embodiments, the antibody comprises a CDR L2 comprising an amino acid sequence of SEQ ID NO: 254 and a CDR L3 comprising an amino acid sequence of SEQ ID NO: 131. In some embodiments, the antibody comprises a CDR L2 comprising an amino acid sequence of SEQ ID NO: 255 and a CDR L3 comprising an amino acid sequence of SEQ ID NO: 129. In some embodiments, the antibody comprises a CDR L2 comprising an amino acid sequence of SEQ ID NO: 255 and a CDR L3 comprising an amino acid sequence of SEQ ID NO: 130. In some embodiments, the antibody comprises a CDR L2 comprising an amino acid sequence of SEQ ID NO: 255 and a CDR L3 comprising an amino acid sequence of SEQ ID NO: 131. In some embodiments, the antibody comprises a CDR L2 comprising an amino acid sequence of SEQ ID NO: 256 and a CDR L3 comprising an amino acid sequence of SEQ ID NO: 129. In some embodiments, the antibody comprises a CDR L2 comprising an amino acid sequence of SEQ ID NO: 256 and a CDR L3 comprising an amino acid sequence of SEQ ID NO: 130. In some embodiments, the antibody comprises a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence selected from a group consisting of SEQ ID NO: 119 and SEQ ID NO: 122; a CDR H2 comprising an amino acid sequence selected from a group consisting of SEQ ID NO: 120, SEQ ID NO: 123, SEQ ID NO: 124, SEQ ID NO: 125, SEQ ID NO: 126, SEQ ID NO: 149, SEQ ID NO: 247, SEQ ID NO: 248, SEQ ID NO: 249 and SEQ ID NO: 250; and a CDR H3 comprising an amino acid sequence of SEQ ID NO: 121.

In some embodiments, the antibody comprises a CDR H1 comprising an amino acid sequence of SEQ ID NO: 119, a CDR H2 comprising an amino acid sequence of SEQ ID NO: 247 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 248 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 249 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 250 and a CDR H3 comprising an amino acid sequence of SEQ ID NO: 121.

In some embodiments, the antibody comprises a CDR H1 comprising an amino acid sequence of SEQ ID NO: 122, a CDR H2 comprising an amino acid sequence of SEQ ID NO: 247 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 248 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 249 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 250 and a CDR H3 comprising an amino acid sequence of SEQ ID NO: 121.

In some embodiments, the antibody comprises a CDR H1 comprising an amino acid sequence of SEQ ID NO: 119, a CDR H2 comprising an amino acid sequence of SEQ ID NO: 120 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 123 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 124 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 125 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 126 and a CDR H3 comprising an amino acid sequence of SEQ ID NO: 121. In some embodiments, the antibody comprises a CDR H1 comprising an amino acid sequence of SEQ ID NO: 119, a CDR H2 comprising an amino acid sequence of SEQ ID NO: 149 and a CDR H3 comprising an amino acid sequence of SEQ ID NO: 121.

In some embodiments, the antibody comprises a CDR H1 comprising an amino acid sequence of SEQ ID NO: 122, a CDR H2 comprising an amino acid sequence of SEQ ID NO: 120 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 123 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 124 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 125 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 126 and a CDR H3 comprising an amino acid sequence of SEQ ID NO: 121. In some embodiments, the antibody comprises a CDR H1 comprising an amino acid sequence of SEQ ID NO: 122, a CDR H2 comprising an amino acid sequence of SEQ ID NO: 149 and a CDR H3 comprising an amino acid sequence of SEQ ID NO: 121.

In some embodiments, the antibody comprises a CDR L1 comprising an amino acid sequence of SEQ ID NO: 127; a CDR L2 comprising an amino acid sequence of SEQ ID NO: 128, SEQ ID NO: 254, SEQ ID NO: 255 or SEQ ID NO: 256; and a CDR L3 comprising an amino acid sequence selected from the group consisting of SEQ ID NO: 129, SEQ ID NO: 130, and SEQ ID NO: 131.

In some embodiments, the antibody comprises a CDR L1 comprising an amino acid sequence of SEQ ID NO: 127, a CDR L2 comprising an amino acid sequence of SEQ ID NO: 254, and a CDR L3 comprising an amino acid sequence of 129. In some embodiments, the antibody comprises a CDR L1 comprising an amino acid sequence of SEQ ID NO: 127, a CDR L2 comprising an amino acid sequence of SEQ ID NO: 254, and a CDR L3 comprising an amino acid sequence of 130. In some embodiments, the antibody comprises a CDR L1 comprising an amino acid sequence of SEQ ID NO: 127, a CDR L2 comprising an amino acid sequence of SEQ ID NO: 254, and a CDR L3 comprising an amino acid sequence of 131.

In some embodiments, the antibody comprises a CDR L1 comprising an amino acid sequence of SEQ ID NO: 127, a CDR L2 comprising an amino acid sequence of SEQ ID NO: 255, and a CDR L3 comprising an amino acid sequence of 129. In some embodiments, the antibody comprises a CDR L1 comprising an amino acid sequence of SEQ ID NO: 127, a CDR L2 comprising an amino acid sequence of SEQ ID NO: 255, and a CDR L3 comprising an amino acid sequence of 130. In some embodiments, the antibody comprises a CDR L1 comprising an amino acid sequence of SEQ ID NO: 127, a CDR L2 comprising an amino acid sequence of SEQ ID NO: 255, and a CDR L3 comprising an amino acid sequence of 131.

In some embodiments, the antibody comprises a CDR L1 comprising an amino acid sequence of SEQ ID NO: 127, a CDR L2 comprising an amino acid sequence of SEQ ID NO: 256, and a CDR L3 comprising an amino acid sequence of 129. In some embodiments, the antibody comprises a CDR L1 comprising an amino acid sequence of SEQ ID NO: 127, a CDR L2 comprising an amino acid sequence of SEQ ID NO: 256, and a CDR L3 comprising an amino acid sequence of 130. In some embodiments, the antibody comprises a CDR L1 comprising an amino acid sequence of SEQ ID NO: 127, a CDR L2 comprising an amino acid sequence of SEQ ID NO: 256, and a CDR L3 comprising an amino acid sequence of 131.

In some embodiments, the antibody comprises a CDR L1 comprising an amino acid sequence of SEQ ID NO: 127, a CDR L2 comprising an amino acid sequence of SEQ ID NO: 128, and a CDR L3 comprising an amino acid sequence of 129. In some embodiments, the antibody comprises a CDR L1 comprising an amino acid sequence of SEQ ID NO: 127, a CDR L2 comprising an amino acid sequence of SEQ ID NO: 128, and a CDR L3 comprising an amino acid sequence of 130. In some embodiments, the antibody comprises a CDR L1 comprising an amino acid sequence of SEQ ID NO: 127, a CDR L2 comprising an amino acid sequence of SEQ ID NO: 128, and a CDR L3 comprising an amino acid sequence of 131.

In some embodiments, the antibody comprises a CDR H1 comprising an amino acid sequence selected from a group consisting of SEQ ID NO: 119 and SEQ ID NO: 122; a CDR H2 comprising an amino acid sequence selected from a group consisting of SEQ ID NO: 120, SEQ ID NO: 123, SEQ ID NO: 124, SEQ ID NO: 125, SEQ ID NO: 126, SEQ ID NO: 149, SEQ ID NO: 247, SEQ ID NO: 248, SEQ ID NO: 249 and SEQ ID NO: 250; a CDR H3 comprising an amino acid sequence of SEQ ID NO: 121; a CDR L1 comprising an amino acid sequence of SEQ ID NO: 127; a CDR L2 comprising an amino acid sequence selected from a group consisting of SEQ ID NO: 128, SEQ ID NO: 254, SEQ ID NO: 255 and SEQ ID NO: 256; and a CDR L3 comprising an amino acid sequence selected from the group consisting of SEQ ID NO: 129, SEQ ID NO: 130, and SEQ ID NO: 131.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 119, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 120, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 123, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 124, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 125, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 126, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 149, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 247, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 248, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 249, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 128 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 254 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 255 and a CDR L3 comprising an amino acid sequence of SEQ ID NO: 131.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 129.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 130.

In some embodiments, the antibody comprises a CDR H1 comprising an amino acid sequence of SEQ ID NO: 122, a CDR H2 comprising an amino acid sequence of SEQ ID NO: 250, a CDR H3 comprising an amino acid sequence of SEQ ID NO: 121, a CDR L1 comprising an amino acid sequence of SEQ ID NO: 127, a CDR L2 comprising an amino acid sequence of SEQ ID NO: 256 and a CDR L3 comprising an amino acid sequence of SEQ ID NO: 131.

In some embodiments, the antibody or antigen binding fragment thereof provided herein comprise CDRs having amino acid sequences of the CDRs contained in VH and VL sequences in Table 6, Table 28, Table 29, Table 31, Table 5 and Table 17 below.

In some embodiments, the antibody comprises a VH comprising CDRs having amino acid sequences of the CDRs contained in the VH comprising an amino acid sequence of SEQ ID NO: 35 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 35 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 35 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 35 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 50 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 50 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 50 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 50 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 54 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 54 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 54 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 54 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 56 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 56 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 56 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 56 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 60 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 60 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 60 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 60 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 181 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 181 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 181 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 181 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 190 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 190 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 190 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 190 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 192 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 192 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 192 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 192 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 194 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 194 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 194 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 194 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 196 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 196 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 196 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 196 and a VL comprising CDRs having amino acid sequences of the CDRs contained in the VL comprising an amino acid sequence of SEQ ID NO: 200.

In some embodiments, the antibody comprises a VH comprising CDRs having amino acid sequences of the CDRs contained in the VH comprising an amino acid sequence of SEQ ID NO: 198 and a VL comprising CDRs having amino acid sequences of the CDRs contained in the VL comprising an amino acid sequence of SEQ ID NO: 40.

In some embodiments, the antibody comprises a VH comprising CDRs having amino acid sequences of the CDRs contained in the VH comprising an amino acid sequence of SEQ ID NO: 198 and a VL comprising CDRs having amino acid sequences of the CDRs contained in the VL comprising an amino acid sequence of SEQ ID NO: 52.

In some embodiments, the antibody comprises a VH comprising CDRs having amino acid sequences of the CDRs contained in the VH comprising an amino acid sequence of SEQ ID NO: 198 and a VL comprising CDRs having amino acid sequences of the CDRs contained in the VL comprising an amino acid sequence of SEQ ID NO: 58.

In some embodiments, the antibody comprises a VH comprising CDRs having amino acid sequences of the CDRs contained in the VH comprising an amino acid sequence of SEQ ID NO: 198 and a VL comprising CDRs having amino acid sequences of the CDRs contained in the VL comprising an amino acid sequence of SEQ ID NO: 200.

The residues from each of these CDR regions are noted in the Sequence Listing provided herein. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering. In certain embodiments, the CDRs in an antibody can be determined according to a combination of various numbering systems, for example, Kabat in combination with Chothia. In certain embodiments, one or more CDRs in an antibody are determined according to Kabat numbering and other CDRs in the antibody are determined according Chothia numbering.

In certain embodiments, the antibody or antigen binding fragment thereof provided herein further comprises one or more FR regions from antibodies provided herein.

TABLE 27

Exemplary mouse frameworks

| | FR1 | FR2 | FR3 | FR4 |
|---|---|---|---|---|
| VH | SEQ ID NO: 132 | SEQ ID NO: 138 | SEQ ID NO: 145 | SEQ ID NO: 158 |
| VL | SEQ ID NO: 160 | SEQ ID NO: 163 | SEQ ID NO: 169 | SEQ ID NO: 171 |

In some embodiments, the antibody provided herein comprises one or more mouse framework regions in Table 27 above.

In some embodiments, the antibody comprises FR H1 comprising an amino acid sequence of SEQ ID NO: 132. In some embodiments, the antibody comprises FR H2 comprising an amino acid sequence of SEQ ID NO: 138. In some embodiments, the antibody comprises FR H3 comprising an amino acid sequence of SEQ ID NO: 145. In some embodiments, the antibody comprises FR H4 comprising an amino acid sequence of SEQ ID NO: 158.

In some embodiments, the antibody comprises FR L1 comprising an amino acid sequence of SEQ ID NO: 160. In some embodiments, the antibody comprises FR L2 comprising an amino acid sequence of SEQ ID NO: 163. In some embodiments, the antibody comprises FR L3 comprising an amino acid sequence of SEQ ID NO: 169. In some embodiments, the antibody comprises FR L4 comprising an amino acid sequence of SEQ ID NO: 171.

In some embodiments, the antibody provided herein comprises a VH comprising FR H1 comprising an amino acid sequence of SEQ ID NO: 132, FR H2 comprising an amino acid sequence of SEQ ID NO: 138, FR H3 comprising an amino acid sequence of SEQ ID NO: 145, and FR H4 comprising an amino acid sequence of SEQ ID NO: 158.

In some embodiments, the antibody provided herein comprises a VL comprising FR L1 comprising an amino acid sequence of SEQ ID NO: 160, FR L2 comprising an amino acid sequence of SEQ ID NO: 163, FR L3 comprising an amino acid sequence of SEQ ID NO: 169, and FR L4 comprising an amino acid sequence of SEQ ID NO: 171.

In some embodiments, the antibody or antigen binding fragment thereof provided herein comprise FRs having amino acid sequences of the FRs contained in VH and VL sequences in Table 28, Table 29, and Table 30 below.

In some embodiments, the antibody comprises a VH comprising FRs having amino acid sequences of the FRs contained in the VH comprising an amino acid sequence of SEQ ID NO: 35 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 35 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 35 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 35 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 50 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 50 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 50 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 50 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 54 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 54 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 54 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 54 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 56 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 56 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 56 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 56 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 60 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 60 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 60 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 60 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 181 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 181 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 181 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 181 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 190 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 190 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 190 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 190 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 192 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 192 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 192 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 192 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 194 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 194 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 194 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 194 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 196 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 196 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 196 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 196 and a VL comprising FRs having amino acid sequences of the FRs contained in the VL comprising an amino acid sequence of SEQ ID NO: 200.

In some embodiments, the antibody comprises a VH comprising FRs having amino acid sequences of the FRs contained in the VH comprising an amino acid sequence of SEQ ID NO: 198 and a VL comprising FRs having amino acid sequences of the FRs contained in the VL comprising an amino acid sequence of SEQ ID NO: 40.

In some embodiments, the antibody comprises a VH comprising FRs having amino acid sequences of the FRs contained in the VH comprising an amino acid sequence of SEQ ID NO: 198 and a VL comprising FRs having amino acid sequences of the FRs contained in the VL comprising an amino acid sequence of SEQ ID NO: 52.

In some embodiments, the antibody comprises a VH comprising FRs having amino acid sequences of the FRs contained in the VH comprising an amino acid sequence of SEQ ID NO: 198 and a VL comprising FRs having amino acid sequences of the FRs contained in the VL comprising an amino acid sequence of SEQ ID NO: 58.

In some embodiments, the antibody comprises a VH comprising FRs having amino acid sequences of the FRs contained in the VH comprising an amino acid sequence of SEQ ID NO: 198 and a VL comprising FRs having amino acid sequences of the FRs contained in the VL comprising an amino acid sequence of SEQ ID NO: 200.

In certain embodiments, the antibody or antigen binding fragment thereof provided herein further comprises one or more FR regions from the humanized antibodies provided herein. FR regions from the humanized antibodies provided herein are described in more detail in Section 5.2.5 below.

Framework regions described herein are determined based upon the boundaries of the CDR numbering system.

In other words, if the CDRs are determined by, e.g., Kabat, IMGT, or Chothia, or any combination thereof, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, and/or the Chothia numbering system, FR2 is defined as the amino acid residues between CDR1 and CDR2 amino acid residues as defined by, e.g., the Kabat numbering system, the IMGT numbering system, and/or the Chothia numbering system, FR3 is defined as the amino acid residues between CDR2 and CDR3 amino acid residues as defined by, e.g., the Kabat numbering system, the IMGT numbering system, and/or the Chothia numbering system, and FR4 is defined as the amino acid residues C-terminal to the CDR3 amino acid residues as defined by, e.g., the Kabat numbering system, the IMGT numbering system, and/or the Chothia numbering system.

In certain embodiments, the antibody or antigen binding fragments provided herein comprises VH and/VL regions of the antibodies provided herein including those described in Section 6 below.

In some embodiments, the antibody or antigen binding fragments provided herein comprises one or more VH sequences listed in Table 28 below.

TABLE 28

VH amino acid sequences of exemplary mouse antibodies

| Heavy Vector ID | VH Name | Variable sequence |
| --- | --- | --- |
| A291 | 41c-VH | SEQ ID NO: 35 |
| A402 | R35B9-VH | SEQ ID NO: 50 |
| A448 | R35B9(Y50G57)-VH | SEQ ID NO: 54 |
| A490 | R35B9(Y50A56G57)-VH | SEQ ID NO: 56 |
| A486 | R35B9(A56)-VH | SEQ ID NO: 60 |
| A437 | R35B9(Y50)-VH | SEQ ID NO: 181 |
| A428 | R35B9(G57)-VH | SEQ ID NO: 190 |
| A435 | R35B9(T28)-VH | SEQ ID NO: 192 |
| A436 | R35B9(T30)-VH | SEQ ID NO: 194 |
| A438 | R35B9(N54)-VH | SEQ ID NO: 196 |
| A450 | 41C(R28Q30R54)-VH | SEQ ID NO: 198 |

In some embodiments, the VH is 41c-VH comprising an amino acid sequence of SEQ ID NO: 35. In some embodiments, the VH is R35B9-VH comprising an amino acid sequence of SEQ ID NO: 50. In some embodiments, the VH is R35B9(Y50G57)-VH comprising an amino acid sequence of SEQ ID NO: 54. In some embodiments, the VH is R35B9(Y50A56G57)-VH comprising an amino acid sequence of SEQ ID NO: 56. In some embodiments, the VH is R35B9(A56)-VH comprising an amino acid sequence of SEQ ID NO: 60. In some embodiments, the VH is R35B9(Y50)-VH comprising an amino acid sequence of SEQ ID NO: 181. In some embodiments, the VH is R35B9(G57)-VH comprising an amino acid sequence of SEQ ID NO: 190. In some embodiments, the VH is R35B9(T28)-VH comprising an amino acid sequence of SEQ ID NO: 192. In some embodiments, the VH is R35B9(T30)-VH comprising an amino acid sequence of SEQ ID NO: 194. In some embodiments, the VH is R35B9(N54)-VH comprising an amino acid sequence of SEQ ID NO: 196. In some embodiments, the VH is 41C(R28Q30R54)-VH comprising an amino acid sequence of SEQ ID NO: 198.

In some embodiments, the antibodies provided herein comprise one or more VL sequences listed in Table 29 below.

TABLE 29

VL amino acid sequences of exemplary mouse antibodies

| Light Vector ID | VL Name | Variable sequence |
| --- | --- | --- |
| A290 | 41c-VL | SEQ ID NO: 40 |
| A403 | R35B9-VL | SEQ ID NO: 52 |
| A439 | R35B9(H98)-VL | SEQ ID NO: 58 |
| A440 | R35B9(F99)-VL | SEQ ID NO: 200 |

In some embodiments, the VL is 41c-VL comprising an amino acid sequence of SEQ ID NO: 40. In some embodiments, the VL is R35B9-VL comprising an amino acid sequence of SEQ ID NO: 52. In some embodiments, the VL is R35B9(H98)-VL comprising an amino acid sequence of SEQ ID NO: 58. In some embodiments, the VL is R35B9(F99)-VL comprising an amino acid sequence of SEQ ID NO: 200.

In yet other embodiments, the antibody provided herein comprises a VH and/or a VL from Table 30 below.

TABLE 30

Amino acid sequences of exemplary mouse antibodies

| Antibody Name | VH | VL |
| --- | --- | --- |
| A291/A290 | SEQ ID NO: 35 | SEQ ID NO: 40 |
| A291/A403 | SEQ ID NO: 35 | SEQ ID NO: 52 |
| A291/A439 | SEQ ID NO: 35 | SEQ ID NO: 58 |
| A291/A440 | SEQ ID NO: 35 | SEQ ID NO: 200 |
| A402/A290 | SEQ ID NO: 50 | SEQ ID NO: 40 |
| A402/A403 | SEQ ID NO: 50 | SEQ ID NO: 52 |
| A402/A439 | SEQ ID NO: 50 | SEQ ID NO: 58 |
| A402/A440 | SEQ ID NO: 50 | SEQ ID NO: 200 |
| A448/A290 | SEQ ID NO: 54 | SEQ ID NO: 40 |
| A448/A403 | SEQ ID NO: 54 | SEQ ID NO: 52 |
| A448/A439 | SEQ ID NO: 54 | SEQ ID NO: 58 |
| A448/A440 | SEQ ID NO: 54 | SEQ ID NO: 200 |
| A490/A290 | SEQ ID NO: 56 | SEQ ID NO: 40 |
| A490/A403 | SEQ ID NO: 56 | SEQ ID NO: 52 |
| A490/A439 | SEQ ID NO: 56 | SEQ ID NO: 58 |
| A490/A440 | SEQ ID NO: 56 | SEQ ID NO: 200 |
| A486/A290 | SEQ ID NO: 60 | SEQ ID NO: 40 |
| A486/A403 | SEQ ID NO: 60 | SEQ ID NO: 52 |
| A486/A439 | SEQ ID NO: 60 | SEQ ID NO: 58 |
| A486/A440 | SEQ ID NO: 60 | SEQ ID NO: 200 |
| A437/A290 | SEQ ID NO: 181 | SEQ ID NO: 40 |
| A437/A403 | SEQ ID NO: 181 | SEQ ID NO: 52 |
| A437/A439 | SEQ ID NO: 181 | SEQ ID NO: 58 |
| A437/A440 | SEQ ID NO: 181 | SEQ ID NO: 200 |
| A428/A290 | SEQ ID NO: 190 | SEQ ID NO: 40 |
| A428/A403 | SEQ ID NO: 190 | SEQ ID NO: 52 |
| A428/A439 | SEQ ID NO: 190 | SEQ ID NO: 58 |
| A428/A440 | SEQ ID NO: 190 | SEQ ID NO: 200 |
| A435/A290 | SEQ ID NO: 192 | SEQ ID NO: 40 |
| A435/A403 | SEQ ID NO: 192 | SEQ ID NO: 52 |
| A435/A439 | SEQ ID NO: 192 | SEQ ID NO: 58 |
| A435/A440 | SEQ ID NO: 192 | SEQ ID NO: 200 |
| A436/A290 | SEQ ID NO: 194 | SEQ ID NO: 40 |
| A436/A403 | SEQ ID NO: 194 | SEQ ID NO: 52 |
| A436/A439 | SEQ ID NO: 194 | SEQ ID NO: 58 |
| A436/A440 | SEQ ID NO: 194 | SEQ ID NO: 200 |
| A438/A290 | SEQ ID NO: 196 | SEQ ID NO: 40 |
| A438/A403 | SEQ ID NO: 196 | SEQ ID NO: 52 |
| A438/A439 | SEQ ID NO: 196 | SEQ ID NO: 58 |
| A438/A440 | SEQ ID NO: 196 | SEQ ID NO: 200 |
| A450/A290 | SEQ ID NO: 198 | SEQ ID NO: 40 |
| A450/A403 | SEQ ID NO: 198 | SEQ ID NO: 52 |
| A450/A439 | SEQ ID NO: 198 | SEQ ID NO: 58 |
| A450/A440 | SEQ ID NO: 198 | SEQ ID NO: 200 |

In some embodiments, the antibody is A291/A290 comprising a VH comprising an amino acid sequence of SEQ ID NO: 35 and a VL comprising an amino acid sequence of SEQ ID NO: 40.

In some embodiments, the antibody is A291/A403 comprising a VH comprising an amino acid sequence of SEQ ID NO: 35 and a VL comprising an amino acid sequence of SEQ ID NO: 52.

In some embodiments, the antibody is A291/A439 comprising a VH comprising an amino acid sequence of SEQ ID NO: 35 and a VL comprising an amino acid sequence of SEQ ID NO: 58.

In some embodiments, the antibody is A291/A440 comprising a VH comprising an amino acid sequence of SEQ ID NO: 35 and a VL comprising an amino acid sequence of SEQ ID NO: 200.

In some embodiments, the antibody is A402/A290 comprising a VH comprising an amino acid sequence of SEQ ID NO: 50 and a VL comprising an amino acid sequence of SEQ ID NO: 40.

In some embodiments, the antibody is A402/A403 comprising a VH comprising an amino acid sequence of SEQ ID NO: 50 and a VL comprising an amino acid sequence of SEQ ID NO: 52.

In some embodiments, the antibody is A402/A439 comprising a VH comprising an amino acid sequence of SEQ ID NO: 50 and a VL comprising an amino acid sequence of SEQ ID NO: 58.

In some embodiments, the antibody is A402/A440 comprising a VH comprising an amino acid sequence of SEQ ID NO: 50 and a VL comprising an amino acid sequence of SEQ ID NO: 200.

In some embodiments, the antibody is A448/A290 comprising a VH comprising an amino acid sequence of SEQ ID NO: 54 and a VL comprising an amino acid sequence of SEQ ID NO: 40.

In some embodiments, the antibody is A448/A403 comprising a VH comprising an amino acid sequence of SEQ ID NO: 54 and a VL comprising an amino acid sequence of SEQ ID NO: 52.

In some embodiments, the antibody is A448/A439 comprising a VH comprising an amino acid sequence of SEQ ID NO: 54 and a VL comprising an amino acid sequence of SEQ ID NO: 58.

In some embodiments, the antibody is A448/A440 comprising a VH comprising an amino acid sequence of SEQ ID NO: 54 and a VL comprising an amino acid sequence of SEQ ID NO: 200.

In some embodiments, the antibody is A490/A290 comprising a VH comprising an amino acid sequence of SEQ ID NO: 56 and a VL comprising an amino acid sequence of SEQ ID NO: 40.

In some embodiments, the antibody is A490/A403 comprising a VH comprising an amino acid sequence of SEQ ID NO: 56 and a VL comprising an amino acid sequence of SEQ ID NO: 52.

In some embodiments, the antibody is A490/A439 comprising a VH comprising an amino acid sequence of SEQ ID NO: 56 and a VL comprising an amino acid sequence of SEQ ID NO: 58.

In some embodiments, the antibody is A490/A440 comprising a VH comprising an amino acid sequence of SEQ ID NO: 56 and a VL comprising an amino acid sequence of SEQ ID NO: 200.

In some embodiments, the antibody is A486/A290 comprising a VH comprising an amino acid sequence of SEQ ID NO: 60 and a VL comprising an amino acid sequence of SEQ ID NO: 40.

In some embodiments, the antibody is A486/A403 comprising a VH comprising an amino acid sequence of SEQ ID NO: 60 and a VL comprising an amino acid sequence of SEQ ID NO: 52.

In some embodiments, the antibody is A486/A439 comprising a VH comprising an amino acid sequence of SEQ ID NO: 60 and a VL comprising an amino acid sequence of SEQ ID NO: 58.

In some embodiments, the antibody is A486/A440 comprising a VH comprising an amino acid sequence of SEQ ID NO: 60 and a VL comprising an amino acid sequence of SEQ ID NO: 200.

In some embodiments, the antibody is A437/A290 comprising a VH comprising an amino acid sequence of SEQ ID NO: 181 and a VL comprising an amino acid sequence of SEQ ID NO: 40.

In some embodiments, the antibody is A437/A403 comprising a VH comprising an amino acid sequence of SEQ ID NO: 181 and a VL comprising an amino acid sequence of SEQ ID NO: 52.

In some embodiments, the antibody is A437/A439 comprising a VH comprising an amino acid sequence of SEQ ID NO: 181 and a VL comprising an amino acid sequence of SEQ ID NO: 58.

In some embodiments, the antibody is A437/A440 comprising a VH comprising an amino acid sequence of SEQ ID NO: 181 and a VL comprising an amino acid sequence of SEQ ID NO: 200.

In some embodiments, the antibody is A428/A290 comprising a VH comprising an amino acid sequence of SEQ ID NO: 190 and a VL comprising an amino acid sequence of SEQ ID NO: 40.

In some embodiments, the antibody is A428/A403 comprising a VH comprising an amino acid sequence of SEQ ID NO: 190 and a VL comprising an amino acid sequence of SEQ ID NO: 52.

In some embodiments, the antibody is A428/A439 comprising a VH comprising an amino acid sequence of SEQ ID NO: 190 and a VL comprising an amino acid sequence of SEQ ID NO: 58.

In some embodiments, the antibody is A428/A440 comprising a VH comprising an amino acid sequence of SEQ ID NO: 190 and a VL comprising an amino acid sequence of SEQ ID NO: 200.

In some embodiments, the antibody is A435/A290 comprising a VH comprising an amino acid sequence of SEQ ID NO: 192 and a VL comprising an amino acid sequence of SEQ ID NO: 40.

In some embodiments, the antibody is A435/A403 comprising a VH comprising an amino acid sequence of SEQ ID NO: 192 and a VL comprising an amino acid sequence of SEQ ID NO: 52.

In some embodiments, the antibody is A435/A439 comprising a VH comprising an amino acid sequence of SEQ ID NO: 192 and a VL comprising an amino acid sequence of SEQ ID NO: 58.

In some embodiments, the antibody is A435/A440 comprising a VH comprising an amino acid sequence of SEQ ID NO: 192 and a VL comprising an amino acid sequence of SEQ ID NO: 200.

In some embodiments, the antibody is A436/A290 comprising a VH comprising an amino acid sequence of SEQ ID NO: 194 and a VL comprising an amino acid sequence of SEQ ID NO: 40.

In some embodiments, the antibody is A436/A403 comprising a VH comprising an amino acid sequence of SEQ ID NO: 194 and a VL comprising an amino acid sequence of SEQ ID NO: 52.

In some embodiments, the antibody is A436/A439 comprising a VH comprising an amino acid sequence of SEQ ID NO: 194 and a VL comprising an amino acid sequence of SEQ ID NO: 58.

In some embodiments, the antibody is A436/A440 comprising a VH comprising an amino acid sequence of SEQ ID NO: 194 and a VL comprising an amino acid sequence of SEQ ID NO: 200.

In some embodiments, the antibody is A438/A290 comprising a VH comprising an amino acid sequence of SEQ ID NO: 196 and a VL comprising an amino acid sequence of SEQ ID NO: 40.

In some embodiments, the antibody is A438/A403 comprising a VH comprising an amino acid sequence of SEQ ID NO: 196 and a VL comprising an amino acid sequence of SEQ ID NO: 52.

In some embodiments, the antibody is A438/A439 comprising a VH comprising an amino acid sequence of SEQ ID NO: 196 and a VL comprising an amino acid sequence of SEQ ID NO: 58.

In some embodiments, the antibody is A438/A440 comprising a VH comprising an amino acid sequence of SEQ ID NO: 196 and a VL comprising an amino acid sequence of SEQ ID NO: 200.

In some embodiments, the antibody is A450/A290 comprising a VH comprising an amino acid sequence of SEQ ID NO: 198 and a VL comprising an amino acid sequence of SEQ ID NO: 40.

In some embodiments, the antibody is A450/A403 comprising a VH comprising an amino acid sequence of SEQ ID NO: 198 and a VL comprising an amino acid sequence of SEQ ID NO: 52.

In some embodiments, the antibody is A450/A439 comprising a VH comprising an amino acid sequence of SEQ ID NO: 198 and a VL comprising an amino acid sequence of SEQ ID NO: 58.

In some embodiments, the antibody is A450/A440 comprising a VH comprising an amino acid sequence of SEQ ID NO: 198 and a VL comprising an amino acid sequence of SEQ ID NO: 200.

In yet another aspect, provided herein are antibodies that compete with one of the antibodies or antigen binding fragments thereof described above. Such antibodies may also bind to the same epitope as one of the above mentioned antibodies, or an overlapping epitope. Antibodies and fragments that compete with or bind to the same epitope as the above-mentioned antibodies are expected to show similar functional properties. The exemplified antigen binding proteins and fragments include those with the VH regions, VL regions and CDRs provided herein, including those in the Sequence Listing provided herein and Tables 26-35.

In certain embodiments, an antibody described herein or an antigen-binding fragment thereof comprises amino acid sequences with certain percent identity relative to the antibodies described above including the exemplary antibodies described in Section 6 below.

The determination of percent identity between two sequences (e.g., amino acid sequences or nucleic acid sequences) can be accomplished using a mathematical algorithm. A preferred, non-limiting example of a mathematical algorithm utilized for the comparison of two sequences is the algorithm of Karlin and Altschul, 1990, *Proc. Natl. Acad. Sci. U.S.A.* 87:2264 2268, modified as in Karlin and Altschul, 1993, *Proc. Natl. Acad. Sci. U.S.A.* 90:5873 5877. Such an algorithm is incorporated into the NBLAST and) (BLAST programs of Altschul et al., 1990, *J. Mol. Biol.* 215:403. BLAST nucleotide searches can be performed with the NBLAST nucleotide program parameters set, e.g., for score=100, word length=12 to obtain nucleotide sequences homologous to a nucleic acid molecules described herein. BLAST protein searches can be performed with the XBLAST program parameters set, e.g., to score 50, word length=3 to obtain amino acid sequences homologous to a protein molecule described herein. To obtain gapped alignments for comparison purposes, Gapped BLAST can be utilized as described in Altschul et aL, 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 35, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 35, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 35, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 35, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 35, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 35, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 35, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 35, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 35, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 35, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 35, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 35, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 50, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 50, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 50, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 50, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 50, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 50, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 50, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 50, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 50, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 50, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 50, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 50, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 54, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 54, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 54, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 54, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 54, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 54, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 54, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 54, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 54, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 54, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 54, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 54, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 56, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 56, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 56, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 56, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 56, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 56, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 56, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 56, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 56, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 56, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 56, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 56, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 60, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 60, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 60, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 60, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 60, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 60, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 60, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 60, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 60, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 60, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 60, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 60, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 181, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 181, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 181, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 181, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 181, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 181, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 181, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 181, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 181, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 181, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 181, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 181, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 190, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 190, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 190, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 190, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 190, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 190, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 190, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 190, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 190, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 190, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 190, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 190, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 192, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 192, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 192, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 192, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 192, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 192, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 192, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 192, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 192, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 192, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 192, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 192, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 194, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 194, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 194, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 194, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 194, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 194, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 194, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 194, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 194, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 194, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 194, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 194, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 196, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 196, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 196, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 196, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 196, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 196, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 196, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 196, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 196, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 196, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 196, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 196, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 198, and/or a VL region having at least 80%, at least 85%, at least 90%, at least 95%, or at least 98% sequence identity to the amino acid sequence of SEQ ID NO: 40, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 198, and/or a VL region comprising CDRs having at least 80%, at least 85%, at least 90%, at least 95%, or at least 98% sequence identity to the amino acid sequence of the CDRs contained in SEQ ID NO: 40, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 198, and/or a VL region comprising VL framework regions having at least 80%, at least 85%, at least 90%, at least 95%, or at least 98% sequence identity to the amino acid sequence the framework regions contained in SEQ ID NO: 40, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 198, and/or a VL region having at least 80%, at least 85%, at least 90%, at least 95%, or at least 98% sequence identity to the amino acid sequence of SEQ ID NO: 52, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 198, and/or a VL region comprising CDRs having at least 80%, at least 85%, at least 90%, at least 95%, or at least 98% sequence identity to the amino acid sequence of the CDRs contained in SEQ ID NO: 52, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 198, and/or a VL region comprising VL framework regions having at least 80%, at least 85%, at least 90%, at least 95%, or at least 98% sequence identity to the amino acid sequence the framework regions contained in SEQ ID NO: 52, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 198, and/or a VL region having at least 80%, at least 85%, at least 90%, at least 95%, or at least 98% sequence identity to the amino acid sequence of SEQ ID NO: 58, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 198, and/or a VL region comprising CDRs having at least 80%, at least 85%, at least 90%, at least 95%, or at least 98% sequence identity to the amino acid sequence of the CDRs contained in SEQ ID NO: 58, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 198, and/or a VL region comprising VL framework regions having at least 80%, at least 85%, at least 90%, at least 95%, or at least 98% sequence identity to the amino acid sequence the framework regions contained in SEQ ID NO: 58, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 198, and/or a VL region having at least 80%, at least 85%, at least 90%, at least 95%, or at least 98% sequence identity to the amino acid sequence of SEQ ID NO: 200, wherein the antibody immunospecifically binds to Fn14.

In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 198, and/or a VL region comprising CDRs having at least 80%, at least 85%, at least 90%, at least 95%, or at least 98% sequence identity to the amino acid sequence of the CDRs contained in SEQ ID NO: 200, wherein the antibody immunospecifically binds to Fn14.

In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 198, and/or a VL region comprising VL framework regions having at least 80%, at least 85%, at least 90%, at least 95%, or at least 98% sequence identity to the amino acid sequence the framework regions contained in SEQ ID NO: 200, wherein the antibody immunospecifically binds to Fn14.

5.2.2 Polyclonal Antibodies

The antibodies of the present disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include an Fn14 polypeptide or a fusion protein thereof. It may be useful to conjugate the immunizing agent to a protein known to be immunogenic in the mammal being immunized or to immunize the mammal with the protein and one or more adjuvants. Examples of such immunogenic proteins include, but are not limited to, keyhole limpet hemocyanin, serum albumin, bovine thyroglobulin, and soybean trypsin inhibitor. Examples of adjuvants which may be employed include Ribi, CpG, Poly (I:C), Freund's complete adjuvant, and MPL-TDM adjuvant (monophosphoryl Lipid A, synthetic trehalose dicorynomycolate). The immunization protocol may be selected by one skilled in the art without undue experimentation. The mammal can then be bled, and the serum assayed for anti-Fn14 antibody titer. If desired, the mammal can be boosted until the antibody titer increases or plateaus. Additionally or alternatively, lymphocytes may be obtained from the immunized animal for fusion and preparation of monoclonal antibodies from hybridoma as described below.

5.2.3 Monoclonal Antibodies

The antibodies of the present disclosure may alternatively be monoclonal antibodies. Monoclonal antibodies may be made using the hybridoma method first described by Kohler et al., 1975, *Nature* 256:495-97, or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice 59-103 (1986)).

The hybridoma cells thus prepared are seeded and grown in a suitable culture medium, which, in certain embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary fusion partner myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, $X_{63}$-Ag8-653 cells available from the American Type Culture Collection (Manassas, VA), and those derived from MOPC-21 and MPC-11 mouse tumors available from the Salk Institute Cell Distribution Center (San Diego, CA). Human myeloma and mouse-human heteromyeloma cell lines also have been described for the production of human monoclonal antibodies (Kozbor, 1984, *Immunol.* 133:3001-05; and Brodeur et al., 1987, *Monoclonal Antibody Production Techniques and Applications* 51-63).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can,for example, be determined by the Scatchard analysis described in Munson et al., 1980, Anal. Biochem. 107:220-39.

Once hybridoma cells that produce antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells, such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, Curr. Opinion in Immunol. 5:256-62 and Phickthun, 1992, Immunol. Revs. 130:151-88.

In some embodiments, an antibody that binds an Fn14 epitope comprises an amino acid sequence of a VH domain and/or an amino acid sequence of a VL domain encoded by a nucleotide sequence that hybridizes to (1) the complement of a nucleotide sequence encoding any one of the VH and/or VL domain described herein under stringent conditions (e.g., hybridization to filter-bound DNA in 6× sodium chloride/sodium citrate (SSC) at about 45° C. followed by one or more washes in 0.2× SSC/0.1% SDS at about 50-65° C.), under highly stringent conditions (e.g., hybridization to filter-bound nucleic acid in 6× SSC at about 45° C. followed by one or more washes in 0.1× SSC/0.2% SDS at about 68° C.), or under other stringent hybridization conditions which are known to those of skill in the art. See, e.g., Current Protocols in Molecular Biology Vol. I, 6.3.1-6.3.6 and 2.10.3 (Ausubel et al. eds., 1989).

In some embodiments, an antibody that binds an Fn14 epitope comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in the Sequence Listing provided herein under stringent conditions (e.g., hybridization to filter-bound DNA in 6× SSC at about 45° C. followed by one or more washes in 0.2× SSC/0.1% SDS at about 50-65° C.), under highly stringent conditions (e.g., hybridization to filter-bound nucleic acid in 6× SSC at about 45° C. followed by one or more washes in 0.1× SSC/0.2% SDS at about 68° C.), or under other stringent hybridization conditions which are known to those of skill in the art (see, e.g., Ausubel et al., supra).

In a further embodiment, monoclonal antibodies or antibody fragments can be isolated from antibody phage libraries generated using the techniques described in, for example, Antibody Phage Display: Methods and Protocols (O'Brien and Aitken eds., 2002). In phage display methods, functional antibody domains are displayed on the surface of phage particles which carry the polynucleotide sequences encoding them. Examples of phage display methods that can be used to make the antibodies described herein include those disclosed in Brinkman et al., 1995, J. Immunol. Methods 182:41-50; Ames et al., 1995, J. Immunol. Methods 184: 177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

In principle, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., 1994, Ann. Rev. Immunol. 12:433-55.

Repertoires of VH and VL genes can be separately cloned by PCR and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., 1993, EMBO J 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, 1992, J. Mol. Biol. 227:381-88.

Screening of the libraries can be accomplished by various techniques known in the art. For example, Fn14 (e.g., an Fn14 polypeptide, fragment, or epitope) can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., 1990, Proteins 8:309-14 and WO 92/09690, and by use of a low coating density of antigen as described in Marks et al., 1992, Biotechnol. 10:779-83.

Anti-Fn14 antibodies can be obtained by designing a suitable antigen screening procedure to select for the phage clone of interest followed by construction of a full length antibody clone using VH and/or VL sequences (e.g., the Fv sequences), or various CDR sequences from VH and VL sequences, from the phage clone of interest and suitable constant region (e.g., Fc) sequences described in Kabat et al., supra.

Antibodies described herein can also, for example, include chimeric antibodies. A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

Antibodies or antigen binding fragments produced using techniques such as those described herein can be isolated using standard, well known techniques. For example, antibodies or antigen binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography. As used herein, an "isolated" or "purified" antibody is substantially free of cellular material or other proteins from the cell or tissue source from which the antibody is derived, or substantially free of chemical precursors or other chemicals when chemically synthesized.

In some specific embodiments, monoclonal antibodies are generated using the methods exemplified in Section 6 below. In some specific embodiments, hybridoma isgenerated using the methods exemplified in Section 6 below. In some specific embodiments, chimeric antibodies are generated using the methods exemplified in Section 6 below.

5.2.4 Antibody Fragments

The present disclosure provides antibodies and antibody fragments that bind to Fn14. In certain circumstances, there are advantages of using antibody fragments rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et aL , 1985, Science 229:81-83). However, these fragments can now be produced directly by recombinant host cells. Fab, Fv, and scFv antibody fragments can all be expressed in and secreted from E. coli or yeast cells, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., 1992, Bio/Technology 10:163-67). According to another approach, F(ab')2 fragments can be isolated directly from recombinant host cell culture. Fab and F(ab')2 fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above. Such linear antibodies may be monospecific or multi-specific, such as bispecific.

Smaller antibody-derived binding structures are the separate variable domains (V domains) also termed single variable domain antibodies (sdAbs). Certain types of organisms, the camelids and cartilaginous fish, possess high affinity single V-like domains mounted on an Fc equivalent domain structure as part of their immune system. (Woolven et al., 1999, Immunogenetics 50: 98-101; and Streltsov et al., 2004, Proc Natl Acad Sci USA. 101:12444-49). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains.

Antibodies provided herein include, but are not limited to, immunoglobulin molecules and immunologically active portions of immunoglobulin molecules, for example, molecules that contain an antigen binding site that bind to an Fn14 epitope. The immunoglobulin molecules provided herein can be of any class (e.g., IgG, IgE, IgM, IgD, and IgA) or any subclass (e.g., IgG1, IgG2, IgG3, IgG4, IgA1, and IgA2) of immunoglobulin molecule.

Variants and derivatives of antibodies include antibody functional fragments that retain the ability to bind to an Fn14 epitope. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single antigen-binding domain comprising an Fab and an additional portion of the heavy chain through the hinge region); F(ab')2 (e.g., two Fab' molecules joined by interchain disulfide bonds in the hinge regions of the heavy chains; the Fab' molecules may be directed toward the same or different epitopes); a bispecific Fab (e.g., a Fab molecule having two antigen binding domains, each of which may be directed to a different epitope); a single chain comprising a variable region, also known as, scFv (e.g., the variable, antigen-binding determinative region of a single light and heavy chain of an antibody linked together by a chain of 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies); a bispecific scFv (e.g., an scFv or a dsFv molecule having two antigen-binding domains, each of which may be directed to a different epitope); a diabody (e.g., a dimerized scFv formed when the VH domain of a first scFv assembles with the VL domain of a second scFv and the VL domain of the first scFv assembles with the VH domain of the second scFv; the two antigen-binding regions of the diabody may be directed towards the same or different epitopes); a triabody (e.g., a trimerized scFv, formed in a manner similar to a diabody, but in which three antigen-binding domains are created in a single complex; the three antigen binding domains may be directed towards the same or different epitopes) ; and a tetrabody (e.g., a tetramerized scFv, formed in a manner similar to a diabody, but in which four antigen-binding domains are created in a single complex; the four antigen binding domains may be directed towards the same or different epitopes).

5.2.5 Humanized Antibodies

The antibodies described herein can, for example, include humanized antibodies, e.g., deimmunized or composite human antibodies.

A humanized antibody can comprise human framework region and human constant region sequences. For example, a humanized antibody can comprise human constant region sequences. In certain embodiments, a humanized antibody can be selected from any class of immunoglobulins, including IgM, IgG, IgD, IgA and IgE, and any isotype, including IgG1, IgG2, IgG3 and IgG4 (e.g., variants of IgG4 and IgG4 nullbody). In certain embodiments, a humanized antibody can comprise kappa or lambda light chain constant sequences.

Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 93/17105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s- 5977s (1995), Couto et al., Cancer Res. 55(8): 1717-22 (1995), Sandhu JS, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

In some embodiments, antibodies provided herein can be humanized antibodies that bind Fn14, including human, cynomolgus macaque, rat and mouse Fn14. For example, humanized antibodies of the present disclosure may comprise one or more CDRs as shown in the Sequence Listing provided herein. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., 1986, Nature 321:522-25; Riechmann et al., 1988, Nature 332: 323-27; and Verhoeyen et al., 1988, Science 239:1534-36), by substituting hypervariable region sequences for the corresponding sequences of a human antibody.

In some cases, the humanized antibodies are constructed by CDR grafting, in which the amino acid sequences of the six CDRs of the parent non-human antibody (e.g., rodent) are grafted onto a human antibody framework. For example, Padlan et al. determined that only about one third of the residues in the CDRs actually contact the antigen, and termed these the "specificity determining residues," or SDRs (Padlan et al., 1995, FASEB J. 9:133-39). In the technique of SDR grafting, only the SDR residues are grafted onto the human antibody framework (see, e.g., Kashmiri et al., 2005, Methods 36:25-34).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence that is closest to that of the rodent may be selected as the human framework for the humanized antibody (Sims et al., 1993, J. Immunol. 151:2296-308; and Chothia et al., 1987, J. Mol. Biol. 196:901-17). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285-89; and Presta et al., 1993, J. Immunol. 151:2623-32). In some cases, the framework is derived from the consensus sequences of the most abundant human subclasses, VL6 subgroup I (VL6I) and VH subgroup III (VHIII). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., 2002, J. Immunol. 169:1119-25).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, 2000, Protein Eng. 13:819-24), Modeller (Sali and Blundell, 1993, J. Mol. Biol. 234:779-815), and Swiss PDB Viewer (Guex and Peitsch, 1997, Electrophoresis 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., 2007, Mol. Immunol. 44:1986-98).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see, e.g., Hoogenboom, 2005, Nat. Biotechnol. 23:1105-16; Dufner et al., 2006, Trends Biotechnol. 24:523-29; Feldhaus et al., 2003, Nat. Biotechnol. 21:163-70; and Schlapschy et al., 2004, Protein Eng. Des. Sel. 17:847-60).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, 1992, J. Mol. Biol. 224:487-99), or from the more limited set of target residues identified by Baca et al. (1997, J. Biol. Chem. 272:10678-84).

In FR shuffling, whole FRs are combined with the non-human CDRs instead of creating combinatorial libraries of selected residue variants (see, e.g., Dall' Acqua et al., 2005, Methods 36:43-60). The libraries may be screened for binding in a two-step process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity, and thermal stability (see, e.g., Damschroder et al., 2007, Mol. Immunol. 44:3049-60).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple subclasses with distinct human V-segment CDRs. Humaneering allows for isolation of antibodies that are 91-96% homologous to human germline gene antibodies (see, e.g., Alfenito, Cambridge Healthtech Institute's Third Annual PEGS, The Protein Engineering Summit, 2007).

The "human engineering" method involves altering a non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., 1994, Protein Engineering 7:805-14; U.S. Pat. Nos. 5,766,886; 5,770,196; 5,821,123; and 5,869,619; and PCT Publication WO 93/11794.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody. Such antibodies can comprise human constant region sequences, e.g., human light chain and/or heavy chain constant regions.

A deimmunized antibody is an antibody in which T-cell epitopes have been removed. Methods for making deimmunized antibodies have been described. See, e.g., Jones et al., Methods Mol Biol. 2009;525:405-23, xiv, and De Groot et al., Cell. Immunol. 244:148-153(2006)). Deimmunized antibodies comprise T-cell epitope-depleted variable regions and human constant regions. Briefly, VH and VL of an antibody are cloned and T-cell epitopes are subsequently identified by testing overlapping peptides derived from the VH and VL of the antibody in a T cell proliferation assay. T cell epitopes are identified via in silico methods to identify peptide binding to human MHC class II. Mutations are introduced in the VH and VL to abrogate binding to human MHC class II. Mutated VH and VL are then utilized to generate the deimmunized antibody.

In some specific embodiments, humanized antibodies are generated using the methods exemplified in Section 6 below.

In some embodiments, the humanized antibodies comprises one or more CDRs listed in Table 26 and/or described in Section 5.2.1 above.

More specifically, in some embodiments, the humanized antibody or antigen binding fragment thereof provided herein comprises:
 (a) a heavy chain variable region (VH) comprising (i) VH complementarity determining region 1 (CDR H1) comprising an amino acid sequence of GYX$_1$FX$_2$DYNMH (SEQ ID NO: 184), wherein X$_1$ is T, I or R, and X$_2$ is T or Q; (ii) VH complementarity determining region 2 (CDR H2) comprising an amino acid sequence of X$_3$INPX$_4$NX$_5$X$_6$TNYNQKFKG (SEQ ID NO: 185), wherein X$_3$ is Y or S, X$_4$ is N or R; X$_5$ is A or G, and X$_6$ is G or W; (iii) VH complementarity determining region 3 (CDR H3) comprising an amino acid sequence of SGWFTY (SEQ ID NO: 121);
 (b) a light chain variable region (VL) comprising (i) VL complementarity determining region 1 (CDR L1) comprising an amino acid sequence of KS SQSLLN-SAGKTYLN (SEQ ID NO: 127); (ii) VL complementarity determining region 2 (CDR L2) comprising an amino acid sequence of LVSQLDS (SEQ ID NO: 128); (iii) VL complementarity determining region 3 (CDR L3) comprising an amino acid sequence of WQGTX$_7$X$_8$PWT (SEQ ID NO: 186), wherein X$_7$ is H or F, and X$_8$ is F or Y.

In some more specific embodiments, the humanized antibody or antigen binding fragment thereof provided herein comprises:
 (a) a heavy chain variable region (VH) comprising (i)VH complementarity determining region 1 (CDR H1) comprising an amino acid sequence of GYIFQDYNMEI (SEQ ID NO: 122); (ii) VH complementarity determining region 2 (CDR H2) comprising an amino acid sequence of X$_3$INPRNX$_5$X$_6$TNYNQKFKG (SEQ ID NO: 187), wherein X$_3$ is Y or S, X$_5$ is A or G; and X$_6$ is G or W; and (iii) VH complementarity determining region 3 (CDR H3) comprising an amino acid sequence of SGWFTY (SEQ ID NO: 121);
 (b) a light chain variable region (VL) comprising (i) VL complementarity determining region 1 (CDR L1) comprising an amino acid sequence of KSSQSLLN-SAGKTYLN (SEQ ID NO: 127); (ii) VL complementarity determining region 2 (CDR L2) comprising an amino acid sequence of LVSQLDS (SEQ ID NO: 128); and (iii) VL complementarity determining region 3 (CDR L3) comprising an amino acid sequence of WQGTX$_7$YPWT (SEQ ID NO: 188), wherein X$_7$ is H or F.

In some embodiments, the antibody or antigen binding fragment thereof comprises:
 (a) a heavy chain variable region (VH) comprising (i) VH complementarity determining region 1 (CDR H1) comprising an amino acid sequence of GYIFQDYNIVIII (SEQ ID NO: 122); (ii) VH complementarity determining region 2 (CDR H2) comprising an amino acid sequence of X$_3$INPRNX$_5$X$_6$TNYNX$_9$KFXioG (SEQ ID NO: 259), wherein X$_3$ is Y or S, X$_5$ is A or G; X$_6$ is G or W, X$_9$ is Q or D, and X$_{10}$ is K, G, H, or D; (iii) VH complementarity determining region 3 (CDR H3) comprising an amino acid sequence of SGWFTY (SEQ ID NO: 121);
 (b) a light chain variable region (VL) comprising (i) VL complementarity determining region 1 (CDR L1) comprising an amino acid sequence of KSSQSLLN-SAGKTYLN (SEQ ID NO: 127); (ii) VL complementarity determining region 2 (CDR L2) comprising an amino acid sequence of LVX$_{11}$X$_{12}$LDX$_{13}$ (SEQ ID NO: 258), wherein X$_{11}$ is S or A, X$_{12}$ is Q or E, and X$_{13}$ is S or D; (iii) VL complementarity determining region 3 (CDR L3) comprising an amino acid sequence of WQGTX$_7$YPWT (SEQ ID NO: 188), wherein X$_7$ is H or F.

In other more specific embodiments, the humanized antibody or antigen binding fragment thereof provided herein comprises one or more CDRs from Table 31 below.

TABLE 31

CDRs of exemplary humanized antibodies

|    | CDR1 | CDR2 | CDR3 |
|----|------|------|------|
| VH | SEQ ID NO: 122 | SEQ ID NO: 123<br>SEQ ID NO: 124<br>SEQ ID NO: 126<br>SEQ ID NO: 247<br>SEQ ID NO: 248<br>SEQ ID NO: 249<br>SEQ ID NO: 250 | SEQ ID NO: 121 |
| VL | SEQ ID NO: 127 | SEQ ID NO: 128<br>SEQ ID NO: 254<br>SEQ ID NO: 255<br>SEQ ID NO: 256 | SEQ ID NO: 130<br>SEQ ID NO: 131 |

Thus, in some more specific embodiments, the humanized antibody or antigen binding fragment thereof provided herein comprises:
 (a) a heavy chain variable region (VH) comprising (i) VH complementarity determining region 1 (CDR H1) comprising an amino acid sequence of SEQ ID NO: 122; (ii) VH complementarity determining region 2 (CDR H2) comprising an amino acid sequence selected from a group consisting of SEQ ID NO: 123, SEQ ID NO: 124, SEQ ID NO: 126, SEQ ID NO: 247, SEQ ID NO: 248, SEQ ID NO: 249, and SEQ ID NO: 250; and (iii) VH complementarity determining region 3 (CDR H3) comprising an amino acid sequence of SEQ ID NO: 121, and
 (b) a light chain variable region (VL) comprising (i) VL complementarity determining region 1 (CDR L1) comprising an amino acid sequence of SEQ ID NO: 127; (ii) VL complementarity determining region 2 (CDR L2) comprising an amino acid sequence selected from a group consisting of SEQ ID NO: 128, SEQ ID NO: 254, SEQ ID NO: 255, and SEQ ID NO: 256; and (iii) VL complementarity determining region 3 (CDR L3) comprising an amino acid sequence selected from a group consisting of SEQ ID NO: 130 and SEQ ID NO: 131.

In other more specific embodiments, the humanized antibody or antigen binding fragment thereof provided herein comprises a VH comprising CDRs comprising amino acid sequences of the CDRs contained in the VH selected from a group consisting of SEQ ID NO: 179, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 106, SEQ ID NO: 108, SEQ ID NO: 110, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225 and SEQ ID NO: 227; and a VL comprising CDRs comprising amino acid sequences of the CDRs contained in the VL selected from a group consisting of SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, SEQ ID NO: 229, SEQ ID NO: 231, SEQ ID NO: 233, SEQ ID NO: 235 and SEQ ID NO: 237.

The residues from each of these CDR regions are noted in the Sequence Listing provided herein. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering. In certain embodiments, the CDRs in an antibody can be determined according to a combination of various numbering systems, for example, Kabat in combination with Chothia. In certain embodiments, one or more CDRs in an antibody are determined according to Kabat numbering and other CDRs in the antibody are determined according Chothia numbering.

In some embodiments, the humanized antibody or antigen binding fragment provided herein further comprises one or more FRs from the humanized antibodies described herein including those in Section 6 below. In some embodiments, the humanized antibody or antigen binding fragment thereof provided herein comprises one or more FR sequences listed in Table 32 below.

TABLE 32

FRs of exemplary humanized antibodies

| | FR1 | FR2 | FR3 | FR4 |
|---|---|---|---|---|
| VH | SEQ ID NO: 133 | SEQ ID NO: 139 | SEQ ID NO: 146 | SEQ ID NO: 159 |
| | SEQ ID NO: 134 | SEQ ID NO: 140 | SEQ ID NO: 147 | |
| | SEQ ID NO: 135 | SEQ ID NO: 141 | SEQ ID NO: 148 | |
| | SEQ ID NO: 136 | SEQ ID NO: 142 | SEQ ID NO: 150 | |
| | SEQ ID NO: 137 | SEQ ID NO: 143 | SEQ ID NO: 151 | |
| | SEQ ID NO: 238 | SEQ ID NO: 144 | SEQ ID NO: 152 | |
| | SEQ ID NO: 239 | SEQ ID NO: 173 | SEQ ID NO: 153 | |
| | | SEQ ID NO: 240 | SEQ ID NO: 154 | |
| | | SEQ ID NO: 241 | SEQ ID NO: 155 | |
| | | SEQ ID NO: 242 | SEQ ID NO: 156 | |
| | | SEQ ID NO: 243 | SEQ ID NO: 157 | |
| | | SEQ ID NO: 244 | SEQ ID NO: 174 | |
| | | SEQ ID NO: 245 | SEQ ID NO: 251 | |
| | | SEQ ID NO: 246 | | |
| VL | SEQ ID NO: 161 | SEQ ID NO: 163 | SEQ ID NO: 170 | SEQ ID NO: 171 |
| | SEQ ID NO: 162 | SEQ ID NO: 164 | | SEQ ID NO: 172 |
| | | SEQ ID NO: 165 | | |
| | | SEQ ID NO: 166 | | |
| | | SEQ ID NO: 167 | | |
| | | SEQ ID NO: 168 | | |
| | | SEQ ID NO: 252 | | |
| | | SEQ ID NO: 253 | | |

In some embodiments, the antibody comprises a FR H1 comprising an amino acid sequence selected from a group consisting of SEQ ID NO: 133, SEQ ID NO: 134, SEQ ID NO: 135, SEQ ID NO: 136, SEQ ID NO: 137, SEQ ID NO: 238 and SEQ ID NO: 239. In some embodiments, the antibody comprises a FR H1 comprising an amino acid sequence of SEQ ID NO: 133. In some embodiments, the antibody comprises a FR H1 comprising an amino acid sequence of SEQ ID NO: 134. In some embodiments, the antibody comprises a FR H1 comprising an amino acid sequence of SEQ ID NO: 135. In some embodiments, the antibody comprises a FR H1 comprising an amino acid sequence of SEQ ID NO: 136. In some embodiments, the antibody comprises a FR H1 comprising an amino acid sequence of SEQ ID NO: 137. In some embodiments, the antibody comprises a FR H1 comprising an amino acid sequence of SEQ ID NO: 238. In some embodiments, the antibody comprises a FR H1 comprising an amino acid sequence of SEQ ID NO: 239.

In some embodiments, the antibody comprises a FR H2 comprising an amino acid sequence selected from a group consisting of SEQ ID NO: 139, SEQ ID NO: 140, SEQ ID NO: 141, SEQ ID NO: 142, and SEQ ID NO: 143, SEQ ID NO: 144, SEQ ID NO: 173, SEQ ID NO: 240, SEQ ID NO: 241, SEQ ID NO: 242, SEQ ID NO: 243, SEQ ID NO: 244, SEQ ID NO: 245 and SEQ ID NO: 246. In some embodiments, the antibody comprises a FR H2 comprising an amino acid sequence of SEQ ID NO: 139. In some embodiments, the antibody comprises a FR H2 comprising an amino acid sequence of SEQ ID NO: 140. In some embodiments, the antibody comprises a FR H2 comprising an amino acid sequence of SEQ ID NO: 141. In some embodiments, the antibody comprises a FR H2 comprising an amino acid sequence of SEQ ID NO: 142. In some embodiments, the antibody comprises a FR H2 comprising an amino acid sequence of SEQ ID NO: 143. In some embodiments, the antibody comprises a FR H2 comprising an amino acid sequence of SEQ ID NO: 144. In some embodiments, the antibody comprises a FR H2 comprising an amino acid sequence of SEQ ID NO: 173. In some embodiments, the antibody comprises a FR H2 comprising an amino acid sequence of SEQ ID NO: 240. In some embodiments, the antibody comprises a FR H2 comprising an amino acid sequence of SEQ ID NO: 241. In some embodiments, the antibody comprises a FR H2 comprising an amino acid sequence of SEQ ID NO: 242. In some embodiments, the antibody comprises a FR H2 comprising an amino acid sequence of SEQ ID NO: 243. In some embodiments, the antibody comprises a FR H2 comprising an amino acid sequence of SEQ ID NO: 244. In some embodiments, the antibody comprises a FR H2 comprising an amino acid sequence of SEQ ID NO: 245. In some embodiments, the antibody comprises a FR H2 comprising an amino acid sequence of SEQ ID NO: 246.

In some embodiments, the antibody comprises a FR H3 comprising an amino acid sequence selected from a group consisting of SEQ ID NO: 146, SEQ ID NO: 147, SEQ ID NO: 148, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 174, and SEQ ID NO: 251. In some embodiments, the antibody comprises a FR H3 comprising an amino acid sequence of SEQ ID NO: 146. In some embodiments, the antibody comprises a FR H3 comprising an amino acid sequence of SEQ ID NO: 147. In some embodiments, the antibody comprises a FR H3 comprising an amino acid sequence of SEQ ID NO: 148. In some embodiments, the antibody comprises a FR H3 comprising an amino acid sequence of SEQ ID NO: 150. In some embodiments, the antibody comprises a FR H3 comprising an amino acid sequence of SEQ ID NO: 151. In some embodiments, the antibody comprises a FR H3 comprising an amino acid sequence of SEQ ID NO: 152. In some embodiments, the antibody comprises a FR H3 comprising an amino acid sequence of SEQ ID NO: 153. In some embodiments, the antibody comprises a FR H3 comprising an amino acid sequence of SEQ ID NO: 154. In some embodiments, the antibody comprises a FR H3 comprising an amino acid sequence of SEQ ID NO: 155. In some embodiments, the antibody comprises a FR H3 comprising an amino acid sequence of SEQ ID NO: 156. In some embodiments, the antibody comprises a FR H3 comprising an amino acid sequence of SEQ ID NO: 157. In some embodiments, the antibody comprises a FR H3 comprising an amino acid sequence of SEQ ID NO: 174. In some embodiments, the antibody comprises a FR H3 comprising an amino acid sequence of SEQ ID NO: 251.

In some embodiments, the antibody comprises a FR H4 comprising an amino acid sequence of SEQ ID NO: 159.

In some embodiments, the antibody comprises a FR L1 comprising an amino acid sequence selected from a group consisting of SEQ ID NO: 161 and SEQ ID NO: 162. In some embodiments, the antibody comprises a FR L1 of SEQ ID NO: 161. In some embodiments, the antibody comprises a FR L1 of SEQ ID NO: 162.

In some embodiments, the antibody comprises a FR L2 comprising an amino acid sequence selected from a group consisting of SEQ ID NO: 163, SEQ ID NO: 164, SEQ ID NO: 165, SEQ ID NO: 166, SEQ ID NO: 167, SEQ ID NO: 168, SEQ ID NO: 252 and SEQ ID NO: 253. In some embodiments, the antibody comprises a FR L2 of SEQ ID NO: 163. In some embodiments, the antibody comprises a FR L2 of SEQ ID NO: 164. In some embodiments, the antibody comprises a FR L2 of SEQ ID NO: 165. In some embodiments, the antibody comprises a FR L2 of SEQ ID NO: 166. In some embodiments, the antibody comprises a FR L2 of SEQ ID NO: 167. In some embodiments, the antibody comprises a FR L2 of SEQ ID NO: 168. In some embodiments, the antibody comprises a FR L2 of SEQ ID NO: 252. In some embodiments, the antibody comprises a FR L2 of SEQ ID NO: 253.

In some embodiments, the antibody comprises a FR L3 of SEQ ID NO: 170.

In some embodiments, the antibody comprises a FR L4 comprising an amino acid sequence selected from a group consisting of SEQ ID NO: 171 and SEQ ID NO: 172. In some embodiments, the antibody comprises a FR L4 of SEQ ID NO: 171. In some embodiments, the antibody comprises a FR L4 of SEQ ID NO: 172.

In some embodiments, the antibody comprises a FR H1 comprising an amino acid sequence of SEQ ID NO: 133, a FR H2 comprising an amino acid sequence of SEQ ID NO: 139, a FR H3 comprising an amino acid sequence of SEQ ID NO: 146, and a FR H4 comprising an amino acid sequence of SEQ ID NO: 159.

In some embodiments, the antibody comprises a FR H1 comprising an amino acid sequence of SEQ ID NO: 133, a FR H2 comprising an amino acid sequence of SEQ ID NO: 142, a FR H3 comprising an amino acid sequence of SEQ ID NO: 146, and a FR H4 comprising an amino acid sequence of SEQ ID NO: 159.

In some embodiments, the antibody comprises a FR H1 comprising an amino acid sequence of SEQ ID NO: 133, a FR H2 comprising an amino acid sequence of SEQ ID NO: 142, a FR H3 comprising an amino acid sequence of SEQ ID NO: 148, and a FR H4 comprising an amino acid sequence of SEQ ID NO: 159.

In some embodiments, the antibody comprises a FR H1 comprising an amino acid sequence of SEQ ID NO: 133, a FR H2 comprising an amino acid sequence of SEQ ID NO: 142, a FR H3 comprising an amino acid sequence of SEQ ID NO: 155, and a FR H4 comprising an amino acid sequence of SEQ ID NO: 159.

In some embodiments, the antibody comprises a FR H1 comprising an amino acid sequence of SEQ ID NO: 133, a FR H2 comprising an amino acid sequence of SEQ ID NO: 143, a FR H3 comprising an amino acid sequence of SEQ ID NO: 152, and a FR H4 comprising an amino acid sequence of SEQ ID NO: 159.

In some embodiments, the antibody comprises a FR H1 comprising an amino acid sequence of SEQ ID NO: 133, a FR H2 comprising an amino acid sequence of SEQ ID NO: 144, a FR H3 comprising an amino acid sequence of SEQ ID NO: 154, and a FR H4 comprising an amino acid sequence of SEQ ID NO: 159.

In some embodiments, the antibody comprises a FR H1 comprising an amino acid sequence of SEQ ID NO: 133, a FR H2 comprising an amino acid sequence of SEQ ID NO: 173, a FR H3 comprising an amino acid sequence of SEQ ID NO: 174, and a FR H4 comprising an amino acid sequence of SEQ ID NO: 159.

In some embodiments, the antibody comprises a FR H1 comprising an amino acid sequence of SEQ ID NO: 134, a FR H2 comprising an amino acid sequence of SEQ ID NO: 140, a FR H3 comprising an amino acid sequence of SEQ ID NO: 147, and a FR H4 comprising an amino acid sequence of SEQ ID NO: 159.

In some embodiments, the antibody comprises a FR H1 comprising an amino acid sequence of SEQ ID NO: 134, a FR H2 comprising an amino acid sequence of SEQ ID NO: 140, a FR H3 comprising an amino acid sequence of SEQ ID NO: 151, and a FR H4 comprising an amino acid sequence of SEQ ID NO: 159.

In some embodiments, the antibody comprises a FR H1 comprising an amino acid sequence of SEQ ID NO: 134, a FR H2 comprising an amino acid sequence of SEQ ID NO: 141, a FR H3 comprising an amino acid sequence of SEQ ID NO: 147, and a FR H4 comprising an amino acid sequence of SEQ ID NO: 159.

In some embodiments, the antibody comprises a FR H1 comprising an amino acid sequence of SEQ ID NO: 134, a FR H2 comprising an amino acid sequence of SEQ ID NO:

141, a FR H3 comprising an amino acid sequence of SEQ ID NO: 150, and a FR H4 comprising an amino acid sequence of SEQ ID NO: 159.

In some embodiments, the antibody comprises a FR H1 comprising an amino acid sequence of SEQ ID NO: 135, a FR H2 comprising an amino acid sequence of SEQ ID NO: 139, a FR H3 comprising an amino acid sequence of SEQ ID NO: 153, and a FR H4 comprising an amino acid sequence of SEQ ID NO: 159.

In some embodiments, the antibody comprises a FR H1 comprising an amino acid sequence of SEQ ID NO: 136, a FR H2 comprising an amino acid sequence of SEQ ID NO: 141, a FR H3 comprising an amino acid sequence of SEQ ID NO: 156, and a FR H4 comprising an amino acid sequence of SEQ ID NO: 159.

In some embodiments, the antibody comprises a FR H1 comprising an amino acid sequence of SEQ ID NO: 136, a FR H2 comprising an amino acid sequence of SEQ ID NO: 240, a FR H3 comprising an amino acid sequence of SEQ ID NO: 156, and a FR H4 comprising an amino acid sequence of SEQ ID NO: 159.

In some embodiments, the antibody comprises a FR H1 comprising an amino acid sequence of SEQ ID NO: 136, a FR H2 comprising an amino acid sequence of SEQ ID NO: 241, a FR H3 comprising an amino acid sequence of SEQ ID NO: 156, and a FR H4 comprising an amino acid sequence of SEQ ID NO: 159.

In some embodiments, the antibody comprises a FR H1 comprising an amino acid sequence of SEQ ID NO: 136, a FR H2 comprising an amino acid sequence of SEQ ID NO: 242, a FR H3 comprising an amino acid sequence of SEQ ID NO: 156, and a FR H4 comprising an amino acid sequence of SEQ ID NO: 159.

In some embodiments, the antibody comprises a FR H1 comprising an amino acid sequence of SEQ ID NO: 136, a FR H2 comprising an amino acid sequence of SEQ ID NO: 243, a FR H3 comprising an amino acid sequence of SEQ ID NO: 156, and a FR H4 comprising an amino acid sequence of SEQ ID NO: 159.

In some embodiments, the antibody comprises a FR H1 comprising an amino acid sequence of SEQ ID NO: 136, a FR H2 comprising an amino acid sequence of SEQ ID NO: 244, a FR H3 comprising an amino acid sequence of SEQ ID NO: 156, and a FR H4 comprising an amino acid sequence of SEQ ID NO: 159.

In some embodiments, the antibody comprises a FR H1 comprising an amino acid sequence of SEQ ID NO: 137, a FR H2 comprising an amino acid sequence of SEQ ID NO: 144, a FR H3 comprising an amino acid sequence of SEQ ID NO: 157, and a FR H4 comprising an amino acid sequence of SEQ ID NO: 159.

In some embodiments, the antibody comprises a FR H1 comprising an amino acid sequence of SEQ ID NO: 238, a FR H2 comprising an amino acid sequence of SEQ ID NO: 245, a FR H3 comprising an amino acid sequence of SEQ ID NO: 251, and a FR H4 comprising an amino acid sequence of SEQ ID NO: 159.

In some embodiments, the antibody comprises a FR H1 comprising an amino acid sequence of SEQ ID NO: 238, a FR H2 comprising an amino acid sequence of SEQ ID NO: 246, a FR H3 comprising an amino acid sequence of SEQ ID NO: 251, and a FR H4 comprising an amino acid sequence of SEQ ID NO: 159.

In some embodiments, the antibody comprises a FR H1 comprising an amino acid sequence of SEQ ID NO: 239, a FR H2 comprising an amino acid sequence of SEQ ID NO: 245, a FR H3 comprising an amino acid sequence of SEQ ID NO: 251, and a FR H4 comprising an amino acid sequence of SEQ ID NO: 159.

In some embodiments, the antibody comprises a FR L1 comprising an amino acid sequence of SEQ ID NO: 161, a FR L2 comprising an amino acid sequence of SEQ ID NO: 252, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO: 252, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 161, a FR L2 comprising an amino acid sequence of SEQ ID NO: 253, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO: 253, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 252, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 252, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 253, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 253, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 161, a FR L2 comprising an amino acid sequence of SEQ ID NO: 163, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO: 164, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO:

165, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO: 166, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO: 167, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO: 168, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 161, a FR L2 comprising an amino acid sequence of SEQ ID NO: 163, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 161, a FR L2 comprising an amino acid sequence of SEQ ID NO: 164, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 161, a FR L2 comprising an amino acid sequence of SEQ ID NO: 165, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 161, a FR L2 comprising an amino acid sequence of SEQ ID NO: 166, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 161, a FR L2 comprising an amino acid sequence of SEQ ID NO: 167, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 161, a FR L2 comprising an amino acid sequence of SEQ ID NO: 168, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 163, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 164, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 165, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 166, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 167, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 168, a FR L3 comprising an amino acid sequence of SEQ ID NO: 170, and a FR L4 comprising an amino acid sequence of SEQ ID NO: 171.

In some embodiments, the antibody comprises a FR L1 comprising an amino acid sequence of SEQ ID NO: 162, a FR L2 comprising an amino acid sequence of SEQ ID NO: 163, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 164, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 165, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 166, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 167, a FR L3 comprising an amino acid sequence of SEQ ID NO: 170, and a FR L4 comprising an amino acid sequence of SEQ ID NO: 172.

In some embodiments, the antibody comprises a FR L1 comprising an amino acid sequence of SEQ ID NO: 162, a FR L2 comprising an amino acid sequence of SEQ ID NO: 168, a FR L3 comprising an amino acid sequence of SEQ ID NO: 170, and a FR L4 comprising an amino acid sequence of SEQ ID NO: 172.

In other more specific embodiments, the humanized antibody or antigen binding fragment thereof provided herein comprises a VH comprising FRs comprising amino acid sequences of the FRs contained in the VH selected from a group consisting of SEQ ID NO: 179, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 106, SEQ ID NO: 108, SEQ ID NO: 110, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225 and SEQ ID NO: 227; and a VL comprising FRs comprising amino acid sequences of the FRs contained in the VL selected from a group consisting of SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, SEQ ID NO: 229, SEQ ID NO: 231, SEQ ID NO: 233, SEQ ID NO: 235 and SEQ ID NO: 237.

As described above, framework regions described herein are determined based upon the boundaries of the CDR numbering system. In other words, if the CDRs are determined by, e.g., Kabat, IMGT, or Chothia, or any combination thereof, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, and/or the Chothia numbering system, FR2 is defined as the amino acid residues between CDR1 and CDR2 amino acid residues as defined by, e.g., the Kabat numbering system, the IMGT numbering system, and/or the Chothia numbering system, FR3 is defined as the amino acid residues between CDR2 and CDR3 amino acid residues as defined by, e.g., the Kabat numbering system, the IMGT numbering system, and/or the Chothia numbering system, and FR4 is defined as the amino acid residues C-terminal to the CDR3 amino acid residues as defined by, e.g., the Kabat numbering system, the IMGT numbering system, and/or the Chothia numbering system.

In some embodiments, the humanized antibody or antigen binding fragment thereof provided herein comprise a VH listed in Table 33 below.

TABLE 33

VH amino acid sequences of exemplary humanized antibodies

| Heavy Vector ID | VH Name | Variable sequence |
|---|---|---|
| A700 | hzR35B9-HV0 | SEQ ID NO: 179 |
| A454 | hzR35B9-HV5a | SEQ ID NO: 66 |
| A455 | hzR35B9-HV5b | SEQ ID NO: 68 |
| A456 | hzR35B9-HV6a | SEQ ID NO: 70 |
| A457 | hzR35B9-HV6b | SEQ ID NO: 72 |
| A458 | hzR35B9-HV6c | SEQ ID NO: 74 |
| A459 | hzR35B9-HV7a | SEQ ID NO: 76 |
| A460 | hzR35B9-HV7b | SEQ ID NO: 78 |
| A461 | hzR35B9-HV7c | SEQ ID NO: 80 |
| A462 | hzR35B9-HV9a | SEQ ID NO: 82 |
| A463 | hzR35B9-HV9b | SEQ ID NO: 84 |
| A464 | hzR35B9-HV10 | SEQ ID NO: 86 |
| A465 | hzR35B9-HV11 | SEQ ID NO: 88 |
| A466 | hzR35B9-HV18 | SEQ ID NO: 90 |
| A512 | hzR35B9(A56)-HV11 | SEQ ID NO: 108 |
| A515 | hzR35B9(Y50A56G57)-HV7b | SEQ ID NO: 110 |
| A553 | hzR35B9(A56)-HV7c | SEQ ID NO: 106 |
| A631 | hzR35B9(A56)-HV12a | SEQ ID NO: 203 |
| A632 | hzR35B9(A56)-HV12b | SEQ ID NO: 205 |
| A633 | hzR35B9(A56)-HV13a | SEQ ID NO: 207 |
| A634 | hzR35B9(A56)-HV13b | SEQ ID NO: 209 |
| A636 | hzR35B9(A56)-HV13d | SEQ ID NO: 211 |
| A638 | hzR35B9(A56)-HV13f | SEQ ID NO: 213 |

TABLE 33-continued

VH amino acid sequences of exemplary humanized antibodies

| Heavy Vector ID | VH Name | Variable sequence |
|---|---|---|
| A639 | hzR35B9(A56)-HV13g | SEQ ID NO: 215 |
| A641 | hzR35B9(A56)-HV16 | SEQ ID NO: 217 |
| A642 | hzR35B9(A56)-HV17a | SEQ ID NO: 219 |
| A643 | hzR35B9(A56)-HV17b | SEQ ID NO: 221 |
| A645 | hzR35B9(A56)-HV17d | SEQ ID NO: 223 |
| A648 | hzR35B9(A56)-HV17g | SEQ ID NO: 225 |
| A650 | hzR35B9(A56)-HV17i | SEQ ID NO: 227 |

In some embodiments, the VH is hzR35B9(A56)-HV12a comprising an amino acid sequence of SEQ ID NO: 203. In some embodiments, the VH is hzR35B9(A56)-HV12b comprising an amino acid sequence of SEQ ID NO: 205. In some embodiments, the VH is hzR35B9(A56)-HV13a comprising an amino acid sequence of SEQ ID NO: 207. In some embodiments, the VH is hzR35B9(A56)-HV13b comprising an amino acid sequence of SEQ ID NO: 209. In some embodiments, the VH is hzR35B9(A56)-HV13d comprising an amino acid sequence of SEQ ID NO: 211. In some embodiments, the VH is hzR35B9(A56)-HV13f comprising an amino acid sequence of SEQ ID NO: 213. In some embodiments, the VH is hzR35B9(A56)-HV13g comprising an amino acid sequence of SEQ ID NO: 215. In some embodiments, the VH is hzR35B9(A56)-HV16 comprising an amino acid sequence of SEQ ID NO: 217. In some embodiments, the VH is hzR35B9(A56)-HV17a comprising an amino acid sequence of SEQ ID NO: 219. In some embodiments, the VH is hzR35B9(A56)-HV17b comprising an amino acid sequence of SEQ ID NO: 221. In some embodiments, the VH is hzR35B9(A56)-HV17d comprising an amino acid sequence of SEQ ID NO: 223. In some embodiments, the VH is hzR35B9(A56)-HV17g comprising an amino acid sequence of SEQ ID NO: 225. In some embodiments, the VH is hzR35B9(A56)-HV17i comprising an amino acid sequence of SEQ ID NO: 227.

In some embodiments, the VH is hzR35B9-HV0 comprising an amino acid sequence of SEQ ID NO: 179. In some embodiments, the VH is hzR35B9-HV5a comprising an amino acid sequence of SEQ ID NO: 66. In some embodiments, the VH is AhzR35B9-HV5b comprising an amino acid sequence of SEQ ID NO: 68. In some embodiments, the VH is hzR35B9-HV6a comprising an amino acid sequence of SEQ ID NO: 70. In some embodiments, the VH is hzR35B9-HV6b comprising an amino acid sequence of SEQ ID NO: 72. In some embodiments, the VH is hzR35B9-HV6c comprising an amino acid sequence of SEQ ID NO: 74. In some embodiments, the VH is hzR35B9-HV7a comprising an amino acid sequence of SEQ ID NO: 76. In some embodiments, the VH is hzR35B9-HV7b comprising an amino acid sequence of SEQ ID NO: 78. In some embodiments, the VH is hzR35B9-HV7c comprising an amino acid sequence of SEQ ID NO: 80. In some embodiments, the VH is hzR35B9-HV9a comprising an amino acid sequence of SEQ ID NO: 82. In some embodiments, the VH is hzR35B9-HV9b comprising an amino acid sequence of SEQ ID NO: 84. In some embodiments, the VH is hzR35B9-HV10 comprising an amino acid sequence of SEQ ID NO: 86. In some embodiments, the VH is hzR35B9-HV11 comprising an amino acid sequence of SEQ ID NO: 88. In some embodiments, the VH is hzR35B9-HV18 comprising an amino acid sequence of SEQ ID NO: 90. In some embodiments, the VH is hzR35B9(A56)-HV11 comprising an amino acid sequence of SEQ ID NO: 108. In some embodiments, the VH is hzR35B9(Y50A56G57)-HV7b comprising an amino acid sequence of SEQ ID NO: 110. In some embodiments, the VH is hzR35B9(A56)-HV7c comprising an amino acid sequence of SEQ ID NO: 106.

In some embodiments, the humanized antibody or antigen binding fragment thereof provided herein comprises a VL listed in Table 34 below.

TABLE 34

VL amino acid sequences of exemplary humanized antibodies

| Light Vector ID | VL Name | Variable sequence |
|---|---|---|
| A467 | hzR35B9-LV0 | SEQ ID NO: 92 |
| A468 | hzR35B9-LV1a | SEQ ID NO: 94 |
| A469 | hzR35B9-LV1b | SEQ ID NO: 96 |
| A470 | hzR35B9-LV3a | SEQ ID NO: 98 |
| A471 | hzR35B9-LV3b | SEQ ID NO: 100 |
| A472 | hzR35B9-LV4 | SEQ ID NO: 102 |
| A473 | hzR35B9-LV5 | SEQ ID NO: 104 |
| A518 | hzR35B9(H98)-LV1a | SEQ ID NO: 112 |
| A651 | hzR35B9(A56)-LV2a | SEQ ID NO: 229 |
| A652 | hzR35B9(A56)-LV2b | SEQ ID NO: 231 |
| A653 | hzR35B9(A56)-LV2c | SEQ ID NO: 233 |
| A654 | hzR35B9(A56)-LV2d | SEQ ID NO: 235 |
| A656 | hzR35B9(A56)-LV2f | SEQ ID NO: 237 |

In some embodiments, the VL is hzR35B9-LV0 comprising an amino acid sequence of SEQ ID NO: 92. In some embodiments, the VL is hzR35B9-LV1a comprising an amino acid sequence of SEQ ID NO: 94. In some embodiments, the VL is hzR35B9-LV1b comprising an amino acid sequence of SEQ ID NO: 96. In some embodiments, the VL is hzR35B9-LV3a comprising an amino acid sequence of SEQ ID NO: 98. In some embodiments, the VL is hzR35B9-LV3b comprising an amino acid sequence of SEQ ID NO: 100. In some embodiments, the VL is hzR35B9-LV4 comprising an amino acid sequence of SEQ ID NO: 102. In some embodiments, the VL is hzR35B9-LV5 comprising an amino acid sequence of SEQ ID NO: 104. In some embodiments, the VL is hzR35B9(H98)-LV1a comprising an amino acid sequence of SEQ ID NO: 112.

In some embodiments, the VL is hzR35B9(A56)-LV2a comprising an amino acid sequence of SEQ ID NO: 229. In some embodiments, the VL is hzR35B9(A56)-LV2b comprising an amino acid sequence of SEQ ID NO: 231. In some embodiments, the VL is hzR35B9(A56)-LV2c comprising an amino acid sequence of SEQ ID NO: 233. In some embodiments, the VL is hzR35B9(A56)-LV2d comprising an amino acid sequence of SEQ ID NO: 235. In some embodiments, the VL is hzR35B9(A56)-LV2f comprising an amino acid sequence of SEQ ID NO: 237.

In certain embodiments, the humanized antibody or antigen binding fragment thereof provided herein comprises VH and/or VL in Table 35.

TABLE 35

Amino acid sequences of exemplary humanized antibodies

| Antibody Name | VH | VL |
|---|---|---|
| A700/A467 | SEQ ID NO: 179 | SEQ ID NO: 92 |
| A700/A468 | SEQ ID NO: 179 | SEQ ID NO: 94 |
| A700/A469 | SEQ ID NO: 179 | SEQ ID NO: 96 |
| A700/A470 | SEQ ID NO: 179 | SEQ ID NO: 98 |
| A700/A471 | SEQ ID NO: 179 | SEQ ID NO: 100 |
| A700/A472 | SEQ ID NO: 179 | SEQ ID NO: 102 |
| A700/A473 | SEQ ID NO: 179 | SEQ ID NO: 104 |
| A700/A518 | SEQ ID NO: 179 | SEQ ID NO: 112 |
| A700/A651 | SEQ ID NO: 179 | SEQ ID NO: 229 |

TABLE 35-continued

Amino acid sequences of exemplary humanized antibodies

| Antibody Name | VH | VL |
|---|---|---|
| A700/A652 | SEQ ID NO: 179 | SEQ ID NO: 231 |
| A700/A653 | SEQ ID NO: 179 | SEQ ID NO: 233 |
| A700/A654 | SEQ ID NO: 179 | SEQ ID NO: 235 |
| A700/A656 | SEQ ID NO: 179 | SEQ ID NO: 237 |
| A454/A467 | SEQ ID NO: 66 | SEQ ID NO: 92 |
| A454/A468 | SEQ ID NO: 66 | SEQ ID NO: 94 |
| A454/A469 | SEQ ID NO: 66 | SEQ ID NO: 96 |
| A454/A470 | SEQ ID NO: 66 | SEQ ID NO: 98 |
| A454/A471 | SEQ ID NO: 66 | SEQ ID NO: 100 |
| A454/A472 | SEQ ID NO: 66 | SEQ ID NO: 102 |
| A454/A473 | SEQ ID NO: 66 | SEQ ID NO: 104 |
| A454/A518 | SEQ ID NO: 66 | SEQ ID NO: 112 |
| A454/A651 | SEQ ID NO: 66 | SEQ ID NO: 229 |
| A454/A652 | SEQ ID NO: 66 | SEQ ID NO: 231 |
| A454/A653 | SEQ ID NO: 66 | SEQ ID NO: 233 |
| A454/A654 | SEQ ID NO: 66 | SEQ ID NO: 235 |
| A454/A656 | SEQ ID NO: 66 | SEQ ID NO: 237 |
| A455/A467 | SEQ ID NO: 68 | SEQ ID NO: 92 |
| A455/A468 | SEQ ID NO: 68 | SEQ ID NO: 94 |
| A455/A469 | SEQ ID NO: 68 | SEQ ID NO: 96 |
| A455/A470 | SEQ ID NO: 68 | SEQ ID NO: 98 |
| A455/A471 | SEQ ID NO: 68 | SEQ ID NO: 100 |
| A455/A472 | SEQ ID NO: 68 | SEQ ID NO: 102 |
| A455/A473 | SEQ ID NO: 68 | SEQ ID NO: 104 |
| A455/A518 | SEQ ID NO: 68 | SEQ ID NO: 112 |
| A455/A651 | SEQ ID NO: 68 | SEQ ID NO: 229 |
| A455/A652 | SEQ ID NO: 68 | SEQ ID NO: 231 |
| A455/A653 | SEQ ID NO: 68 | SEQ ID NO: 233 |
| A455/A654 | SEQ ID NO: 68 | SEQ ID NO: 235 |
| A455/A656 | SEQ ID NO: 68 | SEQ ID NO: 237 |
| A456/A467 | SEQ ID NO: 70 | SEQ ID NO: 92 |
| A456/A468 | SEQ ID NO: 70 | SEQ ID NO: 94 |
| A456/A469 | SEQ ID NO: 70 | SEQ ID NO: 96 |
| A456/A470 | SEQ ID NO: 70 | SEQ ID NO: 98 |
| A456/A471 | SEQ ID NO: 70 | SEQ ID NO: 100 |
| A456/A472 | SEQ ID NO: 70 | SEQ ID NO: 102 |
| A456/A473 | SEQ ID NO: 70 | SEQ ID NO: 104 |
| A456/A518 | SEQ ID NO: 70 | SEQ ID NO: 112 |
| A456/A651 | SEQ ID NO: 70 | SEQ ID NO: 229 |
| A456/A652 | SEQ ID NO: 70 | SEQ ID NO: 231 |
| A456/A653 | SEQ ID NO: 70 | SEQ ID NO: 233 |
| A456/A654 | SEQ ID NO: 70 | SEQ ID NO: 235 |
| A456/A656 | SEQ ID NO: 70 | SEQ ID NO: 237 |
| A457/A467 | SEQ ID NO: 72 | SEQ ID NO: 92 |
| A457/A468 | SEQ ID NO: 72 | SEQ ID NO: 94 |
| A457/A469 | SEQ ID NO: 72 | SEQ ID NO: 96 |
| A457/A470 | SEQ ID NO: 72 | SEQ ID NO: 98 |
| A457/A471 | SEQ ID NO: 72 | SEQ ID NO: 100 |
| A457/A472 | SEQ ID NO: 72 | SEQ ID NO: 102 |
| A457/A473 | SEQ ID NO: 72 | SEQ ID NO: 104 |
| A457/A518 | SEQ ID NO: 72 | SEQ ID NO: 112 |
| A457/A651 | SEQ ID NO: 72 | SEQ ID NO: 229 |
| A457/A652 | SEQ ID NO: 72 | SEQ ID NO: 231 |
| A457/A653 | SEQ ID NO: 72 | SEQ ID NO: 233 |
| A457/A654 | SEQ ID NO: 72 | SEQ ID NO: 235 |
| A457/A656 | SEQ ID NO: 72 | SEQ ID NO: 237 |
| A458/A467 | SEQ ID NO: 74 | SEQ ID NO: 92 |
| A458/A468 | SEQ ID NO: 74 | SEQ ID NO: 94 |
| A458/A469 | SEQ ID NO: 74 | SEQ ID NO: 96 |
| A458/A470 | SEQ ID NO: 74 | SEQ ID NO: 98 |
| A458/A471 | SEQ ID NO: 74 | SEQ ID NO: 100 |
| A458/A472 | SEQ ID NO: 74 | SEQ ID NO: 102 |
| A458/A473 | SEQ ID NO: 74 | SEQ ID NO: 104 |
| A458/A518 | SEQ ID NO: 74 | SEQ ID NO: 112 |
| A458/A651 | SEQ ID NO: 74 | SEQ ID NO: 229 |
| A458/A652 | SEQ ID NO: 74 | SEQ ID NO: 231 |
| A458/A653 | SEQ ID NO: 74 | SEQ ID NO: 233 |
| A458/A654 | SEQ ID NO: 74 | SEQ ID NO: 235 |
| A458/A656 | SEQ ID NO: 74 | SEQ ID NO: 237 |
| A459/A467 | SEQ ID NO: 76 | SEQ ID NO: 92 |
| A459/A468 | SEQ ID NO: 76 | SEQ ID NO: 94 |
| A459/A469 | SEQ ID NO: 76 | SEQ ID NO: 96 |
| A459/A470 | SEQ ID NO: 76 | SEQ ID NO: 98 |
| A459/A471 | SEQ ID NO: 76 | SEQ ID NO: 100 |
| A459/A472 | SEQ ID NO: 76 | SEQ ID NO: 102 |
| A459/A473 | SEQ ID NO: 76 | SEQ ID NO: 104 |

TABLE 35-continued

Amino acid sequences of exemplary humanized antibodies

| Antibody Name | VH | VL |
|---|---|---|
| A459/A518 | SEQ ID NO: 76 | SEQ ID NO: 112 |
| A459/A651 | SEQ ID NO: 76 | SEQ ID NO: 229 |
| A459/A652 | SEQ ID NO: 76 | SEQ ID NO: 231 |
| A459/A653 | SEQ ID NO: 76 | SEQ ID NO: 233 |
| A459/A654 | SEQ ID NO: 76 | SEQ ID NO: 235 |
| A459/A656 | SEQ ID NO: 76 | SEQ ID NO: 237 |
| A460/A467 | SEQ ID NO: 78 | SEQ ID NO: 92 |
| A460/A468 | SEQ ID NO: 78 | SEQ ID NO: 94 |
| A460/A469 | SEQ ID NO: 78 | SEQ ID NO: 96 |
| A460/A470 | SEQ ID NO: 78 | SEQ ID NO: 98 |
| A460/A471 | SEQ ID NO: 78 | SEQ ID NO: 100 |
| A460/A472 | SEQ ID NO: 78 | SEQ ID NO: 102 |
| A460/A473 | SEQ ID NO: 78 | SEQ ID NO: 104 |
| A460/A518 | SEQ ID NO: 78 | SEQ ID NO: 112 |
| A460/A651 | SEQ ID NO: 78 | SEQ ID NO: 229 |
| A460/A652 | SEQ ID NO: 78 | SEQ ID NO: 231 |
| A460/A653 | SEQ ID NO: 78 | SEQ ID NO: 233 |
| A460/A654 | SEQ ID NO: 78 | SEQ ID NO: 235 |
| A460/A656 | SEQ ID NO: 78 | SEQ ID NO: 237 |
| A461/A467 | SEQ ID NO: 80 | SEQ ID NO: 92 |
| A461/A468 | SEQ ID NO: 80 | SEQ ID NO: 94 |
| A461/A469 | SEQ ID NO: 80 | SEQ ID NO: 96 |
| A461/A470 | SEQ ID NO: 80 | SEQ ID NO: 98 |
| A461/A471 | SEQ ID NO: 80 | SEQ ID NO: 100 |
| A461/A472 | SEQ ID NO: 80 | SEQ ID NO: 102 |
| A461/A473 | SEQ ID NO: 80 | SEQ ID NO: 104 |
| A461/A518 | SEQ ID NO: 80 | SEQ ID NO: 112 |
| A461/A651 | SEQ ID NO: 80 | SEQ ID NO: 229 |
| A461/A652 | SEQ ID NO: 80 | SEQ ID NO: 231 |
| A461/A653 | SEQ ID NO: 80 | SEQ ID NO: 233 |
| A461/A654 | SEQ ID NO: 80 | SEQ ID NO: 235 |
| A461/A656 | SEQ ID NO: 80 | SEQ ID NO: 237 |
| A462/A467 | SEQ ID NO: 82 | SEQ ID NO: 92 |
| A462/A468 | SEQ ID NO: 82 | SEQ ID NO: 94 |
| A462/A469 | SEQ ID NO: 82 | SEQ ID NO: 96 |
| A462/A470 | SEQ ID NO: 82 | SEQ ID NO: 98 |
| A462/A471 | SEQ ID NO: 82 | SEQ ID NO: 100 |
| A462/A472 | SEQ ID NO: 82 | SEQ ID NO: 102 |
| A462/A473 | SEQ ID NO: 82 | SEQ ID NO: 104 |
| A462/A518 | SEQ ID NO: 82 | SEQ ID NO: 112 |
| A462/A651 | SEQ ID NO: 82 | SEQ ID NO: 229 |
| A462/A652 | SEQ ID NO: 82 | SEQ ID NO: 231 |
| A462/A653 | SEQ ID NO: 82 | SEQ ID NO: 233 |
| A462/A654 | SEQ ID NO: 82 | SEQ ID NO: 235 |
| A462/A656 | SEQ ID NO: 82 | SEQ ID NO: 237 |
| A463/A467 | SEQ ID NO: 84 | SEQ ID NO: 92 |
| A463/A468 | SEQ ID NO: 84 | SEQ ID NO: 94 |
| A463/A469 | SEQ ID NO: 84 | SEQ ID NO: 96 |
| A463/A470 | SEQ ID NO: 84 | SEQ ID NO: 98 |
| A463/A471 | SEQ ID NO: 84 | SEQ ID NO: 100 |
| A463/A472 | SEQ ID NO: 84 | SEQ ID NO: 102 |
| A463/A473 | SEQ ID NO: 84 | SEQ ID NO: 104 |
| A463/A518 | SEQ ID NO: 84 | SEQ ID NO: 112 |
| A463/A651 | SEQ ID NO: 84 | SEQ ID NO: 229 |
| A463/A652 | SEQ ID NO: 84 | SEQ ID NO: 231 |
| A463/A653 | SEQ ID NO: 84 | SEQ ID NO: 233 |
| A463/A654 | SEQ ID NO: 84 | SEQ ID NO: 235 |
| A463/A656 | SEQ ID NO: 84 | SEQ ID NO: 237 |
| A464/A467 | SEQ ID NO: 86 | SEQ ID NO: 92 |
| A464/A468 | SEQ ID NO: 86 | SEQ ID NO: 94 |
| A464/A469 | SEQ ID NO: 86 | SEQ ID NO: 96 |
| A464/A470 | SEQ ID NO: 86 | SEQ ID NO: 98 |
| A464/A471 | SEQ ID NO: 86 | SEQ ID NO: 100 |
| A464/A472 | SEQ ID NO: 86 | SEQ ID NO: 102 |
| A464/A473 | SEQ ID NO: 86 | SEQ ID NO: 104 |
| A464/A518 | SEQ ID NO: 86 | SEQ ID NO: 112 |
| A464/A651 | SEQ ID NO: 86 | SEQ ID NO: 229 |
| A464/A652 | SEQ ID NO: 86 | SEQ ID NO: 231 |
| A464/A653 | SEQ ID NO: 86 | SEQ ID NO: 233 |
| A464/A654 | SEQ ID NO: 86 | SEQ ID NO: 235 |
| A464/A656 | SEQ ID NO: 86 | SEQ ID NO: 237 |
| A465/A467 | SEQ ID NO: 88 | SEQ ID NO: 92 |
| A465/A468 | SEQ ID NO: 88 | SEQ ID NO: 94 |
| A465/A469 | SEQ ID NO: 88 | SEQ ID NO: 96 |
| A465/A470 | SEQ ID NO: 88 | SEQ ID NO: 98 |
| A465/A471 | SEQ ID NO: 88 | SEQ ID NO: 100 |
| A465/A472 | SEQ ID NO: 88 | SEQ ID NO: 102 |
| A465/A473 | SEQ ID NO: 88 | SEQ ID NO: 104 |
| A465/A518 | SEQ ID NO: 88 | SEQ ID NO: 112 |
| A465/A651 | SEQ ID NO: 88 | SEQ ID NO: 229 |
| A465/A652 | SEQ ID NO: 88 | SEQ ID NO: 231 |
| A465/A653 | SEQ ID NO: 88 | SEQ ID NO: 233 |
| A465/A654 | SEQ ID NO: 88 | SEQ ID NO: 235 |
| A465/A656 | SEQ ID NO: 88 | SEQ ID NO: 237 |
| A466/A467 | SEQ ID NO: 90 | SEQ ID NO: 92 |
| A466/A468 | SEQ ID NO: 90 | SEQ ID NO: 94 |
| A466/A469 | SEQ ID NO: 90 | SEQ ID NO: 96 |
| A466/A470 | SEQ ID NO: 90 | SEQ ID NO: 98 |
| A466/A471 | SEQ ID NO: 90 | SEQ ID NO: 100 |
| A466/A472 | SEQ ID NO: 90 | SEQ ID NO: 102 |
| A466/A473 | SEQ ID NO: 90 | SEQ ID NO: 104 |
| A466/A518 | SEQ ID NO: 90 | SEQ ID NO: 112 |
| A466/A651 | SEQ ID NO: 90 | SEQ ID NO: 229 |
| A466/A652 | SEQ ID NO: 90 | SEQ ID NO: 231 |
| A466/A653 | SEQ ID NO: 90 | SEQ ID NO: 233 |
| A466/A654 | SEQ ID NO: 90 | SEQ ID NO: 235 |
| A466/A656 | SEQ ID NO: 90 | SEQ ID NO: 237 |
| A512/A467 | SEQ ID NO: 108 | SEQ ID NO: 92 |
| A512/A468 | SEQ ID NO: 108 | SEQ ID NO: 94 |
| A512/A469 | SEQ ID NO: 108 | SEQ ID NO: 96 |
| A512/A470 | SEQ ID NO: 108 | SEQ ID NO: 98 |
| A512/A471 | SEQ ID NO: 108 | SEQ ID NO: 100 |
| A512/A472 | SEQ ID NO: 108 | SEQ ID NO: 102 |
| A512/A473 | SEQ ID NO: 108 | SEQ ID NO: 104 |
| A512/A518 | SEQ ID NO: 108 | SEQ ID NO: 112 |
| A512/A651 | SEQ ID NO: 108 | SEQ ID NO: 229 |
| A512/A652 | SEQ ID NO: 108 | SEQ ID NO: 231 |
| A512/A653 | SEQ ID NO: 108 | SEQ ID NO: 233 |
| A512/A654 | SEQ ID NO: 108 | SEQ ID NO: 235 |
| A512/A656 | SEQ ID NO: 108 | SEQ ID NO: 237 |
| A515/A467 | SEQ ID NO: 110 | SEQ ID NO: 92 |
| A515/A468 | SEQ ID NO: 110 | SEQ ID NO: 94 |
| A515/A469 | SEQ ID NO: 110 | SEQ ID NO: 96 |
| A515/A470 | SEQ ID NO: 110 | SEQ ID NO: 98 |
| A515/A471 | SEQ ID NO: 110 | SEQ ID NO: 100 |
| A515/A472 | SEQ ID NO: 110 | SEQ ID NO: 102 |
| A515/A473 | SEQ ID NO: 110 | SEQ ID NO: 104 |
| A515/A518 | SEQ ID NO: 110 | SEQ ID NO: 112 |
| A515/A651 | SEQ ID NO: 110 | SEQ ID NO: 229 |
| A515/A652 | SEQ ID NO: 110 | SEQ ID NO: 231 |
| A515/A653 | SEQ ID NO: 110 | SEQ ID NO: 233 |
| A515/A654 | SEQ ID NO: 110 | SEQ ID NO: 235 |
| A515/A656 | SEQ ID NO: 110 | SEQ ID NO: 237 |
| A553/A467 | SEQ ID NO: 106 | SEQ ID NO: 92 |
| A553/A468 | SEQ ID NO: 106 | SEQ ID NO: 94 |
| A553/A469 | SEQ ID NO: 106 | SEQ ID NO: 96 |
| A553/A470 | SEQ ID NO: 106 | SEQ ID NO: 98 |
| A553/A471 | SEQ ID NO: 106 | SEQ ID NO: 100 |
| A553/A472 | SEQ ID NO: 106 | SEQ ID NO: 102 |
| A553/A473 | SEQ ID NO: 106 | SEQ ID NO: 104 |
| A553/A518 | SEQ ID NO: 106 | SEQ ID NO: 112 |
| A553/A651 | SEQ ID NO: 106 | SEQ ID NO: 229 |
| A553/A652 | SEQ ID NO: 106 | SEQ ID NO: 231 |
| A553/A653 | SEQ ID NO: 106 | SEQ ID NO: 233 |
| A553/A654 | SEQ ID NO: 106 | SEQ ID NO: 235 |
| A553/A656 | SEQ ID NO: 106 | SEQ ID NO: 237 |
| A631/A467 | SEQ ID NO: 203 | SEQ ID NO: 92 |
| A631/A468 | SEQ ID NO: 203 | SEQ ID NO: 94 |
| A631/A469 | SEQ ID NO: 203 | SEQ ID NO: 96 |
| A631/A470 | SEQ ID NO: 203 | SEQ ID NO: 98 |
| A631/A471 | SEQ ID NO: 203 | SEQ ID NO: 100 |
| A631/A472 | SEQ ID NO: 203 | SEQ ID NO: 102 |
| A631/A473 | SEQ ID NO: 203 | SEQ ID NO: 104 |
| A631/A518 | SEQ ID NO: 203 | SEQ ID NO: 112 |
| A631/A651 | SEQ ID NO: 203 | SEQ ID NO: 229 |
| A631/A652 | SEQ ID NO: 203 | SEQ ID NO: 231 |
| A631/A653 | SEQ ID NO: 203 | SEQ ID NO: 233 |
| A631/A654 | SEQ ID NO: 203 | SEQ ID NO: 235 |
| A631/A656 | SEQ ID NO: 203 | SEQ ID NO: 237 |
| A632/A467 | SEQ ID NO: 205 | SEQ ID NO: 92 |
| A632/A468 | SEQ ID NO: 205 | SEQ ID NO: 94 |
| A632/A469 | SEQ ID NO: 205 | SEQ ID NO: 96 |

TABLE 35-continued

Amino acid sequences of exemplary humanized antibodies

| Antibody Name | VH | VL |
|---|---|---|
| A632/A470 | SEQ ID NO: 205 | SEQ ID NO: 98 |
| A632/A471 | SEQ ID NO: 205 | SEQ ID NO: 100 |
| A632/A472 | SEQ ID NO: 205 | SEQ ID NO: 102 |
| A632/A473 | SEQ ID NO: 205 | SEQ ID NO: 104 |
| A632/A518 | SEQ ID NO: 205 | SEQ ID NO: 112 |
| A632/A651 | SEQ ID NO: 205 | SEQ ID NO: 229 |
| A632/A652 | SEQ ID NO: 205 | SEQ ID NO: 231 |
| A632/A653 | SEQ ID NO: 205 | SEQ ID NO: 233 |
| A632/A654 | SEQ ID NO: 205 | SEQ ID NO: 235 |
| A632/A656 | SEQ ID NO: 205 | SEQ ID NO: 237 |
| A633/A467 | SEQ ID NO: 207 | SEQ ID NO: 92 |
| A633/A468 | SEQ ID NO: 207 | SEQ ID NO: 94 |
| A633/A469 | SEQ ID NO: 207 | SEQ ID NO: 96 |
| A633/A470 | SEQ ID NO: 207 | SEQ ID NO: 98 |
| A633/A471 | SEQ ID NO: 207 | SEQ ID NO: 100 |
| A633/A472 | SEQ ID NO: 207 | SEQ ID NO: 102 |
| A633/A473 | SEQ ID NO: 207 | SEQ ID NO: 104 |
| A633/A518 | SEQ ID NO: 207 | SEQ ID NO: 112 |
| A633/A651 | SEQ ID NO: 207 | SEQ ID NO: 229 |
| A633/A652 | SEQ ID NO: 207 | SEQ ID NO: 231 |
| A633/A653 | SEQ ID NO: 207 | SEQ ID NO: 233 |
| A633/A654 | SEQ ID NO: 207 | SEQ ID NO: 235 |
| A633/A656 | SEQ ID NO: 207 | SEQ ID NO: 237 |
| A634/A467 | SEQ ID NO: 209 | SEQ ID NO: 92 |
| A634/A468 | SEQ ID NO: 209 | SEQ ID NO: 94 |
| A634/A469 | SEQ ID NO: 209 | SEQ ID NO: 96 |
| A634/A470 | SEQ ID NO: 209 | SEQ ID NO: 98 |
| A634/A471 | SEQ ID NO: 209 | SEQ ID NO: 100 |
| A634/A472 | SEQ ID NO: 209 | SEQ ID NO: 102 |
| A634/A473 | SEQ ID NO: 209 | SEQ ID NO: 104 |
| A634/A518 | SEQ ID NO: 209 | SEQ ID NO: 112 |
| A634/A651 | SEQ ID NO: 209 | SEQ ID NO: 229 |
| A634/A652 | SEQ ID NO: 209 | SEQ ID NO: 231 |
| A634/A653 | SEQ ID NO: 209 | SEQ ID NO: 233 |
| A634/A654 | SEQ ID NO: 209 | SEQ ID NO: 235 |
| A634/A656 | SEQ ID NO: 209 | SEQ ID NO: 237 |
| A636/A467 | SEQ ID NO: 211 | SEQ ID NO: 92 |
| A636/A468 | SEQ ID NO: 211 | SEQ ID NO: 94 |
| A636/A469 | SEQ ID NO: 211 | SEQ ID NO: 96 |
| A636/A470 | SEQ ID NO: 211 | SEQ ID NO: 98 |
| A636/A471 | SEQ ID NO: 211 | SEQ ID NO: 100 |
| A636/A472 | SEQ ID NO: 211 | SEQ ID NO: 102 |
| A636/A473 | SEQ ID NO: 211 | SEQ ID NO: 104 |
| A636/A518 | SEQ ID NO: 211 | SEQ ID NO: 112 |
| A636/A651 | SEQ ID NO: 211 | SEQ ID NO: 229 |
| A636/A652 | SEQ ID NO: 211 | SEQ ID NO: 231 |
| A636/A653 | SEQ ID NO: 211 | SEQ ID NO: 233 |
| A636/A654 | SEQ ID NO: 211 | SEQ ID NO: 235 |
| A636/A656 | SEQ ID NO: 211 | SEQ ID NO: 237 |
| A638/A467 | SEQ ID NO: 213 | SEQ ID NO: 92 |
| A638/A468 | SEQ ID NO: 213 | SEQ ID NO: 94 |
| A638/A469 | SEQ ID NO: 213 | SEQ ID NO: 96 |
| A638/A470 | SEQ ID NO: 213 | SEQ ID NO: 98 |
| A638/A471 | SEQ ID NO: 213 | SEQ ID NO: 100 |
| A638/A472 | SEQ ID NO: 213 | SEQ ID NO: 102 |
| A638/A473 | SEQ ID NO: 213 | SEQ ID NO: 104 |
| A638/A518 | SEQ ID NO: 213 | SEQ ID NO: 112 |
| A638/A651 | SEQ ID NO: 213 | SEQ ID NO: 229 |
| A638/A652 | SEQ ID NO: 213 | SEQ ID NO: 231 |
| A638/A653 | SEQ ID NO: 213 | SEQ ID NO: 233 |
| A638/A654 | SEQ ID NO: 213 | SEQ ID NO: 235 |
| A638/A656 | SEQ ID NO: 213 | SEQ ID NO: 237 |
| A639/A467 | SEQ ID NO: 215 | SEQ ID NO: 92 |
| A639/A468 | SEQ ID NO: 215 | SEQ ID NO: 94 |
| A639/A469 | SEQ ID NO: 215 | SEQ ID NO: 96 |
| A639/A470 | SEQ ID NO: 215 | SEQ ID NO: 98 |
| A639/A471 | SEQ ID NO: 215 | SEQ ID NO: 100 |
| A639/A472 | SEQ ID NO: 215 | SEQ ID NO: 102 |
| A639/A473 | SEQ ID NO: 215 | SEQ ID NO: 104 |
| A639/A518 | SEQ ID NO: 215 | SEQ ID NO: 112 |
| A639/A651 | SEQ ID NO: 215 | SEQ ID NO: 229 |
| A639/A652 | SEQ ID NO: 215 | SEQ ID NO: 231 |
| A639/A653 | SEQ ID NO: 215 | SEQ ID NO: 233 |
| A639/A654 | SEQ ID NO: 215 | SEQ ID NO: 235 |
| A639/A656 | SEQ ID NO: 215 | SEQ ID NO: 237 |
| A641/A467 | SEQ ID NO: 217 | SEQ ID NO: 92 |
| A641/A468 | SEQ ID NO: 217 | SEQ ID NO: 94 |
| A641/A469 | SEQ ID NO: 217 | SEQ ID NO: 96 |
| A641/A470 | SEQ ID NO: 217 | SEQ ID NO: 98 |
| A641/A471 | SEQ ID NO: 217 | SEQ ID NO: 100 |
| A641/A472 | SEQ ID NO: 217 | SEQ ID NO: 102 |
| A641/A473 | SEQ ID NO: 217 | SEQ ID NO: 104 |
| A641/A518 | SEQ ID NO: 217 | SEQ ID NO: 112 |
| A641/A651 | SEQ ID NO: 217 | SEQ ID NO: 229 |
| A641/A652 | SEQ ID NO: 217 | SEQ ID NO: 231 |
| A641/A653 | SEQ ID NO: 217 | SEQ ID NO: 233 |
| A641/A654 | SEQ ID NO: 217 | SEQ ID NO: 235 |
| A641/A656 | SEQ ID NO: 217 | SEQ ID NO: 237 |
| A642/A467 | SEQ ID NO: 219 | SEQ ID NO: 92 |
| A642/A468 | SEQ ID NO: 219 | SEQ ID NO: 94 |
| A642/A469 | SEQ ID NO: 219 | SEQ ID NO: 96 |
| A642/A470 | SEQ ID NO: 219 | SEQ ID NO: 98 |
| A642/A471 | SEQ ID NO: 219 | SEQ ID NO: 100 |
| A642/A472 | SEQ ID NO: 219 | SEQ ID NO: 102 |
| A642/A473 | SEQ ID NO: 219 | SEQ ID NO: 104 |
| A642/A518 | SEQ ID NO: 219 | SEQ ID NO: 112 |
| A642/A651 | SEQ ID NO: 219 | SEQ ID NO: 229 |
| A642/A652 | SEQ ID NO: 219 | SEQ ID NO: 231 |
| A642/A653 | SEQ ID NO: 219 | SEQ ID NO: 233 |
| A642/A654 | SEQ ID NO: 219 | SEQ ID NO: 235 |
| A642/A656 | SEQ ID NO: 219 | SEQ ID NO: 237 |
| A643/A467 | SEQ ID NO: 221 | SEQ ID NO: 92 |
| A643/A468 | SEQ ID NO: 221 | SEQ ID NO: 94 |
| A643/A469 | SEQ ID NO: 221 | SEQ ID NO: 96 |
| A643/A470 | SEQ ID NO: 221 | SEQ ID NO: 98 |
| A643/A471 | SEQ ID NO: 221 | SEQ ID NO: 100 |
| A643/A472 | SEQ ID NO: 221 | SEQ ID NO: 102 |
| A643/A473 | SEQ ID NO: 221 | SEQ ID NO: 104 |
| A643/A518 | SEQ ID NO: 221 | SEQ ID NO: 112 |
| A643/A651 | SEQ ID NO: 221 | SEQ ID NO: 229 |
| A643/A652 | SEQ ID NO: 221 | SEQ ID NO: 231 |
| A643/A653 | SEQ ID NO: 221 | SEQ ID NO: 233 |
| A643/A654 | SEQ ID NO: 221 | SEQ ID NO: 235 |
| A643/A656 | SEQ ID NO: 221 | SEQ ID NO: 237 |
| A645/A467 | SEQ ID NO: 223 | SEQ ID NO: 92 |
| A645/A468 | SEQ ID NO: 223 | SEQ ID NO: 94 |
| A645/A469 | SEQ ID NO: 223 | SEQ ID NO: 96 |
| A645/A470 | SEQ ID NO: 223 | SEQ ID NO: 98 |
| A645/A471 | SEQ ID NO: 223 | SEQ ID NO: 100 |
| A645/A472 | SEQ ID NO: 223 | SEQ ID NO: 102 |
| A645/A473 | SEQ ID NO: 223 | SEQ ID NO: 104 |
| A645/A518 | SEQ ID NO: 223 | SEQ ID NO: 112 |
| A645/A651 | SEQ ID NO: 223 | SEQ ID NO: 229 |
| A645/A652 | SEQ ID NO: 223 | SEQ ID NO: 231 |
| A645/A653 | SEQ ID NO: 223 | SEQ ID NO: 233 |
| A645/A654 | SEQ ID NO: 223 | SEQ ID NO: 235 |
| A645/A656 | SEQ ID NO: 223 | SEQ ID NO: 237 |
| A648/A467 | SEQ ID NO: 225 | SEQ ID NO: 92 |
| A648/A468 | SEQ ID NO: 225 | SEQ ID NO: 94 |
| A648/A469 | SEQ ID NO: 225 | SEQ ID NO: 96 |
| A648/A470 | SEQ ID NO: 225 | SEQ ID NO: 98 |
| A648/A471 | SEQ ID NO: 225 | SEQ ID NO: 100 |
| A648/A472 | SEQ ID NO: 225 | SEQ ID NO: 102 |
| A648/A473 | SEQ ID NO: 225 | SEQ ID NO: 104 |
| A648/A518 | SEQ ID NO: 225 | SEQ ID NO: 112 |
| A648/A651 | SEQ ID NO: 225 | SEQ ID NO: 229 |
| A648/A652 | SEQ ID NO: 225 | SEQ ID NO: 231 |
| A648/A653 | SEQ ID NO: 225 | SEQ ID NO: 233 |
| A648/A654 | SEQ ID NO: 225 | SEQ ID NO: 235 |
| A648/A656 | SEQ ID NO: 225 | SEQ ID NO: 237 |
| A650/A467 | SEQ ID NO: 227 | SEQ ID NO: 92 |
| A650/A468 | SEQ ID NO: 227 | SEQ ID NO: 94 |
| A650/A469 | SEQ ID NO: 227 | SEQ ID NO: 96 |
| A650/A470 | SEQ ID NO: 227 | SEQ ID NO: 98 |
| A650/A471 | SEQ ID NO: 227 | SEQ ID NO: 100 |
| A650/A472 | SEQ ID NO: 227 | SEQ ID NO: 102 |
| A650/A473 | SEQ ID NO: 227 | SEQ ID NO: 104 |
| A650/A518 | SEQ ID NO: 227 | SEQ ID NO: 112 |

TABLE 35-continued

Amino acid sequences of exemplary humanized antibodies

| Antibody Name | VH | VL |
|---|---|---|
| A650/A651 | SEQ ID NO: 227 | SEQ ID NO: 229 |
| A650/A652 | SEQ ID NO: 227 | SEQ ID NO: 231 |
| A650/A653 | SEQ ID NO: 227 | SEQ ID NO: 233 |
| A650/A654 | SEQ ID NO: 227 | SEQ ID NO: 235 |
| A650/A656 | SEQ ID NO: 227 | SEQ ID NO: 237 |

In some embodiments, the antibody is A631/A467 comprising a VH comprising an amino acid sequence of SEQ ID NO: 203 and a VL comprising an amino acid sequence of SEQ ID NO: 92. In some embodiments, the antibody is A631/A468 comprising a VH comprising an amino acid sequence of SEQ ID NO: 203 and a VL comprising an amino acid sequence of SEQ ID NO: 94. In some embodiments, the antibody is A631/A469 comprising a VH comprising an amino acid sequence of SEQ ID NO: 203 and a VL comprising an amino acid sequence of SEQ ID NO: 96. In some embodiments, the antibody is A631/A470 comprising a VH comprising an amino acid sequence of SEQ ID NO: 203 and a VL comprising an amino acid sequence of SEQ ID NO: 98. In some embodiments, the antibody is A631/A471 comprising a VH comprising an amino acid sequence of SEQ ID NO: 203 and a VL comprising an amino acid sequence of SEQ ID NO: 100. In some embodiments, the antibody is A631/A472 comprising a VH comprising an amino acid sequence of SEQ ID NO: 203 and a VL comprising an amino acid sequence of SEQ ID NO: 102. In some embodiments, the antibody is A631/A473 comprising a VH comprising an amino acid sequence of SEQ ID NO: 203 and a VL comprising an amino acid sequence of SEQ ID NO: 104. In some embodiments, the antibody is A631/A518 comprising a VH comprising an amino acid sequence of SEQ ID NO: 203 and a VL comprising an amino acid sequence of SEQ ID NO: 112. In some embodiments, the antibody is A631/A651 comprising a VH comprising an amino acid sequence of SEQ ID NO: 203 and a VL comprising an amino acid sequence of SEQ ID NO: 229. In some embodiments, the antibody is A631/A652 comprising a VH comprising an amino acid sequence of SEQ ID NO: 203 and a VL comprising an amino acid sequence of SEQ ID NO: 231. In some embodiments, the antibody is A631/A653 comprising a VH comprising an amino acid sequence of SEQ ID NO: 203 and a VL comprising an amino acid sequence of SEQ ID NO: 233. In some embodiments, the antibody is A631/A654 comprising a VH comprising an amino acid sequence of SEQ ID NO: 203 and a VL comprising an amino acid sequence of SEQ ID NO: 235. In some embodiments, the antibody is A631/A656 comprising a VH comprising an amino acid sequence of SEQ ID NO: 203 and a VL comprising an amino acid sequence of SEQ ID NO: 237.

In some embodiments, the antibody is A632/A467 comprising a VH comprising an amino acid sequence of SEQ ID NO: 205 and a VL comprising an amino acid sequence of SEQ ID NO: 92. In some embodiments, the antibody is A632/A468 comprising a VH comprising an amino acid sequence of SEQ ID NO: 205 and a VL comprising an amino acid sequence of SEQ ID NO: 94. In some embodiments, the antibody is A632/A469 comprising a VH comprising an amino acid sequence of SEQ ID NO: 205 and a VL comprising an amino acid sequence of SEQ ID NO: 96. In some embodiments, the antibody is A632/A470 comprising a VH comprising an amino acid sequence of SEQ ID NO: 205 and a VL comprising an amino acid sequence of SEQ ID NO: 98. In some embodiments, the antibody is A632/A471 comprising a VH comprising an amino acid sequence of SEQ ID NO: 205 and a VL comprising an amino acid sequence of SEQ ID NO: 100. In some embodiments, the antibody is A632/A472 comprising a VH comprising an amino acid sequence of SEQ ID NO: 205 and a VL comprising an amino acid sequence of SEQ ID NO: 102. In some embodiments, the antibody is A632/A473 comprising a VH comprising an amino acid sequence of SEQ ID NO: 205 and a VL comprising an amino acid sequence of SEQ ID NO: 104. In some embodiments, the antibody is A632/A518 comprising a VH comprising an amino acid sequence of SEQ ID NO: 205 and a VL comprising an amino acid sequence of SEQ ID NO: 112. In some embodiments, the antibody is A632/A651 comprising a VH comprising an amino acid sequence of SEQ ID NO: 205 and a VL comprising an amino acid sequence of SEQ ID NO: 229. In some embodiments, the antibody is A632/A652 comprising a VH comprising an amino acid sequence of SEQ ID NO: 205 and a VL comprising an amino acid sequence of SEQ ID NO: 231. In some embodiments, the antibody is A632/A653 comprising a VH comprising an amino acid sequence of SEQ ID NO: 205 and a VL comprising an amino acid sequence of SEQ ID NO: 233. In some embodiments, the antibody is A632/A654 comprising a VH comprising an amino acid sequence of SEQ ID NO: 205 and a VL comprising an amino acid sequence of SEQ ID NO: 235. In some embodiments, the antibody is A632/A656 comprising a VH comprising an amino acid sequence of SEQ ID NO: 205 and a VL comprising an amino acid sequence of SEQ ID NO: 237.

In some embodiments, the antibody is A633/A467 comprising a VH comprising an amino acid sequence of SEQ ID NO: 207 and a VL comprising an amino acid sequence of SEQ ID NO: 92. In some embodiments, the antibody is A633/A468 comprising a VH comprising an amino acid sequence of SEQ ID NO: 207 and a VL comprising an amino acid sequence of SEQ ID NO: 94. In some embodiments, the antibody is A633/A469 comprising a VH comprising an amino acid sequence of SEQ ID NO: 207 and a VL comprising an amino acid sequence of SEQ ID NO: 96. In some embodiments, the antibody is A633/A470 comprising a VH comprising an amino acid sequence of SEQ ID NO: 207 and a VL comprising an amino acid sequence of SEQ ID NO: 98. In some embodiments, the antibody is A633/A471 comprising a VH comprising an amino acid sequence of SEQ ID NO: 207 and a VL comprising an amino acid sequence of SEQ ID NO: 100. In some embodiments, the antibody is A633/A472 comprising a VH comprising an amino acid sequence of SEQ ID NO: 207 and a VL comprising an amino acid sequence of SEQ ID NO: 102. In some embodiments, the antibody is A633/A473 comprising a VH comprising an amino acid sequence of SEQ ID NO: 207 and a VL comprising an amino acid sequence of SEQ ID NO: 104. In some embodiments, the antibody is A633/A518 comprising a VH comprising an amino acid sequence of SEQ ID NO: 207 and a VL comprising an amino acid sequence of SEQ ID NO: 112. In some embodiments, the antibody is A633/A651 comprising a VH comprising an amino acid sequence of SEQ ID NO: 207 and a VL comprising an amino acid sequence of SEQ ID NO: 229. In some embodiments, the antibody is A633/A652 comprising a VH comprising an amino acid sequence of SEQ ID NO: 207 and a VL comprising an amino acid sequence of SEQ ID NO: 231. In some embodiments, the antibody is A633/A653 comprising a VH comprising an amino acid sequence of SEQ ID NO: 207 and a VL comprising an amino acid sequence of SEQ ID NO: 233. In some embodiments, the antibody is A633/A654 comprising a VH comprising an amino acid sequence of SEQ ID NO: 207 and a VL comprising an amino acid sequence of SEQ ID NO: 235. In some embodiments, the antibody is A633/A656 comprising a VH comprising an amino acid sequence of SEQ ID NO: 207 and a VL comprising an amino acid sequence of SEQ ID NO: 237.

In some embodiments, the antibody is A634/A467 comprising a VH comprising an amino acid sequence of SEQ ID NO: 209 and a VL comprising an amino acid sequence of SEQ ID NO: 92. In some embodiments, the antibody is A634/A468 comprising a VH comprising an amino acid sequence of SEQ ID NO: 209 and a VL comprising an amino acid sequence of SEQ ID NO: 94. In some embodiments, the antibody is A634/A469 comprising a VH comprising an amino acid sequence of SEQ ID NO: 209 and a VL comprising an amino acid sequence of SEQ ID NO: 96. In some embodiments, the antibody is A634/A470 comprising a VH comprising an amino acid sequence of SEQ ID NO: 209 and a VL comprising an amino acid sequence of SEQ ID NO: 98. In some embodiments, the antibody is A634/A471 comprising a VH comprising an amino acid sequence of SEQ ID NO: 209 and a VL comprising an amino acid sequence of SEQ ID NO: 100. In some embodiments, the antibody is A634/A472 comprising a VH comprising an amino acid sequence of SEQ ID NO: 209 and a VL comprising an amino acid sequence of SEQ ID NO: 102. In some embodiments, the antibody is A634/A473 comprising a VH comprising an amino acid sequence of SEQ ID NO: 209 and a VL comprising an amino acid sequence of SEQ ID NO: 104. In some embodiments, the antibody is A634/A518 comprising a VH comprising an amino acid sequence of SEQ ID NO: 209 and a VL comprising an amino acid sequence of SEQ ID NO: 112. In some embodiments, the antibody is A634/A651 comprising a VH comprising an amino acid sequence of SEQ ID NO: 209 and a VL comprising an amino acid sequence of SEQ ID NO: 229. In some embodiments, the antibody is A634/A652 comprising a VH comprising an amino acid sequence of SEQ ID NO: 209 and a VL comprising an amino acid sequence of SEQ ID NO: 231. In some embodiments, the antibody is A634/A653 comprising a VH comprising an amino acid sequence of SEQ ID NO: 209 and a VL comprising an amino acid sequence of SEQ ID NO: 233. In some embodiments, the antibody is A634/A654 comprising a VH comprising an amino acid sequence of SEQ ID NO: 209 and a VL comprising an amino acid sequence of SEQ ID NO: 235. In some embodiments, the antibody is A634/A656 comprising a VH comprising an amino acid sequence of SEQ ID NO: 209 and a VL comprising an amino acid sequence of SEQ ID NO: 237.

In some embodiments, the antibody is A636/A467 comprising a VH comprising an amino acid sequence of SEQ ID NO: 211 and a VL comprising an amino acid sequence of SEQ ID NO: 92. In some embodiments, the antibody is A636/A468 comprising a VH comprising an amino acid sequence of SEQ ID NO: 211 and a VL comprising an amino acid sequence of SEQ ID NO: 94. In some embodiments, the antibody is A636/A469 comprising a VH comprising an amino acid sequence of SEQ ID NO: 211 and a VL comprising an amino acid sequence of SEQ ID NO: 96. In some embodiments, the antibody is A636/A470 comprising a VH comprising an amino acid sequence of SEQ ID NO: 211 and a VL comprising an amino acid sequence of SEQ ID NO: 98. In some embodiments, the antibody is A636/A471 comprising a VH comprising an amino acid sequence of SEQ ID NO: 211 and a VL comprising an amino acid sequence of SEQ ID NO: 100. In some embodiments, the antibody is A636/A472 comprising a VH comprising an amino acid sequence of SEQ ID NO: 211 and a VL comprising an amino acid sequence of SEQ ID NO: 102. In some embodiments, the antibody is A636/A473 comprising a VH comprising an amino acid sequence of SEQ ID NO: 211 and a VL comprising an amino acid sequence of SEQ ID NO: 104. In some embodiments, the antibody is A636/A518 comprising a VH comprising an amino acid sequence of SEQ ID NO: 211 and a VL comprising an amino acid sequence of SEQ ID NO: 112. In some embodiments, the antibody is A636/A651 comprising a VH comprising an amino acid sequence of SEQ ID NO: 211 and a VL comprising an amino acid sequence of SEQ ID NO: 229. In some embodiments, the antibody is A636/A652 comprising a VH comprising an amino acid sequence of SEQ ID NO: 211 and a VL comprising an amino acid sequence of SEQ ID NO: 231. In some embodiments, the antibody is A636/A653 comprising a VH comprising an amino acid sequence of SEQ ID NO: 211 and a VL comprising an amino acid sequence of SEQ ID NO: 233. In some embodiments, the antibody is A636/A654 comprising a VH comprising an amino acid sequence of SEQ ID NO: 211 and a VL comprising an amino acid sequence of SEQ ID NO: 235. In some embodiments, the antibody is A636/A656 comprising a VH comprising an amino acid sequence of SEQ ID NO: 211 and a VL comprising an amino acid sequence of SEQ ID NO: 237.

In some embodiments, the antibody is A638/A467 comprising a VH comprising an amino acid sequence of SEQ ID NO: 213 and a VL comprising an amino acid sequence of SEQ ID NO: 92. In some embodiments, the antibody is A638/A468 comprising a VH comprising an amino acid sequence of SEQ ID NO: 213 and a VL comprising an amino acid sequence of SEQ ID NO: 94. In some embodiments, the antibody is A638/A469 comprising a VH comprising an amino acid sequence of SEQ ID NO: 213 and a VL comprising an amino acid sequence of SEQ ID NO: 96. In some embodiments, the antibody is A638/A470 comprising a VH comprising an amino acid sequence of SEQ ID NO: 213 and a VL comprising an amino acid sequence of SEQ ID NO: 98. In some embodiments, the antibody is A638/A471 comprising a VH comprising an amino acid sequence of SEQ ID NO: 213 and a VL comprising an amino acid sequence of SEQ ID NO: 100. In some embodiments, the antibody is A638/A472 comprising a VH comprising an amino acid sequence of SEQ ID NO: 213 and a VL comprising an amino acid sequence of SEQ ID NO: 102. In some embodiments, the antibody is A638/A473 comprising a VH comprising an amino acid sequence of SEQ ID NO: 213 and a VL comprising an amino acid sequence of SEQ ID NO: 104. In some embodiments, the antibody is A638/A518 comprising a VH comprising an amino acid sequence of SEQ ID NO: 213 and a VL comprising an amino acid sequence of SEQ ID NO: 112. In some embodiments, the antibody is A638/A651 comprising a VH comprising an amino acid sequence of SEQ ID NO: 213 and a VL comprising an amino acid sequence of SEQ ID NO: 229. In some embodiments, the antibody is A638/A652 comprising a VH comprising an amino acid sequence of SEQ ID NO: 213 and a VL comprising an amino acid sequence of SEQ ID NO: 231. In some embodiments, the antibody is A638/A653 comprising a VH comprising an amino acid sequence of SEQ ID NO: 213 and a VL comprising an amino acid sequence of SEQ ID NO: 233. In some embodiments, the antibody is A638/A654 comprising a VH comprising an amino acid sequence of SEQ ID NO: 213 and a VL comprising an amino acid sequence of SEQ ID NO: 235. In some embodiments, the antibody is A638/A656 comprising a VH comprising an amino acid sequence of SEQ ID NO: 213 and a VL comprising an amino acid sequence of SEQ ID NO: 237.

In some embodiments, the antibody is A639/A467 comprising a VH comprising an amino acid sequence of SEQ ID NO: 215 and a VL comprising an amino acid sequence of SEQ ID NO: 92. In some embodiments, the antibody is A639/A468 comprising a VH comprising an amino acid sequence of SEQ ID NO: 215 and a VL comprising an amino acid sequence of SEQ ID NO: 94. In some embodiments, the antibody is A639/A469 comprising a VH comprising an amino acid sequence of SEQ ID NO: 215 and a VL comprising an amino acid sequence of SEQ ID NO: 96. In some embodiments, the antibody is A639/A470 comprising a VH comprising an amino acid sequence of SEQ ID NO: 215 and a VL comprising an amino acid sequence of SEQ ID NO: 98. In some embodiments, the antibody is A639/A471 comprising a VH comprising an amino acid sequence of SEQ ID NO: 215 and a VL comprising an amino acid sequence of SEQ ID NO: 100. In some embodiments, the antibody is A639/A472 comprising a VH comprising an amino acid sequence of SEQ ID NO: 215 and a VL comprising an amino acid sequence of SEQ ID NO: 102. In some embodiments, the antibody is A639/A473 comprising a VH comprising an amino acid sequence of SEQ ID NO: 215 and a VL comprising an amino acid sequence of SEQ ID NO: 104. In some embodiments, the antibody is A639/A518 comprising a VH comprising an amino acid sequence of SEQ ID NO: 215 and a VL comprising an amino acid sequence of SEQ ID NO: 112. In some embodiments, the antibody is A639/A651 comprising a VH comprising an amino acid sequence of SEQ ID NO: 215 and a VL comprising an amino acid sequence of SEQ ID NO: 229. In some embodiments, the antibody is A639/A652 comprising a VH comprising an amino acid sequence of SEQ ID NO: 215 and a VL comprising an amino acid sequence of SEQ ID NO: 231. In some embodiments, the antibody is A639/A653 comprising a VH comprising an amino acid sequence of SEQ ID NO: 215 and a VL comprising an amino acid sequence of SEQ ID NO: 233. In some embodiments, the antibody is A639/A654 comprising a VH comprising an amino acid sequence of SEQ ID NO: 215 and a VL comprising an amino acid sequence of SEQ ID NO: 235. In some embodiments, the antibody is A639/A656 comprising a VH comprising an amino acid sequence of SEQ ID NO: 215 and a VL comprising an amino acid sequence of SEQ ID NO: 237.

In some embodiments, the antibody is A641/A467 comprising a VH comprising an amino acid sequence of SEQ ID NO: 217 and a VL comprising an amino acid sequence of SEQ ID NO: 92. In some embodiments, the antibody is A641/A468 comprising a VH comprising an amino acid sequence of SEQ ID NO: 217 and a VL comprising an amino acid sequence of SEQ ID NO: 94. In some embodiments, the antibody is A641/A469 comprising a VH comprising an amino acid sequence of SEQ ID NO: 217 and a VL comprising an amino acid sequence of SEQ ID NO: 96. In some embodiments, the antibody is A641/A470 comprising a VH comprising an amino acid sequence of SEQ ID NO: 217 and a VL comprising an amino acid sequence of SEQ ID NO: 98. In some embodiments, the antibody is A641/A471 comprising a VH comprising an amino acid sequence of SEQ ID NO: 217 and a VL comprising an amino acid sequence of SEQ ID NO: 100. In some embodiments, the antibody is A641/A472 comprising a VH comprising an amino acid sequence of SEQ ID NO: 217 and a VL comprising an amino acid sequence of SEQ ID NO: 102. In some embodiments, the antibody is A641/A473 comprising a VH comprising an amino acid sequence of SEQ ID NO: 217 and a VL comprising an amino acid sequence of SEQ ID NO: 104. In some embodiments, the antibody is A641/A518 comprising a VH comprising an amino acid sequence of SEQ ID NO: 217 and a VL comprising an amino acid sequence of SEQ ID NO: 112. In some embodiments, the antibody is A641/A651 comprising a VH comprising an amino acid sequence of SEQ ID NO: 217 and a VL comprising an amino acid sequence of SEQ ID NO: 229. In some embodiments, the antibody is A641/A652 comprising a VH comprising an amino acid sequence of SEQ ID NO: 217 and a VL comprising an amino acid sequence of SEQ ID NO: 231. In some embodiments, the antibody is A641/A653 comprising a VH comprising an amino acid sequence of SEQ ID NO: 217 and a VL comprising an amino acid sequence of SEQ ID NO: 233. In some embodiments, the antibody is A641/A654 comprising a VH comprising an amino acid sequence of SEQ ID NO: 217 and a VL comprising an amino acid sequence of SEQ ID NO: 235. In some embodiments, the antibody is A641/A656 comprising a VH comprising an amino acid sequence of SEQ ID NO: 217 and a VL comprising an amino acid sequence of SEQ ID NO: 237.

In some embodiments, the antibody is A642/A467 comprising a VH comprising an amino acid sequence of SEQ ID NO: 219 and a VL comprising an amino acid sequence of SEQ ID NO: 92. In some embodiments, the antibody is A642/A468 comprising a VH comprising an amino acid sequence of SEQ ID NO: 219 and a VL comprising an amino acid sequence of SEQ ID NO: 94. In some embodiments, the antibody is A642/A469 comprising a VH comprising an amino acid sequence of SEQ ID NO: 219 and a VL comprising an amino acid sequence of SEQ ID NO: 96. In some embodiments, the antibody is A642/A470 comprising a VH comprising an amino acid sequence of SEQ ID NO: 219 and a VL comprising an amino acid sequence of SEQ ID NO: 98. In some embodiments, the antibody is A642/A471 comprising a VH comprising an amino acid sequence of SEQ ID NO: 219 and a VL comprising an amino acid sequence of SEQ ID NO: 100. In some embodiments, the antibody is A642/A472 comprising a VH comprising an amino acid sequence of SEQ ID NO: 219 and a VL comprising an amino acid sequence of SEQ ID NO: 102. In some embodiments, the antibody is A642/A473 comprising a VH comprising an amino acid sequence of SEQ ID NO: 219 and a VL comprising an amino acid sequence of SEQ ID NO: 104. In some embodiments, the antibody is A642/A518 comprising a VH comprising an amino acid sequence of SEQ ID NO: 219 and a VL comprising an amino acid sequence of SEQ ID NO: 112. In some embodiments, the antibody is A642/A651 comprising a VH comprising an amino acid sequence of SEQ ID NO: 219 and a VL comprising an amino acid sequence of SEQ ID NO: 229. In some embodiments, the antibody is A642/A652 comprising a VH comprising an amino acid sequence of SEQ ID NO: 219 and a VL comprising an amino acid sequence of SEQ ID NO: 231. In some embodiments, the antibody is A642/A653 comprising a VH comprising an amino acid sequence of SEQ ID NO: 219 and a VL comprising an amino acid sequence of SEQ ID NO: 233. In some embodiments, the antibody is A642/A654 comprising a VH comprising an amino acid sequence of SEQ ID NO: 219 and a VL comprising an amino acid sequence of SEQ ID NO: 235. In some embodiments, the antibody is A642/A656 comprising a VH comprising an amino acid sequence of SEQ ID NO: 219 and a VL comprising an amino acid sequence of SEQ ID NO: 237.

In some embodiments, the antibody is A643/A467 comprising a VH comprising an amino acid sequence of SEQ ID NO: 221 and a VL comprising an amino acid sequence of SEQ ID NO: 92. In some embodiments, the antibody is A643/A468 comprising a VH comprising an amino acid sequence of SEQ ID NO: 221 and a VL comprising an amino acid sequence of SEQ ID NO: 94. In some embodiments, the antibody is A643/A469 comprising a VH comprising an amino acid sequence of SEQ ID NO: 221 and a VL comprising an amino acid sequence of SEQ ID NO: 96. In some embodiments, the antibody is A643/A470 comprising a VH comprising an amino acid sequence of SEQ ID NO: 221 and a VL comprising an amino acid sequence of SEQ ID NO: 98. In some embodiments, the antibody is A643/A471 comprising a VH comprising an amino acid sequence of SEQ ID NO: 221 and a VL comprising an amino acid sequence of SEQ ID NO: 100. In some embodiments, the antibody is A643/A472 comprising a VH comprising an amino acid sequence of SEQ ID NO: 221 and a VL comprising an amino acid sequence of SEQ ID NO: 102. In some embodiments, the antibody is A643/A473 comprising a VH comprising an amino acid sequence of SEQ ID NO: 221 and a VL comprising an amino acid sequence of SEQ ID NO: 104. In some embodiments, the antibody is A643/A518 comprising a VH comprising an amino acid sequence of SEQ ID NO: 221 and a VL comprising an amino acid sequence of SEQ ID NO: 112. In some embodiments, the antibody is A643/A651 comprising a VH comprising an amino acid sequence of SEQ ID NO: 221 and a VL comprising an amino acid sequence of SEQ ID NO: 229. In some embodiments, the antibody is A643/A652 comprising a VH comprising an amino acid sequence of SEQ ID NO: 221 and a VL comprising an amino acid sequence of SEQ ID NO: 231. In some embodiments, the antibody is A643/A653 comprising a VH comprising an amino acid sequence of SEQ ID NO: 221 and a VL comprising an amino acid sequence of SEQ ID NO: 233. In some embodiments, the antibody is A643/A654 comprising a VH comprising an amino acid sequence of SEQ ID NO: 221 and a VL comprising an amino acid sequence of SEQ ID NO: 235. In some embodiments, the antibody is A643/A656 comprising a VH comprising an amino acid sequence of SEQ ID NO: 221 and a VL comprising an amino acid sequence of SEQ ID NO: 237.

In some embodiments, the antibody is A645/A467 comprising a VH comprising an amino acid sequence of SEQ ID NO: 223 and a VL comprising an amino acid sequence of SEQ ID NO: 92. In some embodiments, the antibody is A645/A468 comprising a VH comprising an amino acid sequence of SEQ ID NO: 223 and a VL comprising an amino acid sequence of SEQ ID NO: 94. In some embodiments, the antibody is A645/A469 comprising a VH comprising an amino acid sequence of SEQ ID NO: 223 and a VL comprising an amino acid sequence of SEQ ID NO: 96. In some embodiments, the antibody is A645/A470 comprising a VH comprising an amino acid sequence of SEQ ID NO: 223 and a VL comprising an amino acid sequence of SEQ ID NO: 98. In some embodiments, the antibody is A645/A471 comprising a VH comprising an amino acid sequence of SEQ ID NO: 223 and a VL comprising an amino acid sequence of SEQ ID NO: 100. In some embodiments, the antibody is A645/A472 comprising a VH comprising an amino acid sequence of SEQ ID NO: 223 and a VL comprising an amino acid sequence of SEQ ID NO: 102. In some embodiments, the antibody is A645/A473 comprising a VH comprising an amino acid sequence of SEQ ID NO: 223 and a VL comprising an amino acid sequence of SEQ ID NO: 104. In some embodiments, the antibody is A645/A518 comprising a VH comprising an amino acid sequence of SEQ ID NO: 223 and a VL comprising an amino acid sequence of SEQ ID NO: 112. In some embodiments, the antibody is A645/A651 comprising a VH comprising an amino acid sequence of SEQ ID NO: 223 and a VL comprising an amino acid sequence of SEQ ID NO: 229. In some embodiments, the antibody is A645/A652 comprising a VH comprising an amino acid sequence of SEQ ID NO: 223 and a VL comprising an amino acid sequence of SEQ ID NO: 231. In some embodiments, the antibody is A645/A653 comprising a VH comprising an amino acid sequence of SEQ ID NO: 223 and a VL comprising an amino acid sequence of SEQ ID NO: 233. In some embodiments, the antibody is A645/A654 comprising a VH comprising an amino acid sequence of SEQ ID NO: 223 and a VL comprising an amino acid sequence of SEQ ID NO: 235. In some embodiments, the antibody is A645/A656 comprising a VH comprising an amino acid sequence of SEQ ID NO: 223 and a VL comprising an amino acid sequence of SEQ ID NO: 237.

In some embodiments, the antibody is A648/A467 comprising a VH comprising an amino acid sequence of SEQ ID NO: 225 and a VL comprising an amino acid sequence of SEQ ID NO: 92. In some embodiments, the antibody is A648/A468 comprising a VH comprising an amino acid sequence of SEQ ID NO: 225 and a VL comprising an amino acid sequence of SEQ ID NO: 94. In some embodiments, the antibody is A648/A469 comprising a VH comprising an amino acid sequence of SEQ ID NO: 225 and a VL comprising an amino acid sequence of SEQ ID NO: 96. In some embodiments, the antibody is A648/A470 comprising a VH comprising an amino acid sequence of SEQ ID NO: 225 and a VL comprising an amino acid sequence of SEQ ID NO: 98. In some embodiments, the antibody is A648/A471 comprising a VH comprising an amino acid sequence of SEQ ID NO: 225 and a VL comprising an amino acid sequence of SEQ ID NO: 100. In some embodiments, the antibody is A648/A472 comprising a VH comprising an amino acid sequence of SEQ ID NO: 225 and a VL comprising an amino acid sequence of SEQ ID NO: 102. In some embodiments, the antibody is A648/A473 comprising a VH comprising an amino acid sequence of SEQ ID NO: 225 and a VL comprising an amino acid sequence of SEQ ID NO: 104. In some embodiments, the antibody is A648/A518 comprising a VH comprising an amino acid sequence of SEQ ID NO: 225 and a VL comprising an amino acid sequence of SEQ ID NO: 112. In some embodiments, the antibody is A648/A651 comprising a VH comprising an amino acid sequence of SEQ ID NO: 225 and a VL comprising an amino acid sequence of SEQ ID NO: 229. In some embodiments, the antibody is A648/A652 comprising a VH comprising an amino acid sequence of SEQ ID NO: 225 and a VL comprising an amino acid sequence of SEQ ID NO: 231. In some embodiments, the antibody is A648/A653 comprising a VH comprising an amino acid sequence of SEQ ID NO: 225 and a VL comprising an amino acid sequence of SEQ ID NO: 233. In some embodiments, the antibody is A648/A654 comprising a VH comprising an amino acid sequence of SEQ ID NO: 225 and a VL comprising an amino acid sequence of SEQ ID NO: 235. In some embodiments, the antibody is A648/A656 comprising a VH comprising an amino acid sequence of SEQ ID NO: 225 and a VL comprising an amino acid sequence of SEQ ID NO: 237.

In some embodiments, the antibody is A650/A467 comprising a VH comprising an amino acid sequence of SEQ ID NO: 227 and a VL comprising an amino acid sequence of SEQ ID NO: 92. In some embodiments, the antibody is A650/A468 comprising a VH comprising an amino acid sequence of SEQ ID NO: 227 and a VL comprising an amino acid sequence of SEQ ID NO: 94. In some embodiments, the antibody is A650/A469 comprising a VH comprising an amino acid sequence of SEQ ID NO: 227 and a VL comprising an amino acid sequence of SEQ ID NO: 96. In some embodiments, the antibody is A650/A470 comprising a VH comprising an amino acid sequence of SEQ ID NO: 227 and a VL comprising an amino acid sequence of SEQ ID NO: 98. In some embodiments, the antibody is A650/A471 comprising a VH comprising an amino acid sequence of SEQ ID NO: 227 and a VL comprising an amino acid sequence of SEQ ID NO: 100. In some embodiments, the antibody is A650/A472 comprising a VH comprising an amino acid sequence of SEQ ID NO: 227 and a VL comprising an amino acid sequence of SEQ ID NO: 102. In some embodiments, the antibody is A650/A473 comprising a VH comprising an amino acid sequence of SEQ ID NO: 227 and a VL comprising an amino acid sequence of SEQ ID NO: 104. In some embodiments, the antibody is A650/A518 comprising a VH comprising an amino acid sequence of SEQ ID NO: 227 and a VL comprising an amino acid sequence of SEQ ID NO: 112. In some embodiments, the antibody is A650/A651 comprising a VH comprising an amino acid sequence of SEQ ID NO: 227 and a VL comprising an amino acid sequence of SEQ ID NO: 229. In some embodiments, the antibody is A650/A652 comprising a VH comprising an amino acid sequence of SEQ ID NO: 227 and a VL comprising an amino acid sequence of SEQ ID NO: 231. In some embodiments, the antibody is A650/A653 comprising a VH comprising an amino acid sequence of SEQ ID NO: 227 and a VL comprising an amino acid sequence of SEQ ID NO: 233. In some embodiments, the antibody is A650/A654 comprising a VH comprising an amino acid sequence of SEQ ID NO: 227 and a VL comprising an amino acid sequence of SEQ ID NO: 235. In some embodiments, the antibody is A650/A656 comprising a VH comprising an amino acid sequence of SEQ ID NO: 227 and a VL comprising an amino acid sequence of SEQ ID NO: 237.

In some embodiments, the antibody is A700/A467 comprising a VH comprising an amino acid sequence of SEQ ID NO: 179 and a VL comprising an amino acid sequence of SEQ ID NO: 92. In some embodiments, the antibody is A700/A468 comprising a VH comprising an amino acid sequence of SEQ ID NO: 179 and a VL comprising an amino acid sequence of SEQ ID NO: 94. In some embodiments, the antibody is A700/A469 comprising a VH comprising an amino acid sequence of SEQ ID NO: 179 and a VL comprising an amino acid sequence of SEQ ID NO: 96. In some embodiments, the antibody is A700/A470 comprising a VH comprising an amino acid sequence of SEQ ID NO: 179 and a VL comprising an amino acid sequence of SEQ ID NO: 98. In some embodiments, the antibody is A700/A471 comprising a VH comprising an amino acid sequence of SEQ ID NO: 179 and a VL comprising an amino acid sequence of SEQ ID NO: 100. In some embodiments, the antibody is A700/A472 comprising a VH comprising an amino acid sequence of SEQ ID NO: 179 and a VL comprising an amino acid sequence of SEQ ID NO: 102. In some embodiments, the antibody is A700/A473 comprising a VH comprising an amino acid sequence of SEQ ID NO: 179 and a VL comprising an amino acid sequence of SEQ ID NO: 104. In some embodiments, the antibody is A700/A518 comprising a VH comprising an amino acid sequence of SEQ ID NO: 179 and a VL comprising an amino acid sequence of SEQ ID NO: 112. In some embodiments, the antibody is A700/A651 comprising a VH comprising an amino acid sequence of SEQ ID NO: 179 and a VL comprising an amino acid sequence of SEQ ID NO: 229. In some embodiments, the antibody is A700/A652 comprising a VH comprising an amino acid sequence of SEQ ID NO: 179 and a VL comprising an amino acid sequence of SEQ ID NO: 231. In some embodiments, the antibody is A700/A653 comprising a VH comprising an amino acid sequence of SEQ ID NO: 179 and a VL comprising an amino acid sequence of SEQ ID NO: 233. In some embodiments, the antibody is A700/A654 comprising a VH comprising an amino acid sequence of SEQ ID NO: 179 and a VL comprising an amino acid sequence of SEQ ID NO: 235. In some embodiments, the antibody is A700/A656 comprising a VH comprising an amino acid sequence of SEQ ID NO: 179 and a VL comprising an amino acid sequence of SEQ ID NO: 237.

In some embodiments, the antibody is A454/A467 comprising a VH comprising an amino acid sequence of SEQ ID NO: 66 and a VL comprising an amino acid sequence of SEQ ID NO: 92. In some embodiments, the antibody is A454/A468 comprising a VH comprising an amino acid sequence of SEQ ID NO: 66 and a VL comprising an amino acid sequence of SEQ ID NO: 94. In some embodiments, the antibody is A454/A469 comprising a VH comprising an amino acid sequence of SEQ ID NO: 66 and a VL comprising an amino acid sequence of SEQ ID NO: 96. In some embodiments, the antibody is A454/A470 comprising a VH comprising an amino acid sequence of SEQ ID NO: 66 and a VL comprising an amino acid sequence of SEQ ID NO: 98. In some embodiments, the antibody is A454/A471 comprising a VH comprising an amino acid sequence of SEQ ID NO: 66 and a VL comprising an amino acid sequence of SEQ ID NO: 100. In some embodiments, the antibody is A454/A472 comprising a VH comprising an amino acid sequence of SEQ ID NO: 66 and a VL comprising an amino acid sequence of SEQ ID NO: 102. In some embodiments, the antibody is A454/A473 comprising a VH comprising an amino acid sequence of SEQ ID NO: 66 and a VL comprising an amino acid sequence of SEQ ID NO: 104. In some embodiments, the antibody is A454/A518 comprising a VH comprising an amino acid sequence of SEQ ID NO: 66 and a VL comprising an amino acid sequence of SEQ ID NO: 112. In some embodiments, the antibody is A454/A651 comprising a VH comprising an amino acid sequence of SEQ ID NO: 66 and a VL comprising an amino acid sequence of SEQ ID NO: 229. In some embodiments, the antibody is A454/A652 comprising a VH comprising an amino acid sequence of SEQ ID NO: 66 and a VL comprising an amino acid sequence of SEQ ID NO: 231. In some embodiments, the antibody is A454/A653 comprising a VH comprising an amino acid sequence of SEQ ID NO: 66 and a VL comprising an amino acid sequence of SEQ ID NO: 233. In some embodiments, the antibody is A454/A654 comprising a VH comprising an amino acid sequence of SEQ ID NO: 66 and a VL comprising an amino acid sequence of SEQ ID NO: 235. In some embodiments, the antibody is A454/A656 comprising a VH comprising an amino acid sequence of SEQ ID NO: 66 and a VL comprising an amino acid sequence of SEQ ID NO: 237.

In some embodiments, the antibody is A455/A467 comprising a VH comprising an amino acid sequence of SEQ ID NO: 68 and a VL comprising an amino acid sequence of SEQ ID NO: 92. In some embodiments, the antibody is A455/A468 comprising a VH comprising an amino acid sequence of SEQ ID NO: 68 and a VL comprising an amino acid sequence of SEQ ID NO: 94. In some embodiments, the antibody is A455/A469 comprising a VH comprising an amino acid sequence of SEQ ID NO: 68 and a VL comprising an amino acid sequence of SEQ ID NO: 96. In some embodiments, the antibody is A455/A470 comprising a VH comprising an amino acid sequence of SEQ ID NO: 68 and a VL comprising an amino acid sequence of SEQ ID NO: 98. In some embodiments, the antibody is A455/A471 comprising a VH comprising an amino acid sequence of SEQ ID NO: 68 and a VL comprising an amino acid sequence of SEQ ID NO: 100. In some embodiments, the antibody is A455/A472 comprising a VH comprising an amino acid sequence of SEQ ID NO: 68 and a VL comprising an amino acid sequence of SEQ ID NO: 102. In some embodiments, the antibody is A455/A473 comprising a VH comprising an amino acid sequence of SEQ ID NO: 68 and a VL comprising an amino acid sequence of SEQ ID NO: 104. In some embodiments, the antibody is A455/A518 comprising a VH comprising an amino acid sequence of SEQ ID NO: 68 and a VL comprising an amino acid sequence of SEQ ID NO: 112. In some embodiments, the antibody is A455/A651 comprising a VH comprising an amino acid sequence of SEQ ID NO: 68 and a VL comprising an amino acid sequence of SEQ ID NO: 229. In some embodiments, the antibody is A455/A652 comprising a VH comprising an amino acid sequence of SEQ ID NO: 68 and a VL comprising an amino acid sequence of SEQ ID NO: 231. In some embodiments, the antibody is A455/A653 comprising a VH comprising an amino acid sequence of SEQ ID NO: 68 and a VL comprising an amino acid sequence of SEQ ID NO: 233. In some embodiments, the antibody is A455/A654 comprising a VH comprising an amino acid sequence of SEQ ID NO: 68 and a VL comprising an amino acid sequence of SEQ ID NO: 235. In some embodiments, the antibody is A455/A656 comprising a VH comprising an amino acid sequence of SEQ ID NO: 68 and a VL comprising an amino acid sequence of SEQ ID NO: 237.

In some embodiments, the antibody is A456/A467 comprising a VH comprising an amino acid sequence of SEQ ID NO: 70 and a VL comprising an amino acid sequence of SEQ ID NO: 92. In some embodiments, the antibody is A456/A468 comprising a VH comprising an amino acid sequence of SEQ ID NO: 70 and a VL comprising an amino acid sequence of SEQ ID NO: 94. In some embodiments, the antibody is A456/A469 comprising a VH comprising an amino acid sequence of SEQ ID NO: 70 and a VL comprising an amino acid sequence of SEQ ID NO: 96. In some embodiments, the antibody is A456/A470 comprising a VH comprising an amino acid sequence of SEQ ID NO: 70 and a VL comprising an amino acid sequence of SEQ ID NO: 98. In some embodiments, the antibody is A456/A471 comprising a VH comprising an amino acid sequence of SEQ ID NO: 70 and a VL comprising an amino acid sequence of SEQ ID NO: 100. In some embodiments, the antibody is A456/A472 comprising a VH comprising an amino acid sequence of SEQ ID NO: 70 and a VL comprising an amino acid sequence of SEQ ID NO: 102. In some embodiments, the antibody is A456/A473 comprising a VH comprising an amino acid sequence of SEQ ID NO: 70 and a VL comprising an amino acid sequence of SEQ ID NO: 104. In some embodiments, the antibody is A456/A518 comprising a VH comprising an amino acid sequence of SEQ ID NO: 70 and a VL comprising an amino acid sequence of SEQ ID NO: 112. In some embodiments, the antibody is A456/A651 comprising a VH comprising an amino acid sequence of SEQ ID NO: 70 and a VL comprising an amino acid sequence of SEQ ID NO: 229. In some embodiments, the antibody is A456/A652 comprising a VH comprising an amino acid sequence of SEQ ID NO: 70 and a VL comprising an amino acid sequence of SEQ ID NO: 231. In some embodiments, the antibody is A456/A653 comprising a VH comprising an amino acid sequence of SEQ ID NO: 70 and a VL comprising an amino acid sequence of SEQ ID NO: 233. In some embodiments, the antibody is A456/A654 comprising a VH comprising an amino acid sequence of SEQ ID NO: 70 and a VL comprising an amino acid sequence of SEQ ID NO: 235. In some embodiments, the antibody is A456/A656 comprising a VH comprising an amino acid sequence of SEQ ID NO: 70 and a VL comprising an amino acid sequence of SEQ ID NO: 237.

In some embodiments, the antibody is A457/A467 comprising a VH comprising an amino acid sequence of SEQ ID NO: 72 and a VL comprising an amino acid sequence of SEQ ID NO: 92. In some embodiments, the antibody is A457/A468 comprising a VH comprising an amino acid sequence of SEQ ID NO: 72 and a VL comprising an amino acid sequence of SEQ ID NO: 94. In some embodiments, the antibody is A457/A469 comprising a VH comprising an amino acid sequence of SEQ ID NO: 72 and a VL comprising an amino acid sequence of SEQ ID NO: 96. In some embodiments, the antibody is A457/A470 comprising a VH comprising an amino acid sequence of SEQ ID NO: 72 and a VL comprising an amino acid sequence of SEQ ID NO: 98. In some embodiments, the antibody is A457/A471 comprising a VH comprising an amino acid sequence of SEQ ID NO: 72 and a VL comprising an amino acid sequence of SEQ ID NO: 100. In some embodiments, the antibody is A457/A472 comprising a VH comprising an amino acid sequence of SEQ ID NO: 72 and a VL comprising an amino acid sequence of SEQ ID NO: 102. In some embodiments, the antibody is A457/A473 comprising a VH comprising an amino acid sequence of SEQ ID NO: 72 and a VL comprising an amino acid sequence of SEQ ID NO: 104. In some embodiments, the antibody is A457/A518 comprising a VH comprising an amino acid sequence of SEQ ID NO: 72 and a VL comprising an amino acid sequence of SEQ ID NO: 112. In some embodiments, the antibody is A457/A651 comprising a VH comprising an amino acid sequence of SEQ ID NO: 72 and a VL comprising an amino acid sequence of SEQ ID NO: 229. In some embodiments, the antibody is A457/A652 comprising a VH comprising an amino acid sequence of SEQ ID NO: 72 and a VL comprising an amino acid sequence of SEQ ID NO: 231. In some embodiments, the antibody is A457/A653 comprising a VH comprising an amino acid sequence of SEQ ID NO: 72 and a VL comprising an amino acid sequence of SEQ ID NO: 233. In some embodiments, the antibody is A457/A654 comprising a VH comprising an amino acid sequence of SEQ ID NO: 72 and a VL comprising an amino acid sequence of SEQ ID NO: 235. In some embodiments, the antibody is A457/A656 comprising a VH comprising an amino acid sequence of SEQ ID NO: 72 and a VL comprising an amino acid sequence of SEQ ID NO: 237.

In some embodiments, the antibody is A458/A467 comprising a VH comprising an amino acid sequence of SEQ ID NO: 74 and a VL comprising an amino acid sequence of SEQ ID NO: 92. In some embodiments, the antibody is A458/A468 comprising a VH comprising an amino acid sequence of SEQ ID NO: 74 and a VL comprising an amino acid sequence of SEQ ID NO: 94. In some embodiments, the antibody is A458/A469 comprising a VH comprising an amino acid sequence of SEQ ID NO: 74 and a VL comprising an amino acid sequence of SEQ ID NO: 96. In some embodiments, the antibody is A458/A470 comprising a VH comprising an amino acid sequence of SEQ ID NO: 74 and a VL comprising an amino acid sequence of SEQ ID NO: 98. In some embodiments, the antibody is A458/A471 comprising a VH comprising an amino acid sequence of SEQ ID NO: 74 and a VL comprising an amino acid sequence of SEQ ID NO: 100. In some embodiments, the antibody is A458/A472 comprising a VH comprising an amino acid sequence of SEQ ID NO: 74 and a VL comprising an amino acid sequence of SEQ ID NO: 102. In some embodiments, the antibody is A458/A473 comprising a VH comprising an amino acid sequence of SEQ ID NO: 74 and a VL comprising an amino acid sequence of SEQ ID NO: 104. In some embodiments, the antibody is A458/A518 comprising a VH comprising an amino acid sequence of SEQ ID NO: 74 and a VL comprising an amino acid sequence of SEQ ID NO: 112. In some embodiments, the antibody is A458/A651 comprising a VH comprising an amino acid sequence of SEQ ID NO: 74 and a VL comprising an amino acid sequence of SEQ ID NO: 229. In some embodiments, the antibody is A458/A652 comprising a VH comprising an amino acid sequence of SEQ ID NO: 74 and a VL comprising an amino acid sequence of SEQ ID NO: 231. In some embodiments, the antibody is A458/A653 comprising a VH comprising an amino acid sequence of SEQ ID NO: 74 and a VL comprising an amino acid sequence of SEQ ID NO: 233. In some embodiments, the antibody is A458/A654 comprising a VH comprising an amino acid sequence of SEQ ID NO: 74 and a VL comprising an amino acid sequence of SEQ ID NO: 235. In some embodiments, the antibody is A458/A656 comprising a VH comprising an amino acid sequence of SEQ ID NO: 74 and a VL comprising an amino acid sequence of SEQ ID NO: 237.

In some embodiments, the antibody is A459/A467 comprising a VH comprising an amino acid sequence of SEQ ID NO: 76 and a VL comprising an amino acid sequence of SEQ ID NO: 92. In some embodiments, the antibody is A459/A468 comprising a VH comprising an amino acid sequence of SEQ ID NO: 76 and a VL comprising an amino acid sequence of SEQ ID NO: 94. In some embodiments, the antibody is A459/A469 comprising a VH comprising an amino acid sequence of SEQ ID NO: 76 and a VL comprising an amino acid sequence of SEQ ID NO: 96. In some embodiments, the antibody is A459/A470 comprising a VH comprising an amino acid sequence of SEQ ID NO: 76 and a VL comprising an amino acid sequence of SEQ ID NO: 98. In some embodiments, the antibody is A459/A471 comprising a VH comprising an amino acid sequence of SEQ ID NO: 76 and a VL comprising an amino acid sequence of SEQ ID NO: 100. In some embodiments, the antibody is A459/A472 comprising a VH comprising an amino acid sequence of SEQ ID NO: 76 and a VL comprising an amino acid sequence of SEQ ID NO: 102. In some embodiments, the antibody is A459/A473 comprising a VH comprising an amino acid sequence of SEQ ID NO: 76 and a VL comprising an amino acid sequence of SEQ ID NO: 104. In some embodiments, the antibody is A459/A518 comprising a VH comprising an amino acid sequence of SEQ ID NO: 76 and a VL comprising an amino acid sequence of SEQ ID NO: 112. In some embodiments, the antibody is A459/A651 comprising a VH comprising an amino acid sequence of SEQ ID NO: 76 and a VL comprising an amino acid sequence of SEQ ID NO: 229. In some embodiments, the antibody is A459/A652 comprising a VH comprising an amino acid sequence of SEQ ID NO: 76 and a VL comprising an amino acid sequence of SEQ ID NO: 231. In some embodiments, the antibody is A459/A653 comprising a VH comprising an amino acid sequence of SEQ ID NO: 76 and a VL comprising an amino acid sequence of SEQ ID NO: 233. In some embodiments, the antibody is A459/A654 comprising a VH comprising an amino acid sequence of SEQ ID NO: 76 and a VL comprising an amino acid sequence of SEQ ID NO: 235. In some embodiments, the antibody is A459/A656 comprising a VH comprising an amino acid sequence of SEQ ID NO: 76 and a VL comprising an amino acid sequence of SEQ ID NO: 237.

In some embodiments, the antibody is A460/A467 comprising a VH comprising an amino acid sequence of SEQ ID NO: 78 and a VL comprising an amino acid sequence of SEQ ID NO: 92. In some embodiments, the antibody is A460/A468 comprising a VH comprising an amino acid sequence of SEQ ID NO: 78 and a VL comprising an amino acid sequence of SEQ ID NO: 94. In some embodiments, the antibody is A460/A469 comprising a VH comprising an amino acid sequence of SEQ ID NO: 78 and a VL comprising an amino acid sequence of SEQ ID NO: 96. In some embodiments, the antibody is A460/A470 comprising a VH comprising an amino acid sequence of SEQ ID NO: 78 and a VL comprising an amino acid sequence of SEQ ID NO: 98. In some embodiments, the antibody is A460/A471 comprising a VH comprising an amino acid sequence of SEQ ID NO: 78 and a VL comprising an amino acid sequence of SEQ ID NO: 100. In some embodiments, the antibody is A460/A472 comprising a VH comprising an amino acid sequence of SEQ ID NO: 78 and a VL comprising an amino acid sequence of SEQ ID NO: 102. In some embodiments, the antibody is A460/A473 comprising a VH comprising an amino acid sequence of SEQ ID NO: 78 and a VL comprising an amino acid sequence of SEQ ID NO: 104. In some embodiments, the antibody is A460/A518 comprising a VH comprising an amino acid sequence of SEQ ID NO: 78 and a VL comprising an amino acid sequence of SEQ ID NO: 112. In some embodiments, the antibody is A460/A651 comprising a VH comprising an amino acid sequence of SEQ ID NO: 78 and a VL comprising an amino acid sequence of SEQ ID NO: 229. In some embodiments, the antibody is A460/A652 comprising a VH comprising an amino acid sequence of SEQ ID NO: 78 and a VL comprising an amino acid sequence of SEQ ID NO: 231. In some embodiments, the antibody is A460/A653 comprising a VH comprising an amino acid sequence of SEQ ID NO: 78 and a VL comprising an amino acid sequence of SEQ ID NO: 233. In some embodiments, the antibody is A460/A654 comprising a VH comprising an amino acid sequence of SEQ ID NO: 78 and a VL comprising an amino acid sequence of SEQ ID NO: 235. In some embodiments, the antibody is A460/A656 comprising a VH comprising an amino acid sequence of SEQ ID NO: 78 and a VL comprising an amino acid sequence of SEQ ID NO: 237.

In some embodiments, the antibody is A461/A467 comprising a VH comprising an amino acid sequence of SEQ ID NO: 80 and a VL comprising an amino acid sequence of SEQ ID NO: 92. In some embodiments, the antibody is A461/A468 comprising a VH comprising an amino acid sequence of SEQ ID NO: 80 and a VL comprising an amino acid sequence of SEQ ID NO: 94. In some embodiments, the antibody is A461/A469 comprising a VH comprising an amino acid sequence of SEQ ID NO: 80 and a VL comprising an amino acid sequence of SEQ ID NO: 96. In some embodiments, the antibody is A461/A470 comprising a VH comprising an amino acid sequence of SEQ ID NO: 80 and a VL comprising an amino acid sequence of SEQ ID NO: 98. In some embodiments, the antibody is A461/A471 comprising a VH comprising an amino acid sequence of SEQ ID NO: 80 and a VL comprising an amino acid sequence of SEQ ID NO: 100. In some embodiments, the antibody is A461/A472 comprising a VH comprising an amino acid sequence of SEQ ID NO: 80 and a VL comprising an amino acid sequence of SEQ ID NO: 102. In some embodiments, the antibody is A461/A473 comprising a VH comprising an amino acid sequence of SEQ ID NO: 80 and a VL comprising an amino acid sequence of SEQ ID NO: 104. In some embodiments, the antibody is A461/A518 comprising a VH comprising an amino acid sequence of SEQ ID NO: 80 and a VL comprising an amino acid sequence of SEQ ID NO: 112. In some embodiments, the antibody is A461/A651 comprising a VH comprising an amino acid sequence of SEQ ID NO: 80 and a VL comprising an amino acid sequence of SEQ ID NO: 229. In some embodiments, the antibody is A461/A652 comprising a VH comprising an amino acid sequence of SEQ ID NO: 80 and a VL comprising an amino acid sequence of SEQ ID NO: 231. In some embodiments, the antibody is A461/A653 comprising a VH comprising an amino acid sequence of SEQ ID NO: 80 and a VL comprising an amino acid sequence of SEQ ID NO: 233. In some embodiments, the antibody is A461/A654comprising a VH comprising an amino acid sequence of SEQ ID NO: 80 and a VL comprising an amino acid sequence of SEQ ID NO: 235. In some embodiments, the antibody is A461/A656 comprising a VH comprising an amino acid sequence of SEQ ID NO: 80 and a VL comprising an amino acid sequence of SEQ ID NO: 237.

In some embodiments, the antibody is A462/A467 comprising a VH comprising an amino acid sequence of SEQ ID NO: 82 and a VL comprising an amino acid sequence of SEQ ID NO: 92. In some embodiments, the antibody is A462/A468 comprising a VH comprising an amino acid sequence of SEQ ID NO: 82 and a VL comprising an amino acid sequence of SEQ ID NO: 94. In some embodiments, the antibody is A462/A469 comprising a VH comprising an amino acid sequence of SEQ ID NO: 82 and a VL comprising an amino acid sequence of SEQ ID NO: 96. In some embodiments, the antibody is A462/A470 comprising a VH comprising an amino acid sequence of SEQ ID NO: 82 and a VL comprising an amino acid sequence of SEQ ID NO: 98. In some embodiments, the antibody is A462/A471 comprising a VH comprising an amino acid sequence of SEQ ID NO: 82 and a VL comprising an amino acid sequence of SEQ ID NO: 100. In some embodiments, the antibody is A462/A472 comprising a VH comprising an amino acid sequence of SEQ ID NO: 82 and a VL comprising an amino acid sequence of SEQ ID NO: 102. In some embodiments, the antibody is A462/A473 comprising a VH comprising an amino acid sequence of SEQ ID NO: 82 and a VL comprising an amino acid sequence of SEQ ID NO: 104. In some embodiments, the antibody is A462/A518 comprising a VH comprising an amino acid sequence of SEQ ID NO: 82 and a VL comprising an amino acid sequence of SEQ ID NO: 112. In some embodiments, the antibody is A462/A651 comprising a VH comprising an amino acid sequence of SEQ ID NO: 82 and a VL comprising an amino acid sequence of SEQ ID NO: 229. In some embodiments, the antibody is A462/A652 comprising a VH comprising an amino acid sequence of SEQ ID NO: 82 and a VL comprising an amino acid sequence of SEQ ID NO: 231. In some embodiments, the antibody is A462/A653 comprising a VH comprising an amino acid sequence of SEQ ID NO: 82 and a VL comprising an amino acid sequence of SEQ ID NO: 233. In some embodiments, the antibody is A462/A654 comprising a VH comprising an amino acid sequence of SEQ ID NO: 82 and a VL comprising an amino acid sequence of SEQ ID NO: 235. In some embodiments, the antibody is A462/A656 comprising a VH comprising an amino acid sequence of SEQ ID NO: 82 and a VL comprising an amino acid sequence of SEQ ID NO: 237.

In some embodiments, the antibody is A463/A467 comprising a VH comprising an amino acid sequence of SEQ ID NO: 84 and a VL comprising an amino acid sequence of SEQ ID NO: 92. In some embodiments, the antibody is A463/A468 comprising a VH comprising an amino acid sequence of SEQ ID NO: 84 and a VL comprising an amino acid sequence of SEQ ID NO: 94. In some embodiments, the antibody is A463/A469 comprising a VH comprising an amino acid sequence of SEQ ID NO: 84 and a VL comprising an amino acid sequence of SEQ ID NO: 96. In some embodiments, the antibody is A463/A470 comprising a VH comprising an amino acid sequence of SEQ ID NO: 84 and a VL comprising an amino acid sequence of SEQ ID NO: 98. In some embodiments, the antibody is A463/A471 comprising a VH comprising an amino acid sequence of SEQ ID NO: 84 and a VL comprising an amino acid sequence of SEQ ID NO: 100. In some embodiments, the antibody is A463/A472 comprising a VH comprising an amino acid sequence of SEQ ID NO: 84 and a VL comprising an amino acid sequence of SEQ ID NO: 102. In some embodiments, the antibody is A463/A473 comprising a VH comprising an amino acid sequence of SEQ ID NO: 84 and a VL comprising an amino acid sequence of SEQ ID NO: 104. In some embodiments, the antibody is A463/A518 comprising a VH comprising an amino acid sequence of SEQ ID NO: 84 and a VL comprising an amino acid sequence of SEQ ID NO: 112. In some embodiments, the antibody is A463/A651 comprising a VH comprising an amino acid sequence of SEQ ID NO: 84 and a VL comprising an amino acid sequence of SEQ ID NO: 229. In some embodiments, the antibody is A463/A652 comprising a VH comprising an amino acid sequence of SEQ ID NO: 84 and a VL comprising an amino acid sequence of SEQ ID NO: 231. In some embodiments, the antibody is A463/A653 comprising a VH comprising an amino acid sequence of SEQ ID NO: 84 and a VL comprising an amino acid sequence of SEQ ID NO: 233. In some embodiments, the antibody is A463/A654comprising a VH comprising an amino acid sequence of SEQ ID NO: 84 and a VL comprising an amino acid sequence of SEQ ID NO: 235. In some embodiments, the antibody is A463/A656 comprising a VH comprising an amino acid sequence of SEQ ID NO: 84 and a VL comprising an amino acid sequence of SEQ ID NO: 237.

In some embodiments, the antibody is A464/A467 comprising a VH comprising an amino acid sequence of SEQ ID NO: 86 and a VL comprising an amino acid sequence of SEQ ID NO: 92. In some embodiments, the antibody is A464/A468 comprising a VH comprising an amino acid sequence of SEQ ID NO: 86 and a VL comprising an amino acid sequence of SEQ ID NO: 94. In some embodiments, the antibody is A464/A469 comprising a VH comprising an amino acid sequence of SEQ ID NO: 86 and a VL comprising an amino acid sequence of SEQ ID NO: 96. In some embodiments, the antibody is A464/A470 comprising a VH comprising an amino acid sequence of SEQ ID NO: 86 and a VL comprising an amino acid sequence of SEQ ID NO: 98. In some embodiments, the antibody is A464/A471 comprising a VH comprising an amino acid sequence of SEQ ID NO: 86 and a VL comprising an amino acid sequence of SEQ ID NO: 100. In some embodiments, the antibody is A464/A472 comprising a VH comprising an amino acid sequence of SEQ ID NO: 86 and a VL comprising an amino acid sequence of SEQ ID NO: 102. In some embodiments, the antibody is A464/A473 comprising a VH comprising an amino acid sequence of SEQ ID NO: 86 and a VL comprising an amino acid sequence of SEQ ID NO: 104. In some embodiments, the antibody is A464/A518 comprising a VH comprising an amino acid sequence of SEQ ID NO: 86 and a VL comprising an amino acid sequence of SEQ ID NO: 112. In some embodiments, the antibody is A464/A651 comprising a VH comprising an amino acid sequence of SEQ ID NO: 86 and a VL comprising an amino acid sequence of SEQ ID NO: 229. In some embodiments, the antibody is A464/A652 comprising a VH comprising an amino acid sequence of SEQ ID NO: 86 and a VL comprising an amino acid sequence of SEQ ID NO: 231. In some embodiments, the antibody is A464/A653 comprising a VH comprising an amino acid sequence of SEQ ID NO: 86 and a VL comprising an amino acid sequence of SEQ ID NO: 233. In some embodiments, the antibody is A464/A654comprising a VH comprising an amino acid sequence of SEQ ID NO: 86 and a VL comprising an amino acid sequence of SEQ ID NO: 235. In some embodiments, the antibody is A464/A656 comprising a VH comprising an amino acid sequence of SEQ ID NO: 86 and a VL comprising an amino acid sequence of SEQ ID NO: 237.

In some embodiments, the antibody is A465/A467 comprising a VH comprising an amino acid sequence of SEQ ID NO: 88 and a VL comprising an amino acid sequence of SEQ ID NO: 92. In some embodiments, the antibody is A465/A468 comprising a VH comprising an amino acid sequence of SEQ ID NO: 88 and a VL comprising an amino acid sequence of SEQ ID NO: 94. In some embodiments, the antibody is A465/A469 comprising a VH comprising an amino acid sequence of SEQ ID NO: 88 and a VL comprising an amino acid sequence of SEQ ID NO: 96. In some embodiments, the antibody is A465/A470 comprising a VH comprising an amino acid sequence of SEQ ID NO: 88 and a VL comprising an amino acid sequence of SEQ ID NO: 98. In some embodiments, the antibody is A465/A471 comprising a VH comprising an amino acid sequence of SEQ ID NO: 88 and a VL comprising an amino acid sequence of SEQ ID NO: 100. In some embodiments, the antibody is A465/A472 comprising a VH comprising an amino acid sequence of SEQ ID NO: 88 and a VL comprising an amino acid sequence of SEQ ID NO: 102. In some embodiments, the antibody is A465/A473 comprising a VH comprising an amino acid sequence of SEQ ID NO: 88 and a VL comprising an amino acid sequence of SEQ ID NO: 104. In some embodiments, the antibody is A465/A518 comprising a VH comprising an amino acid sequence of SEQ ID NO: 88 and a VL comprising an amino acid sequence of SEQ ID NO: 112. In some embodiments, the antibody is A465/A651 comprising a VH comprising an amino acid sequence of SEQ ID NO: 88 and a VL comprising an amino acid sequence of SEQ ID NO: 229. In some embodiments, the antibody is A465/A652 comprising a VH comprising an amino acid sequence of SEQ ID NO: 88 and a VL comprising an amino acid sequence of SEQ ID NO: 231. In some embodiments, the antibody is A465/A653 comprising a VH comprising an amino acid sequence of SEQ ID NO: 88 and a VL comprising an amino acid sequence of SEQ ID NO: 233. In some embodiments, the antibody is A465/A654comprising a VH comprising an amino acid sequence of SEQ ID NO: 88 and a VL comprising an amino acid sequence of SEQ ID NO: 235. In some embodiments, the antibody is A465/A656 comprising a VH comprising an amino acid sequence of SEQ ID NO: 88 and a VL comprising an amino acid sequence of SEQ ID NO: 237.

In some embodiments, the antibody is A466/A467 comprising a VH comprising an amino acid sequence of SEQ ID NO: 90 and a VL comprising an amino acid sequence of SEQ ID NO: 92. In some embodiments, the antibody is A466/A468 comprising a VH comprising an amino acid sequence of SEQ ID NO: 90 and a VL comprising an amino acid sequence of SEQ ID NO: 94. In some embodiments, the antibody is A466/A469 comprising a VH comprising an amino acid sequence of SEQ ID NO: 90 and a VL comprising an amino acid sequence of SEQ ID NO: 96. In some embodiments, the antibody is A466/A470 comprising a VH comprising an amino acid sequence of SEQ ID NO: 90 and a VL comprising an amino acid sequence of SEQ ID NO: 98. In some embodiments, the antibody is A466/A471 comprising a VH comprising an amino acid sequence of SEQ ID NO: 90 and a VL comprising an amino acid sequence of SEQ ID NO: 100. In some embodiments, the antibody is A466/A472 comprising a VH comprising an amino acid sequence of SEQ ID NO: 90 and a VL comprising an amino acid sequence of SEQ ID NO: 102. In some embodiments, the antibody is A466/A473 comprising a VH comprising an amino acid sequence of SEQ ID NO: 90 and a VL comprising an amino acid sequence of SEQ ID NO: 104. In some embodiments, the antibody is A466/A518 comprising a VH comprising an amino acid sequence of SEQ ID NO: 90 and a VL comprising an amino acid sequence of SEQ ID NO: 112. In some embodiments, the antibody is A466/A651 comprising a VH comprising an amino acid sequence of SEQ ID NO: 90 and a VL comprising an amino acid sequence of SEQ ID NO: 229. In some embodiments, the antibody is A466/A652 comprising a VH comprising an amino acid sequence of SEQ ID NO: 90 and a VL comprising an amino acid sequence of SEQ ID NO: 231. In some embodiments, the antibody is A466/A653 comprising a VH comprising an amino acid sequence of SEQ ID NO: 90 and a VL comprising an amino acid sequence of SEQ ID NO: 233. In some embodiments, the antibody is A466/A654comprising a VH comprising an amino acid sequence of SEQ ID NO: 90 and a VL comprising an amino acid sequence of SEQ ID NO: 235. In some embodiments, the antibody is A466/A656 comprising a VH comprising an amino acid sequence of SEQ ID NO: 90 and a VL comprising an amino acid sequence of SEQ ID NO: 237.

In some embodiments, the antibody is A512/A467 comprising a VH comprising an amino acid sequence of SEQ ID NO: 108 and a VL comprising an amino acid sequence of SEQ ID NO: 92. In some embodiments, the antibody is A512/A468 comprising a VH comprising an amino acid sequence of SEQ ID NO: 108 and a VL comprising an amino acid sequence of SEQ ID NO: 94. In some embodiments, the antibody is A512/A469 comprising a VH comprising an amino acid sequence of SEQ ID NO: 108 and a VL comprising an amino acid sequence of SEQ ID NO: 96. In some embodiments, the antibody is A512/A470 comprising a VH comprising an amino acid sequence of SEQ ID NO: 108 and a VL comprising an amino acid sequence of SEQ ID NO: 98. In some embodiments, the antibody is A512/A471 comprising a VH comprising an amino acid sequence of SEQ ID NO: 108 and a VL comprising an amino acid sequence of SEQ ID NO: 100. In some embodiments, the antibody is A512/A472 comprising a VH comprising an amino acid sequence of SEQ ID NO: 108 and a VL comprising an amino acid sequence of SEQ ID NO: 102. In some embodiments, the antibody is A512/A473 comprising a VH comprising an amino acid sequence of SEQ ID NO: 108 and a VL comprising an amino acid sequence of SEQ ID NO: 104. In some embodiments, the antibody is A512/A518 comprising a VH comprising an amino acid sequence of SEQ ID NO: 108 and a VL comprising an amino acid sequence of SEQ ID NO: 112. In some embodiments, the antibody is A512/A651 comprising a VH comprising an amino acid sequence of SEQ ID NO: 108 and a VL comprising an amino acid sequence of SEQ ID NO: 229. In some embodiments, the antibody is A512/A652 comprising a VH comprising an amino acid sequence of SEQ ID NO: 108 and a VL comprising an amino acid sequence of SEQ ID NO: 231. In some embodiments, the antibody is A512/A653 comprising a VH comprising an amino acid sequence of SEQ ID NO: 108 and a VL comprising an amino acid sequence of SEQ ID NO: 233. In some embodiments, the antibody is A512/A654comprising a VH comprising an amino acid sequence of SEQ ID NO: 108 and a VL comprising an amino acid sequence of SEQ ID NO: 235. In some embodiments, the antibody is A512/A656 comprising a VH comprising an amino acid sequence of SEQ ID NO: 108 and a VL comprising an amino acid sequence of SEQ ID NO: 237.

In some embodiments, the antibody is A515/A467 comprising a VH comprising an amino acid sequence of SEQ ID NO: 110 and a VL comprising an amino acid sequence of SEQ ID NO: 92. In some embodiments, the antibody is A515/A468 comprising a VH comprising an amino acid sequence of SEQ ID NO: 110 and a VL comprising an amino acid sequence of SEQ ID NO: 94. In some embodiments, the antibody is A515/A469 comprising a VH comprising an amino acid sequence of SEQ ID NO: 110 and a VL comprising an amino acid sequence of SEQ ID NO: 96. In some embodiments, the antibody is A515/A470 comprising a VH comprising an amino acid sequence of SEQ ID NO: 110 and a VL comprising an amino acid sequence of SEQ ID NO: 98. In some embodiments, the antibody is A515/A471 comprising a VH comprising an amino acid sequence of SEQ ID NO: 110 and a VL comprising an amino acid sequence of SEQ ID NO: 100. In some embodiments, the antibody is A515/A472 comprising a VH comprising an amino acid sequence of SEQ ID NO: 110 and a VL comprising an amino acid sequence of SEQ ID NO: 102. In some embodiments, the antibody is A515/A473 comprising a VH comprising an amino acid sequence of SEQ ID NO: 110 and a VL comprising an amino acid sequence of SEQ ID NO: 104. In some embodiments, the antibody is A515/A518 comprising a VH comprising an amino acid sequence of SEQ ID NO: 110 and a VL comprising an amino acid sequence of SEQ ID NO: 112. In some embodiments, the antibody is A515/A651 comprising a VH comprising an amino acid sequence of SEQ ID NO: 110 and a VL comprising an amino acid sequence of SEQ ID NO: 229. In some embodiments, the antibody is A515/A652 comprising a VH comprising an amino acid sequence of SEQ ID NO: 110 and a VL comprising an amino acid sequence of SEQ ID NO: 231. In some embodiments, the antibody is A515/A653 comprising a VH comprising an amino acid sequence of SEQ ID NO: 110 and a VL comprising an amino acid sequence of SEQ ID NO: 233. In some embodiments, the antibody is A515/A654comprising a VH comprising an amino acid sequence of SEQ ID NO: 110 and a VL comprising an amino acid sequence of SEQ ID NO: 235. In some embodiments, the antibody is A515/A656 comprising a VH comprising an amino acid sequence of SEQ ID NO: 110 and a VL comprising an amino acid sequence of SEQ ID NO: 237.

In some embodiments, the antibody is A553/A467 comprising a VH comprising an amino acid sequence of SEQ ID NO: 106 and a VL comprising an amino acid sequence of SEQ ID NO: 92. In some embodiments, the antibody is A553/A468 comprising a VH comprising an amino acid sequence of SEQ ID NO: 106 and a VL comprising an amino acid sequence of SEQ ID NO: 94. In some embodiments, the antibody is A553/A469 comprising a VH comprising an amino acid sequence of SEQ ID NO: 106 and a VL comprising an amino acid sequence of SEQ ID NO: 96. In some embodiments, the antibody is A553/A470 comprising a VH comprising an amino acid sequence of SEQ ID NO: 106 and a VL comprising an amino acid sequence of SEQ ID NO: 98. In some embodiments, the antibody is A553/A471 comprising a VH comprising an amino acid sequence of SEQ ID NO: 106 and a VL comprising an amino acid sequence of SEQ ID NO: 100. In some embodiments, the antibody is A553/A472 comprising a VH comprising an amino acid sequence of SEQ ID NO: 106 and a VL comprising an amino acid sequence of SEQ ID NO: 102. In some embodiments, the antibody is A553/A473 comprising a VH comprising an amino acid sequence of SEQ ID NO: 106 and a VL comprising an amino acid sequence of SEQ ID NO: 104. In some embodiments, the antibody is A553/A518 comprising a VH comprising an amino acid sequence of SEQ ID NO: 106 and a VL comprising an amino acid sequence of SEQ ID NO: 112. In some embodiments, the antibody is A553/A651 comprising a VH comprising an amino acid sequence of SEQ ID NO: 106 and a VL comprising an amino acid sequence of SEQ ID NO: 229. In some embodiments, the antibody is A553/A652 comprising a VH comprising an amino acid sequence of SEQ ID NO: 106 and a VL comprising an amino acid sequence of SEQ ID NO: 231. In some embodiments, the antibody is A553/A653 comprising a VH comprising an amino acid sequence of SEQ ID NO: 106 and a VL comprising an amino acid sequence of SEQ ID NO: 233. In some embodiments, the antibody is A553/A654comprising a VH comprising an amino acid sequence of SEQ ID NO: 106 and a VL comprising an amino acid sequence of SEQ ID NO: 235. In some embodiments, the antibody is A553/A656 comprising a VH comprising an amino acid sequence of SEQ ID NO: 106 and a VL comprising an amino acid sequence of SEQ ID NO: 237.

In yet another aspect, provided herein are antibodies that compete with one of the humanized antibody or antigen binding fragment thereof described above. Such antibodies may also bind to the same epitope as one of the above mentioned antibodies, or an overlapping epitope. Antibodies and fragments that compete with or bind to the same epitope as the above-mentioned antibodies are expected to show similar functional properties.

In certain embodiments, an antibody described herein or an antigen-binding fragment thereof comprises amino acid sequences with certain percent identity relative to the humanized antibodies described above. The percent identity between two sequences can be determined using techniques similar to those described above, with or without allowing gaps. In calculating percent identity, typically only exact matches are counted.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 179, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 179, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 179, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 66, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 66, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 66, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 68, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 68, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 68, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 70, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 70, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 70, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 72, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 72, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 72, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 74, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 74, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 74, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 76, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 76, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 76, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 78, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 78, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 78, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 80, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 80, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 80, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95% or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 82, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 82, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 82, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 84, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 84, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 84, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 86, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 86, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 86, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 88, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 88, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 88, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 90, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 90, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 90, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 110, and/or a VL region having at least 80%, at least 85%, at least 90%, at least 95%, or at least 98% sequence identity to the amino acid sequence of SEQ ID NO: 231, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 110, and/or a VL region comprising CDRs having at least 80%, at least 85%, at least 90%, at least 95%, or at least 98% sequence identity to the amino acid sequence of the CDRs contained in SEQ ID NO: 231, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 110, and/or a VL region comprising VL framework regions having at least 80%, at least 85%, at least 90%, at least 95%, or at least 98% sequence identity to the amino acid sequence the framework regions contained in SEQ ID NO: 231, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 106, and/or a VL region having at least 80%, at least 85%, at least 90%, at least 95%, or at least 98% sequence identity to the amino acid sequence of SEQ ID NO: 231, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 106, and/or a VL region comprising CDRs having at least 80%, at least 85%, at least 90%, at least 95%, or at least 98% sequence identity to the amino acid sequence of the CDRs contained in SEQ ID NO: 231, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 106, and/or a VL region comprising VL framework regions having at least 80%, at least 85%, at least 90%, at least 95%, or at least 98% sequence identity to the amino acid sequence the framework regions contained in SEQ ID NO: 231, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 235, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 235, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 235, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 203, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 203, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 203, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 229, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 229, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 229, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 231, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 231, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 231, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 209, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 209, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 209, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 211, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 211, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 211, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 221, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 221, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 221, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 233, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 233, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 233, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 205, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 205, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 205, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 223, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 223, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 223, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 229, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 229, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 229, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 231, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 231, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 231, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 233, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 233, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 233, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 235, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 235, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 235, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 225, and/or a VL region having at least 80%, at least 85%, at least 90%, at least 95%, or at least 98% sequence identity to the amino acid sequence of SEQ ID NO: 237, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 225, and/or a VL region comprising CDRs having at least 80%, at least 85%, at least 90%, at least 95%, or at least 98% sequence identity to the amino acid sequence of the CDRs contained in SEQ ID NO: 237, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 225, and/or a VL region comprising VL framework regions having at least 80%, at least 85%, at least 90%, at least 95%, or at least 98% sequence identity to the amino acid sequence the framework regions contained in SEQ ID NO: 237, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 215, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 215, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 215, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 108, and/or a VL region having at least 80%, at least 85%, at least 90%, at least 95%, or at least 98% sequence identity to the amino acid sequence of SEQ ID NO: 237, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 108, and/or a VL region comprising CDRs having at least 80%, at least 85%, at least 90%, at least 95%, or at least 98% sequence identity to the amino acid sequence of the CDRs contained in SEQ ID NO: 237, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 108, and/or a VL region comprising VL framework regions having at least 80%, at least 85%, at least 90%, at least 95%, or at least 98% sequence identity to the amino acid sequence the framework regions contained in SEQ ID NO: 237, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 207, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 207, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 207, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 213, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 213, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 213, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 229, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 229, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 229, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 231, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 231, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 231, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 233, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 233, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 233, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 235, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 235, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 235, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 217, and/or a VL region having at least 80%, at least 85%, at least 90%, at least 95%, or at least 98% sequence identity to the amino acid sequence of SEQ ID NO: 237, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 217, and/or a VL region comprising CDRs having at least 80%, at least 85%, at least 90%, at least 95%, or at least 98% sequence identity to the amino acid sequence of the CDRs contained in SEQ ID NO: 237, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 217, and/or a VL region comprising VL framework regions having at least 80%, at least 85%, at least 90%, at least 95%, or at least 98% sequence identity to the amino acid sequence the framework regions contained in SEQ ID NO: 237, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 219, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 219, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 219, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 92, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 92, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 92, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 94, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 94, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 94, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 96, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 96, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 96, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 98, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 98, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 98, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 100, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 100, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 100, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 102, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 102, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 102, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 104, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 104, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 104, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 112, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 112, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 112, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 229, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 229, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 229, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 231, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 231, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 231, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 233, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 233, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 233, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 235, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 235, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 235, wherein the antibody immunospecifically binds to Fn14.

In certain embodiments, an antibody provided herein or an antigen-binding fragment thereof comprises a VH region having at least 80%, at least 85%, at least 90%, at least 95%, or at least 98% sequence identity to the amino acid sequence of SEQ ID NO: 227, and/or a VL region having at least 80%, at least 85%, at least 90%, at least 95%, or at least 98% sequence identity to the amino acid sequence of SEQ ID NO: 237, wherein the antibody immunospecifically binds to Fn14. In certain embodiments, an antibody provided herein or an antigen-binding fragment thereof comprises a VH region comprising CDRs having at least 80%, at least 85%, at least 90%, at least 95%, or at least 98% sequence identity to the amino acid sequence of the CDRs contained in SEQ ID NO: 227, and/or a VL region comprising CDRs having at least 80%, at least 85%, at least 90%, at least 95%, or at least 98% sequence identity to the amino acid sequence of the CDRs contained in SEQ ID NO: 237, wherein the antibody immunospecifically binds to Fn14. In certain embodiments, an antibody provided herein or an antigen-binding fragment thereof comprises a VH region comprising VH framework regions having at least 80%, at least 85%, at least 90%, at least 95%, or at least 98% sequence identity to the amino acid sequence of the framework regions contained in SEQ ID NO: 227, and/or a VL region comprising VL framework regions having at least 80%, at least 85%, at least 90%, at least 95%, or at least 98% sequence identity to the amino acid sequence the framework regions contained in SEQ ID NO: 237, wherein the antibody immunospecifically binds to Fn14.

5.2.6 Human Antibodies

In specific embodiments, the antibody is a fully human anti-human antibody. Fully human antibodies may be produced by any method known in the art. Human anti-Fn14 antibodies provided herein, e.g., dual antagonist antibody binding to Fn14, can be constructed by combining Fv clone variable domain sequence(s) selected from human-derived phage display libraries with known human constant domain sequences(s). Alternatively, human monoclonal antibodies of the present disclosure can be made by the hybridoma method. Human myeloma and mouse-human heteromyeloma cell lines for the production of human monoclonal antibodies have been described, for example, by Kozbor, 1984, J. Immunol. 133:3001-05; Brodeur et al., Monoclonal Antibody Production Techniques and Applications 51-63 (1987); and Boerner et a/., 1991, J. Immunol. 147:86-95.

It is also possible to produce transgenic animals (e.g., mice) that are capable, upon immunization, of producing a full repertoire of human antibodies in the absence of endogenous immunoglobulin production. Transgenic mice that express human antibody repertoires have been used to generate high-affinity human sequence monoclonal antibodies against a wide variety of potential drug targets (see, e.g., Jakobovits, A., 1995, Curr. Opin. Biotechnol. 6(5):561-66; BrUggemann and Taussing, 1997, Curr. Opin. Biotechnol. 8(4):455-58; U.S. Pat. Nos. 6,075,181 and 6,150,584; and Lonberg et al., 2005, Nature Biotechnol. 23:1117-25).

Alternatively, the human antibody may be prepared via immortalization of human B lymphocytes producing an antibody directed against a target antigen (e.g., such B lymphocytes may be recovered from an individual or may have been immunized in vitro) (see, e.g., Cole et aL, Monoclonal Antibodies and Cancer Therapy (1985); Boerner et al., 1991, J. Immunol. 147(1):86-95; and U.S. Pat. No. 5,750,373).

Gene shuffling can also be used to derive human antibodies from non-human, for example, rodent, antibodies, where the human antibody has similar affinities and specificities to the starting non-human antibody. According to this method, which is also called "epitope imprinting" or "guided selection," either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone (e.g., the epitope guides (imprints) the choice of the human chain partner). When the process is repeated in order to replace the remaining non-human chain, a human antibody is obtained (see, e.g., PCT WO 93/06213; and Osbourn et al., 2005, Methods 36:61-68). Unlike traditional humanization of non-human antibodies by CDR grafting, this technique provides completely human antibodies, which have no FR or CDR residues of non-human origin. Examples of guided selection to humanize mouse antibodies towards cell surface antigens include the folate-binding protein present on ovarian cancer cells (see, e.g., Figini et al., 1998, Cancer Res. 58:991-96) and CD147, which is highly expressed on hepatocellular carcinoma (see, e.g., Bao et al., 2005, Cancer Biol. Ther. 4:1374-80).

A potential disadvantage of the guided selection approach is that shuffling of one antibody chain while keeping the other constant could result in epitope drift. In order to maintain the epitope recognized by the non-human antibody, CDR retention can be applied (see, e.g., Klimka et al., 2000, Br. J. Cancer. 83:252-60; and Beiboer et al., 2000, J. Mol. Biol. 296:833-49). In this method, the non-human VH CDR3 is commonly retained, as this CDR may be at the center of the antigen-binding site and may be the most important region of the antibody for antigen recognition. In some instances, however, VH CDR3 and VL CDR3, as well as VH CDR2, VL CDR2, and VL CDR1 of the non-human antibody may be retained.

5.2.7 Multispecific Antibodies

Multispecific antibodies such as bispecific antibodies are monoclonal antibodies that have binding specificities for at least two different antigens. In certain embodiments, the multispecific antibodies can be constructed based on the sequences of the antibodies provided herein, e.g., the CDR sequences listed in the Sequence Listing provided herein. In certain embodiments, the multispecific antibodies provided herein are bispecific antibodies. In certain embodiments, bispecific antibodies are mouse, chimeric, human or humanized antibodies. In certain embodiments, one of the binding specificities is for Fn14 and the other is for any other antigen. In some embodiments, one of the binding specificities is for Fn14 and the other is for another antigen such as a cytokine or chemokine. In certain embodiments, bispecific antibodies may bind to two different epitopes of Fn14. Bispecific antibodies can be prepared as full length antibodies or antibody fragments (e.g., F(ab')2 bispecific antibodies).

Methods for making multispecific antibodies are known in the art, such as, by co-expression of two immunoglobulin heavy chain-light chain pairs, where the two heavy chains have different specificities (see, e.g., Milstein and Cuello, 1983, Nature 305:537-40). For further details of generating multispecific antibodies (e.g., bispecific antibodies), see, for example, Bispecific Antibodies (Kontermann ed., 2011).

5.2.8 Multivalent Antibodies

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (e.g., two polypeptide chains), wherein the polypeptide chain(s) comprise two or more variable domains. For instance, the polypeptide chain(s) may comprise VD1-$(X_1)$n-VD2-$(X_2)$n-Fc, wherein VD1 is a first variable domain, VD2 is a second variable domain, Fc is one polypeptide chain of an Fc region, $X_1$ and $X_2$ represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (e.g., four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

5.2.9 Fc Engineering

It may be desirable to modify an antibody provided herein by Fc engineering. In certain embodiments, the modification to the Fc region of the antibody results in the decrease or elimination of an effector function of the antibody. In certain embodiments, the effector function is ADCC, ADCP, and/or CDC. In some embodiments, the effector function is ADCC. In other embodiments, the effector function is ADCP. In other embodiments, the effector function is CDC. In one embodiment, the effector function is ADCC and ADCP. In one embodiment, the effector function is ADCC and CDC. In one embodiment, the effector function is ADCP and CDC. In one embodiment, the effector function is ADCC, ADCP and CDC. This may be achieved by introducing one or more amino acid substitutions in an Fc region of the antibody.

To increase the serum half-life of the antibody, one may incorporate a salvage receptor binding epitope into the antibody (especially an antibody fragment), for example, as described in U.S. Pat. No. 5,739,277. Term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

5.2.10 Alternative Binding Agents

The present disclosure encompasses non-immunoglobulin binding agents that specifically bind to the same epitope as an antibody disclosed herein. In some embodiments, a non-immunoglobulin binding agent is identified as an agent that displaces or is displaced by an antibody of the present disclosure in a competitive binding assay. These alternative binding agents may include, for example, any of the engineered protein scaffolds known in the art. Such scaffolds may comprise one or more CDRs as shown in Tables 24. Such scaffolds include, for example, anticalins, which are based upon the lipocalin scaffold, a protein structure characterized by a rigid beta-barrel that supports four hypervariable loops which form the ligand binding site. Novel binding specificities may be engineered by targeted random mutagenesis in the loop regions, in combination with functional display and guided selection (see, e.g., Skerra, 2008, FEBS J. 275:2677-83). Other suitable scaffolds may include, for example, adnectins, or monobodies, based on the tenth extracellular domain of human fibronectin III (see, e.g., Koide and Koide, 2007, Methods Mol. Biol. 352: 95-109); affibodies, based on the Z domain of staphylococcal protein A (see, e.g., Nygren et al., 2008, FEBS J. 275:2668-76); DARPins, based on ankyrin repeat proteins (see, e.g., Stumpp et al., 2008, Drug. Discov. Today 13:695-701); fynomers, based on the SH3 domain of the human Fyn protein kinase (see, e.g., Grabulovski et al., 2007, J. Biol. Chem. 282:3196-204); affitins, based on Sac7d from Sulfolobus acidolarius (see, e.g., Krehenbrink et al., 2008, J. Mol. Biol. 383:1058-68); affilins, based on human y-B-crystallin (see, e.g., Ebersbach et al., 2007, J. Mol. Biol. 372:172-85); avimers, based on the A domain of membrane receptor proteins (see, e.g., Silverman et al., 2005, Biotechnol. 23:1556-61); cysteine-rich knottin peptides (see, e.g., Kolmar, 2008, FEBS J. 275:2684-90); and engineered Kunitz-type inhibitors (see, e.g., Nixon and Wood, 2006, Curr. Opin. Drug. Discov. Dev. 9:261-68). For a review, see, for example, Gebauer and Skerra, 2009, Curr. Opin. Chem. Biol. 13:245-55.

5.2.11 Antibody Variants

In some embodiments, amino acid sequence modification(s) of the antibodies or antigen binding fragments that bind to Fn14 provided herein are contemplated. For example, it may be desirable to improve the binding affinity and/or other biological properties of the antibody, including but not limited to specificity, thermostability, expression level, effector functions, glycosylation, reduced immunogenicity, or solubility. Thus, in addition to the antibodies described herein, it is contemplated that antibody variants can be prepared. For example, antibody variants can be prepared by introducing appropriate nucleotide changes into the encoding DNA, and/or by synthesis of the desired antibody or polypeptide. Those skilled in the art would appreciate that amino acid changes may alter post-translational processes of the antibody, such as changing the number or position of glycosylation sites or altering the membrane anchoring characteristics.

In some embodiments, antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

Variations may be a substitution, deletion, or insertion of one or more codons encoding the antibody or polypeptide that results in a change in the amino acid sequence as compared with the native sequence antibody or polypeptide. Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the full-length or mature native sequence.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Alternatively, conservative (e.g., within an amino acid group with similar properties and/or side chains) substitutions may be made, so as to maintain or not significantly change the properties. Amino acids may be grouped according to similarities in the properties of their side chains (see, e.g., Lehninger, Biochemistry 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions entail exchanging a member of one of these classes for another class. Such substituted residues also may be introduced into the conservative substitution sites or, into the remaining (non-conserved) sites. Accordingly, in one embodiment, an antibody or antigen binding fragment thereof that binds to an Fn14 epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of an antibody described herein, for examples, the antibodies described in Section 6 below.

In one embodiment, an antibody or antigen-binding fragment thereof that binds to an Fn14 epitope comprises an amino acid sequence that is at least 35% identical to the amino acid sequence of an antibody described herein. In one embodiment, an antibody or antigen-binding fragment thereof that binds to an Fn14 epitope comprises an amino acid sequence that is at least 40% identical to the amino acid sequence of an antibody described herein. In one embodiment, an antibody or antigen-binding fragment thereof that binds to an Fn14 epitope comprises an amino acid sequence that is at least 45% identical to the amino acid sequence of an antibody described herein. In one embodiment, an antibody or antigen-binding fragment thereof that binds to an Fn14 epitope comprises an amino acid sequence that is at least 50% identical to the amino acid sequence of an antibody described herein. In one embodiment, an antibody or antigen-binding fragment thereof that binds to an Fn14 epitope comprises an amino acid sequence that is at least 55% identical to the amino acid sequence of an antibody described herein. In one embodiment, an antibody or antigen-binding fragment thereof that binds to an Fn14 epitope comprises an amino acid sequence that is at least 60% identical to the amino acid sequence of an antibody described herein. In one embodiment, an antibody or antigen-binding fragment thereof that binds to an Fn14 epitope comprises an amino acid sequence that is at least 65% identical to the amino acid sequence of an antibody described herein. In one embodiment, an antibody or antigen-binding fragment thereof that binds to an Fn14 epitope comprises an amino acid sequence that is at least 70% identical to the amino acid sequence of an antibody described herein. In one embodiment, an antibody or antigen-binding fragment thereof that binds to an Fn14 epitope comprises an amino acid sequence that is at least 75% identical to the amino acid sequence of an antibody described herein. In one embodiment, an antibody or antigen-binding fragment thereof that binds to an Fn14 epitope comprises an amino acid sequence that is at least 80% identical to the amino acid sequence of an antibody described herein. In one embodiment, an antibody or antigen-binding fragment thereof that binds to an Fn14 epitope comprises an amino acid sequence that is at least 90% identical to the amino acid sequence of an antibody described herein. In one embodiment, an antibody or antigen-binding fragment thereof that binds to an Fn14 epitope comprises an amino acid sequence that is at least 95% identical to the amino acid sequence of an antibody described herein. In one embodiment, an antibody or antigen-binding fragment thereof that binds to an Fn14 comprises an amino acid sequence that is at least 99% identical to the amino acid sequence of an antibody described herein.

In some embodiments, provided herein is an antibody or antigen binding fragment thereof that binds to an Fn14 epitope and comprises a VH region comprising an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in the Sequence Listing provided herein, and/or a VL region comprising an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in the Sequence Listing provided herein.

In some embodiments, provided herein is an antibody or antigen binding fragment thereof that binds to an Fn14 epitope and comprises a VH region comprising an amino acid sequence that is at least 35% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 40% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 45% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 50% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 55% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 60% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 65% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 70% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 75% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 80% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 85% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 90% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 95% identical to an amino acid sequence depicted in the Sequence Listing provided herein and Tables 26-35. In some embodiments, provided herein is an antibody or antigen binding fragment thereof that binds to an Fn14 epitope and comprises a VH region comprising an amino acid sequence that is at least 99% identical to an amino acid sequence depicted in the Sequence Listing provided herein and Tables 26-35.

In some embodiments, provided herein is an antibody or antigen binding fragment thereof that binds to an Fn14 epitope and comprises a VL region comprising an amino acid sequence that is at least 35% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 40% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 45% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 50% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 55% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 60% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 65% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 70% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 75% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 80% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 85% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 90% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 95% identical to an amino acid sequence depicted in the Sequence Listing provided herein and Tables 26-35. In some embodiments, provided herein is an antibody or antigen binding fragment thereof that binds to an Fn14 epitope and comprises a VL region comprising an amino acid sequence that is at least 99% identical to an amino acid sequence depicted in the Sequence Listing provided herein and Tables 26-35.

In yet another embodiment, an antibody or antigen binding fragment thereof that binds to an Fn14 epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence and/or a VL CDR amino acid sequence depicted in the Sequence Listing provided herein and Tables 26-35.

In yet another embodiment, an antibody or antigen binding fragment thereof that binds to an Fn14 epitope comprises a VH CDR and/or a VL CDR amino acid sequence that is at least 35% identical to a VH CDR amino acid sequence depicted and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 40% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 45% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 50% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 55% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 60% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 65% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 70% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 75% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 80% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 85% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 90% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 95% identical to a VH CDR amino acid sequence and/or a VL CDR amino acid sequence depicted in the Sequence Listing provided herein and Tables 26-35. In yet another embodiment, an antibody or antigen binding fragment thereof that binds to an Fn14 epitope comprises a VH CDR and/or a VL CDR amino acid sequence that is at least 99% identical to a VH CDR amino acid sequence and/or a VL CDR amino acid sequence depicted in the Sequence Listing provided herein and Tables 26-35.

The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce the anti-Fn14 antibody variant DNA.

Any cysteine residue not involved in maintaining the proper conformation of the antibody provided herein also may be substituted, for example, with another amino acid, such as alanine or serine, to improve the oxidative stability of the molecule and to prevent aberrant crosslinking. Conversely, cysteine bond(s) may be added to the antibody to improve its stability (e.g., where the antibody is an antibody fragment such as an Fv fragment).

In some embodiments, an antibody molecule of the present disclosure is a "de-immunized" antibody. A "de-immunized" antibody is an antibody derived from a humanized or chimeric antibody, which has one or more alterations in its amino acid sequence resulting in a reduction of immunogenicity of the antibody, compared to the respective original non-de-immunized antibody. One of the procedures for generating such antibody mutants involves the identification and removal of T-cell epitopes of the antibody molecule. In a first step, the immunogenicity of the antibody molecule can be determined by several methods, for example, by in vitro determination of T-cell epitopes or in silico prediction of such epitopes, as known in the art. Once the critical residues for T-cell epitope function have been identified, mutations can be made to remove immunogenicity and retain antibody activity. For review, see, for example, Jones et al., 2009, Methods in Molecular Biology 525:405-23.

5.2.12 In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed on the surface of an organism (e.g., phage, bacteria, yeast, or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review, see, for example, Hoogenboom, 2002, Methods. Mol. Biol. 178:1-37; and Bradbury and Marks, 2004, J. Immunol. Methods 290:29-49.

In a yeast display system (see, e.g., Boder et al., 1997, Nat. Biotech. 15:553-57; and Chao et al., 2006, Nat. Protocols 1:755-68), the antibody may be fused to the adhesion subunit of the yeast agglutinin protein Aga2p, which attaches to the yeast cell wall through disulfide bonds to Agalp. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., 1999, J. Mol. Biol. 292:949-56). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., 2004, Gene 342:211-18).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see, e.g., Fukuda et al., 2006, Nucleic Acids Res. 34:e127). In mRNA display, a covalent bond between antibody and mRNA is established using puromycin as an adaptor molecule (Wilson et al., 2001, Proc. Natl. Acad. Sci. USA 98:3750-55).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

In some embodiments, mammalian display systems may be used.

Diversity may also be introduced into the CDRs of the antibody libraries in a targeted manner or via random introduction. The former approach includes sequentially targeting all the CDRs of an antibody via a high or low level of mutagenesis or targeting isolated hot spots of somatic hypermutations (see, e.g., Ho et al., 2005, J. Biol. Chem. 280:607-17) or residues suspected of affecting affinity on experimental basis or structural reasons. Diversity may also be introduced by replacement of regions that are naturally diverse via DNA shuffling or similar techniques (see, e.g., Lu et al., 2003, J. Biol. Chem. 278:43496-507; U.S. Pat. Nos. 5,565,332 and 6,989,250). Alternative techniques target hypervariable loops extending into framework-region residues (see, e.g., Bond et al., 2005, J. Mol. Biol. 348:699-709) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, the antibodies can be immobilized onto solid supports, columns, pins, or cellulose/poly(vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, 2005, Nature Biotechnology 23:1105-16; Quiroz and Sinclair, 2010, Revista Ingeneria Biomedia 4:39-51; and references therein.

In some specific embodiments, antibody affinity maturation can be performed using the methods exemplified in Section 6 below.

5.2.13 Antibody Modifications

Covalent modifications of the antibodies binding to Fn14 provided herein are included within the scope of the present disclosure. Covalent modifications include reacting targeted amino acid residues of an antibody with an organic derivatizing agent that is capable of reacting with selected side chains or the N- or C- terminal residues of the antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains (see, e.g., Creighton, Proteins: Structure and Molecular Properties 79-86 (1983)), acetylation of the N-terminal amine, and amidation of any C-terminal carboxyl group.

Other types of covalent modification of the antibody provided herein included within the scope of this present disclosure include altering the native glycosylation pattern of the antibody or polypeptide (see, e.g., Beck et al., 2008, Curr. Pharm. Biotechnol. 9:482-501; and Walsh, 2010, Drug Discov. Today 15:773-80), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192; or 4,179,337.

An antibody of the present disclosure may also be modified to form chimeric molecules comprising the antibody fused to another, heterologous polypeptide or amino acid sequence, for example, an epitope tag (see, e.g., Terpe, 2003, Appl. Microbiol. Biotechnol. 60:523-33) or the Fc region of an IgG molecule (see, e.g., Aruffo, Antibody Fusion Proteins 221-42 (Chamow and Ashkenazi eds., 1999)).

Also provided herein are fusion proteins comprising an antibody provided herein that binds to Fn14 and a heterologous polypeptide.

Also provided herein are panels of antibodies that bind to an Fn14 antigen. In specific embodiments, the panels of antibodies have different association rates, different dissociation rates, different affinities for an Fn14 antigen, and/or different specificities for an Fn14 antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96-well or 384-well plates, for assays such as ELISAs.

5.2.14 Immunoconjugates

The present disclosure also provides conjugates comprising any one of the antibodies of the present disclosure covalently bound by a synthetic linker to one or more non-antibody agents.

In some embodiments, antibodies provided herein are conjugated or recombinantly fused, e.g., to a therapeutic agent (e.g., a cytotoxic agent) or a diagnostic or detectable molecule. The conjugated or recombinantly fused antibodies can be useful, for example, for treating or preventing a disease or disorder such as an Fn14-mediated disease. The conjugated or recombinantly fused antibodies can be useful, for example, for monitoring or prognosing the onset, development, progression, and/or severity of an Fn14-mediated disease.

Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, but not limited to, an acridinium based compound or a HALOTAG; radioactive materials, such as, but not limited to, iodine (131I, 125I, 123I, and 121I,), carbon (14C), sulfur (35S), tritium (3H), indium (115In, 113In, 112In, and 111In), technetium (99Tc), thallium (201Ti), gallium (68Ga and 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, or 117Sn; positron emitting metals using various positron emission tomographies; and non-radioactive paramagnetic metal ions.

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, or about 100 amino acids) to generate fusion proteins, as well as uses thereof. In particular, provided herein are fusion proteins comprising an antigen-binding fragment of an antibody provided herein (e.g., CDR1, CDR2, and/or CDR3) and a heterologous protein, polypeptide, or peptide. In one embodiment, the heterologous protein, polypeptide, or peptide that the antibody is fused to is useful for targeting the antibody to a particular cell type.

Moreover, antibodies provided herein can be fused to marker or "tag" sequences, such as a peptide, to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-24, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767-78), and the "FLAG" tag.

Methods for fusing or conjugating moieties (including polypeptides) to antibodies are known (see, e.g., Arnon et al., Monoclonal Antibodies for Immunotargeting of Drugs in Cancer Therapy, in Monoclonal Antibodies and Cancer Therapy 243-56 (Reisfeld et al. eds., 1985); Hellstrom et al., Antibodies for Drug Delivery, in Controlled Drug Delivery 623-53 (Robinson et al. eds., 2d ed. 1987); Thorpe, Antibody Carriers of Cytotoxic Agents in Cancer Therapy: A Review, in Monoclonal Antibodies: Biological and Clinical Applications 475-506 (Pinchera et al. eds., 1985); Analysis, Results, and Future Prospective of the Therapeutic Use of Radiolabeled Antibody in Cancer Therapy, in Monoclonal Antibodies for Cancer Detection and Therapy 303-16 (Baldwin et aL eds., 1985); Thorpe et al., 1982,Immunol. Rev. 62:119-58; U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., 1991, Proc. Natl. Acad. Sci. USA, 88: 10535-39; Traunecker et al., 1988, Nature, 331:84-86; Zheng et al., 1995, J. Immunol. 154:5590-600; and Vil et al., 1992, Proc. Natl. Acad. Sci. USA 89:11337-41).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the antibodies as provided herein, including, for example, antibodies with higher affinities and lower dissociation rates (see, e.g., U.S. Pat. Nos. 5,605,793; 5,811, 238; 5,830,721; 5,834,252; and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-13). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described, for example, in U.S. Pat. No. 4,676,980.

Antibodies as provided herein may also be attached to solid supports, which are particularly useful for immunoassays or purification of the target antigen. Such solid supports include, but are not limited to, glass, cellulose, polyacrylamide, nylon, polystyrene, polyvinyl chloride, or polypropylene.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., 1992, Cancer Res. 52:127-31; and U.S. Pat. No. 5,208,020), thioether linkers, or hydrophilic linkers designed to evade multidrug transporter-mediated resistance (see, e.g., Kovtun et al., 2010, Cancer Res. 70:2528-37).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate). The present disclosure further contemplates that conjugates of antibodies and agents may be prepared using any suitable methods as disclosed in the art (see, e.g., Bioconjugate Techniques (Hermanson ed., 2d ed. 2008)).

Conventional conjugation strategies for antibodies and agents have been based on random conjugation chemistries involving the c-amino group of Lys residues or the thiol group of Cys residues, which results in heterogeneous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., 2008, J. Immunol. Meth. 332: 41-52; and Junutula et al., 2008, Nature Biotechnol. 26:925-32). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., 2008, Proc. Natl. Acad. Sci. USA 105: 12451-56; and Hofer et al., 2009, Biochemistry 48(50): 12047-57).

5.3 Polynucleotides

In certain embodiments, the disclosure encompasses polynucleotides that encode the antibodies described herein. The term "polynucleotides that encode a polypeptide" encompasses a polynucleotide that includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, a polynucleotide comprises the coding sequence for a polypeptide fused in the same reading frame to a polynucleotide which aids, for example, in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In certain embodiments, a polynucleotide comprises the coding sequence for a polypeptide fused in the same reading frame to a marker or tag sequence. For example, in some embodiments, a marker sequence is a hexa-histidine tag supplied by a vector that allows efficient purification of the polypeptide fused to the marker in the case of a bacterial host. In some embodiments, a marker is used in conjunction with other affinity tags.

In certain embodiments, the polynucleotide provided herein is selected from the polynucleotides listed in the Sequence Listing provided herein or any combinations thereof. In certain embodiments, the polynucleotide provided herein is selected from the polynucleotides listed in Table 36 below.

TABLE 36

Polynucleotide sequences of exemplary mouse antibodies

| Antibody Name | VH | VL |
|---|---|---|
| A291/A290 | SEQ ID NO: 34 | SEQ ID NO: 39 |
| A291/A403 | SEQ ID NO: 34 | SEQ ID NO: 51 |
| A291/A439 | SEQ ID NO: 34 | SEQ ID NO: 57 |
| A291/A440 | SEQ ID NO: 34 | SEQ ID NO: 199 |
| A402/A290 | SEQ ID NO: 49 | SEQ ID NO: 39 |
| A402/A403 | SEQ ID NO: 49 | SEQ ID NO: 51 |
| A402/A439 | SEQ ID NO: 49 | SEQ ID NO: 57 |
| A402/A440 | SEQ ID NO: 49 | SEQ ID NO: 199 |
| A448/A290 | SEQ ID NO: 53 | SEQ ID NO: 39 |
| A448/A403 | SEQ ID NO: 53 | SEQ ID NO: 51 |
| A448/A439 | SEQ ID NO: 53 | SEQ ID NO: 57 |
| A448/A440 | SEQ ID NO: 53 | SEQ ID NO: 199 |
| A490/A290 | SEQ ID NO: 55 | SEQ ID NO: 39 |
| A490/A403 | SEQ ID NO: 55 | SEQ ID NO: 51 |
| A490/A439 | SEQ ID NO: 55 | SEQ ID NO: 57 |
| A490/A440 | SEQ ID NO: 55 | SEQ ID NO: 199 |
| A486/A290 | SEQ ID NO: 59 | SEQ ID NO: 39 |
| A486/A403 | SEQ ID NO: 59 | SEQ ID NO: 51 |
| A486/A439 | SEQ ID NO: 59 | SEQ ID NO: 57 |
| A486/A440 | SEQ ID NO: 59 | SEQ ID NO: 199 |
| A437/A290 | SEQ ID NO: 180 | SEQ ID NO: 39 |
| A437/A403 | SEQ ID NO: 180 | SEQ ID NO: 51 |
| A437/A439 | SEQ ID NO: 180 | SEQ ID NO: 57 |
| A437/A440 | SEQ ID NO: 180 | SEQ ID NO: 199 |
| A428/A290 | SEQ ID NO: 189 | SEQ ID NO: 39 |
| A428/A403 | SEQ ID NO: 189 | SEQ ID NO: 51 |
| A428/A439 | SEQ ID NO: 189 | SEQ ID NO: 57 |
| A428/A440 | SEQ ID NO: 189 | SEQ ID NO: 199 |
| A435/A290 | SEQ ID NO: 191 | SEQ ID NO: 39 |
| A435/A403 | SEQ ID NO: 191 | SEQ ID NO: 51 |
| A435/A439 | SEQ ID NO: 191 | SEQ ID NO: 57 |
| A435/A440 | SEQ ID NO: 191 | SEQ ID NO: 199 |
| A436/A290 | SEQ ID NO: 193 | SEQ ID NO: 39 |
| A436/A403 | SEQ ID NO: 193 | SEQ ID NO: 51 |
| A436/A439 | SEQ ID NO: 193 | SEQ ID NO: 57 |
| A436/A440 | SEQ ID NO: 193 | SEQ ID NO: 199 |
| A438/A290 | SEQ ID NO: 195 | SEQ ID NO: 39 |
| A438/A403 | SEQ ID NO: 195 | SEQ ID NO: 51 |
| A438/A439 | SEQ ID NO: 195 | SEQ ID NO: 57 |
| A438/A440 | SEQ ID NO: 195 | SEQ ID NO: 199 |
| A450/A290 | SEQ ID NO: 197 | SEQ ID NO: 39 |
| A450/A403 | SEQ ID NO: 197 | SEQ ID NO: 51 |
| A450/A439 | SEQ ID NO: 197 | SEQ ID NO: 57 |
| A450/A440 | SEQ ID NO: 197 | SEQ ID NO: 199 |

In some embodiments, the polynucleotide comprises a VH nucleotide sequence of SEQ ID NO: 34 and/or a VL nucleotide sequence of SEQ ID NO: 39. In some embodiments, the polynucleotide comprises a VH nucleotide sequence of SEQ ID NO: 34 and/or a VL nucleotide sequence of SEQ ID NO: 51. In some embodiments, the polynucleotide comprises a VH nucleotide sequence of SEQ ID NO: 34 and/or a VL nucleotide sequence of SEQ ID NO: 57. In some embodiments, the polynucleotide comprises a VH nucleotide sequence of SEQ ID NO: 34 and/or a VL nucleotide sequence of SEQ ID NO: 199.

In some embodiments, the polynucleotide comprises a VH nucleotide sequence of SEQ ID NO: 49 and/or a VL nucleotide sequence of SEQ ID NO: 39. In some embodiments, the polynucleotide comprises a VH nucleotide sequence of SEQ ID NO: 49 and/or a VL nucleotide sequence of SEQ ID NO: 51. In some embodiments, the polynucleotide comprises a VH nucleotide sequence of SEQ ID NO: 49 and/or a VL nucleotide sequence of SEQ ID NO: 57. In some embodiments, the polynucleotide comprises a VH nucleotide sequence of SEQ ID NO: 49 and/or a VL nucleotide sequence of SEQ ID NO: 199.

In some embodiments, the polynucleotide comprises a VH nucleotide sequence of SEQ ID NO: 53 and/or a VL nucleotide sequence of SEQ ID NO: 39. In some embodiments, the polynucleotide comprises a VH nucleotide sequence of SEQ ID NO: 53 and/or a VL nucleotide sequence of SEQ ID NO: 51. In some embodiments, the polynucleotide comprises a VH nucleotide sequence of SEQ ID NO: 53 and/or a VL nucleotide sequence of SEQ ID NO: 57. In some embodiments, the polynucleotide comprises a VH nucleotide sequence of SEQ ID NO: 53 and/or a VL nucleotide sequence of SEQ ID NO: 199.

In some embodiments, the polynucleotide comprises a VH nucleotide sequence of SEQ ID NO: 55 and/or a VL nucleotide sequence of SEQ ID NO: 39. In some embodiments, the polynucleotide comprises a VH nucleotide sequence of SEQ ID NO: 55 and/or a VL nucleotide sequence of SEQ ID NO: 51. In some embodiments, the polynucleotide comprises a VH nucleotide sequence of SEQ ID NO: 55 and/or a VL nucleotide sequence of SEQ ID NO: 57. In some embodiments, the polynucleotide comprises a VH nucleotide sequence of SEQ ID NO: 55 and/or a VL nucleotide sequence of SEQ ID NO: 199.

In some embodiments, the polynucleotide comprises a VH nucleotide sequence of SEQ ID NO: 59 and/or a VL nucleotide sequence of SEQ ID NO: 39. In some embodiments, the polynucleotide comprises a VH nucleotide sequence of SEQ ID NO: 59 and/or a VL nucleotide sequence of SEQ ID NO: 51. In some embodiments, the polynucleotide comprises a VH nucleotide sequence of SEQ ID NO: 59 and/or a VL nucleotide sequence of SEQ ID NO: 57. In some embodiments, the polynucleotide comprises a VH nucleotide sequence of SEQ ID NO: 59 and/or a VL nucleotide sequence of SEQ ID NO: 199.

In some embodiments, the polynucleotide comprises a VH nucleotide sequence of SEQ ID NO: 180 and/or a VL nucleotide sequence of SEQ ID NO: 39. In some embodiments, the polynucleotide comprises a VH nucleotide sequence of SEQ ID NO: 180 and/or a VL nucleotide sequence of SEQ ID NO: 51. In some embodiments, the polynucleotide comprises a VH nucleotide sequence of SEQ ID NO: 180 and/or a VL nucleotide sequence of SEQ ID NO: 57. In some embodiments, the polynucleotide comprises a VH nucleotide sequence of SEQ ID NO: 180 and/or a VL nucleotide sequence of SEQ ID NO: 199.

In some embodiments, the polynucleotide comprises a VH nucleotide sequence of SEQ ID NO: 189 and/or a VL nucleotide sequence of SEQ ID NO: 39. In some embodiments, the polynucleotide comprises a VH nucleotide sequence of SEQ ID NO: 189 and/or a VL nucleotide sequence of SEQ ID NO: 51. In some embodiments, the polynucleotide comprises a VH nucleotide sequence of SEQ ID NO: 189 and/or a VL nucleotide sequence of SEQ ID NO: 57. In some embodiments, the polynucleotide comprises a VH nucleotide sequence of SEQ ID NO: 189 and/or a VL nucleotide sequence of SEQ ID NO: 199.

In some embodiments, the polynucleotide comprises a VH nucleotide sequence of SEQ ID NO: 191 and/or a VL nucleotide sequence of SEQ ID NO: 39. In some embodiments, the polynucleotide comprises a VH nucleotide sequence of SEQ ID NO: 191 and/or a VL nucleotide sequence of SEQ ID NO: 51. In some embodiments, the polynucleotide comprises a VH nucleotide sequence of SEQ ID NO: 191 and/or a VL nucleotide sequence of SEQ ID NO: 57. In some embodiments, the polynucleotide comprises a VH nucleotide sequence of SEQ ID NO: 191 and/or a VL nucleotide sequence of SEQ ID NO: 199.

In some embodiments, the polynucleotide comprises a VH nucleotide sequence of SEQ ID NO: 193 and/or a VL nucleotide sequence of SEQ ID NO: 39. In some embodiments, the polynucleotide comprises a VH nucleotide sequence of SEQ ID NO: 193 and/or a VL nucleotide sequence of SEQ ID NO: 51. In some embodiments, the polynucleotide comprises a VH nucleotide sequence of SEQ ID NO: 193 and/or a VL nucleotide sequence of SEQ ID NO: 57. In some embodiments, the polynucleotide comprises a VH nucleotide sequence of SEQ ID NO: 193 and/or a VL nucleotide sequence of SEQ ID NO: 199.

In some embodiments, the polynucleotide comprises a VH nucleotide sequence of SEQ ID NO: 195 and/or a VL nucleotide sequence of SEQ ID NO: 39. In some embodiments, the polynucleotide comprises a VH nucleotide sequence of SEQ ID NO: 195 and/or a VL nucleotide sequence of SEQ ID NO: 51. In some embodiments, the polynucleotide comprises a VH nucleotide sequence of SEQ ID NO: 195 and/or a VL nucleotide sequence of SEQ ID NO: 57. In some embodiments, the polynucleotide comprises a VH nucleotide sequence of SEQ ID NO: 195 and/or a VL nucleotide sequence of SEQ ID NO: 199.

In some embodiments, the polynucleotide comprises a VH nucleotide sequence of SEQ ID NO: 197 and/or a VL nucleotide sequence of SEQ ID NO: 39. In some embodiments, the polynucleotide comprises a VH nucleotide sequence of SEQ ID NO: 197 and/or a VL nucleotide sequence of SEQ ID NO: 51. In some embodiments, the polynucleotide comprises a VH nucleotide sequence of SEQ ID NO: 197 and/or a VL nucleotide sequence of SEQ ID NO: 57. In some embodiments, the polynucleotide comprises a VH nucleotide sequence of SEQ ID NO: 197 and/or a VL nucleotide sequence of SEQ ID NO: 199.

In some embodiments, the polynucleotide provided herein is selected from Table 37 below.

TABLE 37

Polynucleotide sequences of humanized antibodies

| Antibody Name | VH | VL |
| --- | --- | --- |
| A454/A467 | SEQ ID NO: 65 | SEQ ID NO: 91 |
| A454/A468 | SEQ ID NO: 65 | SEQ ID NO: 93 |
| A454/A469 | SEQ ID NO: 65 | SEQ ID NO: 95 |
| A454/A470 | SEQ ID NO: 65 | SEQ ID NO: 97 |
| A454/A471 | SEQ ID NO: 65 | SEQ ID NO: 99 |
| A454/A472 | SEQ ID NO: 65 | SEQ ID NO: 101 |
| A454/A473 | SEQ ID NO: 65 | SEQ ID NO: 103 |
| A454/A518 | SEQ ID NO: 65 | SEQ ID NO: 111 |
| A454/A651 | SEQ ID NO: 65 | SEQ ID NO: 228 |
| A454/A652 | SEQ ID NO: 65 | SEQ ID NO: 230 |
| A454/A653 | SEQ ID NO: 65 | SEQ ID NO: 232 |
| A454/A654 | SEQ ID NO: 65 | SEQ ID NO: 234 |
| A454/A656 | SEQ ID NO: 65 | SEQ ID NO: 236 |
| A455/A467 | SEQ ID NO: 67 | SEQ ID NO: 91 |
| A455/A468 | SEQ ID NO: 67 | SEQ ID NO: 93 |
| A455/A469 | SEQ ID NO: 67 | SEQ ID NO: 95 |
| A455/A470 | SEQ ID NO: 67 | SEQ ID NO: 97 |
| A455/A471 | SEQ ID NO: 67 | SEQ ID NO: 99 |
| A455/A472 | SEQ ID NO: 67 | SEQ ID NO: 101 |
| A455/A473 | SEQ ID NO: 67 | SEQ ID NO: 103 |
| A455/A518 | SEQ ID NO: 67 | SEQ ID NO: 111 |
| A455/A651 | SEQ ID NO: 67 | SEQ ID NO: 228 |
| A455/A652 | SEQ ID NO: 67 | SEQ ID NO: 230 |
| A455/A653 | SEQ ID NO: 67 | SEQ ID NO: 232 |
| A455/A654 | SEQ ID NO: 67 | SEQ ID NO: 234 |
| A455/A656 | SEQ ID NO: 67 | SEQ ID NO: 236 |
| A456/A467 | SEQ ID NO: 69 | SEQ ID NO: 91 |
| A456/A468 | SEQ ID NO: 69 | SEQ ID NO: 93 |
| A456/A469 | SEQ ID NO: 69 | SEQ ID NO: 95 |
| A456/A470 | SEQ ID NO: 69 | SEQ ID NO: 97 |
| A456/A471 | SEQ ID NO: 69 | SEQ ID NO: 99 |
| A456/A472 | SEQ ID NO: 69 | SEQ ID NO: 101 |
| A456/A473 | SEQ ID NO: 69 | SEQ ID NO: 103 |
| A456/A518 | SEQ ID NO: 69 | SEQ ID NO: 111 |
| A456/A651 | SEQ ID NO: 69 | SEQ ID NO: 228 |
| A456/A652 | SEQ ID NO: 69 | SEQ ID NO: 230 |
| A456/A653 | SEQ ID NO: 69 | SEQ ID NO: 232 |
| A456/A654 | SEQ ID NO: 69 | SEQ ID NO: 234 |
| A456/A656 | SEQ ID NO: 69 | SEQ ID NO: 236 |
| A457/A467 | SEQ ID NO: 71 | SEQ ID NO: 91 |
| A457/A468 | SEQ ID NO: 71 | SEQ ID NO: 93 |
| A457/A469 | SEQ ID NO: 71 | SEQ ID NO: 95 |
| A457/A470 | SEQ ID NO: 71 | SEQ ID NO: 97 |
| A457/A471 | SEQ ID NO: 71 | SEQ ID NO: 99 |
| A457/A472 | SEQ ID NO: 71 | SEQ ID NO: 101 |

TABLE 37-continued

Polynucleotide sequences of humanized antibodies

| Antibody Name | VH | VL |
|---|---|---|
| A457/A473 | SEQ ID NO: 71 | SEQ ID NO: 103 |
| A457/A518 | SEQ ID NO: 71 | SEQ ID NO: 111 |
| A457/A651 | SEQ ID NO: 71 | SEQ ID NO: 228 |
| A457/A652 | SEQ ID NO: 71 | SEQ ID NO: 230 |
| A457/A653 | SEQ ID NO: 71 | SEQ ID NO: 232 |
| A457/A654 | SEQ ID NO: 71 | SEQ ID NO: 234 |
| A457/A656 | SEQ ID NO: 71 | SEQ ID NO: 236 |
| A458/A467 | SEQ ID NO: 73 | SEQ ID NO: 91 |
| A458/A468 | SEQ ID NO: 73 | SEQ ID NO: 93 |
| A458/A469 | SEQ ID NO: 73 | SEQ ID NO: 95 |
| A458/A470 | SEQ ID NO: 73 | SEQ ID NO: 97 |
| A458/A471 | SEQ ID NO: 73 | SEQ ID NO: 99 |
| A458/A472 | SEQ ID NO: 73 | SEQ ID NO: 101 |
| A458/A473 | SEQ ID NO: 73 | SEQ ID NO: 103 |
| A458/A518 | SEQ ID NO: 73 | SEQ ID NO: 111 |
| A458/A651 | SEQ ID NO: 73 | SEQ ID NO: 228 |
| A458/A652 | SEQ ID NO: 73 | SEQ ID NO: 230 |
| A458/A653 | SEQ ID NO: 73 | SEQ ID NO: 232 |
| A458/A654 | SEQ ID NO: 73 | SEQ ID NO: 234 |
| A458/A656 | SEQ ID NO: 73 | SEQ ID NO: 236 |
| A459/A467 | SEQ ID NO: 75 | SEQ ID NO: 91 |
| A459/A468 | SEQ ID NO: 75 | SEQ ID NO: 93 |
| A459/A469 | SEQ ID NO: 75 | SEQ ID NO: 95 |
| A459/A470 | SEQ ID NO: 75 | SEQ ID NO: 97 |
| A459/A471 | SEQ ID NO: 75 | SEQ ID NO: 99 |
| A459/A472 | SEQ ID NO: 75 | SEQ ID NO: 101 |
| A459/A473 | SEQ ID NO: 75 | SEQ ID NO: 103 |
| A459/A518 | SEQ ID NO: 75 | SEQ ID NO: 111 |
| A459/A651 | SEQ ID NO: 75 | SEQ ID NO: 228 |
| A459/A652 | SEQ ID NO: 75 | SEQ ID NO: 230 |
| A459/A653 | SEQ ID NO: 75 | SEQ ID NO: 232 |
| A459/A654 | SEQ ID NO: 75 | SEQ ID NO: 234 |
| A459/A656 | SEQ ID NO: 75 | SEQ ID NO: 236 |
| A460/A467 | SEQ ID NO: 77 | SEQ ID NO: 91 |
| A460/A468 | SEQ ID NO: 77 | SEQ ID NO: 93 |
| A460/A469 | SEQ ID NO: 77 | SEQ ID NO: 95 |
| A460/A470 | SEQ ID NO: 77 | SEQ ID NO: 97 |
| A460/A471 | SEQ ID NO: 77 | SEQ ID NO: 99 |
| A460/A472 | SEQ ID NO: 77 | SEQ ID NO: 101 |
| A460/A473 | SEQ ID NO: 77 | SEQ ID NO: 103 |
| A460/A518 | SEQ ID NO: 77 | SEQ ID NO: 111 |
| A460/A651 | SEQ ID NO: 77 | SEQ ID NO: 228 |
| A460/A652 | SEQ ID NO: 77 | SEQ ID NO: 230 |
| A460/A653 | SEQ ID NO: 77 | SEQ ID NO: 232 |
| A460/A654 | SEQ ID NO: 77 | SEQ ID NO: 234 |
| A460/A656 | SEQ ID NO: 77 | SEQ ID NO: 236 |
| A461/A467 | SEQ ID NO: 79 | SEQ ID NO: 91 |
| A461/A468 | SEQ ID NO: 79 | SEQ ID NO: 93 |
| A461/A469 | SEQ ID NO: 79 | SEQ ID NO: 95 |
| A461/A470 | SEQ ID NO: 79 | SEQ ID NO: 97 |
| A461/A471 | SEQ ID NO: 79 | SEQ ID NO: 99 |
| A461/A472 | SEQ ID NO: 79 | SEQ ID NO: 101 |
| A461/A473 | SEQ ID NO: 79 | SEQ ID NO: 103 |
| A461/A518 | SEQ ID NO: 79 | SEQ ID NO: 111 |
| A461/A651 | SEQ ID NO: 79 | SEQ ID NO: 228 |
| A461/A652 | SEQ ID NO: 79 | SEQ ID NO: 230 |
| A461/A653 | SEQ ID NO: 79 | SEQ ID NO: 232 |
| A461/A654 | SEQ ID NO: 79 | SEQ ID NO: 234 |
| A461/A656 | SEQ ID NO: 79 | SEQ ID NO: 236 |
| A462/A467 | SEQ ID NO: 81 | SEQ ID NO: 91 |
| A462/A468 | SEQ ID NO: 81 | SEQ ID NO: 93 |
| A462/A469 | SEQ ID NO: 81 | SEQ ID NO: 95 |
| A462/A470 | SEQ ID NO: 81 | SEQ ID NO: 97 |
| A462/A471 | SEQ ID NO: 81 | SEQ ID NO: 99 |
| A462/A472 | SEQ ID NO: 81 | SEQ ID NO: 101 |
| A462/A473 | SEQ ID NO: 81 | SEQ ID NO: 103 |
| A462/A518 | SEQ ID NO: 81 | SEQ ID NO: 111 |
| A462/A651 | SEQ ID NO: 81 | SEQ ID NO: 228 |
| A462/A652 | SEQ ID NO: 81 | SEQ ID NO: 230 |
| A462/A653 | SEQ ID NO: 81 | SEQ ID NO: 232 |
| A462/A654 | SEQ ID NO: 81 | SEQ ID NO: 234 |
| A462/A656 | SEQ ID NO: 81 | SEQ ID NO: 236 |
| A463/A467 | SEQ ID NO: 83 | SEQ ID NO: 91 |
| A463/A468 | SEQ ID NO: 83 | SEQ ID NO: 93 |
| A463/A469 | SEQ ID NO: 83 | SEQ ID NO: 95 |
| A463/A470 | SEQ ID NO: 83 | SEQ ID NO: 97 |
| A463/A471 | SEQ ID NO: 83 | SEQ ID NO: 99 |
| A463/A472 | SEQ ID NO: 83 | SEQ ID NO: 101 |
| A463/A473 | SEQ ID NO: 83 | SEQ ID NO: 103 |
| A463/A518 | SEQ ID NO: 83 | SEQ ID NO: 111 |
| A463/A651 | SEQ ID NO: 83 | SEQ ID NO: 228 |
| A463/A652 | SEQ ID NO: 83 | SEQ ID NO: 230 |
| A463/A653 | SEQ ID NO: 83 | SEQ ID NO: 232 |
| A463/A654 | SEQ ID NO: 83 | SEQ ID NO: 234 |
| A463/A656 | SEQ ID NO: 83 | SEQ ID NO: 236 |
| A464/A467 | SEQ ID NO: 85 | SEQ ID NO: 91 |
| A464/A468 | SEQ ID NO: 85 | SEQ ID NO: 93 |
| A464/A469 | SEQ ID NO: 85 | SEQ ID NO: 95 |
| A464/A470 | SEQ ID NO: 85 | SEQ ID NO: 97 |
| A464/A471 | SEQ ID NO: 85 | SEQ ID NO: 99 |
| A464/A472 | SEQ ID NO: 85 | SEQ ID NO: 101 |
| A464/A473 | SEQ ID NO: 85 | SEQ ID NO: 103 |
| A464/A518 | SEQ ID NO: 85 | SEQ ID NO: 111 |
| A464/A651 | SEQ ID NO: 85 | SEQ ID NO: 228 |
| A464/A652 | SEQ ID NO: 85 | SEQ ID NO: 230 |
| A464/A653 | SEQ ID NO: 85 | SEQ ID NO: 232 |
| A464/A654 | SEQ ID NO: 85 | SEQ ID NO: 234 |
| A464/A656 | SEQ ID NO: 85 | SEQ ID NO: 236 |
| A465/A467 | SEQ ID NO: 87 | SEQ ID NO: 91 |
| A465/A468 | SEQ ID NO: 87 | SEQ ID NO: 93 |
| A465/A469 | SEQ ID NO: 87 | SEQ ID NO: 95 |
| A465/A470 | SEQ ID NO: 87 | SEQ ID NO: 97 |
| A465/A471 | SEQ ID NO: 87 | SEQ ID NO: 99 |
| A465/A472 | SEQ ID NO: 87 | SEQ ID NO: 101 |
| A465/A473 | SEQ ID NO: 87 | SEQ ID NO: 103 |
| A465/A518 | SEQ ID NO: 87 | SEQ ID NO: 111 |
| A465/A651 | SEQ ID NO: 87 | SEQ ID NO: 228 |
| A465/A652 | SEQ ID NO: 87 | SEQ ID NO: 230 |
| A465/A653 | SEQ ID NO: 87 | SEQ ID NO: 232 |
| A465/A654 | SEQ ID NO: 87 | SEQ ID NO: 234 |
| A465/A656 | SEQ ID NO: 87 | SEQ ID NO: 236 |
| A466/A467 | SEQ ID NO: 89 | SEQ ID NO: 91 |
| A466/A468 | SEQ ID NO: 89 | SEQ ID NO: 93 |
| A466/A469 | SEQ ID NO: 89 | SEQ ID NO: 95 |
| A466/A470 | SEQ ID NO: 89 | SEQ ID NO: 97 |
| A466/A471 | SEQ ID NO: 89 | SEQ ID NO: 99 |
| A466/A472 | SEQ ID NO: 89 | SEQ ID NO: 101 |
| A466/A473 | SEQ ID NO: 89 | SEQ ID NO: 103 |
| A466/A518 | SEQ ID NO: 89 | SEQ ID NO: 111 |
| A466/A651 | SEQ ID NO: 89 | SEQ ID NO: 228 |
| A466/A652 | SEQ ID NO: 89 | SEQ ID NO: 230 |
| A466/A653 | SEQ ID NO: 89 | SEQ ID NO: 232 |
| A466/A654 | SEQ ID NO: 89 | SEQ ID NO: 234 |
| A466/A656 | SEQ ID NO: 89 | SEQ ID NO: 236 |
| A512/A467 | SEQ ID NO: 107 | SEQ ID NO: 91 |
| A512/A468 | SEQ ID NO: 107 | SEQ ID NO: 93 |
| A512/A469 | SEQ ID NO: 107 | SEQ ID NO: 95 |
| A512/A470 | SEQ ID NO: 107 | SEQ ID NO: 97 |
| A512/A471 | SEQ ID NO: 107 | SEQ ID NO: 99 |
| A512/A472 | SEQ ID NO: 107 | SEQ ID NO: 101 |
| A512/A473 | SEQ ID NO: 107 | SEQ ID NO: 103 |
| A512/A518 | SEQ ID NO: 107 | SEQ ID NO: 111 |
| A512/A651 | SEQ ID NO: 107 | SEQ ID NO: 228 |
| A512/A652 | SEQ ID NO: 107 | SEQ ID NO: 230 |
| A512/A653 | SEQ ID NO: 107 | SEQ ID NO: 232 |
| A512/A654 | SEQ ID NO: 107 | SEQ ID NO: 234 |
| A512/A656 | SEQ ID NO: 107 | SEQ ID NO: 236 |
| A515/A467 | SEQ ID NO: 109 | SEQ ID NO: 91 |
| A515/A468 | SEQ ID NO: 109 | SEQ ID NO: 93 |
| A515/A469 | SEQ ID NO: 109 | SEQ ID NO: 95 |
| A515/A470 | SEQ ID NO: 109 | SEQ ID NO: 97 |
| A515/A471 | SEQ ID NO: 109 | SEQ ID NO: 99 |
| A515/A472 | SEQ ID NO: 109 | SEQ ID NO: 101 |
| A515/A473 | SEQ ID NO: 109 | SEQ ID NO: 103 |
| A515/A518 | SEQ ID NO: 109 | SEQ ID NO: 111 |
| A515/A651 | SEQ ID NO: 109 | SEQ ID NO: 228 |
| A515/A652 | SEQ ID NO: 109 | SEQ ID NO: 230 |
| A515/A653 | SEQ ID NO: 109 | SEQ ID NO: 232 |
| A515/A654 | SEQ ID NO: 109 | SEQ ID NO: 234 |
| A515/A656 | SEQ ID NO: 109 | SEQ ID NO: 236 |
| A553/A467 | SEQ ID NO: 105 | SEQ ID NO: 91 |
| A553/A468 | SEQ ID NO: 105 | SEQ ID NO: 93 |

TABLE 37-continued

Polynucleotide sequences of humanized antibodies

| Antibody Name | VH | VL |
|---|---|---|
| A553/A469 | SEQ ID NO: 105 | SEQ ID NO: 95 |
| A553/A470 | SEQ ID NO: 105 | SEQ ID NO: 97 |
| A553/A471 | SEQ ID NO: 105 | SEQ ID NO: 99 |
| A553/A472 | SEQ ID NO: 105 | SEQ ID NO: 101 |
| A553/A473 | SEQ ID NO: 105 | SEQ ID NO: 103 |
| A553/A518 | SEQ ID NO: 105 | SEQ ID NO: 111 |
| A553/A651 | SEQ ID NO: 105 | SEQ ID NO: 228 |
| A553/A652 | SEQ ID NO: 105 | SEQ ID NO: 230 |
| A553/A653 | SEQ ID NO: 105 | SEQ ID NO: 232 |
| A553/A654 | SEQ ID NO: 105 | SEQ ID NO: 234 |
| A553/A656 | SEQ ID NO: 105 | SEQ ID NO: 236 |
| A631/A467 | SEQ ID NO: 202 | SEQ ID NO: 91 |
| A631/A468 | SEQ ID NO: 202 | SEQ ID NO: 93 |
| A631/A469 | SEQ ID NO: 202 | SEQ ID NO: 95 |
| A631/A470 | SEQ ID NO: 202 | SEQ ID NO: 97 |
| A631/A471 | SEQ ID NO: 202 | SEQ ID NO: 99 |
| A631/A472 | SEQ ID NO: 202 | SEQ ID NO: 101 |
| A631/A473 | SEQ ID NO: 202 | SEQ ID NO: 103 |
| A631/A518 | SEQ ID NO: 202 | SEQ ID NO: 111 |
| A631/A651 | SEQ ID NO: 202 | SEQ ID NO: 228 |
| A631/A652 | SEQ ID NO: 202 | SEQ ID NO: 230 |
| A631/A653 | SEQ ID NO: 202 | SEQ ID NO: 232 |
| A631/A654 | SEQ ID NO: 202 | SEQ ID NO: 234 |
| A631/A656 | SEQ ID NO: 202 | SEQ ID NO: 236 |
| A632/A467 | SEQ ID NO: 204 | SEQ ID NO: 91 |
| A632/A468 | SEQ ID NO: 204 | SEQ ID NO: 93 |
| A632/A469 | SEQ ID NO: 204 | SEQ ID NO: 95 |
| A632/A470 | SEQ ID NO: 204 | SEQ ID NO: 97 |
| A632/A471 | SEQ ID NO: 204 | SEQ ID NO: 99 |
| A632/A472 | SEQ ID NO: 204 | SEQ ID NO: 101 |
| A632/A473 | SEQ ID NO: 204 | SEQ ID NO: 103 |
| A632/A518 | SEQ ID NO: 204 | SEQ ID NO: 111 |
| A632/A651 | SEQ ID NO: 204 | SEQ ID NO: 228 |
| A632/A652 | SEQ ID NO: 204 | SEQ ID NO: 230 |
| A632/A653 | SEQ ID NO: 204 | SEQ ID NO: 232 |
| A632/A654 | SEQ ID NO: 204 | SEQ ID NO: 234 |
| A632/A656 | SEQ ID NO: 204 | SEQ ID NO: 236 |
| A633/A467 | SEQ ID NO: 206 | SEQ ID NO: 91 |
| A633/A468 | SEQ ID NO: 206 | SEQ ID NO: 93 |
| A633/A469 | SEQ ID NO: 206 | SEQ ID NO: 95 |
| A633/A470 | SEQ ID NO: 206 | SEQ ID NO: 97 |
| A633/A471 | SEQ ID NO: 206 | SEQ ID NO: 99 |
| A633/A472 | SEQ ID NO: 206 | SEQ ID NO: 101 |
| A633/A473 | SEQ ID NO: 206 | SEQ ID NO: 103 |
| A633/A518 | SEQ ID NO: 206 | SEQ ID NO: 111 |
| A633/A651 | SEQ ID NO: 206 | SEQ ID NO: 228 |
| A633/A652 | SEQ ID NO: 206 | SEQ ID NO: 230 |
| A633/A653 | SEQ ID NO: 206 | SEQ ID NO: 232 |
| A633/A654 | SEQ ID NO: 206 | SEQ ID NO: 234 |
| A633/A656 | SEQ ID NO: 206 | SEQ ID NO: 236 |
| A634/A467 | SEQ ID NO: 208 | SEQ ID NO: 91 |
| A634/A468 | SEQ ID NO: 208 | SEQ ID NO: 93 |
| A634/A469 | SEQ ID NO: 208 | SEQ ID NO: 95 |
| A634/A470 | SEQ ID NO: 208 | SEQ ID NO: 97 |
| A634/A471 | SEQ ID NO: 208 | SEQ ID NO: 99 |
| A634/A472 | SEQ ID NO: 208 | SEQ ID NO: 101 |
| A634/A473 | SEQ ID NO: 208 | SEQ ID NO: 103 |
| A634/A518 | SEQ ID NO: 208 | SEQ ID NO: 111 |
| A634/A651 | SEQ ID NO: 208 | SEQ ID NO: 228 |
| A634/A652 | SEQ ID NO: 208 | SEQ ID NO: 230 |
| A634/A653 | SEQ ID NO: 208 | SEQ ID NO: 232 |
| A634/A654 | SEQ ID NO: 208 | SEQ ID NO: 234 |
| A634/A656 | SEQ ID NO: 208 | SEQ ID NO: 236 |
| A636/A467 | SEQ ID NO: 210 | SEQ ID NO: 91 |
| A636/A468 | SEQ ID NO: 210 | SEQ ID NO: 93 |
| A636/A469 | SEQ ID NO: 210 | SEQ ID NO: 95 |
| A636/A470 | SEQ ID NO: 210 | SEQ ID NO: 97 |
| A636/A471 | SEQ ID NO: 210 | SEQ ID NO: 99 |
| A636/A472 | SEQ ID NO: 210 | SEQ ID NO: 101 |
| A636/A473 | SEQ ID NO: 210 | SEQ ID NO: 103 |
| A636/A518 | SEQ ID NO: 210 | SEQ ID NO: 111 |
| A636/A651 | SEQ ID NO: 210 | SEQ ID NO: 228 |
| A636/A652 | SEQ ID NO: 210 | SEQ ID NO: 230 |
| A636/A653 | SEQ ID NO: 210 | SEQ ID NO: 232 |
| A636/A654 | SEQ ID NO: 210 | SEQ ID NO: 234 |
| A636/A656 | SEQ ID NO: 210 | SEQ ID NO: 236 |
| A638/A467 | SEQ ID NO: 212 | SEQ ID NO: 91 |
| A638/A468 | SEQ ID NO: 212 | SEQ ID NO: 93 |
| A638/A469 | SEQ ID NO: 212 | SEQ ID NO: 95 |
| A638/A470 | SEQ ID NO: 212 | SEQ ID NO: 97 |
| A638/A471 | SEQ ID NO: 212 | SEQ ID NO: 99 |
| A638/A472 | SEQ ID NO: 212 | SEQ ID NO: 101 |
| A638/A473 | SEQ ID NO: 212 | SEQ ID NO: 103 |
| A638/A518 | SEQ ID NO: 212 | SEQ ID NO: 111 |
| A638/A651 | SEQ ID NO: 212 | SEQ ID NO: 228 |
| A638/A652 | SEQ ID NO: 212 | SEQ ID NO: 230 |
| A638/A653 | SEQ ID NO: 212 | SEQ ID NO: 232 |
| A638/A654 | SEQ ID NO: 212 | SEQ ID NO: 234 |
| A638/A656 | SEQ ID NO: 212 | SEQ ID NO: 236 |
| A639/A467 | SEQ ID NO: 214 | SEQ ID NO: 91 |
| A639/A468 | SEQ ID NO: 214 | SEQ ID NO: 93 |
| A639/A469 | SEQ ID NO: 214 | SEQ ID NO: 95 |
| A639/A470 | SEQ ID NO: 214 | SEQ ID NO: 97 |
| A639/A471 | SEQ ID NO: 214 | SEQ ID NO: 99 |
| A639/A472 | SEQ ID NO: 214 | SEQ ID NO: 101 |
| A639/A473 | SEQ ID NO: 214 | SEQ ID NO: 103 |
| A639/A518 | SEQ ID NO: 214 | SEQ ID NO: 111 |
| A639/A651 | SEQ ID NO: 214 | SEQ ID NO: 228 |
| A639/A652 | SEQ ID NO: 214 | SEQ ID NO: 230 |
| A639/A653 | SEQ ID NO: 214 | SEQ ID NO: 232 |
| A639/A654 | SEQ ID NO: 214 | SEQ ID NO: 234 |
| A639/A656 | SEQ ID NO: 214 | SEQ ID NO: 236 |
| A641/A467 | SEQ ID NO: 216 | SEQ ID NO: 91 |
| A641/A468 | SEQ ID NO: 216 | SEQ ID NO: 93 |
| A641/A469 | SEQ ID NO: 216 | SEQ ID NO: 95 |
| A641/A470 | SEQ ID NO: 216 | SEQ ID NO: 97 |
| A641/A471 | SEQ ID NO: 216 | SEQ ID NO: 99 |
| A641/A472 | SEQ ID NO: 216 | SEQ ID NO: 101 |
| A641/A473 | SEQ ID NO: 216 | SEQ ID NO: 103 |
| A641/A518 | SEQ ID NO: 216 | SEQ ID NO: 111 |
| A641/A651 | SEQ ID NO: 216 | SEQ ID NO: 228 |
| A641/A652 | SEQ ID NO: 216 | SEQ ID NO: 230 |
| A641/A653 | SEQ ID NO: 216 | SEQ ID NO: 232 |
| A641/A654 | SEQ ID NO: 216 | SEQ ID NO: 234 |
| A641/A656 | SEQ ID NO: 216 | SEQ ID NO: 236 |
| A642/A467 | SEQ ID NO: 218 | SEQ ID NO: 91 |
| A642/A468 | SEQ ID NO: 218 | SEQ ID NO: 93 |
| A642/A469 | SEQ ID NO: 218 | SEQ ID NO: 95 |
| A642/A470 | SEQ ID NO: 218 | SEQ ID NO: 97 |
| A642/A471 | SEQ ID NO: 218 | SEQ ID NO: 99 |
| A642/A472 | SEQ ID NO: 218 | SEQ ID NO: 101 |
| A642/A473 | SEQ ID NO: 218 | SEQ ID NO: 103 |
| A642/A518 | SEQ ID NO: 218 | SEQ ID NO: 111 |
| A642/A651 | SEQ ID NO: 218 | SEQ ID NO: 228 |
| A642/A652 | SEQ ID NO: 218 | SEQ ID NO: 230 |
| A642/A653 | SEQ ID NO: 218 | SEQ ID NO: 232 |
| A642/A654 | SEQ ID NO: 218 | SEQ ID NO: 234 |
| A642/A656 | SEQ ID NO: 218 | SEQ ID NO: 236 |
| A643/A467 | SEQ ID NO: 220 | SEQ ID NO: 91 |
| A643/A468 | SEQ ID NO: 220 | SEQ ID NO: 93 |
| A643/A469 | SEQ ID NO: 220 | SEQ ID NO: 95 |
| A643/A470 | SEQ ID NO: 220 | SEQ ID NO: 97 |
| A643/A471 | SEQ ID NO: 220 | SEQ ID NO: 99 |
| A643/A472 | SEQ ID NO: 220 | SEQ ID NO: 101 |
| A643/A473 | SEQ ID NO: 220 | SEQ ID NO: 103 |
| A643/A518 | SEQ ID NO: 220 | SEQ ID NO: 111 |
| A643/A651 | SEQ ID NO: 220 | SEQ ID NO: 228 |
| A643/A652 | SEQ ID NO: 220 | SEQ ID NO: 230 |
| A643/A653 | SEQ ID NO: 220 | SEQ ID NO: 232 |
| A643/A654 | SEQ ID NO: 220 | SEQ ID NO: 234 |
| A643/A656 | SEQ ID NO: 220 | SEQ ID NO: 236 |
| A645/A467 | SEQ ID NO: 222 | SEQ ID NO: 91 |
| A645/A468 | SEQ ID NO: 222 | SEQ ID NO: 93 |
| A645/A469 | SEQ ID NO: 222 | SEQ ID NO: 95 |
| A645/A470 | SEQ ID NO: 222 | SEQ ID NO: 97 |
| A645/A471 | SEQ ID NO: 222 | SEQ ID NO: 99 |
| A645/A472 | SEQ ID NO: 222 | SEQ ID NO: 101 |
| A645/A473 | SEQ ID NO: 222 | SEQ ID NO: 103 |
| A645/A518 | SEQ ID NO: 222 | SEQ ID NO: 111 |
| A645/A651 | SEQ ID NO: 222 | SEQ ID NO: 228 |
| A645/A652 | SEQ ID NO: 222 | SEQ ID NO: 230 |
| A645/A653 | SEQ ID NO: 222 | SEQ ID NO: 232 |

TABLE 37-continued

Polynucleotide sequences of humanized antibodies

| Antibody Name | VH | VL |
|---|---|---|
| A645/A654 | SEQ ID NO: 222 | SEQ ID NO: 234 |
| A645/A656 | SEQ ID NO: 222 | SEQ ID NO: 236 |
| A648/A467 | SEQ ID NO: 224 | SEQ ID NO: 91 |
| A648/A468 | SEQ ID NO: 224 | SEQ ID NO: 93 |
| A648/A469 | SEQ ID NO: 224 | SEQ ID NO: 95 |
| A648/A470 | SEQ ID NO: 224 | SEQ ID NO: 97 |
| A648/A471 | SEQ ID NO: 224 | SEQ ID NO: 99 |
| A648/A472 | SEQ ID NO: 224 | SEQ ID NO: 101 |
| A648/A473 | SEQ ID NO: 224 | SEQ ID NO: 103 |
| A648/A518 | SEQ ID NO: 224 | SEQ ID NO: 111 |
| A648/A651 | SEQ ID NO: 224 | SEQ ID NO: 228 |
| A648/A652 | SEQ ID NO: 224 | SEQ ID NO: 230 |
| A648/A653 | SEQ ID NO: 224 | SEQ ID NO: 232 |
| A648/A654 | SEQ ID NO: 224 | SEQ ID NO: 234 |
| A648/A656 | SEQ ID NO: 224 | SEQ ID NO: 236 |
| A650/A467 | SEQ ID NO: 226 | SEQ ID NO: 91 |
| A650/A468 | SEQ ID NO: 226 | SEQ ID NO: 93 |
| A650/A469 | SEQ ID NO: 226 | SEQ ID NO: 95 |
| A650/A470 | SEQ ID NO: 226 | SEQ ID NO: 97 |
| A650/A471 | SEQ ID NO: 226 | SEQ ID NO: 99 |
| A650/A472 | SEQ ID NO: 226 | SEQ ID NO: 101 |
| A650/A473 | SEQ ID NO: 226 | SEQ ID NO: 103 |
| A650/A518 | SEQ ID NO: 226 | SEQ ID NO: 111 |
| A650/A651 | SEQ ID NO: 226 | SEQ ID NO: 228 |
| A650/A652 | SEQ ID NO: 226 | SEQ ID NO: 230 |
| A650/A653 | SEQ ID NO: 226 | SEQ ID NO: 232 |
| A650/A654 | SEQ ID NO: 226 | SEQ ID NO: 234 |
| A650/A656 | SEQ ID NO: 226 | SEQ ID NO: 236 |

In some embodiments, the polynucleotide comprises a VH nucleotide sequence of SEQ ID NO: 202 and/or a VL nucleotide sequence of SEQ ID NO: 91. In some embodiments, the polynucleotide comprises a VH nucleotide sequence of SEQ ID NO: 202 and/or a VL nucleotide sequence of SEQ ID NO: 93. In some embodiments, the polynucleotide comprises a VH nucleotide sequence of SEQ ID NO: 202 and/or a VL nucleotide sequence of SEQ ID NO: 95. In some embodiments, the polynucleotide comprises a VH nucleotide sequence of SEQ ID NO: 202 and/or a VL nucleotide sequence of SEQ ID NO: 97. In some embodiments, the polynucleotide comprises a VH nucleotide sequence of SEQ ID NO: 202 and/or a VL nucleotide sequence of SEQ ID NO: 99. In some embodiments, the polynucleotide comprises a VH nucleotide sequence of SEQ ID NO: 202 and/or a VL nucleotide sequence of SEQ ID NO: 101. In some embodiments, the polynucleotide comprises a VH nucleotide sequence of SEQ ID NO: 202 and/or a VL nucleotide sequence of SEQ ID NO: 103. In some embodiments, the polynucleotide comprises a VH nucleotide sequence of SEQ ID NO: 202 and/or a VL nucleotide sequence of SEQ ID NO: 111. In some embodiments, the polynucleotide comprises a VH nucleotide sequence of SEQ ID NO: 202 and/or a VL nucleotide sequence of SEQ ID NO: 228. In some embodiments, the polynucleotide comprises a VH nucleotide sequence of SEQ ID NO: 202 and/or a VL nucleotide sequence of SEQ ID NO: 230. In some embodiments, the polynucleotide comprises a VH nucleotide sequence of SEQ ID NO: 202 and/or a VL nucleotide sequence of SEQ ID NO: 232. In some embodiments, the polynucleotide comprises a VH nucleotide sequence of SEQ ID NO: 202 and/or a VL nucleotide sequence of SEQ ID NO: 234. In some embodiments, the polynucleotide comprises a VH nucleotide sequence of SEQ ID NO: 202 and/or a VL nucleotide sequence of SEQ ID NO: 236.

In some embodiments, the polynucleotide comprises a VH nucleotide sequence of SEQ ID NO: 204 and/or a VL nucleotide sequence of SEQ ID NO: 91. In some embodiments, the polynucleotide comprises a VH nucleotide sequence of SEQ ID NO: 204 and/or a VL nucleotide sequence of SEQ ID NO: 93. In some embodiments, the polynucleotide comprises a VH nucleotide sequence of SEQ ID NO: 204 and/or a VL nucleotide sequence of SEQ ID NO: 95. In some embodiments, the polynucleotide comprises a VH nucleotide sequence of SEQ ID NO: 204 and/or a VL nucleotide sequence of SEQ ID NO: 97. In some embodiments, the polynucleotide comprises a VH nucleotide sequence of SEQ ID NO: 204 and/or a VL nucleotide sequence of SEQ ID NO: 99. In some embodiments, the polynucleotide comprises a VH nucleotide sequence of SEQ ID NO: 204 and/or a VL nucleotide sequence of SEQ ID NO: 101. In some embodiments, the polynucleotide comprises a VH nucleotide sequence of SEQ ID NO: 204 and/or a VL nucleotide sequence of SEQ ID NO: 103. In some embodiments, the polynucleotide comprises a VH nucleotide sequence of SEQ ID NO: 204 and/or a VL nucleotide sequence of SEQ ID NO: 111. In some embodiments, the polynucleotide comprises a VH nucleotide sequence of SEQ ID NO: 204 and/or a VL nucleotide sequence of SEQ ID NO: 228. In some embodiments, the polynucleotide comprises a VH nucleotide sequence of SEQ ID NO: 204 and/or a VL nucleotide sequence of SEQ ID NO: 230. In some embodiments, the polynucleotide comprises a VH nucleotide sequence of SEQ ID NO: 204 and/or a VL nucleotide sequence of SEQ ID NO: 232. In some embodiments, the polynucleotide comprises a VH nucleotide sequence of SEQ ID NO: 204 and/or a VL nucleotide sequence of SEQ ID NO: 234. In some embodiments, the polynucleotide comprises a VH nucleotide sequence of SEQ ID NO: 204 and/or a VL nucleotide sequence of SEQ ID NO: 236.

In some embodiments, the polynucleotide comprises a VH nucleotide sequence of SEQ ID NO: 206 and/or a VL nucleotide sequence of SEQ ID NO: 91. In some embodiments, the polynucleotide comprises a VH nucleotide sequence of SEQ ID NO: 206 and/or a VL nucleotide sequence of SEQ ID NO: 93. In some embodiments, the polynucleotide comprises a VH nucleotide sequence of SEQ ID NO: 206 and/or a VL nucleotide sequence of SEQ ID NO: 95. In some embodiments, the polynucleotide comprises a VH nucleotide sequence of SEQ ID NO: 206 and/or a VL nucleotide sequence of SEQ ID NO: 97. In some embodiments, the polynucleotide comprises a VH nucleo-tide sequence of SEQ ID NO: 206 and/or a VL nucleotide sequence of SEQ ID NO: 99. In some embodiments, the polynucleotide comprises a VH nucleotide sequence of SEQ ID NO: 206 and/or a VL nucleotide sequence of SEQ ID NO: 101. In some embodiments, the polynucleotide comprises a VH nucleotide sequence of SEQ ID NO: 206 and/or a VL nucleotide sequence of SEQ ID NO: 103. In some embodiments, the polynucleotide comprises a VH nucleotide sequence of SEQ ID NO: 206 and/or a VL nucleotide sequence of SEQ ID NO: 111. In some embodiments, the polynucleotide comprises a VH nucleotide sequence of SEQ ID NO: 206 and/or a VL nucleotide sequence of SEQ ID NO: 228. In some embodiments, the polynucleotide comprises a VH nucleotide sequence of SEQ ID NO: 206 and/or a VL nucleotide sequence of SEQ ID NO: 230. In some embodiments, the polynucleotide comprises a VH nucleotide sequence of SEQ ID NO: 206 and/or a VL nucleotide sequence of SEQ ID NO: 232. In some embodiments, the polynucleotide comprises a VH nucleotide sequence of SEQ ID NO: 206 and/or a VL nucleotide sequence of SEQ ID NO: 234. In some embodiments, the polynucleotide comprises a VH nucleotide sequence of SEQ ID NO: 206 and/or a VL nucleotide sequence of SEQ ID NO: 236.

In some embodiments, the polynucleotide comprises a VH nucleotide sequence of SEQ ID NO: 208 and/or a VL nucleotide sequence of SEQ ID NO: 91. In some embodiments, the polynucleotide comprises a VH nucleotide sequence of SEQ ID NO: 208 and/or a VL nucleotide sequence of SEQ ID NO: 93. In some embodiments, the polynucleotide comprises a VH nucleotide sequence of SEQ ID NO: 208 and/or a VL nucleotide sequence of SEQ ID NO: 95. In some embodiments, the polynucleotide comprises a VH nucleotide sequence of SEQ ID NO: 208 and/or a VL nucleotide sequence of SEQ ID NO: 97. In some embodiments, the polynucleotide comprises a VH nucleotide sequence of SEQ ID NO: 208 and/or a VL nucleotide sequence of SEQ ID NO: 99. In some embodiments, the polynucleotide comprises a VH nucleotide sequence of SEQ ID NO: 208 and/or a VL nucleotide sequence of SEQ ID NO: 101. In some embodiments, the polynucleotide comprises a VH nucleotide sequence of SEQ ID NO: 208 and/or a VL nucleotide sequence of SEQ ID NO: 103. In some embodiments, the polynucleotide comprises a VH nucleotide sequence of SEQ ID NO: 208 and/or a VL nucleotide sequence of SEQ ID NO: 111. In some embodiments, the polynucleotide comprises a VH nucleotide sequence of SEQ ID NO: 208 and/or a VL nucleotide sequence of SEQ ID NO: 228. In some embodiments, the polynucleotide comprises a VH nucleotide sequence of SEQ ID NO: 208 and/or a VL nucleotide sequence of SEQ ID NO: 230. In some embodiments, the polynucleotide comprises a VH nucleotide sequence of SEQ ID NO: 208 and/or a VL nucleotide sequence of SEQ ID NO: 232. In some embodiments, the polynucleotide comprises a VH nucleotide sequence of SEQ ID NO: 208 and/or a VL nucleotide sequence of SEQ ID NO: 234. In some embodiments, the polynucleotide comprises a VH nucleotide sequence of SEQ ID NO: 208 and/or a VL nucleotide sequence of SEQ ID NO: 236.

In some embodiments, the polynucleotide comprises a VH nucleotide sequence of SEQ ID NO: 210 and/or a VL nucleotide sequence of SEQ ID NO: 91. In some embodiments, the polynucleotide comprises a VH nucleotide sequence of SEQ ID NO: 210 and/or a VL nucleotide sequence of SEQ ID NO: 93. In some embodiments, the polynucleotide comprises a VH nucleotide sequence of SEQ ID NO: 210 and/or a VL nucleotide sequence of SEQ ID NO: 95. In some embodiments, the polynucleotide comprises a VH nucleotide sequence of SEQ ID NO: 210 and/or a VL nucleotide sequence of SEQ ID NO: 97. In some embodiments, the polynucleotide comprises a VH nucleotide sequence of SEQ ID NO: 210 and/or a VL nucleotide sequence of SEQ ID NO: 99. In some embodiments, the polynucleotide comprises a VH nucleotide sequence of SEQ ID NO: 210 and/or a VL nucleotide sequence of SEQ ID NO: 101. In some embodiments, the polynucleotide comprises a VH nucleotide sequence of SEQ ID NO: 210 and/or a VL nucleotide sequence of SEQ ID NO: 103. In some embodiments, the polynucleotide comprises a VH nucleotide sequence of SEQ ID NO: 210 and/or a VL nucleotide sequence of SEQ ID NO: 111. In some embodiments, the polynucleotide comprises a VH nucleotide sequence of SEQ ID NO: 210 and/or a VL nucleotide sequence of SEQ ID NO: 228. In some embodiments, the polynucleotide comprises a VH nucleotide sequence of SEQ ID NO: 210 and/or a VL nucleotide sequence of SEQ ID NO: 230. In some embodiments, the polynucleotide comprises a VH nucleotide sequence of SEQ ID NO: 210 and/or a VL nucleotide sequence of SEQ ID NO: 232. In some embodiments, the polynucleotide comprises a VH nucleotide sequence of SEQ ID NO: 210 and/or a VL nucleotide sequence of SEQ ID NO: 234. In some embodiments, the polynucleotide comprises a VH nucleotide sequence of SEQ ID NO: 210 and/or a VL nucleotide sequence of SEQ ID NO: 236.

In some embodiments, the polynucleotide comprises a VH nucleotide sequence of SEQ ID NO: 212 and/or a VL nucleotide sequence of SEQ ID NO: 91. In some embodiments, the polynucleotide comprises a VH nucleotide sequence of SEQ ID NO: 212 and/or a VL nucleotide sequence of SEQ ID NO: 93. In some embodiments, the polynucleotide comprises a VH nucleotide sequence of SEQ ID NO: 212 and/or a VL nucleotide sequence of SEQ ID NO: 95. In some embodiments, the polynucleotide comprises a VH nucleotide sequence of SEQ ID NO: 212 and/or a VL nucleotide sequence of SEQ ID NO: 97. In some embodiments, the polynucleotide comprises a VH nucleotide sequence of SEQ ID NO: 212 and/or a VL nucleotide sequence of SEQ ID NO: 99. In some embodiments, the polynucleotide comprises a VH nucleotide sequence of SEQ ID NO: 212 and/or a VL nucleotide sequence of SEQ ID NO: 101. In some embodiments, the polynucleotide comprises a VH nucleotide sequence of SEQ ID NO: 212 and/or a VL nucleotide sequence of SEQ ID NO: 103. In some embodiments, the polynucleotide comprises a VH nucleotide sequence of SEQ ID NO: 212 and/or a VL nucleotide sequence of SEQ ID NO: 111. In some embodiments, the polynucleotide comprises a VH nucleotide sequence of SEQ ID NO: 212 and/or a VL nucleotide sequence of SEQ ID NO: 228. In some embodiments, the polynucleotide comprises a VH nucleotide sequence of SEQ ID NO: 212 and/or a VL nucleotide sequence of SEQ ID NO: 230. In some embodiments, the polynucleotide comprises a VH nucleotide sequence of SEQ ID NO: 212 and/or a VL nucleotide sequence of SEQ ID NO: 232. In some embodiments, the polynucleotide comprises a VH nucleotide sequence of SEQ ID NO: 212 and/or a VL nucleotide sequence of SEQ ID NO: 234. In some embodiments, the polynucleotide comprises a VH nucleotide sequence of SEQ ID NO: 212 and/or a VL nucleotide sequence of SEQ ID NO: 236.

In some embodiments, the polynucleotide comprises a VH nucleotide sequence of SEQ ID NO: 214 and/or a VL nucleotide sequence of SEQ ID NO: 91. In some embodiments, the polynucleotide comprises a VH nucleotide sequence of SEQ ID NO: 214 and/or a VL nucleotide sequence of SEQ ID NO: 93. In some embodiments, the polynucleotide comprises a VH nucleotide sequence of SEQ ID NO: 214 and/or a VL nucleotide sequence of SEQ ID NO: 95. In some embodiments, the polynucleotide comprises a VH nucleotide sequence of SEQ ID NO: 214 and/or a VL nucleotide sequence of SEQ ID NO: 97. In some embodiments, the polynucleotide comprises a VH nucleotide sequence of SEQ ID NO: 214 and/or a VL nucleotide sequence of SEQ ID NO: 99. In some embodiments, the polynucleotide comprises a VH nucleotide sequence of SEQ ID NO: 214 and/or a VL nucleotide sequence of SEQ ID NO: 101. In some embodiments, the polynucleotide comprises a VH nucleotide sequence of SEQ ID NO: 214 and/or a VL nucleotide sequence of SEQ ID NO: 103. In some embodiments, the polynucleotide comprises a VH nucleotide sequence of SEQ ID NO: 214 and/or a VL nucleotide sequence of SEQ ID NO: 111. In some embodiments, the polynucleotide comprises a VH nucleotide sequence of SEQ ID NO: 214 and/or a VL nucleotide sequence of SEQ ID NO: 228. In some embodiments, the polynucleotide comprises a VH nucleotide sequence of SEQ ID NO: 214 and/or a VL nucleotide sequence of SEQ ID NO: 230. In some embodiments, the polynucleotide comprises a VH nucleotide sequence of SEQ ID NO: 214 and/or a VL nucleotide sequence of SEQ ID NO: 232. In some embodiments, the polynucleotide comprises a VH nucleotide sequence of SEQ ID NO: 214 and/or a VL nucleotide sequence of SEQ ID NO: 234. In some embodiments, the polynucleotide comprises a VH nucleotide sequence of SEQ ID NO: 214 and/or a VL nucleotide sequence of SEQ ID NO: 236.

In some embodiments, the polynucleotide comprises a VH nucleotide sequence of SEQ ID NO: 216 and/or a VL nucleotide sequence of SEQ ID NO: 91. In some embodiments, the polynucleotide comprises a VH nucleotide sequence of SEQ ID NO: 216 and/or a VL nucleotide sequence of SEQ ID NO: 93. In some embodiments, the polynucleotide comprises a VH nucleotide sequence of SEQ ID NO: 216 and/or a VL nucleotide sequence of SEQ ID NO: 95. In some embodiments, the polynucleotide comprises a VH nucleotide sequence of SEQ ID NO: 216 and/or a VL nucleotide sequence of SEQ ID NO: 97. In some embodiments, the polynucleotide comprises a VH nucleotide sequence of SEQ ID NO: 216 and/or a VL nucleotide sequence of SEQ ID NO: 99. In some embodiments, the polynucleotide comprises a VH nucleotide sequence of SEQ ID NO: 216 and/or a VL nucleotide sequence of SEQ ID NO: 101. In some embodiments, the polynucleotide comprises a VH nucleotide sequence of SEQ ID NO: 216 and/or a VL nucleotide sequence of SEQ ID NO: 103. In some embodiments, the polynucleotide comprises a VH nucleotide sequence of SEQ ID NO: 216 and/or a VL nucleotide sequence of SEQ ID NO: 111. In some embodiments, the polynucleotide comprises a VH nucleotide sequence of SEQ ID NO: 216 and/or a VL nucleotide sequence of SEQ ID NO: 228. In some embodiments, the polynucleotide comprises a VH nucleotide sequence of SEQ ID NO: 216 and/or a VL nucleotide sequence of SEQ ID NO: 230. In some embodiments, the polynucleotide comprises a VH nucleotide sequence of SEQ ID NO: 216 and/or a VL nucleotide sequence of SEQ ID NO: 232. In some embodiments, the polynucleotide comprises a VH nucleotide sequence of SEQ ID NO: 216 and/or a VL nucleotide sequence of SEQ ID NO: 234. In some embodiments, the polynucleotide comprises a VH nucleotide sequence of SEQ ID NO: 216 and/or a VL nucleotide sequence of SEQ ID NO: 236.

In some embodiments, the polynucleotide comprises a VH nucleotide sequence of SEQ ID NO: 218 and/or a VL nucleotide sequence of SEQ ID NO: 91. In some embodiments, the polynucleotide comprises a VH nucleotide sequence of SEQ ID NO: 218 and/or a VL nucleotide sequence of SEQ ID NO: 93. In some embodiments, the polynucleotide comprises a VH nucleotide sequence of SEQ ID NO: 218 and/or a VL nucleotide sequence of SEQ ID NO: 95. In some embodiments, the polynucleotide comprises a VH nucleotide sequence of SEQ ID NO: 218 and/or a VL nucleotide sequence of SEQ ID NO: 97. In some embodiments, the polynucleotide comprises a VH nucleotide sequence of SEQ ID NO: 218 and/or a VL nucleotide sequence of SEQ ID NO: 99. In some embodiments, the polynucleotide comprises a VH nucleotide sequence of SEQ ID NO: 218 and/or a VL nucleotide sequence of SEQ ID NO: 101. In some embodiments, the polynucleotide comprises a VH nucleotide sequence of SEQ ID NO: 218 and/or a VL nucleotide sequence of SEQ ID NO: 103. In some embodiments, the polynucleotide comprises a VH nucleotide sequence of SEQ ID NO: 218 and/or a VL nucleotide sequence of SEQ ID NO: 111. In some embodiments, the polynucleotide comprises a VH nucleotide sequence of SEQ ID NO: 218 and/or a VL nucleotide sequence of SEQ ID NO: 228. In some embodiments, the polynucleotide comprises a VH nucleotide sequence of SEQ ID NO: 218 and/or a VL nucleotide sequence of SEQ ID NO: 230. In some embodiments, the polynucleotide comprises a VH nucleotide sequence of SEQ ID NO: 218 and/or a VL nucleotide sequence of SEQ ID NO: 232. In some embodiments, the polynucleotide comprises a VH nucleotide sequence of SEQ ID NO: 218 and/or a VL nucleotide sequence of SEQ ID NO: 234. In some embodiments, the polynucleotide comprises a VH nucleotide sequence of SEQ ID NO: 218 and/or a VL nucleotide sequence of SEQ ID NO: 236.

In some embodiments, the polynucleotide comprises a VH nucleotide sequence of SEQ ID NO: 220 and/or a VL nucleotide sequence of SEQ ID NO: 91. In some embodiments, the polynucleotide comprises a VH nucleotide sequence of SEQ ID NO: 220 and/or a VL nucleotide sequence of SEQ ID NO: 93. In some embodiments, the polynucleotide comprises a VH nucleotide sequence of SEQ ID NO: 220 and/or a VL nucleotide sequence of SEQ ID NO: 95. In some embodiments, the polynucleotide comprises a VH nucleotide sequence of SEQ ID NO: 220 and/or a VL nucleotide sequence of SEQ ID NO: 97. In some embodiments, the polynucleotide comprises a VH nucleotide sequence of SEQ ID NO: 220 and/or a VL nucleotide sequence of SEQ ID NO: 99. In some embodiments, the polynucleotide comprises a VH nucleotide sequence of SEQ ID NO: 220 and/or a VL nucleotide sequence of SEQ ID NO: 101. In some embodiments, the polynucleotide comprises a VH nucleotide sequence of SEQ ID NO: 220 and/or a VL nucleotide sequence of SEQ ID NO: 103. In some embodiments, the polynucleotide comprises a VH nucleotide sequence of SEQ ID NO: 220 and/or a VL nucleotide sequence of SEQ ID NO: 111. In some embodiments, the polynucleotide comprises a VH nucleotide sequence of SEQ ID NO: 220 and/or a VL nucleotide sequence of SEQ ID NO: 228. In some embodiments, the polynucleotide comprises a VH nucleotide sequence of SEQ ID NO: 220 and/or a VL nucleotide sequence of SEQ ID NO: 230. In some embodiments, the polynucleotide comprises a VH nucleotide sequence of SEQ ID NO: 220 and/or a VL nucleotide sequence of SEQ ID NO: 232. In some embodiments, the polynucleotide comprises a VH nucleotide sequence of SEQ ID NO: 220 and/or a VL nucleotide sequence of SEQ ID NO: 234. In some embodiments, the polynucleotide comprises a VH nucleotide sequence of SEQ ID NO: 220 and/or a VL nucleotide sequence of SEQ ID NO: 236.

In some embodiments, the polynucleotide comprises a VH nucleotide sequence of SEQ ID NO: 222 and/or a VL nucleotide sequence of SEQ ID NO: 91. In some embodiments, the polynucleotide comprises a VH nucleotide sequence of SEQ ID NO: 222 and/or a VL nucleotide sequence of SEQ ID NO: 93. In some embodiments, the polynucleotide comprises a VH nucleotide sequence of SEQ ID NO: 222 and/or a VL nucleotide sequence of SEQ ID NO: 95. In some embodiments, the polynucleotide comprises a VH nucleotide sequence of SEQ ID NO: 222 and/or a VL nucleotide sequence of SEQ ID NO: 97. In some embodiments, the polynucleotide comprises a VH nucleotide sequence of SEQ ID NO: 222 and/or a VL nucleotide sequence of SEQ ID NO: 99. In some embodiments, the polynucleotide comprises a VH nucleotide sequence of SEQ ID NO: 222 and/or a VL nucleotide sequence of SEQ ID NO: 101. In some embodiments, the polynucleotide comprises a VH nucleotide sequence of SEQ ID NO: 222 and/or a VL nucleotide sequence of SEQ ID NO: 103. In some embodiments, the polynucleotide comprises a VH nucleotide sequence of SEQ ID NO: 222 and/or a VL nucleotide sequence of SEQ ID NO: 111. In some embodiments, the polynucleotide comprises a VH nucleotide sequence of SEQ ID NO: 222 and/or a VL nucleotide sequence of SEQ ID NO: 228. In some embodiments, the polynucleotide comprises a VH nucleotide sequence of SEQ ID NO: 222 and/or a VL nucleotide sequence of SEQ ID NO: 230. In some embodiments, the polynucleotide comprises a VH nucleotide sequence of SEQ ID NO: 222 and/or a VL nucleotide sequence of SEQ ID NO: 232. In some embodiments, the polynucleotide comprises a VH nucleotide sequence of SEQ ID NO: 222 and/or a VL nucleotide sequence of SEQ ID NO: 234. In some embodiments, the polynucleotide comprises a VH nucleotide sequence of SEQ ID NO: 222 and/or a VL nucleotide sequence of SEQ ID NO: 236.

In some embodiments, the polynucleotide comprises a VH nucleotide sequence of SEQ ID NO: 224 and/or a VL nucleotide sequence of SEQ ID NO: 91. In some embodiments, the polynucleotide comprises a VH nucleotide sequence of SEQ ID NO: 224 and/or a VL nucleotide sequence of SEQ ID NO: 93. In some embodiments, the polynucleotide comprises a VH nucleotide sequence of SEQ ID NO: 224 and/or a VL nucleotide sequence of SEQ ID NO: 95. In some embodiments, the polynucleotide comprises a VH nucleotide sequence of SEQ ID NO: 224 and/or a VL nucleotide sequence of SEQ ID NO: 97. In some embodiments, the polynucleotide comprises a VH nucleotide sequence of SEQ ID NO: 224 and/or a VL nucleotide sequence of SEQ ID NO: 99. In some embodiments, the polynucleotide comprises a VH nucleotide sequence of SEQ ID NO: 224 and/or a VL nucleotide sequence of SEQ ID NO: 101. In some embodiments, the polynucleotide comprises a VH nucleotide sequence of SEQ ID NO: 224 and/or a VL nucleotide sequence of SEQ ID NO: 103. In some embodiments, the polynucleotide comprises a VH nucleotide sequence of SEQ ID NO: 224 and/or a VL nucleotide sequence of SEQ ID NO: 111. In some embodiments, the polynucleotide comprises a VH nucleotide sequence of SEQ ID NO: 224 and/or a VL nucleotide sequence of SEQ ID NO: 228. In some embodiments, the polynucleotide comprises a VH nucleotide sequence of SEQ ID NO: 224 and/or a VL nucleotide sequence of SEQ ID NO: 230. In some embodiments, the polynucleotide comprises a VH nucleotide sequence of SEQ ID NO: 224 and/or a VL nucleotide sequence of SEQ ID NO: 232. In some embodiments, the polynucleotide comprises a VH nucleotide sequence of SEQ ID NO: 224 and/or a VL nucleotide sequence of SEQ ID NO: 234. In some embodiments, the polynucleotide comprises a VH nucleotide sequence of SEQ ID NO: 224 and/or a VL nucleotide sequence of SEQ ID NO: 236.

In some embodiments, the polynucleotide comprises a VH nucleotide sequence of SEQ ID NO: 226 and/or a VL nucleotide sequence of SEQ ID NO: 91. In some embodiments, the polynucleotide comprises a VH nucleotide sequence of SEQ ID NO: 226 and/or a VL nucleotide sequence of SEQ ID NO: 93. In some embodiments, the polynucleotide comprises a VH nucleotide sequence of SEQ ID NO: 226 and/or a VL nucleotide sequence of SEQ ID NO: 95. In some embodiments, the polynucleotide comprises a VH nucleotide sequence of SEQ ID NO: 226 and/or a VL nucleotide sequence of SEQ ID NO: 97. In some embodiments, the polynucleotide comprises a VH nucleotide sequence of SEQ ID NO: 226 and/or a VL nucleotide sequence of SEQ ID NO: 99. In some embodiments, the polynucleotide comprises a VH nucleotide sequence of SEQ ID NO: 226 and/or a VL nucleotide sequence of SEQ ID NO: 101. In some embodiments, the polynucleotide comprises a VH nucleotide sequence of SEQ ID NO: 226 and/or a VL nucleotide sequence of SEQ ID NO: 103. In some embodiments, the polynucleotide comprises a VH nucleotide sequence of SEQ ID NO: 226 and/or a VL nucleotide sequence of SEQ ID NO: 111. In some embodiments, the polynucleotide comprises a VH nucleotide sequence of SEQ ID NO: 226 and/or a VL nucleotide sequence of SEQ ID NO: 228. In some embodiments, the polynucleotide comprises a VH nucleotide sequence of SEQ ID NO: 226 and/or a VL nucleotide sequence of SEQ ID NO: 230. In some embodiments, the polynucleotide comprises a VH nucleotide sequence of SEQ ID NO: 226 and/or a VL nucleotide sequence of SEQ ID NO: 232. In some embodiments, the polynucleotide comprises a VH nucleotide sequence of SEQ ID NO: 226 and/or a VL nucleotide sequence of SEQ ID NO: 234. In some embodiments, the polynucleotide comprises a VH nucleotide sequence of SEQ ID NO: 226 and/or a VL nucleotide sequence of SEQ ID NO: 236.

In some embodiments, the polynucleotide comprises a VH nucleotide sequence of SEQ ID NO: 65 and/or a VL nucleotide sequence of SEQ ID NO: 91. In some embodiments, the polynucleotide comprises a VH nucleotide sequence of SEQ ID NO: 65 and/or a VL nucleotide sequence of SEQ ID NO: 93. In some embodiments, the polynucleotide comprises a VH nucleotide sequence of SEQ ID NO: 65 and/or a VL nucleotide sequence of SEQ ID NO: 95. In some embodiments, the polynucleotide comprises a VH nucleotide sequence of SEQ ID NO: 65 and/or a VL nucleotide sequence of SEQ ID NO: 97. In some embodiments, the polynucleotide comprises a VH nucleotide sequence of SEQ ID NO: 65 and/or a VL nucleotide sequence of SEQ ID NO: 99. In some embodiments, the polynucleotide comprises a VH nucleotide sequence of SEQ ID NO: 65 and/or a VL nucleotide sequence of SEQ ID NO: 101. In some embodiments, the polynucleotide comprises a VH nucleotide sequence of SEQ ID NO: 65 and/or a VL nucleotide sequence of SEQ ID NO: 103. In some embodiments, the polynucleotide comprises a VH nucleotide sequence of SEQ ID NO: 65 and/or a VL nucleotide sequence of SEQ ID NO: 111. In some embodiments, the polynucleotide comprises a VH nucleotide sequence of SEQ ID NO: 65 and/or a VL nucleotide sequence of SEQ ID NO: 228. In some embodiments, the polynucleotide comprises a VH nucleotide sequence of SEQ ID NO: 65 and/or a VL nucleotide sequence of SEQ ID NO: 230. In some embodiments, the polynucleotide comprises a VH nucleotide sequence of SEQ ID NO: 65 and/or a VL nucleotide sequence of SEQ ID NO: 232. In some embodiments, the polynucleotide comprises a VH nucleotide sequence of SEQ ID NO: 65 and/or a VL nucleotide sequence of SEQ ID NO: 234. In some embodiments, the polynucleotide comprises a VH nucleotide sequence of SEQ ID NO: 65 and/or a VL nucleotide sequence of SEQ ID NO: 236.

In some embodiments, the polynucleotide comprises a VH nucleotide sequence of SEQ ID NO: 67 and/or a VL nucleotide sequence of SEQ ID NO: 91. In some embodiments, the polynucleotide comprises a VH nucleotide sequence of SEQ ID NO: 67 and/or a VL nucleotide sequence of SEQ ID NO: 93. In some embodiments, the polynucleotide comprises a VH nucleotide sequence of SEQ ID NO: 67 and/or a VL nucleotide sequence of SEQ ID NO: 95. In some embodiments, the polynucleotide comprises a VH nucleotide sequence of SEQ ID NO: 67 and/or a VL nucleotide sequence of SEQ ID NO: 97. In some embodiments, the polynucleotide comprises a VH nucleotide sequence of SEQ ID NO: 67 and/or a VL nucleotide sequence of SEQ ID NO: 99. In some embodiments, the polynucleotide comprises a VH nucleotide sequence of SEQ ID NO: 67 and/or a VL nucleotide sequence of SEQ ID NO: 101. In some embodiments, the polynucleotide comprises a VH nucleotide sequence of SEQ ID NO: 67 and/or a VL nucleotide sequence of SEQ ID NO: 103. In some embodiments, the polynucleotide comprises a VH nucleotide sequence of SEQ ID NO: 67 and/or a VL nucleotide sequence of SEQ ID NO: 111. In some embodiments, the polynucleotide comprises a VH nucleotide sequence of SEQ ID NO: 67 and/or a VL nucleotide sequence of SEQ ID NO: 228. In some embodiments, the polynucleotide comprises a VH nucleotide sequence of SEQ ID NO: 67 and/or a VL nucleotide sequence of SEQ ID NO: 230. In some embodiments, the polynucleotide comprises a VH nucleotide sequence of SEQ ID NO: 67 and/or a VL nucleotide sequence of SEQ ID NO: 232. In some embodiments, the polynucleotide comprises a VH nucleotide sequence of SEQ ID NO: 67 and/or a VL nucleotide sequence of SEQ ID NO: 234. In some embodiments, the polynucleotide comprises a VH nucleotide sequence of SEQ ID NO: 67 and/or a VL nucleotide sequence of SEQ ID NO: 236.

In some embodiments, the polynucleotide comprises a VH nucleotide sequence of SEQ ID NO: 69 and/or a VL nucleotide sequence of SEQ ID NO: 91. In some embodiments, the polynucleotide comprises a VH nucleotide sequence of SEQ ID NO: 69 and/or a VL nucleotide sequence of SEQ ID NO: 93. In some embodiments, the polynucleotide comprises a VH nucleotide sequence of SEQ ID NO: 69 and/or a VL nucleotide sequence of SEQ ID NO: 95. In some embodiments, the polynucleotide comprises a VH nucleotide sequence of SEQ ID NO: 69 and/or a VL nucleotide sequence of SEQ ID NO: 97. In some embodiments, the polynucleotide comprises a VH nucleotide sequence of SEQ ID NO: 69 and/or a VL nucleotide sequence of SEQ ID NO: 99. In some embodiments, the polynucleotide comprises a VH nucleotide sequence of SEQ ID NO: 69 and/or a VL nucleotide sequence of SEQ ID NO: 101. In some embodiments, the polynucleotide comprises a VH nucleotide sequence of SEQ ID NO: 69 and/or a VL nucleotide sequence of SEQ ID NO: 103. In some embodiments, the polynucleotide comprises a VH nucleotide sequence of SEQ ID NO: 69 and/or a VL nucleotide sequence of SEQ ID NO: 111. In some embodiments, the polynucleotide comprises a VH nucleotide sequence of SEQ ID NO: 69 and/or a VL nucleotide sequence of SEQ ID NO: 228. In some embodiments, the polynucleotide comprises a VH nucleotide sequence of SEQ ID NO: 69 and/or a VL nucleotide sequence of SEQ ID NO: 230. In some embodiments, the polynucleotide comprises a VH nucleotide sequence of SEQ ID NO: 69 and/or a VL nucleotide sequence of SEQ ID NO: 232. In some embodiments, the polynucleotide comprises a VH nucleotide sequence of SEQ ID NO: 69 and/or a VL nucleotide sequence of SEQ ID NO: 234. In some embodiments, the polynucleotide comprises a VH nucleotide sequence of SEQ ID NO: 69 and/or a VL nucleotide sequence of SEQ ID NO: 236.

In some embodiments, the polynucleotide comprises a VH nucleotide sequence of SEQ ID NO: 71 and/or a VL nucleotide sequence of SEQ ID NO: 91. In some embodiments, the polynucleotide comprises a VH nucleotide sequence of SEQ ID NO: 71 and/or a VL nucleotide sequence of SEQ ID NO: 93. In some embodiments, the polynucleotide comprises a VH nucleotide sequence of SEQ ID NO: 71 and/or a VL nucleotide sequence of SEQ ID NO: 95. In some embodiments, the polynucleotide comprises a VH nucleotide sequence of SEQ ID NO: 71 and/or a VL nucleotide sequence of SEQ ID NO: 97. In some embodiments, the polynucleotide comprises a VH nucleotide sequence of SEQ ID NO: 71 and/or a VL nucleotide sequence of SEQ ID NO: 99. In some embodiments, the polynucleotide comprises a VH nucleotide sequence of SEQ ID NO: 71 and/or a VL nucleotide sequence of SEQ ID NO: 101. In some embodiments, the polynucleotide comprises a VH nucleotide sequence of SEQ ID NO: 71 and/or a VL nucleotide sequence of SEQ ID NO: 103. In some embodiments, the polynucleotide comprises a VH nucleotide sequence of SEQ ID NO: 71 and/or a VL nucleotide sequence of SEQ ID NO: 111. In some embodiments, the polynucleotide comprises a VH nucleotide sequence of SEQ ID NO: 71 and/or a VL nucleotide sequence of SEQ ID NO: 228. In some embodiments, the polynucleotide comprises a VH nucleotide sequence of SEQ ID NO: 71 and/or a VL nucleotide sequence of SEQ ID NO: 230. In some embodiments, the polynucleotide comprises a VH nucleotide sequence of SEQ ID NO: 71 and/or a VL nucleotide sequence of SEQ ID NO: 232. In some embodiments, the polynucleotide comprises a VH nucleotide sequence of SEQ ID NO: 71 and/or a VL nucleotide sequence of SEQ ID NO: 234. In some embodiments, the polynucleotide comprises a VH nucleotide sequence of SEQ ID NO: 71 and/or a VL nucleotide sequence of SEQ ID NO: 236.

In some embodiments, the polynucleotide comprises a VH nucleotide sequence of SEQ ID NO: 73 and/or a VL nucleotide sequence of SEQ ID NO: 91. In some embodiments, the polynucleotide comprises a VH nucleotide sequence of SEQ ID NO: 73 and/or a VL nucleotide sequence of SEQ ID NO: 93. In some embodiments, the polynucleotide comprises a VH nucleotide sequence of SEQ ID NO: 73 and/or a VL nucleotide sequence of SEQ ID NO: 95. In some embodiments, the polynucleotide comprises a VH nucleotide sequence of SEQ ID NO: 73 and/or a VL nucleotide sequence of SEQ ID NO: 97. In some embodiments, the polynucleotide comprises a VH nucleotide sequence of SEQ ID NO: 73 and/or a VL nucleotide sequence of SEQ ID NO: 99. In some embodiments, the polynucleotide comprises a VH nucleotide sequence of SEQ ID NO: 73 and/or a VL nucleotide sequence of SEQ ID NO: 101. In some embodiments, the polynucleotide comprises a VH nucleotide sequence of SEQ ID NO: 73 and/or a VL nucleotide sequence of SEQ ID NO: 103. In some embodiments, the polynucleotide comprises a VH nucleotide sequence of SEQ ID NO: 73 and/or a VL nucleotide sequence of SEQ ID NO: 111. In some embodiments, the polynucleotide comprises a VH nucleotide sequence of SEQ ID NO: 73 and/or a VL nucleotide sequence of SEQ ID NO: 228. In some embodiments, the polynucleotide comprises a VH nucleotide sequence of SEQ ID NO: 73 and/or a VL nucleotide sequence of SEQ ID NO: 230. In some embodiments, the polynucleotide comprises a VH nucleotide sequence of SEQ ID NO: 73 and/or a VL nucleotide sequence of SEQ ID NO: 232. In some embodiments, the polynucleotide comprises a VH nucleotide sequence of SEQ ID NO: 73 and/or a VL nucleotide sequence of SEQ ID NO: 234. In some embodiments, the polynucleotide comprises a VH nucleotide sequence of SEQ ID NO: 73 and/or a VL nucleotide sequence of SEQ ID NO: 236.

In some embodiments, the polynucleotide comprises a VH nucleotide sequence of SEQ ID NO: 75 and/or a VL nucleotide sequence of SEQ ID NO: 91. In some embodiments, the polynucleotide comprises a VH nucleotide sequence of SEQ ID NO: 75 and/or a VL nucleotide sequence of SEQ ID NO: 93. In some embodiments, the polynucleotide comprises a VH nucleotide sequence of SEQ ID NO: 75 and/or a VL nucleotide sequence of SEQ ID NO: 95. In some embodiments, the polynucleotide comprises a VH nucleotide sequence of SEQ ID NO: 75 and/or a VL nucleotide sequence of SEQ ID NO: 97. In some embodiments, the polynucleotide comprises a VH nucleotide sequence of SEQ ID NO: 75 and/or a VL nucleotide sequence of SEQ ID NO: 99. In some embodiments, the polynucleotide comprises a VH nucleotide sequence of SEQ ID NO: 75 and/or a VL nucleotide sequence of SEQ ID NO: 101. In some embodiments, the polynucleotide comprises a VH nucleotide sequence of SEQ ID NO: 75 and/or a VL nucleotide sequence of SEQ ID NO: 103. In some embodiments, the polynucleotide comprises a VH nucleotide sequence of SEQ ID NO: 75 and/or a VL nucleotide sequence of SEQ ID NO: 111. In some embodiments, the polynucleotide comprises a VH nucleotide sequence of SEQ ID NO: 75 and/or a VL nucleotide sequence of SEQ ID NO: 228. In some embodiments, the polynucleotide comprises a VH nucleotide sequence of SEQ ID NO: 75 and/or a VL nucleotide sequence of SEQ ID NO: 230. In some embodiments, the polynucleotide comprises a VH nucleotide sequence of SEQ ID NO: 75 and/or a VL nucleotide sequence of SEQ ID NO: 232. In some embodiments, the polynucleotide comprises a VH nucleotide sequence of SEQ ID NO: 75 and/or a VL nucleotide sequence of SEQ ID NO: 234. In some embodiments, the polynucleotide comprises a VH nucleotide sequence of SEQ ID NO: 75 and/or a VL nucleotide sequence of SEQ ID NO: 236.

In some embodiments, the polynucleotide comprises a VH nucleotide sequence of SEQ ID NO: 77 and/or a VL nucleotide sequence of SEQ ID NO: 91. In some embodiments, the polynucleotide comprises a VH nucleotide sequence of SEQ ID NO: 77 and/or a VL nucleotide sequence of SEQ ID NO: 93. In some embodiments, the polynucleotide comprises a VH nucleotide sequence of SEQ ID NO: 77 and/or a VL nucleotide sequence of SEQ ID NO: 95. In some embodiments, the polynucleotide comprises a VH nucleotide sequence of SEQ ID NO: 77 and/or a VL nucleotide sequence of SEQ ID NO: 97. In some embodiments, the polynucleotide comprises a VH nucleotide sequence of SEQ ID NO: 77 and/or a VL nucleotide sequence of SEQ ID NO: 99. In some embodiments, the polynucleotide comprises a VH nucleotide sequence of SEQ ID NO: 77 and/or a VL nucleotide sequence of SEQ ID NO: 101. In some embodiments, the polynucleotide comprises a VH nucleotide sequence of SEQ ID NO: 77 and/or a VL nucleotide sequence of SEQ ID NO: 103. In some embodiments, the polynucleotide comprises a VH nucleotide sequence of SEQ ID NO: 77 and/or a VL nucleotide sequence of SEQ ID NO: 111. In some embodiments, the polynucleotide comprises a VH nucleotide sequence of SEQ ID NO: 77 and/or a VL nucleotide sequence of SEQ ID NO: 228. In some embodiments, the polynucleotide comprises a VH nucleotide sequence of SEQ ID NO: 77 and/or a VL nucleotide sequence of SEQ ID NO: 230. In some embodiments, the polynucleotide comprises a VH nucleotide sequence of SEQ ID NO: 77 and/or a VL nucleotide sequence of SEQ ID NO: 232. In some embodiments, the polynucleotide comprises a VH nucleotide sequence of SEQ ID NO: 77 and/or a VL nucleotide sequence of SEQ ID NO: 234. In some embodiments, the polynucleotide comprises a VH nucleotide sequence of SEQ ID NO: 77 and/or a VL nucleotide sequence of SEQ ID NO: 236.

In some embodiments, the polynucleotide comprises a VH nucleotide sequence of SEQ ID NO: 79 and/or a VL nucleotide sequence of SEQ ID NO: 91. In some embodiments, the polynucleotide comprises a VH nucleotide sequence of SEQ ID NO: 79 and/or a VL nucleotide sequence of SEQ ID NO: 93. In some embodiments, the polynucleotide comprises a VH nucleotide sequence of SEQ ID NO: 79 and/or a VL nucleotide sequence of SEQ ID NO: 95. In some embodiments, the polynucleotide comprises a VH nucleotide sequence of SEQ ID NO: 79 and/or a VL nucleotide sequence of SEQ ID NO: 97. In some embodiments, the polynucleotide comprises a VH nucleotide sequence of SEQ ID NO: 79 and/or a VL nucleotide sequence of SEQ ID NO: 99. In some embodiments, the polynucleotide comprises a VH nucleotide sequence of SEQ ID NO: 79 and/or a VL nucleotide sequence of SEQ ID NO: 101. In some embodiments, the polynucleotide comprises a VH nucleotide sequence of SEQ ID NO: 79 and/or a VL nucleotide sequence of SEQ ID NO: 103. In some embodiments, the polynucleotide comprises a VH nucleotide sequence of SEQ ID NO: 79 and/or a VL nucleotide sequence of SEQ ID NO: 111. In some embodiments, the polynucleotide comprises a VH nucleotide sequence of SEQ ID NO: 79 and/or a VL nucleotide sequence of SEQ ID NO: 228. In some embodiments, the polynucleotide comprises a VH nucleotide sequence of SEQ ID NO: 79 and/or a VL nucleotide sequence of SEQ ID NO: 230. In some embodiments, the polynucleotide comprises a VH nucleotide sequence of SEQ ID NO: 79 and/or a VL nucleotide sequence of SEQ ID NO: 232. In some embodiments, the polynucleotide comprises a VH nucleotide sequence of SEQ ID NO: 79 and/or a VL nucleotide sequence of SEQ ID NO: 234. In some embodiments, the polynucleotide comprises a VH nucleotide sequence of SEQ ID NO: 79 and/or a VL nucleotide sequence of SEQ ID NO: 236.

In some embodiments, the polynucleotide comprises a VH nucleotide sequence of SEQ ID NO: 81 and/or a VL nucleotide sequence of SEQ ID NO: 91. In some embodiments, the polynucleotide comprises a VH nucleotide sequence of SEQ ID NO: 81 and/or a VL nucleotide sequence of SEQ ID NO: 93. In some embodiments, the polynucleotide comprises a VH nucleotide sequence of SEQ ID NO: 81 and/or a VL nucleotide sequence of SEQ ID NO: 95. In some embodiments, the polynucleotide comprises a VH nucleotide sequence of SEQ ID NO: 81 and/or a VL nucleotide sequence of SEQ ID NO: 97. In some embodiments, the polynucleotide comprises a VH nucleotide sequence of SEQ ID NO: 81 and/or a VL nucleotide sequence of SEQ ID NO: 99. In some embodiments, the polynucleotide comprises a VH nucleotide sequence of SEQ ID NO: 81 and/or a VL nucleotide sequence of SEQ ID NO: 101. In some embodiments, the polynucleotide comprises a VH nucleotide sequence of SEQ ID NO: 81 and/or a VL nucleotide sequence of SEQ ID NO: 103. In some embodiments, the polynucleotide comprises a VH nucleotide sequence of SEQ ID NO: 81 and/or a VL nucleotide sequence of SEQ ID NO: 111. In some embodiments, the polynucleotide comprises a VH nucleotide sequence of SEQ ID NO: 81 and/or a VL nucleotide sequence of SEQ ID NO: 228. In some embodiments, the polynucleotide comprises a VH nucleotide sequence of SEQ ID NO: 81 and/or a VL nucleotide sequence of SEQ ID NO: 230. In some embodiments, the polynucleotide comprises a VH nucleotide sequence of SEQ ID NO: 81 and/or a VL nucleotide sequence of SEQ ID NO: 232. In some embodiments, the polynucleotide comprises a VH nucleotide sequence of SEQ ID NO: 81 and/or a VL nucleotide sequence of SEQ ID NO: 234. In some embodiments, the polynucleotide comprises a VH nucleotide sequence of SEQ ID NO: 81 and/or a VL nucleotide sequence of SEQ ID NO: 236.

In some embodiments, the polynucleotide comprises a VH nucleotide sequence of SEQ ID NO: 83 and/or a VL nucleotide sequence of SEQ ID NO: 91. In some embodiments, the polynucleotide comprises a VH nucleotide sequence of SEQ ID NO: 83 and/or a VL nucleotide sequence of SEQ ID NO: 93. In some embodiments, the polynucleotide comprises a VH nucleotide sequence of SEQ ID NO: 83 and/or a VL nucleotide sequence of SEQ ID NO: 95. In some embodiments, the polynucleotide comprises a VH nucleotide sequence of SEQ ID NO: 83 and/or a VL nucleotide sequence of SEQ ID NO: 97. In some embodiments, the polynucleotide comprises a VH nucleotide sequence of SEQ ID NO: 83 and/or a VL nucleotide sequence of SEQ ID NO: 99. In some embodiments, the polynucleotide comprises a VH nucleotide sequence of SEQ ID NO: 83 and/or a VL nucleotide sequence of SEQ ID NO: 101. In some embodiments, the polynucleotide comprises a VH nucleotide sequence of SEQ ID NO: 83 and/or a VL nucleotide sequence of SEQ ID NO: 103. In some embodiments, the polynucleotide comprises a VH nucleotide sequence of SEQ ID NO: 83 and/or a VL nucleotide sequence of SEQ ID NO: 111. In some embodiments, the polynucleotide comprises a VH nucleotide sequence of SEQ ID NO: 83 and/or a VL nucleotide sequence of SEQ ID NO: 228. In some embodiments, the polynucleotide comprises a VH nucleotide sequence of SEQ ID NO: 83 and/or a VL nucleotide sequence of SEQ ID NO: 230. In some embodiments, the polynucleotide comprises a VH nucleotide sequence of SEQ ID NO: 83 and/or a VL nucleotide sequence of SEQ ID NO: 232. In some embodiments, the polynucleotide comprises a VH nucleotide sequence of SEQ ID NO: 83 and/or a VL nucleotide sequence of SEQ ID NO: 234. In some embodiments, the polynucleotide comprises a VH nucleotide sequence of SEQ ID NO: 83 and/or a VL nucleotide sequence of SEQ ID NO: 236.

In some embodiments, the polynucleotide comprises a VH nucleotide sequence of SEQ ID NO: 85 and/or a VL nucleotide sequence of SEQ ID NO: 91. In some embodiments, the polynucleotide comprises a VH nucleotide sequence of SEQ ID NO: 85 and/or a VL nucleotide sequence of SEQ ID NO: 93. In some embodiments, the polynucleotide comprises a VH nucleotide sequence of SEQ ID NO: 85 and/or a VL nucleotide sequence of SEQ ID NO: 95. In some embodiments, the polynucleotide comprises a VH nucleotide sequence of SEQ ID NO: 85 and/or a VL nucleotide sequence of SEQ ID NO: 97. In some embodiments, the polynucleotide comprises a VH nucleotide sequence of SEQ ID NO: 85 and/or a VL nucleotide sequence of SEQ ID NO: 99. In some embodiments, the polynucleotide comprises a VH nucleotide sequence of SEQ ID NO: 85 and/or a VL nucleotide sequence of SEQ ID NO: 101. In some embodiments, the polynucleotide comprises a VH nucleotide sequence of SEQ ID NO: 85 and/or a VL nucleotide sequence of SEQ ID NO: 103. In some embodiments, the polynucleotide comprises a VH nucleotide sequence of SEQ ID NO: 85 and/or a VL nucleotide sequence of SEQ ID NO: 111. In some embodiments, the polynucleotide comprises a VH nucleotide sequence of SEQ ID NO: 85 and/or a VL nucleotide sequence of SEQ ID NO: 228. In some embodiments, the polynucleotide comprises a VH nucleotide sequence of SEQ ID NO: 85 and/or a VL nucleotide sequence of SEQ ID NO: 230. In some embodiments, the polynucleotide comprises a VH nucleotide sequence of SEQ ID NO: 85 and/or a VL nucleotide sequence of SEQ ID NO: 232. In some embodiments, the polynucleotide comprises a VH nucleotide sequence of SEQ ID NO: 85 and/or a VL nucleotide sequence of SEQ ID NO: 234. In some embodiments, the polynucleotide comprises a VH nucleotide sequence of SEQ ID NO: 85 and/or a VL nucleotide sequence of SEQ ID NO: 236.

In some embodiments, the polynucleotide comprises a VH nucleotide sequence of SEQ ID NO: 87 and/or a VL nucleotide sequence of SEQ ID NO: 91. In some embodiments, the polynucleotide comprises a VH nucleotide sequence of SEQ ID NO: 87 and/or a VL nucleotide sequence of SEQ ID NO: 93. In some embodiments, the polynucleotide comprises a VH nucleotide sequence of SEQ ID NO: 87 and/or a VL nucleotide sequence of SEQ ID NO: 95. In some embodiments, the polynucleotide comprises a VH nucleotide sequence of SEQ ID NO: 87 and/or a VL nucleotide sequence of SEQ ID NO: 97. In some embodiments, the polynucleotide comprises a VH nucleotide sequence of SEQ ID NO: 87 and/or a VL nucleotide sequence of SEQ ID NO: 99. In some embodiments, the polynucleotide comprises a VH nucleotide sequence of SEQ ID NO: 87 and/or a VL nucleotide sequence of SEQ ID NO: 101. In some embodiments, the polynucleotide comprises a VH nucleotide sequence of SEQ ID NO: 87 and/or a VL nucleotide sequence of SEQ ID NO: 103. In some embodiments, the polynucleotide comprises a VH nucleotide sequence of SEQ ID NO: 87 and/or a VL nucleotide sequence of SEQ ID NO: 111. In some embodiments, the polynucleotide comprises a VH nucleotide sequence of SEQ ID NO: 87 and/or a VL nucleotide sequence of SEQ ID NO: 228. In some embodiments, the polynucleotide comprises a VH nucleotide sequence of SEQ ID NO: 87 and/or a VL nucleotide sequence of SEQ ID NO: 230. In some embodiments, the polynucleotide comprises a VH nucleotide sequence of SEQ ID NO: 87 and/or a VL nucleotide sequence of SEQ ID NO: 232. In some embodiments, the polynucleotide comprises a VH nucleotide sequence of SEQ ID NO: 87 and/or a VL nucleotide sequence of SEQ ID NO: 234. In some embodiments, the polynucleotide comprises a VH nucleotide sequence of SEQ ID NO: 87 and/or a VL nucleotide sequence of SEQ ID NO: 236.

In some embodiments, the polynucleotide comprises a VH nucleotide sequence of SEQ ID NO: 89 and/or a VL nucleotide sequence of SEQ ID NO: 91. In some embodiments, the polynucleotide comprises a VH nucleotide sequence of SEQ ID NO: 89 and/or a VL nucleotide sequence of SEQ ID NO: 93. In some embodiments, the polynucleotide comprises a VH nucleotide sequence of SEQ ID NO: 89 and/or a VL nucleotide sequence of SEQ ID NO: 95. In some embodiments, the polynucleotide comprises a VH nucleotide sequence of SEQ ID NO: 89 and/or a VL nucleotide sequence of SEQ ID NO: 97. In some embodiments, the polynucleotide comprises a VH nucleotide sequence of SEQ ID NO: 89 and/or a VL nucleotide sequence of SEQ ID NO: 99. In some embodiments, the polynucleotide comprises a VH nucleotide sequence of SEQ ID NO: 89 and/or a VL nucleotide sequence of SEQ ID NO: 101. In some embodiments, the polynucleotide comprises a VH nucleotide sequence of SEQ ID NO: 89 and/or a VL nucleotide sequence of SEQ ID NO: 103. In some embodiments, the polynucleotide comprises a VH nucleotide sequence of SEQ ID NO: 89 and/or a VL nucleotide sequence of SEQ ID NO: 111. In some embodiments, the polynucleotide comprises a VH nucleotide sequence of SEQ ID NO: 89 and/or a VL nucleotide sequence of SEQ ID NO: 228. In some embodiments, the polynucleotide comprises a VH nucleotide sequence of SEQ ID NO: 89 and/or a VL nucleotide sequence of SEQ ID NO: 230. In some embodiments, the polynucleotide comprises a VH nucleotide sequence of SEQ ID NO: 89 and/or a VL nucleotide sequence of SEQ ID NO: 232. In some embodiments, the polynucleotide comprises a VH nucleotide sequence of SEQ ID NO: 89 and/or a VL nucleotide sequence of SEQ ID NO: 234. In some embodiments, the polynucleotide comprises a VH nucleotide sequence of SEQ ID NO: 89 and/or a VL nucleotide sequence of SEQ ID NO: 236.

In some embodiments, the polynucleotide comprises a VH nucleotide sequence of SEQ ID NO: 107 and/or a VL nucleotide sequence of SEQ ID NO: 91. In some embodiments, the polynucleotide comprises a VH nucleotide sequence of SEQ ID NO: 107 and/or a VL nucleotide sequence of SEQ ID NO: 93. In some embodiments, the polynucleotide comprises a VH nucleotide sequence of SEQ ID NO: 107 and/or a VL nucleotide sequence of SEQ ID NO: 95. In some embodiments, the polynucleotide comprises a VH nucleotide sequence of SEQ ID NO: 107 and/or a VL nucleotide sequence of SEQ ID NO: 97. In some embodiments, the polynucleotide comprises a VH nucleotide sequence of SEQ ID NO: 107 and/or a VL nucleotide sequence of SEQ ID NO: 99. In some embodiments, the polynucleotide comprises a VH nucleotide sequence of SEQ ID NO: 107 and/or a VL nucleotide sequence of SEQ ID NO: 101. In some embodiments, the polynucleotide comprises a VH nucleotide sequence of SEQ ID NO: 107 and/or a VL nucleotide sequence of SEQ ID NO: 103. In some embodiments, the polynucleotide comprises a VH nucleotide sequence of SEQ ID NO: 107 and/or a VL nucleotide sequence of SEQ ID NO: 111. In some embodiments, the polynucleotide comprises a VH nucleotide sequence of SEQ ID NO: 107 and/or a VL nucleotide sequence of SEQ ID NO: 228. In some embodiments, the polynucleotide comprises a VH nucleotide sequence of SEQ ID NO: 107 and/or a VL nucleotide sequence of SEQ ID NO: 230. In some embodiments, the polynucleotide comprises a VH nucleotide sequence of SEQ ID NO: 107 and/or a VL nucleotide sequence of SEQ ID NO: 232. In some embodiments, the polynucleotide comprises a VH nucleotide sequence of SEQ ID NO: 107 and/or a VL nucleotide sequence of SEQ ID NO: 234. In some embodiments, the polynucleotide comprises a VH nucleotide sequence of SEQ ID NO: 107 and/or a VL nucleotide sequence of SEQ ID NO: 236.

In some embodiments, the polynucleotide comprises a VH nucleotide sequence of SEQ ID NO: 109 and/or a VL nucleotide sequence of SEQ ID NO: 91. In some embodiments, the polynucleotide comprises a VH nucleotide sequence of SEQ ID NO: 109 and/or a VL nucleotide sequence of SEQ ID NO: 93. In some embodiments, the polynucleotide comprises a VH nucleotide sequence of SEQ ID NO: 109 and/or a VL nucleotide sequence of SEQ ID NO: 95. In some embodiments, the polynucleotide comprises a VH nucleotide sequence of SEQ ID NO: 109 and/or a VL nucleotide sequence of SEQ ID NO: 97. In some embodiments, the polynucleotide comprises a VH nucleotide sequence of SEQ ID NO: 109 and/or a VL nucleotide sequence of SEQ ID NO: 99. In some embodiments, the polynucleotide comprises a VH nucleotide sequence of SEQ ID NO: 109 and/or a VL nucleotide sequence of SEQ ID NO: 101. In some embodiments, the polynucleotide comprises a VH nucleotide sequence of SEQ ID NO: 109 and/or a VL nucleotide sequence of SEQ ID NO: 103. In some embodiments, the polynucleotide comprises a VH nucleotide sequence of SEQ ID NO: 109 and/or a VL nucleotide sequence of SEQ ID NO: 111.

In some embodiments, the polynucleotide comprises a VH nucleotide sequence of SEQ ID NO: 109 and/or a VL nucleotide sequence of SEQ ID NO: 228. In some embodiments, the polynucleotide comprises a VH nucleotide sequence of SEQ ID NO: 109 and/or a VL nucleotide sequence of SEQ ID NO: 230. In some embodiments, the polynucleotide comprises a VH nucleotide sequence of SEQ ID NO: 109 and/or a VL nucleotide sequence of SEQ ID NO: 232. In some embodiments, the polynucleotide comprises a VH nucleotide sequence of SEQ ID NO: 109 and/or a VL nucleotide sequence of SEQ ID NO: 234. In some embodiments, the polynucleotide comprises a VH nucleotide sequence of SEQ ID NO: 109 and/or a VL nucleotide sequence of SEQ ID NO: 236.

In some embodiments, the polynucleotide comprises a VH nucleotide sequence of SEQ ID NO: 105 and/or a VL nucleotide sequence of SEQ ID NO: 91. In some embodiments, the polynucleotide comprises a VH nucleotide sequence of SEQ ID NO: 105 and/or a VL nucleotide sequence of SEQ ID NO: 93. In some embodiments, the polynucleotide comprises a VH nucleotide sequence of SEQ ID NO: 105 and/or a VL nucleotide sequence of SEQ ID NO: 95. In some embodiments, the polynucleotide comprises a VH nucleotide sequence of SEQ ID NO: 105 and/or a VL nucleotide sequence of SEQ ID NO: 97. In some embodiments, the polynucleotide comprises a VH nucleotide sequence of SEQ ID NO: 105 and/or a VL nucleotide sequence of SEQ ID NO: 99. In some embodiments, the polynucleotide comprises a VH nucleotide sequence of SEQ ID NO: 105 and/or a VL nucleotide sequence of SEQ ID NO: 101. In some embodiments, the polynucleotide comprises a VH nucleotide sequence of SEQ ID NO: 105 and/or a VL nucleotide sequence of SEQ ID NO: 103. In some embodiments, the polynucleotide comprises a VH nucleotide sequence of SEQ ID NO: 105 and/or a VL nucleotide sequence of SEQ ID NO: 111. In some embodiments, the polynucleotide comprises a VH nucleotide sequence of SEQ ID NO: 105 and/or a VL nucleotide sequence of SEQ ID NO: 228. In some embodiments, the polynucleotide comprises a VH nucleotide sequence of SEQ ID NO: 105 and/or a VL nucleotide sequence of SEQ ID NO: 230. In some embodiments, the polynucleotide comprises a VH nucleotide sequence of SEQ ID NO: 105 and/or a VL nucleotide sequence of SEQ ID NO: 232. In some embodiments, the polynucleotide comprises a VH nucleotide sequence of SEQ ID NO: 105 and/or a VL nucleotide sequence of SEQ ID NO: 234. In some embodiments, the polynucleotide comprises a VH nucleotide sequence of SEQ ID NO: 105 and/or a VL nucleotide sequence of SEQ ID NO: 236.

The present disclosure further relates to variants of the polynucleotides described herein, wherein the variant encodes, for example, fragments, analogs, and/or derivatives of a polypeptide. In certain embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising an antibody or antigen binding fragment thereof described herein.

As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In certain embodiments, the present disclosure provides a polynucleotide comprising a nucleotide sequence at least about 80% identical, at least about 85% identical, at least about 90% identical, at least about 95% identical, and in some embodiments, at least about 96%, 97%, 98% or 99% identical to a polynucleotide listed in the Sequence Listing provided herein.

In certain embodiments, the present disclosure provides a polynucleotide comprising a nucleotide sequence at least about 80% identical, at least about 85% identical, at least about 90% identical, at least about 95% identical, and in some embodiments, at least about 96%, 97%, 98% or 99% identical to a polynucleotide selected from the polynucleotides listed in Table 36 and Table 37 above.

In certain embodiments, the polynucleotide provided herein further comprises one or more signal sequences before the VH and/or VL sequences listed in Table 36 and Table 37 above.

In certain embodiments, a polynucleotide is isolated. In certain embodiments, a polynucleotide is substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises one or more expression vectors comprising polynucleotide molecules. In some embodiments, a host cell comprises a polynucleotide molecule. In some embodiments, a host cell comprises one or more polynucleotide molecules. Construction of the vectors provided herein is exemplified in Section 6 below.

5.4 Methods of Making the Antibodies

In yet another aspect, provided herein are methods for making the various antibodies or antigen binding fragments provided herein.

Recombinant expression of an antibody provided herein (e.g., a full-length antibody, heavy and/or light chain of an antibody, or a single chain antibody provided herein) that immunospecifically binds to an Fn14 antigen (e.g., Fn14) requires construction of an expression vector containing a polynucleotide that encodes the antibody. Once a polynucleotide encoding an antibody molecule, heavy or light chain of an antibody, or fragment thereof (such as, but not necessarily, containing the heavy and/or light chain variable domain) provided herein has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule provided herein, a heavy or light chain of an antibody, a heavy or light chain variable domain of an antibody or a fragment thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody provided herein. Thus, also provided herein are host cells containing a polynucleotide encoding an antibody provided herein or fragments thereof, or a heavy or light chain thereof, or fragment thereof, or a single chain antibody provided herein, operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules provided herein (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule provided herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing antibody coding sequences; or mammalian cell systems (e.g., COS, CHO, BHK, 293, NSO, and 3T3 cells)

harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In some embodiments, antibodies provided herein are produced in CHO cells. In a specific embodiment, the expression of nucleotide sequences encoding antibodies provided herein which immunospecifically bind to an Fn14 antigen is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et a , 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NSO (a murine myeloma cell line that does not endogenously produce any immunoglobulin chains), CRL7O3O and HsS78Bst cells. In some embodiments, fully human monoclonal antibodies provided herein are produced in mammalian cells, such as CHO cells.

For long-term, high-yield production of recombinant proteins, stable expression can be utilized. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors provided herein, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains may comprise cDNA or genomic DNA.

Once an antibody molecule provided herein has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies provided herein can be fused to heterologous polypeptide sequences described herein or otherwise known in the art to facilitate purification. Certain methods of making the antibodies or fragments thereof provided herein are described in Section 6 below.

5.5 Pharmaceutical Compositions

In one aspect, the present disclosure further provides pharmaceutical compositions comprising at least one antibody or antigen binding fragment thereof of the present disclosure. In some embodiments, a pharmaceutical composition comprises therapeutically effective amount of an antibody or antigen binding fragment thereof provided herein and a pharmaceutically acceptable excipient.

Pharmaceutical compositions comprising an antibody or antigen binding fragment thereof are prepared for storage by mixing the fusion protein having the desired degree of purity with optional physiologically acceptable excipients (see, e.g., Remington, *Remington's Pharmaceutical Sciences* (18th ed. 1980)) in the form of aqueous solutions or lyophilized or other dried forms.

The antibody or antigen binding fragment thereof of the present disclosure may be formulated in any suitable form for delivery to a target cell/tissue, e.g., as microcapsules or macroemulsions (Remington, supra; Park et al., 2005, Molecules 10:146-61; Malik et al., 2007, Curr. Drug. Deliv. 4:141-51), as sustained release formulations (Putney and Burke, 1998, Nature Biotechnol. 16:153-57), or in liposomes (Maclean et al., 1997, Int. J. Oncol. 11:325-32; Kontermann, 2006, Curr. Opin. Mol. Ther. 8:39-45).

An antibody or antigen binding fragment thereof provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles, and nanocapsules) or in macroemulsions. Such techniques are disclosed, for example, in Remington, supra.

Various compositions and delivery systems are known and can be used with an antibody or antigen binding fragment thereof as described herein, including, but not limited to, encapsulation in liposomes, microparticles, microcapsules, recombinant cells capable of expressing the antibody or antigen binding fragment thereof, receptor-mediated endocytosis (see, e.g., Wu and Wu, 1987, J. Biol. Chem. 262:4429-32), construction of a nucleic acid as part of a retroviral or other vector, etc. In another embodiment, a composition can be provided as a controlled release or sustained release system. In one embodiment, a pump may be used to achieve controlled or sustained release (see, e.g., Langer, supra; Sefton, 1987, Crit. Ref. Biomed. Eng. 14:201-40; Buchwald et al., 1980, Surgery 88:507-16; and Saudek et al., 1989, N. Engl. J. Med. 321:569-74). In another embodiment, polymeric materials can be used to achieve controlled or sustained release of a prophylactic or therapeutic agent (e.g., an antibody or antigen binding fragment thereof as described herein) or a composition provided herein (see, e.g., *Medical Applications of Controlled Release* (Langer and Wise eds., 1974); *Controlled Drug Bioavailability, Drug Product Design and Performance* (Smolen and Ball eds., 1984); Ranger and Peppas, 1983, J. Macromol. Sci. Rev. Macromol. Chem. 23:61-126; Levy et al., 1985, Science 228:190-92; During et al., 1989, Ann. Neurol. 25:351-56; Howard et al., 1989, J. Neurosurg. 71:105-12; U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of a particular target tissue, for example, the nasal passages or lungs, thus requiring only a fraction of the systemic dose (see, e.g., Goodson, Medical Applications of Controlled Release Vol. 2, 115-38 (1984)). Controlled release systems are discussed, for example, by Langer, 1990, Science 249:1527-33. Any technique known to one of skill in the art can be used to produce sustained release formulations comprising one or more antibody or antigen binding fragment thereof as described herein (see, e.g., U.S. Pat. No. 4,526,938, PCT publication Nos. WO 91/05548 and WO 96/20698, Ning et al., 1996, Radiotherapy & Oncology 39:179-89; Song et al., 1995, PDA J. of Pharma. Sci. & Tech. 50:372-97; Cleek et aL, 1997, Pro. Int'l. Symp. Control. Rel. Bioact. Mater. 24:853-54; and Lam et al., 1997, Proc. Int'l. Symp. Control Rel. Bioact. Mater. 24:759-60).

5.6 Methods of Using the Antibodies and Pharmaceutical Compositions

In one aspect, provided herein is a method of attenuating an activity of Fn14 on a cell, comprising exposing the cell to an effective amount of an antibody or antigen binding fragment thereof provided herein.

In some embodiments, the antibody provided herein attenuates an Fn14 activity by at least about 10%. In some embodiments, the antibody provided herein attenuates an Fn14 activity by at least about 20%. In some embodiments, the antibody provided herein attenuates an Fn14 activity by at least about 30%. In some embodiments, the antibody provided herein attenuates an Fn14 activity by at least about 40%. In some embodiments, the antibody provided herein attenuates an Fn14 activity by at least about 50%. In some embodiments, the antibody provided herein attenuates an Fn14 activity by at least about 60%. In some embodiments, the antibody provided herein attenuates an Fn14 activity by at least about 70%. In some embodiments, the antibody provided herein attenuates an Fn14 activity by at least about 80%. In some embodiments, the antibody provided herein attenuates an Fn14 activity by at least about 90%. In some embodiments, the antibody provided herein attenuates an Fn14 activity by at least about 95%. In certain embodiments, the antibody described herein can attenuate (e.g., partially attenuate) an Fn14 activity by at least about 15% to about 65%. In certain embodiments, the antibody described herein can attenuate (e.g., partially attenuate) an Fn14 activity by at least about 20% to about 65%. In certain embodiments, the antibody described herein can attenuate (e.g., partially attenuate) an Fn14 activity by at least about 30% to about 65%.

A non-limiting example of an Fn14 activity is Fn14 mediated signaling. Thus, in certain embodiments, provided herein is a method of attenuating (e.g., partially attenuating) Fn14 mediated signaling in a cell, comprising exposing the cell to an effective amount of an antibody or antigen binding fragment thereof provided herein.

In some embodiments, the antibody provided herein attenuates Fn14 mediated signaling by at least about 10%. In some embodiments, the antibody provided herein attenuates Fn14 mediated signaling by at least about 20%. In some embodiments, the antibody provided herein attenuates Fn14 mediated signaling by at least about 30%. In some embodiments, the antibody provided herein attenuates Fn14 mediated signaling by at least about 40%. In some embodiments, the antibody provided herein attenuates Fn14 mediated signaling by at least about 50%. In some embodiments, the antibody provided herein attenuates Fn14 mediated signaling by at least about 60%. In some embodiments, the antibody provided herein attenuates Fn14 mediated signaling by at least about 70%. In some embodiments, the antibody provided herein attenuates Fn14 mediated signaling by at least about 80%. In some embodiments, the antibody provided herein attenuates Fn14 mediated signaling by at least about 90%. In some embodiments, the antibody provided herein attenuates Fn14 mediated signaling by at least about 95%. In certain embodiments, the antibody described herein can attenuate (e.g., partially attenuate) Fn14 mediated signaling by at least about 15% to about 65%. In certain embodiments, the antibody described herein can attenuate (e.g., partially attenuate) Fn14 mediated signaling by at least about 20% to about 65%. In certain embodiments, the antibody described herein can attenuate (e.g., partially attenuate) Fn14 mediated signaling by at least about 30% to about 65%.

Another non-limiting example of an Fn14 activity is binding to TWEAK. Thus, in certain embodiments, provided herein is a method of attenuating (e.g., partially attenuating) the binding of Fn14 to TWEAK, comprising exposing a cell to an effective amount of an antibody or antigen binding fragment thereof provided herein.

In some embodiments, the antibody provided herein attenuates the binding of Fn14 to TWEAK by at least about 10%. In some embodiments, the antibody provided herein attenuates the binding of Fn14 to TWEAK by at least about 20%. In some embodiments, the antibody provided herein attenuates the binding of Fn14 to TWEAK by at least about 30%. In some embodiments, the antibody provided herein attenuates the binding of Fn14 to TWEAK by at least about 40%. In some embodiments, the antibody provided herein attenuates the binding of Fn14 to TWEAK by at least about 50%. In some embodiments, the antibody provided herein attenuates the binding of Fn14 to TWEAK by at least about 60%. In some embodiments, the antibody provided herein attenuates the binding of Fn14 to TWEAK by at least about 70%. In some embodiments, the antibody provided herein attenuates the binding of Fn14 to TWEAK by at least about 80%. In some embodiments, the antibody provided herein attenuates the binding of Fn14 to TWEAK by at least about 90%. In some embodiments, the antibody provided herein attenuates the binding of Fn14 to TWEAK by at least about 95%. In certain embodiments, the antibody described herein can attenuate (e.g., partially attenuate) the binding of Fn14 to TWEAK by at least about 15% to about 65%. In certain embodiments, the antibody described herein can attenuate (e.g., partially attenuate) the binding of Fn14 to TWEAK by at least about 20% to about 65%. In certain embodiments, the antibody described herein can attenuate (e.g., partially attenuate) the binding of Fn14 to TWEAK by at least about 30% to about 65%.

Yet another non-limiting example of an Fn14 activity is signaling mediated by TWEAK. Thus, in certain embodiments, provided herein is a method of attenuating (e.g., partially attenuating) TWEAK mediated signaling in a cell, comprising exposing the cell to an effective amount of an antibody or antigen binding fragment thereof provided herein.

In some embodiments, the antibody provided herein attenuates TWEAK mediated signaling by at least about 10%. In some embodiments, the antibody provided herein attenuates TWEAK mediated signaling by at least about 20%. In some embodiments, the antibody provided herein attenuates TWEAK mediated signaling by at least about 30%. In some embodiments, the antibody provided herein attenuates TWEAK mediated signaling by at least about 40%. In some embodiments, the antibody provided herein attenuates TWEAK mediated signaling by at least about 50%. In some embodiments, the antibody provided herein attenuates TWEAK mediated signaling by at least about 60%. In some embodiments, the antibody provided herein attenuates TWEAK mediated signaling by at least about 70%. In some embodiments, the antibody provided herein attenuates TWEAK mediated signaling by at least about 80%. In some embodiments, the antibody provided herein attenuates TWEAK mediated signaling by at least about 90%. In some embodiments, the antibody provided herein attenuates TWEAK mediated signaling by at least about 95%. In certain embodiments, the antibody described herein can attenuate (e.g., partially attenuate) TWEAK mediated signaling by at least about 15% to about 65%. In certain embodiments, the antibody described herein can attenuate (e.g., partially attenuate) TWEAK mediated signaling by at least about 20% to about 65%. In certain embodiments, the antibody described herein can attenuate (e.g., partially attenuate) TWEAK mediated signaling by at least about 30% to about 65%.

Yet another non-limiting example of an Fn14 activity is related to levels of cytokines and/or chemokines that are induced by TWEAK (e.g., through binding of TWEAK to Fn14). In some embodiments, the one or more cytokines and/or chemokines are selected from a group consisting of IL-8, CCL2, IL-1β, TGFβ, CCL21, TNFα, IL-6, CXCL1, CCL3, CCL4, CXCL12, CCLS, CXCL10, and CXCL16.

In one embodiment, the Fn14 activity is related to IL-8 secretion. Thus, in certain embodiments, provided herein is a method of inhibiting IL-8 secretion in a cell, comprising exposing the cell to an effective amount of an antibody or antigen binding fragment thereof provided herein.

In one embodiment, an antibody provided herein inhibits IL-8 secretion by at least about 5%. In one embodiment, an antibody provided herein inhibits IL-8 secretion by at least about 10%. In one embodiment, an antibody provided herein inhibits IL-8 secretion by at least about 15%. In one embodiment, an antibody provided herein inhibits IL-8 secretion by at least about 20%. In one embodiment, an antibody provided herein inhibits IL-8 secretion by at least about 25%. In one embodiment, an antibody provided herein inhibits IL-8 secretion by at least about 30%. In one embodiment, an antibody provided herein inhibits IL-8 secretion by at least about 35%. In one embodiment, an antibody provided herein inhibits IL-8 secretion by at least about 40%. In one embodiment, an antibody provided herein inhibits IL-8 secretion by at least about 45%. In one embodiment, an antibody provided herein inhibits IL-8 secretion by at least about 50%. In one embodiment, an antibody provided herein inhibits IL-8 secretion by at least about 55%. In one embodiment, an antibody provided herein inhibits IL-8 secretion by at least about 60%. In one embodiment, an antibody provided herein inhibits IL-8 secretion by at least about 65%. In one embodiment, an antibody provided herein inhibits IL-8 secretion by at least about 70%. In one embodiment, an antibody provided herein inhibits IL-8 secretion by at least about 75%. In one embodiment, an antibody provided herein inhibits IL-8 secretion by at least about 80%. In one embodiment, an antibody provided herein inhibits IL-8 secretion by at least about 85%. In one embodiment, an antibody provided herein inhibits IL-8 secretion by at least about 90%. In one embodiment, an antibody provided herein inhibits IL-8 secretion by at least about 95%. In one embodiment, an antibody provided herein inhibits IL-8 secretion by at least about 96%. In one embodiment, an antibody provided herein inhibits IL-8 secretion by at least about 97%. In one embodiment, an antibody provided herein inhibits IL-8 secretion by at least about 98%. In one embodiment, an antibody provided herein inhibits IL-8 secretion by at least about 99%.

In another embodiment, the Fn14 activity is related to ICAM-1 expression. Thus, in certain embodiments, provided herein is a method of inhibiting ICAM-1 expression in a cell, comprising exposing the cell to an effective amount of an antibody or antigen binding fragment thereof provided herein.

In one embodiment, an antibody provided herein inhibits ICAM-1 expression by at least about 5%. In one embodiment, an antibody provided herein inhibits ICAM-1 expression by at least about 10%. In one embodiment, an antibody provided herein inhibits ICAM-1 expression by at least about 15%. In one embodiment, an antibody provided herein inhibits ICAM-1 expression by at least about 20%. In one embodiment, an antibody provided herein inhibits ICAM-1 expression by at least about 25%. In one embodiment, an antibody provided herein inhibits ICAM-1 expression by at least about 30%. In one embodiment, an antibody provided herein inhibits ICAM-1 expression by at least about 35%. In one embodiment, an antibody provided herein inhibits ICAM-1 expression by at least about 40%. In one embodiment, an antibody provided herein inhibits ICAM-1 expression by at least about 45%. In one embodiment, an antibody provided herein inhibits ICAM-1 expression by at least about 50%. In one embodiment, an antibody provided herein inhibits ICAM-1 expression by at least about 55%. In one embodiment, an antibody provided herein inhibits ICAM-1 expression by at least about 60%. In one embodiment, an antibody provided herein inhibits ICAM-1 expression by at least about 65%. In one embodiment, an antibody provided herein inhibits ICAM-1 expression by at least about 70%. In one embodiment, an antibody provided herein inhibits ICAM-1 expression by at least about 75%. In one embodiment, an antibody provided herein inhibits ICAM-1 expression by at least about 80%. In one embodiment, an antibody provided herein inhibits ICAM-1 expression by at least about 85%. In one embodiment, an antibody provided herein inhibits ICAM-1 expression by at least about 90%. In one embodiment, an antibody provided herein inhibits ICAM-1 expression by at least about 95%. In one embodiment, an antibody provided herein inhibits ICAM-1 expression by at least about 96%. In one embodiment, an antibody provided herein inhibits ICAM-1 expression by at least about 97%. In one embodiment, an antibody provided herein inhibits ICAM-1 expression by at least about 98%. In one embodiment, an antibody provided herein inhibits ICAM-1 expression by at least about 99%.

In another embodiment, the Fn14 activity is related to CCL2 expression. Thus, in certain embodiments, provided herein is a method of inhibiting CCL2 expression in a cell, comprising exposing the cell to an effective amount of an antibody or antigen binding fragment thereof provided herein.

In one embodiment, an antibody provided herein inhibits CCL2 expression by at least about 5%. In one embodiment, an antibody provided herein inhibits CCL2 expression by at least about 10%. In one embodiment, an antibody provided herein inhibits CCL2 expression by at least about 15%. In one embodiment, an antibody provided herein inhibits CCL2 expression by at least about 20%. In one embodiment, an antibody provided herein inhibits CCL2 expression by at least about 25%. In one embodiment, an antibody provided herein inhibits CCL2 expression by at least about 30%. In one embodiment, an antibody provided herein inhibits CCL2 expression by at least about 35%. In one embodiment, an antibody provided herein inhibits CCL2 expression by at least about 40%. In one embodiment, an antibody provided herein inhibits CCL2 expression by at least about 45%. In one embodiment, an antibody provided herein inhibits CCL2 expression by at least about 50%. In one embodiment, an antibody provided herein inhibits CCL2 expression by at least about 55%. In one embodiment, an antibody provided herein inhibits CCL2 expression by at least about 60%. In one embodiment, an antibody provided herein inhibits CCL2 expression by at least about 65%. In one embodiment, an antibody provided herein inhibits CCL2 expression by at least about 70%. In one embodiment, an antibody provided herein inhibits CCL2 expression by at least about 75%. In one embodiment, an antibody provided herein inhibits CCL2 expression by at least about 80%. In one embodiment, an antibody provided herein inhibits CCL2 expression by at least about 85%. In one embodiment, an antibody provided herein inhibits CCL2 expression by at least about 90%. In one embodiment, an antibody provided herein inhibits CCL2 expression by at least about 95%. In one embodiment, an antibody provided herein inhibits CCL2 expression by at least about 96%. In one embodiment, an antibody provided herein inhibits CCL2 expression by at least about 97%. In one embodiment, an antibody provided herein inhibits CCL2 expression by at least about 98%. In one embodiment, an antibody provided herein inhibits CCL2 expression by at least about 99%.

In another aspect, provided herein is a method of treating a disease or disorder in a subject comprising administering to the subject an effective amount of an antibody or antigen binding fragment thereof provided herein. In one embodiment, the disease or disorder is an Fn14-mediated disease or disorder. In one embodiment, the disease or disorder is TWEAK-mediated disease or disorder. In some embodiments, the disease or disorder is selected from a group consisting of autoimmune and/or inflammatory diseases affecting joints, skin, kidney, liver, intestine, heart, lung, or muscle, wherein optionally the disease or disorder is selected from a group consisting of rheumatoid arthritis, bullous pemphigoid, discoid cutaneous lupus, urticarial vasculitis, Henoch-Schonlein Purpura, IgA nephrophathy, atopic dermatitis (atopic eczema), psoriasis (psoriasis vulgaris), seborrheic eczema, asthma, proteinuric kidney disease, liver disease, lupus nephritis, polymyositis, dermatomyositis, calcineurin inhibitor induced nephrotoxicity, myotonic dystrophy, cardiac dysfunction and failure, Alport syndrome, ulcerative colitis, Crohn's disease, cutaneous vasculitis, cachexia, and inflammatory bowel disease, and wherein optionally the disease or disorder is related to fibrosis and optionally selected from a group consisting of tissue fibrosis, idiopathic pulmonary fibrosis, interstitial lung disease, scleroderma (systemic sclerosis), cancer, cancer-associated cachexia, muscle wasting, keloids, inclusion body myositis, and tissue remodeling (see, e.g., van kuijk A.W.R., et al., Ann. Rheum. Dis. 2010, 69: 301; Dharmapatni A. ASSK, et al., Arthritis Res. & Ther. 2011, 13: R51; Liu Y., et al., J. Invest. Dermatol. 2017, 137: 1512; Liu Y., et al., Frontiers in Immunol. 2017, 8: 651; Li M., et al., J. Dermatol. 2013, 40: 891; Chen T., et al., Clin. and Exp. Immunol. 2011, 166: 64; Sasaki Y., et al., BMC Nephrol. 2015, 16: 27; Sidler D., et al., Nature Communications 2017, 8: 15395; Zimmermann M., et al., J. Allergy Clin. Immunol. 2011, 127: 200; Chen Y., et al., PLoS ONE 2011, 6: e22202; Cheng H., et al., Exp. Dermatol. 2016, 25: 32; Bilgic O., et al., Cytokine 2016, 77: 10; Sanchez-Nino M. D., et al., Biochimica et Biophysica Acta 2013, 1832: 2232; Wilhelm A., et al., J. Pathol. 2016, 239: 109; Michaelson J. S., et al., J. Autoimmun. 2012, 39: 130; Peng Q., et al., Arthritis Res. & Ther. 2014, 16: R26; Claus M., et al., Am. J. Transplant. 2018, 18: 1636; Yadava R. S., et al., Human Molecular Genetics 2015, 24: 2035; Jain M., et al., Circulation 2009, 119: 2058; Ortiz A., et al., Eur J. Pharmacol. 2015, 759: 205; Kawashima R., et al., Gastroenterol. 2011, 141: 2119; Kaplan M., et al., Inflamm Bowel Dis. 2016, 22: 615; Kaplan M., et al., Inflamm Bowel Dis. 2016, 22: 615; Chen T., et al., PLoS ONE 2013, 8: e56830; Johnston, A.J., et al., 2015, Cell 162(6):1365-78; Dohi, T., et al., 2009, Gastroenterology 136(3):912-23).

Also provided herein is a method of treatment of a disease or disorder, wherein the subject is administered one or more therapeutic agents in combination with the antibody or antigen-binding fragment thereof provided herein. Methods of administration and dosing is described in more detail in Section 5.7 below.

In another aspect, provided herein is the use of the antibody or antigen binding fragment thereof provided herein in the manufacture of a medicament for treating a disease or disorder in a subject.

In another aspect, provided herein is the use of a pharmaceutical composition provided herein in the manufacture of a medicament for treating a disease or disorder in a subject.

In another aspect, provided herein is the use of an antibody or antigen binding fragment thereof provided herein in the manufacture of a medicament, wherein the medicament is for use in a method for detecting the presence of an Fn14 in a biological sample, the method comprising contacting the biological sample with the antibody under conditions permissive for binding of the antibody to the Fn14 protein, and detecting whether a complex is formed between the antibody and the Fn14 protein.

In other aspects, the antibodies and fragments thereof of the present disclosure are useful for detecting the presence of an Fn14 in a biological sample. The term "detecting" as used herein encompasses quantitative or qualitative detection. In certain embodiments, a biological sample comprises bodily fluid, a cell, or a tissue. Diagnostic assays and methods are described in more detail in Section 5.9 below.

5.7 Methods of Administration and Dosing

In a specific embodiment, provided herein is a composition for use in the prevention and/or treatment of a disease or condition comprising an antibody or antigen binding fragment thereof provided herein. In one embodiment, provided herein is a composition for use in the prevention of a disease or condition, wherein the composition comprises an antibody or antigen binding fragment thereof provided herein. In one embodiment, provided herein is a composition for use in the treatment of a disease or condition, wherein the composition comprises an antibody or antigen binding fragment thereof provided herein. In some embodiments, the disease or condition is an Fn14-mediated disease. In some embodiments, the disease or condition is a TWEAK-mediated disease. In some embodiments, the disease or disorder is selected from a group consisting of autoimmune and/or inflammatory diseases affecting joints, skin, kidney, liver, intestine, heart, lung, or muscle, wherein optionally the disease or disorder is selected from a group consisting of rheumatoid arthritis, bullous pemphigoid, discoid cutaneous lupus, urticarial vasculitis, Henoch-Schonlein Purpura, IgA nephrophathy, atopic dermatitis (atopic eczema), psoriasis (psoriasis vulgaris), seborrheic eczema, asthma, proteinuric kidney disease, liver disease, lupus nephritis, polymyositis, dermatomyositis, calcineurin inhibitor induced nephrotoxicity, myotonic dystrophy, cardiac dysfunction and failure, Alport syndrome, ulcerative colitis, Crohn's disease, cutaneous vasculitis, cachexia, and inflammatory bowel disease, and wherein optionally the disease or disorder is related to fibrosis and optionally selected from a group consisting of tissue fibrosis, idiopathic pulmonary fibrosis, interstitial lung disease, scleroderma (systemic sclerosis), cancer, cancer-associated cachexia, muscle wasting, keloids, inclusion body myositis, and tissue remodeling.

In certain embodiments, the subject is a subject in need thereof. In some embodiments, the subject has the disease or condition. In other embodiments, the subject is at risk of having the disease or condition. In some embodiments, the administration results in the prevention, management, treatment or amelioration of the disease or condition.

In one embodiment, provided herein is a composition for use in the prevention and/or treatment of a symptom of a disease or condition, wherein the composition comprises an antibody or antigen binding fragment thereof provided herein. In one embodiment, provided herein is a composition for use in the prevention of a symptom of a disease or condition, wherein the composition comprises an antibody or antigen binding fragment thereof provided herein. In one embodiment, provided herein is a composition for use in the treatment of a symptom of a disease or condition, wherein the composition comprises an antibody or antigen binding fragment thereof provided herein. In some embodiments, the disease or condition is an Fn14-mediated and/or TWEAK mediated disease. In some embodiments, the disease or disorder is selected from a group consisting of autoimmune and/or inflammatory diseases affecting joints, skin, kidney, liver, intestine, heart, lung, or muscle, wherein optionally the disease or disorder is selected from a group consisting of rheumatoid arthritis, bullous pemphigoid, discoid cutaneous lupus, urticarial vasculitis, Henoch-Schonlein Purpura, IgA nephrophathy, atopic dermatitis (atopic eczema), psoriasis (psoriasis vulgaris), seborrheic eczema, asthma, proteinuric kidney disease, liver disease, lupus nephritis, polymyositis, dermatomyositis, calcineurin inhibitor induced nephrotoxicity, myotonic dystrophy, cardiac dysfunction and failure, Alport syndrome, ulcerative colitis, Crohn's disease, cutaneous vasculitis, cachexia, and inflammatory bowel disease, and wherein optionally the disease or disorder is related to fibrosis and optionally selected from a group consisting of tissue fibrosis, idiopathic pulmonary fibrosis, interstitial lung disease, scleroderma (systemic sclerosis), cancer, cancer-associated cachexia, muscle wasting, keloids, inclusion body myositis, and tissue remodeling.

In certain embodiments, the subject is a subject in need thereof. In some embodiments, the subject has the disease or condition. In other embodiments, the subject is at risk of having the disease or condition. In some embodiments, the administration results in the prevention or treatment of the symptom of the disease or condition.

In another embodiment, provided herein is a method of preventing and/or treating a disease or condition in a subject, comprising administering an effective amount of an antibody or antigen binding fragment thereof provided herein. In one embodiment, provided herein is a method of preventing a disease or condition in a subject, comprising administering an effective amount of an antibody or antigen binding fragment thereof provided herein. In one embodiment, provided herein is a method of treating a disease or condition in a subject, comprising administering an effective amount of an antibody or antigen binding fragment thereof provided herein. In some embodiments, the disease or condition is an Fn14-mediated and/or TWEAK mediated disease. In some embodiments, the disease or disorder is selected from a group consisting of autoimmune and/or inflammatory diseases affecting joints, skin, kidney, liver, intestine, heart, lung, or muscle, wherein optionally the disease or disorder is selected from a group consisting of rheumatoid arthritis, bullous pemphigoid, discoid cutaneous lupus, urticarial vasculitis, Henoch-Schonlein Purpura, IgA nephrophathy, atopic dermatitis (atopic eczema), psoriasis (psoriasis vulgaris), seborrheic eczema, asthma, proteinuric kidney disease, liver disease, lupus nephritis, polymyositis, dermatomyositis, calcineurin inhibitor induced nephrotoxicity, myotonic dystrophy, cardiac dysfunction and failure, Alport syndrome, ulcerative colitis, Crohn's disease, cutaneous vasculitis, cachexia, and inflammatory bowel disease, and wherein optionally the disease or disorder is related to fibrosis and optionally selected from a group consisting of tissue fibrosis, idiopathic pulmonary fibrosis, interstitial lung disease, scleroderma (systemic sclerosis), cancer, cancer-associated cachexia, muscle wasting, keloids, inclusion body myositis, and tissue remodeling.

In certain embodiments, the subject is a subject in need thereof. In some embodiments, the subject has the disease or condition. In other embodiments, the subject is at risk of having the disease or condition. In some embodiments, the administration results in the prevention or treatment of the disease or condition.

In another embodiment, provided herein is a method of preventing and/or treating a symptom of a disease or condition in a subject, comprising administering an effective amount of an antibody or antigen binding fragment thereof provided herein. In one embodiment, provided herein is a method of preventing a symptom of a disease or condition in a subject, comprising administering an effective amount of an antibody or antigen binding fragment thereof provided herein. In one embodiment, provided herein is a method of treating a symptom of a disease or condition in a subject, comprising administering an effective amount of an antibody or antigen binding fragment thereof provided herein. In some embodiments, the disease or condition is an Fn14-mediated and/or TWEAK mediated disease. In some embodiments, the disease or disorder is selected from a group consisting of autoimmune and/or inflammatory diseases affecting joints, skin, kidney, liver, intestine, heart, lung, or muscle, wherein optionally the disease or disorder is selected from a group consisting of rheumatoid arthritis, bullous pemphigoid, discoid cutaneous lupus, urticarial vasculitis, Henoch-Schonlein Purpura, IgA nephrophathy, atopic dermatitis (atopic eczema), psoriasis (psoriasis vulgaris), seborrheic eczema, asthma, proteinuric kidney disease, liver disease, lupus nephritis, polymyositis, dermatomyositis, calcineurin inhibitor induced nephrotoxicity, myotonic dystrophy, cardiac dysfunction and failure, Alport syndrome, ulcerative colitis, Crohn's disease, cutaneous vasculitis, cachexia, and inflammatory bowel disease, and wherein optionally the disease or disorder is related to fibrosis and optionally selected from a group consisting of tissue fibrosis, idiopathic pulmonary fibrosis, interstitial lung disease, scleroderma (systemic sclerosis), cancer, cancer-associated cachexia, muscle wasting, keloids, inclusion body myositis, and tissue remodeling.

In certain embodiments, the subject is a subject in need thereof. In some embodiments, the subject has the disease or condition. In other embodiments, the subject is at risk of having the disease or condition. In some embodiments, the administration results in the prevention or treatment of the symptom of the disease or condition.

Also provided herein are methods of preventing and/or treating a disease or condition by administrating to a subject of an effective amount of an antibody or antigen binding fragment thereof provided herein, or pharmaceutical composition comprising an antibody or antigen binding fragment thereof provided herein. In one aspect, the antibody or antigen binding fragment thereof is substantially purified (i.e., substantially free from substances that limit its effect or produce undesired side-effects). The subject administered a therapy can be a mammal such as non-primate (e.g., cows, pigs, horses, cats, dogs, rats etc.) or a primate (e.g., a monkey, such as a cynomolgus macaque monkey, or a human). In a one embodiment, the subject is a human. In another embodiment, the subject is a human with a disease or condition.

Various delivery systems are known and can be used to administer a prophylactic or therapeutic agent (e.g., an antibody or antigen binding fragment thereof provided herein), including, but not limited to, encapsulation in liposomes, microparticles, microcapsules, recombinant cells capable of expressing the antibody or antigen binding fragment thereof, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., an antibody or antigen binding fragment thereof provided herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody or antigen binding fragment thereof provided herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition provided herein locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. In some embodiments, when administering an antibody or antigen binding fragment thereof provided herein, care must be taken to use materials to which the antibody or antigen binding fragment thereof does not absorb.

In another embodiment, a prophylactic or therapeutic agent, or a composition provided herein can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a prophylactic or therapeutic agent, or a composition provided herein can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibody provided herein) or a composition provided herein (see e.g., Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more antibody or antigen binding fragment thereof provided herein. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition provided herein is a nucleic acid encoding a prophylactic or therapeutic agent (e.g., an antibody or antigen binding fragment thereof provided herein), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition provided herein comprises one, two or more antibodies or antigen binding fragments thereof provided herein. In another embodiment, a composition provided herein comprises one, two or more antibodies or antigen binding fragments thereof provided herein and a prophylactic or therapeutic agent other than an antibody or antigen binding fragment thereof provided herein. In one embodiment, the agents are known to be useful for or have been or are currently used for the prevention, management, treatment and/or amelioration of a disease or condition. In addition to prophylactic or therapeutic agents, the compositions provided herein may also comprise an excipient.

The compositions provided herein include bulk drug compositions useful in the manufacture of pharmaceutical compositions (e.g., compositions that are suitable for administration to a subject or patient) that can be used in the preparation of unit dosage forms. In an embodiment, a composition provided herein is a pharmaceutical composition. Such compositions comprise a prophylactically or therapeutically effective amount of one or more prophylactic or therapeutic agents (e.g., an antibody or antigen binding fragment thereof provided herein or other prophylactic or therapeutic agent), and a pharmaceutically acceptable excipient. The pharmaceutical compositions can be formulated to be suitable for the route of administration to a subject.

In a specific embodiment, the term "excipient" can also refer to a diluent, adjuvant (e.g., Freunds' adjuvant (complete or incomplete) or vehicle. Pharmaceutical excipients can be sterile liquids, such as water and oils, including those of petroleum, animal, vegetable or synthetic origin, such as peanut oil, soybean oil, mineral oil, sesame oil and the like. Water is an exemplary excipient when the pharmaceutical composition is administered intravenously. Saline solutions and aqueous dextrose and glycerol solutions can also be employed as liquid excipients, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in Remington's Pharmaceutical Sciences (1990) Mack Publishing Co., Easton, PA Such compositions will contain a prophylactically or therapeutically effective amount of the antibody or antigen binding fragment thereof provided herein, such as in purified form, together with a suitable amount of excipient so as to provide the form for proper administration to the patient. The formulation should suit the mode of administration.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

An antibody or antigen binding fragment thereof provided herein can be packaged in a hermetically sealed container such as an ampoule or sachette indicating the quantity of antibody. In one embodiment, the antibody or antigen binding fragment thereof is supplied as a dry sterilized lyophilized powder or water free concentrate in a hermetically sealed container and can be reconstituted, e.g., with water or saline to the appropriate concentration for administration to a subject. The lyophilized antibody or antigen binding fragment thereof can be stored at between 2 and 8° C. in its original container and the antibody or antigen binding fragment thereof can be administered within 12 hours, such as within 6 hours, within 5 hours, within 3 hours, or within 1 hour after being reconstituted. In an alternative embodiment, an antibody or antigen binding fragment thereof provided herein is supplied in liquid form in a hermetically sealed container indicating the quantity and concentration of the antibody.

The compositions provided herein can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a prophylactic or therapeutic agent (e.g., an antibody or antigen binding fragment thereof provided herein), or a composition provided herein that will be effective in the prevention and/or treatment of a disease or condition can be determined by standard clinical techniques. In addition, in vitro assays may optionally be employed to help identify optimal dosage ranges. The precise dose to be employed in the formulation will also depend on the route of administration, and the seriousness of a disease or condition, and should be decided according to the judgment of the practitioner and each patient's circumstances.

Effective doses may be extrapolated from dose-response curves derived from in vitro or animal model test systems.

In certain embodiments, the route of administration for a dose of an antibody or antigen binding fragment thereof provided herein to a patient is intranasal, intramuscular, intravenous, subcutaneous, or a combination thereof, but other routes described herein are also acceptable. Each dose may or may not be administered by an identical route of administration. In some embodiments, an antibody or antigen binding fragment thereof provided herein may be administered via multiple routes of administration simultaneously or subsequently to other doses of the same or a different antibody or antigen binding fragment thereof provided herein.

In certain embodiments, the antibody or antigen binding fragment thereof provided herein are administered prophylactically or therapeutically to a subject. The antibody or antigen binding fragment thereof provided herein can be prophylactically or therapeutically administered to a subject so as to prevent, lessen or ameliorate a disease or symptom thereof.

5.8 Gene Therapy

In a specific embodiment, nucleic acids comprising sequences encoding antibodies or functional derivatives thereof, are administered to a subject for use in a method provided herein, for example, to prevent, manage, treat and/or ameliorate an Fn14-mediated disease, disorder or condition, by way of gene therapy. Such therapy encompasses that performed by the administration to a subject of an expressed or expressible nucleic acid. In an embodiment, the nucleic acids produce their encoded antibody, and the antibody mediates a prophylactic or therapeutic effect.

Any of the methods for recombinant gene expression (or gene therapy) available in the art can be used.

For general review of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB IECH 11(5): 155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a specific embodiment, a composition comprises nucleic acids encoding an antibody provided herein, the nucleic acids being part of an expression vector that expresses the antibody or chimeric proteins or heavy or light chains thereof in a suitable host. In particular, such nucleic acids have promoters, such as heterologous promoters, operably linked to the antibody coding region, the promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, 1989, Proc. Natl. Acad. Sci. USA 86:8932-8935; Zijlstra et al., 1989, Nature 342:435-438). In some embodiments, the expressed antibody molecule is a single chain antibody; alternatively, the nucleic acid sequences include sequences encoding both the heavy and light chains, or fragments thereof, of the antibody.

Delivery of the nucleic acids into a subject can be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where the sequences are expressed to produce the encoded product. This can be accomplished by any of numerous methods known in the art, e.g., by constructing them as part of an appropriate nucleic acid expression vector and administering the vector so that the sequences become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or coating with lipids or cell surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO93/14188, WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In a specific embodiment, viral vectors that contains nucleic acid sequences encoding an antibody are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding the antibody to be used in gene therapy can be cloned into one or more vectors, which facilitates delivery of the gene into a subject. More detail about retroviral vectors can be found in Boesen et al., 1994, Biotherapy 6:291-302, which describes the use of a retroviral vector to deliver the MDR1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in the recombinant production of antibodies. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang et al., 1995, Gene Therapy 2:775-783. In a specific embodiment, adenovirus vectors are used.

Adeno-associated virus (AAV) can also be utilized (Walsh et al., 1993, Proc. Soc. Exp. Biol. Med. 204:289-300; and U.S. Pat. No. 5,436,146). In a specific embodiment, AAV vectors are used to express an anti-Fn14 antibody as provided herein. In certain embodiments, the AAV comprises a nucleic acid encoding a VH domain. In other embodiments, the AAV comprises a nucleic acid encoding a VL domain. In certain embodiments, the AAV comprises a nucleic acid encoding a VH domain and a VL domain. In some embodiments of the methods provided herein, a subject is administered an AAV comprising a nucleic acid encoding a VH domain and an AAV comprising a nucleic acid encoding a VL domain. In other embodiments, a subject is administered an AAV comprising a nucleic acid encoding a VH domain and a VL domain. In certain embodiments, the VH and VL domains are over-expressed.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and can be used in accordance with the methods provided herein, provided that the necessary developmental and physiological functions of the recipient cells are not disrupted. The technique should provide for the stable transfer of the nucleic acid to the cell, so that the nucleic acid is expressible by the cell, such as heritable and expressible by its cell progeny.

The resulting recombinant cells can be delivered to a subject by various methods known in the art. Recombinant blood cells (e.g., hematopoietic stem or progenitor cells) can be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a specific embodiment, the cell used for gene therapy is autologous to the subject.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the methods provided herein (see e.g., PCT Publication WO 94/08598; Stemple and Anderson, 1992, Cell 7 1:973-985; Rheinwald, 1980, Meth. Cell Bio. 21A: 229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.9 Diagnostic Assays and Methods

Labeled antibodies and derivatives and analogs thereof, which immunospecifically bind to an Fn14 antigen can be used for diagnostic purposes to detect, diagnose, or monitor an Fn14-mediated disease. Thus, provided herein are methods for the detection of an Fn14-mediated disease comprising: (a) assaying the expression of an Fn14 antigen in cells or a tissue sample of a subject using one or more antibodies provided herein that immunospecifically bind to the Fn14 antigen; and (b) comparing the level of the Fn14 antigen with a control level, e.g., levels in normal tissue samples (e.g., from a patient not having an Fn14-mediated disease, or from the same patient before disease onset), whereby an increase in the assayed level of Fn14 antigen compared to the control level of the Fn14 antigen is indicative of an Fn14-mediated disease.

Also provided herein is a diagnostic assay for diagnosing an Fn14-mediated disease comprising: (a) assaying for the level of an Fn14 antigen in cells or a tissue sample of an individual using one or more antibodies provided herein that immunospecifically bind to an Fn14 antigen; and (b) comparing the level of the Fn14 antigen with a control level, e.g., levels in normal tissue samples, whereby an increase in the assayed Fn14 antigen level compared to the control level of the Fn14 antigen is indicative of an Fn14-mediated disease. In certain embodiments, provided herein is a method of treating an Fn14-mediated disease in a subject, comprising: (a) assaying for the level of an Fn14 antigen in cells or a tissue sample of the subject using one or more antibodies provided herein that immunospecifically bind to an Fn14 antigen; and (b) comparing the level of the Fn14 antigen with a control level, e.g., levels in normal tissue samples, whereby an increase in the assayed Fn14 antigen level compared to the control level of the Fn14 antigen is indicative of an Fn14-mediated disease. In some embodiments, the method further comprises (c) administering an effective amount of an antibody provided herein to the subject identified as having the Fn14-mediated disease. A more definitive diagnosis of an Fn14-mediated disease may allow health professionals to employ preventative measures or aggressive treatment earlier thereby preventing the development or further progression of the Fn14-mediated disease.

Antibodies provided herein can be used to assay Fn14 antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin.

One aspect provided herein is the detection and diagnosis of an Fn14-mediated disease in a human. In one embodiment, diagnosis comprises: a) administering (for example, parenterally, subcutaneously, or intraperitoneally) to a subject an effective amount of a labeled antibody that immunospecifically binds to an Fn14 antigen; b) waiting for a time interval following the administering for permitting the labeled antibody to concentrate at sites in the subject where the Fn14 antigen is expressed (and for unbound labeled molecule to be cleared to background level); c) determining background level; and d) detecting the labeled antibody in the subject, such that detection of labeled antibody above the background level indicates that the subject has an Fn14-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99Tc. The labeled antibody will then accumulate at the location of cells which contain the specific protein. In vivo tumor imaging is described in S.W. Burchiel et al., "Immunopharmacokinetics of Radiolabeled Antibodies and Their Fragments." (Chapter 13 in Tumor Imaging: The Radiochemical Detection of Cancer, S.W. Burchiel and B.A. Rhodes, eds., Masson Publishing Inc. (1982).

Depending on several variables, including the type of label used and the mode of administration, the time interval following the administration for permitting the labeled antibody to concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of an Fn14-mediated disease is carried out by repeating the method for diagnosing the an Fn14-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods provided herein include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U .S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.10 Kits

Also provided herein are kits comprising an antibody (e.g., an anti-Fn14 antibody) provided herein, or a composition (e.g., a pharmaceutical composition) thereof, packaged into suitable packaging material. A kit optionally includes a label or packaging insert including a description of the components or instructions for use in vitro, in vivo, or ex vivo, of the components therein.

The term "packaging material" refers to a physical structure housing the components of the kit. The packaging material can maintain the components sterilely, and can be made of material commonly used for such purposes (e.g., paper, corrugated fiber, glass, plastic, foil, ampoules, vials, tubes, etc.).

Kits provided herein can include labels or inserts. Labels or inserts include "printed matter," e.g., paper or cardboard, separate or affixed to a component, a kit or packing material (e.g., a box), or attached to, for example, an ampoule, tube, or vial containing a kit component. Labels or inserts can additionally include a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media, or memory type cards. Labels or inserts can include information identifying manufacturer information, lot numbers, manufacturer location, and date.

Kits provided herein can additionally include other components. Each component of the kit can be enclosed within an individual container, and all of the various containers can be within a single package. Kits can also be designed for cold storage. A kit can further be designed to contain antibodies provided herein, or cells that contain nucleic acids encoding the antibodies provided herein. The cells in the kit can be maintained under appropriate storage conditions until ready to use.

Also provided herein are panels of antibodies that immunospecifically bind to an Fn14 antigen. In specific embodiments, provided herein are panels of antibodies having different association rate constants different dissociation rate constants, different affinities for Fn14 antigen, and/or different specificities for an Fn14 antigen. In certain embodiments, provided herein are panels of about 10, preferably about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1,000, 1,000-2,500, 2,500-5,000, 5,000-25,000, 25,000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

6. EXAMPLES

The following is a description of various methods and materials used in the studies, and are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present invention. Efforts have been made to ensure accuracy with respect to numbers used (e.g., amounts, percentages, etc.), but some experimental errors and deviations should be accounted for.

Example 1

Generation of Mouse Anti-Human Fn14 Antagonist, Non-Agonist Antibodies with Cross-Reactivity to Mouse, Rat, and Cynomolgus Macaque Fn14

This example illustrates the method for generating exemplary mouse anti-human Fn14 antagonist antibodies provided herein. It is to be understood that the exemplary Fn14 antibodies described in this example are not intended to represent the full scope of the present invention.

Antigen Preparation

Mammalian expression vectors for producing recombinant full-length human, mouse and cynomolgus macaque (i.e., Macaca fascicularis) Fn14 proteins were prepared. Specifically, DNA sequences encoding human, mouse and cynomolgus macaque Fn14 were synthesized by DNA Craft artificial gene synthesis at Fasmac (Kanagawa, Japan), and are shown in polynucleotide sequences SEQ ID NOs: 1, 5 and 9, respectively. The DNA encoding human Fn14 has a polynucleotide sequence of SEQ ID NO: 1, and the encoded human Fn14 has an amino acid sequence of SEQ ID NO: 2 (accession no. NP 057723). The DNA encoding mouse Fn14 has a polynucleotide sequence of SEQ ID NO: 5, and the encoded mouse Fn14 has an amino acid sequence of SEQ ID NO: 6 (accession no. NP 038777.2). The DNA encoding rat Fn14 has a polynucleotide sequence of SEQ ID NO: 7, and the encoded rat Fn14 has an amino acid sequence of SEQ ID NO: 8 (accession no. NP 851600). The DNA encoding cynomolgus macaque Fn14 has a polynucleotide sequence of SEQ ID NO: 9, and the encoded cynomolgus macaque Fn14 has an amino acid sequence of SEQ ID NO: 10 (accession no. XP 005591081.1). Nucleotide and amino acid sequences of Fn14 protein from various sources are listed in Table 13 below.

TABLE 13

Nucleotide and amino acid sequences of Fn14 proteins

| Description | Sequence (SEQ ID NO) |
|---|---|
| Human Fn14 (full length) nucleotide sequence | ATGGCTCGGGGCTCGCTGCGCCGGTTGCTGCGGCTCCTCGTG CTGGGGCTCTGGCTGGCGTTGCTGCGCTCCGTGGCCGGGGAG CAAGCGCCAGGCACCGCCCCCTGCTCCCGCGGCAGCTCCTGG AGCGCGGACCTGGACAAGTGCATGGACTGCGCGTCTTGCAG GGCGCGACCGCACAGCGACTTCTGCCTGGGCTGCGCTGCAG CACCTCCTGCCCCCTTCCGGCTGCTTTGGCCCATCCTTGGGG GCGCTCTGAGCCTGACCTTCGTGCTGGGGCTGCTTTCTGGCT TTTTGGTCTGGAGACGATGCCGCAGGAGAGAGAAGTTCACC ACCCCCATAGAGGAGACCGGCGGAGAGGGCTGCCCAGCTGT GGCGCTGATCCAG (SEQ ID NO: 1) |
| Human Fn14 (full length) amino acid sequence | MARGSLRRLLRLLVLGLWLALLRSVAGEQAPGTAPCSRGSSWS ADLDKCMDCASCRARPHSDFCLGCAAAPPAPFRLLWPILGGAL SLTFVLGLLSGFLVWRRCRRREKFTTPIEETGGEGCPAVALIQ (SEQ ID NO: 2) |
| human Fn14 mature, extracellular domain (aa28-75) (nucleotide sequence) | GAGCAAGCGCCAGGCACCGCCCCCTGCTCCCGCGGCAGCTC CTGGAGCGCGGACCTGGACAAGTGCATGGACTGCGCGTCTT GCAGGGCGCGACCGCACAGCGACTTCTGCCTGGGCTGCGCT GCAGCACCTCCTGCCCCCTTC (SEQ ID NO: 3) |
| human Fn14 mature, extracellular domain (aa28-75) (amino acid sequence) | EQAPGTAPCSRGSSWSADLDKCMDCASCRARPHSDFCLGCAA APPAPF (SEQ ID NO: 4) |
| mouse Fn14 (full length) nucleotide sequence | ATGGCTTCGGCTTGGCCGCGGTCTCTGCCGCAGATCCTCGTG TTGGGATTCGGCTTGGTGTTGATGCGCGCCGCGGCCGGGGAG CAAGCACCAGGCACCTCCCCATGCTCTAGCGGCAGCTCCTGG AGCGCGGACCTCGACAAGTGCATGGACTGCGCCTTCTTGTCCA GCGCGACCACACAGCGACTTCTGCCTGGGATGCGCCGCAGC ACCTCCTGCCCACTTCAGGCTACTGTGGCCCATTCTGGGGGG CGCTCTTAGTCTGGTCCTGGTTTTGGCGCTGGTTTCTAGTTTC CTGGTCTGGAGAAGATGCCGCCGGAGAGAAAAGTTTACTAC CCCCATAGAGGAGACTGGTGGAGAGGGCTGCCCAGGTGTGG CACTGATCCAG (SEQ ID NO: 5) |
| mouse Fn14 (full length) amino acid sequence | MASAWPRSLPQILVLGFGLVLMRAAAGEQAPGTSPCSSGSSWS ADLDKCMDCASCPARPHSDFCLGCAAAPPAHFRLLWPILGGAL SLVLVLALVSSFLVWRRCRRREKFTTPIEETGGEGCPGVALIQ (SEQ ID NO: 6) |
| rat Fn14 (full length) nucleotide sequence | ATGGCTCCGGGTTGGCCGCGGCCTCTGCCGCAGCTCCTCGTG TTGGGATTCGGGTTGGTGTTGATACGCGCCACGGCCGGGGA GCAAGCACCAGGCAACGCCCCATGCTCAAGCGGCAGCTCCT GGAGCGCGGACCTCGACAAGTGCATGGACTGCGCTTCTTGTC CAGCGCGACCACACAGCGACTTCTGCCTGGGATGCGCAGCA GCACCTCCTGCCCACTTCAGGATGCTATGGCCCATTCTGGGA GGCGCTCTTAGTCTGGCCCTGGTTTTGGCGCTGGTTTCTGGTT TCCTGGTCTGGAGACGATGCCGCCGGAGAGAAAAGTTTACT ACCCCCATAGAGGAGACTGGTGGAGAAGGCTGCCCAGGTGT GGCACTGATCCAG (SEQ ID NO: 7) |
| rat Fn14 (full length) amino acid sequence | MAPGWPRPLPQLLVLGFGLVLIRATAGEQAPGNAPCSSGSSWS ADLDKCMDCASCPARPHSDFCLGCAAAPPAHFRMLWPILGGA LSLALVLALVSGFLVWRRCRRREKFTTPIEETGGEGCPGVALIQ (SEQ ID NO: 8) |
| cynomolgus macaque (Macaca fascicularis) Fn14 (full length) nucleotide sequence | ATGGCTCGGGGTTCGCTGCGCCGGTTGCTGCGGCTCCTCGTG CTGGGGCTCTGGCTGGCGTTGCTGCGCTCCGTGGCTGGGGAG CAAGCGCCAGGCACCGCCCCCTGCTCCCACGGCAGTTCCTGG AGCGCGGACCTGGACAAGTGCATGGACTGCGCGTCTTGCAG GGCGCGACCGCACAGCGACTTCTGCCTGGGCTGCTCTGCGGC ACCTCCTGCCCCCTTCCGGCTGCTTTGGCCCATCCTTGGGGG CGCTCTGAGTCTGACCTTCGTGCTGGGGCTGCTTTCTGGCTTT CTGGTCTGGAGACGATGCCGCAGGAGAGAGAAGTTCACCAC CCCCATAGAGGAGACCGGCGGAGAGGGCTGCCCAGCTGTGG CGCTGATCCAGTGA (SEQ ID NO: 9) |
| cynomolgus macaque (Macaca fascicularis) Fn14 (full length) amino acid sequence | MARGSLRRLLRLLVLGLWLALLRSVAGEQAPGTAPCSHGSSWS ADLDKCMDCASCRARPHSDFCLGCSAAPPAPFRLLWPILGGAL SLTFVLGLLSGFLVWRRCRRREKFTTPIEETGGEGCPAVALIQ (SEQ ID NO: 10) |

Following gene synthesis, DNA coding for the full length Fn14 for each respective species was amplified from synthesized DNA by PCR using primers adding appropriate 5' and 3' flanking DNA for insertion into mammalian expression vectors pCI or pSI (Promega, Madison, Wisconsin). After joining insert and vector by ligase-independent cloning (Seamless Cloning and Assembly Enzyme Mix, cat# A14606, Invitrogen/GeneArt, Carlsbad, California), the resulting plasmids were validated by Sanger sequencing.

To generate antigens for antibody binding assays, pC1 or pS1 expression vectors for human, cynomolgus macaque or mouse Fn14 (described above) were transiently transfected into 293F cells using the FreeStyle 293 Expression System (cat# K900001, Life Technologies/Invitrogen, Carlsbad, California). Cells were used in flow cytometry experiments two days after transfection.

The nucleotide and amino acid sequences of human Fn14 used for immunization are SEQ ID NO: 1 and SEQ ID NO: 2, respectively (see Table 13). To generate an antigen for immunization, a CHO-K1 cell pool stably expressing surface human Fn14 was generated by electroporation of plasmid pKTABEX-TC26-hFn14 (Kyowa Hakko Kirin, described in WO2013005649) into CHO-K1 cells (European Collection of Authenticated Cell Cultures (ECACC), cat# 85051005, Port Down, United Kingdom) using a Cell Line Nucleofector™ Kit V (Catalog # VCA-1003, Lonza, Basil, Switzerland) according to the manufacturer's instructions, followed by selection of cells containing plasmid-expressed antibiotic resistance. After several weeks of antibiotic selection, surviving cells were confirmed to express surface human Fn14 by antibody binding in flow cytometry.

Cloning His-SUMO-Fn14

A mammalian expression vector was generated for mammalian expression of a soluble protein consisting of amino acids 28-75 of the extracellular domain of human Fn14 protein, shown in SEQ ID NO: 4, fused at the amino-terminus to a tandem 6× histidine and mutant SUMO tag (His-SUMO) to produce a soluble His-SUMO-huFn14 protein. The mature protein nucleotide and amino acid sequences are SEQ ID NO: 11 and SEQ ID NO: 12, respectively, as shown below.

```
His-SUMO-hFn14 nucleotide sequence:
                                        (SEQ ID NO: 11)
CATCATCACCACCATCACGGGTCCCTGCAGGACTCAGAAGTCAATCAAGA

AGCTAAGCCAGAGGTCAAGCCAGAAGTCAAGCCTGAGACTCACATCAATT

TAAAGGTGTCCGATGGATCTTCAGAGATCTTCTTCAAGATCAAAAAGACC

ACTCCTTTAAGAAGGCTGATGGAAGCGTTCGCTAAAAGACAGGGTAAGGA

AATGGACTCCTTAACGTTCTTGTACGACGGTATTGAAATTCAAGCTGATC

AGACCCCTGAAGATTTGGACATGGAGGATAACGATATTATTGAGGCTCAC

CGCGAACAGATTGGAGGTGAGCAAGCGCCAGGCACCGCCCCCTGCTCCCG

CGGCAGCTCCTGGAGCGCGGACCTGGACAAGTGCATGGACTGCGCGTCTT

GCAGGGCGCGACCGCACAGCGACTTCTGCCTGGGCTGCGCTGCAGCACCT

CCTGCCCCCTTCTAA.
```

```
His-SUMO-hFn14 amino acid sequence:
                                        (SEQ ID NO: 12)
HHHHHHGSLQDSEVNQEAKPEVKPEVKPETHINLKVSDGSSEIFFKIKKT

TPLRRLMEAFAKRQGKEMDSLTFLYDGIEIQADQTPEDLDMEDNDITEAH

REQIGGEQAPGTAPCSRGSSWSADLDKCMDCASCRARPHSDFCLGCAAAP

PAPF.
```

When attached at the amino-terminus of a protein, the SUMO tag can be removed completely by SUMO protease, leaving no tag-derived amino acids on the amino-terminus of the SUMO-processed protein of interest. This SUMO tag mutant (Lucigen, Middleton, Wisconsin) has been engineered by amino acid substitution such that it is resistant to desumoylation by natural eukaryotic SUMO protease, but can be cleaved by an engineered mutant SUMO protease, called SUMO Expresso Protease (cat# 30801-2, Lucigen, Middleton, Wisconsin).

Expression vector cloning was performed using methods known to those skilled in the art. Briefly, using overlapping PCR, cDNA coding for the amino-terminal His-SUMO tag (nucleotide SEQ ID NO: 21, amino acid SEQ ID NO: 22) was fused in frame with cDNA coding for the extracellular domain of human Fn14 (amino acids 28-75) (nucleotide SEQ ID NO: 3, amino acid SEQ ID NO: 4), while at the same time adding a eukaryotic signal peptide sequence directly 5' of the 6× His tag. In one PCR reaction, DNA coding for His-SUMO tag was amplified from the Lucigen prokaryotic expression vector component found in the Expresso T7 SUMO Cloning and Expression System kit (cat# 49003, Lucigen, Middleton, Wisconsin) using DNA primers that added 5' DNA coding for a mammalian IgG signal peptide and 3' DNA sequence homologous to in frame DNA coding for the amino-terminus of mature human Fn14 (all PCR reactions were performed using KOD Hot Start DNA Polymerase, cat# 71086, Millipore Sigma, Burlington, Massachusetts). Simultaneously, a second PCR reaction amplified DNA coding for the extracellular domain of mature human Fn14 (amino acids 28-75) using a forward primer with no additional nucleotides and a reverse primer that added a 3' stop codon after the codon for Fn14 amino acid 75. The DNA products of these two PCR reactions were purified by agarose gel electrophoresis and gel extraction (QIAquick Gel Extraction Kit, cat# 28704, QIAGEN, Hilden, Germany), then combined as template in a subsequent PCR reaction in which the overlapping two DNA templates annealed to each other and were elongated into a single cDNA strand with 5' and 3' flanking primers which added 5' and 3' overhangs for ligase-independent cloning into pcDNA3.4 (Invitrogen, cat# A14697, Carlsbad, California) digested with NheI and EcoRI (NEB, Ipswich, Massachusetts) using ligase-independent cloning, as per the manufacturer's product manual (Seamless Cloning and Assembly Enzyme Mix, cat# A14606, Life Technologies/Invitrogen/GeneArt, Carlsbad, California). The resulting plasmid was verified by Sanger sequencing.

The polynucleotide and amino acid sequences of the His-SUMO protein tag are as follows:

```
His-SUMO nucleotide sequence:
                                        (SEQ ID NO: 21)
CATCATCACCACCATCACGGGTCCCTGCAGGACTCAGAAGTCAATCAAGA

AGCTAAGCCAGAGGTCAAGCCAGAAGTCAAGCCTGAGACTCACATCAATT
```

```
-continued
TAAAGGTGTCCGATGGATCTTCAGAGATCTTCTTCAAGATCAAAAAGACC

ACTCCTTTAAGAAGGCTGATGGAAGCGTTCGCTAAAAGACAGGGTAAGGA

AATGGACTCCTTAACGTTCTTGTACGACGGTATTGAAATTCAAGCTGATC

AGACCCCTGAAGATTTGGACATGGAGGATAACGATATTATTGAGGCTCAC

CGCGAACAGATTGGAGGT.

His-His-SUMO amino acid sequence:
                                    (SEQ ID NO: 22)
HHHHHHGSLQDSEVNQEAKPEVKPEVKPETHINLKVSDGSSEIFFKIKKT

TPLRRLMEAFAKRQGKEMDSLTFLYDGIEIQADQTPEDLDMEDNDIMAHR

EQIGG.
```

Cloning Soluble Human, Mouse and Cynomolgus Macaque Fn14-GST

Mammalian expression vectors were generated for production of the extracellular domain of either human, mouse or cynomolgus monkey (Macaca fascicularis) Fn14 (aa 28-75) fused to the amino-terminus of glutathione S-transferase (GST) via a linker peptide (linker amino acid sequence is GTLEVLFQGP, and the GST nucleotide and amino acid sequences are shown in SEQ ID NO: 19 and SEQ ID NO: 20, respectively). Vectors were constructed by first ligating DNA coding for GST into mammalian expression vector, INPEP4 (Biogen/IDEC), digested with ApaI and BamHI. The GST-coding DNA was PCR amplified from sequence synthesized by Fasmac (Kanagawa, Japan) with primers adding 5' and 3' DNA suitable for ligation into the vector. The completed vector, INPEP4-GST, was confirmed by Sanger sequencing. Subsequently, DNA coding for Fn14 amino acids 1-75 (including the endogenous signal peptide, amino acid sequence 1-27) was amplified by PCR using primers adding flanking 5' and 3' DNA suitable for ligation into BglII and KpnI sites of digested INPEP4-GST vector described above. After ligation, a single Fn14-GST vector clone for each Fn14 species listed above was confirmed by Sanger sequencing. Subsequently, these Fn14-GST DNA sequences were also subcloned into mammalian expression vector pTC27 (Kyowa Hakko Kirin) by cut-and-paste digestion and ligation using the flanking BglII and BamHI restriction sites. These vectors were also confirmed by Sanger sequencing. Complete nucleotide sequences for human-, mouse- and cynomolgus macaque-Fn14-GST are shown in SEQ ID NOs: 13, 17 and 15, respectively, and the respective amino acid translations are shown in SEQ ID NOs: 14, 18 and 16 (see Table 14).

TABLE 14

Nucleotide and amino acid sequences of Fn14-GST

| Description | Sequence (SEQ ID NO) |
| --- | --- |
| human Fn14-GST nucleotide sequence | ATGGCTCGGGGCTCGCTGCGCCGGTTGCTGCGGCTCCTCGTGCTGGGGCTC TGGCTGGCGTTGCTGCGCTCCGTGGCCGGGGAGCAAGCGCCAGGCACCGCC CCCTGCTCCCGCGGCAGCTCCTGGAGCGCGGACCTGGACAAGTGCATGGAC TGCGCGTCTTGCAGGGCGCGACCGCACAGCGACTTCTGCCTGGGCTGCGCT GCAGCACCTCCTGCCCCCTTCGGTACCCTGGAAGTTCTGTTCCAGGGGCCC ATGTCCCCTATACTAGGTTATTGGAAAATTAAGGGCCTTGTGCAACCCACT CGACTTCTTTTGGAATATCTTGAAGAAAAATATGAAGAGCATTTGTATGAG CGCGATGAAGGTGATAAATGGCGAAACAAAAAGTTTGAATTGGGTTTGGAG TTTCCCAATCTTCCTTATTATATTGATGGTGATGTTAAATTAACACAGTCT ATGGCCATCATACGTTATATAGCTGACAAGCACAACATGTTGGGTGGTTGT CCAAAAGAGCGTGCAGAGATTTCAATGCTTGAAGGAGCGGTTTTGGATATT AGATACGGTGTTTCGAGAATTGCATATAGTAAAGACTTTGAAACTCTCAAA GTTGATTTTCTTAGCAAGCTACCTGAAATGCTGAAAATGTTCGAAGATCGT TTATGTCATAAAACATATTTAAATGGTGATCATGTAACCCATCCTGACTTC ATGTTGTATGACGCTCTTGATGTTGTTTTATACATGGACCCAATGTGCCTG GATGCGTTCCCAAAATTAGTTTGTTTTAAAAAACGTATTGAAGCTATCCCA CAAATTGATAAGTACTTGAAATCCAGCAAGTATATAGCATGGCCTTTGCAG GGCTGGCAAGCCACGTTTGGTGGTGGCGACCATCCTCCAAAATCGGATTGA (SEQ ID NO: 13) |
| human Fn14-GST amino acid sequence | MARGSLRRLLRLLVLGLWLALLRSVAGEQAPGTAPCSRGSSWSADLDKCMD CASCRARPHSDFCLGCAAAPPAPFGTLEVLFQGPMSPILGYVVKIKGLVQP TRLLLEYLEEKYEEHLYERDEGDKWRNKKFELGLEFPNLPYYIDGDVKLTQ SMAIIRYIADKHNMLGGCPKERAEISMLEGAVLDIRYGVSRIAYSKDFETL KVDFLSKLPEMLKMFEDRLCHKTYLNGDHVTEIPDFMLYDALDVVLYMDPM CLDAFPKLVCFKKRIEAIPQIDKYLKSSKYIAWPLQGWQATFGGGDEIPPK SD (SEQ ID NO: 14) |
| cyno Fn14-GST (Macaca fascicularis) nucleotide sequence | ATGGCTCGGGGCTCGCTGCGCCGGTTGCTGCGGCTCCTCGTGCTGGGGCTC TGGCTGGCGTTGCTGCGCTCCGTGGCCGGGGAGCAAGCGCCAGGCACCGCC CCCTGCTCCCACGGCAGCTCCTGGAGCGCGGACCTGGACAAGTGCATGGAC TGCGCGTCTTGCAGGGCGCGACCGCACAGCGACTTCTGCCTGGGCTGCTCC GCAGCACCTCCTGCCCCCTTCGGTACCCTGGAAGTTCTGTTCCAGGGGCCC ATGTCCCCTATACTAGGTTATTGGAAAATTAAGGGCCTTGTGCAACCCACT CGACTTCTTTTGGAATATCTTGAAGAAAAATATGAAGAGCATTTGTATGAG CGCGATGAAGGTGATAAATGGCGAAACAAAAAGTTTGAATTGGGTTTGGAG TTTCCCAATCTTCCTTATTATATTGATGGTGATGTTAAATTAACACAGTCT ATGGCCATCATACGTTATATAGCTGACAAGCACAACATGTTGGGTGGTTGT CCAAAAGAGCGTGCAGAGATTTCAATGCTTGAAGGAGCGGTTTTGGATATT AGATACGGTGTTTCGAGAATTGCATATAGTAAAGACTTTGAAACTCTCAAA GTTGATTTTCTTAGCAAGCTACCTGAAATGCTGAAAATGTTCGAAGATCGT TTATGTCATAAAACATATTTAAATGGTGATCATGTAACCCATCCTGACTTC ATGTTGTATGACGCTCTTGATGTTGTTTTATACATGGACCCAATGTGCCTG GATGCGTTCCCAAAATTAGTTTGTTTTAAAAAACGTATTGAAGCTATCCCA |

TABLE 14-continued

Nucleotide and amino acid sequences of Fn14-GST

| Description | Sequence (SEQ ID NO) |
|---|---|
| | CAAATTGATAAGTACTTGAAATCCAGCAAGTATATAGCATGGCCTTTGCAG<br>GGCTGGCAAGCCACGTTTGGTGGTGGCGACCATCCTCCAAAATCGGAT<br>(SEQ ID NO: 15) |
| cyno Fn14-GST<br>(*Macaca fascicularis*)<br>amino acid sequence | MARGSLRRLLRLLVLGLWLALLRSVAGEQAPGTAPCSHGSSWSADLDKCMD<br>CASCRARPHSDFCLGCSAAPPAPFGTLEVLFQGPMSPILGYVVKIKGLVQP<br>TRLLLEYLEEKYEEHLYERDEGDKWRNKKFELGLEFPNLPYYIDGDVKLTQ<br>SMAIIRYIADKHNMLGGCPKERAEISMLEGAVLDIRYGVSRIAYSKDFETL<br>KVDFLSKLPEMLKMFEDRLCHKTYLNGDHVTEIPDFMLYDALDVVLYMDPM<br>CLDAFPKLVCFKKRIEAIPQIDKYLKSSKYIAWPLQGWQATFGGGDEIPPK<br>SD<br>(SEQ ID NO: 16) |
| mouse Fn14-GST<br>nucleotide sequence | ATGGCTTCGGCTTGGCCGCGGTCTCTGCCGCAGATCCTCGTGTTGGGATTC<br>GGCTTGGTGTTGATGCGCGCCGCGGCCGGGGAGCAAGCACCAGGCACCTCC<br>CCATGCTCTAGCGGCAGCTCCTGGAGCGCGGACCTCGACAAGTGCATGGAC<br>TGCGCTTCTTGTCCAGCGCGACCACACAGCGACTTCTGCCTGGGATGCGCC<br>GCAGCACCTCCTGCCCACTTCGGTACCCTGGAAGTTCTGTTCCAGGGGCCC<br>ATGTCCCTATACTAGGTTATTGGAAAATTAAGGGCCTTGTGCAACCCACT<br>CGACTTCTTTTGGAATATCTTGAAGAAAATATGAAGAGCATTTGTATGAG<br>CGCGATGAAGGTGATAAATGGCGAAACAAAAAGTTTGAATTGGGTTTGGAG<br>TTTCCCAATCTTCCTTATTATATTGATGGTGATGTTAAATTAACACAGTCT<br>ATGGCCATCATACGTTATATAGCTGACAAGCACAACATGTTGGGTGGTTGT<br>CCAAAAGAGCGTGCAGAGATTTCAATGCTTGAAGGAGCGGTTTTGGATATT<br>AGATACGGTGTTTCGAGAATTGCATATAGTAAAGACTTTGAAACTCTCAAA<br>GTTGATTTTCTTAGCAAGCTACCTGAAATGCTGAAAATGTTCGAAGATCGT<br>TTATGTCATAAAACATATTTAAATGGTGATCATGTAACCCATCCTGACTTC<br>ATGTTGTATGACGCTCTTGATGTTGTTTTATACATGGACCCAATGTGCCTG<br>GATGCGTTCCCAAAATTAGTTTGTTTTAAAAAACGTATTGAAGCTATCCCA<br>CAAATTGATAAGTACTTGAAATCCAGCAAGTATATAGCATGGCCTTTGCAG<br>GGCTGGCAAGCCACGTTTGGTGGTGGCGACCATCCTCCAAAATCGGATTGA<br>(SEQ ID NO: 17) |
| mouse Fn14-GST<br>amino acid sequence | MASAWPRSLPQILVLGFGLVLMRAAAGEQAPGTSPCSSGSSWSADLDKCMD<br>CASCPARPHSDFCLGCAAAPPAHFGTLEVLFQGPMSPILGYWKIKGLVQPT<br>RLLLEYLEEKYEEHLYERDEGDKWRNKKFELGLEFPNLPYYIDGDVKLTQS<br>MAIIRYIADKHNMLGGCPKERAEISMLEGAVLDIRYGVSRIAYSKDFETLK<br>VDFLSKLPEMLKMFEDRLCHKTYLNGDHVTHPDFMLYDALDVVLYMDPMCL<br>DAFPKLVCFKKRIEAIPQIDKYLKSSKYIAWPLQGWQATFGGGDEIPPKSD<br>(SEQ ID NO: 18) |
| GST nucleotide<br>sequence | ATGTCCCCTATACTAGGTTATTGGAAAATTAAGGGCCTTGTGCAACCCACT<br>CGACTTCTTTTGGAATATCTTGAAGAAAATATGAAGAGCATTTGTATGAG<br>CGCGATGAAGGTGATAAATGGCGAAACAAAAAGTTTGAATTGGGTTTGGAG<br>TTTCCCAATCTTCCTTATTATATTGATGGTGATGTTAAATTAACACAGTCT<br>ATGGCCATCATACGTTATATAGCTGACAAGCACAACATGTTGGGTGGTTGT<br>CCAAAAGAGCGTGCAGAGATTTCAATGCTTGAAGGAGCGGTTTTGGATATT<br>AGATACGGTGTTTCGAGAATTGCATATAGTAAAGACTTTGAAACTCTCAAA<br>GTTGATTTTCTTAGCAAGCTACCTGAAATGCTGAAAATGTTCGAAGATCGT<br>TTATGTCATAAAACATATTTAAATGGTGATCATGTAACCCATCCTGACTTC<br>ATGTTGTATGACGCTCTTGATGTTGTTTTATACATGGACCCAATGTGCCTG<br>GATGCGTTCCCAAAATTAGTTTGTTTTAAAAAACGTATTGAAGCTATCCCA<br>CAAATTGATAAGTACTTGAAATCCAGCAAGTATATAGCATGGCCTTTGCAG<br>GGCTGGCAAGCCACGTTTGGTGGTGGCGACCATCCTCCAAAATCGGAT<br>(SEQ ID NO: 19) |
| GST amino acid<br>sequence | MSPILGYWKIKGLVQPTRLLLEYLEEKYEEHLYERDEGDKWRNKKFELGLE<br>FPNLPYYIDGDVKLTQSMAIIRYIADKHNMLGGCPKERAEISMLEGAVLDI<br>RYGVSRIAYSKDFETLKVDFLSKLPEMLKMFEDRLCHKTYLNGDHVTHPDF<br>MLYDALDVVLYMDPMCLDAFPKLVCFKKRIEAIPQIDKYLKSSKYIAWPLQ<br>GWQATFGGGDEIPPKSD<br>(SEQ ID NO: 20) |

Immunization

BALB/c mice and Fn14 knockout (KO) mice were used for immunization. BALB/c mice were purchased from Charles River Laboratories Japan Inc. Fn14 KO mice were prepared using the method described in the examples of WO2014007198. hFn14/CHO-K1 cells stably expressing hFn14 expression vector were used as immunogens. hFn14/CHO-K1 cells were collected and resuspended in 200 μL of Sigma Adjuvant System (cat# S6322, MillporeSigma, Burlington, Massachusetts) or saline, then administered intraperitoneally ($2.5 \times 10^6$ cells per animal). Plasmid hFn14 expression vector DNA was prepared with In vivo jetPEI kit (cat# 201-10G, PolyPlus-transfection, Strasbourg, France). DNA:jetPEI was mixed at a ratio of 10:1. 50 μg DNA was administered intraperitoneally or intravenously per animal.

Balb/c or Fn14 knockout (KO) mice were immunized intraperitoneally (i.p.) with human Fn14 (hFn14) transfected CHO-K1 cells in Sigma adjuvant system as described. Five days after the first immunization, mice received a boost injection of Fn14 transfected cells followed ten days later by a final boost consisting of 50 μg Fn14 DNA/5 μL jet-PEI. All injections were administered intraperitoneally. Three days after the final boost, mice were sacrificed and spleens were removed and processed for hybridoma generation.

Hybridoma Generation

Hybridomas were generated from spleen cells isolated from Balb/c or Fn14 knockout (KO) mice immunized with human Fn14 (hFn14) transfected CHO-K1 cells in Sigma adjuvant system as described. Following removal of spleens from immunized mice, spleens were cut into pieces and gently homogenized into a single cell suspension in PBS.

To generate hybridomas, spleen cells from the single cell suspension were fused with mouse myeloma cells Sp2/0 (American Type Culture Collection (ATCC): CRL1581). Spleen cell suspensions were pelleted by centrifugation (1500 rpm, 3 min) and Red Blood Cell Lysing Buffer (Sigma) was added to the cell pellet on ice. Next, the cells were washed twice with DMEM (Gibco) and subjected to cell fusion.

Mouse myeloma cells Sp2/0 that were cultured in DMEM with 10% FBS were used for cell fusion. Sp2/0 and mouse spleen cells were mixed at a ratio of 5:1 (Sp2/0:spleen cells), followed by centrifugation (1500 rpm, 3 min). 1 mL of polyethylene glycol –1500 (Roche Diagnostics) was slowly added to the cell pellet with gentle rocking, followed by 5 mL DMEM with gentle rocking and then a final 10 mL of DMEM was added. The cell solution was incubated for 5 min at 37° C. then centrifuged (1500 rpm, 3 min). The resulting cell pellet was resuspended in complete medium (DMEM containing 10% FBS, 50 μmol/L 2-mercaptoethanol, 50 μg/mL insulin, 10 ng/mL IL-6) at a cell density of $1 \times 10^6$ cells/mL. 100 μL of cell suspension was seeded per well of 96-well plates. The plates were incubated at 37° C. with 5% $CO_2$.

After 16 hours, successfully fused hybridoma cells were subject to selection by culture in HAT containing media (cat# H0262, Sigma, St. Louis, Missouri). 100 μL of 2× HAT-containing medium (the medium described above with 2× HAT media supplement (Sigma)) was added to each well of cell suspension in 96-well plates and the plates were incubated at 37° C. with 5% $CO_2$. The medium was changed 3× per week with HAT-containing medium until the cells reached a density suitable for screening. Screening was performed using hybridoma culture supernatants or purified antibodies.

Seven hybridoma clones were selected based on the screening for antigen binding. The Balb/c derived monoclonal antibodies tested were 17A3, 24A8, 6A5 and 35A2, and Fn14 KO mouse-derived monoclonal antibodies were KO41c, KO42d and KO43b.

Fn14 Specific Hybridoma Antigen Binding Screening Assay

Cell culture supernatants from seven selected hybridoma clones were evaluated for binding of antibodies directed against Fn14 expressed on different cell lines. The Balb/c derived monoclonal antibodies tested were 17A3, 24A8, 6A5 and 35A2, and Fn14 KO mouse-derived monoclonal antibodies were KO41c, KO42d and KO43b.

Specifically, the binding activity of hybridoma culture supernatants or purified antibodies to Fn14-expressing cells was evaluated by flow cytometry (FCM). The cell lines evaluated by FCM were Fn14-transfected human embryonic kidney 293F cells (ThermoFisher, cat# R79007) and two cell lines endogenously expressing Fn14, human kidney-derived HK2 cells (ATCC, cat# CRL-2190) and rat kidney-derived NRK-52E cells (Japanese Collection of Research Biore-sources Cell Bank (JCRB), cat# IF050480). For FCM analysis, Fn14-expressing cells were harvested using 0.25% trypsin-EDTA (Nacalai Tesque), washed with PBS, and resuspended in SM (Staining Medium: PBS containing 2% FBS, 1 mM EDTA, 0.05% sodium azide). Cells were then seeded in a 96-well plate at $1 \times 10^5$ cells per well. Hybridoma supernatant or purified antibody (1 μg/mL final concentration) was added and the cells were incubated at 4° C. for 60 minutes. Cells were then washed with SM, resuspended in goat F(ab')2 anti-mouse IgG-PE (Southern Biotech Inc.), diluted 1:500 in SM and incubated at 4° C. for 60 minutes. Cells were washed with SM and finally resuspended in 50 μL of SM. Fluorescence intensity was measured by FCM (BD Biosciences, FACS CantoII) and the data were analyzed using FlowJo software (Tomy Digital Biology Co., Ltd.).

Figure 1:
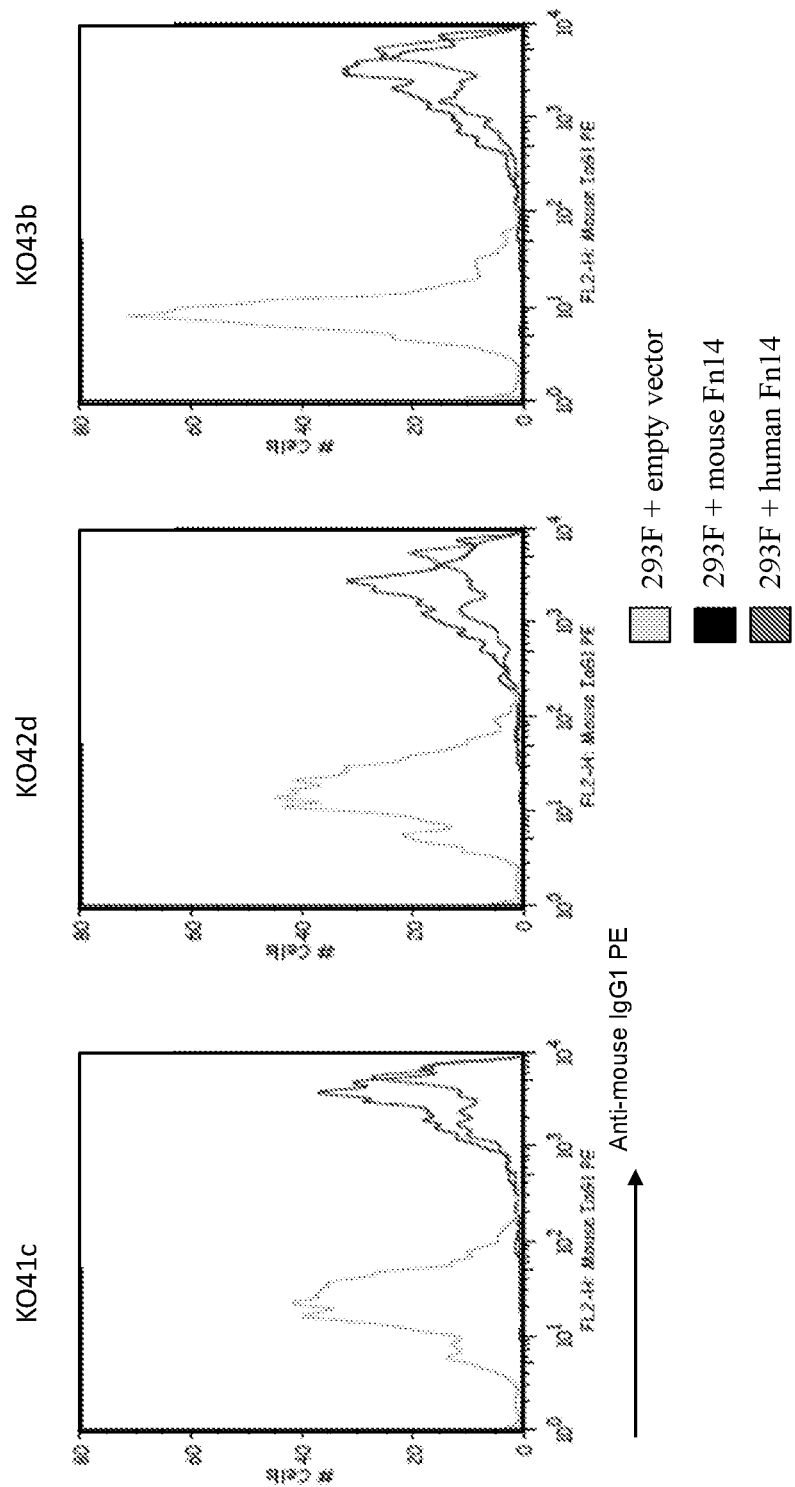

More specifically, cells expressing both mouse and human Fn14 exhibited a shift in fluorescence intensity following incubation with KO41c, KO42d and KO43b supernatants when compared with negative control cells transfected with empty vector (see FIG. 1). This result indicates that Fn14 KO mouse-derived monoclonal antibodies bound to both mouse and human Fn14.

Figure 2A:
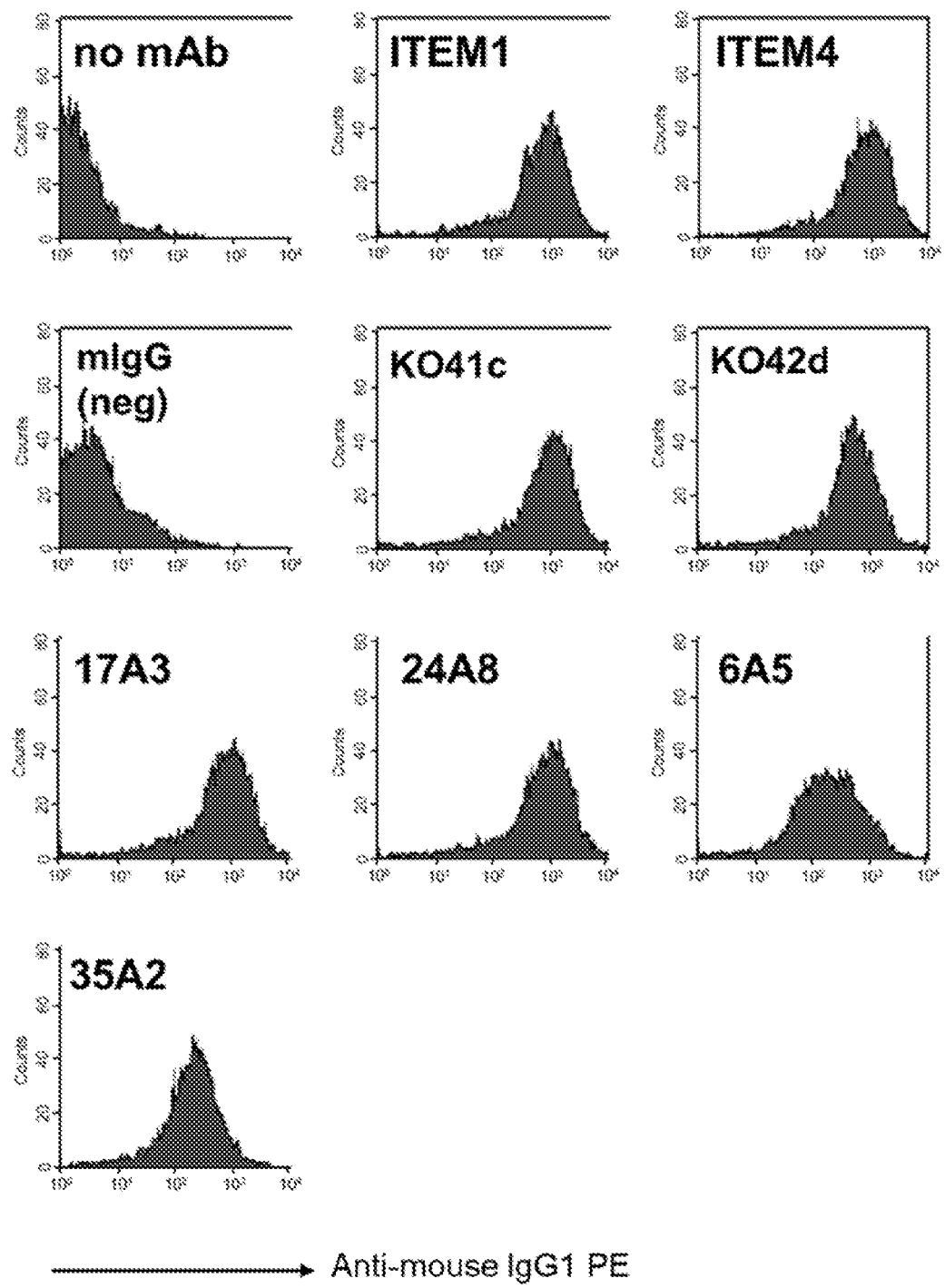
Figure 2B:
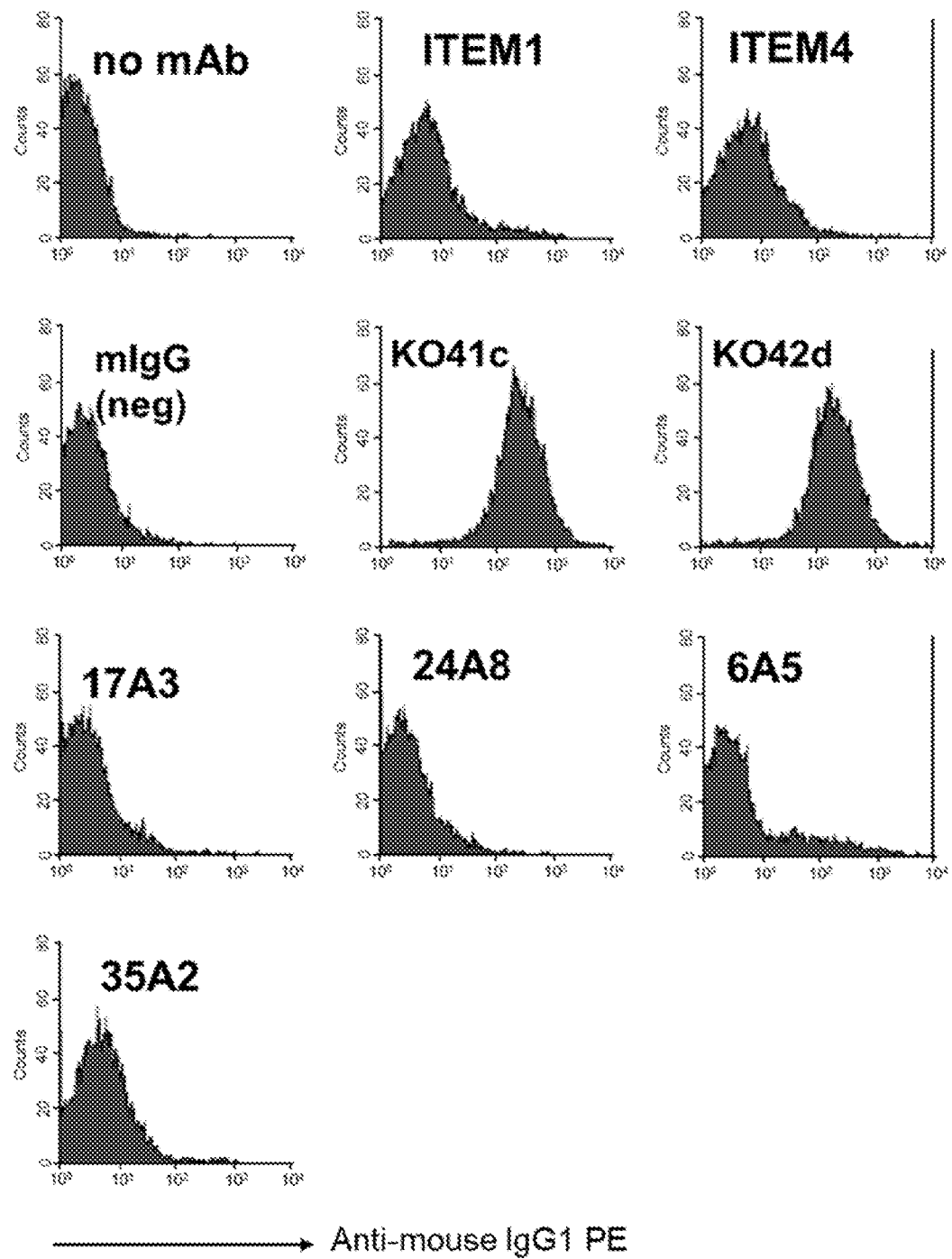

The following anti-Fn14 antibodies were evaluated in these assays: commercial monoclonal antibodies ITEM-1, ITEM-4 (see Nakayama M. et al., 2003, J. Immunol. 170: 341-348), Fn14 KO mouse-derived monoclonal antibodies KO41c, KO42d and KO43b, and Balb/c derived monoclonal antibodies 17A3, 24A8, 6A5 and 35A2. Antibodies derived from Fn14 KO mice (KO41c, KO42d and KO43b) bound to human and mouse Fn14, as well as rat Fn14 (KO43b not tested) (see FIG. 1 and FIGS. 2A and 2B). Antibodies derived from BALB/c mice were able to bind human Fn14 but not rat Fn14 (see FIGS. 2A and 2B).

Fn14 Specific Hybridoma TWEAK Neutralization Screening Assay

The biological activity of the purified Fn14 antibodies was evaluated by screening their ability to neutralize the Fn14-mediated induction of CCL2 expression by TNF-like weak inducer of apoptosis (TWEAK). The ability of Fn14 antibodies to attenuate TWEAK-induced CCL2 gene expression in HK2 and NRK-52E cells was measured by real-time PCR. HK2 cells or NRK-52E cells were harvested and seeded into 24-well cell culture microplates at $2 \times 10^5$ cells per well, then incubated with 30 ng/mL human TWEAK (hTWEAK) (R&D Systems, cat# 1090-TW-025) and 10 μg/mL of the candidate purified mouse antibodies at 37° C. with 5% $CO_2$. After a 6 hour incubation, the medium was removed and total RNA was extracted using an RNeasy Mini Kit and QIA shredder (QIAGEN). Next, RNA was reverse transcribed using PrimeScrip RT Master Mix (Takara-bio). To quantify CCL2 expression, real-time PCR was performed using the prepared cDNA and specific primers for human and rat CCL2 genes. The primer sets (human CCL2, rat CCL2, human GAPDH, and rat GAPDH) were purchased from Takara-bio's Bio's Perfect Real Time Primer Support System. The experiment was performed using SYBR Premix Ex Taq II (Takara-bio) and 7900HT Fast Real Time PCR System (Applied Biosystems). CCL2 expression data were normalized relative to GAPDH expression.

Figure 3A:
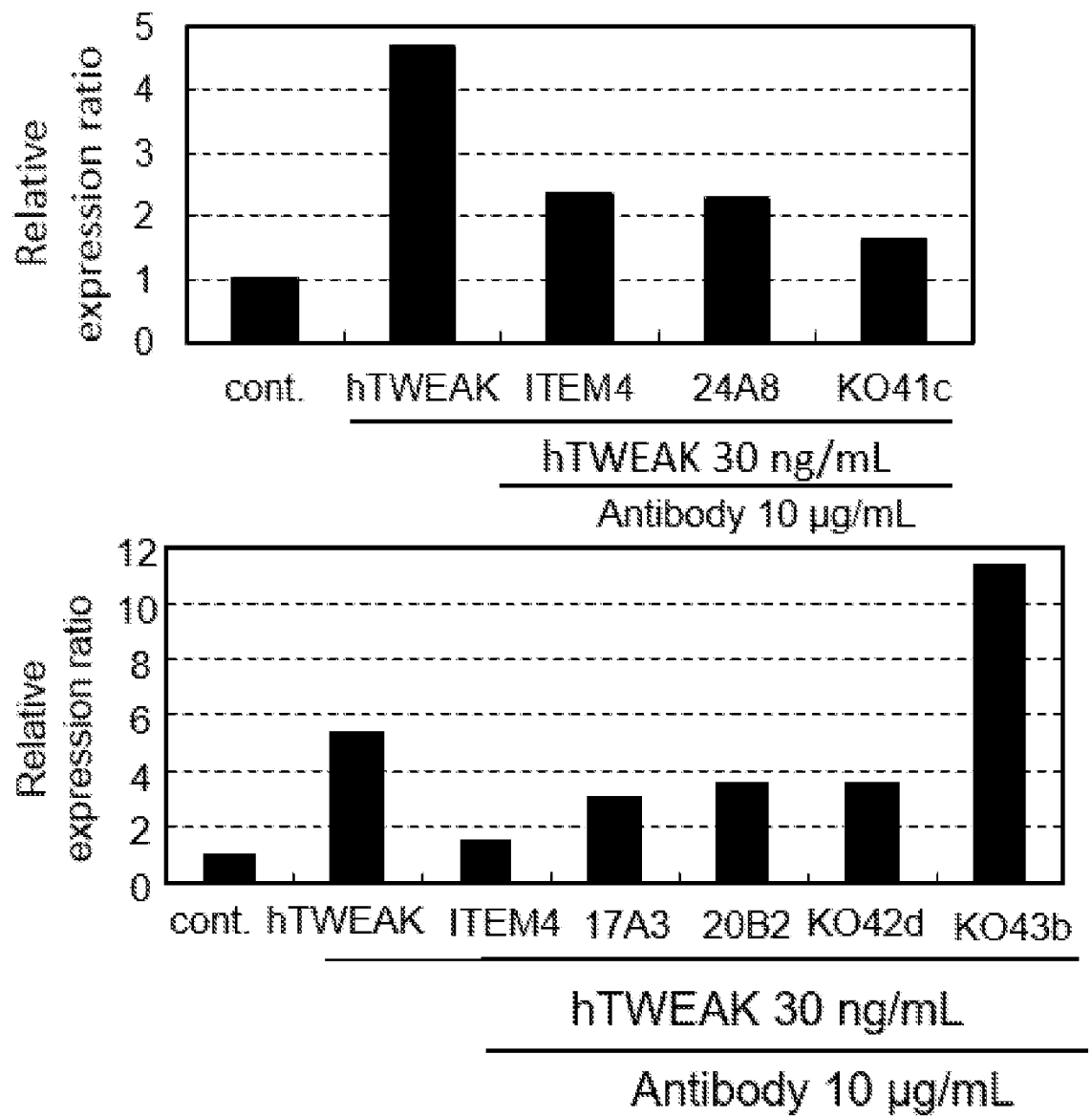
Figure 3B:
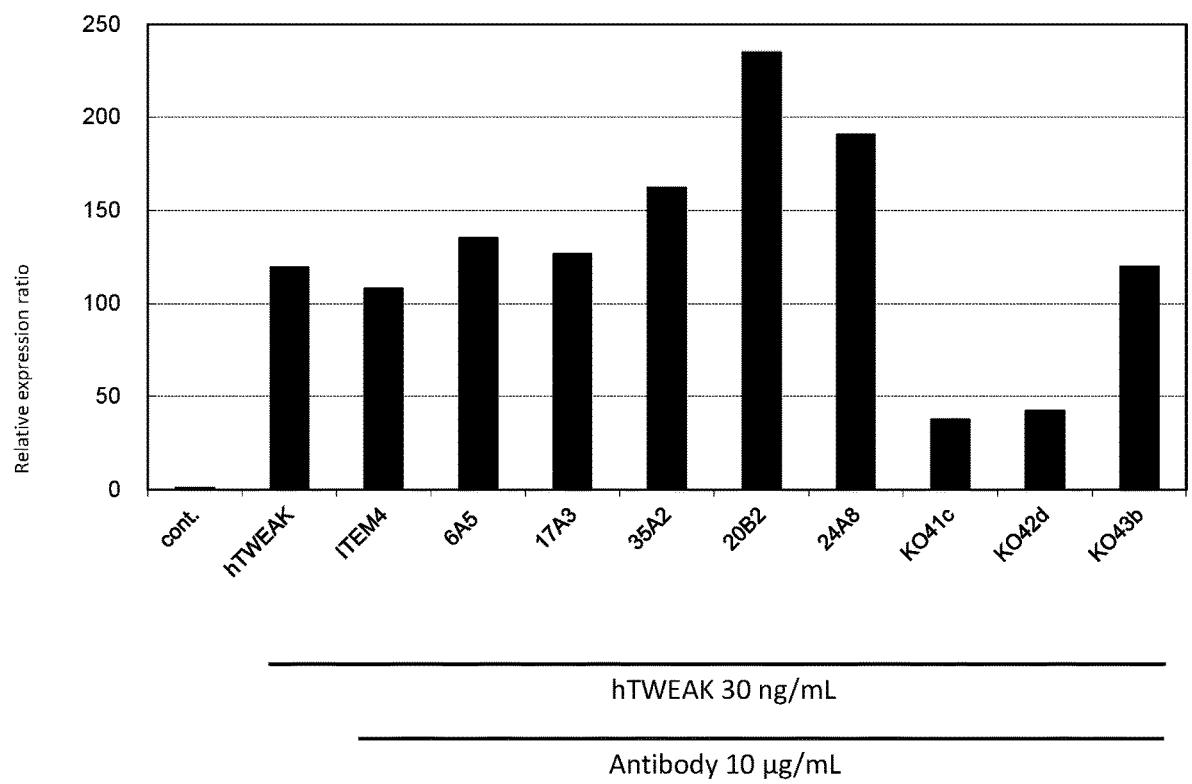

In human kidney HK2 cells, candidate Fn14 antibodies 17A3, 20B2, 24A8, KO41c and KO42d showed antagonist activity against human Fn14 by reducing hTWEAK-induced expression of CCL2 (FIG. 3A). On the other hand, only KO41c and KO42d exhibited antagonist activity against rat Fn14 in rat kidney NRK-52E cells (FIG. 3B). This result is in agreement with data showing that the BALB/c derived mAbs were unable to bind rat Fn14 (see FIGS. 2A and 2B). KO43b did not demonstrate antagonist activity in HK2 cells, and the activity of 6A5 and 3 5A2 antibodies was not tested in the assay with HK2 cells (commercially-available Fn14 antibody (ITEM4) was used as a positive control).

NF-κB Luciferase Reporter Screening Assay in NRK-52E Cells

An NF-κB luciferase reporter screening assay was utilized to further evaluate the antagonist activity of candidate Fn14 monoclonal antibodies. NRK52E-A15/Luc cells were prepared, in which the rat kidney derived cell line, NRK-52E, endogenously expresses Fn14. Stimulation of these cells with hTWEAK results in the upregulation of downstream genes such as CCL2 (chemokine C-C motif ligand 2) and ICAM1 (Intercellular Adhesion Molecule 1, also known as CD54, Cluster of Differentiation 54). Given that NRK-52E cells are responsive to TWEAK/Fn14 engagement, proliferate quickly, and are favorable to the generation of stable transfectants, they were chosen to generate an NF-κB/Luciferase reporter cell line. pGL4.32 [luc2P/NFκB-RE/Hygro] vector (Promega) was introduced into NRK-52E cells using FuGENE HD Transfection Reagent (Roche). Three days later, the cells were plated at limiting dilution in a 96 well plate in culture medium (DMEM containing 5% FBS) and 0.3 mg/mL hygromycin B (WAKO) was added to the medium to obtain a single clonal strain. A stable strain (A15) with the capability to produce luciferase after stimulation with hTWEAK or hTNFα was obtained. Luciferase activity was measured using the Steady-Glo Luciferase Assay System (Promega). Briefly, 100 μL of substrate solution was added to each well, mixed, then luciferase activity was measured using a Veritas Microplate Luminometer (Promega). Ligand (hTWEAK or hTNFα, R & D Systems) was added to the NRK52E-A15 cells at concentrations of 0.1, 0.5, 1, 5, 10, 50 and 100 ng/mL and luciferase activity was measured after 6 hours. 5 ng/mL of TWEAK stimulation was sufficient to induce luciferase activity with an SB ratio greater than 5.

Figure 4A:
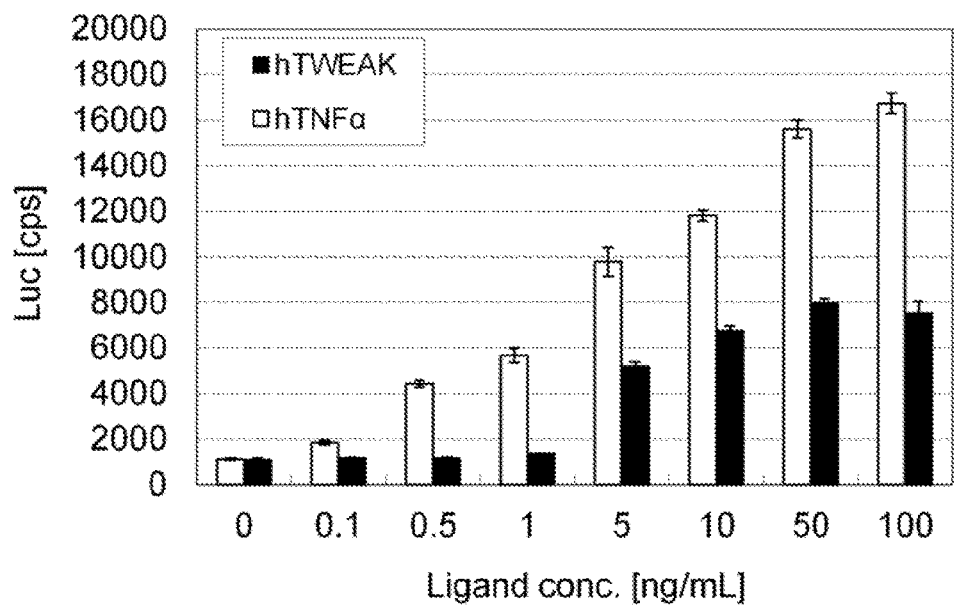

The ability of Fn14 candidate antibodies to neutralize hTWEAK-stimulated NF-κB-Luciferase activity was tested in NRK52E-A15/Luc cells. NRK52E-A15/Luc cells harboring a NFκB-Luciferase reporter were stimulated with hTWEAK or human tumor necrosis factor alpha (hTNFα), a stimulus known to activate NF-κB, at indicated concentrations (0-100 ng/mL). NF-κB-Luciferase activity was reported as counts per second measured on a luminometer (Luc [cps]). Results indicate that, similar to TNFα, hTWEAK induced NFκB activation in a dose dependent manner (see FIG. 4A).

Figure 4B:
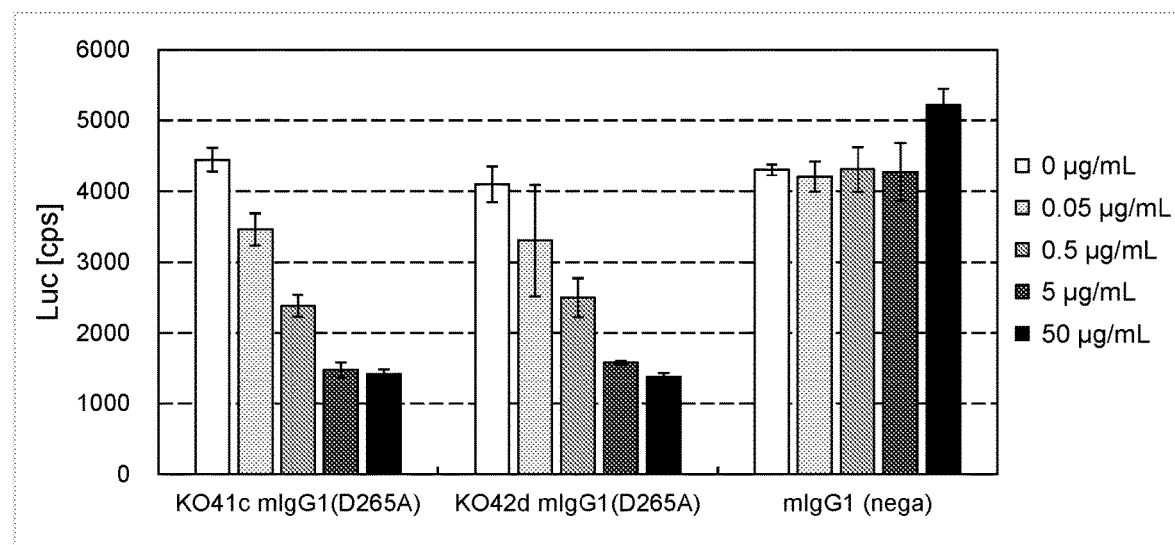

Cells were stimulated with hTWEAK (5 ng/mL) in the presence of indicated concentrations of purified anti-Fn14 mAbs, KO41c and KO42d, or control mouse IgG1 antibody (0-50 μg/mL) (see FIG. 4B). Anti-Fn14 monoclonal antibodies KO41c and KO42d neutralized hTWEAK NF-κB activation in a dose-dependent manner compared with a mIgG1 isotype control antibody (nega) (see FIG. 4B).

Example 2

Mouse Antibody Preparation And Sequence Analysis

Cloning of Genes Encoding VII and VL of Anti-Fn14 Antibody from Hybridoma Cells

Nucleotide sequences of antibody variable regions were determined by sequencing VH and VL genes isolated by 5' RACE-PCR amplification from RNA extracted from clonal hybridoma cells. Total RNA was prepared from 1 ×10$^6$ hybridoma cells producing KO41c and KO42d antibody using an RNeasy Mini Kit (cat# 74104, QIAGEN, Hilden, Germany) and QIA shredder (cat# 79654, QIAGEN, Hilden, Germany). First strand cDNA was synthesized using 1 Kg of total RNA for each hybridoma using a SMARTer RACE cDNA Amplification Kit (cat# 634859, Clontech, Mountain View, California). cDNA sequence for each unique VH and VL was obtained using first strand cDNA as the template. PCR was performed using combinations of primers specific to mouse IgG2a, mouse IgG2b, and the universal primer A (provided in SMARTer® RACE cDNA Amplification Kit), to amplify the VH cDNA fragment of each antibody. In addition, PCR was performed using primers specific to mouse Ig(x) and the universal primer A in order to amplify the VL cDNA fragment of each antibody. Subsequently, each PCR reaction was subjected to gel electrophoresis and amplified fragments were purified using a QlAquick Gel Extraction Kit (cat# 28704, QIAGEN, Hilden, Germany). Each of the gene fragments obtained was inserted into the pCR4 vector using a Zero Blunt TOPO PCR Cloning Kit for Sequencing (cat# K280020, Life Technologies, Carlsbad, California).

The resulting plasmids containing amplified variable gene nucleotide sequences were introduced into E. coli DHSa for amplification and selected for using the appropriate antibiotic on LB-agar plates. DNA plasmids were subsequently amplified by growing individual bacterial clones in liquid LB culture, under antibiotic selection, and then plasmids were extracted using an auto-plasmid-isolator (Kurabo).

Complete sequence for the VH and VL of each antibody clone was determined by Sanger sequencing of the PCR-derived inserts from multiple plasmids for each clone using M13F/R primers. The consensus nucleotide sequence for each was determined to be the full-length VH or VL cDNA (including the putative ATG initiation codon at the 5'-terminus). The respective VH and VL amino acid sequences were deduced from these.

Analysis of Variable Region Sequences

The complete VH nucleotide sequences of antibodies KO41c and KO42d are represented by SEQ ID NOs: 31 and 41, respectively. The complete amino acid sequences including the signal sequence, deduced from these nucleotide sequences, are represented by SEQ ID NOs: 32 and 42, respectively. The complete VL nucleotide sequences of antibodies KO41c and KO42d are represented by SEQ ID NOs: 36 and 45, respectively. The complete amino acid sequences including the signal sequence, deduced from these nucleotide sequences, are represented by SEQ ID NOs:

37 and 46, respectively. The VH amino acid sequences of KO41c and KO42d excluding the signal sequence are represented by SEQ ID NOs: 35 and 44, respectively. The VL amino acid sequences of KO41c and KO42d excluding the signal are represented by SEQ ID NOs: 40 and 48, respectively (see Table 15).

TABLE 15

VH and VL nucleotide and amino acid sequences of antibodies KO41c and KO42d.

| Description | Sequences (SEQ ID NO) |
|---|---|
| 41C-VH (with signal peptide) (not codon optimized) | ATGGGATGGAGCTGGATCTTTCTCTTTCTCCTGTCAGAAACTGCAGGTGTCC TCTCTGAGGTCCAGCTGCAACAGTCTGGACCTGAGCTGGTGAAGCCTGGGGC TTCAGTGAAGATGTCCTGCAAGGCTTCTGGATACACATTCACTGACTACAAC ATGCACTGGGTGAAGCAGAGCCATGGAAAGAGCCTTGAATGGATTGGATATA TTAACCCTAACAATGGTGGTACTAACTACAACCAGAAGTTCAAGGGCAAGGC CACATTGACTGTAAACAAGTCCTCCAGGTCAGCCTACATGGAGTTCCGCAGC CTGACATCGGAGGATTCTGCAGTCTATTACTGTGCCTCGTCGGGATGGTTTA CTTACTGGGGCCAAGGGACTCTGGTCACTGTCTCTGCA (SEQ ID NO: 31) |
| 41C-VH (with signal peptide) | MGWSWIFLFLLSETAGVLSEVQLQQSGPELVKPGASVKMSCKASGYTFTDYN MHWVKQSHGKSLEWIGYINPNNGGTNYNQKFKGKATLTVNKSSRSAYMEFRS LTSEDSAVYYCASSGWFTYWGQGTLVTVSA (SEQ ID NO: 32) |
| 41C-VH (no signal peptide) (not codon optimized) | GAGGTCCAGCTGCTCCAGTCTGGACCTGAGCTGGTGAAGCCTGTGGCTTCAG TGAAGATGTCCTGCAAGGCTTCTGGATACACATTCACTGACTACAACATTCA CTGGGTGAAGCAGAGCCATGGAAAGAGCCTTGAGTGGATTGGATATATTAAC CCTAACAATGGTGTTACTGGCTACAACCAGAAGTTCAGGGGCAAGGCCACAT TGACTGTTAACAGGTCCTCCAACACAGCCTACATGGACCTCCGCAGCCTGAC ATCGGAGGATTCTGCAGTCTATTACTGTACAAGACGCTATGGTGACTACGTC CATGCTATGGACTGCTGGGGTCAAGGAACCTCAGTCACCGTCTCCTCA (SEQ ID NO: 33) |
| 41C-VH (no signal peptide) (codon optimized) | GAAGTGCAGCTGCAGCAGTCTGGCCCCGAGCTCGTGAAACCTGGCGCCTCCG TGAAGATGTCCTGCAAGGCCTCCGGCTACACCTTCACCGACTACAACATGCA CTGGGTCAAGCAGTCCCACGGCAAGTCCCTGGAATGGATCGGCTACATCAAC CCCAACAACGGCGGCACCAACTACAACCAGAAGTTCAAGGGCAAGGCTACCC TGACCGTGAACAAGTCCTCCAGATCCGCCTACATGGAATTTCGGTCCCTGAC CTCCGAGGACTCCGCCGTGTACTACTGCGCCTCCTCTGGCTGGTTCACCTAC TGGGGCCAGGGCACCCTCGTGACCGTGTCTGCT (SEQ ID NO: 34) |
| 41C-VH (no signal peptide) | EVQLQQSGPELVKPGASVKMSCKASGYTFTDYNMHWVKQSHGKSLEWIGYIN PNNGGTNYNQKFKGKATLTVNKSSRSAYMEFRSLTSEDSAVYYCASSGWFTY WGQGTLVTVSA (SEQ ID NO: 35) |
| 41C-VL (with signal peptide) (not codon optimized) | ATGATGAGTCCTGCCCAGTTCCTGTTTCTGTTAGTGCTCTGGATTCGGGAAA CCAACGGTGATGTTGTGATGACCCAGACTCCACTCACTTTGTCGGTTGCCAT TGGACAACCAGCCTCCATCTCTTGCAAGTCAAGTCAGAGCCTCTTAAATAGT GCTGGAAAGACATATTTGAATTGGTTGTTACAGAGGCCAGGCCAGTCTCCAA AGCGCCTAATTTATCTGGTGTCTCAACTGGACTCTGGAGTCCCTGACAGGTT CACTGGCAGTGGATCAGGGACAGATTTCACACTGAAAATCAGCAGAGTGGAG GCTGAGGATTTGGGAGTTTATTATTGCTGGCAAGGTACACATTTTCCGTGGA CGTTCGGTGGAGGCACCAAGCTGGAAATCAAA (SEQ ID NO: 36) |
| 41C-VL (with signal peptide) | MMSPAQFLFLLVLWIRETNGDVVMTQTPLTLSVAIGQPASISCKSSQSLLNS AGKTYLNWLLQRPGQSPKRLIYLVSQLDSGVPDRFTGSGSGTDFTLKISRVE AEDLGVYYCWQGTHFPWTFGGGTKLEIK (SEQ ID NO: 37) |
| 41C-VL (no signal peptide) (not codon optimized) | GATGTTGTGATGACCCAGACTCCACTCACTTTGTCGGTTGCCATTGGACAAC CAGCCTCCATCTCTTGCAAGTCAAGTCAGAGCCTCTTAAATAGTGCTGGAAA GACATATTTGAATTGGTTGTTACAGAGGCCAGGCCAGTCTCCAAAGCGCCTA ATTTATCTGGTGTCTCAACTGGACTCTGGAGTCCCTGACAGGTTCACTGGCA GTGGATCAGGGACAGATTTCACACTGAAAATCAGCAGAGTGGAGGCTGAGGA TTTGGGAGTTTATTATTGCTGGCAAGGTACACATTTTCCGTGGACGTTCGGT GGAGGCACCAAGCTGGAAATCAAA (SEQ ID NO: 38) |
| 41C-VL (no signal peptide) (codon optimized) | GACGTCGTGATGACCCAGACCCCCCTGACACTGTCTGTGGCCATCGGCCAGC CTGCCTCCATCTCCTGCAAGTCCTCCCAGTCCCTGCTGAACTCCGCCGGCAA GACCTACCTGAACTGGCTGCTGCAGCGGCCTGGCCAGTCCCCCAAGAGACTG ATCTACCTGGTGTCCCAGCTGGACTCCGGCGTGCCCGATAGATTCACCGGCT CTGGCTCTGGCACCGACTTCACCCTGAAGATCAGCCGGGTGGAAGCCGAGGA CCTGGGCGTGTACTACTGCTGGCAGGGCACCCACTTCCCTTGGACCTTTGGC GGAGGCACCAAGCTGGAAATCAAG (SEQ ID NO: 39) |

TABLE 15-continued

VH and VL nucleotide and amino acid sequences of antibodies KO41c and KO42d.

| Description | Sequences (SEQ ID NO) |
| --- | --- |
| 41C-VL (no signal peptide) | DVVMTQTPLTLSVAIGQPASISCKSSQSLLNSAGKTYLNWLLQRPGQSPKRL IYLVSQLDSGVPDRFTGSGSGTDFTLKISRVEAEDLGVYYCWQGTHFPWTFG GGTKLEIK (SEQ ID NO: 40) |
| 42d-VH (with signal peptide) | ATGGGATGGAGCTGGATCTTTCTCTTTCTCCTGTCAGAAACTGCAGGTGTCC TCTCTGAGGTCCAGCTGCTCCAGTCTGGACCTGAGCTGGTGAAGCCTGTGGC TTCAGTGAAGATGTCCTGCAAGGCTTCTGGATACACATTCACTGACTACAAC ATTCACTGGGTGAAGCAGAGCCATGGAAAGAGCCTTGAGTGGATTGGATATA TTAACCCTAACAATGGTGTTACTGGCTACAACCAGAAGTTCAGGGGCAAGGC CACATTGACTGTTAACAGGTCCTCCAACACAGCCTACATGGACCTCCGCAGC CTGACATCGGAGGATTCTGCAGTCTATTACTGTACAAGACGCTATGGTGACT ACGTCCATGCTATGGACTGCTGGGGTCAAGGAACCTCAGTCACCGTCTCCTC A (SEQ ID NO: 41) |
| 42d-VH (with signal peptide) | MGWSWIFLFLLSETAGVLSEVQLLQSGPELVKPVASVKMSCKASGYTFTDYN IHWVKQSHGKSLEWIGYINPNNGVTGYNQKFRGKATLTVNRSSNTAYMDLRS LTSEDSAVYYCTRRYGDYVHAMDCWGQGTSVTVSS (SEQ ID NO: 42) |
| 42d-VH (no signal peptide) | GAGGTCCAGCTGCTCCAGTCTGGACCTGAGCTGGTGAAGCCTGTGGCTTCAG TGAAGATGTCCTGCAAGGCTTCTGGATACACATTCACTGACTACAACATTCA CTGGGTGAAGCAGAGCCATGGAAAGAGCCTTGAGTGGATTGGATATATTAAC CCTAACAATGGTGTTACTGGCTACAACCAGAAGTTCAGGGGCAAGGCCACAT TGACTGTTAACAGGTCCTCCAACACAGCCTACATGGACCTCCGCAGCCTGAC ATCGGAGGATTCTGCAGTCTATTACTGTACAAGACGCTATGGTGACTACGTC CATGCTATGGACTGCTGGGGTCAAGGAACCTCAGTCACCGTCTCCTCA (SEQ ID NO: 43) |
| 42d-VH (no signal peptide) | EVQLLQSGPELVKPVASVKMSCKASGYTFTDYNIHWVKQSHGKSLEWIGYIN PNNGVTGYNQKFRGKATLTVNRSSNTAYMDLRSLTSEDSAVYYCTRRYGDYV HAMDCWGQGTSVTVSS (SEQ ID NO: 44) |
| 42d-VL (with signal peptide) | ATGGACATGAGGGCTCCTGCACAGATTTTTGGCTTCTTGTTGCTCTTGTTTC CAGGTACCAGATGTGACATCCAGATGACCCAGTCTCCATCCTCCTTATCTGC CTCTCTGGGAGAAAGAGTCAGTCTCACTTGTCGGGCAAGTCAGGACATTGGT AGTAGGTTAAACTGGCTTCAGCAGGAACCAGATGGAACTATTAAACGCCTGA TCTACGCCACATCCAGTTTAGATTCTGGTGTCCCCAAAAGGTTCAGTGGCAG TAGGTCTGGGTCAGATTATTCTCTCACCATCAGCAGCCTTGAGTCTGAAGAT TTTGTAGACTATTACTGTCTACAATATGCTAGTTCTCCGTACACATTCGGAG GGGGGACCAAGCTGGAAATAAAA (SEQ ID NO: 45) |
| 42d-VL (with signal peptide) | MDMRAPAQIFGFLLLLFPGTRCDIQMTQSPSSLSASLGERVSLTCRASQDIG SRLNWLQQEPDGTIKRLIYATSSLDSGVPKRFSGSRSGSDYSLTISSLESED FVDYYCLQYASSPYTFGGGTKLEIK (SEQ ID NO: 46) |
| 42d-VL (no signal peptide) | GACATCCAGATGACCCAGTCTCCATCCTCCTTATCTGCCTCTCTGGGAGAAA GAGTCAGTCTCACTTGTCGGGCAAGTCAGGACATTGGTAGTAGGTTAAACTG GCTTCAGCAGGAACCAGATGGAACTATTAAACGCCTGATCTACGCCACATCC AGTTTAGATTCTGGTGTCCCCAAAAGGTTCAGTGGCAGTAGGTCTGGGTCAG ATTATTCTCTCACCATCAGCAGCCTTGAGTCTGAAGATTTTGTAGACTATTA CTGTCTACAATATGCTAGTTCTCCGTACACATTCGGAGGGGGGACCAAGCTG GAAATAAAA (SEQ ID NO: 47) |
| 42d-VL (no signal peptide) | DIQMTQSPSSLSASLGERVSLTCRASQDIGSRLNWLQQEPDGTIKRLIYATS SLDSGVPKRFSGSRSGSDYSLTISSLESEDFVDYYCLQYASSPYTFGGGTKL EIK (SEQ ID NO: 48) |

Compared to the known sequence data of mouse antibody (see Sequences of Proteins of Immunological Interest, US Dept. Health and Human Services (1991)), the isolated cDNAs are found to be full-length cDNAs including the secretory signal sequence, which encode KO41c antibody and KO42d antibody, respectively. CDRs of VH and VL of each monoclonal antibody were identified by comparison with the known antibody amino acid sequence. Complementarity Determining Regions (CDR)s were defined using the Kabat definition (See Kabat et al. (1991) Sequences of Proteins of Immunological Interest, Fifth Edition, U.S. Department of Health and Human Services, NIH Publication No. 91-3242), except for VH CDR1 (also called HCDR1 or CDR H1), for which a combination of the Cho (Chothia and Lesk, 1987, J. Mol. Biol. 196:901-17) and Kabat definitions was used instead. Specifically, the amino-terminus of the HCDR1 was defined by using Chothia while the carboxy-terminus was defined by Kabat, and all amino acids beween those borders are included.

The amino acid sequences of HCDR1, HCDR2 and HCDR3 from the KO41c VH are represented by SEQ ID NOs: 119, 120 and 121, respectively. The amino acid sequences of LCDR1, LCDR2 and LCDR3 from the KO41c VL are represented by SEQ ID NOs: 127, 128 and 129, respectively. The amino acid sequences of CDR1, CDR2 and CDR3 of VH from the KO42d VH are represented by SEQ ID NOs: 113, 114 and 115, respectively. The amino acid sequences of CDR1, CDR2 and CDR3 from the KO42d VL are represented by SEQ ID NOs: 116, 117 and 118, respectively. The VH, VL, and CDR amino acid sequences of 41c and 41d antibodies are summarized in Table 16 below.

shown in SEQ ID NO: 37, the 41c VL amino acid sequence without signal sequence is shown in SEQ ID NO: 40. The amino acid sequences of the complete, mature 41c mIgG1 (D265A), kappa antibody heavy and light chain are represented by concatenation of VH SEQ ID NO: 35 with IgG constant SEQ ID NO: 26, and VL SEQ ID NO: 40 with kappa constant SEQ ID NO: 24, respectively.

Additional antibody expression vectors for production of various recombinant mouse IgG1(D265A), kappa antibodies were generated using similar, standard methods known to those skilled in the art, but used a generic mouse IgG or kappa signal sequence for the heavy or light chain expression, respectively. For example, an expression vector for mouse IgG1(D265A) heavy chain of 41c with an exogenous signal peptide was generated by amplifying the cDNA coding for the 41c variable heavy chain (VH), using primers which added 5' and 3' overlapping sequence for ligase-independent cloning into mammalian expression vector,

TABLE 16

Amino acid sequences of VH, VL and CDRs of KO41c and KO42d

| | KO41c (41c) | KO42d (42d) |
|---|---|---|
| VH | EVQLQQSGPELVKPGASVKMSCKASGYTFTDYNMH WVKQSHGKSLEWIGYINPNNGGTNYNQKFKGKATL TVNKSSRSAYMEFRSLTSEDSAVYYCASSGWFTYW GQGTLVTVSA (SEQ ID NO: 35) | EVQLLQSGPELVKPVASVKMSCKASGYTFTDYNIH WVKQSHGKSLEWIGYINPNNGVTGYNQKFRGKATL TVNRSSNTAYMDLRSLTSEDSAVYYCTRRYGDYVH AMDCWGQGTSVTVSS (SEQ ID NO: 44) |
| HCDR1 | GYTFTDYNMH (SEQ ID NO: 119) | GYTFTDYNIH (SEQ ID NO: 113) |
| HCDR2 | YINPNNGGTNYNQKFKG (SEQ ID NO: 120) | YINPNNGVTGYNQKFRG (SEQ ID NO: 114) |
| HCDR3 | SGWFTY (SEQ ID NO: 121) | RYGDYVHAMDC (SEQ ID NO: 115) |
| VL | DVVMTQTPLTLSVAIGQPASISCKSSQSLLNSAGK TYLNWLLQRPGQSPKRLIYLVSQLDSGVPDRFTGS GSGTDFTLKISRVEAEDLGVYYCWQGTHFPWTFGG GTKLEIK (SEQ ID NO: 40) | DIQMTQSPSSLSASLGERVSLTCRASQDIGSRLNW LQQEPDGTIKRLIYATSSLDSGVPKRFSGSRSGSD YSLTISSLESEDFVDYYCLQYASSPYTFGGGTKLE IK (SEQ ID NO: 48) |
| LCDR1 | KSSQSLLNSAGKTYLN (SEQ ID NO: 127) | RASQDIGSRLN (SEQ ID NO: 116) |
| LCDR2 | LVSQLDS (SEQ ID NO: 128) | ATSSLDS (SEQ ID NO: 117) |
| LCDR3 | WQGTHFPWT (SEQ ID NO: 129) | LQYASSPYT (SEQ ID NO: 118) |

Cloning Antibody Expression Vectors

Antibody clone KO41c (41c) was reformatted to a recombinant mouse IgG1(D265A), kappa antibody. DNA coding for the signal peptide and VH region of clone 41c (shown in nucleotide SEQ ID NO: 31) was amplified by PCR using primers adding 5' and 3' flanking DNA suitable for insertion into a mammalian expression vector, in frame with DNA coding for mouse IgG1 chain constant region (carrying the D265Å mutation known to reduce IgG Fc binding to FcγRs) (Baudino et al., J Immunol, 2008,181(9):6664). DNA coding for signal peptide and 41c VL (shown in nucleotide SEQ ID NO: 36) was similarly inserted into a mammalian expression vector, in frame with DNA coding for a mouse kappa constant sequence (shown in nucleotide SEQ ID NO: 23). The amino acid sequence of 41c VH, with signal peptide is shown in SEQ ID NO: 32, the 41c VH amino acid sequence without signal sequence is shown in SEQ ID NO: 35. The amino acid sequence of 41c VL, with signal peptide is pTC26-spmIgG1(D265A) (Kyowa Hakko Kirin), or pcDNA3.4-spmIgG1(D265A) (modified from pcDNA3.4, Life Technologies/Invitrogen, Carlsbad California) digested with restriction endonucleases, Sfol and NruI (New England Biolabs, Ipswich, Massachusetts). When inserted into the digested vector using a Seamless Cloning and Assembly Enzyme Mix (cat# A14606, Life Technologies/Invitrogen/GeneArt, Carlsbad, California), as per the manufacturer's instructions, the VH cDNA is in-frame between a 5' sequence coding for a mouse IgG signal peptide, and a 3' sequence coding for mouse IgG1(D265A) constant domain (shown in nucleotide SEQ ID NO: 25 and amino acid SEQ ID NO: 26).

Similarly, an expression vector for the mouse kappa light chain of 41c was generated by amplifying the cDNA coding for the 41c variable light chain (VL), using primers which added 5' and 3' overlapping sequence for ligase-independent cloning into mammalian expression vector, pTC26-spmK (Kyowa Hakko Kirin) or pcDNA3.4-spmK (modified from pcDNA3.4, Life Technologies/Invitrogen, Carlsbad, California), digested with restriction endonucleases, SfoI and NruI (New England Biolabs). When inserted into the digested vector using a Seamless Cloning and Assembly Enzyme Mix (cat# A14606, Life Technologies/Invitrogen/GeneArt, Carlsbad, California), as per the manufacturer's instructions, the VL cDNA is in frame between a 5' sequence coding for a mouse kappa signal peptide, and a 3' sequence coding for mouse kappa constant domain (nucleotide SEQ ID NO: 23 coding for amino acid SEQ ID NO: 24).

This process was performed in the same way for all other antibody clones expressed as mouse IgG1(D265A), kappa. In this way, expression vectors for anti-Fn14 antibody clone CRCBT-06-002 (CRCBT) were generated from synthesized cDNAs (performed by Invitrogen/GeneArt, Regensburg, Germany) that code for the VH and VL sequences for CRCBT-06-002 (described in US2013/0273036 A1), which were then used as template for PCR and subcloned into mouse IgG1 (D265A), kappa expression vectors in the same manner described above. All plasmid sequences were validated by Sanger sequencing.

Certain constant domain sequences mentioned above are listed below:

Mouse IgG1(D265A) constant domain nucleotide sequence:
(SEQ ID NO: 25)
GCCAAAACGACACCCCCGTCTGTCTATCCACTGGCCCCTGGATCTGCTGC

CCAAACTAACTCCATGGTGACCCTGGGATGCCTGGTCAAGGGCTATTTCC

CTGAGCCAGTGACAGTGACCTGGAACTCTGGCTCCCTGTCCAGCGGTGTG

CACACCTTCCCAGCTGTCCTGGAGTCTGACCTCTACACTCTGAGCAGCTC

AGTGACTGTCCCCTCCAGCCCTCGGCCCAGCGAGACCGTCACCTGCAACG

TTGCCCACCCGGCCAGCAGCACCAAGGTGGACAAGAAAATTGTGCCCAGG

GATTGTGGTTGTAAGCCTTGCATATGTACAGTCCCAGAAGTATCATCTGT

CTTCATCTTCCCCCCAAAGCCCAAGGATGTGCTCACCATTACTCTGACTC

CTAAGGTCACGTGTGTTGTGGTAGcCATCAGCAAGGATGATCCCGAGGTC

CAGTTCAGCTGGTTTGTAGATGATGTGGAGGTGCACACAGCTCAGACGCA

ACCCCGGGAGGAGCAGTTCAACAGCACTTTCCGCTCAGTCAGTGAACTTC

CCATCATGCACCAGGACTGGCTCAATGGCAAGGAGTTCAAATGCAGGGTC

AACAGTGCAGCTTTCCCTGCCCCCATCGAGAAAACCATCTCCAAAACCAA

AGGCAGACCGAAGGCTCCACAGGTGTACACCATTCCACCTCCCAAGGAGC

AGATGGCCAAGGATAAAGTCAGTCTGACCTGCATGATAACAGACTTCTTC

CCTGAAGACATTACTGTGGAGTGGCAGTGGAATGGGCAGCCAGCGGAGAA

CTACAAGAACACTCAGCCCATCATGAACACGAATGGCTCTTACTTCGTCT

ACAGCAAGCTCAATGTGCAGAAGAGCAACTGGGAGGCAGGAAATACTTTC

ACCTGCTCTGTGTTACATGAGGGCCTGCACAACCACCATACTGAGAAGAG

CCTCTCCCACTCTCCTGGTAAA

Mouse IgG1(D265A) constant domain amino acid sequence
(SEQ ID NO: 26)
AKTTPPSVYPLAPGSAAQTNSMVTLGCLVKGYFPEPVTVTWNSGSLSSGV

HTFPAVLESDLYTLSSSVTVPSSPRPSETVTCNVAHPASSTKVDKKIVPR

-continued
DCGCKPCICTVPEVSSVFIFPPKPKDVLTITLTPKVTCVVVAISKDDPEV

QFSWFVDDVEVHTAQTQPREEQFNSTFRSVSELPIMHQDWLNGKEFKCRV

NSAAFPAPIEKTISKTKGRPKAPQVYTIPPPKEQMAKDKVSLTCMITDFF

PEDITVEWQWNGQPAENYKNTQPIMNTNGSYFVYSKLNVQKSNWEAGNTF

TCSVLHEGLHNHHTEKSLSHSPGK

Mouse kappa constant domain nucleotide sequence:
(SEQ ID NO: 23)
CGAGCTGATGCTGCACCAACTGTATCCATCTTCCCACCATCCAGTGAGCA

GTTAACATCTGGAGGTGCCTCAGTCGTGTGCTTCTTGAACAACTTCTACC

CCAAAGACATCAATGTCAAGTGGAAGATTGATGGCAGTGAACGACAAAAT

GGCGTCCTGAACAGTTGGACTGATCAGGACAGCAAAGACAGCACCTACAG

CATGAGCAGCACCCTCACGTTGACCAAGGACGAGTATGAACGACATAACA

GCTATACCTGTGAGGCCACTCACAAGACATCAACTTCACCCATCGTCAAG

AGCTTCAACAGGAATGAGTGT

Mouse kappa constant domain amino acid sequence:
(SEQ ID NO: 24)
RADAAPTVSIFPPSSEQLTSGGASVVCFLNNFYPKDINVKWKIDGSERQN

GVLNSWTDQDSKDSTYSMSSTLTLTKDEYERHNSYTCEATEIKTSTSPIV

KSFNRNEC

Example 3

Production and Purification of Recombinant Antibodies and Proteins from Mammalian Cells Production of recombinant antibodies from mammalian cells was done using either the Freestyle293, Expi293 or ExpiCHO transient expression systems (cat# s K900001, A14635 and A29133, respectively, Life Technologies/Invitrogen, Carlsbad, California). Separate mammalian expression vectors for the heavy chain and the light chain were combined in a one-to-one or one-to-three ratio, respectively, and transfected using the methods described in the manufacturer's manuals. Five to ten days after transfection, culture media was collected and clarified by centrifugation followed by 0.22 micron filtration (such as cat# S2GPUO5RE, Stericup® Filter Units, EMD Millipore, Bedford, Massachusetts).

Production of all Fn14-GST and His-SUMO-Fn14 recombinant proteins was done using either the Freestyle293 or Expi293 transient expression systems, following the methods described in the manufacturer's manual (cat# s K900001 and A14635, respectively, Invitrogen, Carlsbad, California), after which protein-containing conditioned medium was clarified, as above, prior to purification or direct use in assays.

Recombinant Antibody Purification

Recombinant mouse monoclonal antibodies were purified from culture media using recombinant MabSelect SuRe Protein-A affinity resin (GE Healthcare Life Sciences, Pittsburgh, PA). The conditioned medium was filtered with a 0.22 μm vacuum filter unit (Millipore, Bedford, MA) and loaded onto a HiTrap MabSelect SuRe column (GE Healthcare Life Sciences, Pittsburgh, PA) of appropriate capacity to match the amount of antibody in the medium. The column was washed thoroughly with 6 column volumes of PBS pH 7.4 (Sigma Aldrich powder pouches), the antibody was eluted with 0.1 M Gly-HCl, 0.15 M NaCl pH 3.6, and neutralized with 1 M Tris-HCl, pH 8.0. Fractions were analyzed by SDS-PAGE and positive fractions were pooled and dialyzed against PBS pH 7.4 (Sigma Aldrich powder pouches). Following dialysis, antibody samples were concentrated with a centrifugal filter concentrator (Vivaspin, 30,000 MVVCO: Sartorius, Goettingen, Germany). Finally, the antibody was filter sterilized using syringe filters with 0.22 µm pore diameter and antibody concentration was determined by the Lowry method. Pyrogen content was determined using FDA-licensed Endosafe-PTS Limulus Amebocyte Lysate (LAL) assay (Charles River Laboratories). The limits of detection for this assay are 1-0.01 EU/mL of endotoxin. If the test was negative, the samples were considered endotoxin free.

Histidine-tagged (His-tag) Protein Purification

His-tag protein was purified using several different methods depending on the specific protein. For example, His-tagged SUMO-Fn14 recombinant protein was purified using immobilized metal ion affinity chromatography (IMAC) (GE Healthcare, cat# 17524701). Other His-tagged recombinant human proteins were purified from culture medium using HisTrap HP affinity column (Ni Sepharose High Performance media precharged with nickel ions (Ni2+)) (GE Healthcare Life Sciences, Pittsburgh, PA). The conditioned medium (culture supernatant) was diluted with 20 mM Tris-HCl pH 8.0, 0.5 M NaCl buffer and filtered with a 0.22 µm vacuum filter unit (Millipore, Bedford, MA). 20 mM imidazole and 1 mM DTT (final concentration) were added just prior to purification. Sample was loaded onto a 5 mL HisTrap HP column (GE Healthcare Life Sciences, Pittsburgh, PA) equilibrated with 20 mM Tris-HCl pH 8.0, 0.5 M NaCl, 20 mM imidazole. Upon sample loading, the column was washed thoroughly with 6 column volumes of 20 mM Tris-HCl pH 8.0, 0.5 M NaCl, 20 mM imidazole. The protein was eluted with 20 mM- 600 mM imidazole gradient over 25 column volumes, and neutralized with 5mM EDTA and 5mM DTT (final concentration). Fractions were analyzed by SDS-PAGE and positive fractions were pooled and dialyzed against PBS pH 7.4 (Sigma Aldrich powder pouches). Following dialysis, protein sample was concentrated with a centrifugal filter concentrator (Vivaspin 30,000 MVVCO: Sartorius, Goettingen, Germany). Finally, the protein was filter sterilized using syringe filters with 0.22 µm pore diameter and protein concentration was determined using the Lowry method. Pyrogen content was determined using FDA-licensed Endosafe-PTS Limulus Amebocyte Lysate (LAL) assay (Charles River Laboratories). The limits of detection for this assay are 1-0.01 EU/mL of endotoxin. If the test was negative, the samples were considered endotoxin free.

Example 4

Affinity Maturation of 41C

The 41c clone was affinity matured through phage display (Smith, G.P., Science, 1985, 228(4705):1315-7) and panning of mutation-randomized libraries of 41c Fab. This work was performed by Abwiz Bio (San Diego, California). To this end, four separate phagemid libraries of 41c Fab were created, each with a single complementarity determining region (CDR) randomized by mutation of select amino acid positions within the targeted CDR: heavy chain CDR1 (HCDR1), heavy chain CDR2 (HCDR2), heavy chain CDR3 (HCDR3) or light chain CDR3 (LCDR3). Phage generated from these libraries were screened by panning on recombinant His-SUMO-Fn14 protein bound to a solid-phase medium. High affinity 41c variants were enriched and clones with enhanced antigen binding were selected.

Specifically, a phagemid for phage surface expression of a 41c Fab was created by sequential insertion of synthetic DNA fragments coding for 41c VH and VL into Abwiz's proprietary phagemid, in-frame with DNA for mouse IgG1 constant heavy 1 (CH1) and kappa constant domains, respectively. Prior to mutational library construction, four separate phagemids were created for the separate library templates by inserting in-frame stop codons into one of the four targeted CDRs (HCDR1, HCDR2, HCDR3 or LCDR3) each in accordance with the CDR that was to be targeted by mutation in that library. This wasimplemented in order to eliminate unmutated phagemid from dominating the library, because the process of mutation is inefficient. The Kunkel method of mutagenesis (Kunkel, T. A., Proc Natl Acad Sci USA, 1985, 82(2):488-92) was used to generate each of the four randomized CDR libraries using the stop-codon-modified (deoxyuracil-containing single-stranded DNA) dU-ssDNA phagemid templates, and oligonucleotides randomized at selected amino acid loci within each library's respective targeted CDR. The number of targeted amino acid loci was constrained to five per CDR to limit the overall theoretical diversity, and to ensure that every clone would be present in the phage pool during selection. Selection of amino acid positions to target for randomization was based on analysis of 41c sequence similarity to germline, bioinformatics-based comparison to antibodies with similar sequences. To maximize diversity of the randomized CDR libraries, NNK codons were used at each mutated CDR position. NNK codons (where each letter stands for a mixture of deoxynucleoside triphosphates, N =adenosine (A)/cytidine (C)/guanosine (G)/thymidine (T), and K =G/T) are a randomized mixture of 32 codons coding for any of the 20 standard amino acids. For the first step of Kunkel mutagenesis, the four 41c phagemids containing stop codons in CDRs were separately transformed into E. colt strain, CJ236. For each library template, phage were produced from the CJ236 cells, and dU-ssDNA was purified from the phage. Randomized oligonucleotide pools, designed based on the principles above, were annealed to the dU-ssDNA templates for each of the libraries, followed by DNA polymerase synthesis of the complementary strand and ligation to create covalently closed circular DNA libraries (CCC-DNA). Library quality wasassessed by sequencing 24 unique colonies from library-transformed E. colt. Each library contained between 72 and 85% recombinant, non-parental open reading frames. Fab-expressing phage for each of the libraries were then produced from transformed E. coli ER2738 cells. The diversity of each library was between 5.3E+08 and 1.4E+09, which was calculated to be 16-42 times the theoretical library diversity.

Each of the phage libraries were then "panned" for binding to His-SUMO-Fn14 protein-coated plates. Phage remaining bound to the Fn14-coated plate were eluted with acid and propagated by infecting E. coli which, in turn, produced more phage for a subsequent round of panning. This process was repeated three times on plates coated with decreasing amounts of His-SUMO-Fn14 protein, and with increasing numbers of washes, in order to select for phage expressing higher affinity 41c variants. Phage from each round were screened by ELISA for specificity of binding to His-SUMO-Fn14, and counter-screened for non-specific binding to His-SUMO protein alone, or bovine serum albumin (BSA). Each round produced phage pools with increased ELISA signal for His-SUMO-Fn14 specific binding but little or no ELISA signal for non-Fn14 proteins.

Phage from round four of panning were used to infect *E. coli*, and the antibody variable regions from individual colonies were sequenced. From the first attempt at affinity maturation, analysis of sequencing data from round four phage showed that HCDR1, HCDR2 and LCDR3 libraries contained a myriad of diverse sequences within their respective mutated CDRs, while the HCDR3 library contained sequences that were parental, or nearly parental.

After quantification of the Fab in sequenced phagemid-infected bacterial supernatant, the relative binding affinity of each Fab to antigen was measured. The amount of Fab protein released into the supernatant was quantified by ELISA, and the relative binding affinity of each Fab to antigen was measured by ELISA by titration on His-SUMO-Fn14-coated plates. The binding of Fab clones to Fn14 was compared to the binding of parental 41c Fab in a parallel assay on the same ELISA plates. While numerous clones showed near-equivalent binding to His-SUMO-Fn14 as parental 41c Fab, none of the clones demonstrated enhanced binding relative to parental 41c.

A second attempt at finding a higher affinity 41c Fab from the randomized libraries was undertaken by creating a single, higher diversity library from the four previously screened libraries. This new, hybrid library was created by using overlapping PCR to combine the randomized CDR portion of each of the three previously panned individual VH libraries, HCDR1, HCDR2 and HCDR3 (from round 3 or round 4 panning) into a single hybrid using overlapping PCR VH library. The randomized CDR from each of the three panned VH libraries, along with some flanking framework, was individually amplified by PCR. Purified PCR product from all three were then combined into a single overlapping PCR reaction that fused all randomized CDRs into a single VH library randomized at all three CDRs. This hybrid VH library DNA was subcloned into the LCDR3 light chain library from round three panning. The resulting library, randomized at four CDRs (HCDR1, HCDR2, HCDR3 and LCDR3), was used to produce new phage, which were subsequently panned for Fn14 binding, using multiple high-stringency wash conditions in parallel. Library phage were exposed to plates coated with either high (100 μM) or low (10 μM) concentrations of His-SUMO-Fn14 for 1.5 hours at 37° C., after which time the plates were washed ten times. Plates were then incubated in wash buffer at 37° C. for either 4 or 18 hours, with or without addition of 0.5 μM soluble His-SUMO-Fn14 protein. After a final wash, plate-bound phage were eluted and propagated as before. The resulting panned library phage were exposed to the same panning method two more times.

Phage remaining after the final panning were cloned by limiting dilution and expanded. From this second attempt, numerous *E. coli* clones infected with either round two or round three panned-phage were isolated.

Phage generated from these libraries were screened by panning on recombinant His-SUMO-Fn14 protein bound to a solid-phase medium. High affinity 41c variants were enriched and clones with enhanced antigen binding were selected.

Selection of Affinity Matured Fab Clones

Affinity matured Fab clones were screened for higher affinity for Fn14 than the parental 41c. Fab secreted from individual clones was assayed for binding titration to Fn14-coated plates by ELISA. To compare clones, Fab protein was quantified for each clone and two replicate antigen binding ELISA titrations were performed as previously described. However, one plate was washed using standard wash conditions, while the replicate plate was washed with a more stringent 1.5 hour wash step incubation at 37° C. Fab clones were ranked by comparing the relative signal in each of these antigen binding ELISAs, measured at approximately 1 nM of Fab. Ten Fab clones with binding similar to, or greater than, that of recombinant parental 41c Fab were selected for further analysis.

Recombinant Fab protein was extracted from *E. coli* infected with phage and the corresponding VH and VL were determined by Sanger sequencing (data not shown). Crude bacterial supernatant containing Fab from these ten clones was analyzed by signal plasmon resonance (SPR) for the relative off-rates (Kd) on His-SUMO-Fn14-coated chips (data not shown). The top seven were reformatted to full mouse IgG1(D265A), kappa antibody, expressed from mammalian cells and purified.

Selection of Affinity Matured Clone R35B9

The selected antibodies were analyzed for biophysical properties, binding affinity in Biacore and activity in in vitro antagonist and agonist functional assays. As discussed in more detail in Example 13 below, based on biophysical properties, increased affinity to hFn14 (see Tables 8 and 9 and FIGS. 5 and 6) and performance in in vitro cell-based assays (see FIGS. 10 and FIGS. 11A, 11B and 11C), clone R35B9 was selected as the lead affinity matured version of 41c and was used in the generation of VH and VL variants.

The VH and VL amino acid sequences for clone R35B9 are shown in SEQ ID NOs 50 and 52, respectively (see Table 18 below). Whole mouse IgG1(D265A), kappa R35B9 antibody was compared to parental clone 41c, and anti-Fn14 antibody CRCBT-06-002 in evaluating its affinity to Fn14 and its performance in in vitro cell-based assays.

Antibody production and sequence analysis of clone R35B9 was performed as described in Examples 2 and 3 above.

The amino acid sequences of VH, VL and CDRs of R35B9 are summarized in the Table 18 below.

TABLE 18

Amino acid sequences of VH, VL and CDRs of R35B9

| VH | EVQLQQSGPELVKPGASVKMSCKASGYIF QDYNMHWVKQSHGKSLEWIGSINPRNGWT NYNQKFKGKATLTVNKSSRSAYMEFRSLT SEDSAVYYCASSGWFTYWGQGTLVTVSA (SEQ ID NO: 50) | VL | DVVMTQTPLTLSVAIGQPASISCKSSQSLL NSAGKTYLNWLLQRPGQSPKRLIYLVSQLD SGVPDRFTGSGSGTDFTLKISRVEAEDLGV YYCWQGTFYPWTFGGGTKLEIK (SEQ ID NO: 52) |
|---|---|---|---|
| HCDR1 | GYIFQDYNMH (SEQ ID NO: 122) | LCDR1 | KSSQSLLNSAGKTYLN (SEQ ID NO: 127) |

TABLE 18-continued

Amino acid sequences of VH, VL and CDRs of R35B9

| | | | | |
|---|---|---|---|---|
| HCDR2 | SINPRNGWTNYNQKFKG (SEQ ID NO: 123) | | LCDR2 | LVSQLDS (SEQ ID NO: 128) |
| HCDR3 | SGWFTY (SEQ ID NO: 121) | | LCDR3 | WQGTFYPWT (SEQ ID NO: 130) |

Parental 41c antibody and affinity matured clone R35B9 are compared Table 19 below. As shown, affinity maturation has resulted in five VH amino acids that differ between the two clones: T28I, T30Q, Y50S, N54R, G57W (in HCDR1 and HCDR2), and two VL amino acid changes, H98F and F99Y (in LCDR3).

TABLE 19

Comparison of 41c and R35B9

| Name | Purpose | Heavy Vector ID | Light Vector ID | HCDR1 | HCDR2 | LCDR3 |
|---|---|---|---|---|---|---|
| 41c (mouse) | parental | A291 | A290 | --T-T----- | Y---N--G--------- | ----HF--- |
| R35B9 (mouse) | affinity matured | A402 | A403 | --I-Q----- | S---R--W--------- | ----FY--- |

Example 5

Generation of R35B9 Variants

Amino acid sequence variants of R35B9 VH and VL were created by mutating cDNA at specific codons using overlapping PCR methods known to those skilled in the art. Briefly, variable region cDNAs were amplified by overlapping PCR using primers containing the desired codon substitutions. The mutated variable sequences were cloned into antibody expression vectors for the desired isotype as described previously. These variants were designed by toggling the amino acid identity, individually or in combination, between that found in 41c and that found in R35B9 at each of the seven (7) amino acid loci that are different between the two clones. R35B9-specific amino acids are comprised of VH amino acids isoleucine at position 28 (Iso28), glutamine at position 30 (Gln30), serine at position 50 (Ser50), arginine at position 54 (Arg54), and tryptophan at position 57 (Trp57), and VL amino acids phenylalanine at position 98 (Phe98) and tyrosine at position 99 (Tyr99).

The VH and VL nucleotide and amino acid sequences of R35B9 and its variants are shown in Table 20 below.

TABLE 20

Nucleotide and amino acid sequences of R35B9 VH and VL and variants.

| Description | Sequence (SEQ ID NO) |
|---|---|
| R35B9-VH | GAGGTGCAGCTGCAGCAAAGCGGCCCGGAGCTGGTGAAACCGGGTGCGAGCGTTA AAATGAGCTGCAAGGCGAGCGGTTACATTTTTCAGGATTATAATATGCATTGGGT TAAACAGAGCCACGGTAAAAGCCTGGAGTGGATCGGCTCTATTAATCCGCGTAAT GGTTGGACCAACTATAACCAAAAGTTCAAAGGCAAGGCGACCCTGACCGTGAACA AGAGCAGCCGTAGCGCGTACATGGAGTTTCGTAGCCTGACCAGCGAAGATAGCGC GGTTTACTATTGCGCGTCTTCGGGGTGGTTCACGTATTGGGGTCAAGGCACCCTG GTGACCGTTAGCGCG (SEQ ID NO: 49) |
| R35B9-VH | EVQLQQSGPELVKPGASVKMSCKASGYIFQDYNMHWVKQSHGKSLEWIGSINPRN GWTNYNQKFKGKATLTVNKSSRSAYMEFRSLTSEDSAVYYCASSGWFTYWGQGTL VTVSA (SEQ ID NO: 50) |
| R35B9-VL | GACGTGGTTATGACCCAAACCCCGCTGACCCTGAGCGTGGCGATTGGTCAGCCGG CGAGCATTAGCTGCAAGAGCAGCCAAAGCCTGCTGAACAGCGCGGGTAAAACCTA CCTGAACTGGCTGCTGCAGCGTCCGGGTCAAAGCCCGAAGCGTCTGATCTATCTG GTGAGCCAGCTGGACAGCGGTGTGCCGGACCGTTTCACCGGTAGCGGTAGCGGCA CCGACTTTACCCTGAAAATTAGCCGTGTGGAGGCGGAAGATCTGGGTGTTTACTA TTGCTGGCAAGGTACTTTTTATCCGTGGACCTTTGGTGGCGGTACCAAGCTGGAG ATCAAA (SEQ ID NO: 51) |
| R35B9-VL | DVVMTQTPLTLSVAIGQPASISCKSSQSLLNSAGKTYLNWLLQRPGQSPKRLIYL VSQLDSGVPDRFTGSGSGTDFTLKISRVEAEDLGVYYCWQGTFYPWTFGGGTKLE IK (SEQ ID NO: 52) |

TABLE 20-continued

Nucleotide and amino acid sequences of R35B9 VH and VL and variants.

| Description | Sequence (SEQ ID NO) |
|---|---|
| R35B9(Y50G57)-VH | GAGGTGCAGCTGCAGCAAAGCGGCCCGGAGCTGGTGAAACCGGGTGCGAGCGTTA<br>AAATGAGCTGCAAGGCGAGCGGTTACATTTTTCAGGATTATAATATGCATTGGGT<br>TAAACAGAGCCACGGTAAAAGCCTGGAGTGGATCGGCTaTATTAATCCGCGTAAT<br>GGTgGGACCAACTATAACCAAAAGTTCAAAGGCAAGGCGACCCTGACCGTGAACA<br>AGAGCAGCCGTAGCGCGTACATGGAGTTTCGTAGCCTGACCAGCGAAGATAGCGC<br>GGTTTACTATTGCGCGTCTTCGGGGTGGTTCACGTATTGGGGTCAAGGCACCCTG<br>GTGACCGTTAGCGCG (SEQ ID NO: 53) |
| R35B9(Y50G57)-VH | EVQLQQSGPELVKPGASVKMSCKASGYIFQDYNMHWVKQSHGKSLEWIGYINPR<br>NGGTNYNQKFKGKATLTVNKSSRSAYMEFRSLTSEDSAVYYCASSGWFTYWGQGT<br>LVTVSA (SEQ ID NO: 54) |
| R35B9(Y50A56G57)-VH | GAGGTGCAGCTGCAGCAAAGCGGCCCGGAGCTGGTGAAACCGGGTGCGAGCGTTA<br>AAATGAGCTGCAAGGCGAGCGGTTACATTTTTCAGGATTATAATATGCATTGGGT<br>TAAACAGAGCCACGGTAAAAGCCTGGAGTGGATCGGCTaTATTAATCCGCGTAAT<br>gccGGGACCAACTATAACCAAAAGTTCAAAGGCAAGGCGACCCTGACCGTGAACA<br>AGAGCAGCCGTAGCGCGTACATGGAGTTTCGTAGCCTGACCAGCGAAGATAGCGC<br>GGTTTACTATTGCGCGTCTTCGGGGTGGTTCACGTATTGGGGTCAAGGCACCCTG<br>GTGACCGTTAGCGCG (SEQ ID NO: 55) |
| R35B9(Y50A56G57)-VH | EVQLQQSGPELVKPGASVKMSCKASGYIFQDYNNHWVKQSHGKSLEWIGYINPRN<br>AGTNYNQKFKGKATLTVNKSSRSAYMEFRSLTSEDSAVYYCASSGWFTYWGQGTL<br>VTVSA (SEQ ID NO: 56) |
| R35B9(H98)-VL | GACGTGGTTATGACCCAAACCCCGCTGACCCTGAGCGTGGCGATTGGTCAGCCGG<br>CGAGCATTAGCTGCAAGAGCAGCCAAAGCCTGCTGAACAGCGCGGGTAAAACCTA<br>CCTGAACTGGCTGCTGCAGCGTCCGGGTCAAAGCCCGAAGCGTCTGATCTATCTG<br>GTGAGCCAGCTGGACAGCGGTGTGCCGGACCGTTTCACCGGTAGCGGTAGCGGCA<br>CCGACTTTACCCTGAAAATTAGCCGTGTGGAGGCGGAAGATCTGGGTGTTTACTA<br>TTGCTGGCAAGGTACTcaTTATCCGTGGACCTTTGGTGGCGGTACCAAGCTGGAG<br>ATCAAA (SEQ ID NO: 57) |
| R35B9(H98)-VL | DVVIVITQTPLTLSVAIGQPASISCKSSQSLLNSAGKTYLNWLLQRPGQSPKRLI<br>YLVSQLDSGVPDRFTGSGSGTDFTLKISRVEAEDLGVYYCWQGTHYPWTFGGGTK<br>LEIK (SEQ ID NO: 58) |
| R35B9(A56)-VH | GAGGTGCAGCTGCAGCAAAGCGGCCCGGAGCTGGTGAAACCGGGTGCGAGCGTTA<br>AAATGAGCTGCAAGGCGAGCGGTTACATTTTTCAGGATTATAATATGCATTGGGT<br>TAAACAGAGCCACGGTAAAAGCCTGGAGTGGATCGGCTCTATTAATCCGCGTAAT<br>GcTTGGACCAACTATAACCAAAAGTTCAAAGGCAAGGCGACCCTGACCGTGAACA<br>AGAGCAGCCGTAGCGCGTACATGGAGTTTCGTAGCCTGACCAGCGAAGATAGCGC<br>GGTTTACTATTGCGCGTCTTCGGGGTGGTTCACGTATTGGGGTCAAGGCACCCTG<br>GTGACCGTTAGCGCG (SEQ ID NO: 59) |
| R35B9(A56)-VH | EVQLQQSGPELVKPGASVKMSCKASGYIFQDYNNHWVKQSHGKSLEWIGSINPRN<br>AWTNYNQKFKGKATLTVNKSSRSAYMEFRSLTSEDSAVYYCASSGWFTYWGQGTLV<br>TVSA (SEQ ID NO: 60) |
| R35B9(Y50)-VH | GAGGTGCAGCTGCAGCAAAGCGGCCCGGAGCTGGTGAAACCGGGTGCGAGCGTTA<br>AAATGAGCTGCAAGGCGAGCGGTTACATTTTTCAGGATTATAATATGCATTGGGT<br>TAAACAGAGCCACGGTAAAAGCCTGGAGTGGATCGGCTaTATTAATCCGCGTAAT<br>GGTTGGACCAACTATAACCAAAAGTTCAAAGGCAAGGCGACCCTGACCGTGAACA<br>AGAGCAGCCGTAGCGCGTACATGGAGTTTCGTAGCCTGACCAGCGAAGATAGCGC<br>GGTTTACTATTGCGCGTCTTCGGGGTGGTTCACGTATTGGGGTCAAGGCACCCTG<br>GTGACCGTTAGCGCG (SEQ ID NO: 180) |
| R35B9(Y50)-VH | EVQLQQSGPELVKPGASVKMSCKASGYIFQDYNMHWVKQSHGKSLEWIGYINPRN<br>GWTNYNQKFKGKATLTVNKSSRSAYMEFRSLTSEDSAVYYCASSGWFTYWGQGTL<br>VTVSA (SEQ ID NO: 181) |
| R35B9(F99)-VL | GACGTGGTTATGACCCAAACCCCGCTGACCCTGAGCGTGGCGATTGGTCAGCCGG<br>CGAGCATTAGCTGCAAGAGCAGCCAAAGCCTGCTGAACAGCGCGGGTAAAACCTA<br>CCTGAACTGGCTGCTGCAGCGTCCGGGTCAAAGCCCGAAGCGTCTGATCTATCTG<br>GTGAGCCAGCTGGACAGCGGTGTGCCGGACCGTTTCACCGGTAGCGGTAGCGGCA<br>CCGACTTTACCCTGAAAATTAGCCGTGTGGAGGCGGAAGATCTGGGTGTTTACTA<br>TTGCTGGCAAGGTACTTTTTtTCCGTGGACCTTTGGTGGCGGTACCAAGCTGGAG<br>ATCAAA (SEQ ID NO: 199) |
| R35B9(F99)-VL | DVVIVITQTPLTLSVAIGQPASISCKSSQSLLNSAGKTYLNWLLQRPGQSPKRLI<br>YLVSQLDSGVPDRFTGSGSGTDFTLKISRVEAEDLGVYYCWQGTFFPWTFGGGTK<br>LEIK (SEQ ID NO: 200) |

The VH, VL and CDR amino acid sequences of R35B9 and its variants are also summarized in Table 1, Table 2 and Table 3 below (see also FIG. 20, FIG. 21, and FIG. 22). The complete R35B9 VH sequence is shown in Table 1 (SEQ ID NO: 50), and amino acid sequences of HCDR1 and HCDR2 containing the substitutions are shown in Table 3 (SEQ ID NOs. 122 and 123, respectively). The complete R35B9 VL sequence is shown in Table 1 (SEQ ID NO: 52), and amino acid sequence of LCDR3 containing the substitutions is shown in Table 2 (SEQ ID NO: 130). Each of these seven amino acids were reverted back individually, or in combination, to the parental 41c identity, specifically to 41c-specific VH amino acids threonine at position 28 (Thr28), threonine at position 30 (Thr30), tyrosine at position 50 (Tyr50), asparagine at position 54 (Asn54), or glycine at position 57 (Gly57), or 41c-specific VL amino acids histidine at position 98 (His98) or phenylalanine at position 99 (Phe99). The complete 41c VH and VL amino acid sequences are show in Table 1 (SEQ ID NO: 35 and 40, respectively), and the 41c HCDR1, HCDR2 and LCDR3 sequences are shown in Table 3 (SEQ ID NOs. 119, and 120) and Table 2 (SEQ ID NO: 129).

TABLE 1

Mouse VH and VL amino acid sequences of Fn14 antagonist monoclonal antibodies

| VH Name (Heavy Vector ID) | Variable Sequence (SEQ ID NO) |
|---|---|
| 41c (A291) | EVQLQQSGPELVKPGASVKMSCKASGYTFTDYNMHWVKQSHGKSLEWIG YINPNNGGTNYNQKFKGKATLTVNKSSRSAYMEFRSLTSEDSAVYYCAS SGWFTYWGQGTLVTVSA (SEQ ID NO: 35) |
| 42d | EVQLLQSGPELVKPVASVKMSCKASGYTFTDYNIHWVKQSHGKSLEWIG YINPNNGVTGYNQKFRGKATLTVNRSSNTAYMDLRSLTSEDSAVYYCTR RYGDYVHAMDCWGQGTSVTVSS (SEQ ID NO: 44) |
| R35B9 (A402, A451) | EVQLQQSGPELVKPGASVKMSCKASGYIFQDYNMHWVKQSHGKSLEWIG SINPRNGWTNYNQKFKGKATLTVNKSSRSAYMEFRSLTSEDSAVYYCAS SGWFTYWGQGTLVTVSA (SEQ ID NO: 50) |
| R35B9(Y50G57) (A448, A474) | EVQLQQSGPELVKPGASVKMSCKASGYIFQDYNMHWVKQSHGKSLEWIG YINPRNGGTNYNQKFKGKATLTVNKSSRSAYMEFRSLTSEDSAVYYCAS SGWFTYWGQGTLVTVSA (SEQ ID NO: 54) |
| R35B9(A56) (A486) | EVQLQQSGPELVKPGASVKMSCKASGYIFQDYNMHWVKQSKGKSLEWIG SINPRNAWTNYNQKFKGKATLTVNKSSRSAYMEFRSLTSEDSAVYYCAS SGWFTYWGQGLTVTVSA (SEQ ID NO: 60) |
| R35B9(Y50A56G57) (A490) | EVQLQQSGPELVKPGASVKMSCKASGYIFQDYNMHWVKQSHGKSLEWIG YINPRNAGTNYNQKFKGKATLTVNKSSRSAYMEFRSLTSEDSAVYYCAS SGWFTYWGQGTLVTVSA (SEQ ID NO: 56) |
| R35B9(Y50) (A437) | EVQLQQSGPELVKPGASVKMSCKASGYIFQDYNMHWVKQSHGKSLEWIG YINPRNGWTNYNQKFKGKATLTVNKSSRSAYMEFRSLTSEDSAVYYCAS SGWGTYWGQGTLVTVSA (SEQ ID NO: 181) |
| VL Name (Light Vector ID) | Variable Sequence (SEQ ID NO) |
| 41c (A290) | DVVMTQTPLTLSVAIGQPASISCKSSQSLLNSAGKTYLNWLLQRPGQSP KRLIYLVSQLDSGVPDRFTGSGSGTDFTLKISRVEAEDLGVYYCWQGTH FPWTFGGGTKLEIK (SEQ ID NO: 40) |
| 42d | DIQMTQSPSSLSASLGERVSLTCRASQDIGSRLNWLQQEPDGTIKRLIY ATSSLDSGVPKRFSGSRSGSDYSLTISSLESEDFVDYYCLQYASSPYTF GGGTKLEIK (SEQ ID NO: 48) |
| R35B9 (A403, A452) | DVVMTQTPLTLSVAIGQPASISCKSSQSLLNSAGKTYLNWLLQRPGQSP KRLIYLVSQLDSGVPDRFTGSGSGTDFTLKISRVEAEDLGVYYCWQGTF YPWTFGGGTKLEIK (SEQ ID NO: 52) |
| R35B9(H98) (A439) | DVVMTQTPLTLSVAIGQPASISCKSSQSLLNSAGKTYLNWLLQRPGQSP KRLIYLVSQLDSGVPDRFTGSGSGTDFTLKISRVEAEDLGVYYCWQGTH YPWTFGGGTKLEIK(SEQ ID NO: 58) |

TABLE 2

VL amino acid sequences broken down into framework and CDR sequences with corresponding SEQ ID NOs.

| Light Name Vector ID | L-FR1 | LCDR1 (Kabat) | L-FR2 | LCDR2 (Kabat) | L-FR3 | LCDR3 (Kabat) | L-FR4 |
|---|---|---|---|---|---|---|---|
| 41c VL (A290, A370) Mouse | DVVMTQTPLTL SVAIGQPASIS C (SEQ ID NO: 160) | KSSQSLLLSAG KTYLN (SEQ ID NO: 127) | WLLQRPGQSPK RLIY (SEQ ID NO: 163) | LVSQLDS (SEQ ID NO: 128) | GVPDRFTGSGS GTDFTLKISRV EAEDLGVYYC (SEQ ID NO: 169) | WQGTHPWT (SEQ ID NO: 129) | FGGGTKLEIK (SEQ ID NO: 171) |

TABLE 2-continued

VL amino acid sequences broken down into framework and CDR sequences with corresponding SEQ ID NOs.

| Light Name (Vector ID) | L-FR1 | LCDR1 (Kabat) | L-FR2 | LCDR2 (Kabat) | L-FR3 | LCDR3 (Kabat) | L-FR4 |
|---|---|---|---|---|---|---|---|
| R35B9 VL (A403, A452) Mouse | DVVMTQTPLTL SVAIGQPASIS C (SEQ ID NO: 160) | KSSQSLLLSAG KTYLN (SEQ ID NO: 127) | WLLQRPGQSPK RLIY (SEQ ID NO: 163) | LVSQLDS (SEQ ID NO: 128) | GVPDRFTGSGS GTDFTLKISRV EAEDLGVYYC (SEQ ID NO: 169) | WGQGTFYPWT (SEQ ID NO: 130) | FGGGTKLEIK (SEQ ID NO: 171) |
| AA102700.1 (N/A) Human | DVVMTQSPLSL PVTLGQPASIS C (SEQ ID NO: 161) | — | WFQQRPGQSPR RLIY (SEQ ID NO: 164) | — | GVPDRFSGSGS GTDFTLKISRV EAEDVGVYYC (SEQ ID NO: 170) | — | FGGGTKVEIK (SEQ ID NO: 172) |
| hzR35B9-LV0 (A467) Humanized | DVVMTQSPLSL PVTLGQPASIS C (SEQ ID NO: 161) | KSSQSLLLSAG KTYLN (SEQ ID NO: 127) | WFQQRPGQSPR RLIY (SEQ ID NO: 164) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9-LV1a (A468) Humanized | DVVMTQSPLSL PVTLGQPASIS C (SEQ ID NO: 161) | KSSQSLLLSAG KTYLN (SEQ ID NO: 127) | WLQQRPGQSPR RLIY (SEQ ID NO: 165) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9-LV1b (A469) Humanized | DVVMTQSPLSL PVTLGQPASIS C (SEQ ID NO: 161) | KSSQSLLLSAG KTYLN (SEQ ID NO: 127) | WFLQRPGQSPR RLIY (SEQ ID NO: 166) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9-LV3a (A470) Humanized | DVVMTQSPLSL PVTIGQPASIS C (SEQ ID NO: 162) | KSSQSLLLSAG KTYLN (SEQ ID NO: 127) | WFLQRPGQSPK RLIY (SEQ ID NO: 167) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9-LV3b (A471) Humanized | DVVMTQSPLSL PVTIGQPASIS C (SEQ ID NO: 162) | KSSQSLLLSAG KTYLN (SEQ ID NO: 127) | WLLQRPGQSPR RLIY (SEQ ID NO: 168) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9-LV4 (A472) Humanized | DVVMTQSPLSL PVTIGQPASIS C (SEQ ID NO: 162) | KSSQSLLLSAG KTYLN (SEQ ID NO: 127) | WLLQRPGQSPK RLIY (SEQ ID NO: 163) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9-LV5 (A473) Humanized | DVVMTQSPLSL PVTIGQPASIS C (SEQ ID NO: 162) | KSSQSLLLSAG KTYLN (SEQ ID NO: 127) | WLLQRPGQSPK RLIY (SEQ ID NO: 163) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKLEIK (SEQ ID NO: 171) |
| hzR35B9(H98)-LV1a (A518) Humanized | DVVMTQSPLSL PVTLGQPASIS C (SEQ ID NO: 161) | KSSQSLLLSAG KTYLN (SEQ ID NO: 127) | WLQQRPGQSPR RLIY (SEQ ID NO: 165) | LVSQLDS (SEQ ID NO: 128) | GVPDRFSGSGS GTDFTLKISRV EAEDVGVYYC (SEQ ID NO: 170) | WQGTHYPWT (SEQ ID NO: 131) | FGGGTKVEIK (SEQ ID NO: 172) |
| hzR35B9(A56)-LV2a (A651) Humanized | DVVMTQSPLSL PVTLGQPASIS C (SEQ ID NO: 161) | KSSQSLLLSAG KTYLN (SEQ ID NO: 127) | WLQQRPGQSPR RGIY (SEQ ID NO: 252) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9(A56)-LV2b (A652) Humanized | DVVMTQSPLSL PVTLGQPASIS C (SEQ ID NO: 161) | KSSQSLLLSAG KTYLN (SEQ ID NO: 127) | WLQQRPGQSPR RLAY (SEQ ID NO: 253) | LVSQLDS (SEQ ID NO: 128) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |

TABLE 2-continued

VL amino acid sequences broken down into framework and CDR sequences with corresponding SEQ ID NOs.

| Light Name (Vector ID) | L-FR1 | LCDR1 (Kabat) | L-FR2 | LCDR2 (Kabat) | L-FR3 | LCDR3 (Kabat) | L-FR4 |
|---|---|---|---|---|---|---|---|
| hzR35B9(A56)-LV2c (A653) Humanized | DVVMTQSPLSL PVTLGQPASIS C (SEQ ID NO: 161) | KSSQSLLLSAG KTYLN (SEQ ID NO: 127) | WLQQRPGQSPR RLIY (SEQ ID NO: 165) | LVSELDS (SEQ ID NO: 255) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9(A56)-LV2d (A654) Humanized | DVVMTQSPLSL PVTLGQPASIS C (SEQ ID NO: 161) | KSSQSLLLSAG KTYLN (SEQ ID NO: 127) | WLQQRPGQSPR RLIY (SEQ ID NO: 165) | LVSQLDD (SEQ ID NO: 254) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |
| hzR35B9(A56)-LV2f (A656) Humanized | DVVMTQSPLSL PVTLGQPASIS C (SEQ ID NO: 161) | KSSQSLLLSAG KTYLN (SEQ ID NO: 127) | WLQQRPGQSPR RLIY (SEQ ID NO: 165) | LVAQLDS (SEQ ID NO: 256) | GVPDRFSGSGS GTDFTLKISRV EAEDVGVYYC (SEQ ID NO: 170) | WGQGTFYPWT (SEQ ID NO: 130) | FGGGTKVEIK (SEQ ID NO: 172) |

TABLE 3

VH amino acid sequences broken down into framework and CDR sequences with corresponding SEQ ID NOs

| Name (Heavy Vector ID) Species | H-FR1 | H-CDR1 (Chothia) | H-FR2 | H-CDR2 (Kabat) | H-FR3 | H-CDR3 (Kabat) | H-FR4 |
|---|---|---|---|---|---|---|---|
| 41c VH (A291, A369) Mouse | EVQLQQSGP ELVKPGASV KMSCKAS (SEQ ID NO: 132) | GYTFTDYNMH (SEQ ID NO: 119) | WVKQSHGKSL EWIG (SEQ ID NO: 138) | YINPNNGGTN YNQKFKG (SEQ ID NO: 120) | KATLTVNKSS RSAYMEFRSL TSEDSAVYYC AS (SEQ ID NO: 145) | SGWFTY (SEQ ID NO: 121) | WGQGTLVTV SA (SEQ ID NO: 158) |
| R35B9 VH (A402) Mouse | EVQLQQSGP ELVKPGASV KMSCKAS (SEQ ID NO: 132) | GYIFQDYNMH (SEQ ID NO: 122) | WVKQSHGKSL EWIG (SEQ ID NO: 138) | SINPRNGWTN YNQKFKG (SEQ ID NO: 123) | KATLTVNKSS RSAYMEFRSL TSEDSAVYYC AS (SEQ ID NO: 145) | SGWFTY (SEQ ID NO: 121) | WGQGTLVTV SA (SEQ ID NO: 158) |
| R35B9(Y50) VH (A437) Mouse | EVQLQQSGP ELVKPGASV KMSCKAS (SEQ ID NO: 132) | GYIFQDYNMH (SEQ ID NO: 122) | WVKQSHGKSL EWIG (SEQ ID NO: 138) | YINPRNGWTN YNQKFKG (SEQ ID NO: 149) | KATLTVNKSS RSAYMEFRSL TSEDSAVYYC AS (SEQ ID NO: 145) | SGWFTY (SEQ ID NO: 121) | WGQGTLVTV SA (SEQ ID NO: 158) |
| R35B9(Y50G57) VH (A447, A474) Mouse | EVQLQQSGP ELVKPGASV KMSCKAS (SEQ ID NO: 132) | GYIFQDYNMH (SEQ ID NO: 122) | WVKQSHGKSL EWIG (SEQ ID NO: 138) | YINPRNGGTN YNQKFKG (SEQ ID NO: 125) | KATLTVNKSS RSAYMEFRSL TSEDSAVYYC AS (SEQ ID NO: 145) | SGWFTY (SEQ ID NO: 121) | WGQGTLVTV SA (SEQ ID NO: 158) |
| hSGHI(1) (N/A) Human Template | QVQLVQSGA EVKKPGASV KVSCKAS (SEQ ID NO: 133) | — | WVRQAPGQGL EWMG (SEQ ID NO: 173) | — | RVTITADTST STAYMELSSL RSEDTAVYYC AR (SEQ ID NO: 174) | — | WGQGTLVTV SS (SEQ ID NO: 159) |
| hzR35B9-HV0 (A700) Humanized | QVQLVQSGA EVKKPGASV KVSCKAS (SEQ ID NO: 133) | GYIFQDYNMH (SEQ ID NO: 122) | WVRQAPGQGL EWMG (SEQ ID NO: 173) | SINPRNGWTN YNQKFKG (SEQ ID NO: 123) | RVTITADTST STAYMELSSL RSEDTAVYYC AR (SEQ ID NO: 174) | SGWFTY (SEQ ID NO: 121) | WGQGTLVTV SS (SEQ ID NO: 159) |

TABLE 3-continued

VH amino acid sequences broken down into framework
and CDR sequences with corresponding SEQ ID NOs

| Name (Heavy Vector ID) Species | H-FR1 | H-CDR1 (Chothia) | H-FR2 | H-CDR2 (Kabat) | H-FR3 | H-CDR3 (Kabat) | H-FR4 |
|---|---|---|---|---|---|---|---|
| hzR35B9-HV5a (A454) Humanized | QVQLVQSGA EVKKPGASV KVSCKAS (SEQ ID NO: 133) | GYIFQDYNMH (SEQ ID NO: 122) | WVRQAPGQGL EWIG (SEQ ID NO: 139) | SINPRNGWTN YNQKFKG (SEQ ID NO: 123) | RATITADTST STAYMELSSL RSEDTAVYYC AS (SEQ ID NO: 146) | SGWFTY (SEQ ID NO: 121) | WGQGTLVTV SS (SEQ ID NO: 159) |
| hzR35B9-HV5b (A455) Humanized | QVQLVQSGA EVVKPGASV KVSCKAS (SEQ ID NO: 134) | GYIFQDYNMH (SEQ ID NO: 122) | WVRQAHGQG LEWMG (SEQ ID NO: 140) | SINPRNGWTN YNQKFKG (SEQ ID NO: 123) | RVTITADTST STAYMELSSL RSEDTAVYYC AS (SEQ ID NO: 147) | SGWFTY (SEQ ID NO: 121) | WGQGTLVTV SS (SEQ ID NO: 159) |
| hzR35B9-HV6b (A456) Humanized | QVQLVQSGA EVVKPGASV KVSCKAS (SEQ ID NO: 134) | GYIFQDYNMH (SEQ ID NO: 122) | WVRQAHGQS LEWMG (SEQ ID NO: 141) | SINPRNGWTN YNQKFKG (SEQ ID NO: 123) | RVTITADTST STAYMELSSL RSEDTAVYYC AS (SEQ ID NO: 147) | SGWFTY (SEQ ID NO: 121) | WGQGTLVTV SS (SEQ ID NO: 159) |
| hzR35B9-HV6b (A457) Humanized | QVQLVQSGA EVKGPGASV KVSCKAS (SEQ ID NO: 133) | GYIFQDYNMH (SEQ ID NO: 122) | WVRQAHGQG LEWIG (SEQ ID NO: 142) | SINPRNGWTN YNQKFKG (SEQ ID NO: 123) | RATITADKST STAYMELSSL RSEDTAVYYC AR (SEQ ID NO: 148) | SGWFTY (SEQ ID NO: 121) | WGQGTLVTV SS (SEQ ID NO: 159) |
| hzR35B9-HV6c (A458) Humanized | QVQLVQSGA EVKGPGASV KVSCKAS (SEQ ID NO: 133) | GYIFQDYNMH (SEQ ID NO: 122) | WVRQAHGQG LEWIG (SEQ ID NO: 142) | SINPRNGWTN YNQKFKG (SEQ ID NO: 123) | RATITADTST STAYMELSSL RSEDTAVYYC AS (SEQ ID NO: 146) | SGWFTY (SEQ ID NO: 121) | WGQGTLVTV SS (SEQ ID NO: 159) |
| hzR35B9-HV7a (A459) Humanized | QVQLVQSGA EVVKPGASV KVSCKAS (SEQ ID NO: 134) | GYIFQDYNMH (SEQ ID NO: 122) | WVRQAHGQS LEWMG (SEQ ID NO: 141) | SINPRNGWTN YNQKFKG (SEQ ID NO: 123) | RVTITADTST RTAYMELSSL RSEDTAVYYC AS (SEQ ID NO: 150) | SGWFTY (SEQ ID NO: 121) | WGQGTLVTV SS (SEQ ID NO: 159) |
| hzR35B9-HV7b (A460) Humanized | QVQLVQSGA EVVKPGASV KVSCKAS (SEQ ID NO: 134) | GYIFQDYNMH (SEQ ID NO: 122) | WVRQAHGQG LEWMG (SEQ ID NO: 140) | SINPRNGWTN YNQKFKG (SEQ ID NO: 123) | RVTITADKST RTAYMELSSL RSEDTAVYYC AS (SEQ ID NO: 151) | SGWFTY (SEQ ID NO: 121) | WGQGTLVTV SS (SEQ ID NO: 159) |
| hzR35B9-HV7c (A461) Humanized | QVQLVQSGA EVKGPGASV KVSCKAS (SEQ ID NO: 133) | GYIFQDYNMH (SEQ ID NO: 122) | WVKQAPGGQ LEWIG (SEQ ID NO: 143) | SINPRNGWTN YNQKFKG (SEQ ID NO: 123) | KATITADTST STAYMELSSL RSEDTAVYYC AS (SEQ ID NO: 152) | SGWFTY (SEQ ID NO: 121) | WGQGTLVTV SS (SEQ ID NO: 159) |
| hzR35B9-HV9a (A462) Humanized | QVQLVQSGA EVKKPGASV KMSCKAS (SEQ ID NO: 135) | GYIFQDYNMH (SEQ ID NO: 122) | WVRQAPGQG LEWIG (SEQ ID NO: 139) | SINPRNGWTN YNQKFKG (SEQ ID NO: 123) | RATLTVDTST STAYMEFSSL RSEDTAVYYC AS (SEQ ID NO: 153) | SGWFTY (SEQ ID NO: 121) | WGQGTLVTV SS (SEQ ID NO: 159) |
| hzR35B9-HV9b (A463) Humanized | QVQLVQSGA EVKGPGASV KVSCKAS (SEQ ID NO: 133) | GYIFQDYNMH (SEQ ID NO: 122) | WVKQAHGQS LEWIG (SEQ ID NO: 144) | SINPRNGWTN YNQKFKG (SEQ ID NO: 123) | RATITADTST STAYMEFSSL RSEDTAVYYC AS (SEQ ID NO: 154) | SGWFTY (SEQ ID NO: 121) | WGQGTLVTV SS (SEQ ID NO: 159) |

TABLE 3-continued

VH amino acid sequences broken down into framework
and CDR sequences with corresponding SEQ ID NOs

| Name (Heavy Vector ID) Species | H-FR1 | H-CDR1 (Chothia) | H-FR2 | H-CDR2 (Kabat) | H-FR3 | H-CDR3 (Kabat) | H-FR4 |
|---|---|---|---|---|---|---|---|
| hzR35B9-HV10 (A464) Humanized | QVQLVQSGA EVKGPGASV KVSCKAS (SEQ ID NO: 133) | GYIFQDYNMH (SEQ ID NO: 122) | WVRQAHGQG LEWIG (SEQ ID NO: 142) | SINPRNGWTN YNQKFKG (SEQ ID NO: 123) | KATITADKST RTAYMEFSSL RSEDTAVYYC AS (SEQ ID NO: 155) | SGWFTY (SEQ ID NO: 121) | WGQGTLVTV SS (SEQ ID NO: 159) |
| hzR35B9-HV11 (A465) Humanized | QVQLVQSGP EVVKPGASV KVSCKAS (SEQ ID NO: 136) | GYIFQDYNMH (SEQ ID NO: 122) | WVRQAHGQS LEWMG (SEQ ID NO: 141) | SINPRNGWTN YNQKFKG (SEQ ID NO: 123) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9-HV18 (A466) Humanized | EVQLVQSGP EVVKPGASV KMSCKAS (SEQ ID NO: 137) | GYIFQDYNMH (SEQ ID NO: 122) | WVKQAHGQS LEWIG (SEQ ID NO: 144) | SINPRNGWTN YNQKFKG (SEQ ID NO: 123) | KATLTVDKST RTAYMEFSSL RSEDTAVYYC AS (SEQ ID NO: 157) | SGWFTY (SEQ ID NO: 121) | WGQGTLVTV SS (SEQ ID NO: 159) |
| hzR35B9(A56)- HV11 (A512) Humanized | QVQLVQSGP EVVKPGASV KVSCKAS (SEQ ID NO: 136) | GYIFQDYNMH (SEQ ID NO: 122) | WVRQAHGQS LEWMG (SEQ ID NO: 141) | SINPRNAWTN YNQKFKG (SEQ ID NO: 124) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9 (Y50A56G57)- VH7b (A515) Humanized | QVQLVQSGA EVVKPGASV KVSCKAS (SEQ ID NO: 134) | GYIFQDYNMH (SEQ ID NO: 122) | WVRQAHGQG LEWMG (SEQ ID NO: 140) | YINPRNAGTN YNQKFKG (SEQ ID NO: 126) | RVTITADKST RTAYMELSSL RSEDTAVYYC AS (SEQ ID NO: 151) | SGWFTY (SEQ ID NO: 121) | WGQGTLVTV SS (SEQ ID NO: 159) |
| hzR35B9(A56)- HV7c (A553) Humanized | QVQLVQSGA EVKGPGASV KVSCKAS (SEQ ID NO: 133) | GYIFQDYNMH (SEQ ID NO: 122) | WVKQAPGGQ LEWIG (SEQ ID NO: 143) | SINPRNAWTN YNQKFKG (SEQ ID NO: 124) | KATITADTST STAYMELSSL RSEDTAVYYC AS (SEQ ID NO: 152) | SGWFTY (SEQ ID NO: 121) | WGQGTLVTV SS (SEQ ID NO: 159) |
| hzR35B9(A56)- HV12a (A631) Humanized | QVQLVQSGP EVVKPGASV KVSCKAS (SEQ ID NO: 136) | GYIFQDYNMH (SEQ ID NO: 122) | WVRQADGQS LEWMG (SEQ ID NO: 240) | SINPRNAWTN YNQKFKG (SEQ ID NO: 124) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9(A56)- HV12b (A632) Humamized | QVQLVQSGP EVVKPGASV KVSCKAS (SEQ ID NO: 136) | GYIFQDYNMH (SEQ ID NO: 122) | WVRQAPGQS LEWMG (SEQ ID NO: 241) | SINPRNAWTN YNQKFKG (SEQ ID NO: 124) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9(A56)- HV13a (A633) Humanized | QVQLVQSGP EVVKPGASV KVSCKAS (SEQ ID NO: 136) | GYIFQDYNMH (SEQ ID NO: 122) | WVREAHGQS LEWMG (SEQ ID NO: 242) | SINPRNAWTN YNQKFKG (SEQ ID NO: 124) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9(A56)- HV13b (A634) Humanized | QVQLVQSGP EVVKPGASV KVSCKAS (SEQ ID NO: 136) | GYIFQDYNMH (SEQ ID NO: 122) | WVRQAHGQS LEWMG (SEQ ID NO: 141) | SINPRNAWTN YNQKFGG (SEQ ID NO: 247) | RATITVDKST RTAYMELSSL RSEDTAVYYC AS (SEQ ID NO: 156) | SGWFTY (SEQ ID NO: 121) | WGQGTLVTV SS (SEQ ID NO: 159) |

TABLE 3-continued

VH amino acid sequences broken down into framework
and CDR sequences with corresponding SEQ ID NOs

| Name (Heavy Vector ID) Species | H-FR1 | H-CDR1 (Chothia) | H-FR2 | H-CDR2 (Kabat) | H-FR3 | H-CDR3 (Kabat) | H-FR4 |
|---|---|---|---|---|---|---|---|
| hzR35B9(A56)-HV13d (A636) Humanized | QVQLVQSGP EVVKPGASV KVSCKAS (SEQ ID NO: 136) | GYIFQDYNMH (SEQ ID NO: 122) | WGRQAGGQS KEWMG (SEQ ID NO: 243) | SINPRNAWTN YNQKFKG (SEQ ID NO: 124) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9(A56)-HV13f (A638) Humanized | QVQLVQSGP EVVKPGASV KVSCKAS (SEQ ID NO: 136) | GYIFQDYNMH (SEQ ID NO: 122) | WVRQAHGQS LEWMG (SEQ ID NO: 141) | SINPRNAWTN YNDKFKG (SEQ ID NO: 249) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9(A56)-HV13g (A639) Humanized | QVQLVQSGP EVVKPGASV KVSCKAS (SEQ ID NO: 136) | GYIFQDYNMH (SEQ ID NO: 122) | WVRQAHGDS LEWMG (SEQ ID NO: 244) | SINPRNAWTN YNQKFKG (SEQ ID NO: 124) | RATITVDKST RTAYMELSSL RSEDTAVYYC AS (SEQ ID NO: 156) | SGWFTY (SEQ ID NO: 121) | WGQGTLVTV SS (SEQ ID NO: 159) |
| hzR35B9(A56)-HV16 (A641) Humanized | QVQLQQSGP EVVKPGASV KVSCKAS (SEQ ID NO: 238) | GYIFQDYNMH (SEQ ID NO: 122) | WVKQAHGQS LEWMG (SEQ ID NO: 245) | SINPRNAWTN YNQKFKG (SEQ ID NO: 124) | KATLTVDKST RTAYMELSSL RSEDTAVYYC AS (SEQ ID NO: 251) | SGWFTY (SEQ ID NO: 121) | WGQGTLVTV SS (SEQ ID NO: 159) |
| hzR35B9(A56)-HV167a (A642) Humanized | QVQLQQSGP EVVKPGASV KVSCKAS (SEQ ID NO: 238) | GYIFQDYNMH (SEQ ID NO: 122) | WVKQGHGQS LEWMG (SEQ ID NO: 246) | SINPRNAWTN YNQKFKG (SEQ ID NO: 124) | KATLTVDKST RTAYMELSSL RSEDTAVYYC AS (SEQ ID NO: 251) | SGWFTY (SEQ ID NO: 121) | WGQGTLVTV SS (SEQ ID NO: 159) |
| hzR35B9(A56)-HV17b (A643) Humanized | QVQLQQSGP EVVKPGASV KVSCKAS (SEQ ID NO: 238) | GYIFQDYNMH (SEQ ID NO: 122) | WVKQAHGQS LEWMG (SEQ ID NO: 245) | SINPRNAWTN YNQKFHG (SEQ ID NO: 250) | KATLTVDKST RTAYMELSSL RSEDTAVYYC AS (SEQ ID NO: 251) | SGWFTY (SEQ ID NO: 121) | WGQGTLVTV SS (SEQ ID NO: 159) |
| hzR35B9(A56)-HV17d (A645) Humanized | QVQLQQSGP EVVKPGASV KVSCKAS (SEQ ID NO: 238) | GYIFQDYNMH (SEQ ID NO: 122) | WVKQAHGQS LEWMG (SEQ ID NO: 245) | SINPRNAWTN YNQKFDG (SEQ ID NO: 248) | KATLTVDKST RTAYMELSSL RSEDTAVYYC AS (SEQ ID NO: 251) | SGWFTY (SEQ ID NO: 121) | WGQGTLVTV SS (SEQ ID NO: 159) |
| hzR35B9(A56)-HV17g (A648) Humanized | QVQLQQSGP EVVKPGASV KVSCKAS (SEQ ID NO: 238) | GYIFQDYNMH (SEQ ID NO: 122) | WVKQAHGQS LEWMG (SEQ ID NO: 245) | SINPRNAWTN YNDKFKG (SEQ ID NO: 249) | KATLTVDKST RTAYMELSSL RSEDTAVYYC AS (SEQ ID NO: 251) | SGWFTY (SEQ ID NO: 121) | WGQGTLVTV SS (SEQ ID NO: 159) |

TABLE 3-continued

VH amino acid sequences broken down into framework and CDR sequences with corresponding SEQ ID NOs

| Name (Heavy Vector ID) Species | H-FR1 | H-CDR1 (Chothia) | H-FR2 | H-CDR2 (Kabat) | H-FR3 | H-CDR3 (Kabat) | H-FR4 |
|---|---|---|---|---|---|---|---|
| hzR35B9(A56)-HV17i (A650) Humamized | QVQLQQSGP EVAKPGASV KVSCKAS (SEQ ID NO: 239) | GYIFQDYNMH (SEQ ID NO: 122) | WVKQAHGQS LEWMG (SEQ ID NO: 245) | SINPRNAWTN YNQKFKG (SEQ ID NO: 124) | KATLTVDKST RTAYMELSSL RSEDTAVYYC AS (SEQ ID NO: 251) | SGWFTY (SEQ ID NO: 121) | WGQGTLVTV SS (SEQ ID NO: 159) |

Whole antibodies were produced using methods described above with various combinations heavy and light chains containing various 41c- and R35B9-derived VH and VL amino acid identities. Exemplary antibodies are listed in Table 21 below. These antibody variants were tested for binding affinity and/or in vitro functional activity.

TABLE 21

R35B39 Variants

| Name | Purpose | Heavy Vector ID | Light Vector ID | CDR-H | CDR-L |
|---|---|---|---|---|---|
| 41c (mouse) | parental | A291 | A290 | 41c | 41c |
| R35B9 (mouse) | affinity matured | A402 | A403 | R35B9 | R35B9 |
| A448/A403 | variant(mo) | A448 | A403 | R35B9(Y50G57) | R35B9 |
| A428/A403 | variant(mo) | A428 | A403 | R35B9(G57) | R35B9 |
| A437/A403 | variant(mo) | A437 | A403 | R35B9(Y50) | R35B9 |
| A402/A440 | variant(mo) | A402 | A440 | R35B9 | R35B9(F99) |
| A402/A439 | variant(mo) | A402 | A439 | R35B9 | R35B9(H98) |
| A402/A290 | variant(mo) | A402 | A290 | R35B9 | 41c |
| A448/A439 | variant(mo) | A448 | A439 | R35B9(Y50G57) | R35B9(H98) |
| A437/A290 | variant(mo) | A437 | A290 | R35B9(Y50) | 41c |
| A448/A290 | variant(mo) | A448 | A290 | R35B9(Y50G57) | 41c |
| A428/A290 | variant(mo) | A428 | A290 | R35B9(G57) | 41c |
| A291/A403 | variant(mo) | A291 | A403 | 41c | R35B9 |
| A436/A403 | variant(mo) | A436 | A403 | R35B9(T30) | R35B9 |
| A438/A403 | variant(mo) | A438 | A403 | R35B9(N54) | R35B9 |
| A291/A449 | variant(mo) | A291 | A449 | 41c | 41C(R101) |
| A435/A403 | variant(mo) | A435 | A403 | R35B9(T28) | R35B9 |
| A450/A290 | variant(mo) | A450 | A290 | 41C(R28Q30R54) | 41c |

As a result, three CDR substitution variants were selected: R35B9(Y50G57) VH, in which R35B9 VH amino acid positions 50 and 57 within HCDR2 were reverted to 41c amino acids tyrosine (Tyr) and glycine (Gly), respectively (VH amino acid sequence shown in Table 1, SEQ ID NO: 54); R35B9(Y50) VH, in which R35B9 VH amino acid position 50 within HCDR2 was reverted to 41c amino acids tyrosine (Tyr) (amino acid sequence shown in Table 1, SEQ ID NO: 181); and R35B9(H98) VL, in which R35B9 VL LCDR3 amino acid position 98 was reverted to 41c amino acid histidine (His) (amino acid sequence shown in Table 1, SEQ ID NO: 58).

Three whole mouse IgG1 (D265A), kappa antibody clones were produced using these variant heavy or light chain variable sequences (see antibodies A448/A439, A437/A290, and A448/A290 bolded in Table 21). Specifically, antibodies A448/A290 and A448/A439 were produced by expressing a heavy chain containing the R35B9(Y50G57) VH (A448) (SEQ ID NO: 54) combined with a light chain containing the 41c VL (A290) (SEQ ID NO: 40), or a light chain light chain containing the R35B9(H98) VL(A439) (SEQ ID NO: 58), respectively. Antibody A437/A290 was produced by expressing a heavy chain containing the R35B9 (Y50) VH (A437) (SEQ ID NO: 181) combined with a light chain light chain containing 41c VL (A290) (SEQ ID NO: 40). Resulting purified antibodies were tested for binding and functional activity in in vitro assays.

Example 6

Functional Assessment of R35B9 Variants

Anti-Fn14 mAb R35B9 Optimized Clones Antagonize TWEAK-Induced IL-8 Expression

The optimized clones were assayed for their ability to block TWEAK-induced IL-8 release in HRMC. HRMC were incubated with 0.8325 nM anti-Fn14 or isotype control mAbs for 30 minutes and then rhTWEAK was added to the wells at 250 ng/mL for 24 h. Supernatants were harvested and tested for IL-8 using an IL-8 ELISA kit. All optimized clones tested (A437/A290, A448/A290, and A448/A439) retained the ability to block TWEAK-induced IL-8 at a level similar to R35B9 and at a superior level compared to CRCBT-06-002 and ITEM-4 at antibody concentrations of 0.125 μg/mL (0.833 nM) (see FIG. 12).

Anti-Fn14 mAb R35B9 Optimized Clones do not Agonize TWEAK-Induced IL-8 Expression Optimized R35B9 clones (i.e., A437/A290, A448/A290, and A448/A439) were also tested for agonist activity in HRMC. All three optimized clones showed no detectable agonist activity (IL-8 release) at a mAb concentration as high as 40 µg/mL (266 nM) which was the highest concentration tested (see FIG. 16A and FIG. 16B). As previously observed, ITEM-4 demonstrates dose-dependent agonist activity at higher mAb concentrations (see FIG. 16A).

Anti-Fn14 mAb R35B9 Optimized Clones Antagonize TWEAK-Induced ICAM-1 Expression

To determine the ability of the optimized clones to block fibrotic mediators, they were tested for their ability to block TWEAK-induced ICAM-1 upregulation on HRMC. The ICAM-1 expression assay was repeated with the addition of three of the optimized clones, A437/A290, A448/A290 and A448/A439. Briefly, HRMC were incubated with media alone or with anti-Fn14 or isotype control mAbs at varied concentrations for 30 minutes and then media with or without rhTWEAK (250 ng/mL) was added to the cells for 24 hours. Cells were dissociated with trypsin and stained for surface ICAM-1 expression. Intensity of surface ICAM-1 expression was measured using a flow cytometer (BD Biosciences Fortessa), gated on live cells.

The results demonstrate that the optimized clones are able to block TWEAK-induced upregulation of surface ICAM-1 to a similar extent, as R35B9 and that all three of these clones are able to block this upregulation better than CRCBT-06-002 and ITEM-4 (FIG. 19 and Table 12).

TABLE 12

Anti-Fn14 R35B9 optimized clones antagonize TWEAK-induced ICAM-1 expression on HRMC

|  | mAb (0.1 µg/mL) | ICAM-1 MFI* |
| --- | --- | --- |
| 250 ng/mL rhTWEAK | 41c | 13,107 |
|  | R35B9 | 5,828 |
|  | A437/A290 | 5,112 |
|  | A448/A290 | 6,429 |
|  | A448/A439 | 5,484 |
|  | ITEM-4 | 9,620 |
|  | CRCBT | 11,785 |
|  | mIgG1 | 33,254 |
|  | mIgG2b | 34,696 |

(MFI* = mean fluorescence intensity.)

Example 7

Removal of Liability Sequence within R35B9 VH

The clones A448/A290 and A448/A439 described above as well as R35B9 were chosen to move forward for humanization and elimination of the potential deamidation site located at heavy chain CDR2. Asparagine residues within antibody CDRs are known to be susceptible to deamidation or isomerization events (Chelius, D., et al., Anal Chem, 2005, 77(18):6004-11; Sydow, J. F., et al., PLoS One, 2014, 9(6):100736), particularly when a glycine residue is bonded at the carboxy side of the asparagine, e.g., Asn-Gly (NG). Such an NG sequence is present in HCDR2 of 41c and R35B9 at positions 55-56. To determine if substitution by other amino acids at either the asparagine or the glycine position is possible while retaining antigen binding, three variants were generated. Either glutamine or aspartic acid was substituted at position 55, represented by Q55 or D55, respectively, or alanine was substituted at position 56 (A56) within a R35B9 heavy chain, and then respective mouse antibodies were produced containing each of the single amino acid substitutions.

Based on Biacore analysis, it was determined that the R35B9(A56) VH single substitution contained in antibody A486/A452 (VH and VL amino acid sequences shown in SEQ ID NOs. 60 and 52, respectively, Table 1) retained the best binding affinity (see Table 4 below). Thus, this A56 substitution was introduced into several R35B9 antibody variants including R35B9(Y50G57) VH (A448) (shown in nucleotide SEQ ID NO: 53 and amino acid SEQ ID NO: 54), creating R35B9(Y50A56G57) VH (A490) (shown in nucleotide SEQ ID NO: 55, amino acid SEQ ID NO: 56, Table 1). It was also used to produce chimeric mouse-human IgG4null, kappa antibody A490/A452 containing R35B9 (Y50A56G57) VH (A490) heavy chain with R35B9 VL light chain (A452) (shown in Table 1, SEQ ID NO: 52).

TABLE 4

Binding kinetics of deamidation fixed R35B9(A56) mAb to human Fn14

|  | His-Sumo-huFn14 Concentration Range 0.111 nM-9 nM | | | |
| --- | --- | --- | --- | --- |
| Anti-Fn14 mAbs | kd (1/s) | ka (1/Ms) | (KD) | Rmax |
| R35B9 (A451/A452) | 9.938E−04 | 7525000 | 0.1321 nM | 31.85 |
| R35B9 (A56) (A486/A452) | 3.541E−04 | 4961000 | 71.38 pM | 61.16 |

Example 8

Humanization of R35B9

Selection of Human Antibody Framework Regions (FR)

Humanized R35B9 variant antibodies, collectively referred to as hzR35B9 antibodies, were designed using various VL and VH amino acid sequences based on sequence homology and immunogenicity risk assessment.

First, in order to select amino acids of known human antibody framework regions (FRs) suitable for the grafting of the amino acid sequences of R35B9 antibody CDRs, the BLASTP database (The National Center for Biotechnology Information) was used to search for amino acid sequences of human antibody FRs having high homology to the amino acid sequences of VL and VH FRs of the R35B9 antibody. The amino acid sequences of FRs shown in GenBank Accession No. AAQ02700.1 (immunoglobulin κ light chain variable region, partial) and PIR Accession No. PN0444 (Ig heavy chain V region precursor—human (fragment)) had the highest homology to the amino acid sequences of FRs of VL and VH of the R35B9 antibody.

Immunogenicity risk prediction was carried out using Epibase In Silico Services for Biotherapeutics (Lonza, Basil Switzerland). The predicted immunogenicity risk of the sequence obtained by grafting the CDR to the FR sequence of the above VH had no significant decrease. Therefore, homology with the human FR consensus sequence reported by Kabat et al. Sequences of Proteins of Immunological Interest, US Dept. Health and Human Services (1991) was compared. hSGHI had the highest homology to FR within the VH of the R35B9 antibody so we then examined transplanting CDRs into hSGHI. When the consensus sequence was used, the predicted immunogenicity risk using hSGHI was preferable to using PN0444.

Generation of Humanized hzR35B9 HV0 and hzR35B9 LV0

Accordingly, the amino acid sequences of LCDR1, LCDR2, and LCDR3 (as defined by Kabat) of the VL of R35B9 shown in SEQ ID NOs: 127, 128, and 130, respectively, were grafted to appropriate positions in the amino acid sequences of AAQ02700.1 FRs to design hzR35B9 LV0 (SEQ ID NO: 92), as shown in Tables 2 and 6.

The amino acid sequences of HCDR1 (comprised of the sequence encompassed by a combination of the Chothia and Kabat definitions) (Al-Lazikani, B., *J Mol Biol,* 1997, 273 (4):927-48), HCDR2, and HCDR3 (as defined by Kabat) of VH of R35B9 shown in SEQ ID NOs: 122, 123, and 121, respectively, were grafted to appropriate positions in the amino acid sequences of hSGHI FRs to design hzR35B9 HV0 (SEQ ID NO: 179), as shown in Tables 3 and 6. This mixture of CDR definitions within the VH was used during humanization because two of the amino acids substitutions in R35B9 VH required for increased affinity for Fn14, isoleucine 28 (Iso28) and glutamine 30 (Gln30), are found outside of the Kabat-defined HCDR1, but are included within the Chothia-defined HCDR1. For this reason, we use a combination of Chothia and Kabat HCDR1 definitions to encompass the entire amino acids sequence that we consider HCDR1.

Generation of Variants of Humanized hzR35B9 HV0 and hzR35B9 LV0

A humanized antibody obtained by merely grafting the amino acid sequences of CDRs of a rodent-derived antibody to the amino acid sequences of FRs of human antibody often exhibits reduced binding activity. In order to overcome such limitation of direct CDR-grafting, FR amino acid residues that are different between mouse and human, and considered to influence the binding activity of the antibody, may be modified from human to rodent sequence. FR amino acid residues considered to influence the binding activity of the antibody were identified and modified as described below. An antibody having the designed hzR35B9 LV0 and hzR35B9 HV0 in VL and VH, respectively, is referred to as hzR35B9 LV0HV0 antibody or simply hzR35B9 LV0HV0. Other hzR35B9 antibodies are designated in the same way.

Computer modeling was used to construct three-dimensional structures of the variable regions of the hzR35B9 LV0HV0 and R35B9 antibodies (Discovery Studio, Accelrys). In the amino acid sequences of VL and VH FRs of hzR35B9 LV0HV0, amino acid residues differing from R35B9 were substituted with the counterpart amino acid residues of the R35B9 antibody to generate new hybrid sequences. Three-dimensional structures were generated and compared among the prepared R35B9, hzR35B9 LV0HV0, and subsequent modified forms in order to identify amino acid residues predicted to influence the binding activity of the mAb. Based on this analysis, the following amino acid FR residues of hzR35B9 LV0HV0 variable region were predicted to change the three-dimensional structure of the antigen binding site and influence mAb binding activity: Leu (15), Phe (41), Gln (42), Arg (50), and Val (109) in SEQ ID NO: 92; and Gln (1), Ala (9), Lys (12), Val (20), Arg (38), Pro (41), Gly (44), Met (48), Arg (67), Val (68), Ile (70), Ala (72), Thr (74), Ser (77), Leu (83), and Arg (98) in SEQ ID NO: 179.

At least one or more of these selected amino acid residues were substituted by the counterpart amino acid residues of R35B9 to design VL and VH of humanized antibodies having various modifications. Specifically, at least one amino acid modification substituting Leu (15) with Ile, Phe (41) with Leu, Gln (42) with Leu, Arg (50) with Lys, and Val (109) with Leu, in SEQ ID NO: 92, was introduced into the VL. In this way, hzR35B9 LV0 (SEQ ID NO: 92), LV1 a (SEQ ID NO: 94), LV1b (SEQ ID NO: 96), LV3a (SEQ ID NO: 98), LV3b (SEQ ID NO: 100), LV4 (SEQ ID NO: 102), and LV5 (SEQ ID NO: 104) were designed as VLs of hzR35B9 antibody, and their respective amino acid sequences are shown in Table 6 (see also FIG. 24).

At least one amino acid modification substituting Gln (1) with Glu, Ala (9) with Pro, Lys (12) with Val, Val (20) with Met, Arg (38) with Lys, Pro (41) with His, Gly (44) with Ser, Met (48) with Ile, Arg (67) with Lys, Val (68) with Ala, Ile (70) with Leu, Ala (72) with Val, Thr (74) with Lys, Ser (77) with Arg, Leu (83) with Phe, and Arg (98) with Ser, in SEQ ID NO: 179, was introduced into the VH. In this way, hzR35B9 HV0 (SEQ ID NO: 179), HV5a (SEQ ID NO: 66), HV5b (SEQ ID NO: 68), HV6a (SEQ ID NO: 70), HV6b (SEQ ID NO: 72), HV6c (SEQ ID NO: 74), HV7a (SEQ ID NO: 76), HV7b (SEQ ID NO: 78), HV7c (SEQ ID NO: 80), HV9a (SEQ ID NO: 82), HV9b (SEQ ID NO: 84), HVI 0 (SEQ ID NO: 86), HV11 (SEQ ID NO: 88), and HV18 (SEQ ID NO: 90) were designed as VHs of hzR35B9 antibody, and their respective amino acid sequences are shown in Table 6 and corresponding nucleotide sequences are shown in Table 22. The CDR and FR sequences in exemplary humanized antibody VH and VL regions are shown in Tables 2-3 above.

TABLE 6

Humanized VH and VL amino acid sequences with corresponding SEQ ID NOs

| Heavy Vector ID | VH Name | Humanized framework | Variable sequence |
| --- | --- | --- | --- |
| A700 | hzR35B9-HV0 | HV0 | QVQLVQSGAEVKKPGASVKVSCKASGYIFQDY NMHWVRQAPGQGLEWMGSINPRNGWTNYNQKF KGRVTITADTSTSTAYMELSSLRSEDTAVYYC ARSGWFTYWGQGTLVTVSS (SEQ ID NO: 179) |
| A454 | hzR35B9-HV5a | HV5a | QVQLVQSGAEVKKPGASVKVSCKASGYIFQDY NMHWVRQAPGQGLEWIGSINPRNGWTNYNQKF KGRATITADTSTSTAYMELSSLRSEDTAVYYC ASSGWFTYWGQGTLVTVSS (SEQ ID NO: 66) |
| A455 | hzR35B9-HV5b | HV5b | QVQLVQSGAEVVKPGASVKVSCKASGYIFQDY NMHWVRQAHGQGLEWMGSINPRNGWTNYNQKF KGRVTITADTSTSTAYMELSSLRSEDTAVYYC ASSGWFTYWGQGTLVTVSS (SEQ ID NO: 68) |

TABLE 6-continued

Humanized VH and VL amino acid sequences with corresponding SEQ ID NOs

| Heavy Vector ID | VH Name | Humanized framework | Variable sequence |
|---|---|---|---|
| A456 | hzR35B9-HV6a | HV6a | QVQLVQSGAEVVKPGASVKVSCKASGYIFQDY NMHWVRQAHGQSLEWMGSINPRNGWTNYNQKF KGRVTITADTSTSTAYMELSSLRSEDTAVYYC ASSGWFTYWGQGTIVTVSS (SEQ ID NO: 70) |
| A457 | hzR35B9-HV6b | HV6b | QVQLVQSGAEVKKPGASVKVSCKASGYIFQDY NMHWVRQAHGQGLEWIGSINPRNGWTNYNQKF KGRATITADKSTSTAYMELSSLRSEDTAVYYC ARSGWFTYWGQGTLVTVSS (SEQ ID NO: 72) |
| A458 | hzR35B9-HV6c | HV6c | QVQLVQSGAEVKKPGASVKVSCKASGYIFQDY NMHWVRQAHGQGLEWIGSINPRNGWTNYNQKF KGRATITADTSTSTAYMELSSLRSEDTAVYYC ASSGWFTYWGQGTLVTVSS (SEQ ID NO: 74) |
| A459 | hzR35B9-HV7a | HV7a | QVQLVQSGAEVVKPGASVKVSCKASGYIFQDY NMHWVRQAHGQSLEWMGSINPRNGWTNYNQKF KGRVTITADTSTRTAYMELSSLRSEDTAVYYC ASSGWFTYWGQGTLVTVSS (SEQ ID NO: 76) |
| A460 | hzR35B9-HV7b | HV7b | QVQLVQSGAEVVKPGASVKVSCKASGYIFQDY NMHWVRQAHGQSLEWMGSINPRNGWTNYNQKF KGRVTITADKSTRTAYMELSSLRSEDTAVYYC ASSGWFTYWGQGTLVTVSS (SEQ ID NO: 78) |
| A461 | hzR35B9-HV7c | HV7c | QVQLVQSGAEVVKPGASVKVSCKASGYIFQDY NMHWVKQAPGQGLEWIGSINPRNGWTNYNQKF KGKATITADTSTSTAYMELSSLRSEDTAVYYC ASSGWFTYWGQGTLVTVSS (SEQ ID NO: 80) |
| A462 | hzR35B9-HV9a | HV9a | QVQLVQSGAEVKKPGASVKMSCKASGYIFQDY NMHWVRQAPGQGLEWIGSINPRNGWTNYNQKF KGRATLTVDTSTSTAYMEFSSLRSEDTAVYYC ASSGWFTYWGQGTLVTVSS (SEQ ID NO: 82) |
| A463 | hzR35B9-HV9b | HV9b | QVQLVQSGAEVKKPGASVKVSCKASGYIFQDY NMHWVKQAHGQGLEWIGSINPRNGWTNYNQKF KGRATITADTSTSTAYMEFSSLRSEDTAVYYC ASSGWFTYWGQGTLVTVSS (SEQ ID NO: 84) |
| A464 | hzR35B9-HV10 | HV10 | QVQLVQSGAEVKKPGASVKVSCKASGYIFQDY NMHWVRQAHGQGLEWIGSINPRNGWTNYNQKF KGKATITADKSTRTAYMEFSSLRSEDTAVYYC ASSGWFTYWGQGTLVTVSS (SEQ ID NO: 86) |
| A465 | hzR35B9-HV11 | HV11 | QVQLVQSGPEVVKPGASVKVSCKASGYIFQDY NMHWVRQAHGQSLEWMGSINPRNGWTNYNQKF KGRATITVDKSTRTAYMELSSLRSEDTAVYYC ASSGWFTYWGQGTLVTVSS (SEQ ID NO: 88) |
| A466 | hzR35B9-HV18 | HV18 | EVQLVQSGPEVVKPGASVKMSCKASGYIFQDY NMHWVKQAHGQSLEWIGSINPRNGWTNYNQKF KGKATLTVDKSTRTAYMEFSSLRSEDTAVYYC ASSGWFTYWGQGTLVTVSS (SEQ ID NO: 90) |

TABLE 6-continued

Humanized VH and VL amino acid sequences with corresponding SEQ ID NOs

| Heavy Vector ID | VH Name | Humanized framework | Variable sequence |
|---|---|---|---|
| A512 | hzR35B9 (A56)-HV11 | HV11 | QVQLVQSGPEVVKPGASVKVSCKASGYIFQDY NMHWVRQAHGQSLEWMGSINPRNAWTNYNQKF KGRATITVDKSTRTAYMELSSLRSEDTAVYYC ASSGWFTYWGQGTLVTVSS (SEQ ID NO: 108) |
| A515 | hzR35B9 (Y50A56G57)- HV7b | HV7b | QVQLVQSGAEVVKPGASVKVSCKASGYIFQDY NMHWVRQAHGQGLEWMGYINPRNAGTNYNQKF KGRVTITADKSTRTAYMELSSLRSEDTAVYYC ASSGWFTYWGQGTLVTVSS (SEQ ID NO: 110) |
| A553 | hzR35B9 (A56)-HV7c | HV7c | QVQLVQSGAEVKKPGASVKVSCKASGYIFQDY NMHWVKQAPGQGLEWIGSINPRNAWTNYNQKF KGKATITADTSTSTAYMELSSLRSEDTAVYYC ASSGWFTYWGQGTLVTVSS (SEQ ID NO: 106) |
| A467 | hzR35B9- LV0 | LV0 | DVVMTQSPLSLPVTLGQPASISCKSSQSLLNS AGKTYLNWFQQRPGQSPRRLIYLVSQLDSGVP DRFSGSGSGTDFTLKISRVEAEDVGVYYCWQG TFYPWTFGGGTKVEIK (SEQ ID NO: 92) |
| A468 | hzR35B9- LV1a | LV1a | DVVMTQSPLSLPVTLGQPASISCKSSQSLLNS AGKTYLNWLQQRPGQSPRRLIYLVSQLDSGVP DRFSGSGSGTDFTLKISRVEAEDVGVYYCWQG TFYPWTFGGGTKVEIK (SEQ ID NO: 94) |
| A469 | hzR35B9- LV1b | LV1b | DVVMTQSPLSLPVTLGQPASISCKSSQSLLNS AGKTYLNWFLQRPGQSPRRLIYLVSQLDSGVP DRFSGSGSGTDFTLKISRVEAEDVGVYYCWQG TFYPWTFGGGTKVEIK (SEQ ID NO: 96) |
| A470 | hzR35B9- LV3a | LV3a | DVVMTQSPLSLPVTIGQPASISCKSSQSLLNS AGKTYLNWFLQRPGQSPRKLIYLVSQLDSGVP DRFSGSGSGTDFTLKISRVEAEDVGVYYCWQG TFYPWTFGGGTKVEIK (SEQ ID NO: 98) |
| A471 | hzK35B9- LV3b | LV3b | DVVMIQSPLSLPVTIGQPASISCKSSQSLLNS AGKTYLNWLLQRPGQSPRRLIYLVSQLDSGVP DRFSGSGSGTDFTLKISRVEAEDVGVYYCWQG TFYPWTFGGGTKVEIK (SEQ ID NO: 100) |
| A472 | hzR35B9- LV4 | LV4 | DVVMTQSPLSLPVTIGQPASISCKSSQSLLNS AGKTYLNWLLQRPGQSPRKLIYLVSQLDSGVP DRFSGSGSGTDFTLKISRVEAEDVGVYYCWQG TFYPWTFGGGTKVEIK (SEQ ID NO: 102) |
| A473 | hzR35B9- LV5 | LV5 | DVVMTQSPLSLPVTIGQPASISCKSSQSLLNS AGKTYLNWLLQRPGQSPRKLIYLVSQLDSGVP DRFSGSGSGTDFTLKISRVEAEDVGVYYCWQG TFYPWTFGGGTKLEIK (SEQ ID NO: 104) |
| A518 | hzR35B9 (H98)-LV1a | LV1a | DVVMTQSPLSLPVTLGQPASISCKSSQSLLNS AGKTYLNWLQQRPGQSPRRLIYLVSQLDSGVP DRFSGSGSGTDFTLKISRVEAEDVGVYYCWQG THYPWTFGGGTKVEIK (SEQ ID NO: 112) |

TABLE 22

Humanized VH and VL nucleotide sequences with corresponding SEQ ID NOs

Sequence (SEQ ID NO)

VH Name hzR35B9-
VH_HV5a
CAAGTGCAACTGGTGCAAAGCGGAGCTGAAGTAAAGAAGCCTGGAGCATCC
GTCAAGGTAAGTTGCAAGGCTAGTGGCTATATCTTCCAGGACTATAATATG
CATTGGGTACGCCAGGCTCCCGGACAAGGGCTGGAGTGGATAGGGAGCATC
AATCCACGCAACGGATGGACCAACTACAATCAGAAGTTCAAAGGACGAGCA
ACTATCACTGCAGATACATCAACCTCCACTGCTTACATGGAATTGAGTTCC
CTGCGTTCCGAAGACACCGCAGTGTACTATTGTGCCAGTTCAGGGTGGTTT
ACTTACTGGGGACAAGGCACACTGGTGACCGTTTCTAGC (SEQ ID NO:
65)

hzR35B9-
VH_HV5b
CAAGTTCAGCTTGTCCAGAGCGGTGCTGAAGTGGTCAAACCAGGCGCAAGT
GTTAAAGTTTCTTGCAAGGCATCTGGATATATTTTTCAGGACTACAACATG
CACTGGGTACGACAAGCCCACGGTCAGGGATTGGAATGGATGGGATCCATC
AACCCCAAGAAACGGTTGGACAAATTACAATCAAAAGTTCAAAGGCAGGGTA
ACAATCACCGCAGACACAAGCACCAGTACCGCTTACATGGAGCTGAGCTCT
TTGAGATCAGAGGACACTGCTGTGTACTATTGCGCATCTAGCGGGTGGTTC
ACTTACTGGGGACAGGGCACTCTTGTGACTGTGAGCTCT (SEQ ID NO:
67)

hzR35B9-
VH_HV6a
CAAGTTCAACTTGTTCAATCAGGCGCAGAAGTAGTGAAACCTGGTGCTTCT
GTGAAGGTGTCATGTAAGGCCAGCGGTTATATCTTTCAGGACTACAATATG
CATTGGGTTCGCCAAGCACATGGGCAGTCCCTGGAGTGGATGGGGTCTATC
AATCCTCGCAATGGCTGGACCAACTATAACCAAAAGTTCAAGGGTAGGGTC
ACTATCACTGCTGACACATCCACCTCTACCGCCTACATGGAATTGTCATCT
TTGCGCTCTGAGGACACTGCTGTGTACTATTGCGCTTCATCAGGCTGGTTC
ACCTATTGGGGACAGGGCACATTGGTGACTGTGTCTTCC (SEQ ID NO:
69)

hzR35B9-
VH_HV6b
CAAGTCCAACTGGTGCAAAGCGGAGCTGAAGTGAAGAAGCCAGGTGCCAGT
GTCAAGGTATCCTGCAAGGCAAGTGGTTATATTTTCCAGGACTATAATATG
CATTGGGTTAGGCAGGCACATGACAGGGGCTCGAATGGATCGGGAGTATT
AACCCACGTAATGGGTGGCTAATTACAACCAGAAGTTCAAAGGAAGGGCC
ACCATTACAGCCGACAAATCAACCTCAACTGCTTATATGGAGCTTAGCAGC
CTGCGTTCTGAGGACACTGCTGTATACTATTGTGCCCGTTCAGGTTGGTTC
ACCTACTGGGGACAGGGCACTCTTGTTACAGTCAGTTCT (SEQ ID NO:
71)

hzR35B9-
VH_HV6c
CAGGTACAGCTCGTTCAAAGCGGTGCCGAGGTAAAAAAGCCTGGGGCCTCT
GTTAAAGTTTCATGCAAGGCCTCAGGATATATCTTTCAAGACTACAACATG
CATTGGGTGCGTCAGGCACATGGCCAGGGCCTCGAATGGATCGGCAGCATA
AATCCACGGAACGGTTGGACCAACTACAACCAGAAATTCAAAGGAAGGGCC
ACTATAACCGCCGACACATCTACTTCTACCGCATACATGGAACTCTCCAGT
CTCAGGTCAGAAGATACAGCCGTCTACTATTGCGCCAGTAGCGGTTGGTTT
ACATACTGGGGGCAAGGAACTCTCGTTACCGTGTCCAGC (SEQ ID NO:
73)

hzR35B9-
VH_HV7a
CAGGTACAACTGGTACAGTCTGGAGCTGAGGTGGTTAAGCCAGGGGCCAGC
GTCAAAGTATCCTGTAAGGCTTCCGGATATATATTCCAGGACTACAATATG
CACTGGGTTCGGCAAGCCCACGGACAATCTCTGGAGTGGATGGGCTCCATC
AATCCCAGGAATGGATGACCAATTACAATCAGAAGTTCAAGGGGCGAGTC
ACAATCACAGCTGATACAAGTACTAGAACCGCTTACATGGAGCTTTCTTCA
TTGAGGTCCGAGGATACAGCTGTCTACTACTGCGCTTCCTCAGGATGGTTT
ACTTATTGGGGTCAAGGAACTCTGGTGACAGTTAGCAGC (SEQ ID NO:
75)

hzR35B9-
VH_HV7b
CAAGTGCAGCTCGTTCAGTCTGGAGCCGAGGTAGTCAAGCCCGGCGCATCT
GTTAAAGTCAGTTGCAAAGCTTCCGGCTATATCTTCCAGGATTACAACATG
CACTGGGTCAGACAGGCTCACGGTCAAGGGCTCGAATGGATGGGAAGTATT
AACCCTCGTAATGGATGGACTAACTATAACCAAAAGTTTAAGGGGAGGGTG
ACTATTCAGCAGATAAGTCTACTCGCACTGCCTATATGGAGCTTAGCTCA
CTCCGCTCCGAAGACACCGCTGTGTATTACTGTGCTAGTTCCGGGTGGTTC
ACCTATTGGGGCAAGGAACTCTTGTAACAGTTTCCTCT (SEQ ID NO:
77)

hzR35B9-
VH_HV7c
CAAGTTCAACTGGTGCAGTCTGGCGCTGAGGTAAAAAAACCCGGCGCCTCT
GTTAAAGTAAGTTGTAAAGCATCTGGGTATATCTTCAAGATTACAACATG
CACTGGGTTAAGCAGGCTCCCGGACAGGGTCTTGAGTGGATAGGGTCCATA
AATCCCCGCAATGGCTGGACTAATTATAACCAAAAGTTCAAAGGAAAAGCC
ACCATCACAGCAGACACCAGTACATCTACCGCCTACATGGAATTGAGTTCT
CTGCGGAGCGAGGATACCGCAGTCTATTACTGCGCCTCATCTGGATGTTT
ACTTACTGGGGTCAGGGCACTCTGGTGACTGTTTCAAGT (SEQ ID NO:
79)

TABLE 22-continued

Humanized VH and VL nucleotide sequences with corresponding SEQ ID NOs

Sequence (SEQ ID NO)

hzR35B9-
VH_HV9a    CAAGTTCAGCTCGTGCAGTCTGGAGCAGAGGTAAAGAAACCCGGCGCATCA
           GTGAAGATGAGTTGTAAGGCTAGTGGTTATATATTCCAGGATTATAATATG
           CACTGGGTACGACAGGCTCCAGGCCAAGGGCTTGAATGGATAGGCAGCATT
           AACCCCCGAAACGGCTGGACTAATTACAACCAGAAATTCAAGGGACGCGCA
           ACCCTCACTGTGGATACTTCCACATCTACTGCTTACATGGAGTTTTCATCA
           CTCAGGTCAGAAGACACAGCAGTGTACTACTGTGCCTCCTCTGGGTGGTTC
           ACATATTGGGGACAAGGCACATTGGTGACAGTCTCCTCT (SEQ ID NO:
           81)

hzR35B9-
VH_HV9b    CAGGTCCAACTGGTACAGTCCGGCGCTGAAGTAAAAAAACCAGGCGCTAGT
           GTCAAGGTATCATGCAAAGCAAGTGGGTATATCTTTCAGGATTATAATATG
           CACTGGGTAAAACAGGCTCACGGCCAATCCCTGGAGTGGATCGGTTCCATC
           AATCCACGGAACGGCTGGACCAACTACAACCAGAAGTTTAAGGGCCGTGCT
           ACCATTACAGCCGACACTAGCACTAGCACAGCTTACATGGAATTCTCCTCC
           CTGCGAAGCGAAGACACCGCAGTGTATTACTGCGCTAGTTCCGGTTGGTTC
           ACTTACTGGGGCCAGGGCACACTCGTCACTGTCTCAAGC (SEQ ID NO:
           83)

hzR35B9-
VH_HV10    CAGGTGCAACTGGTGCAATCTGGGGCAGAAGTTAAAAAACCAGGCGCTAGC
           GTAAAAGTTTCTTGCAAAGCAAGTGGGTACATATTCCAAGATTACAATATG
           CATTGGGTCAGGCAGGCCCACGGTCAGGGATTGGAGTGGATCGGCTCTATC
           AACCCTAGAAATGGTTGGACTAACTACAACCAGAAGTTCAAAGGGAAAGCC
           ACCATTACCGCCGATAAATCCACCAGGACAGCCTATATGGAGTTTTCTAGC
           CTTCGTAGCGAAGACACCGCTGTGTATTATTGCGCTTCAGTGGATGGTTC
           ACTTATTGGGTCAGGGGACCTTGGTCACTGTTAGTTCT (SEQ ID NO:
           85)

hzR35B9-
VH_HV11    CAAGTTCAACTTGTCCAATCCGGTCCAGAAGTCGTAAAACCAGGTGCTAGT
           GTGAAAGTCTCATGCAAGGCTTCAGGCTACATATTTCAAGACTATAATATG
           CATTGGGTTAGACAGGCACACGGTCAGTCACTGGAATGGATGGGGTCAATC
           AACCCTCGCAACGGATGGACAAATTACAACCAAAAGTTCAAGGGAGAGCT
           ACTATCACTGTCGATAAATCTACCAGAACAGCTTACATGGAGCTGAGTAGT
           CTGAGATCAGAGGACACCGCCGTCTACTATTGTGCTTCTTCTGGGTGGTTT
           ACATACTGGGGGCAGGGGACACTGGTGACTGTGAGTTCT (SEQ ID NO:
           87)

hzR35B9-
VH_HV18    GAGGTCCAACTGGTTCAAAGTGGACCAGAGGTGGTGAAACCAGGAGCTAGC
           GTAAAAATGAGCTGTAAGGCTTCAGGTTATATCTTTCAGGATTACAACATG
           CACTGGGTAAAACAAGCCCACGGCCAGTCTCTCGAATGGATTGGGTCAATC
           AATCCCCGAAACGGTTGGACAAACTATAATCAGAAATTCAAAGGTAAAGCA
           ACATTGACTGTTGACAAATCAACCAGGACCGCATACATGGAGTTTTCATCC
           CTGCGTAGTGAAGACACTGCTGTTTACTACTGTGCTAGTTCTGGGTGGTTC
           ACTTACTGGGGGCAGGGAACTCTTGTCACTGTTTCTTCA (SEQ ID NO:
           89)

VL Name hzR35B9-
VL_LV0     GACGTAGTGATGACTCAGAGCCCTCTGTCACTCCCCGTCACACTGGGACAA
           CCAGCTTCCATCTCCTGCAAGTCATCTCAATCTTTGTTGAATAGCGCAGGA
           AAGACATACCTGAACTGGTTCCAACAACGCCCTGGTCAAAGCCCACGCAGG
           CTGATCTATTTGGTAAGTCAACTGGATAGCGGAGTACCTGACCGTTTCTCT
           GGAAGTGGAAGTGGTACTGACTTCACCTTGAAAATCTCCAGGGTTGAAGCC
           GAGGACGTGGGGGTGTATTACTGTTGGCAAGGTACTTTCTACCCTTGGACT
           TTCGGCGGCGGTACCAAGGTAGAGATTAAA (SEQ ID NO: 91)

hzR35B9-
VL_LV1a    GATGTAGTAATGACCCAGTCCCCACTTAGCTTGCCCGTTACACTCGGCCAA
           CCCGCAAGCATATCTTGCAAATCCAGTCAGAGCCTCCTGAACTCTGCTGGA
           AAGACCTATCTGAATTGGCTTCAACAACGTCCCGGTCAATCCCCCAGACGA
           CTTATCTACTTGGTAAGTCAGCTTGACTCCGGGGTTCCAGACAGGTTTTCC
           GGATCTGGAAGTGGAACTGATTTTACACTCAAAATTAGTCGAGTCGAGGCC
           GAAGACGTGGGTGTCTATTATTGCTGGCAAGGCACCTTTTATCCATGGACT
           TTTGGTGGGGGCACCAAGGTTGAAATTAAG (SEQ ID NO: 93)

hzR35B9-
VL_LV1b    GATGTTGTGATGACACAAAGTCCTCTGAGCCTTCCAGTCACATTGGGTCAG
           CCTGCATCTATTAGTTGTAAGAGCAGTCAATCACTGCTGAATAGTGCCGGA
           AAAACATACTTGAATTGGTTCCTTCAGCGCCCAGGCCAGTCTCCTCGGCGG
           TTGATTTATCTTGTCTCAACTGGATTCTGGTGTCCCCGATAGATTTTCA
           GGTTCAGGGTCAGGGACCGATTTTACACTGAAGATTTCTCGCGTCGAGGCA
           GAGGACGTTGGGGTTATTACTGTTGGCAGGGAACATTTTATCCATGGACA
           TTCGGGGGAGGAACCAAGGTAGAGATTAAA (SEQ ID NO: 95)

hzR35B9-
VL_LV3a    GACGTAGTTATGACTCAGTCTCCACTCTCTCTCCCCGTGACCATTGGACAG
           CCTGCATCAATATCCTGCAAAAGTAGCCAGTCCTTGCTCAACTCAGCCGGT
           AAAACCTACCTCAACTGGTTCCTTCAGCGCCCCGGTCAGTCTCCAAAGCGT
           TTGATATACCTGGTGAGTCAACTCGACTCAGGTGTCCCCGATCGCTTCTCT

TABLE 22-continued

Humanized VH and VL nucleotide sequences with corresponding SEQ ID NOs

| | Sequence (SEQ ID NO) |
|---|---|
| | GGGAGCGGTTCAGGCACAGATTTTACTCTCAAAATATCCAGAGTTGAAGCT<br>GAAGACGTTGGGGTTTACTATTGCTGGCAGGGAACATTCTATCCTTGGACT<br>TTTGGAGGAGGCACAAAGGTTGAGATCAAG (SEQ ID NO: 97) |
| hzR35B9-<br>VL_LV3b | GACGTTGTAATGACCCAAAGTCCACTGTCACTTCCCGTAACCATAGGGCAA<br>CCCGCCAGCATCTCCTGCAAATCATCCCAAAGTCTTCTTAACAGTGCCGGA<br>AAAACATACTTGAACTGGCTCTTGCAGAGGCCAGGGCAATCTCCTCGACGA<br>CTGATATACCTTGTATCCCAGTTGGATTCTGGCGTGCCCGACAGATTCAGT<br>GGAAGCGGATCTGGCACAGACTTTACCCTTAAAATCAGCCGCGTGGAGGCC<br>GAGGATGTTGGAGTGTACTACTGTTGGCAAGGAACATTTTACCCTTGGACC<br>TTTGGCGGGGGGACCAAAGTCGAGATAAAG (SEQ ID NO: 99) |
| hzR35B9-<br>VL_LV4 | GATGTCGTGATGACACAAAGTCCCCTGAGCTTGCCCGTAACTATTGGGCAA<br>CCAGCCTCTATCTCTTGTAAATCATCACAATCTTTGCTCAATTCTGCTGGC<br>AAGACATACCTTAACTGGCTTTTGCAACGCCCTGGTCAAAGCCCTAAGAGA<br>TTGATTTATCTCGTCAGCCAGCTGGACTCTGGGGTCCCAGATCGCTTTAGT<br>GGGTCAGGCTCTGGAACCGACTTCACACTGAAGATCTCCAGGGTTGAAGCC<br>GAGGATGTAGGGGTTTATTACTGTTGGCAAGGCACCTTTTATCCCTGGACT<br>TTTGGGGGCGGCACCAAGGTCGAAATAAAG (SEQ ID NO: 101) |
| hzR35B9-<br>VL_LV5 | GATGTTGTCATGACTCAATCACCATTGAGCCTCCCCGTGACAATAGGCCAG<br>CCTGCTTCCATTTCCTGTAAGTCAAGCCAGAGTCTGCTTAATAGTGCCGGG<br>AAGACCTATCTGAACTGGCTCTTGCAGAGACCAGGACAATCTCCAAAACGG<br>TTGATCTACCTGGTCAGCCAGTTGGACAGCGGCGTTCCAGATCGATTCAGT<br>GGCAGTGGATCTGGAACTGATTTTACCTTGAAGATTAGTAGAGTAGAGGCA<br>GAGGACGTGGGAGTATATTACTGCTGGCAGGGAACCTTCTACCCCTGGACC<br>TTTGGCGGCGGCACCAAGCTCGAGATCAAA (SEQ ID NO: 103) |
| hzR35B9<br>(A56)-<br>VH_HV7c | CAAGTTCAACTGGTGCAGTCTGGCGCTGAGGTAAAAAAACCCGGCGCCTCT<br>GTTAAAGTAAGTTGTAAAGCATCTGGGTATATCTTTCAAGATTACAACATG<br>CACTGGGTTAAGCAGGCTCCCGGACAGGGTCTTGAGTGGATAGGGTCCATA<br>AATCCCCGCAATGcCTGGACTAATTATAACCAAAAGTTCAAAGGAAAAGCC<br>ACCATCACAGCAGACACCAGTACATCTACCGCCTACATGGAATTGAGTTCT<br>CTGCGGAGCGAGGATACCGCAGTCTATTACTGCGCCTCATCTGGATGGTTT<br>ACTTACTGGGGTCAGGGCACTCTGGTGACTGTTTCAAGT (SEQ ID NO:<br>105) |
| hzR35B9<br>(A56)-<br>VH_HV11 | CAAGTTCAACTTGTCCAATCCGGTCCAGAAGTCGTAAAACCAGGTGCTAGT<br>GTGAAAGTCTCATGCAAGGCTTCAGGCTACATATTTCAAGACTATAATATG<br>CATTGGGTTAGACAGGCACACGGTCAGTCACTGGAATGGATGGGGTCAATC<br>AACCCTCGCAACGCCTGGACAAATTACAACCAAAAGTTCAAAGGGAGAGCT<br>ACTATCACTGTCGATAAATCTACCAGAACAGCTTACATGGAGCTGAGTAGT<br>CTGAGATCAGAGGACACCGCCGTCTACTATTGTGCTTCTTCTGGGTGGTTT<br>ACATACTGGGGCAGGGGACACTGGTGACTGTGAGTTCT (SEQ ID NO:<br>107) |
| hzR35B9<br>(Y50A56G57)-<br>VH_HV7b | CAAGTGCAGCTCGTTCAGTCTGGAGCCGAGGTAGTCAAGCCCGGCGCATCT<br>GTTAAAGTCAGTTGCAAAGCTTCCGGCTATATCTTCCAGGATTACAACATG<br>CACTGGGTCAGACAGGCTCACGGTCAAGGGCTCGAATGGATGGGAtaTATT<br>AACCCTCGTAATGCCGGGACTAACTATAACCAAAAGTTTAAGGGGAGGGTG<br>ACTATTACAGCAGATAAGTCTACTCGCACTGCCTATATGGAGCTTAGCTCA<br>CTCCGCTCCGAAGACACCGCTGTGTATTACTGTGCTAGTTCCGGGTGGTTC<br>ACCTATTGGGGGCAAGGAACTCTTGTAACAGTTTCCTCT (SEQ ID NO:<br>109) |
| hzR35B9<br>(H98)-<br>VL_LV1a | GATGTAGTAATGACCCAGTCCCCACTTAGCTTGCCCGTTACACTCGGCCAA<br>CCCGCAAGCATATCTTGCAAATCCAGTCAGAGCCTCCTGAACTCTGCTGGA<br>AAGACCTATCTGAATTGGCTTCAACAACGTCCGGTCAATCCCCCAGACGA<br>CTTATCTACTTGGTAAGTCAGCTTGACTCCGGGGTTCCAGACAGGTTTTCC<br>GGATCTGGAAGTGGAACTGATTTTACACTCAAAATTAGTCGAGTGAGGCC<br>GAAGACGTGGGTGTCTATTATTGCTGGCAAGGCACCcaTTATCCATGGACT<br>TTTGGTGGGGGCACCAAGGTTGAAATTAAG (SEQ ID NO: 111) |

Example 9

Introducing CDR Variations into Humanized Antibodies

Several humanized frameworks of R35B9 VH and VL were chosen based on favorable activity, and selected CDR amino acid substitutions were introduced (see Table 6).

Three substitutions were introduced into hzR35B9 HV7b VH (tyrosine at position 50 (Tyr50), alanine at position 56 (Ala56) and glycine at position 57 (Gly57) to create a heavy chain with the hzR35B9(Y50A56G57) HV7b VH (A515) variable region (shown in nucleotide SEQ ID NO: 109 and amino acid SEQ ID NO: 110). One substitution was introduced into hzR35B9 HV7c VH (alanine at position 56 (A56)) to create a heavy chain with the hzR35B9(A56) HV7c VH (A553) variable region (shown in nucleotide SEQ ID NO: 105 and amino acid SEQ ID NO: 106). One substitution was introduced into hzR35B9 HV11 VH (alanine at position 56 (A56) to create a heavy chain with the hzR35B9(A56) HV11 VH (A512) variable region (shown in nucleotide SEQ ID NO: 107 and amino acid SEQ ID NO: 108).

One substitution was introduced into hzR35B9 LV1a VL (histidine at position 98 (H98)) to create a light chain with the hzR35B9(H98) LV1a VL (A518) variable region (shown in nucleotide SEQ ID NO: 111 and amino acid SEQ ID NO: 112).

These heavy and light chains were used to produce several humanized antibodies (see Tables 5 and 6): antibody A512/A468 comprised of heavy chain containing hzR35B9 (A56) HV11 VH (A512) (amino acid SEQ ID NO: 108) and light chain containing hzR35B9 LV1a VL (A468) (amino acid SEQ ID NO: 94); antibody A515/A518 comprised of a heavy chain containing hzR35B9(Y50A56G57) HV7b VH (A515) variable region (amino acid SEQ ID NO: 110) and light chain containing hzR35B9(H98) LV1a VL (A518) variable region (amino acid SEQ ID NO: 112); and antibody A553/A472 comprised of a heavy chain containing hzR35B9(A56) HV7c VH (A553) (SEQ ID NO: 106) and light chain containing hzR35B9 LV4 VL (A472) variable region (amino acid SEQ ID NO: 102).

Example 10

Further Engineered Humanized Antibodies

Humanized antibody clone A512/A468 (expressing heavy and light chains containing VH and VL amino acid sequences of SEQ ID NOs. 108 and 94, respectively) was further engineered. Based on the A512 VH and A468 VL sequences, thirteen heavy chains with variant VH sequences and five light chains with variant VL sequences were generated using methods described previously.

Variant VH sequences include at least one amino acid modification substituting Val (5) with Gln, Val (12) with Ala, Val (37) with Gly, Arg (38) with Lys, Gln (39) with Glu, Ala (40) with Gly, His (41) with Asp or Pro, Glu (43) with Asp, Gln (62) with Asp, Lys (65) with Gly or Asp or His, Arg (67) with Lys, or Ile (70) with Leu. In this way HV12a (SEQ ID NO: 203), HV12b (SEQ ID NO: 205), HV13a (SEQ ID NO: 207), HV13b (SEQ ID NO: 209), HV13d (SEQ ID NO: 211), HV13f (SEQ ID NO: 213), HV13g (SEQ ID NO: 215), HV16 (SEQ ID NO: 217), HV17a (SEQ ID NO: 219), HV17b (SEQ ID NO: 221), HV17d (SEQ ID NO: 223), HV17g (SEQ ID NO: 225), and HV17i (SEQ ID NO: 227) were designed as VH variants of hzR35B9 antibody clone A512. Nucleotide and amino acid sequences of these variant VH sequences based on A512 are shown in Table 5 below (see also FIG. 22 to FIG. 24).

TABLE 5

Nucleotide and amino acid sequences of variant VH sequences based on A512

| VH Name | Sequence (SEQ ID NO) |
|---|---|
| hzR35B9(A56)-HV12a (A631) | CAAGTTCAACTTGTCCAATCCGGTCCAGAAGTCGTAAAACCA GGTGCTAGTGTGAAAGTCTCATGCAAGGCTTCAGGCTACATA TTTCAAGACTATAATATGCATTGGGTTAGACAGGCAGACGGT CAGTCACTGGAATGGATGGGGTCAATCAACCCTCGCAACGCC TGGACAAATTACAACCAAAAGTTCAAAGGGAGAGCTACTATC ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 202) |
| hzR35B9(A56)-HV12a (A631) | QVQLVQSGPEVVKPGASVKVSCKASGYIFQDYNMHWVRQADG QSLEWMGSINPRNAWTNYNQKFKGRATITVDKSTRTAYMELS SLRSEDTAVYYCASSGWFTYWGQGTLVTVSS (SEQ ID NO: 203) |
| hzR35B9(A56)-HV12b (A632) | CAAGTTCAACTTGTCCAATCCGGTCCAGAAGTCGTAAAACCA GGTGCTAGTGTGAAAGTCTCATGCAAGGCTTCAGGCTACATA TTTCAAGACTATAATATGCATTGGGTTAGACAGGCACCCGGT CAGTCACTGGAATGGATGGGGTCAATCAACCCTCGCAACGCC TGGACAAATTACAACCAAAAGTTCAAAGGGAGAGCTACTATC ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 204) |
| hzR35B9(A56)-HV12b (A632) | QVQLVQSGPEVVKPGASVKVSCKASGYIFQDYNMHWVRQAPG QSLEWMGSINPRNAWTNYNQKFKGRATITVDKSTRTAYMELS SLRSEDTAVYYCASSGWFTYWGQGTLVTVSS (SEQ ID NO: 205) |
| hzR35B9(A56)-HV13a (A633) | CAAGTTCAACTTGTCCAATCCGGTCCAGAAGTCGTAAAACCA GGTGCTAGTGTGAAAGTCTCATGCAAGGCTTCAGGCTACATA TTTCAAGACTATAATATGCATTGGGTTAGAGAAGCACACGGT CAGTCACTGGAATGGATGGGGTCAATCAACCCTCGCAACGCC TGGACAAATTACAACCAAAAGTTCAAAGGGAGAGCTACTATC ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 206) |

TABLE 5-continued

Nucleotide and amino acid sequences of variant
VH sequences based on A512

| VH Name | Sequence (SEQ ID NO) |
|---|---|
| hzR35B9(A56)-HV13a (A633) | QVQLVQSGPEVVKPGASVKVSCKASGYIFQDYNMHWVREAHGQSLEWMGSINPRNAWTNYNQKFKGRATITVDKSTRTAYMELSSLRSEDTAVYYCASSGWFTYWGQGTLVTVSS (SEQ ID NO: 207) |
| hzR35B9(A56)-HV13b (A634) | CAAGTTCAACTTGTCCAATCCGGTCCAGAAGTCGTAAAACCAGGTGCTAGTGTGAAAGTCTCATGCAAGGCTTCAGGCTACATATTTCAAGACTATAATATGCATTGGGTTAGACAGGCACACGGTCAGTCACTGGAATGGATGGGGTCAATCAACCCTCGCAACGCCTGGACAAATTACAACCAAAAGTTCGGAGGGAGAGCTACTATCACTGTCGATAAATCTACCAGAACAGCTTACATGGAGCTGAGTAGTCTGAGATCAGAGGACACCGCCGTCTACTATTGTGCTTCTTCTGGGTGGTTTACATACTGGGGCAGGGGACACTGGTGACTGTGAGTTCT (SEQ ID NO: 208) |
| hzR35B9(A56)-HV13b (A634) | QVQLVQSGPEVVKPGASVKVSCKASGYIFQDYNMHWVRQAHGQSLEWMGSINPRNAWTNYNQKFGGRATITVDKSTRTAYMELSSLRSEDTAVYYCASSGWFTYWGQGTLVTVSS (SEQ ID NO: 209) |
| hzR35B9(A56)-HV13d (A636) | CAAGTTCAACTTGTCCAATCCGGTCCAGAAGTCGTAAAACCAGGTGCTAGTGTGAAAGTCTCATGCAAGGCTTCAGGCTACATATTTCAAGACTATAATATGCATTGGGGCAGACAGGCACACGGTCAGTCACTGGAATGGATGGGGTCAATCAACCCTCGCAACGCCTGGACAAATTACAACCAAAAGTTCAAAGGGAGAGCTACTATCACTGTCGATAAATCTACCAGAACAGCTTACATGGAGCTGAGTAGTCTGAGATCAGAGGACACCGCCGTCTACTATTGTGCTTCTTCTGGGTGGTTTACATACTGGGGCAGGGGACACTGGTGACTGTGAGTTCT (SEQ ID NO: 210) |
| hzR35B9(A56)-HV13d (A636) | QVQLVQSGPEVVKPGASVKVSCKASGYIFQDYNMHWGRQAHGQSLEWMGSINPRNAWTNYNQKFKGRATITVDKSTRTAYMELSSLRSEDTAVYYCASSGWFTYWGQGTLVTVSS (SEQ ID NO: 211) |
| hzR35B9(A56)-HV13f (A638) | CAAGTTCAACTTGTCCAATCCGGTCCAGAAGTCGTAAAACCAGGTGCTAGTGTGAAAGTCTCATGCAAGGCTTCAGGCTACATATTTCAAGACTATAATATGCATTGGGTTAGACAGGCACACGGTCAGTCACTGGAATGGATGGGGTCAATCAACCCTCGCAACGCCTGGACAAATTACAACGATAAGTTCAAAGGGAGAGCTACTATCACTGTCGATAAATCTACCAGAACAGCTTACATGGAGCTGAGTAGTCTGAGATCAGAGGACACCGCCGTCTACTATTGTGCTTCTTCTGGGTGGTTTACATACTGGGGCAGGGGACACTGGTGACTGTGAGTTCT (SEQ ID NO: 212) |
| hzR35B9(A56)-HV13f (A638) | QVQLVQSGPEVVKPGASVKVSCKASGYIFQDYNMHWVRQAHGQSLEWMGSINPRNAWTNYNDKFKGRATITVDKSTRTAYMELSSLRSEDTAVYYCASSGWFTYWGQGTLVTVSS (SEQ ID NO: 213) |
| hzR35B9(A56)-HV13g (A639) | CAAGTTCAACTTGTCCAATCCGGTCCAGAAGTCGTAAAACCAGGTGCTAGTGTGAAAGTCTCATGCAAGGCTTCAGGCTACATATTTCAAGACTATAATATGCATTGGGTTAGACAGGCACACGGTGACTCACTGGAATGGATGGGGTCAATCAACCCTCGCAACGCCTGGACAAATTACAACCAAAAGTTCAAAGGGAGAGCTACTATCACTGTCGATAAATCTACCAGAACAGCTTACATGGAGCTGAGTAGTCTGAGATCAGAGGACACCGCCGTCTACTATTGTGCTTCTTCTGGGTGGTTTACATACTGGGGCAGGGGACACTGGTGACTGTGAGTTCT (SEQ ID NO: 214) |
| hzR35B9(A56)-HV13g (A639) | QVQLVQSGPEVVKPGASVKVSCKASGYIFQDYNMHWVRQAHGDSLEWMGSINPRNAWTNYNQKFKGRATITVDKSTRTAYMELSSLRSEDTAVYYCASSGWFTYWGQGTLVTVSS (SEQ ID NO: 215) |
| hzR35B9(A56)-HV16 (A641) | CAAGTTCAACTTCAGCAATCCGGTCCAGAAGTCGTAAAACCAGGTGCTAGTGTGAAAGTCTCATGCAAGGCTTCAGGCTACATATTTCAAGACTATAATATGCATTGGGTTAAACAGGCACACGGTCAGTCACTGGAATGGATGGGGTCAATCAACCCTCGCAACGCCTGGACAAATTACAACCAAAAGTTCAAAGGGAAAGCTACTCTGACTGTCGATAAATCTACCAGAACAGCTTACATGGAGCTGAGTAGTCTGAGATCAGAGGACACCGCCGTCTACTATTGTGCTTCTTCTGGGTGGTTTACATACTGGGGCAGGGGACACTGGTGACTGTGAGTTCT (SEQ ID NO: 216) |

TABLE 5-continued

Nucleotide and amino acid sequences of variant VH sequences based on A512

| VH Name | Sequence (SEQ ID NO) |
|---|---|
| hzR35B9(A56)-HV16 (A641) | QVQLQQSGPEVVKPGASVKVSCKASGYIFQDYNMHWVKQAHG QSLEWMGSINPRNAWTNYNQKFKGKATLTVDKSTRTAYMELS SLRSEDTAVYYCASSGWFTYWGQGTLVTVSS (SEQ ID NO: 217) |
| hzR35B9(A56)-HV17a (A642) | CAAGTTCAACTTCAGCAATCCGGTCCAGAAGTCGTAAAACCA GGTGCTAGTGTGAAAGTCTCATGCAAGGCTTCAGGCTACATA TTTCAAGACTATAATATGCATTGGGTTAAACAGGGACACGGT CAGTCACTGGAATGGATGGGGTCAATCAACCCTCGCAACGCC TGGACAAATTACAACCAAAAGTTCAAAGGGAAAGCTACTCTG ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 218) |
| hzR35B9(A56)-HV17a (A642) | QVQLQQSGPEVVKPGASVKVSCKASGYIFQDYNMHWVKQGHG QSLEWMGSINPRNAWTNYNQKFKGKATLTVDKSTRTAYMELS SLRSEDTAVYYCASSGWFTYWGQGTLVTVSS (SEQ ID NO: 219) |
| hzR35B9(A56)-HV17b (A643) | CAAGTTCAACTTCAGCAATCCGGTCCAGAAGTCGTAAAACCA GGTGCTAGTGTGAAAGTCTCATGCAAGGCTTCAGGCTACATA TTTCAAGACTATAATATGCATTGGGTTAAACAGGCACACGGT CAGTCACTGGAATGGATGGGGTCAATCAACCCTCGCAACGCC TGGACAAATTACAACCAAAAGTTCCACGGGAAAGCTACTCTG ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 220) |
| hzR35B9(A56)-HV17b (A643) | QVQLQQSGPEVVKPGASVKVSCKASGYIFQDYNMHWVKQAHG QSLEWMGSINPRNAWTNYNQKFHGKATLTVDKSTRTAYMELS SLRSEDTAVYYCASSGWFTYWGQGTLVTVSS (SEQ ID NO: 221) |
| hzR35B9(A56)-HV17d (A645) | CAAGTTCAACTTCAGCAATCCGGTCCAGAAGTCGTAAAACCA GGTGCTAGTGTGAAAGTCTCATGCAAGGCTTCAGGCTACATA TTTCAAGACTATAATATGCATTGGGTTAAACAGGCACACGGT CAGTCACTGGAATGGATGGGGTCAATCAACCCTCGCAACGCC TGGACAAATTACAACCAAAAGTTCGACGGGAAAGCTACTCTG ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 222) |
| hzR35B9(A56)-HV17d (A645) | QVQLQQSGPEVVKPGASVKVSCKASGYIFQDYNMHWVKQAHG QSLEWMGSINPRNAWTNYNQKFDGKATLTVDKSTRTAYMELS SLRSEDTAVYYCASSGWFTYWGQGTLVTVSS (SEQ ID NO: 223) |
| hzR35B9(A56)-HV17g (A648) | CAAGTTCAACTTCAGCAATCCGGTCCAGAAGTCGTAAAACCA GGTGCTAGTGTGAAAGTCTCATGCAAGGCTTCAGGCTACATA TTTCAAGACTATAATATGCATTGGGTTAAACAGGCACACGGT CAGTCACTGGAATGGATGGGGTCAATCAACCCTCGCAACGCC TGGACAAATTACAACGACAAGTTCAAAGGGAAAGCTACTCTG ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 224) |
| hzR35B9(A56)-HV17g (A648) | QVQLQQSGPEVVKPGASVKVSCKASGYIFQDYNMHWVKQAHG QSLEWMGSINPRNAWTNYNDKFKGKATLTVDKSTRTAYMELS SLRSEDTAVYYCASSGWFTYWGQGTLVTVSS (SEQ ID NO: 225) |
| hzR35B9(A56)-HV17i (A650) | CAAGTTCAACTTCAGCAATCCGGTCCAGAAGTCGCCAAACCA GGTGCTAGTGTGAAAGTCTCATGCAAGGCTTCAGGCTACATA TTTCAAGACTATAATATGCATTGGGTTAAACAGGCACACGGT CAGTCACTGGAATGGATGGGGTCAATCAACCCTCGCAACGCC TGGACAAATTACAACCAAAAGTTCAAAGGGAAAGCTACTCTG ACTGTCGATAAATCTACCAGAACAGCTTACATGGAGCTGAGT AGTCTGAGATCAGAGGACACCGCCGTCTACTATTGTGCTTCT TCTGGGTGGTTTACATACTGGGGCAGGGGACACTGGTGACT GTGAGTTCT (SEQ ID NO: 226) |

TABLE 5-continued

Nucleotide and amino acid sequences of variant VH sequences based on A512

| VH Name | Sequence (SEQ ID NO) |
|---|---|
| hzR35B9(A56)-HV17i (A650) | QVQLQQSGPEVAKPGASVKVSCKASGYIFQDYNMHWVKQAHG QSLEWMGSINPRNAWTNYNQKFKGKATLTVDKSTRTAYMELS SLRSEDTAVYYCASSGWFTYWGQGTLVTVSS (SEQ ID NO: 227) |

Variant VL sequences include at least one amino acid modification substituting Leu (52) for Gly, Ile (53) with Ala, Ser (57) with Ala, Gln (58) with Glu, or Ser (61) with Asp. In this way LV2a (SEQ ID NO: 229), LV2b (SEQ ID NO: 231), LV2c (SEQ ID NO: 233), LV2d (SEQ ID NO: 235), and LV2f (SEQ ID NO: 237) were designed as VL variants of hzR35B9 antibody clone A468. Nucleotide and amino acid sequences of variant VL sequences based on A468 are shown in Table 17 (see also FIG. 21, FIG. 23 and FIG. 24).

TABLE 17

Nucleotide and amino acid sequences of variant VL sequences based on A468

| | |
|---|---|
| hzR35B9 (A56)- LV2a (A651) | GATGTAGTAATGACCCAGTCCCCACTTAGCTTGCCCGTTA CACTCGGCCAACCCGCAAGCATATCTTGCAAATCCAGTCA GAGCCTCCTGAACTCTGCTGGAAAGACCTATCTGAATTGG CTTCAACAACGTCCCGGTCAATCCCCCAGACGAGGTATCT ACTTGGTAAGTCAGCTTGACTCCGGGGTTCCAGACAGGTT TTCCGGATCTGGAAGTGGAACTGATTTTACACTCAAAATT AGTCGAGTCGAGGCCGAAGACGTGGGTGTCTATTATTGCT GGCAAGGCACCTTTTATCCATGGACTTTTGGTGGGGGCAC CAAGGTTGAAATTAAG (SEQ ID NO: 228) |
| hzR35B9 (A56)- LV2a (A651) | DVVMTQSPLSLPVTLGQPASISCKSSQSLLNSAGKTYLNW LQQRPGQSPRRGIYLVSQLDSGVPDRFSGSGSGTDFTLKI SRVEAEDVGVYYCWQGTFYPWTFGGGTKVEIK (SEQ ID NO: 229) |
| hzR35B9 (A56)- LV2b (A652) | GATGTAGTAATGACCCAGTCCCCACTTAGCTTGCCCGTTA CACTCGGCCAACCCGCAAGCATATCTTGCAAATCCAGTCA GAGCCTCCTGAACTCTGCTGGAAAGACCTATCTGAATTGG CTTCAACAACGTCCCGGTCAATCCCCCAGACGACTTGCCT ACTTGGTAAGTCAGCTTGACTCCGGGGTTCCAGACAGGTT TTCCGGATCTGGAAGTGGAACTGATTTTACACTCAAAATT AGTCGAGTCGAGGCCGAAGACGTGGGTGTCTATTATTGCT GGCAAGGCACCTTTTATCCATGGACTTTTGGTGGGGGCAC CAAGGTTGAAATTAAG (SEQ ID NO: 230) |
| hzR35B9 (A56)- LV2b (A652) | DVVMTQSPLSLPVTLGQPASISCKSSQSLLNSAGKTYLNW LQQRPGQSPRRLAYLVSQLDSGVPDRFSGSGSGTDFTLKI SRVEAEDVGVYYCWQGTFYPWTFGGGTKVEIK (SEQ ID NO: 231) |
| hzR35B9 (A56)- LV2c (A653) | GATGTAGTAATGACCCAGTCCCCACTTAGCTTGCCCGTTA CACTCGGCCAACCCGCAAGCATATCTTGCAAATCCAGTCA GAGCCTCCTGAACTCTGCTGGAAAGACCTATCTGAATTGG CTTCAACAACGTCCCGGTCAATCCCCCAGACGACTTATCT ACTTGGTAAGTGAGCTTGACTCCGGGGTTCCAGACAGGTT TTCCGGATCTGGAAGTGGAACTGATTTTACACTCAAAATT AGTCGAGTCGAGGCCGAAGACGTGGGTGTCTATTATTGCT GGCAAGGCACCTTTTATCCATGGACTTTTGGTGGGGGCAC CAAGGTTGAAATTAAG (SEQ ID NO: 232) |
| hzR35B9 (A56)- LV2c (A653) | DVVMTQSPLSLPVTLGQPASISCKSSQSLLNSAGKTYLNW LQQRPGQSPRRLIYLVSELDSGVPDRFSGSGSGTDFTLKI SRVEAEDVGVYYCWQGTFYPWTFGGGTKVEIK (SEQ ID NO: 233) |
| hzR35B9 (A56)- LV2d (A654) | GATGTAGTAATGACCCAGTCCCCACTTAGCTTGCCCGTTA CACTCGGCCAACCCGCAAGCATATCTTGCAAATCCAGTCA GAGCCTCCTGAACTCTGCTGGAAAGACCTATCTGAATTGG CTTCAACAACGTCCCGGTCAATCCCCCAGACGACTTATCT ACTTGGTAAGTCAGCTTGACGACGGGGTTCCAGACAGGTT TTCCGGATCTGGAAGTGGAACTGATTTTACACTCAAAATT AGTCGAGTCGAGGCCGAAGACGTGGGTGTCTATTATTGCT GGCAAGGCACCTTTTATCCATGGACTTTTGGTGGGGGCAC CAAGGTTGAAATTAAG (SEQ ID NO: 234) |
| hzR35B9 (A56)- LV2d (A654) | DVVMTQSPLSLPVTLGQPASISCKSSQSLLNSAGKTYLNW LQQRPGQSPRRLIYLVSQLDDGVPDRFSGSGSGTDFTLKI SRVEAEDVGVYYCWQGTFYPWTFGGGTKVEIK (SEQ ID NO: 235) |
| hzR35B9 (A56)- LV2f (A656) | GATGTAGTAATGACCCAGTCCCCACTTAGCTTGCCCGTTA CACTCGGCCAACCCGCAAGCATATCTTGCAAATCCAGTCA GAGCCTCCTGAACTCTGCTGGAAAGACCTATCTGAATTGG CTTCAACAACGTCCCGGTCAATCCCCCAGACGACTTATCT ACTTGGTAGCCCAGCTTGACTCCGGGGTTCCAGACAGGTT TTCCGGATCTGGAAGTGGAACTGATTTTACACTCAAAATT AGTCGAGTCGAGGCCGAAGACGTGGGTGTCTATTATTGCT GGCAAGGCACCTTTTATCCATGGACTTTTGGTGGGGGCAC CAAGGTTGAAATTAAG (SEQ ID NO: 236) |
| hzR35B9 (A56)- LV2f (A656) | DVVMTQSPLSLPVTLGQPASISCKSSQSLLNSAGKTYLNW LQQRPGQSPRRLIYLVAQLDSGVPDRFSGSGSGTDFTLKI SRVEAEDVGVYYCWQGTFYPWTFGGGTKVEIK (SEQ ID NO: 237) |

Using methods described previously, these further-engineered VH and VL were cloned into expression vectors, and the resulting heavy and light chains were co-expressed with various heavy or light chains described previously to generate additional antibodies. In this way, among others, antibodies A512/A654 (containing VH and VL amino acid SEQ ID NOs. 108 and 235, respectively), A631/A468 (containing VH and VL amino acid SEQ ID NOs. 203 and 94, respectively), A512/A651 (containing VH and VL amino acid SEQ ID NOs. 108 and 229, respectively), A512/A652 (containing VH and VL amino acid SEQ ID NOs. 108 and 231, respectively), A634/A468 (containing VH and VL amino acid SEQ ID NOs. 209 and 94, respectively), A636/A468 (containing VH and VL amino acid SEQ ID NOs. 211 and 94, respectively), A643/A468 (containing VH and VL amino acid SEQ ID NOs. 221 and 94, respectively), A512/A653 (containing VH and VL amino acid SEQ ID NOs. 108 and 233, respectively), A632/A468 (containing VH and VL amino acid SEQ ID NOs. 205 and 94, respectively), A645/A468 (containing VH and VL amino acid SEQ ID NOs. 223 and 94, respectively), A648/A468 (containing VH and VL amino acid SEQ ID NOs. 225 and 94, respectively), A650/A468 (containing VH and VL amino acid SEQ ID NOs. 227 and 94, respectively), A639/A468 (containing VH and VL amino acid SEQ ID NOs. 215 and 94, respectively), A512/A656 (containing VH and VL amino acid SEQ ID NOs. 108 and 237, respectively), A633/A468 (containing VH and VL amino acid SEQ ID NOs. 207 and 94, respectively), A638/A468 (containing VH and VL amino acid SEQ ID NOs. 213 and 94, respectively), A641/A468 (containing VH and VL amino acid SEQ ID NOs. 217 and 94, respectively), A642/A468 (containing VH and VL amino acid SEQ ID NOs. 219 and 94, respectively) were produced as shown in FIG. 23.

Example 11

Functional Analysis of Humanized Antibodies

These humanized antibodies were tested for antagonist activity in rhTWEAK stimulated HRMC using the method described above. Briefly, HRMC were incubated with 0.833 nM humanized anti-Fn14 antibodies, mouse/human chimeric CRCBT-06-002 (mu/huCRCBT), ITEM-4 or isotype control mAbs for 30 minutes at 37° C. and then rhTWEAK was added to the wells at 250 ng/mL for 24 hours. Supernatants were harvested and tested for IL-8 using an IL-8 ELISA kit. Each of the humanized anti-Fn14 clones was able to block TWEAK-induced IL-8 secretion significantly better than mu/huCRCBT-06-002 and ITEM-4. Data were analyzed using unpaired t test, comparing IL-8 reduction.

A512/A468, A553/A472 and A515/A518 showed superior activity compared to mouse/human chimeric CRCBT-06-002 and ITEM-4 at antibody concentration of 0.125 μg/mL (0.833 nM) (see FIG. 13).

Humanized clones A512/A468, A515/A518, and A553/A472 were also tested for agonist activity in HRMC. Briefly, HRMC were incubated with 250 ng/mL rhTWEAK (positive control) or media alone (negative control) and humanized anti-Fn14, mouse/human chimeric CRCBT-06-002 (mu/huCRCBT), ITEM-4 or isotype control mAbs for 24 h. Supernatants were harvested and tested for IL-8 using an IL-8 ELISA kit. Each of the tested anti-Fn14 mAb clones induced minimal amounts of IL-8 release, similar to that observed for isotype control hIgG4-nullbody mAb or supernatant alone (see FIG. 17). These data show that the panel of humanized anti-Fn14 mAb clones (A512/A468, A515/A518, and A553/A472) do not induce inflammatory chemokines from human cells and demonstrate an advantage over previously described anti-Fn14 mAbs that do show agonist activity in vitro.

Example 12

Production of Humanized Antibodies

Mammalian expression vectors for expression of full length humanized heavy or light chains were fabricated for expression of all of the VH and VL designs described above.

Synthesized DNA fragments coding for each of the designed variable sequences (custom DNA synthesis, Invitrogen/GeneArt, Regensburg, Germany) were fused to appropriately digested mammalian expression vectors such that each variable region was joined in frame with an N-terminal signal peptide and C-terminal human constant region. Expression vectors for production of chimeric mouse-human or humanized IgG4 Nullbody, kappa antibodies were generated using the same methods as those described above for construction of mouse IgG1(D265A), kappa heavy and light chain antibody expression vectors, with the exception that the primers for PCR amplification of the VH and VL cDNAs added the appropriate 5' and 3' sequences for ligase-independent cloning into mammalian heavy chain expression vectors pKTABEX-TC26-sphuG4null (Kyowa Hakko Kirin) or pcDNA3.4-sphuG4null, digested with NruI and NheI, and light chain expression vector pKTABEX-TC26-sphuK (KHK) or pcDNA3.4-sphuK, digested with SfoI and BsiWI. All constructed plasmid sequences were validated by Sanger sequencing. Human IgG4 Nullbody® constant domain (nucleotide SEQ ID NO: 29 coding for amino acid SEQ ID NO: 30) contains three amino acid substitutions: proline substituted for serine at position 228 (S228P) (Eu numbering), lysine substitution for arginine at position 409 (R409K) (Eu numbering) to reduce intermolecular dissociation of heavy chains to form half antibodies (see U.S. Pat. No. 8,911,726B2) (Angal, S., et al., Mol Immunol, 1993, 30(1):105) and glutamic acid substitution for leucine at position 235 (L235E) (Eu numbering) to reduce FcγR interaction (Alegre, M.L. et al., *J Immunol,* 1992, 148(11):3461). Human kappa constant nucleotide sequence used is SEQ ID: NO 27 coding for amino acid sequence is SEQ ID NO: 28. In this way, expression vectors for antibodies 41c, R35B9, variants of R35B9, humanized R35B9, variants of humanized R35B9 and chimeric CRCBT-06-002 were fabricated. Human constant domain sequences mentioned above are also listed below.

Human Kappa constant domain nucleotide sequence:
(SEQ ID NO: 27)
CGTACGGTGGCTGCACCATCTGTCTTCATCTTCCCGCCATCTGATGAGCA

GTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGT

AACTCCCAGGAGAGTGTCACAGAGCAGGACAGCAAGGACAGCACCTACAG

CCTCAGCAGCACCCTGACGCTGAGCAAAGCAGACTACGAGAAACACAAAG

TCTACGCCTGCGAAGTCACCCATCAGGGCCTGAGCTCGCCCGTCACAAAG

AGCTTCAACAGGGGAGAGTGT

Human Kappa constant domain amino acid sequence:
(SEQ ID NO: 28)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Human IgG4null constant domain nucleotide sequence:
(SEQ ID NO: 29)
GCTAGCACCAAGGGGCCATCCGTCTTCCCCCTGGCGCCCTGCTCCAGGAG

CACCTCCGAGAGCACAGCCGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACGAAGACCTACACCTGCA

ACGTAGATCACAAGCCCAGCAACACCAAGGTGGACAAGAGAGTTGAGTCC

AAATATGGTCCCCCATGCCCACCATGCCCAGCACCTGAGTTCGAGGGGGG

ACCATCAGTCTTCCTGTTCCCCCCAAAACCCAAGGACACTCTCATGATCT

CCCGGACCCCTGAGGTCACGTGCGTGGTGGTGGACGTGAGCCAGGAAGAC

CCCGAGGTCCAGTTCAACTGGTACGTGGATGGCGTGGAGGTGCATAATGC

CAAGACAAAGCCGCGGGAGGAGCAGTTCAACAGCACGTACCGTGTGGTCA

GCGTCCTCACCGTCCTGCACCAGGACTGGCTGAACGGCAAGGAGTACAAG

TGCAAGGTCTCCAACAAAGGCCTCCCGTCCTCCATCGAGAAAACCATCTC

CAAAGCCAAAGGGCAGCCCCGAGAGCCACAGGTGTACACCCTGCCCCCAT

-continued

```
CCCAGGAGGAGATGACCAAGAACCAGGTCAGCCTGACCTGCCTGGTCAAA

GGCTTCTACCCCAGCGACATCGCCGTGGAGTGGGAGAGCAATGGGCAGCC

GGAGAACAACTACAAGACCACGCCTCCCGTGCTGGACTCCGACGGCTCCT

TCTTCCTCTACAGCAAGCTAACCGTGGACAAGAGCAGGTGGCAGGAGGGG

AATGTCTTCTCATGCTCCGTGATGCATGAGGCTCTGCACAACCACTACAC

ACAGAAGAGCCTCTCCCTGTCTCTGGGTAAA
```

Human IgG4null constant domain amino acid sequence:

(SEQ ID NO: 30)

```
ASTKGPSVFPLAPCSRSTSESTAALGCLVKDYFPEPVTVSWNSGALTSGV

HTFPAVLQSSGLYSLSSVVTVPSSSLGTKTYTCNVDEIKPSNTKVDKRVE

SKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLV

KGFYPSDIAVEWESNGQPENNYKTTPPVLDSDGSFFLYSKLTVDKSRWQE

GNVFSCSVMHEALHNHYTQKSLSLSLGK.
```

Using these vectors, various combinations of humanized R35B9 VH and VL frameworks were used to produce whole antibody by transient expression from Expi293 cells and purified, as described previously. Exemplary humanized antibodies are shown in FIG. 23. Resulting antibodies were tested for binding and functional activity.

Example 13

Biacore Analysis of Anti-Fn14 Antibodies Binding to Fn14

Antibody Fab Generation

The affinity of four recombinant anti-Fn14 mAbs (41c, R35B9, CRCBT-06-002, ITEM-4) to human and cynomolgus macaque GST-Fn14 was measured using Biacore assays. Fab antibody fragments for the following mAbs 41c, R35B9, CRCBT-06-002, ITEM-4 were obtained using the mouse IgG1 Fab and F(ab')2 preparation kit (Thermo Fisher Scientific, # 44980) following manufacturer's instructions provided in the kit. Following enzymatic digestion, the samples were analyzed by SDS-PAGE to confirm Fab fragment generation and subsequently dialyzed against PBS pH 7.4 (Sigma Aldrich powder pouches). Following dialysis, protein sample was concentrated with a centrifugal filter concentrator (Vivaspin 3,500 MWCO: Sartorius, Goettingen, Germany). The protein was further purified by size exclusion chromatography to remove any contaminants or degradation products. The fractions were analyzed by SDS-PAGE and the positive fractions were pooled and dialyzed against PBS pH 7.4 (Sigma Aldrich powder pouches).

Determination of Anti-Fn14 mAb Species Cross-Reactivity (Human, Cynomolgus Macaque and Mouse Fn14) and Affinities to Human and Cynomolgus Macaque Fn14

In order to kinetically analyze the binding activity of anti-Fn14 mouse antibodies 41c, R35B9, and CRCBT-06-002 to recombinant human and cynomolgus macaque Fn14 proteins, the binding activity was measured by surface plasmon resonance method (SPR). Antibodies were generated as described herein. All of the following procedures were carried out using a Biacore T200 (GE Healthcare Bio-Sciences). To determine antibody affinity to human Fn14, recombinant human His-SUMO-Fn14 was immobilized on a CM5 sensor chip (GE Healthcare Bio-Sciences) by amine coupling chemistry. In particular, the kinetic assay was carried out by immobilizing on the chip approximately 20-30 RU of recombinant protein, in order to achieve a low protein immobilization level. To determine antibody affinity to cynomolgus macaque Fn14, polyclonal anti-GST antibodies were immobilized on a CM5 sensor chip (GE Healthcare Bio-Sciences) by amine coupling chemistry. In particular, after immobilizing approximately 1500 RU of anti-GST capture antibody onto the chip, cynomolgus macaque GST-Fn14 in culture supernatant was allowed to run for 5 minutes at a flow rate of 30 µL/min in order to achieve a low capture level of approximately 20 RU. Thereafter, antibody Fab fragments, serially diluted from a high concentration, were allowed to run at a flow rate of 30 µL/min onto the chip for 300 seconds. The dissociation time was 1800 seconds and the binding curves were measured at 25° C. Regeneration was performed with 10 mM glycine pH 1.5 for 30 seconds. The raw data were double referenced by subtraction of the signals from a reference flow cell without immobilized ligand and a buffer blank.

Figure 5:
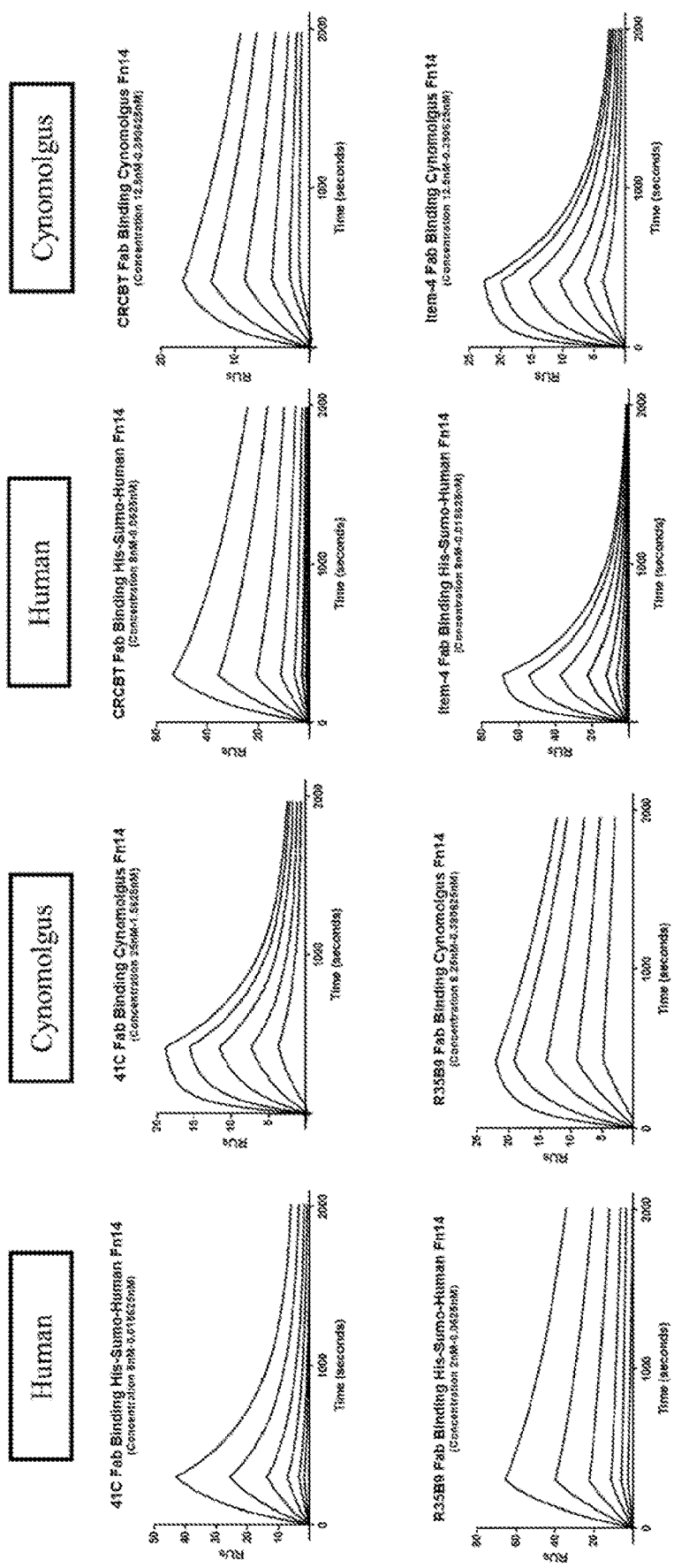
FIG. 5 depicts sensorgrams of individual anti-Fn14 Fab binding to human or cynomolgus macaque Fn14 by Biacore.

A sensorgram corresponding to each concentration was obtained (see FIG. 5). Analysis was carried out using a 1:1 Langmuir fit model using the analysis software attached to the apparatus, Biacore T200 Evaluation software (Biacore), thereby calculating an association rate constant ka [M-1s-1] and a dissociation rate constant kd [s-1] for the recombinant Fn14 proteins. Using these data, equilibrium dissociation constants, $K_D$ (kd/ka), of individual antibodies were obtained. Cross-reactivity of anti-Fn14 mouse antibodies to recombinant mouse GST-Fn14 protein was measured as described above. In particular, Fab antibody fragments at concentrations of 20 nM and 10 nM were allowed to run at a flow rate of 30 µL/min onto the chip for 300 seconds. The dissociation time was 1800 seconds and the binding curves were measured at 25° C.

According to the analysis, anti-Fn14 monoclonal antibody R35B9 had significantly higher affinity for the human Fn14 protein than the rest of the antibodies tested, with an apparent $K_D$ value in the picomolar range (see Table 8 below). The $K_D$ for R35B9 binding to hFn14 was measured at 0.208 nM while the $K_D$ for the other anti-Fn14 antibodies tested was as follows: 0.765 nM (CRCBT-06-002), 1.620 nM (ITEM-4) and 1.978 nM (41c) (see Table 8). Affinity to cynomolgus macaque Fn14 was also tested, yielding similar $K_D$ results, with the mAbs maintaining the same rank order as was observed for human Fn14 (see Table 9 below). It was also demonstrated that all antibodies tested bound to mouse Fn14 protein (see FIG. 6A).

TABLE 8

Binding kinetics of Fn14 Fabs to human Fn14

| Analyte | Amine Coupled | Fitting Model | ka (1/Ms) | kd (1/s) | KD (nM) | KD (nM) Average (Std Dev) |
|---|---|---|---|---|---|---|
| R35B9 Fab LM042817 | His- | 1:1 Binding | 3067000 | 6.302E−04 | 0.2055 | 0.208 |
|  | Sumo-huFn14 | 1:1 Binding | 2030000 | 4.271E−04 | 0.2104 | (+/0.00347) |
| CRCBT-06-002 Fab LM111816 | His- | 1:1 Binding | 887600 | 4.930E−04 | 0.8589 | 0.7654 |
|  | Sumo-huFn14 | 1:1 Binding | 806500 | 5.418E−04 | 0.6719 | (+/−0.1322) |
| 41C Fab LM101416 | His- | 1:1 Binding | 1128000 | 2.423E−03 | 2.148 | 1.978 |
|  | Sumo-huFn14 | 1:1 Binding | 1472000 | 2.661E−03 | 1.808 | (+/−0.2404) |
| Item 4 Fab LM021617 | His- | 1:1 Binding | 1682000 | 3.037E−03 | 1.805 | 1.6195 |
|  | Sumo-huFn14 | 1:1 Binding | 1942000 | 2.785E−03 | 1.434 | (+/−0.2623) |

TABLE 9

Binding kinetics of Fn14 Fabs to cynomolgus macaque Fn14

| Analyte | Captured by antiGST | Fitting Model | ka (1/Ms) | kd (1/s) | KD (nM) | KD (nM) Average (Std Dev) |
|---|---|---|---|---|---|---|
| R35B9 Fab LM042817 | CynoFn14 | 1:1 Binding | 1457000 | 3.424E−04 | 0.235 | 0.2285 (+/−0.00926) |
|  |  | 1:1 Binding | 1714000 | 3.804E−04 | 0.2219 |  |
| CRCBT-06-002 Fab LM111816 | CynoFn14 | 1:1 Binding | 486200 | 4.017E−04 | 0.8262 | 0.76205 (+/−0.0907) |
|  |  | 1:1 Binding | 554500 | 3.869E−04 | 0.6979 |  |
| 41C Fab LM101416 | CynoFn14 | 1:1 Binding | 441200 | 1.534E−03 | 3.476 | 3.38 (+/−0.1386) |
|  |  | 1:1 Binding | 678400 | 2.226E−03 | 3.280 |  |
| Item 4 Fab LM021617 | CynoFn14 | 1:1 Binding | 1308000 | 1.1819E−03 | 1.390 | 1.298 (+/−0.1308) |
|  |  | 1:1 Binding | 1680000 | 2.024E−03 | 1.205 |  |

Alternatively, using a method referred to as "single cycle kinetics," the His-Sumo-Fn14 was injected with increasing concentrations in a single cycle, the surface not being regenerated between injections. Specifically, anti-human Fc specific antibodies were immobilized on a CM5 sensor chip (cat# BR100012, GE Healthcare Life Sciences, Pittsburgh, Pennsylvania) by an amine coupling chemistry. Thereafter, humanized anti-Fn14 antibodies were captured at approximately 200 RUs, followed by injections of increasing concentrations of recombinant human His-Sumo-Fn14 protein. The association time was 120 seconds, and the final dissociation time was 900 seconds. At the end of the analyte injections, the surface was regenerated with 3M $MgCl_2$ for 30s. The raw data were double referenced by subtraction of the signals from a reference flow cell without immobilized ligand and a buffer blank. The sensorgram corresponding to each concentration was obtained (see FIG. 6B). The analysis was carried out using a 1:1 Langmuir fit model, using the analysis software attached to the apparatus, Biacore T200 Evaluation software, thereby calculating an association rate constant ka [M-1s-1] and a dissociation rate constant kd [s-1] for the recombinant Fn14 protein (see Table 24. Humanization of anti-Fn14 antibodies did not affect affinity for human Fn14, as shown in Table 24.

TABLE 24

Binding kinetics of Fn14 mAbs to human Fn14

| Ligand | Fitting Model | ka (1/Ms) | kd (1/s) | KD (nM) | KD (nM) Average (Std Dev) |
|---|---|---|---|---|---|
| A512/ A468 | 1:1 Binding | 3.003e6 | 6.794e−4 | 2.262e−10 | 2.06E−10 |
|  | 1:1 Binding | 3.432e6 | 6.643e−4 | 1.936e−10 | (1.77E−11) |
|  | 1:1 Binding | 3.307e6 | 6.523e−4 | 1.973e−10 |  |
| A515/ A518 | 1:1 Binding | 3.113e6 | 1.435e−3 | 4.611e−10 | 4.70E−10 |
|  | 1:1 Binding | 3.248e6 | 1.537e−3 | 4.734e−10 | (8.33E−12) |
|  | 1:1 Binding | 3.15e6 | 1.501e−3 | 4.766e−10 |  |
| A553/ A472 | 1:1 Binding | 2.150e6 | 8.036e−4 | 3.738e−10 | 3.58E−10 |
|  | 1:1 Binding | 2.342e6 | 8.119e−4 | 3.466e−10 | (1.40E−11) |
|  | 1:1 Binding | 2.26e6 | 7.989e−4 | 3.535e−10 |  |
| A641/ A468 | 1:1 Binding | 2.889e6 | 7.556e−4 | 2.615e−10 | 2.56E−10 |
|  | 1:1 Binding | 3.108e6 | 7.734e−4 | 2.489e−10 | (6.56E−12) |
|  | 1:1 Binding | 2.97e6 | 7.639e−4 | 2.573e−10 |  |
| A648/ A468 | 1:1 Binding | 2.776e6 | 5.312e−4 | 1.914e−10 | 2.22E−10 |
|  | 1:1 Binding | 3.193e6 | 7.556e−4 | 2.367e−10 | (2.66E−11) |
|  | 1:1 Binding | 3.128e6 | 7.42e−4 | 2.372e−10 |  |
| A650/ A468 | 1:1 Binding | 3.304e6 | 8.712e−4 | 2.636e−10 | 2.78E−10 |
|  | 1:1 Binding | 2.936e6 | 8.43e−4 | 2.871e−10 | (1.21E−11) |
|  | 1:1 Binding | 2.923e6 | 8.249e−4 | 2.822e−10 |  |

Example 14

Epitope Mapping of Anti-Fn14 Antibodies Binding to Fn14 Peptides

An Octet-based assay was employed to perform epitope mapping for binding of anti-Fn14 mAbs to two subdomains of the extracellular domain of hFn14. Subdomain 1 consisted of AA30-50 and Subdomain 2 consisted of AA51-70.

A ForteBio Octet Qke instrument (ForteBio) was used to measure the ability of purified antibodies to bind Fn14 peptides. The assays were performed at 30° C. in 96-well half area plates (Grenier, cat# 675076), with agitation set to 1000 rpm, in kinetic buffer (provided in the assay kit) to minimize nonspecific interactions. Biosensor tips were equilibrated in kinetic buffer for 600 s prior to use. Soluble biotinylated peptides (20 µg/ml, Subdomain 1 (AA30-50): APGTAPCSRGSSWSADLDKCM-[K-Ahx-biotin]-amide (SEQ ID NO: 182) and Subdomain 2 (AA51-70): DCASCRARPHSDFCLGCAAA-[K-Ahx-biotin]-amide (SEQ ID NO: 183) synthesized by 21' Century Biochemicals) in kinetic buffer were immobilized on streptavidin-coated biosensors (ForteBio, cat# 18-5020) for 300 seconds. Typical capture variability within a row of eight tips did not exceed 0.1 nm. Purified antibodies (20 µg/ml) were allowed to bind the immobilized peptides. Association was measured for 300 seconds, using the high sensitivity kinetics setting. To characterize the binding properties of the antibody candidates, the response (nm) at t =120 seconds from the start of the association step was recorded. All values were compared to a control sample (isotype antibody).

The results showed that 41c and R35B9 bind to Subdomain 1 of Fn14, whereas CRCBT-06-002 and ITEM-4 bind to Subdomain 2 of the protein (see FIG. 7). This demonstrates that 41c and the affinity matured R35B9 antibodies bind to an epitope of Fn14 that is distinct from the epitope(s) recognized by previously described anti-Fn14 mAbs CRCBT-06-002 and ITEM-4.

Example 15

Production of Recombinant Proteins for Crystallography

Cloning of His-tagged 41c Fab for Crystallization Studies

For the purpose of crystallization, a recombinant Fab fragment of 41c with a C-terminal 6xHistidine heavy chain tag was produced from bacteria. To accomplish this, 41c VL and VH DNA sequences were subcloned into a bacterial expression vector such that a Fab fragment of 41c would be expressed, comprised of a full length 41c mouse kappa light chain, and a 41c mouse IgG1 heavy chain fragment (allele IGHG1*02), through constant domain amino acid # 220 (Eu numbering), followed by a seven amino acid linker (TSGQAGQ, single amino acid code) and C-terminal 6xHistidine tag. Each cDNA was inserted into the vector in-frame with a 5' pelB prokaryotic signal peptide which directs the attached protein to the prokaryotic periplasmic space. Restriction endonuclease sites used for vector insertion at the junction of the pelB cDNA and VH or VL sequences coded for two additional amino acids that were not removed during cleavage of the pelB signal peptide during protein synthesis, leaving two non-immunoglobulin amino acids at the amino terminus of the 41c heavy and light chain, Leu-Glu or Ser-Arg, respectively. The amino acid sequences of the mature mouse 41c-His Fab light chain and heavy chain with C-term His tag are SEQ ID NO: 176, SEQ ID NO: 175, respectively.

Bacterial Production of 41c-His Fab

Escherichia coli (E. coli) bacterial strain, ER2738, was used to produce 41c-His Fab protein, using methods known to those skilled in the art. Briefly, a single plasmid-transformed bacterial colony was inoculated in LB medium and cultured, with shaking, at 37° C. until the optical density of the culture, measured at a 600 nm wavelength (OD600), was between 0.6 and 1, at which time the bacteria were induced to produce protein by addition of Isopropyl ß-D-1-thiogalactopyranoside (IPTG) to the culture at a final concentration of 1 mM. Four to six hours after induction, the culture supernatant, containing Fab protein that had leaked from the periplasmic space, was clarified by centrifugation, concentrated and buffer-exchanged with 50 mM phosphate buffer (pH 8.0) containing 300 mM NaCl and 10 mM imidazole. Protein was then precipitated from the sample by adding ammonium sulfate to make a 60% solution, weight/volume. The precipitated protein fraction was then dialyzed against 50 mM phosphate buffer, pH 8.0, containing 0.3 M NaCl. The concentrated and buffer-exchanged sample was purified as described above. After purification, the resulting 41c-His Fab was estimated to be >95% pure, by SDS-PAGE, and was confirmed to bind Fn14 in ELISA and Biacore.

Cloning and Production of His-tagged R35B9 Fab for Crystallization Studies

A vector for prokaryotic expression of mouse IgG1, kappa Fab of R35B9 was generated. In PCR reaction # 1, the entire R35B9 mouse kappa light chain DNA was amplified from a mammalian expression vector by PCR, using three overlapping forward primers adding DNA for a 5' pelB signal sequence as well as a 15 nucleotide 5' extension overlapping the appropriate region of the restriction digested prokaryotic expression vector, pFLAG-CTS (Sigma-Aldrich), and one reverse primer adding a 6xHistidine tag and 3' flanking DNA to be used for fusion to DNA amplified in PCR reaction # 2. In PCR reaction # 2, DNA coding for the Tac promoter plus the pelB signal peptide was amplified from vector pFLAG-CTS (Sigma-Aldrich) by PCR using a forward primer adding 5' flanking DNA sequence overlapping the 3' end of the PCR reaction # 1, and a reverse primer annealing to and amplifying the 3' end of the pelB signal peptide, and overlapping the 5' DNA sequence from the product of PCR reaction # 3. In PCR reaction # 3, DNA coding for the Fab portion of R35B9 heavy chain fragment (including the entire VH through amino acid # 221 of the mouse IgG1 (allele IGHG1*01) constant hinge region (Eu numbering) was amplified from a previously construct mammalian expression vector using a forward primer adding 5' DNA coding for the pelB signal sequence, which also overlaps the 3' DNA sequence of PCR reaction # 2, and a reverse primer adding a 3' 6xHistidine tag. Using the combined purified DNA fragments from the three previous PCR reactions as template, a fourth PCR reaction was performed which fused all three overlapping DNA fragments into a single pe1B-light chain-promoter-pelB heavy chain-His fragment with 5' and 3' DNA extension for ligation into pFLAG-CTS digested with NdeI and SalI, downstream of a Tac promoter.

Amplified DNA was gel purified and ligated into a restriction digested prokaryotic expression vector using GeneArt Seamless Cloning kit as per the manufacturer's instructions (cat# A14606, Invitrogen/GeneArt, Carlsbad, California). The vector sequence was validated by Sanger sequencing. The amino acid sequences of the mature mouse R35B9-His Fab light chain and heavy chain with C-term His tag are SEQ ID NO: 178, SEQ ID NO: 177, respectively, and are as shown in Table 23 below.

TABLE 23

Amino acid sequences of proteins for crystallization

| | |
|---|---|
| 41C mIgG1 heavy chain for crystal | LEEVQLQQSGPELVKPGASVKMSCKASGYTFTDYNMHWVKQSHGKS LEWIGYINPNNGGTNYNQKFKGKATLTVNKSSRSAYMEFRSLTSED SAVYYCASSGWFTYWGQGTLVTVSAAKTTPPSVYPLAPGSAAQTNS MVTLGCLVKGYFPEPVTVTWNSGSLSSGVHTFPAVLQSDLYTLSSS VTVPSSTWPSETVTCNVAHPASSTKVDKKIVPRDCTSGQAGQHHHH HH (SEQ ID NO: 175) |
| 41C mK light chain for crystal | SRDVVMTQTPLTLSVAIGQPASISCKSSQSLLNSAGKTYLNWLLQR PGQSPKRLIYLVSQLDSGVPDRFTGSGSGTDFTLKISRVEAEDLGV YYCWQGTHFPWTFGGGTKLEIKRADAAPTVSIFPPSSEQLTSGGAS VVCFLNNFYPKDINVKWKIDGSERQNGVLNSWTDQDSKDSTYSMSS TLTLTKDEYERHNSYTCEATHKTSTSPIVKSFNRNEC (SEQ ID NO: 176) |
| R35B9 mIgG1 heavy fab frag for crystal | EVQLQQSGPELVKPGASVKMSCKASGYIFQDYNMHWVKQSHGKSLE WIGSINPRNGWTNYNQKFKGKATLTVNKSSRSAYMEFRSLTSEDSA VYYCASSGWFTYWGQGTLVTVSAAKTTPPSVYPLAPGSAAQTNSMV TLGCLVKGYFPEPVTVTWNSGSLSSGVHTFPAVLESDLYTLSSSVT VPSSPRPSETVTCNVAHPASSTKVDKKIVPRDCGHHHHHH (SEQ ID NO: 177) |
| R35B9 mK light chain for crystal | DVVMTQTPLTLSVAIGQPASISCKSSQSLLNSAGKTYLNWLLQRPG QSPKRLIYLVSQLDSGVPDRFTGSGSGTDFTLKISRVEAEDLGVYY CWQGTFYPWTFGGGTKLEIKRADAAPTVSIFPPSSEQLTSGGASVV CFLNNFYPKDINVKWKIDGSERQNGVLNSWTDQDSKDSTYSMSSTL TLTKDEYERHNSYTCEATHKTSTSPIVKSFNRNEC (SEQ ID NO: 178) |

Bacterial Production of R35B9-His-Fab

The R35B9 Fab-His expression vector was transformed into bacterial strain W3110 and a single ampicillin-resistant clone was grown in liquid LB-broth +ampicillin for 6-8 hours while shaking at 225 rpm at 37° C. 100 µL of the culture was seeded into 100 mL of LB-broth +ampicillin and incubated while shaking at 225 rpm at 37° C. overnight. The next day, an absorbance OD600 measurement was taken, and a large volume of LB-broth +ampicillin were seeded at OD600 of ~0.05-01 This culture was incubated as before until OD600 reached between 0.6-1.0, at which point the cells were gently pelleted and the supernatant was discarded. The bacterial pallet was resuspended in a volume of pre-warmed 37° C. M9 broth (1×M9 minimal salts (Sigma-Aldrich, cat# M6030) supplemented with 0.4% glucose, 2 mM MgSO4 and 0.1 mM CaCl2) equal to the original culture volume, incubated as before for 1 hour, then moved to a 22° C. incubator shaking at 225 rpm.

Expression was induced by adding IPTG to 0.5 mM and incubating overnight. Cells were pelleted by centrifugation and supernatant discarded. The Fab protein was released from the bacterial periplasm by resuspending the cell pellet in TS buffer (200 mM Tris-HCl, pH 8.0, 500 mM sucrose) and incubating on ice for 30-60 minutes. The bacteria were again pelleted by centrifugation and the TS buffer containing released Fab was sterile filtered through a 0.22 µm vacuum filter unit (Millipore, Bedford, MA) then further processed for Fab enrichment by Ni-NTA chromatography.

Production of Recombinant Fn14 for Crystallization Studies

Cleaved, untagged human Fn14 for crystallization studies was obtained by enzymatic treatment of His-SUMO-Fn14 with SUMO Express protease, according to the manufacturer's protocol (Lucigen, cat# 30801-2). The His-SUMO-Fn14 was prepared as shown in Example 1 above.

After cleavage, the mixture was applied to an IMAC column (GE Healthcare, cat# 17524701), and the free target protein was recovered in the flow-through while the SUMO tag and SUMO Express Protease remained bound to the IMAC matrix. The Fn14 protein was further purified by size exclusion chromatography to remove any contaminants or uncleaved material. The fractions were analyzed by SDS-PAGE and the positive fractions were pooled and dialyzed against PBS pH 7.4 (Sigma Aldrich powder pouches).

Recombinant 41c-His and R35B9-His Fab Purification

Recombinant His-tagged Fabs were purified from culture media using HisTrap HP affinity column (Ni Sepharose High Performance media precharged with nickel ions (Ni2+)) (GE Healthcare Life Sciences, cat# 17524701). The conditioned medium (culture supernatant) was diluted with 50 mM sodium phosphate, pH 8.0, 0.3 M NaCl buffer and filtered with a 0.22 µm vacuum filter unit (Millipore, Bedford, MA). Imidazole was added to a final concentration of 20 mM just prior the purification. Sample was loaded onto a 5 mL HisTrap HP column (GE Healthcare Life Sciences, cat# 17524801) equilibrated with 50 mM sodium phosphate, pH 8.0, 0.3 M NaCl buffer, 20 mM imidazole. Upon sample loading, the column was washed thoroughly with 6 column volumes of 50 mM sodium phosphate, pH 8.0, 0.3 M NaCl buffer, 20 mM imidazole. The protein was eluted with 20 mM-600 mM imidazole gradient over 25 column volumes, and neutralized with 5 mM EDTA (final concentration). The fractions were analyzed by SDS-PAGE and the positive fractions were pooled and dialyzed against PBS pH 7.4 (Sigma Aldrich powder pouches). Following dialysis, the protein sample was concentrated with a centrifugal filter concentrator (Vivaspin 3,500 MWCO: Sartorius, Goettingen, Germany). The protein was further purified by size exclusion chromatography to remove any contaminants or degradation products. The fractions were analyzed by SDS-PAGE and the positive fractions were pooled and dialyzed against PBS pH 7.4 (Sigma Aldrich powder pouches).

Example 16

Crystal Structure of the 41C-His Fab or R35B9-His Fab—Fn14 Complexes

Crystallization Methods

Purified Fn14 and His-tagged 41c Fab or R35B9 Fab proteins were mixed in a 1:1 stoichiometric ratio, concentrated to 1 mg/mL and then subjected to crystallization. Initial crystallization trials were performed in a 96-well format using a nano-liter dispensing liquid handling robot (Phoenix, Art Robbins Ltd.) while mixing 0.15 μL protein with 0.15 μL precipitant from different commercially available crystallization screens (JCSG core+and JCSG core 1 screens). Over 200 crystallization conditions were tested using the sitting drop vapor diffusion method and crystallization trails were carried out at both 4° C. and 22° C. Optimization of all crystallization conditions was performed manually by both hanging drop and sitting drop methods. Crystals were obtained in various conditions containing PEG 3350 or PEG 6000 as the common precipitant and were grown over 3 days.

The crystals of Fn14-41c-His Fab complex used for X-ray diffraction experiments were grown by sitting drop vapor diffusion method by equilibrating a mixture containing 1 μL of protein complex (1 mg/mL Fn14-41c-His Fab complex in 1X PBS buffer at pH 7.0) and 1 μL of reservoir solution containing 20% (w/v) PEG3350 and 0.2 M K/Na tartrate, against 1 mL of reservoir solution.

Similarly, the crystals of Fn14 -R35B9-His Fab complex were obtained by hanging drop vapor diffusion method in a crystallization solution containing 0.1M citric acid pH 5.0, 20% WN PEG 6000. All crystals were flash-cooled in liquid nitrogen in their crystallization buffer containing 20% glycerol for subsequent data collection.

Data Collection and Refinement

Native diffraction data for different crystals was collected remotely at Stanford Synchrotron Radiation Light Source (SSRL) beam line 9-2 using a PILATUS 6M PAD detector at a wavelength of 0.97 Å and a temperature of 100 K. Each image was collected with 0.15 degree oscillation and a 1.25 second exposure time. The collected images were processed and scaled using HKL2000 (Otwinowski, Z. and W. Minor, *Methods Enzymol.*, 1997, 276:307-326) to an overall resolution of 1.76 Å for Fn14-41c-His Fab complex and 2.25 Å for Fn14 -R35B9-His Fab complex. The crystals of Fn14-41c Fab complex belong to the space group P21221 (sg 18), with unit cell dimensions: a=68.46 Å, b=75.96 Å, c=102.64 Å, α=β=γ=90°, while the crystals of Fn14-R35B9 Fab complex belong to the space group P1, with unit cell dimensions: a=89.81 Å, b=102.38 Å, c=120.95 Å, α=89.4°, β=82.9°, γ=85.8°.

The position of 41c-His Fab in the asymmetric unit was determined by molecular replacement method PHASER-MR (McCoy, A. J., et al., *Acta Crystallogr.*, 2005, D61(4): 458-464) using the L and H chain of the mouse IgG1 Fab F124 (anti-hepatitis B surface antigen mAb, PDB ID 1F11) separately, as a starting search model. Starting with initial phases obtained by MR, first the 41c-His Fab model was built gradually by cycles of iterative model building and subsequently Fn14 was manually built into the Fo-Fc electron density map using COOT (Emsley, P., et al., *Acta Crystallogr D Biol Crystallogr*, 2004, 60(12):2126-32; Emsley, P., et al., *Acta Crystallogr D Biol Crystallogr.*, 2010. 66(4):486-501). At the final stages of refinement, water molecules were added automatically using Refmac program with ARP/wARP function.

The final model was refined in PHENIX/REFMAC (Murshudov, G.N., et al., *Acta Crystallogr.*, 1997, D53:240-255) to 1.76 Å resolution with residual factors R/Rfree=16.4/19.4. The structure had good geometry with 4 residues (0.89%) as outliers and 97.6% residues in favored region of the Ramachandran plot. Correspondingly, the structure of Fn14 -R35B9-His Fab complex was determined by molecular replacement using the phase information obtained from Fn14-41c-His Fab complex and the structure was refined to 2.3 Å with residual factors R/Rfree=20.9/23.3. The data collection and refinement statistics are summarized in Table 7.

TABLE 7

Data collection and refinement statistics for the Fn14 - 41c-His Fab and Fn14 - R35B9-His Fab complexes

| Data collection statistics | Fn14 - 41c-His Fab complex | Fn14 - R35B9-His Fab complex |
| --- | --- | --- |
| PDB ID | | |
| Space group | $P2_122_1$ | P1 |
| Cell dimension | | |
| a, b, c, (Å) | 68.5, 76.0, 102.6 | 89.8, 102.4, 121.0 |
| a, b, g(°) | 90.00 90.00 90.00 | 89.40, 82.91, 85.86 |
| Resolution range (Å) [outer shell] | 40-1.76 (1.8-1.76) | 50-2.25 (2.33-2.25) |
| No. of unique reflections | 53620 | 193245 |
| $R_{meas}$ (%) | 10.2 (58.2) | 13.5 (65.2) |
| $R_{pim}$ (%) | 4.4 (26.9) | 6.3 (34.8) |
| Multiplicity | 4.9 (4.2) | 4.2 (3.0) |
| Average I/σI | 15.4 (1.96) | 21.4 (1.6) |
| Completeness (%) | 99.4 (99.0) | 95.8 (85.7) |
| Refinement statistics | | |
| No. atoms | 4049 | 29279 |
| Protein | 3623 | 28238 |
| Ligand | 34 | 30 |
| Water | 392 | 1011 |
| Ramachandran plot (%) | | |
| Favored | 97.56 | 97.99 |
| Allowed | 1.56 | 1.53 |
| Outliers | 0.89 | 0.47 |
| R.m.s. deviations | | |
| Bonds (Å) | 0.015 | 0.015 |
| Angles (°) | 1.72 | 1.73 |
| B-factors (Å$^2$) | | |
| Protein | 19.21 | 53.23 |
| ligand | 80.63 | 73.3 |
| Water | 29.6 | 54.5 |
| R factor (%) | 16.4 | 18.9 |
| $R_{free}$ (%) | 19.4 | 22.3 |

Crystal Structure of 41c-His Fab—Fn14 Complex

The complex formed between 41c-His Fab and Fn14 was found to contain one molecule of 41c-His Fab and one molecule of Fn14 in an asymmetric unit. The final model consists of 41c-His Fab light chain residues 1-218 and heavy chain residues 1-216 in each monomer. Proper electron density was observed for Fn14 residues 32-68 of SEQ ID NO: 2, while the construct used for complex formation contains residues 28-75. In the crystal structure, Fn14 stabilization occurs by interacting with both the heavy and light chains of the 41c-His Fab. Fn14 binds at the deep crevice formed by the complementary determining region (CDR) loops from both the heavy and light chains (Part A of FIG. 8). The area of the heavy chain and Fn14 interface is 442 Å2, with 14 residues from Fn14 and 11 residues from the heavy chain region of 41c-His Fab involved. Similarly, the interface between Fn14 and the light chain of 41c-His Fab has 5 and 7 involved residues, respectively, with a total interface area of 174 A2. An electron density map demonstrating residues from Fn14 that are in contact with the light chain loops L1 and L2 of the 41c-His Fab molecule is shown in Part B of FIG. 8. Hence, the heavy chain makes a greater contribution to Fn14 contact in comparison to light chain.

Fn14 forms multiple polar contacts with all three CDR loops of the heavy chain (H1, H2 and H3), involving both main and side chain interactions. Hydrogen bond interactions are formed as follows: Fn14 residues Lys 48 and Cys 49 with Tyr 32 and Asp 31 of the H1 loop on 41c-His Fab, respectively; Fn14 residues Gly 32, Thr 33 and Pro 35 and the heavy chain CDR2 loop of 41c-His Fab; Fn14 residues Asp 45 and Asp 47 and the H3 loop of 41c-His Fab (Part C of FIG. 8). Additionally, van der Waal's interactions between Ala44 of Fn14 and Trp101 of 41 c-His Fab H3 are observed.

Ionic interactions are observed between Fn14 and L1 of 41c-His Fab, while no such interactions are formed with L2 and L3. Fn14 makes polar contacts with Lys 35 and Tyr 37 of the L1 loop (41c-His Fab) in which Asp 45 of Fn14 forms a salt bridge with Lys 35 (Part D of FIG. 8). Additionally, Leu46 of Fn14 forms a hydrophobic interaction with Leu 55 of L2 on 41c-His Fab. L3 is the only CDR that does not interact with Fn14 residues. In total, Fn14 makes 14 polar contacts with the Fab, including two salt bridges, additionally, three van der Waal's interactions are observed (see Table 10).

Crystal Structure of R35B9-His Fab — Fn14 Complex

The crystals of Fn14 -R35B9-His Fab contain a total of 8 individual complexes in the asymmetric unit with all 8 copies superposing perfectly with each other. The structure showed that the Fn14 interacting residues of variable heavy and light chain region of Fab are conserved between 41c and R35B9 variant. The 41c and R35B9 variant of Fab differs in the composition of amino acids at H1 and H2 loop regions and among the three CDR regions of heavy chain, the H2 and H3 loops of both Fab molecules superpose absolutely while the H1 region showed major degree of variation (Part A of FIG. 9). In the H1 loop, the replacement of Thr 28 to Ile 28 causes key conformational change in the whole H1 loop region (Part B of FIG. 9), due to which the aromatic ring of Tyr 27 clashes with the side chain of Ile 28 and hence the Tyr 27 now adopts a completely different orientation in R35B9-His Fab. This allows the OH group of aromatic Tyr 27 to form hydrogen-bonding contact with Lys 48 of Fn14 (Table 11, Part C of FIG. 9). In the same H1 loop, replacement of Thr 30 with Gln 30 did not play any role towards contributing in the interaction with Fn14. Similarly, in the H2 loop, the replacement of Tyr 50 to Ser 50, Asn 54 to Arg 54 and Gly 57 to Trp 57 did not yield any conformation change in the Fab molecule. Indeed, the Tyr 50 now hydrophobically contacts with Trp 57 thereby stabilizing each other in the variable region of heavy chain. Even though Asn 54 is replaced with long chain amino acid Arg 54, due to the lack of charged residues in the N-terminal region of Fn14, Arg 54 interacts only with the main chain carbonyl group of Pro 35 in Fn14 and also can form hydrogen-bonding contact with sulfhydryl group of Cys 49 of Fn14 (Part C of FIG. 9). Compared to 41c Fab, the light chain CDR1 loop of R35B9 showed minor conformational adjustment by moving ~3 Å forward towards Fn14 and hence the Tyr 37 of L1 region of R35B9 Fab could form hydrogen-bonding contact with main chain atoms of Ala 44 of Fn14 (Part D of FIG. 9).

TABLE 10

Interactions between Fn14 and heavy chain/light chain regions of 41c-His Fab

| Antigen residues (Fn14) | Antibody residues (41c Fab) | Hydrogen bonding distance (Å) |
|---|---|---|
| Polar interactions of Fn14 with heavy chain region of 41c Fab | | |
| CYS 49 [N] | ASP 31 [O] | 2.82 |
| LYS 48 [NZ] | TYR 32 [OH] | 3.00 |
| GLY 32 [N] | ASN 54 [O] | 3.67 |
| PRO 35 [O] | ASN 52 [ND2] | 2.88 |
| PRO 35 [O] | ASN 54 [ND2] | 2.80 |
| THR 33 [O] | ASN 55 [ND2] | 2.72 |
| ASP 47 [OD2] | GLY 100 [N] | 3.07 |
| ASP 47 [O] | GLY 100 [N] | 2.75 |
| ASP 47 [OD2] | TRP 101 [N] | 2.91 |
| ASP 45 [O] | TRP 101 [NE1] | 2.86 |
| ASP 47 [O] | SER 99 [OH] | 2.80 |
| Polar interactions of Fn14 with light chain region of 41c Fab | | |
| ASP 45 [OD1] | TYR 37 [OH] | 2.63 |
| ASP 45 [OD2] | LYS 35 [NZ] | 2.69 |

| | | Salt bridge distance (Å) |
|---|---|---|
| ASP 45 [OD1] | LYS 35 [NZ] | 3.08 |
| ASP 45 [OD2] | LYS 35 [NZ] | 2.69 |
| Vander Waal contacts between Fn14 and 41c Fab | | |
| TRP 42 | ASN 33 (HC) | 4.21 |
| ALA 44 | TRP 101 (HC) | 3.34 |
| LEU 46 | LEU 55 (LC) | 4.40 |

TABLE 11

Interactions between Fn14 and heavy chain/light chain regions of R35B9-His Fab

| Antigen residues (Fn14) | Antibody residues (R35B9 Fab) | Hydrogen bonding distance (Å) |
|---|---|---|
| Polar interactions of Fn14 with heavy chain region of R35B9 Fab | | |
| CYS 49 [N] | ASP 31 [O] | 2.95 |
| LYS 48 [NZ] | TYR 32 [OH] | 3.30 |
| LYS 48 [NZ] | TYR 27 [OH] | 3.56 |
| PRO 35 [O] | ASN 52 [ND2] | 3.58 |
| PRO 35 [O] | ARG 54 [NH2] | 2.85 |
| CYS 49 [SG] | ARG 54 [NH2] | 3.00 |
| THR 33 [O] | ASN 55 [ND2] | 3.33 |
| ALA 34 [O] | ASN 55 [ND2] | 3.78 |
| ASP 47 [OD2] | GLY 100 [N] | 2.96 |
| ASP 47 [OD2] | TRP 101 [N] | 2.99 |
| ASP 47 [O] | GLY 100 [N] | 2.71 |
| ASP 45 [O] | TRP 101 [NE1] | 2.97 |
| ASP 47 [O] | SER 99 [OG] | 2.80 |
| Polar interactions of Fn14 with light chain region of R35B9 Fab | | |
| ASP 45 [OD1] | TYR 37 [OH] | 2.55 |
| ASP 45 [OD1] | LYS 35 [NZ] | 3.45 |
| ASP 45 [OD2] | LYS 35 [NZ] | 3.14 |
| Ala 44 (O) | TYR 37 [OH] | 3.58 |
| Ala 44 (N) | TYR 37 [OH] | 3.42 |

| | | Salt bridge distance (Å) |
|---|---|---|
| ASP 45 [OD1] | LYS 35 [NZ] | 3.45 |
| ASP 45 [OD2] | LYS 35 [NZ] | 3.14 |

Example 17

Assessment Of Antagonist Activity of Anti-Fn14 Monoclonal Antibodies In Vitro ELISA Using Primary Human Renal Mesangial Cells Human Renal Mesanginal Cells (HRMC) were purchased from ScienCell Research Laboratories (cat# 4200) and cultured according to the manufacturer's instructions. 96-well flat bottom cell culture plates (Costar, cat# 3596) were coated for 30 minutes at 37° C. with poly-L-lysine solution (ScienCell, cat# 0413) at 17.5 ng/mL in deionized water. After 30 minutes, the poly-L-lysine solution was removed and the wells were washed with sterile deionized water. HRMC were plated onto the poly-L-lysine coated plates at 25,000 cells/well in 100 µL Mesangial cell media (Scien-Cell, cat# 4201). Cells were allowed to adhere to the well for 1-2 hours at 37° C. with 5% $CO_2$. Next, test antibodies were diluted to 4× final concentration in Mesangial cell media and 50 µL of diluted antibodies or media was added to appropriate wells. Antibodies and cells were placed in a 37° C. 5% $CO_2$ incubator for 30 minutes. Recombinant human TWEAK (R&D Systems, cat# 1090-TW) was diluted to 4×(1000 ng/mL) in Mesangial cell media and 50 µL of rhTWEAK (antagonist assay) or media (agonist assay and no rhTWEAK controls) was added to each well. The plates were placed in a 37° C. 5% $CO_2$ incubator overnight. 24 hours later, the plates were removed from the incubator and centrifuged at 314×g for 3 minutes at room temperature. Supernatants were collected and placed into a 96 well round-bottom polypropylene plate (Costar, cat# 3879), the plate was sealed and placed at −20° C. until further analysis could be done. IL-8 levels in the supernatant were assayed by ELISA (R&D Systems, cat# DY208).

To assay the ability of anti-Fn14 mAbs to block TWEAK-induced IL-8 release, HRMC were plated and anti-Fn14 antibodies were added to the cells at 0.156 µg/mL (1.04 nM) prior to addition of rhTWEAK. After 24 hours, supernatants were collected and assayed for IL-8 release. In this assay, R35B9 was able to block TWEAK-mediated induction of IL-8 release by HRMC significantly better than 41c ($p<0.0001$ vs. R35B9), CRCBT-06-002 ($p<0.0001$ vs. R35B9) and ITEM-4 ($p<0.0001$ vs. R35B9). The results demonstrate the superiority of R35B9 over previously described antibodies in the ability to block an inflammatory response induced by the TWEAK-Fn14 pathway (see FIG. 10).

Antagonist and Agonist Assays in A375 Cells

The ability of these same anti-Fn14 mAbs to block TWEAK-induced IL-8 in A375 human melanoma cells was also assayed. A375 cells (human melanoma) were purchased from American Type Culture Collection (ATCC, cat# CRL-1619) and cultured according to the manufacturer's instructions. A375 were plated onto 96-well flat bottom cell culture plates (Costar, cat# 3596) at 200,000 cells/well in 100 µL of culture media. Cells were allowed to adhere to the well for 2 hours at 37° C. with 5% $CO_2$. Next, test antibodies were diluted to 4× final concentration in culture media and 50 µL of diluted antibodies or media was added to appropriate wells. Antibodies and cells were placed in a 37° C. 5% $CO_2$ incubator for 30 minutes. Recombinant human TWEAK (R&D Systems, cat# 1090-TW) was diluted to 4×(1200 ng/mL) in culture media and 50 µL of rhTWEAK (antagonist assay) or media (agonist assay and no rhTWEAK controls) was added to each well. The plates were placed in a 37° C. 5% $CO_2$ incubator overnight. 24 hours later, the plates were removed from the incubator, centrifuged at 314×g for 10 minutes at room temperature. Supernatants were collected and placed into a 96 well round-bottom polypropylene plate (Costar, cat# 3879), the plate was sealed and placed at −20° C. until further analysis could be done. IL-8 levels in the supernatant were assayed by ELISA (R&D Systems, cat# DY208).

R35B9 was superior to 41c ($p<0.0001$ vs. R35B9), CRCBT-06-002 ($p<0.0001$ vs. R35B9) and ITEM-4 ($p<0.0001$ vs. R35B9) at 2.5 µg/mL (16.7 nM) (FIG. 11A), and better than 41c ($p<0.0001$ vs. R35B9) and ITEM-4 ($p<0.01$ vs. R35B9) at 10 µg/mL (66.7 nM) (FIG. 11B). R35B9 exhibited similar inhibitory effect compared to CRCBT-06-002 and ITEM-4 at higher antibody concentrations (266.7 nM) (see FIG. 11C). These data provide evidence for the potency of R35B9 to neutralize TWEAK-induced IL-8 release from a variety of TWEAK-responsive cells.

To determine whether or not the anti-Fn14 mAbs induced IL-8 release in the absence of rhTWEAK (agonist activity), cells (HRMC or A375) were exposed to anti-Fn14 mAbs in a dose-titration series starting at 40 µg/ml (267 nM) with 2-fold serial dilutions to 0.5 ng/mL (0.004 nM). When tested using HRMC, agonist activity was consistently observed for ITEM-4 and occasionally observed for CRCBT-06-002 at higher concentrations of antibody. Importantly, neither 41c nor R35B9 demonstrated agonist activity at any concentration tested (FIG. 14).

Similar results were obtained using a similar agonist assay in A375 cells (FIG. 15). A375 cells were incubated with 300 ng/mL rhTWEAK, anti-Fn14 or isotype control mAbs for 24 hours. Supernatants were harvested and tested for IL-8 using an IL-8 ELISA kit. In the case of developing therapeutic blocking antibodies, agonist activity is undesirable, therefore, this assay indicated an advantage to 41c and R35B9 based on a lack of agonist activity.

Based on biophysical properties, increased affinity to hFn14 (Tables 8 and 9 and FIGS. 5 and 6) and performance in in vitro cell-based assays (FIGS. 10 and 11), clone R35B9 was selected as the lead affinity matured version of 41c and was used in the generation of VH and VL variants as described in further detail above.

Assessment of Anti-Fn14 mAbs to Modulate Expression of Fibrotic-Related Proteins To determine the ability of anti-Fn14 antibodies to block fibrotic mediators, they were tested for their ability to block TWEAK-induced ICAM-1 upregulation on HRMC. Primary HRMC were purchased from ScienCell Research Laboratories (cat# 4200) and cultured according to the manufacturer's instructions. 6-well flat bottom cell culture plates (Costar, cat# 3516) were coated for 30 minutes at 37° C. with poly-L-lysine solution (ScienCell, cat# 0413) at 17.5 µg/mL in deionized water. After 30 minutes, the poly-L-lysine solution was removed and the wells were washed with sterile deionized water. HRMC were plated onto the poly-L-lysine coated plates at 700,000 cells/well in 2 mL Mesangial cell media (ScienCell, cat# 4201). Cells were allowed to adhere to the well for 1-2 hours at 37° C. with 5% $CO_2$. Next, test antibodies were diluted to 4× final concentration in Mesangial cell media and 1 mL of diluted antibodies or media was added to each well of cells. Antibodies and cells were placed in a 37° C. 5% CO2 incubator for 30 minutes. Recombinant human TWEAK (R&D Systems, cat# 1090-TW) was diluted to 4×(1000 ng/mL) in Mesangial cell media and 1 mL of rhTWEAK (antagonist assay) or media (agonist assay and no rhTWEAK controls) was added to appropriate wells. The plates were placed in a 37° C. 5% $CO_2$ incubator overnight. 24 hours later, the plates were removed from the incubator and supernatants were removed. Wells of cells were rinsed with 1 mL of PBS (Gibco, cat# 10010-023) followed by exposure to 0.25% trypsin (Gibco, cat# 25200-072) diluted 1:1 with PBS for a final trypsin concentration of 0.125%. Each well was incubated with 1 mL 0.125% trypsin at 37° C. for 1-2 minutes followed by the addition of 1 mL complete Mesangial cell media. Next, the dissociated cells were harvested into 15 mL conical tubes (Falcon, cat# 352097) and centrifuged at 350×g for six minutes. Supernatant was removed from each tube and the cells were resuspended in 100 µL FACS buffer (PBS, 1% FBS) and transferred to a 96-well round-bottom polypropylene plate (Costar, cat# 3879). Plates were centrifuged at 350×g for 3 minutes at room temperature. Supernatant was removed and cell pellet was lightly vortexed. Cells were resuspended in 100 µL/well of Fc block (10 µg/mL human IgG (Jackson Immunoresearch, cat# 009-00-003) in FACS buffer) and incubated on ice for ten minutes. Next 100 µÅ FACS buffer was added to each well and the plate was centrifuged as described above. Cells were then washed twice more as follows: supernatants removed, plate gently vortexed, cells washed in 200 µL FACS buffer and centrifuged at 350×g, room temperature for 3 minutes. 100 µL of fixable live/dead stain, Zombie Aqua (Biolegend, cat# 423101) was added to each well and the cells were incubated for 15 minutes at room temperature. Cells were then washed as described previously. Next, 100 µL of PE-labeled anti-ICAM-1 mAb (Biolegend, cat# 322708, clone HCD54, 5 µL/test) or PE-labeled isotype control (Biolegend, cat# 400114, clone MOPC-21, 5 µL/test) diluted in FACS buffer was added to each well and the plates were incubated on ice for 30 minutes. At the end of the incubation, cells were washed as previously described and fixed by adding 100 µL/well fix buffer (1% paraformaldehyde in PBS) and incubating on ice for 5 minutes. Cells were then washed with FACS buffer as described above and 30,000 events were collected using a Fortessa (BD Biosciences). Data analysis was performed using FlowJo and GraphPad Prism.

Fn14 mAb R35B9 Antagonizes TWEAK-Induced ICAM-1 Expression

Anti-Fn14 mAbs were shown to block TWEAK-induced upregulation of ICAM-1, with R35B9 having superior blocking ability compared to 41c, CRCBT-06-002 and ITEM-4 (R35B9 vs. 41c p<0.0001, R35B9 vs. CRCBT-06-002 p<0.0001, R35B9 vs. ITEM-4 p<0.0001, One-way ANOVA, both mAb concentrations tested) (FIG. 18). This indicates that R35B9 may be more efficacious at blocking fibrotic mediators such as TWEAK-induced upregulation of ICAM-1 expression.

Assessment of Anti-Fn14 mAbs to Block TWEAK Binding to Fn14 Expressed on Cells

HRMC cells were incubated with individual antibodies at various concentrations (0.015625-1 ng/mL) for 30 minutes at room temperature. Recombinant human TWEAK (R&D Systems, Cat# 1090-TW/CF) was then added to the cells and incubated for 45 minutes at room temperature. Binding of TWEAK to HRMC cells was detected with a biotinylated goat-anti-human TWEAK (R&D Systems, Cat# BAF1090) followed by streptavidin-PE (Biolegend, Cat# 405204). Stained cells were acquired on a Fortessa. % TWEAK blocking was calculated using the following formula: 100-(Geometric mean fluorescence intensity of sample—Geometric mean fluorescence intensity of cells without TWEAK)/(Geometric mean fluorescence intensity— TWEAK alone with no antibody—Geometric mean fluorescence intensity of cells without TWEAK)*100.

Anti-Fn14 mAbs were incubated with HRMC at various concentrations before recombinant human TWEAK was added to the cells. Antibodies A512/A468, A515/A518, A553/A472 were shown to block TWEAK binding to Fn14 expressed on HRMC cells in a dose dependent manner (see FIG. 25). The results demonstrate that humanized anti-Fn14 mAbs block TWEAK binding to Fn14 expressed on cells.

Example 18

Assessment of Activities of Further Engineered Humanized Anti-Fn14 Antibodies

Additional studies were performed to analyze the further engineered humanized antibodies generated in Example 10 above as follows.

Functional Assays Using HaCaT Cells and Human Epidermal Keratinocytes

RANTES assay: HaCaT cells were purchased from AddexBio (cat#T0020001), and cultured according to the manufacturer's instructions. Human primary adult keratinocytes were purchased from Cell Applications Inc. (cat# 102-05a), and cultured according to the manufacturer's instructions. Cells were plated onto 96 well flat-bottom plates at 20,000 cells per well in 100 µL of DMEM complete media for HaCaT cells (DMEM (Thermo Fisher cat# 10313-021) with 10% Fetal Bovine Serum (FBS), 1% penicillin— streptomycin , 1% L-glutamine and 1% Na-Pyruvate. Completed DMEM, or Epivita Serum Free Complete Media for adult keratinocytes (Cell Applications Inc. cat# 141-500a). Cells were allowed to adhere to the wells for 2-3 hours at 37° C. with 5% $CO_2$. Next, media was removed, and test antibodies diluted to 2× final concentration or media were added to appropriate wells. Antibodies and cells were placed in a 37° C. 5% $CO_2$ incubator for 30 minutes. Recombinant human TWEAK (R&D Systems, cat# 1090-TW) diluted to 2× final concentration (200 ng/mL) or media was added to appropriate wells. The plates were placed in a 37° C. 5% $CO_2$ incubator for 48 hours. Supernatants were collected and RANTES levels in the supernatant were assayed by ELISA (R&D Systems, cat#DY278-05)

Apoptosis assay: Human primary neonatal keratinocytes were purchased from Cell Applications Inc. (cat# 102-05n), and cultured according to the manufacturer's instructions. Cells were plated onto 6 well plates at 160,000 cells per well in 2 mL of media (Epivita Serum Free Complete Media for neonatal keratinocytes, Cell Applications Inc. cat# 141-500). Cells were allowed to adhere to the wells for 2-3 hours at 37° C. with 5% $CO_2$. Next, media was removed, and cells were treated with test antibodies at 1.5 ng/mL, and recombinant human TWEAK (R&D Systems, cat# 1090-TW) at 100 ng/mL, TNFα (Peprotech, cat# 300-01a-50 µg) at 10 ng/mL, the combination of TWEAK and TNFα or media. The plates were placed in a 37° C. 5% CO2 incubator for 72 hours. Cells were harvested using TrypLE Express (Thermo Fisher, cat# 12604013), stained with Annexin V and 7-AAD (FITC Annexin V apoptosis detection kit, Biolegend, cat# 640922), and acquired on an LSR Fortessa (BD Biosciences). Data analysis was performed using FlowJo.

ICAM-1 assay: HaCaT cells were cultured according to the manufacturer's instructions. HaCaT cells were plated onto 12-well plates at 300,000 cells per well in 1 mL DMEM complete media. Cells were allowed to adhere to the well for 2 hours at 37° C. with 5% $CO_2$. Next, test antibodies were diluted to 4× final concentration in DMEM complete media and 500 µL of diluted antibodies or media was added to each well of cells. Antibodies and cells were placed in a 37° C.

5% CO2 incubator for 30 minutes. Recombinant human TWEAK was diluted to 4× final concentration (400 ng/mL) in DMEM complete media and 500 µL of TWEAK or media was added to appropriate wells. The plates were placed in a 37° C. 5% CO2 incubator for 48 hours. Cells were then harvested using Accutase buffer (Innovative Cell Technologies, cat#AT-104), stained with Zombie aqua (BioLegend, cat# 423102), APC-anti-human ICAM-1 (BioLegend, cat# 353112) or isotype control antibody (BioLegend, cat# 400122). Cells were then washed with FACS buffer and 30,000 events were collected using an LSR Fortessa (BD Biosciences). Data analysis was performed using FlowJo.

Human primary neonatal keratinocytes were cultured according to the manufacturer's instructions. Keratinocytes were plated onto 12-well plates at 150,000 cells per well in 1 mL of media (Epivita Serum Free Complete Media for neonatal keratinocytes. Cells were allowed to adhere to the well for 2 hours at 37° C. with 5% $CO_2$. Next, test antibodies were diluted to 4× final concentration in Epivita media and 500 µL of diluted antibodies or media was added to each well of cells. Antibodies and cells were placed in a 37° C. 5% CO2 incubator for 30 minutes. Recombinant human TWEAK was diluted to 4× final concentration (400 ng/mL) in Epivita media and 500 µL of TWEAK or media was added to appropriate wells. The plates were placed in a 37° C. 5% CO2 incubator for 48 hours. Cells were then harvested using Accutase buffer (Innovative Cell Technologies, cat#AT-104), stained with Zombie aqua (BioLegend, cat# 423102), APC-anti-human ICAM-1 (BioLegend, cat# 353112). Cells were then washed with FACS buffer and 30,000 events were collected using an LSR Fortessa (BD Biosciences). Data analysis was performed using FlowJo.

Functional Assays Using Human Dermal Fibroblasts

Human primary dermal fibroblasts were purchased from Cell Applications Inc. (cat# 106-05n), and cultured according to the manufacturer's instructions. Cells were plated onto 96 well flat-bottom plates at 20,000 cells per well in 100 µL of media (Human Dermal Fibroblast Growth Medium, Xeno-free, Cell Applications Inc. cat# 116XF-500). Cells were allowed to adhere to the wells for 2-3 hours at 37° C. with 5% $CO_2$. Next, media was removed, and test antibodies diluted to 2× final concentration or media were added to appropriate wells. The plates were placed in a 37° C. 5% CO2 incubator for 30 minutes. Recombinant human TWEAK diluted to 2× final concentration (200 ng/mL) or media was added to appropriate wells. The plates were placed in a 37° C. 5% CO2 incubator for 48 hours. Supernatants were collected and IL-6 levels in the supernatant were assayed by ELISA (Thermo Fisher, cat# 88-7066-86).

Results

As described above, humanized antibody A512/A468 was further engineered to reduce sequence liabilities. Twenty further engineered anti-Fn14 mAbs were tested for their ability to inhibit TWEAK-induced IL-8 production from HRMC. HRMC were plated and anti-Fn14 antibodies were added to the cells at various concentrations prior to addition of TWEAK. After 24 hours, supernatants were collected and assayed for IL-8 release. In this assay, all 20 additional clones, A631/A468, A634/A468, A635/A468, A636/A468, A512/A652, A648/A468, A650/A468 (see FIG. 26A), A512/A653, A633/A468, A638/A468, A641/A468, A642/A468, A647/A468, A512/A656 (see FIG. 26B), A632/A468, A639/A468, A643/A468, A645/A468, A512/A651, and A512/A654 (see FIG. 26C) showed dose-dependent inhibition of IL-8 production.

Moreover, several clones exhibited similar or better inhibitory activity compared to the original clone A512/A468. In addition, A631/A468, A512/A652, A648/A468, A650/A468, A641/A468, A642/A468, A639/A468, A643/A468, and A512/A654 were able to block TWEAK mediated IL-8 release from HRMC significantly more than the CRCBT-06-002 anti-Fn14 mAb (see FIG. 27A) resulting in lower IC50s (see FIG. 27B).

To determine whether or not these further engineered anti-Fn14 mAbs had any agonist activity, i.e. induced IL-8 release in the absence of TWEAK, HRMC were exposed to anti-Fn14 mAbs in a dose-titration series starting at 40 ng/ml (266.67 nM) with a 4-fold serial dilution to 0.5 ng/mL (0.26 nM). Agonist activity was consistently observed for ITEM-4, in particular at higher concentrations of antibody, and therefore, ITEM-4 served as a positive control in the assay. As shown in FIGS. 28A-28C, the majority of the clones did not show agonist activity except for two clones, A635/A468 (see FIG. 28A) and A647/A468 (see FIG. 28B), which induced IL-8 production in the absence of TWEAK, similarly to ITEM-4.

To determine if anti-Fn14 antibodies blocked chemokine production by keratinocytes, humanized anti-Fn14 antibodies were tested for their ability to block TWEAK induced RANTES production by HaCaT cells and human primary epidermal keratinocytes. Firstly, HaCaT cells or human adult primary epidermal keratinocytes were incubated with the Fn14 monoclonal antibodies at various concentrations. Next, the cells were stimulated with 100 ng/mL TWEAK for 48 hours. Cell supernatants were then harvested and tested for RANTES production. Humanized anti-Fn14 mAbs, A512/A468, A515/A518, and A553/A472, markedly inhibited RANTES release from HaCaTs (see FIG. 29A) and human adult primary keratinocytes (see FIG. 29B) in a dose-dependent manner. Furthermore, the antibodies were able to completely suppress RANTES production in a dose dependent manner. This demonstrates that these humanized anti-Fn14 monoclonal antibodies, A512/A468, A515/A518, and A553/A472, are efficacious in blocking chemokine production by keratinocytes.

To determine if anti-Fn14 monoclonal antibodies blocked TWEAK induced apoptosis, humanized anti-Fn14 antibodies A512/A468, A515/A518, and A553/A472 were incubated at 1.5 µg/mL with human neonatal primary epidermal keratinocytes in the presence of TWEAK (100 ng/mL), TNFα (10 ng/mL) or the combination of TWEAK and TNFα for 72 hours. Cells were then collected, stained with Annexin V and 7-AAD, and analyzed on an LSR Fortessa. TWEAK induced more Annexin V, 7-AAD double positive late apoptotic cells than TNFα on neonatal epidermal keratinocytes, and the combination of TWEAK and TNFα induced the highest percentage of late apoptotic cells. Humanized anti-Fn14 antibodies, A512/A468, A515/A518, and A553/A472, reduced the percentage of TWEAK induced apoptotic cells (see FIG. 30). These same Fn14 mAbs also reduced the percentage of apoptotic cells in keratinocytes treated with a combination of TWEAK and TNFα to levels induced by TNFα alone (see FIG. 30).

To determine if anti-Fn14 monoclonal antibodies A512/A468, A515/A518, and A553/A472 block fibrotic mediators and adhesion molecules directing leukocyte migration, they were tested for their ability to block TWEAK induced ICAM-1 upregulation on HaCaT cells and human neonatal epidermal keratinocytes. First, anti-Fn14 or isotype control mAbs were added to HaCaT cells at various concentrations or to neonatal epidermal keratinocytes at 1 µg/mL. Next, the cells were stimulated with 100 ng/mL TWEAK for 48 hours. Cells were then harvested and stained for surface expression of ICAM-1. TWEAK induced upregulation of ICAM-1 expression on HaCaT cells (see FIG. 31A) and neonatal epidermal keratinocytes (see FIG. 31B). Humanized anti-Fn14 monoclonal antibodies, A512/A468, A515/A518, and A553/A472, inhibited ICAM-1 upregulation on HaCaT cells in a dose-dependent manner and was able to completely suppress ICAM-1 upregulation with increasing mAb concentrations (see FIG. 31A). Similarly, at 1 µg/mL, A512/A468 substantially inhibited the upregulation of ICAM-1 on primary keratinocytes, while the isotype control antibody did not have any effect (see FIG. 31B).

To determine if anti-Fn14 monoclonal antibodies A512/A468, A515/A518, and A553/A472 block cytokine production by dermal fibroblasts, they were tested for their ability to block TWEAK induced IL-6 production by dermal fibroblasts. First, anti-Fn14 or isotype control mAbs were incubated with dermal fibrobalsts at various concentrations followed by TWEAK (100 ng/mL) stimulation for 48 hours. Supernatants were collected and IL-6 was quantified. TWEAK induced IL-6 production by dermal fibroblasts (see FIG. 32), and humanized anti-Fn14 monoclonal antibodies, A512/A468, A515/A518, and A553/A472, completely suppressed IL-6 release in a dose-dependent manner with A512/A468 being the most potent (see FIG. 32).

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed:

1. An antibody or antigen binding fragment thereof that binds to Fn14, wherein the antibody or antigen binding fragment thereof is an antagonist of Fn14, wherein the antibody or antigen binding fragment thereof comprises:
   (a) a heavy chain variable region (VH) comprising
   (i) VH complementarity determining region 1 (CDR H1) comprising an amino acid sequence of GYX$_1$FX$_2$DYNMH (SEQ ID NO: 184), wherein X$_1$ is T, I or R, and X$_2$ is T or Q;
   (ii) VH complementarity determining region 2 (CDR H2) comprising an amino acid sequence of X$_3$INPX$_4$NX$_5$X$_6$TNYNX$_9$KFX$_{10}$G (SEQ ID NO: 257), wherein X$_3$ is Y or S, X$_4$ is N or R, X$_5$ is A or G, X$_6$ is G or W, X$_9$ is Q or D, and X$_{10}$ is K, G, H, or D; and
   (iii) VH complementarity determining region 3 (CDR H3) comprising an amino acid sequence of SGWFTY (SEQ ID NO: 121); and
   (b) a light chain variable region (VL) comprising
   (i) VL complementarity determining region 1 (CDR L1) comprising an amino acid sequence of KSSQSLLNSAGKTYLN (SEQ ID NO: 127);
   (ii) VL complementarity determining region 2 (CDR L2) comprising an amino acid sequence of LVX$_{11}$X$_{12}$LDX$_{13}$ (SEQ ID NO: 258), wherein X$_{11}$ is S or A, X$_{12}$ is Q or E, and X$_{13}$ is S or D; and
   (iii) VL complementarity determining region 3 (CDR L3) comprising an amino acid sequence of WQGTX$_7$X$_8$PWT (SEQ ID NO: 186), wherein X$_7$ is H or F, and X$_8$ is F or Y,
   and wherein
   (a) the antibody or antigen binding fragment thereof is not an agonist of Fn14;
   (b) the antibody or antigen binding fragment thereof binds human, cynomolgus macaque, rat and mouse Fn14; and/or
   (c) the antibody or antigen binding fragment thereof binds subdomain 1 comprising amino acids 30-50 of human Fn14 having an amino acid sequence of SEQ ID NO: 2.

2. The antibody or antigen binding fragment thereof of claim 1, wherein the antigen binding fragment is selected from a group consisting of a Fab, a Fab', a F(ab')2, a Fv, a scFv, a dsFv, a diabody, a triabody, a tetrabody, and a multispecific antibody formed from antibody fragments.

3. The antibody or antigen binding fragment thereof of claim 1, wherein: (i) the antibody is a mouse antibody; (ii) the antibody is a chimeric antibody; or (iii) the antibody or antigen binding fragment is a humanized antibody or antigen binding fragment thereof.

4. The antibody or antigen binding fragment thereof of claim 1, wherein the antibody or antigen binding fragment thereof comprises:
   (a) a heavy chain variable region (VH) comprising
   (i) VH complementarity determining region 1 (CDR H1) comprising an amino acid sequence selected from a group consisting of SEQ ID NO: 119 and SEQ ID NO: 122;
   (ii) VH complementarity determining region 2 (CDR H2) comprising an amino acid sequence selected from a group consisting of SEQ ID NO: 120, SEQ ID NO: 123, SEQ ID NO: 124, SEQ ID NO: 125, SEQ ID NO: 126, SEQ ID NO: 149; SEQ ID NO: 247, SEQ ID NO: 248, SEQ ID NO: 249, and SEQ ID NO: 250; and
   (iii) VH complementarity determining region 3 (CDR H3) comprising an amino acid sequence of SEQ ID NO: 121, and
   (b) a light chain variable region (VL) comprising
   (i) VL complementarity determining region 1 (CDR L1) comprising an amino acid sequence of SEQ ID NO: 127;
   (ii) VL complementarity determining region 2 (CDR L2) comprising an amino acid sequence selected from a group consisting of SEQ ID NO: 128, SEQ ID NO: 254, SEQ ID NO: 255, and SEQ ID NO: 256; and
   (iii) VL complementarity determining region 3 (CDR L3) comprising an amino acid sequence selected from a group consisting of SEQ ID NO: 129, SEQ ID NO: 130, and SEQ ID NO: 131.

5. The antibody or antigen binding fragment thereof of claim 1, wherein the antibody or antigen binding fragment thereof comprises:
- (i) a CDR H1 of SEQ ID NO: 122, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 130;
- (ii) a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 130;
- (iii) a CDR H1 of SEQ ID NO: 122, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 130;
- (iv) a CDR H1 of SEQ ID NO: 122, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 130;
- (v) a CDR H1 of SEQ ID NO: 122, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 130;
- (vi) a CDR H1 of SEQ ID NO: 122, a CDR H2 of SEQ ID NO: 123, a CDR H3 of SEQ ID NO: 121, a CDR L1 of SEQ ID NO: 127, a CDR L2 of SEQ ID NO: 128, and a CDR L3 of SEQ ID NO: 131;
- (vii) a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 128, and a CDR L3 of SEQ ID NO: 131;
- (viii) a CDR H1 of SEQ ID NO: 122, a CDR H2 of SEQ ID NO: 125, a CDR H3 of SEQ ID NO: 121, a CDR L1 of SEQ ID NO: 127, a CDR L2 of SEQ ID NO: 128, and a CDR L3 of SEQ ID NO: 131;
- (ix) a CDR H1 of SEQ ID NO: 122, a CDR H2 of SEQ ID NO: 126, a CDR H3 of SEQ ID NO: 121, a CDR L1 of SEQ ID NO: 127, a CDR L2 of SEQ ID NO: 128, and a CDR L3 of SEQ ID NO: 131;
- (x) a CDR H1 of SEQ ID NO: 122, a CDR H2 of SEQ ID NO: 149, a CDR H3 of SEQ ID NO: 121, a CDR L1 of SEQ ID NO: 127, a CDR L2 of SEQ ID NO: 128, and a CDR L3 of SEQ ID NO: 131;
- (xi) a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 254, and a CDR L3 of SEQ ID NO: 130;
- (xii) a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 255, and a CDR L3 of SEQ ID NO: 130;
- (xiii) a CDR H1 of SEQ ID NO: 122, a CDR H2 of SEQ ID NO: 124, a CDR H3 of SEQ ID NO: 121, a CDR L1 of SEQ ID NO: 127, a CDR L2 of SEQ ID NO: 256, and a CDR L3 of SEQ ID NO: 130;
- (xiv) a CDR H1 of SEQ ID NO: 122, a CDR H2 of SEQ ID NO: 247, a CDR H3 of SEQ ID NO: 121, a CDR L1 of SEQ ID NO: 127, a CDR L2 of SEQ ID NO: 128, and a CDR L3 of SEQ ID NO: 130;
- (xv) a CDR H1 of SEQ ID NO: 122, a CDR H2 of SEQ ID NO: 247, a CDR H3 of SEQ ID NO: 121, a CDR L1 of SEQ ID NO: 127, a CDR L2 of SEQ ID NO: 254, and a CDR L3 of SEQ ID NO: 130;
- (xvi) a CDR H1 of SEQ ID NO: 122, a CDR H2 of SEQ ID NO: 247, a CDR H3 of SEQ ID NO: 121, a CDR L1 of SEQ ID NO: 127, a CDR L2 of SEQ ID NO: 255, and a CDR L3 of SEQ ID NO: 130;
- (xvii) a CDR H1 of SEQ ID NO: 122, a CDR H2 of SEQ ID NO: 247, a CDR H3 of SEQ ID NO: 121, a CDR L1 of SEQ ID NO: 127, a CDR L2 of SEQ ID NO: 256, and a CDR L3 of SEQ ID NO: 130;
- (xviii) a CDR H1 of SEQ ID NO: 122, a CDR H2 of SEQ ID NO: 248, a CDR H3 of SEQ ID NO: 121, a CDR L1 of SEQ ID NO: 127, a CDR L2 of SEQ ID NO: 128, and a CDR L3 of SEQ ID NO: 130;
- (xix) a CDR H1 of SEQ ID NO: 122, a CDR H2 of SEQ ID NO: 248, a CDR H3 of SEQ ID NO: 121, a CDR L1 of SEQ ID NO: 127, a CDR L2 of SEQ ID NO: 254, and a CDR L3 of SEQ ID NO: 130;
- (xx) a CDR H1 of SEQ ID NO: 122, a CDR H2 of SEQ ID NO: 248, a CDR H3 of SEQ ID NO: 121, a CDR L1 of SEQ ID NO: 127, a CDR L2 of SEQ ID NO: 255, and a CDR L3 of SEQ ID NO: 130;
- (xxi) a CDR H1 of SEQ ID NO: 122, a CDR H2 of SEQ ID NO: 248, a CDR H3 of SEQ ID NO: 121, a CDR L1 of SEQ ID NO: 127, a CDR L2 of SEQ ID NO: 256, and a CDR L3 of SEQ ID NO: 130;
- (xxii) a CDR H1 of SEQ ID NO: 122, a CDR H2 of SEQ ID NO: 249, a CDR H3 of SEQ ID NO: 121, a CDR L1 of SEQ ID NO: 127, a CDR L2 of SEQ ID NO: 128, and a CDR L3 of SEQ ID NO: 130;
- (xxiii) a CDR H1 of SEQ ID NO: 122, a CDR H2 of SEQ ID NO: 249, a CDR H3 of SEQ ID NO: 121, a CDR L1 of SEQ ID NO: 127, a CDR L2 of SEQ ID NO: 254, and a CDR L3 of SEQ ID NO: 130;
- (xxiv) a CDR H1 of SEQ ID NO: 122, a CDR H2 of SEQ ID NO: 249, a CDR H3 of SEQ ID NO: 121, a CDR L1 of SEQ ID NO: 127, a CDR L2 of SEQ ID NO: 255, and a CDR L3 of SEQ ID NO: 130;
- (xxv) a CDR H1 of SEQ ID NO: 122, a CDR H2 of SEQ ID NO: 249, a CDR H3 of SEQ ID NO: 121, a CDR L1 of SEQ ID NO: 127, a CDR L2 of SEQ ID NO: 256, and a CDR L3 of SEQ ID NO: 130;
- (xxvi) a CDR H1 of SEQ ID NO: 122, a CDR H2 of SEQ ID NO: 250, a CDR H3 of SEQ ID NO: 121, a CDR L1 of SEQ ID NO: 127, a CDR L2 of SEQ ID NO: 128, and a CDR L3 of SEQ ID NO: 130;
- (xxvii) a CDR H1 of SEQ ID NO: 122, a CDR H2 of SEQ ID NO: 250, a CDR H3 of SEQ ID NO: 121, a CDR L1 of SEQ ID NO: 127, a CDR L2 of SEQ ID NO: 254, and a CDR L3 of SEQ ID NO: 130;
- (xxviii) a CDR H1 of SEQ ID NO: 122, a CDR H2 of SEQ ID NO: 250, a CDR H3 of SEQ ID NO: 121, a CDR L1 of SEQ ID NO: 127, a CDR L2 of SEQ ID NO: 255, and a CDR L3 of SEQ ID NO: 130; or
- (xxix) a CDR H1 of SEQ ID NO: 122, a CDR H2 of SEQ ID NO: 250, a CDR H3 of SEQ ID NO: 121, a CDR L1 of SEQ ID NO: 127, a CDR L2 of SEQ ID NO: 256, and a CDR L3 of SEQ ID NO: 130.

6. The antibody or antigen binding fragment thereof of claim 1, wherein the antibody or antigen binding fragment thereof comprises:
a VH comprising an amino acid sequence selected from a group consisting of SEQ ID NO: 179, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 106, SEQ ID NO: 108, SEQ ID NO: 110, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, and SEQ ID NO: 227; and a VL comprising an amino acid sequence selected from a group consisting of SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 112, SEQ ID NO: 229, SEQ ID NO: 231, SEQ ID NO: 233, SEQ ID NO: 235, and SEQ ID NO: 237.

7. The antibody or antigen binding fragment thereof of claim 1, wherein the antibody or antigen binding fragment thereof is conjugated to an agent.

8. A pharmaceutical composition comprising the antibody or antigen binding fragment of claim 1 and a pharmaceutically acceptable excipient.

9. A method of treating a disease or disorder comprising administering a therapeutically effective amount of the antibody or antigen binding fragment thereof of claim 1 to a subject, wherein the disease or disorder is a disease or disorder mediated, induced and/or prolonged by Fn14 and/or TWEAK.

10. The method of claim 9, wherein the disease or disorder is selected from a group consisting of autoimmune and/or inflammatory diseases affecting joints, skin, kidney, liver, intestine, heart, lung, or muscle, wherein optionally the disease or disorder is selected from a group consisting of rheumatoid arthritis, bullous pemphigoid, discoid cutaneous lupus, urticarial vasculitis, Henoch-Schonlein Purpura, IgA nephropathy, atopic dermatitis (atopic eczema), psoriasis, seborrheic eczema, asthma, proteinuric kidney disease, liver disease, lupus nephritis, polymyositis, dermatomyositis, calcineurin inhibitor induced nephrotoxicity, myotonic dystrophy, cardiac dysfunction and failure, Alport syndrome, ulcerative colitis, Crohn's disease, cutaneous vasculitis, cachexia, and inflammatory bowel disease, and wherein optionally the disease or disorder is related to fibrosis and optionally selected from a group consisting of tissue fibrosis, idiopathic pulmonary fibrosis, interstitial lung disease, scleroderma, cancer, cancer-associated cachexia, muscle wasting, keloids, inclusion body myositis, and tissue remodeling.

11. A polynucleotide comprising nucleotide sequences encoding the antibody or antigen binding fragment thereof of claim 1 or a portion thereof.

12. A vector comprising the polynucleotide of claim 11.

13. A cell comprising the polynucleotide of claim 11.

14. A cell comprising the vector of claim 12.

15. A method of making an antibody or antigen binding fragment thereof comprising culturing the cell of claim 13 to express the antibody or antigen binding fragment thereof.

16. The antibody or antigen binding fragment thereof of claim 6, wherein the antibody or antigen binding fragment thereof comprises:
 (i) a VH of SEQ ID NO: 108 and a VL of SEQ ID NO: 94,
 (ii) a VH of SEQ ID NO: 106 and a VL of SEQ ID NO: 102,
 (iii) a VH of SEQ ID NO: 217 and a VL of SEQ ID NO: 94,
 (iv) a VH of SEQ ID NO: 227 and a VL of SEQ ID NO: 94,
 (v) a VH of SEQ ID NO: 203 and a VL of SEQ ID NO: 94,
 (vi) a VH of SEQ ID NO: 108 and a VL of SEQ ID NO: 231,
 (vii) a VH of SEQ ID NO: 219 and a VL of SEQ ID NO: 94,
 (viii) a VH of SEQ ID NO: 215 and a VL of SEQ ID NO: 94,
 (ix) a VH of SEQ ID NO: 110 and a VL of SEQ ID NO: 112,
 (x) a VH of SEQ ID NO: 108 and a VL of SEQ ID NO: 235,
 (xi) a VH of SEQ ID NO: 225 and a VL of SEQ ID NO: 94, or
 (xii) a VH of SEQ ID NO: 221 and a VL of SEQ ID NO: 94.

* * * * *

SEQUENCE LISTING

<160> NUMBER OF SEQ ID NOS: 259

<210> SEQ ID NO 1
<211> LENGTH: 387
<212> TYPE: DNA
<213> ORGANISM: Homo sapiens
<220> FEATURE:
<223> OTHER INFORMATION: Human Fn14 (full length)

<400> SEQUENCE: 1

```
atggctcggg gctcgctgcg ccggttgctg cggctcctcg tgctggggct ctggctggcg      60
ttgctgcgct ccgtggccgg ggagcaagcg ccaggcaccg cccctgctc ccgcggcagc      120 tcctggagcg cggacctgga caagtgcatg gactgcgcgt cttgcagggc gcgaccgcac      180
agcgacttct gcctgggctg cgctgcagca cctcctgccc ccttccggct gctttggccc      240
atccttgggg gcgctctgag cctgaccttc gtgctggggc tgctttctgg cttttttggtc      300 tggagacgat gccgcaggag agagaagttc accaccccca tagaggagac cggcggagag      360
ggctgcccag ctgtggcgct gatccag                                           387
```

<210> SEQ ID NO 2
<211> LENGTH: 129
<212> TYPE: PRT
<213> ORGANISM: Homo sapiens
<220> FEATURE:
<223> OTHER INFORMATION: Human Fn14 (full length)

<400> SEQUENCE: 2

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
        50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Glu Lys Phe Thr Thr
                100                 105                 110

Pro Ile Glu Glu Thr Gly Gly Glu Gly Cys Pro Ala Val Ala Leu Ile
                115                 120                 125
```

Gln

<210> SEQ ID NO 3
<211> LENGTH: 144
<212> TYPE: DNA
<213> ORGANISM: Homo sapiens
<220> FEATURE:
<223> OTHER INFORMATION: human Fn14 fragment used for immunization
      (aa28-75)

<400> SEQUENCE: 3

```
gagcaagcgc caggcaccgc ccctgctcc cgcggcagct cctggagcgc ggacctggac     60
aagtgcatgg actgcgcgtc ttgcagggcg cgaccgcaca gcgacttctg cctgggctgc    120
gctgcagcac ctcctgcccc cttc                                           144
```

<210> SEQ ID NO 4
<211> LENGTH: 48
<212> TYPE: PRT
<213> ORGANISM: Homo sapiens
<220> FEATURE:
<223> OTHER INFORMATION: human Fn14 fragment used for immunization
      (aa28-75)

<400> SEQUENCE: 4

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Pro Ala Pro Phe
        35                  40                  45

<210> SEQ ID NO 5
<211> LENGTH: 387
<212> TYPE: DNA
<213> ORGANISM: Mouse
<220> FEATURE:
<223> OTHER INFORMATION: mouse Fn14 (full length)

<400> SEQUENCE: 5

```
atggcttcgg cttggccgcg gtctctgccg cagatcctcg tgttgggatt cggcttggtg     60
ttgatgcgcg ccgcggccgg ggagcaagca ccaggcacct ccccatgctc tagcggcagc    120
tcctggagcg cggacctcga caagtgcatg gactgcgctt cttgtccagc cgaccacac    180
agcgacttct gcctgggatg cgccgcagca cctcctgccc acttcaggct actgtggccc    240
attctggggg gcgctcttag tctggtcctg gttttggcgc tggtttctag tttcctggtc    300
tggagaagat gccgccggag agaaaagttt actaccccca tagaggagac tggtggagag    360
ggctgcccag gtgtggcact gatccag                                        387
```

<210> SEQ ID NO 6
<211> LENGTH: 129
<212> TYPE: PRT
<213> ORGANISM: Mouse
<220> FEATURE:
<223> OTHER INFORMATION: mouse Fn14 (full length)

<400> SEQUENCE: 6

Met Ala Ser Ala Trp Pro Arg Ser Leu Pro Gln Ile Leu Val Leu Gly
1               5                   10                  15

Phe Gly Leu Val Leu Met Arg Ala Ala Ala Gly Glu Gln Ala Pro Gly
            20                  25                  30

```
Thr Ser Pro Cys Ser Ser Gly Ser Ser Trp Ser Ala Asp Leu Asp Lys
        35                  40                  45

Cys Met Asp Cys Ala Ser Cys Pro Ala Arg Pro His Ser Asp Phe Cys
 50                  55                  60

Leu Gly Cys Ala Ala Ala Pro Pro Ala His Phe Arg Leu Leu Trp Pro
 65                  70                  75                  80

Ile Leu Gly Gly Ala Leu Ser Leu Val Leu Val Leu Ala Leu Val Ser
                 85                  90                  95

Ser Phe Leu Val Trp Arg Arg Cys Arg Arg Arg Glu Lys Phe Thr Thr
                100                 105                 110

Pro Ile Glu Glu Thr Gly Gly Glu Gly Cys Pro Gly Val Ala Leu Ile
                115                 120                 125

Gln

<210> SEQ ID NO 7
<211> LENGTH: 387
<212> TYPE: DNA
<213> ORGANISM: Rattus
<220> FEATURE:
<223> OTHER INFORMATION: rat Fn14 (full length)

<400> SEQUENCE: 7
atggctccgg gttggccgcg gcctctgccg cagctcctcg tgttgggatt cgggttggtg    60
ttgatacgcg ccacggccgg ggagcaagca ccaggcaacg ccccatgctc aagcggcagc   120
tcctggagcg cggacctcga caagtgcatg gactgcgctt cttgtccagc gcgaccacac   180
agcgacttct gcctgggatg cgcagcagca cctcctgccc acttcaggat gctatggccc   240
attctgggag cgctcttagt ctggccctg gttttggcgc tggtttctgg tttcctggtc   300
tggagacgat gccgccggag agaaaagttt actaccccca tagaggagac tggtggagaa   360
ggctgcccag gtgtggcact gatccag                                      387

<210> SEQ ID NO 8
<211> LENGTH: 129
<212> TYPE: PRT
<213> ORGANISM: Rattus
<220> FEATURE:
<223> OTHER INFORMATION: rat Fn14 (full length)

<400> SEQUENCE: 8

Met Ala Pro Gly Trp Pro Arg Pro Leu Pro Gln Leu Leu Val Leu Gly
 1               5                  10                  15

Phe Gly Leu Val Leu Ile Arg Ala Thr Ala Gly Glu Gln Ala Pro Gly
                 20                  25                  30

Asn Ala Pro Cys Ser Ser Gly Ser Ser Trp Ser Ala Asp Leu Asp Lys
                 35                  40                  45

Cys Met Asp Cys Ala Ser Cys Pro Ala Arg Pro His Ser Asp Phe Cys
 50                  55                  60

Leu Gly Cys Ala Ala Ala Pro Pro Ala His Phe Arg Met Leu Trp Pro
 65                  70                  75                  80

Ile Leu Gly Gly Ala Leu Ser Leu Ala Leu Val Leu Ala Leu Val Ser
                 85                  90                  95

Gly Phe Leu Val Trp Arg Arg Cys Arg Arg Arg Glu Lys Phe Thr Thr
                100                 105                 110

Pro Ile Glu Glu Thr Gly Gly Glu Gly Cys Pro Gly Val Ala Leu Ile
                115                 120                 125

Gln
```

<210> SEQ ID NO 9
<211> LENGTH: 390
<212> TYPE: DNA
<213> ORGANISM: Macaca fascicularis
<220> FEATURE:
<223> OTHER INFORMATION: cynomolgus (Macaca fascicularis) Fn14 (full length)

<400> SEQUENCE: 9

```
atggctcggg gttcgctgcg ccggttgctg cggctcctcg tgctgggggct ctggctggcg      60
ttgctgcgct ccgtggctgg ggagcaagcg ccaggcaccg cccccctgctc ccacggcagt     120
tcctggagcg cggacctgga caagtgcatg gactgcgcgt cttgcagggc gcgaccgcac     180
agcgacttct gcctgggctg ctctgcggca cctcctgccc ccttccggct gctttggccc     240
atccttgggg gcgctctgag tctgaccttc gtgctggggc tgctttctgg ctttctggtc     300
tggagacgat gccgcaggag agagaagttc accaccccca tagaggagac cggcggagag     360
ggctgcccag ctgtggcgct gatccagtga                                      390
```

<210> SEQ ID NO 10
<211> LENGTH: 129
<212> TYPE: PRT
<213> ORGANISM: Macaca fascicularis
<220> FEATURE:
<223> OTHER INFORMATION: cynomolgus (Macaca fascicularis) Fn14 (full length)

<400> SEQUENCE: 10

```
Met Ala Arg Gly Ser Leu Arg Arg Leu Leu Arg Leu Leu Val Leu Gly
1               5                   10                  15
Leu Trp Leu Ala Leu Leu Arg Ser Val Ala Gly Glu Gln Ala Pro Gly
            20                  25                  30
Thr Ala Pro Cys Ser His Gly Ser Ser Trp Ser Ala Asp Leu Asp Lys
        35                  40                  45
Cys Met Asp Cys Ala Ser Cys Arg Ala Arg Pro His Ser Asp Phe Cys
    50                  55                  60
Leu Gly Cys Ser Ala Ala Pro Pro Ala Pro Phe Arg Leu Leu Trp Pro
65                  70                  75                  80
Ile Leu Gly Gly Ala Leu Ser Leu Thr Phe Val Leu Gly Leu Leu Ser
                85                  90                  95
Gly Phe Leu Val Trp Arg Arg Cys Arg Arg Arg Glu Lys Phe Thr Thr
            100                 105                 110
Pro Ile Glu Glu Thr Gly Gly Glu Gly Cys Pro Ala Val Ala Leu Ile
        115                 120                 125
Gln
```

<210> SEQ ID NO 11
<211> LENGTH: 465
<212> TYPE: DNA
<213> ORGANISM: Homo sapiens
<220> FEATURE:
<223> OTHER INFORMATION: His-SUMO-hFn14

<400> SEQUENCE: 11

```
catcatcacc accatcacgg gtccctgcag gactcagaag tcaatcaaga agctaagcca       60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
```

```
gctaaaagac agggtaagga aatggactcc ttaacgttct tgtacgacgg tattgaaatt    240
caagctgatc agacccctga agatttggac atggaggata acgatattat tgaggctcac    300
cgcgaacaga ttggaggtga gcaagcgcca ggcaccgccc cctgctcccg cggcagctcc    360
tggagcgcgg acctggacaa gtgcatggac tgcgcgtctt gcagggcgcg accgcacagc    420
gacttctgcc tgggctgcgc tgcagcacct cctgcccct tctaa                     465
```

<210> SEQ ID NO 12
<211> LENGTH: 154
<212> TYPE: PRT
<213> ORGANISM: Homo sapiens
<220> FEATURE:
<223> OTHER INFORMATION: His-SUMO-hFn14

<400> SEQUENCE: 12

```
His His His His His His Gly Ser Leu Gln Asp Ser Glu Val Asn Gln
  1               5                  10                  15

Glu Ala Lys Pro Glu Val Lys Pro Glu Val Lys Pro Glu Thr His Ile
             20                  25                  30

Asn Leu Lys Val Ser Asp Gly Ser Ser Glu Ile Phe Phe Lys Ile Lys
         35                  40                  45

Lys Thr Thr Pro Leu Arg Arg Leu Met Glu Ala Phe Ala Lys Arg Gln
     50                  55                  60

Gly Lys Glu Met Asp Ser Leu Thr Phe Leu Tyr Asp Gly Ile Glu Ile
 65                  70                  75                  80

Gln Ala Asp Gln Thr Pro Glu Asp Leu Asp Met Glu Asp Asn Asp Ile
                 85                  90                  95

Ile Glu Ala His Arg Glu Gln Ile Gly Gly Glu Gln Ala Pro Gly Thr
            100                 105                 110

Ala Pro Cys Ser Arg Gly Ser Ser Trp Ser Ala Asp Leu Asp Lys Cys
        115                 120                 125

Met Asp Cys Ala Ser Cys Arg Ala Arg Pro His Ser Asp Phe Cys Leu
    130                 135                 140

Gly Cys Ala Ala Ala Pro Pro Ala Pro Phe
145                 150
```

<210> SEQ ID NO 13
<211> LENGTH: 918
<212> TYPE: DNA
<213> ORGANISM: Homo sapiens
<220> FEATURE:
<223> OTHER INFORMATION: human Fn14-GST

<400> SEQUENCE: 13

```
atggctcggg gctcgctgcg ccggttgctg cggctcctcg tgctggggct ctggctggcg     60
ttgctgcgct ccgtggccgg ggagcaagcg ccaggcaccg cccctgctc ccgcggcagc    120 tcctggagcg cggacctgga caagtgcatg gactgcgcgt cttgcagggc gcgaccgcac    180
agcgacttct gcctgggctg cgctgcagca cctcctgccc ccttcggtac cctggaagtt    240
ctgttccagg ggcccatgtc ccctatacta ggttattgga aaattaaggg ccttgtgcaa    300
cccactcgac ttcttttgga atatcttgaa gaaaaatatg aagagcattt gtatgagcgc    360
gatgaaggtg ataaatggcg aaacaaaaag tttgaattgg gtttggagtt tcccaatctt    420
ccttattata ttgatggtga tgttaaatta acacagtcta tggccatcat acgttatata    480
gctgacaagc acaacatgtt gggtggttgt ccaaaagagc gtgcagagat ttcaatgctt    540
gaaggagcgg ttttggatat tagatacggt gtttcgagaa ttgcatatag taaagacttt    600
```

-continued

```
gaaactctca aagttgattt tcttagcaag ctacctgaaa tgctgaaaat gttcgaagat    660
cgtttatgtc ataaaacata tttaaatggt gatcatgtaa cccatcctga cttcatgttg    720
tatgacgctc ttgatgttgt tttatacatg gacccaatgt gcctggatgc gttcccaaaa    780
ttagtttgtt ttaaaaaacg tattgaagct atcccacaaa ttgataagta cttgaaatcc    840
agcaagtata tagcatggcc tttgcagggc tggcaagcca cgtttggtgg tggcgaccat    900
cctccaaaat cggattga                                                  918
```

```
<210> SEQ ID NO 14
<211> LENGTH: 305
<212> TYPE: PRT
<213> ORGANISM: Homo sapiens
<220> FEATURE:
<223> OTHER INFORMATION: human Fn14-GST

<400> SEQUENCE: 14
```

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Gly Thr Leu Glu Val
65                  70                  75                  80

Leu Phe Gln Gly Pro Met Ser Pro Ile Leu Gly Tyr Trp Lys Ile Lys
                85                  90                  95

Gly Leu Val Gln Pro Thr Arg Leu Leu Leu Glu Tyr Leu Glu Glu Lys
            100                 105                 110

Tyr Glu Glu His Leu Tyr Glu Arg Asp Glu Gly Asp Lys Trp Arg Asn
        115                 120                 125

Lys Lys Phe Glu Leu Gly Leu Glu Phe Pro Asn Leu Pro Tyr Tyr Ile
    130                 135                 140

Asp Gly Asp Val Lys Leu Thr Gln Ser Met Ala Ile Ile Arg Tyr Ile
145                 150                 155                 160

Ala Asp Lys His Asn Met Leu Gly Gly Cys Pro Lys Glu Arg Ala Glu
                165                 170                 175

Ile Ser Met Leu Glu Gly Ala Val Leu Asp Ile Arg Tyr Gly Val Ser
            180                 185                 190

Arg Ile Ala Tyr Ser Lys Asp Phe Glu Thr Leu Lys Val Asp Phe Leu
        195                 200                 205

Ser Lys Leu Pro Glu Met Leu Lys Met Phe Glu Asp Arg Leu Cys His
    210                 215                 220

Lys Thr Tyr Leu Asn Gly Asp His Val Thr His Pro Asp Phe Met Leu
225                 230                 235                 240

Tyr Asp Ala Leu Asp Val Val Leu Tyr Met Asp Pro Met Cys Leu Asp
                245                 250                 255

Ala Phe Pro Lys Leu Val Cys Phe Lys Lys Arg Ile Glu Ala Ile Pro
            260                 265                 270

Gln Ile Asp Lys Tyr Leu Lys Ser Lys Tyr Ile Ala Trp Pro Leu
        275                 280                 285

Gln Gly Trp Gln Ala Thr Phe Gly Gly Gly Asp His Pro Pro Lys Ser
    290                 295                 300

Asp
305

<210> SEQ ID NO 15
<211> LENGTH: 915
<212> TYPE: DNA
<213> ORGANISM: Macaca fascicularis
<220> FEATURE:
<223> OTHER INFORMATION: cyno Fn14-GST (Macaca fascicularis)

<400> SEQUENCE: 15

```
atggctcggg gctcgctgcg ccggttgctg cggctcctcg tgctgggget ctggctggcg      60
ttgctgcgct ccgtggccgg ggagcaagcg ccaggcaccg ccccctgctc ccacggcagc     120
tcctggagcg cggacctgga caagtgcatg gactgcgcgt cttgcagggc gcgaccgcac     180
agcgacttct gcctgggctg ctccgcagca cctcctgccc ccttcggtac cctggaagtt     240
ctgttccagg ggcccatgtc cctatacta ggttattgga aaattaaggg ccttgtgcaa      300
cccactcgac ttcttttgga atatcttgaa gaaaaatatg aagagcattt gtatgagcgc     360
gatgaaggtg ataaatggcg aaacaaaaag tttgaattgg gtttggagtt cccaatctt     420
ccttattata ttgatggtga tgttaaatta acacagtcta tggccatcat acgttatata     480
gctgacaagc acaacatgtt gggtggttgt ccaaaagagc gtgcagagat ttcaatgctt     540
gaaggagcgg ttttggatat tagatacggt gtttcgagaa ttgcatatag taaagacttt     600
gaaactctca agttgatttt tcttagcaag ctacctgaaa tgctgaaaat gttcgaagat     660
cgtttatgtc ataaaacata tttaaatggt gatcatgtaa cccatcctga cttcatgttg     720
tatgacgctc ttgatgttgt tttatacatg gacccaatgt gcctggatgc gttcccaaaa     780
ttagtttgtt ttaaaaaacg tattgaagct atcccacaaa ttgataagta cttgaaatcc     840
agcaagtata tagcatggcc tttgcagggc tggcaagcca cgtttggtgg tggcgaccat     900
cctccaaaat cggat                                                    915
```

<210> SEQ ID NO 16
<211> LENGTH: 305
<212> TYPE: PRT
<213> ORGANISM: Macaca fascicularis
<220> FEATURE:
<223> OTHER INFORMATION: cyno Fn14-GST (Macaca fascicularis)

<400> SEQUENCE: 16

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser His Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ser Ala Ala Pro Pro Ala Pro Phe Gly Thr Leu Glu Val
65                  70                  75                  80

Leu Phe Gln Gly Pro Met Ser Pro Ile Leu Gly Tyr Trp Lys Ile Lys
                85                  90                  95

Gly Leu Val Gln Pro Thr Arg Leu Leu Leu Glu Tyr Leu Glu Glu Lys
            100                 105                 110

Tyr Glu Glu His Leu Tyr Glu Arg Asp Glu Gly Asp Lys Trp Arg Asn
        115                 120                 125
```

-continued

```
Lys Lys Phe Glu Leu Gly Leu Glu Phe Pro Asn Leu Pro Tyr Tyr Ile
    130                 135                 140

Asp Gly Asp Val Lys Leu Thr Gln Ser Met Ala Ile Ile Arg Tyr Ile
145                 150                 155                 160

Ala Asp Lys His Asn Met Leu Gly Gly Cys Pro Lys Glu Arg Ala Glu
                165                 170                 175

Ile Ser Met Leu Glu Gly Ala Val Leu Asp Ile Arg Tyr Gly Val Ser
                180                 185                 190

Arg Ile Ala Tyr Ser Lys Asp Phe Glu Thr Leu Lys Val Asp Phe Leu
            195                 200                 205

Ser Lys Leu Pro Glu Met Leu Lys Met Phe Glu Asp Arg Leu Cys His
        210                 215                 220

Lys Thr Tyr Leu Asn Gly Asp His Val Thr His Pro Asp Phe Met Leu
225                 230                 235                 240

Tyr Asp Ala Leu Asp Val Val Leu Tyr Met Asp Pro Met Cys Leu Asp
                245                 250                 255

Ala Phe Pro Lys Leu Val Cys Phe Lys Lys Arg Ile Glu Ala Ile Pro
                260                 265                 270

Gln Ile Asp Lys Tyr Leu Lys Ser Ser Lys Tyr Ile Ala Trp Pro Leu
            275                 280                 285

Gln Gly Trp Gln Ala Thr Phe Gly Gly Gly Asp His Pro Pro Lys Ser
        290                 295                 300

Asp
305

<210> SEQ ID NO 17
<211> LENGTH: 918
<212> TYPE: DNA
<213> ORGANISM: Mouse
<220> FEATURE:
<223> OTHER INFORMATION: mouse Fn14-GST

<400> SEQUENCE: 17
atggcttcgg cttggccgcg gtctctgccg cagatcctcg tgttgggatt cggcttggtg      60
ttgatgcgcg ccgcggccgg ggagcaagca ccaggcacct ccccatgctc tagcggcagc     120
tcctggagcg cggacctcga caagtgcatg gactgcgctt cttgtccagc gcgaccacac     180
agcgacttct gcctgggatg cgccgcagca cctcctgccc acttcggtac cctggaagtt     240
ctgttccagg ggcccatgtc ccctatacta ggttattgga aaattaaggg ccttgtgcaa     300
cccactcgac ttcttttgga atatcttgaa gaaaaatatg aagagcattt gtatgagcgc     360
gatgaaggtg ataaatggcg aaacaaaaag tttgaattgg gtttggagtt cccaatctt     420 ccttattata ttgatggtga tgttaaatta acacagtcta tggccatcat acgttatata     480
gctgacaagc acaacatgtt gggtggttgt ccaaaagagc gtgcagagat tcaatgctt     540 gaaggagcgg ttttggatat tagatacggt gtttcgagaa ttgcatatag taaagacttt     600
gaaactctca agttgatttt tcttagcaag ctacctgaaa tgctgaaaat gttcgaagat     660
cgtttatgtc ataaaacata tttaaatggt gatcatgtaa cccatcctga cttcatgttg     720
tatgacgctc ttgatgttgt tttatacatg gacccaatgt gcctggatgc gttcccaaaa     780
ttagtttgtt ttaaaaaacg tattgaagct atcccacaaa ttgataagta cttgaaatcc     840
agcaagtata tagcatggcc tttgcagggc tggcaagcca cgtttggtgg tggcgaccat     900
cctccaaaat cggattga                                                  918
```

-continued

```
<210> SEQ ID NO 18
<211> LENGTH: 305
<212> TYPE: PRT
<213> ORGANISM: Mouse
<220> FEATURE:
<223> OTHER INFORMATION: mouse Fn14-GST

<400> SEQUENCE: 18

Met Ala Ser Ala Trp Pro Arg Ser Leu Pro Gln Ile Leu Val Leu Gly
1               5                   10                  15

Phe Gly Leu Val Leu Met Arg Ala Ala Ala Gly Glu Gln Ala Pro Gly
            20                  25                  30

Thr Ser Pro Cys Ser Ser Gly Ser Ser Trp Ser Ala Asp Leu Asp Lys
        35                  40                  45

Cys Met Asp Cys Ala Ser Cys Pro Ala Arg Pro His Ser Asp Phe Cys
    50                  55                  60

Leu Gly Cys Ala Ala Ala Pro Pro Ala Pro His Phe Gly Thr Leu Glu Val
65                  70                  75                  80

Leu Phe Gln Gly Pro Met Ser Pro Ile Leu Gly Tyr Trp Lys Ile Lys
                85                  90                  95

Gly Leu Val Gln Pro Thr Arg Leu Leu Leu Glu Tyr Leu Glu Glu Lys
            100                 105                 110

Tyr Glu Glu His Leu Tyr Glu Arg Asp Glu Gly Asp Lys Trp Arg Asn
        115                 120                 125

Lys Lys Phe Glu Leu Gly Leu Glu Phe Pro Asn Leu Pro Tyr Tyr Ile
130                 135                 140

Asp Gly Asp Val Lys Leu Thr Gln Ser Met Ala Ile Ile Arg Tyr Ile
145                 150                 155                 160

Ala Asp Lys His Asn Met Leu Gly Gly Cys Pro Lys Glu Arg Ala Glu
                165                 170                 175

Ile Ser Met Leu Glu Gly Ala Val Leu Asp Ile Arg Tyr Gly Val Ser
            180                 185                 190

Arg Ile Ala Tyr Ser Lys Asp Phe Glu Thr Leu Lys Val Asp Phe Leu
        195                 200                 205

Ser Lys Leu Pro Glu Met Leu Lys Met Phe Glu Asp Arg Leu Cys His
    210                 215                 220

Lys Thr Tyr Leu Asn Gly Asp His Val Thr His Pro Asp Phe Met Leu
225                 230                 235                 240

Tyr Asp Ala Leu Asp Val Val Leu Tyr Met Asp Pro Met Cys Leu Asp
                245                 250                 255

Ala Phe Pro Lys Leu Val Cys Phe Lys Lys Arg Ile Glu Ala Ile Pro
            260                 265                 270

Gln Ile Asp Lys Tyr Leu Lys Ser Ser Lys Tyr Ile Ala Trp Pro Leu
        275                 280                 285

Gln Gly Trp Gln Ala Thr Phe Gly Gly Asp His Pro Pro Lys Ser
    290                 295                 300

Asp
305

<210> SEQ ID NO 19
<211> LENGTH: 660
<212> TYPE: DNA
<213> ORGANISM: Artificial Sequence
<220> FEATURE:
<223> OTHER INFORMATION: GST

<400> SEQUENCE: 19
```

```
atgtcccctc tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca   600 tggcctttgc agggctggca agccacgttt ggtggtggcg accatcctcc aaaatcggat   660
```

<210> SEQ ID NO 20
<211> LENGTH: 220
<212> TYPE: PRT
<213> ORGANISM: Artificial Sequence
<220> FEATURE:
<223> OTHER INFORMATION: GST

<400> SEQUENCE: 20

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp
    210                 215                 220
```

<210> SEQ ID NO 21
<211> LENGTH: 318
<212> TYPE: DNA

<213> ORGANISM: Artificial Sequence
<220> FEATURE:
<223> OTHER INFORMATION: His-SUMO

<400> SEQUENCE: 21

```
catcatcacc accatcacgg gtccctgcag gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
gctaaaagac agggtaagga aatggactcc ttaacgttct tgtacgacgg tattgaaatt     240
caagctgatc agacccctga agatttggac atggaggata cgatattat tgaggctcac      300
cgcgaacaga ttggaggt                                                    318
```

<210> SEQ ID NO 22
<211> LENGTH: 106
<212> TYPE: PRT
<213> ORGANISM: Artificial Sequence
<220> FEATURE:
<223> OTHER INFORMATION: His-SUMO

<400> SEQUENCE: 22

```
His His His His His His Gly Ser Leu Gln Asp Ser Glu Val Asn Gln
1               5                   10                  15
Glu Ala Lys Pro Glu Val Lys Pro Glu Val Lys Pro Glu Thr His Ile
            20                  25                  30
Asn Leu Lys Val Ser Asp Gly Ser Ser Glu Ile Phe Phe Lys Ile Lys
        35                  40                  45
Lys Thr Thr Pro Leu Arg Arg Leu Met Glu Ala Phe Ala Lys Arg Gln
    50                  55                  60
Gly Lys Glu Met Asp Ser Leu Thr Phe Leu Tyr Asp Gly Ile Glu Ile
65                  70                  75                  80
Gln Ala Asp Gln Thr Pro Glu Asp Leu Asp Met Glu Asp Asn Asp Ile
                85                  90                  95
Ile Glu Ala His Arg Glu Gln Ile Gly Gly
            100                 105
```

<210> SEQ ID NO 23
<211> LENGTH: 321
<212> TYPE: DNA
<213> ORGANISM: Mouse
<220> FEATURE:
<223> OTHER INFORMATION: mouse kappa constant

<400> SEQUENCE: 23

```
cgagctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga cagttggac tgatcaggac       180
agcaaagaca gcacctacag catgagcagc accctcacgt tgaccaagga cgagtatgaa     240
cgacataaca gctatacctg tgaggccact cacaagacat caacttcacc catcgtcaag     300
agcttcaaca ggaatgagtg t                                                321
```

<210> SEQ ID NO 24
<211> LENGTH: 107
<212> TYPE: PRT
<213> ORGANISM: Mouse
<220> FEATURE:
<223> OTHER INFORMATION: mouse kappa constant

<400> SEQUENCE: 24

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 25
<211> LENGTH: 972
<212> TYPE: DNA
<213> ORGANISM: Mouse
<220> FEATURE:
<223> OTHER INFORMATION: mouse IgG1 (D265A) constant

<400> SEQUENCE: 25

```
gccaaaacga cacccccgtc tgtctatcca ctggcccctg gatctgctgc ccaaactaac      60
tccatggtga ccctgggatg cctggtcaag ggctatttcc ctgagccagt gacagtgacc     120
tggaactctg gctccctgtc cagcggtgtg cacaccttcc cagctgtcct ggagtctgac     180
ctctacactc tgagcagctc agtgactgtc cctccagcc tcggcccag cgagaccgtc       240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
cccccaaagc ccaaggatgt gctcaccatt actctgactc taaggtcac gtgtgttgtg      420
gtagccatca gcaaggatga tcccgaggtc cagttcagct ggtttgtaga tgatgtggag     480
gtgcacacag ctcagacgca accccgggag gagcagttca acagcacttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatggccaa ggataaagtc    720
agtctgacct gcatgataac agacttcttc cctgaagaca ttactgtgga gtggcagtgg    780
aatgggcagc cagcggagaa ctacaagaac actcagccca tcatgaacac gaatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aa                                                        972
```

<210> SEQ ID NO 26
<211> LENGTH: 324
<212> TYPE: PRT
<213> ORGANISM: Mouse
<220> FEATURE:
<223> OTHER INFORMATION: mouse IgG1(D265A) constant

<400> SEQUENCE: 26

Ala Lys Thr Thr Pro Pro Ser Val Tyr Pro Leu Ala Pro Gly Ser Ala
1               5                   10                  15

```
Ala Gln Thr Asn Ser Met Val Thr Leu Gly Cys Leu Val Lys Gly Tyr
            20                  25                  30
Phe Pro Glu Pro Val Thr Val Thr Trp Asn Ser Gly Ser Leu Ser Ser
            35                  40                  45
Gly Val His Thr Phe Pro Ala Val Leu Glu Ser Asp Leu Tyr Thr Leu
 50                  55                  60
Ser Ser Ser Val Thr Val Pro Ser Ser Pro Arg Pro Ser Glu Thr Val
 65                  70                  75                  80
Thr Cys Asn Val Ala His Pro Ala Ser Ser Thr Lys Val Asp Lys Lys
                 85                  90                  95
Ile Val Pro Arg Asp Cys Gly Cys Lys Pro Cys Ile Cys Thr Val Pro
            100                 105                 110
Glu Val Ser Ser Val Phe Ile Phe Pro Pro Lys Pro Lys Asp Val Leu
            115                 120                 125
Thr Ile Thr Leu Thr Pro Lys Val Thr Cys Val Val Val Ala Ile Ser
130                 135                 140
Lys Asp Asp Pro Glu Val Gln Phe Ser Trp Phe Val Asp Asp Val Glu
145                 150                 155                 160
Val His Thr Ala Gln Thr Gln Pro Arg Glu Glu Gln Phe Asn Ser Thr
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
        195                 200                 205
Ile Glu Lys Thr Ile Ser Lys Thr Lys Gly Arg Pro Lys Ala Pro Gln
            210                 215                 220
Val Tyr Thr Ile Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Thr Gln
            260                 265                 270
Pro Ile Met Asn Thr Asn Gly Ser Tyr Phe Val Tyr Ser Lys Leu Asn
            275                 280                 285
Val Gln Lys Ser Asn Trp Glu Ala Gly Asn Thr Phe Thr Cys Ser Val
        290                 295                 300
Leu His Glu Gly Leu His Asn His Thr Glu Lys Ser Leu Ser His
305                 310                 315                 320
Ser Pro Gly Lys

<210> SEQ ID NO 27
<211> LENGTH: 321
<212> TYPE: DNA
<213> ORGANISM: Homo sapiens
<220> FEATURE:
<223> OTHER INFORMATION: human kappa constant

<400> SEQUENCE: 27
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
```

```
agcttcaaca ggggagagtg t                                              321
```

<210> SEQ ID NO 28
<211> LENGTH: 107
<212> TYPE: PRT
<213> ORGANISM: Homo sapiens
<220> FEATURE:
<223> OTHER INFORMATION: human kappa constant

<400> SEQUENCE: 28

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 29
<211> LENGTH: 981
<212> TYPE: DNA
<213> ORGANISM: Homo sapiens
<220> FEATURE:
<223> OTHER INFORMATION: human IgG4 null constant

<400> SEQUENCE: 29

```
gctagcacca aggggccatc cgtcttcccc ctggcgccct gctccaggag cacctccgag     60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc cccatgccc accatgccca gcacctgagt tcgaggggggg accatcagtc     360 ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaagcta accgtggaca agagcaggtg gcaggagggg    900
aatgtcttct catgctccgt gatgcatgag gctctgcaca accactacac acagaagagc    960
ctctccctgt ctctgggtaa a                                              981
```

```
<210> SEQ ID NO 30
<211> LENGTH: 327
<212> TYPE: PRT
<213> ORGANISM: Homo sapiens
<220> FEATURE:
<223> OTHER INFORMATION: human IgG4 null constant

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 31
<211> LENGTH: 402
<212> TYPE: DNA
<213> ORGANISM: Artificial Sequence
<220> FEATURE:
<223> OTHER INFORMATION: 41C-VH (with signal peptide) (not codon
``` optimized)

<400> SEQUENCE: 31

```
atgggatgga gctggatctt tctctttctc ctgtcagaaa ctgcaggtgt cctctctgag    60
gtccagctgc aacagtctgg acctgagctg gtgaagcctg gggcttcagt gaagatgtcc   120
tgcaaggctt ctggatacac attcactgac tacaacatgc actgggtgaa gcagagccat   180
ggaaagagcc ttgaatggat tggatatatt aaccctaaca atggtggtac taactacaac   240
cagaagttca aggcaaggc cacattgact gtaaacaagt cctccaggtc agcctacatg    300
gagttccgca gcctgacatc ggaggattct gcagtctatt actgtgcctc gtcgggatgg   360
tttacttact ggggccaagg gactctggtc actgtctctg ca                     402
```

<210> SEQ ID NO 32
<211> LENGTH: 134
<212> TYPE: PRT
<213> ORGANISM: Artificial Sequence
<220> FEATURE:
<223> OTHER INFORMATION: 41C-VH (with signal peptide) (not codon
      optimized)

<400> SEQUENCE: 32

```
Met Gly Trp Ser Trp Ile Phe Leu Phe Leu Leu Ser Glu Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Ser His Gly Lys Ser Leu
    50                  55                  60

Glu Trp Ile Gly Tyr Ile Asn Pro Asn Asn Gly Gly Thr Asn Tyr Asn
65                  70                  75                  80

Gln Lys Phe Lys Gly Lys Ala Thr Leu Thr Val Asn Lys Ser Ser Arg
                85                  90                  95

Ser Ala Tyr Met Glu Phe Arg Ser Leu Thr Ser Glu Asp Ser Ala Val
            100                 105                 110

Tyr Tyr Cys Ala Ser Ser Gly Trp Phe Thr Tyr Trp Gly Gln Gly Thr
        115                 120                 125

Leu Val Thr Val Ser Ala
    130
```

<210> SEQ ID NO 33
<211> LENGTH: 360
<212> TYPE: DNA
<213> ORGANISM: Mouse
<220> FEATURE:
<223> OTHER INFORMATION: 41C-VH (no signal peptide) (not codon
      optimized)

<400> SEQUENCE: 33

```
gaggtccagc tgctccagtc tggacctgag ctggtgaagc ctgtggcttc agtgaagatg    60
tcctgcaagg cttctggata cacattcact gactacaaca ttcactgggt gaagcagagc   120
catggaaaga gccttgagtg gattggatat attaacccta caatggtgt tactggctac   180
aaccagaagt tcaggggcaa ggccacattg actgttaaca ggtcctccaa cacagcctac   240
atggacctcc gcagcctgac atcggaggat tctgcagtct attactgtac aagacgctat   300
ggtgactacg tccatgctat ggactgctgg ggtcaaggaa cctcagtcac cgtctcctca   360
```

<210> SEQ ID NO 34
<211> LENGTH: 345
<212> TYPE: DNA
<213> ORGANISM: Mouse
<220> FEATURE:
<223> OTHER INFORMATION: 41C-VH (no signal peptide) [codon optimized]

<400> SEQUENCE: 34

```
gaagtgcagc tgcagcagtc tggccccgag ctcgtgaaac ctggcgcctc cgtgaagatg      60
tcctgcaagg cctccggcta caccttcacc gactacaaca tgcactgggt caagcagtcc     120
cacggcaagt ccctggaatg gatcggctac atcaacccca caacggcgg caccaactac      180
aaccagaagt tcaagggcaa ggctaccctg accgtgaaca gtcctccag atccgcctac      240
atggaatttc ggtccctgac ctccgaggac tccgccgtgt actactgcgc ctcctctggc     300
tggttcacct actggggcca gggcaccctc gtgaccgtgt ctgct                     345
```

<210> SEQ ID NO 35
<211> LENGTH: 115
<212> TYPE: PRT
<213> ORGANISM: Mouse
<220> FEATURE:
<223> OTHER INFORMATION: 41C-VH (no signal peptide)

<400> SEQUENCE: 35

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Gly Thr Asn Tyr Asn Gln Lys Phe
    50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
        115
```

<210> SEQ ID NO 36
<211> LENGTH: 396
<212> TYPE: DNA
<213> ORGANISM: Artificial Sequence
<220> FEATURE:
<223> OTHER INFORMATION: 41C-VL (with signal peptide) (not codon optimized)

<400> SEQUENCE: 36

```
atgatgagtc ctgcccagtt cctgtttctg ttagtgctct ggattcggga aaccaacggt      60
gatgttgtga tgacccagac tccactcact ttgtcggttg ccattggaca accagcctcc     120
atctcttgca gtcaagtca gagcctctta aatagtgctg gaagacata tttgaattgg       180
ttgttacaga ggccaggcca gtctccaaag cgcctaattt atctggtgtc tcaactggac     240
tctggagtcc ctgacaggtt cactggcagt ggatcaggga cagatttcac actgaaaatc     300
agcagagtgg aggctgagga tttgggagtt tattattgct ggcaaggtac acattttccg     360
```
tggacgttcg gtggaggcac caagctggaa atcaaa 396

<210> SEQ ID NO 37
<211> LENGTH: 132
<212> TYPE: PRT
<213> ORGANISM: Artificial Sequence
<220> FEATURE:
<223> OTHER INFORMATION: 41C-VL (with signal peptide) (not codon
      optimized)

<400> SEQUENCE: 37

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Ala Ile Gly Gln Pro Ala Ser Ile Ser Cys Lys Ser Ser Gln Ser
        35                  40                  45

Leu Leu Asn Ser Ala Gly Lys Thr Tyr Leu Asn Trp Leu Leu Gln Arg
    50                  55                  60

Pro Gly Gln Ser Pro Lys Arg Leu Ile Tyr Leu Val Ser Gln Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Trp Thr Phe Gly Gly Gly Thr Lys
        115                 120                 125

Leu Glu Ile Lys
    130

<210> SEQ ID NO 38
<211> LENGTH: 336
<212> TYPE: DNA
<213> ORGANISM: Mouse
<220> FEATURE:
<223> OTHER INFORMATION: 41C-VL (no signal peptide) (not codon
      optimized)

<400> SEQUENCE: 38
gatgttgtga tgacccagac tccactcact ttgtcggttg ccattggaca accagcctcc    60
atctcttgca agtcaagtca gagcctctta aatagtgctg gaaagacata tttgaattgg   120
ttgttacaga ggccaggcca gtctccaaag cgcctaattt atctggtgtc tcaactggac   180
tctggagtcc ctgacaggtt cactggcagt ggatcaggga cagatttcac actgaaaatc   240
agcagagtgg aggctgagga tttgggagtt tattattgct ggcaaggtac acattttccg   300
tggacgttcg gtggaggcac caagctggaa atcaaa                              336

<210> SEQ ID NO 39
<211> LENGTH: 336
<212> TYPE: DNA
<213> ORGANISM: Mouse
<220> FEATURE:
<223> OTHER INFORMATION: 41C-VL (no signal peptide) (codon optimized)

<400> SEQUENCE: 39
gacgtcgtga tgacccagac ccccctgaca ctgtctgtgg ccatcggcca gcctgcctcc    60
atctcctgca gtcctcccca gtccctgctg aactccgccg gcaagaccta cctgaactgg   120
ctgctgcagc ggcctggcca gtcccccaag agactgatct acctggtgtc ccagctggac   180

```
tccggcgtgc ccgatagatt caccggctct ggctctggca ccgacttcac cctgaagatc    240
agccgggtgg aagccgagga cctgggcgtg tactactgct ggcagggcac ccacttccct    300
tggacctttg gcggaggcac caagctggaa atcaag                              336
```

<210> SEQ ID NO 40
<211> LENGTH: 112
<212> TYPE: PRT
<213> ORGANISM: Mouse
<220> FEATURE:
<223> OTHER INFORMATION: 41C-VL (no signal peptide)

<400> SEQUENCE: 40

```
Asp Val Val Met Thr Gln Thr Pro Leu Thr Leu Ser Val Ala Ile Gly
1               5                   10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Leu Gln Arg Pro Gly Gln Ser
        35                  40                  45

Pro Lys Arg Leu Ile Tyr Leu Val Ser Gln Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110
```

<210> SEQ ID NO 41
<211> LENGTH: 417
<212> TYPE: DNA
<213> ORGANISM: Artificial Sequence
<220> FEATURE:
<223> OTHER INFORMATION: 42d-VH (with signal peptide)

<400> SEQUENCE: 41

```
atgggatgga gctggatctt tctctttctc ctgtcagaaa ctgcaggtgt cctctctgag     60
gtccagctgc tccagtctgg acctgagctg gtgaagcctg tggcttcagt gaagatgtcc    120
tgcaaggctt ctggatacac attcactgac tacaacattc actgggtgaa gcagagccat    180
ggaaagagcc ttgagtggat tggatatatt aaccctaaca atggtgttac tggctacaac    240
cagaagttca gggcaaggc cacattgact gttaacaggt cctccaacac agcctacatg    300
gacctccgca gcctgacatc ggaggattct gcagtctatt actgtacaag acgctatggt    360
gactacgtcc atgctatgga ctgctggggt caaggaacct cagtcaccgt ctcctca       417
```

<210> SEQ ID NO 42
<211> LENGTH: 139
<212> TYPE: PRT
<213> ORGANISM: Artificial Sequence
<220> FEATURE:
<223> OTHER INFORMATION: 42d-VH (with signal peptide)

<400> SEQUENCE: 42

```
Met Gly Trp Ser Trp Ile Phe Leu Phe Leu Leu Ser Glu Thr Ala Gly
1               5                   10                  15

Val Leu Ser Glu Val Gln Leu Leu Gln Ser Gly Pro Glu Leu Val Lys
            20                  25                  30

Pro Val Ala Ser Val Lys Met Ser Cys Lys Ala Ser Gly Tyr Thr Phe
        35                  40                  45
```

```
Thr Asp Tyr Asn Ile His Trp Val Lys Gln Ser His Gly Lys Ser Leu
    50                  55                  60

Glu Trp Ile Gly Tyr Ile Asn Pro Asn Asn Gly Val Thr Gly Tyr Asn
65                  70                  75                  80

Gln Lys Phe Arg Gly Lys Ala Thr Leu Thr Val Asn Arg Ser Ser Asn
                85                  90                  95

Thr Ala Tyr Met Asp Leu Arg Ser Leu Thr Ser Glu Asp Ser Ala Val
            100                 105                 110

Tyr Tyr Cys Thr Arg Arg Tyr Gly Asp Tyr Val His Ala Met Asp Cys
            115                 120                 125

Trp Gly Gln Gly Thr Ser Val Thr Val Ser Ser
    130                 135
```

```
<210> SEQ ID NO 43
<211> LENGTH: 360
<212> TYPE: DNA
<213> ORGANISM: Artificial Sequence
<220> FEATURE:
<223> OTHER INFORMATION: 42d-VH (no signal peptide)

<400> SEQUENCE: 43
gaggtccagc tgctccagtc tggacctgag ctggtgaagc ctgtggcttc agtgaagatg    60
tcctgcaagg cttctggata cacattcact gactacaaca ttcactgggt gaagcagagc   120
catggaaaga gccttgagtg gattggatat attaaccccta acaatggtgt tactggctac   180
aaccagaagt tcaggggcaa ggccacattg actgttaaca ggtcctccaa cacagcctac   240
atggacctcc gcagcctgac atcggaggat tctgcagtct attactgtac aagacgctat   300
ggtgactacg tccatgctat ggactgctgg ggtcaaggaa cctcagtcac cgtctcctca   360
```

```
<210> SEQ ID NO 44
<211> LENGTH: 120
<212> TYPE: PRT
<213> ORGANISM: Artificial Sequence
<220> FEATURE:
<223> OTHER INFORMATION: 42d-VH (no signal peptide)

<400> SEQUENCE: 44

Glu Val Gln Leu Leu Gln Ser Gly Pro Glu Leu Val Lys Pro Val Ala
1               5                   10                  15

Ser Val Lys Met Ser Cys Lys Ala Ser Gly Tyr Thr Phe Thr Asp Tyr
                20                  25                  30

Asn Ile His Trp Val Lys Gln Ser His Gly Lys Ser Leu Glu Trp Ile
            35                  40                  45

Gly Tyr Ile Asn Pro Asn Asn Gly Val Thr Gly Tyr Asn Gln Lys Phe
    50                  55                  60

Arg Gly Lys Ala Thr Leu Thr Val Asn Arg Ser Ser Asn Thr Ala Tyr
65                  70                  75                  80

Met Asp Leu Arg Ser Leu Thr Ser Glu Asp Ser Ala Val Tyr Tyr Cys
                85                  90                  95

Thr Arg Arg Tyr Gly Asp Tyr Val His Ala Met Asp Cys Trp Gly Gln
            100                 105                 110

Gly Thr Ser Val Thr Val Ser Ser
        115                 120
```

```
<210> SEQ ID NO 45
<211> LENGTH: 387
<212> TYPE: DNA
```

<210> SEQ ID NO 45 (implied continuation)

```
<213> ORGANISM: Artificial Sequence
<220> FEATURE:
<223> OTHER INFORMATION: 42d-VL (with signal peptide)

<400> SEQUENCE: 45
atggacatga gggctcctgc acagattttt ggcttcttgt tgctcttgtt tccaggtacc      60
agatgtgaca tccagatgac ccagtctcca tcctccttat ctgcctctct gggagaaaga    120
gtcagtctca cttgtcgggc aagtcaggac attggtagta ggttaaactg gcttcagcag    180
gaaccagatg gaactattaa acgcctgatc tacgccacat ccagtttaga ttctggtgtc    240
cccaaaaggt tcagtggcag taggtctggg tcagattatt ctctcaccat cagcagcctt    300
gagtctgaag attttgtaga ctattactgt ctacaatatg ctagttctcc gtacacattc    360 ggaggggga ccaagctgga aataaaa                                          387

<210> SEQ ID NO 46
<211> LENGTH: 129
<212> TYPE: PRT
<213> ORGANISM: Artificial Sequence
<220> FEATURE:
<223> OTHER INFORMATION: 42d-VL (with signal peptide)

<400> SEQUENCE: 46
```

Met Asp Met Arg Ala Pro Ala Gln Ile Phe Gly Phe Leu Leu Leu Leu
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Ser Arg Leu Asn Trp Leu Gln Gln Glu Pro Asp Gly
    50                  55                  60

Thr Ile Lys Arg Leu Ile Tyr Ala Thr Ser Ser Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Val Asp Tyr Tyr Cys Leu Gln
            100                 105                 110

Tyr Ala Ser Ser Pro Tyr Thr Phe Gly Gly Gly Thr Lys Leu Glu Ile
        115                 120                 125

Lys

```
<210> SEQ ID NO 47
<211> LENGTH: 321
<212> TYPE: DNA
<213> ORGANISM: Artificial Sequence
<220> FEATURE:
<223> OTHER INFORMATION: 42d-VL (no signal peptide)

<400> SEQUENCE: 47
gacatccaga tgacccagtc tccatcctcc ttatctgcct ctctgggaga aagagtcagt      60
ctcacttgtc gggcaagtca ggacattggt agtaggttaa actggcttca gcaggaacca    120
gatggaacta ttaaacgcct gatctacgcc acatccagtt tagattctgg tgtccccaaa    180
aggttcagtg gcagtaggtc tgggtcagat tattctctca ccatcagcag ccttgagtct    240
gaagattttg tagactatta ctgtctacaa tatgctagtt ctccgtacac attcggaggg    300
gggaccaagc tggaaataaa a                                               321
```

```
<210> SEQ ID NO 48
<211> LENGTH: 107
<212> TYPE: PRT
<213> ORGANISM: Artificial Sequence
<220> FEATURE:
<223> OTHER INFORMATION: 42d-VL (no signal peptide)

<400> SEQUENCE: 48

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Arg
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

<210> SEQ ID NO 49
<211> LENGTH: 345
<212> TYPE: DNA
<213> ORGANISM: Mouse
<220> FEATURE:
<223> OTHER INFORMATION: R35B9-VH

<400> SEQUENCE: 49
gaggtgcagc tgcagcaaag cggcccggag ctggtgaaac cgggtgcgag cgttaaaatg      60
agctgcaagg cgagcggtta catttttcag gattataata tgcattgggt taaacagagc     120
cacggtaaaa gcctggagtg gatcggctct attaatccgc gtaatggttg gaccaactat     180
aaccaaaagt tcaaaggcaa ggcgaccctg accgtgaaca agagcagccg tagcgcgtac     240
atggagtttc gtagcctgac cagcgaagat agcgcggttt actattgcgc gtcttcgggg     300
tggttcacgt attggggtca aggcaccctg gtgaccgtta gcgcg                     345

<210> SEQ ID NO 50
<211> LENGTH: 115
<212> TYPE: PRT
<213> ORGANISM: Mouse
<220> FEATURE:
<223> OTHER INFORMATION: R35B9-VH

<400> SEQUENCE: 50

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ser His Gly Lys Ser Leu Glu Trp Ile
        35                  40                  45

Gly Ser Ile Asn Pro Arg Asn Gly Trp Thr Asn Tyr Asn Gln Lys Phe
    50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95
```

Ala Ser Ser Gly Trp Phe Thr Tyr Trp Gly Gln Gly Thr Leu Val Thr
            100                 105                 110

Val Ser Ala
        115

<210> SEQ ID NO 51
<211> LENGTH: 336
<212> TYPE: DNA
<213> ORGANISM: Mouse
<220> FEATURE:
<223> OTHER INFORMATION: R35B9-VL

<400> SEQUENCE: 51
gacgtggtta tgacccaaac cccgctgacc ctgagcgtgg cgattggtca gccggcgagc      60
attagctgca agagcagcca aagcctgctg aacagcgcgg gtaaaaccta cctgaactgg     120
ctgctgcagc gtccgggtca aagcccgaag cgtctgatct atctggtgag ccagctggac     180
agcggtgtgc cggaccgttt caccggtagc ggtagcggca ccgactttac cctgaaaatt     240
agccgtgtgg aggcggaaga tctgggtgtt tactattgct ggcaaggtac tttttatccg     300
tggacctttg gtggcggtac caagctggag atcaaa                               336

<210> SEQ ID NO 52
<211> LENGTH: 112
<212> TYPE: PRT
<213> ORGANISM: Mouse
<220> FEATURE:
<223> OTHER INFORMATION: R35B9-VL

<400> SEQUENCE: 52

Asp Val Val Met Thr Gln Thr Pro Leu Thr Leu Ser Val Ala Ile Gly
1               5                   10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Leu Gln Arg Pro Gly Gln Ser
        35                  40                  45

Pro Lys Arg Leu Ile Tyr Leu Val Ser Gln Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr Phe Tyr Pro Trp Thr Phe Gly Gly Gly Thr Lys Leu Glu Ile Lys
            100                 105                 110

<210> SEQ ID NO 53
<211> LENGTH: 345
<212> TYPE: DNA
<213> ORGANISM: Mouse
<220> FEATURE:
<223> OTHER INFORMATION: R35B9(Y50G57)-VH

<400> SEQUENCE: 53
gaggtgcagc tgcagcaaag cggcccggag ctggtgaaac cgggtgcgag cgttaaaatg      60
agctgcaagg cgagcggtta cattttcag gattataata tgcattgggt taaacagagc     120
cacggtaaaa gcctggagtg gatcggctat attaatccgc gtaatggtgg gaccaactat     180
aaccaaaagt tcaaaggcaa ggcgaccctg accgtgaaca gagcagccg tagcgcgtac     240 atggagtttc gtagcctgac cagcgaagat agcgcggttt actattgcgc gtcttcgggg     300

```
tggttcacgt attggggtca aggcaccctg gtgaccgtta gcgcg          345
```

<210> SEQ ID NO 54
<211> LENGTH: 115
<212> TYPE: PRT
<213> ORGANISM: Mouse
<220> FEATURE:
<223> OTHER INFORMATION: R35B9(Y50G57)-VH

<400> SEQUENCE: 54

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ser His Gly Lys Ser Leu Glu Trp Ile
        35                  40                  45

Gly Tyr Ile Asn Pro Arg Asn Gly Gly Thr Asn Tyr Asn Gln Lys Phe
    50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
        115
```

<210> SEQ ID NO 55
<211> LENGTH: 345
<212> TYPE: DNA
<213> ORGANISM: Mouse
<220> FEATURE:
<223> OTHER INFORMATION: R35B9(Y50A56G57)-VH

<400> SEQUENCE: 55

```
gaggtgcagc tgcagcaaag cggcccggag ctggtgaaac cgggtgcgag cgttaaaatg     60
agctgcaagg cgagcggtta cattttcag gattataata tgcattgggt taaacagagc    120
cacggtaaaa gcctggagtg gatcggctat attaatccgc gtaatgccgg accaactat    180 aaccaaaagt tcaaaggcaa ggcgaccctg accgtgaaca gagcagccg tagcgcgtac    240 atggagtttc gtagcctgac cagcgaagat agcgcggttt actattgcgc gtcttcgggg    300
tggttcacgt attggggtca aggcaccctg gtgaccgtta gcgcg                    345
```

<210> SEQ ID NO 56
<211> LENGTH: 115
<212> TYPE: PRT
<213> ORGANISM: Mouse
<220> FEATURE:
<223> OTHER INFORMATION: R35B9(Y50A56G57)-VH

<400> SEQUENCE: 56

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ser His Gly Lys Ser Leu Glu Trp Ile
        35                  40                  45

Gly Tyr Ile Asn Pro Arg Asn Ala Gly Thr Asn Tyr Asn Gln Lys Phe
```

```
                     50                  55                  60
Lys Gly Lys Ala Thr Leu Thr Val Asn Lys Ser Ser Arg Ser Ala Tyr
 65                  70                  75                  80

Met Glu Phe Arg Ser Leu Thr Ser Glu Asp Ser Ala Val Tyr Tyr Cys
                 85                  90                  95

Ala Ser Ser Gly Trp Phe Thr Tyr Trp Gly Gln Gly Thr Leu Val Thr
            100                 105                 110

Val Ser Ala
       115

<210> SEQ ID NO 57
<211> LENGTH: 336
<212> TYPE: DNA
<213> ORGANISM: Mouse
<220> FEATURE:
<223> OTHER INFORMATION: R35B9(H98)-VL

<400> SEQUENCE: 57
gacgtggtta tgacccaaac cccgctgacc ctgagcgtgg cgattggtca gccggcgagc      60
attagctgca agagcagcca aagcctgctg aacagcgcgg gtaaaaccta cctgaactgg     120
ctgctgcagc gtccgggtca aagcccgaag cgtctgatct atctggtgag ccagctggac     180
agcggtgtgc cggaccgttt caccggtagc ggtagcggca ccgactttac cctgaaaatt     240
agccgtgtgg aggcggaaga tctgggtgtt tactattgct ggcaaggtac tcattatccg     300 tggaccttg gtggcggtac caagctggag atcaaa                                336

<210> SEQ ID NO 58
<211> LENGTH: 112
<212> TYPE: PRT
<213> ORGANISM: Mouse
<220> FEATURE:
<223> OTHER INFORMATION: R35B9(H98)-VL

<400> SEQUENCE: 58

Asp Val Val Met Thr Gln Thr Pro Leu Thr Leu Ser Val Ala Ile Gly
  1               5                  10                  15

Gln Pro Ala Ser Ile Ser Cys Lys Ser Ser Gln Ser Leu Leu Asn Ser
             20                  25                  30

Ala Gly Lys Thr Tyr Leu Asn Trp Leu Leu Gln Arg Pro Gly Gln Ser
         35                  40                  45

Pro Lys Arg Leu Ile Tyr Leu Val Ser Gln Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Tyr Pro Trp Thr Phe Gly Gly Gly Thr Lys Leu Glu Ile Lys
            100                 105                 110

<210> SEQ ID NO 59
<211> LENGTH: 345
<212> TYPE: DNA
<213> ORGANISM: Mouse
<220> FEATURE:
<223> OTHER INFORMATION: R35B9(A56)-VH

<400> SEQUENCE: 59
gaggtgcagc tgcagcaaag cggcccggag ctggtgaaaac cgggtgcgag cgttaaaatg     60
```

```
agctgcaagg cgagcggtta cattttcag gattataata tgcattgggt taaacagagc    120
cacggtaaaa gcctggagtg gatcggctct attaatccgc gtaatgcttg gaccaactat    180
aaccaaaagt tcaaaggcaa ggcgaccctg accgtgaaca agagcagccg tagcgcgtac    240
atggagtttc gtagcctgac cagcgaagat agcgcggttt actattgcgc gtcttcgggg    300
tggttcacgt attggggtca aggcaccctg gtgaccgtta gcgcg                    345
```

```
<210> SEQ ID NO 60
<211> LENGTH: 115
<212> TYPE: PRT
<213> ORGANISM: Mouse
<220> FEATURE:
<223> OTHER INFORMATION: R35B9(A56)-VH

<400> SEQUENCE: 60

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ser His Gly Lys Ser Leu Glu Trp Ile
        35                  40                  45

Gly Ser Ile Asn Pro Arg Asn Ala Trp Thr Asn Tyr Asn Gln Lys Phe
    50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
        115
```

```
<210> SEQ ID NO 61
<211> LENGTH: 357
<212> TYPE: DNA
<213> ORGANISM: Artificial Sequence
<220> FEATURE:
<223> OTHER INFORMATION: CRCBT-06-002_VH (no signal peptide)

<400> SEQUENCE: 61
gaagtgaagc tgcagcagag cggcggagga ctggtgcagc ctggcggatc tatgaagctg     60
agctgtgtgg ccagcggctt caccttcagc tactactgga tgaactgggt cgcgcagagc    120
cccgagcagg gcctggaatg gatcgccgaa atcagactgc agagcaacga ctaccccacc    180
cactacgccg agagcgtgaa gggcagattc accatcagcc gggacgacag caagaacagc    240
gtgtacctgc agatgaacaa cctgcggccc gaggacaccg gcatctacta ctgcgcctgc    300
agatacgccg actacttcga ccactggggc cagggcacaa ccctgaccgt gtcatct      357
```

```
<210> SEQ ID NO 62
<211> LENGTH: 119
<212> TYPE: PRT
<213> ORGANISM: Artificial Sequence
<220> FEATURE:
<223> OTHER INFORMATION: CRCBT-06-002_VH (no signal peptide)

<400> SEQUENCE: 62

Glu Val Lys Leu Gln Gln Ser Gly Gly Gly Leu Val Gln Pro Gly Gly
1               5                   10                  15
```

```
Ser Met Lys Leu Ser Cys Val Ala Ser Gly Phe Thr Phe Ser Tyr Tyr
            20                  25                  30

Trp Met Asn Trp Val Arg Gln Ser Pro Glu Gln Gly Leu Glu Trp Ile
        35                  40                  45

Ala Glu Ile Arg Leu Gln Ser Asn Asp Tyr Pro Thr His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Asn Leu Arg Pro Glu Asp Thr Gly Ile Tyr
                85                  90                  95

Tyr Cys Ala Cys Arg Tyr Ala Asp Tyr Phe Asp His Trp Gly Gln Gly
            100                 105                 110

Thr Thr Leu Thr Val Ser Ser
            115
```

<210> SEQ ID NO 63
<211> LENGTH: 333
<212> TYPE: DNA
<213> ORGANISM: Artificial Sequence
<220> FEATURE:
<223> OTHER INFORMATION: CRCBT-06-002_VL (no signal peptide)

<400> SEQUENCE: 63

```
gacaccgtgc tgacccagag ccctgcttct ctggtggtgt ccctgggcca gagagccacc    60
atcagctgta gagccagcca gagcgtgtcc accagcgact acagctacat ccactggtat   120
cagcagaagc ccggccagcc ccccaagttc ctgattaagt acgccagcaa ccgggacagc   180
ggcgtgcccg ccagattttc tggcagcggc tctggcaccg acttcaccct gaacatccac   240
cccgtggaag aggacgatac cgccatctac tactgccagc acagctggga gatccccccc   300
acatttggag ccggcaccaa gctggaactg cag                                333
```

<210> SEQ ID NO 64
<211> LENGTH: 111
<212> TYPE: PRT
<213> ORGANISM: Artificial Sequence
<220> FEATURE:
<223> OTHER INFORMATION: CRCBT-06-002_VL (no signal peptide)

<400> SEQUENCE: 64

```
Asp Thr Val Leu Thr Gln Ser Pro Ala Ser Leu Val Val Ser Leu Gly
1               5                   10                  15

Gln Arg Ala Thr Ile Ser Cys Arg Ala Ser Gln Ser Val Ser Thr Ser
            20                  25                  30

Asp Tyr Ser Tyr Ile His Trp Tyr Gln Gln Lys Pro Gly Gln Pro Pro
        35                  40                  45

Lys Phe Leu Ile Lys Tyr Ala Ser Asn Arg Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Asp Thr Ala Ile Tyr Tyr Cys Gln His Ser Trp
                85                  90                  95

Glu Ile Pro Pro Thr Phe Gly Ala Gly Thr Lys Leu Glu Leu Gln
            100                 105                 110
```

<210> SEQ ID NO 65
<211> LENGTH: 345
<212> TYPE: DNA
<213> ORGANISM: Homo sapiens
<220> FEATURE:
<223> OTHER INFORMATION: hzR35B9-VH_HV5a

<400> SEQUENCE: 65

```
caagtgcaac tggtgcaaag cggagctgaa gtaaagaagc ctggagcatc cgtcaaggta      60
agttgcaagg ctagtggcta tatcttccag gactataata tgcattgggt acgccaggct     120
cccggacaag ggctggagtg gatagggagc atcaatccac gcaacggatg gaccaactac     180
aatcagaagt tcaaaggacg agcaactatc actgcagata catcaacctc cactgcttac     240
atggaattga gttccctgcg ttccgaagac accgcagtgt actattgtgc cagttcaggg     300
tggtttactt actggggaca aggcacactg gtgaccgttt ctagc                     345
```

<210> SEQ ID NO 66
<211> LENGTH: 115
<212> TYPE: PRT
<213> ORGANISM: Homo sapiens
<220> FEATURE:
<223> OTHER INFORMATION: hzR35B9-VH_HV5a

<400> SEQUENCE: 66

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ile Phe Gln Asp Tyr
            20                  25                  30

Asn Met His Trp Val Arg Gln Ala Pro Gly Gln Gly Leu Glu Trp Ile
        35                  40                  45

Gly Ser Ile Asn Pro Arg Asn Gly Trp Thr Asn Tyr Asn Gln Lys Phe
    50                  55                  60

Lys Gly Arg Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115
```

<210> SEQ ID NO 67
<211> LENGTH: 345
<212> TYPE: DNA
<213> ORGANISM: Homo sapiens
<220> FEATURE:
<223> OTHER INFORMATION: hzR35B9-VH_HV5b

<400> SEQUENCE: 67

```
caagttcagc ttgtccagag cggtgctgaa gtggtcaaac caggcgcaag tgttaaagtt      60
tcttgcaagg catctggata tatttttcag gactacaaca tgcactgggt acgacaagcc     120
cacggtcagg gattggaatg gatgggatcc atcaacccaa gaaacggttg gacaaattac     180
aatcaaaagt tcaaaggcag ggtaacaatc accgcagaca caagcaccag taccgcttac     240
atggagctga gctctttgag atcagaggac actgctgtgt actattgcgc atctagcggg     300
tggttcactt actggggaca gggcactctt gtgactgtga gctct                     345
```

<210> SEQ ID NO 68
<211> LENGTH: 115
<212> TYPE: PRT
<213> ORGANISM: Homo sapiens
<220> FEATURE:

<223> OTHER INFORMATION: hzR35B9-VH_HV5b

<400> SEQUENCE: 68

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Gly Leu Glu Trp Met
        35                  40                  45

Gly Ser Ile Asn Pro Arg Asn Gly Trp Thr Asn Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 69
<211> LENGTH: 345
<212> TYPE: DNA
<213> ORGANISM: Homo sapiens
<220> FEATURE:
<223> OTHER INFORMATION: hzR35B9-VH_HV6a

<400> SEQUENCE: 69
caagttcaac ttgttcaatc aggcgcagaa gtagtgaaac ctggtgcttc tgtgaaggtg      60
tcatgtaagg ccagcggtta tatctttcag gactacaata tgcattgggt tcgccaagca     120
catgggcagt ccctggagtg gatggggtct atcaatcctc gcaatggctg gaccaactat     180
aaccaaaagt tcaagggtag ggtcactatc actgctgaca catccacctc taccgcctac     240
atggaattgt catctttgcg ctctgaggac actgctgtgt actattgcgc ttcatcaggc     300
tggttcacct attggggaca gggcacattg gtgactgtgt cttcc                     345

<210> SEQ ID NO 70
<211> LENGTH: 115
<212> TYPE: PRT
<213> ORGANISM: Homo sapiens
<220> FEATURE:
<223> OTHER INFORMATION: hzR35B9-VH_HV6a

<400> SEQUENCE: 70

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Ser Leu Glu Trp Met
        35                  40                  45

Gly Ser Ile Asn Pro Arg Asn Gly Trp Thr Asn Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr

-continued

```
              100                 105                 110
Val Ser Ser
        115
```

<210> SEQ ID NO 71
<211> LENGTH: 345
<212> TYPE: DNA
<213> ORGANISM: Homo sapiens
<220> FEATURE:
<223> OTHER INFORMATION: hzR35B9-VH_HV6b

<400> SEQUENCE: 71

```
caagtccaac tggtgcaaag cggagctgaa gtgaagaagc caggtgccag tgtcaaggta      60
tcctgcaagg caagtggtta tattttccag gactataata tgcattgggt taggcaggca     120
catggacagg gctcgaatg gatcgggagt attaacccac gtaatgggtg gactaattac      180
aaccagaagt tcaaaggaag ggccaccatt acagccgaca aatcaacctc aactgcttat     240
atggagctta gcagcctgcg ttctgaggac actgctgtat actattgtgc ccgttcaggt     300
tggttcacct actggggaca gggcactctt gttacagtca gttct                     345
```

<210> SEQ ID NO 72
<211> LENGTH: 115
<212> TYPE: PRT
<213> ORGANISM: Homo sapiens
<220> FEATURE:
<223> OTHER INFORMATION: hzR35B9-VH_HV6b

<400> SEQUENCE: 72

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Gln Asp Tyr
            20                  25                  30
Asn Met His Trp Val Arg Gln Ala His Gly Gln Gly Leu Glu Trp Ile
        35                  40                  45
Gly Ser Ile Asn Pro Arg Asn Gly Trp Thr Asn Tyr Asn Gln Lys Phe
    50                  55                  60
Lys Gly Arg Ala Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Gly Trp Phe Thr Tyr Trp Gly Gln Gly Thr Leu Val Thr
            100                 105                 110
Val Ser Ser
        115
```

<210> SEQ ID NO 73
<211> LENGTH: 345
<212> TYPE: DNA
<213> ORGANISM: Homo sapiens
<220> FEATURE:
<223> OTHER INFORMATION: hzR35B9-VH_HV6c

<400> SEQUENCE: 73

```
caggtacagc tcgttcaaag cggtgccgag gtaaaaaagc ctggggcctc tgttaaagtt      60
tcatgcaagg cctcaggata tatctttcaa gactacaaca tgcattgggt gcgtcaggca     120
catggccagg gctcgaatg gatcggcagc ataaatccac ggaacggttg gaccaactac      180
aaccagaaat tcaaaggaag ggccactata accgccgaca catctacttc taccgcatac     240
```

```
atggaactct ccagtctcag gtcagaagat acagccgtct actattgcgc cagtagcggt      300
tggtttacat actgggggca aggaactctc gttaccgtgt ccagc                     345
```

<210> SEQ ID NO 74
<211> LENGTH: 115
<212> TYPE: PRT
<213> ORGANISM: Homo sapiens
<220> FEATURE:
<223> OTHER INFORMATION: hzR35B9-VH_HV6c

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Gly Leu Glu Trp Ile
        35                  40                  45

Gly Ser Ile Asn Pro Arg Asn Gly Trp Thr Asn Tyr Asn Gln Lys Phe
    50                  55                  60

Lys Gly Arg Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 75
<211> LENGTH: 345
<212> TYPE: DNA
<213> ORGANISM: Homo sapiens
<220> FEATURE:
<223> OTHER INFORMATION: hzR35B9-VH_HV7a

<400> SEQUENCE: 75

```
caggtacaac tggtacagtc tggagctgag gtggttaagc caggggccag cgtcaaagta      60
tcctgtaagg cttccggata tatattccag gactacaata tgcactgggt tcggcaagcc     120
cacggacaat ctctggagtg gatgggctcc atcaatccca ggaatggatg gaccaattac     180
aatcagaagt tcaaggggcg agtcacaatc acagctgata caagtactag aaccgcttac     240
atggagcttt cttcattgag gtccgaggat acagctgtct actactgcgc ttcctcagga     300
tggtttactt attggggtca aggaactctg gtgacagtta gcagc                     345
```

<210> SEQ ID NO 76
<211> LENGTH: 115
<212> TYPE: PRT
<213> ORGANISM: Homo sapiens
<220> FEATURE:
<223> OTHER INFORMATION: hzR35B9-VH_HV7a

<400> SEQUENCE: 76

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Ser Leu Glu Trp Met
        35                  40                  45

```
Gly Ser Ile Asn Pro Arg Asn Gly Trp Thr Asn Tyr Asn Gln Lys Phe
    50                  55                  60

Lys Gly Arg Val Thr Ile Thr Ala Asp Thr Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Ser Ser Gly Trp Phe Thr Tyr Trp Gly Gln Gly Thr Leu Val Thr
            100                 105                 110

Val Ser Ser
    115

<210> SEQ ID NO 77
<211> LENGTH: 345
<212> TYPE: DNA
<213> ORGANISM: Homo sapiens
<220> FEATURE:
<223> OTHER INFORMATION: hzR35B9-VH_HV7b

<400> SEQUENCE: 77
caagtgcagc tcgttcagtc tggagccgag gtagtcaagc ccggcgcatc tgttaaagtc      60
agttgcaaag cttccggcta tatcttccag gattacaaca tgcactgggt cagacaggct     120
cacggtcaag ggctcgaatg gatgggaagt attaaccctc gtaatggatg gactaactat     180
aaccaaaagt ttaaggggag ggtgactatt acagcagata gtctactcg cactgcctat      240 atggagctta gctcactccg ctccgaagac accgctgtgt attactgtgc tagttccggg     300
tggttcacct attgggggca aggaactctt gtaacagttt cctct                     345

<210> SEQ ID NO 78
<211> LENGTH: 115
<212> TYPE: PRT
<213> ORGANISM: Homo sapiens
<220> FEATURE:
<223> OTHER INFORMATION: hzR35B9-VH_HV7b

<400> SEQUENCE: 78

Gln Val Gln Leu Val Gln Ser Gly Ala Glu Val Val Lys Pro Gly Ala
 1               5                  10                  15

Ser Val Lys Val Ser Cys Lys Ala Ser Gly Tyr Ile Phe Gln Asp Tyr
                 20                  25                  30

Asn Met His Trp Val Arg Gln Ala His Gly Gln Gly Leu Glu Trp Met
             35                  40                  45

Gly Ser Ile Asn Pro Arg Asn Gly Trp Thr Asn Tyr Asn Gln Lys Phe
    50                  55                  60

Lys Gly Arg Val Thr Ile Thr Ala Asp Lys Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Ser Ser Gly Trp Phe Thr Tyr Trp Gly Gln Gly Thr Leu Val Thr
            100                 105                 110

Val Ser Ser
    115

<210> SEQ ID NO 79
<211> LENGTH: 345
<212> TYPE: DNA
<213> ORGANISM: Homo sapiens
<220> FEATURE:
<223> OTHER INFORMATION: hzR35B9-VH_HV7c
```

<400> SEQUENCE: 79

```
caagttcaac tggtgcagtc tggcgctgag gtaaaaaaac ccggcgcctc tgttaaagta      60
agttgtaaag catctgggta tatctttcaa gattacaaca tgcactgggt taagcaggct     120
cccggacagg gtcttgagtg gatagggtcc ataaatcccc gcaatggctg gactaattat     180
aaccaaaagt tcaaaggaaa agccaccatc acagcagaca ccagtacatc taccgcctac     240 atgaattga gttctctgcg gagcgaggat accgcagtct attactgcgc ctcatctgga      300
tggtttactt actggggtca gggcactctg gtgactgttt caagt                     345
```

<210> SEQ ID NO 80
<211> LENGTH: 115
<212> TYPE: PRT
<213> ORGANISM: Homo sapiens
<220> FEATURE:
<223> OTHER INFORMATION: hzR35B9-VH_HV7c

<400> SEQUENCE: 80

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Lys Gln Ala Pro Gly Gln Gly Leu Glu Trp Ile
        35                  40                  45

Gly Ser Ile Asn Pro Arg Asn Gly Trp Thr Asn Tyr Asn Gln Lys Phe
    50                  55                  60

Lys Gly Lys Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115
```

<210> SEQ ID NO 81
<211> LENGTH: 345
<212> TYPE: DNA
<213> ORGANISM: Homo sapiens
<220> FEATURE:
<223> OTHER INFORMATION: hzR35B9-VH_HV9a

<400> SEQUENCE: 81

```
caagttcagc tcgtgcagtc tggagcagag gtaaagaaac ccggcgcatc agtgaagatg      60
agttgtaagg ctagtggtta tatattccag gattataata tgcactgggt acgacaggct     120
ccaggccaag ggcttgaatg gatagcagc attaacccc gaaacggctg gactaattac      180
aaccagaaat tcaagggacg cgcaaccctc actgtggata cttccacatc tactgcttac     240
atggagtttt catcactcag gtcagaagac acagcagtgt actactgtgc ctcctctggg     300
tggttcacat attggggaca aggcacattg gtgacagtct cctct                     345
```

<210> SEQ ID NO 82
<211> LENGTH: 115
<212> TYPE: PRT
<213> ORGANISM: Homo sapiens
<220> FEATURE:
<223> OTHER INFORMATION: hzR35B9-VH_HV9a

<400> SEQUENCE: 82

```
Gln Val Gln Leu Val Gln Ser Gly Ala Glu Val Lys Lys Pro Gly Ala
1               5                   10                  15
Ser Val Lys Met Ser Cys Lys Ala Ser Gly Tyr Ile Phe Gln Asp Tyr
            20                  25                  30
Asn Met His Trp Val Arg Gln Ala Pro Gly Gln Gly Leu Glu Trp Ile
        35                  40                  45
Gly Ser Ile Asn Pro Arg Asn Gly Trp Thr Asn Tyr Asn Gln Lys Phe
    50                  55                  60
Lys Gly Arg Ala Thr Leu Thr Val Asp Thr Ser Thr Ser Thr Ala Tyr
65                  70                  75                  80
Met Glu Phe Ser Ser Leu Arg Ser Glu Asp Thr Ala Val Tyr Tyr Cys
                85                  90                  95
Ala Ser Ser Gly Trp Phe Thr Tyr Trp Gly Gln Gly Thr Leu Val Thr
            100                 105                 110
Val Ser Ser
        115
```

<210> SEQ ID NO 83
<211> LENGTH: 345
<212> TYPE: DNA
<213> ORGANISM: Homo sapiens
<220> FEATURE:
<223> OTHER INFORMATION: hzR35B9-VH_HV9b

<400> SEQUENCE: 83

```
caggtccaac tggtacagtc cggcgctgaa gtaaaaaaac caggcgctag tgtcaaggta    60
tcatgcaaag caagtgggta tatctttcag gattataata tgcactgggt aaaacaggct   120
cacggccaat ccctggagtg gatcggttcc atcaatccac ggaacggctg gaccaactac   180
aaccagaagt ttaagggccg tgctaccatt acagccgaca ctagcactag cacagcttac   240
atggaattct cctccctgcg aagcgaagac accgcagtgt attactgcgc tagttccggt   300
tggttcactt actggggcca gggcacactc gtcactgtct caagc                   345
```

<210> SEQ ID NO 84
<211> LENGTH: 115
<212> TYPE: PRT
<213> ORGANISM: Homo sapiens
<220> FEATURE:
<223> OTHER INFORMATION: hzR35B9-VH_HV9b

<400> SEQUENCE: 84

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Gln Asp Tyr
            20                  25                  30
Asn Met His Trp Val Lys Gln Ala His Gly Gln Ser Leu Glu Trp Ile
        35                  40                  45
Gly Ser Ile Asn Pro Arg Asn Gly Trp Thr Asn Tyr Asn Gln Lys Phe
    50                  55                  60
Lys Gly Arg Ala Thr Ile Thr Ala Asp Thr Ser Thr Ser Thr Ala Tyr
65                  70                  75                  80
Met Glu Phe Ser Ser Leu Arg Ser Glu Asp Thr Ala Val Tyr Tyr Cys
                85                  90                  95
Ala Ser Ser Gly Trp Phe Thr Tyr Trp Gly Gln Gly Thr Leu Val Thr
            100                 105                 110
Val Ser Ser
```

```
                115

<210> SEQ ID NO 85
<211> LENGTH: 345
<212> TYPE: DNA
<213> ORGANISM: Homo sapiens
<220> FEATURE:
<223> OTHER INFORMATION: hzR35B9-VH_HV10

<400> SEQUENCE: 85
caggtgcaac tggtgcaatc tggggcagaa gttaaaaaac caggcgctag cgtaaaagtt      60
tcttgcaaag caagtgggta catattccaa gattacaata tgcattgggt caggcaggcc     120
cacggtcagg gattggagtg gatcggctct atcaaccctc gaaatggttg gactaactac     180
aaccagaagt tcaaaggaaa agccaccatt accgccgata atccaccag acagcctat       240 atggagtttt ctagccttcg tagcgaagac accgctgtgt attattgcgc ttctagtgga     300
tggttcactt attggggtca ggggaccttg gtcactgtta gttct                     345

<210> SEQ ID NO 86
<211> LENGTH: 115
<212> TYPE: PRT
<213> ORGANISM: Homo sapiens
<220> FEATURE:
<223> OTHER INFORMATION: hzR35B9-VH_HV10

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Gly Leu Glu Trp Ile
        35                  40                  45

Gly Ser Ile Asn Pro Arg Asn Gly Trp Thr Asn Tyr Asn Gln Lys Phe
    50                  55                  60

Lys Gly Lys Ala Thr Ile Thr Ala Asp Lys Ser Thr Arg Thr Ala Tyr
65                  70                  75                  80

Met Glu Phe Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 87
<211> LENGTH: 345
<212> TYPE: DNA
<213> ORGANISM: Homo sapiens
<220> FEATURE:
<223> OTHER INFORMATION: hzR35B9-VH_HV11

<400> SEQUENCE: 87
caagttcaac ttgtccaatc cggtccagaa gtcgtaaaac caggtgctag tgtgaaagtc      60
tcatgcaagg cttcaggcta catatttcaa gactataata tgcattgggt tagacaggca     120
cacggtcagt cactggaatg gatggggtca atcaaccctc gcaacggatg gacaaattac     180
aaccaaaagt tcaagggag agctactatc actgtcgata atctaccag aacagcttac      240 atggagctga gtagtctgag atcagaggac accgccgtct actattgtgc ttcttctggg     300
tggtttacat actgggggca ggggacactg gtgactgtga gttct                     345
```

<210> SEQ ID NO 88
<211> LENGTH: 115
<212> TYPE: PRT
<213> ORGANISM: Homo sapiens
<220> FEATURE:
<223> OTHER INFORMATION: hzR35B9-VH_HV11

<400> SEQUENCE: 88

Gln Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Ser Leu Glu Trp Met
        35                  40                  45

Gly Ser Ile Asn Pro Arg Asn Gly Trp Thr Asn Tyr Asn Gln Lys Phe
    50                  55                  60

Lys Gly Arg Ala Thr Ile Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 89
<211> LENGTH: 345
<212> TYPE: DNA
<213> ORGANISM: Homo sapiens
<220> FEATURE:
<223> OTHER INFORMATION: hzR35B9-VH_HV18

<400> SEQUENCE: 89
gaggtccaac tggttcaaag tggaccagag gtggtgaaac caggagctag cgtaaaaatg      60
agctgtaagg cttcaggtta tatctttcag gattacaaca tgcactgggt aaaacaagcc    120
cacggccagt ctctcgaatg gattgggtca atcaatcccc gaacggttg acaaactat    180 aatcagaaat tcaaaggtaa agcaacattg actgttgaca atcaaccag gaccgcatac    240 atggagtttt catccctgcg tagtgaagac actgctgttt actactgtgc tagttctggg    300
tggttcactt actgggggca gggaactctt gtcactgttt cttca                    345

<210> SEQ ID NO 90
<211> LENGTH: 115
<212> TYPE: PRT
<213> ORGANISM: Homo sapiens
<220> FEATURE:
<223> OTHER INFORMATION: hzR35B9-VH_HV18

<400> SEQUENCE: 90

Glu Val Gln Leu Val Gln Ser Gly Pro Glu Val Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ala His Gly Gln Ser Leu Glu Trp Ile
        35                  40                  45

Gly Ser Ile Asn Pro Arg Asn Gly Trp Thr Asn Tyr Asn Gln Lys Phe
    50                  55                  60

```
Lys Gly Lys Ala Thr Leu Thr Val Asp Lys Ser Thr Arg Thr Ala Tyr
 65                  70                  75                  80

Met Glu Phe Ser Ser Leu Arg Ser Glu Asp Thr Ala Val Tyr Tyr Cys
                 85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 91
<211> LENGTH: 336
<212> TYPE: DNA
<213> ORGANISM: Homo sapiens
<220> FEATURE:
<223> OTHER INFORMATION: hzR35B9-VL_LV0

<400> SEQUENCE: 91
gacgtagtga tgactcagag ccctctgtca ctccccgtca cactgggaca accagcttcc      60
atctcctgca agtcatctca atctttgttg aatagcgcag gaaagacata cctgaactgg     120
ttccaacaac gccctggtca aagcccacgc aggctgatct atttggtaag tcaactggat     180
agcggagtac ctgaccgttt ctctggaagt ggaagtggta ctgacttcac cttgaaaatc     240
tccagggttg aagccgagga cgtgggggtg tattactgtt ggcaaggtac tttctaccct     300
tggactttcg gcggcggtac caaggtagag attaaa                              336

<210> SEQ ID NO 92
<211> LENGTH: 112
<212> TYPE: PRT
<213> ORGANISM: Homo sapiens
<220> FEATURE:
<223> OTHER INFORMATION: hzR35B9-VL_LV0

<400> SEQUENCE: 92

Asp Val Val Met Thr Gln Ser Pro Leu Ser Leu Pro Val Thr Leu Gly
  1               5                  10                  15

Gln Pro Ala Ser Ile Ser Cys Lys Ser Ser Gln Ser Leu Leu Asn Ser
             20                  25                  30

Ala Gly Lys Thr Tyr Leu Asn Trp Phe Gln Gln Arg Pro Gly Gln Ser
         35                  40                  45

Pro Arg Arg Leu Ile Tyr Leu Val Ser Gln Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr Phe Tyr Pro Trp Thr Phe Gly Gly Gly Thr Lys Val Glu Ile Lys
            100                 105                 110

<210> SEQ ID NO 93
<211> LENGTH: 336
<212> TYPE: DNA
<213> ORGANISM: Homo sapiens
<220> FEATURE:
<223> OTHER INFORMATION: hzR35B9-VL_LV1a

<400> SEQUENCE: 93
gatgtagtaa tgacccagtc cccacttagc ttgcccgtta cactcggcca acccgcaagc      60
atatcttgca aatccagtca gagcctcctg aactctgctg gaaagaccta tctgaattgg     120
```

```
cttcaacaac gtcccggtca atcccccaga cgacttatct acttggtaag tcagcttgac    180
tccggggttc cagacaggtt ttccggatct ggaagtggaa ctgattttac actcaaaatt    240
agtcgagtcg aggccgaaga cgtgggtgtc tattattgct ggcaaggcac ctttttatcca   300 tggactttg gtgggggcac caaggttgaa attaag                               336
```

<210> SEQ ID NO 94
<211> LENGTH: 112
<212> TYPE: PRT
<213> ORGANISM: Homo sapiens
<220> FEATURE:
<223> OTHER INFORMATION: hzR35B9-VL_LV1a

<400> SEQUENCE: 94

```
Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Asn Ser
            20                  25                  30

Ala Gly Lys Thr Tyr Leu Asn Trp Leu Gln Gln Arg Pro Gly Gln Ser
        35                  40                  45

Pro Arg Arg Leu Ile Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
                100                 105                 110
```

<210> SEQ ID NO 95
<211> LENGTH: 336
<212> TYPE: DNA
<213> ORGANISM: Homo sapiens
<220> FEATURE:
<223> OTHER INFORMATION: hzR35B9-VL_LV1b

<400> SEQUENCE: 95

```
gatgttgtga tgacacaaag tcctctgagc cttccagtca cattgggtca gcctgcatct    60
attagttgta agagcagtca atcactgctg aatagtgccg gaaaaacata cttgaattgg    120
ttccttcagc gcccaggcca gtctcctcgg cggttgattt atcttgtgtc tcaactggat    180
tctggtgtcc ccgatagatt ttcaggttca gggtcaggga ccgattttac actgaagatt    240
tctcgcgtcg aggcagagga cgttgggggtt tattactgtt ggcagggaac attttatcca   300
tggacattcg ggggaggaac caaggtagag attaaa                               336
```

<210> SEQ ID NO 96
<211> LENGTH: 112
<212> TYPE: PRT
<213> ORGANISM: Homo sapiens
<220> FEATURE:
<223> OTHER INFORMATION: hzR35B9-VL_LV1b

<400> SEQUENCE: 96

```
Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Asn Ser
            20                  25                  30

Ala Gly Lys Thr Tyr Leu Asn Trp Phe Leu Gln Arg Pro Gly Gln Ser
        35                  40                  45
```

```
Pro Arg Arg Leu Ile Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
 65              70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
            100                 105                 110
```

```
<210> SEQ ID NO 97
<211> LENGTH: 336
<212> TYPE: DNA
<213> ORGANISM: Homo sapiens
<220> FEATURE:
<223> OTHER INFORMATION: hzR35B9-VL_LV3a

<400> SEQUENCE: 97
gacgtagtta tgactcagtc tccactctct ctccccgtga ccattggaca gcctgcatca      60
atatcctgca aaagtagcca gtccttgctc aactcagccg gtaaaaccta cctcaactgg    120
ttccttcagc gccccggtca gtctccaaag cgtttgatat acctggtgag tcaactcgac    180
tcaggtgtcc ccgatcgctt ctctgggagc ggttcaggca cagattttac tctcaaaata    240
tccagagttg aagctgaaga cgttggggtt tactattgct ggcagggaac attctatcct    300 tggactttg gaggaggcac aaaggttgag atcaag                              336
```

```
<210> SEQ ID NO 98
<211> LENGTH: 112
<212> TYPE: PRT
<213> ORGANISM: Homo sapiens
<220> FEATURE:
<223> OTHER INFORMATION: hzR35B9-VL_LV3a

<400> SEQUENCE: 98

Asp Val Val Met Thr Gln Ser Pro Leu Ser Leu Pro Val Thr Ile Gly
  1               5                  10                  15

Gln Pro Ala Ser Ile Ser Cys Lys Ser Ser Gln Ser Leu Leu Asn Ser
             20                  25                  30

Ala Gly Lys Thr Tyr Leu Asn Trp Phe Leu Gln Arg Pro Gly Gln Ser
         35                  40                  45

Pro Lys Arg Leu Ile Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
 65              70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
            100                 105                 110
```

```
<210> SEQ ID NO 99
<211> LENGTH: 336
<212> TYPE: DNA
<213> ORGANISM: Homo sapiens
<220> FEATURE:
<223> OTHER INFORMATION: hzR35B9-VL_LV3b

<400> SEQUENCE: 99
gacgttgtaa tgacccaaag tccactgtca cttcccgtaa ccataggca acccgccagc       60 atctcctgca atcatccca agtcttctt aacagtgccg gaaaaacata cttgaactgg      120
```

```
ctcttgcaga ggccagggca atctcctcga cgactgatat accttgtatc ccagttggat    180
tctggcgtgc ccgacagatt cagtggaagc ggatctggca cagactttac ccttaaaatc    240
agccgcgtgg aggccgagga tgttggagtg tactactgtt ggcaaggaac attttaccct    300
tggacctttg gcgggggac caaagtcgag ataaag                               336
```

<210> SEQ ID NO 100
<211> LENGTH: 112
<212> TYPE: PRT
<213> ORGANISM: Homo sapiens
<220> FEATURE:
<223> OTHER INFORMATION: hzR35B9-VL_LV3b

<400> SEQUENCE: 100

```
Asp Val Val Met Thr Gln Ser Pro Leu Ser Leu Pro Val Thr Ile Gly
1               5                   10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Leu Gln Arg Pro Gly Gln Ser
        35                  40                  45

Pro Arg Arg Leu Ile Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
            100                 105                 110
```

<210> SEQ ID NO 101
<211> LENGTH: 336
<212> TYPE: DNA
<213> ORGANISM: Homo sapiens
<220> FEATURE:
<223> OTHER INFORMATION: hzR35B9-VL_LV4

<400> SEQUENCE: 101

```
gatgtcgtga tgacacaaag tccccctgagc ttgcccgtaa ctattgggca accagcctct    60
atctcttgta atcatcaca atctttgctc aattctgctg gcaagacata ccttaactgg    120
cttttgcaac gccctggtca aagccctaag agattgattt atctcgtcag ccagctggac    180
tctggggtcc cagatcgctt tagtgggtca ggctctggaa ccgacttcac actgaagatc    240 tccaggggttg aagccgagga tgtaggggtt tattactgtt ggcaaggcac cttttatccc    300
tggacttttg ggggcggcac caaggtcgaa ataaag                              336
```

<210> SEQ ID NO 102
<211> LENGTH: 112
<212> TYPE: PRT
<213> ORGANISM: Homo sapiens
<220> FEATURE:
<223> OTHER INFORMATION: hzR35B9-VL_LV4

<400> SEQUENCE: 102

```
Asp Val Val Met Thr Gln Ser Pro Leu Ser Leu Pro Val Thr Ile Gly
1               5                   10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Leu Gln Arg Pro Gly Gln Ser
```

```
                    35                  40                  45

Pro Lys Arg Leu Ile Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
                100                 105                 110

<210> SEQ ID NO 103
<211> LENGTH: 336
<212> TYPE: DNA
<213> ORGANISM: Homo sapiens
<220> FEATURE:
<223> OTHER INFORMATION: hzR35B9-VL_LV5

<400> SEQUENCE: 103
gatgttgtca tgactcaatc accattgagc ctccccgtga caataggcca gcctgcttcc      60
atttcctgta agtcaagcca gagtctgctt aatagtgccg ggaagaccta tctgaactgg    120
ctcttgcaga gaccaggaca atctccaaaa cggttgatct acctggtcag ccagttggac    180
agcggcgttc cagatcgatt cagtggcagt ggatctggaa ctgattttac cttgaagatt    240
agtagagtag aggcagagga cgtgggagta tattactgct ggcagggaac cttctacccc    300
tggacctttg gcggcggcac caagctcgag atcaaa                              336

<210> SEQ ID NO 104
<211> LENGTH: 112
<212> TYPE: PRT
<213> ORGANISM: Homo sapiens
<220> FEATURE:
<223> OTHER INFORMATION: hzR35B9-VL_LV5

<400> SEQUENCE: 104

Asp Val Val Met Thr Gln Ser Pro Leu Ser Leu Pro Val Thr Ile Gly
1               5                   10                  15

Gln Pro Ala Ser Ile Ser Cys Lys Ser Ser Gln Ser Leu Leu Asn Ser
                20                  25                  30

Ala Gly Lys Thr Tyr Leu Asn Trp Leu Leu Gln Arg Pro Gly Gln Ser
            35                  40                  45

Pro Lys Arg Leu Ile Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Leu Glu Ile Lys
                100                 105                 110

<210> SEQ ID NO 105
<211> LENGTH: 345
<212> TYPE: DNA
<213> ORGANISM: Homo sapiens
<220> FEATURE:
<223> OTHER INFORMATION: hzR35B9(A56)-VH_HV7c

<400> SEQUENCE: 105
caagttcaac tggtgcagtc tggcgctgag gtaaaaaaac ccggcgcctc tgttaaagta     60
```

```
agttgtaaag catctgggta tatctttcaa gattacaaca tgcactgggt taagcaggct    120
cccggacagg gtcttgagtg gatagggtcc ataaatcccc gcaatgcctg gactaattat    180
aaccaaaagt tcaaaggaaa agccaccatc acagcagaca ccagtacatc taccgcctac    240 atgaattga gttctctgcg gagcgaggat accgcagtct attactgcgc ctcatctgga    300
tggtttactt actggggtca gggcactctg gtgactgttt caagt                    345
```

```
<210> SEQ ID NO 106
<211> LENGTH: 115
<212> TYPE: PRT
<213> ORGANISM: Homo sapiens
<220> FEATURE:
<223> OTHER INFORMATION: hzR35B9(A56)-VH_HV7c

<400> SEQUENCE: 106
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Lys Gln Ala Pro Gly Gln Gly Leu Glu Trp Ile
        35                  40                  45

Gly Ser Ile Asn Pro Arg Asn Ala Trp Thr Asn Tyr Asn Gln Lys Phe
    50                  55                  60

Lys Gly Lys Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

```
<210> SEQ ID NO 107
<211> LENGTH: 345
<212> TYPE: DNA
<213> ORGANISM: Homo sapiens
<220> FEATURE:
<223> OTHER INFORMATION: hzR35B9(A56)-VH_HV11

<400> SEQUENCE: 107
caagttcaac ttgtccaatc cggtccagaa gtcgtaaaac caggtgctag tgtgaaagtc    60
tcatgcaagg cttcaggcta catatttcaa gactataata tgcattgggt tagacaggca    120
cacggtcagt cactggaatg gatgggtca atcaaccctc gcaacgcctg acaaattac    180 aaccaaaagt tcaagggag agctactatc actgtcgata aatctaccag aacagcttac    240
atggagctga gtagtctgag atcagaggac accgccgtct actattgtgc ttcttctggg    300
tggtttacat actggggca ggggacactg gtgactgtga gttct                    345
```

```
<210> SEQ ID NO 108
<211> LENGTH: 115
<212> TYPE: PRT
<213> ORGANISM: Homo sapiens
<220> FEATURE:
<223> OTHER INFORMATION: hzR35B9(A56)-VH_HV11

<400> SEQUENCE: 108
```

Gln Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Ser Leu Glu Trp Met
        35                  40                  45

Gly Ser Ile Asn Pro Arg Asn Ala Trp Thr Asn Tyr Asn Gln Lys Phe
    50                  55                  60

Lys Gly Arg Ala Thr Ile Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 109
<211> LENGTH: 345
<212> TYPE: DNA
<213> ORGANISM: Homo sapiens
<220> FEATURE:
<223> OTHER INFORMATION: hzR35B9(Y50A56G57)-VH_HV7b

<400> SEQUENCE: 109
caagtgcagc tcgttcagtc tggagccgag gtagtcaagc ccggcgcatc tgttaaagtc      60
agttgcaaag cttccggcta tatcttccag gattacaaca tgcactgggt cagacaggct     120
cacggtcaag gctcgaatg gatgggatat attaaccctc gtaatgccgg actaactat      180 aaccaaaagt ttaaggggag ggtgactatt acagcagata agtctactcg cactgcctat     240
atggagctta gctcactccg ctccgaagac accgctgtgt attactgtgc tagttccggg     300
tggttcacct attgggggca aggaactctt gtaacagttt cctct                     345

<210> SEQ ID NO 110
<211> LENGTH: 115
<212> TYPE: PRT
<213> ORGANISM: Homo sapiens
<220> FEATURE:
<223> OTHER INFORMATION: hzR35B9(Y50A56G57)-VH_HV7b

<400> SEQUENCE: 110

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala His Gly Gln Gly Leu Glu Trp Met
        35                  40                  45

Gly Tyr Ile Asn Pro Arg Asn Ala Gly Thr Asn Tyr Asn Gln Lys Phe
    50                  55                  60

Lys Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 111

```
<211> LENGTH: 336
<212> TYPE: DNA
<213> ORGANISM: Homo sapiens
<220> FEATURE:
<223> OTHER INFORMATION: hzR35B9(H98)-VL_LV1a

<400> SEQUENCE: 111
gatgtagtaa tgacccagtc cccacttagc ttgcccgtta cactcggcca acccgcaagc     60
atatcttgca aatccagtca gagcctcctg aactctgctg gaaagaccta tctgaattgg    120
cttcaacaac gtcccggtca atcccccaga cgacttatct acttggtaag tcagcttgac    180
tccggggttc cagacaggtt ttccggatct ggaagtggaa ctgattttac actcaaaatt    240
agtcgagtcg aggccgaaga cgtgggtgtc tattattgct ggcaaggcac ccattatcca    300 tggactttg gtgggggcac caaggttgaa attaag                               336

<210> SEQ ID NO 112
<211> LENGTH: 112
<212> TYPE: PRT
<213> ORGANISM: Homo sapiens
<220> FEATURE:
<223> OTHER INFORMATION: hzR35B9(H98)-VL_LV1a

<400> SEQUENCE: 112
```

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Gln Gln Arg Pro Gly Gln Ser
        35                  40                  45

Pro Arg Arg Leu Ile Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Tyr Pro Trp Thr Phe Gly Gly Gly Thr Lys Val Glu Ile Lys
            100                 105                 110

```
<210> SEQ ID NO 113
<211> LENGTH: 10
<212> TYPE: PRT
<213> ORGANISM: Mouse
<220> FEATURE:
<223> OTHER INFORMATION: HCDR1 42d

<400> SEQUENCE: 113
```

Gly Tyr Thr Phe Thr Asp Tyr Asn Ile His
1               5                   10

```
<210> SEQ ID NO 114
<211> LENGTH: 17
<212> TYPE: PRT
<213> ORGANISM: Mouse
<220> FEATURE:
<223> OTHER INFORMATION: HCDR2 42d

<400> SEQUENCE: 114
```

Tyr Ile Asn Pro Asn Asn Gly Val Thr Gly Tyr Asn Gln Lys Phe Arg
1               5                   10                  15

Gly

```
<210> SEQ ID NO 115
<211> LENGTH: 11
<212> TYPE: PRT
<213> ORGANISM: Mouse
<220> FEATURE:
<223> OTHER INFORMATION: HCDR3 42d

<400> SEQUENCE: 115

Arg Tyr Gly Asp Tyr Val His Ala Met Asp Cys
1               5                   10

<210> SEQ ID NO 116
<211> LENGTH: 11
<212> TYPE: PRT
<213> ORGANISM: Mouse
<220> FEATURE:
<223> OTHER INFORMATION: LCDR1 42d

<400> SEQUENCE: 116

Arg Ala Ser Gln Asp Ile Gly Ser Arg Leu Asn
1               5                   10

<210> SEQ ID NO 117
<211> LENGTH: 7
<212> TYPE: PRT
<213> ORGANISM: Mouse
<220> FEATURE:
<223> OTHER INFORMATION: LCDR2 42d

<400> SEQUENCE: 117

Ala Thr Ser Ser Leu Asp Ser
1               5

<210> SEQ ID NO 118
<211> LENGTH: 9
<212> TYPE: PRT
<213> ORGANISM: Mouse
<220> FEATURE:
<223> OTHER INFORMATION: LCDR3 42d

<400> SEQUENCE: 118

Leu Gln Tyr Ala Ser Ser Pro Tyr Thr
1               5

<210> SEQ ID NO 119
<211> LENGTH: 10
<212> TYPE: PRT
<213> ORGANISM: Mouse
<220> FEATURE:
<223> OTHER INFORMATION: HCDR1 41c

<400> SEQUENCE: 119

Gly Tyr Thr Phe Thr Asp Tyr Asn Met His
1               5                   10

<210> SEQ ID NO 120
<211> LENGTH: 17
<212> TYPE: PRT
<213> ORGANISM: Mouse
<220> FEATURE:
<223> OTHER INFORMATION: HCDR2 41c

<400> SEQUENCE: 120

Tyr Ile Asn Pro Asn Asn Gly Gly Thr Asn Tyr Asn Gln Lys Phe Lys
1               5                   10                  15

Gly
```

```
<210> SEQ ID NO 121
<211> LENGTH: 6
<212> TYPE: PRT
<213> ORGANISM: Mouse
<220> FEATURE:
<223> OTHER INFORMATION: HCDR3 all 41c and R35B9-related antibodies

<400> SEQUENCE: 121

Ser Gly Trp Phe Thr Tyr
1               5

<210> SEQ ID NO 122
<211> LENGTH: 10
<212> TYPE: PRT
<213> ORGANISM: Mouse
<220> FEATURE:
<223> OTHER INFORMATION: HCDR1 R35B9

<400> SEQUENCE: 122

Gly Tyr Ile Phe Gln Asp Tyr Asn Met His
1               5                   10

<210> SEQ ID NO 123
<211> LENGTH: 17
<212> TYPE: PRT
<213> ORGANISM: Mouse
<220> FEATURE:
<223> OTHER INFORMATION: HCDR2 R35B9

<400> SEQUENCE: 123

Ser Ile Asn Pro Arg Asn Gly Trp Thr Asn Tyr Asn Gln Lys Phe Lys
1               5                   10                  15

Gly

<210> SEQ ID NO 124
<211> LENGTH: 17
<212> TYPE: PRT
<213> ORGANISM: Mouse
<220> FEATURE:
<223> OTHER INFORMATION: HCDR2 R35B9(A56)

<400> SEQUENCE: 124

Ser Ile Asn Pro Arg Asn Ala Trp Thr Asn Tyr Asn Gln Lys Phe Lys
1               5                   10                  15

Gly

<210> SEQ ID NO 125
<211> LENGTH: 17
<212> TYPE: PRT
<213> ORGANISM: Mouse
<220> FEATURE:
<223> OTHER INFORMATION: HCDR2 R35B9(Y50G57)

<400> SEQUENCE: 125

Tyr Ile Asn Pro Arg Asn Gly Gly Thr Asn Tyr Asn Gln Lys Phe Lys
1               5                   10                  15

Gly

<210> SEQ ID NO 126
<211> LENGTH: 17
<212> TYPE: PRT
<213> ORGANISM: Mouse
<220> FEATURE:
<223> OTHER INFORMATION: HCDR2 R35B9(Y50A56G57)
```

```
<400> SEQUENCE: 126

Tyr Ile Asn Pro Arg Asn Ala Gly Thr Asn Tyr Asn Gln Lys Phe Lys
1               5                   10                  15
Gly

<210> SEQ ID NO 127
<211> LENGTH: 16
<212> TYPE: PRT
<213> ORGANISM: Mouse
<220> FEATURE:
<223> OTHER INFORMATION: LCDR1 all 41c and R35B9-related antibodies

<400> SEQUENCE: 127

Lys Ser Ser Gln Ser Leu Leu Asn Ser Ala Gly Lys Thr Tyr Leu Asn
1               5                   10                  15

<210> SEQ ID NO 128
<211> LENGTH: 7
<212> TYPE: PRT
<213> ORGANISM: Mouse
<220> FEATURE:
<223> OTHER INFORMATION: LCDR2 all 41c and R35B9-related antibodies

<400> SEQUENCE: 128

Leu Val Ser Gln Leu Asp Ser
1               5

<210> SEQ ID NO 129
<211> LENGTH: 9
<212> TYPE: PRT
<213> ORGANISM: Mouse
<220> FEATURE:
<223> OTHER INFORMATION: LCDR3 41C

<400> SEQUENCE: 129

Trp Gln Gly Thr His Phe Pro Trp Thr
1               5

<210> SEQ ID NO 130
<211> LENGTH: 9
<212> TYPE: PRT
<213> ORGANISM: Mouse
<220> FEATURE:
<223> OTHER INFORMATION: LCDR3 R35B9 mouse and humanized

<400> SEQUENCE: 130

Trp Gln Gly Thr Phe Tyr Pro Trp Thr
1               5

<210> SEQ ID NO 131
<211> LENGTH: 9
<212> TYPE: PRT
<213> ORGANISM: Mouse
<220> FEATURE:
<223> OTHER INFORMATION: LCDR3 R35B9(H98)

<400> SEQUENCE: 131

Trp Gln Gly Thr His Tyr Pro Trp Thr
1               5

<210> SEQ ID NO 132
<211> LENGTH: 25
<212> TYPE: PRT
<213> ORGANISM: Mouse
<220> FEATURE:
```

```
<223> OTHER INFORMATION: H-FR1 mouse R35B9 and 41c

<400> SEQUENCE: 132

Glu Val Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 133
<211> LENGTH: 25
<212> TYPE: PRT
<213> ORGANISM: Homo sapiens
<220> FEATURE:
<223> OTHER INFORMATION: H-FR1 humanized HV0, HV5a,HV6b, HV6c, HV7c,
      HV9b, HV10

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 134
<211> LENGTH: 25
<212> TYPE: PRT
<213> ORGANISM: Homo sapiens
<220> FEATURE:
<223> OTHER INFORMATION: H-FR1 humanized HV5b, HV6a, HV7a, HV7b

<400> SEQUENCE: 134

Gln Val Gln Leu Val Gln Ser Gly Ala Glu Val Val Lys Pro Gly Ala
1               5                   10                  15

Ser Val Lys Val Ser Cys Lys Ala Ser
            20                  25

<210> SEQ ID NO 135
<211> LENGTH: 25
<212> TYPE: PRT
<213> ORGANISM: Homo sapiens
<220> FEATURE:
<223> OTHER INFORMATION: H-FR1 humanized HV9a

<400> SEQUENCE: 135

Gln Val Gln Leu Val Gln Ser Gly Ala Glu Val Lys Lys Pro Gly Ala
1               5                   10                  15

Ser Val Lys Met Ser Cys Lys Ala Ser
            20                  25

<210> SEQ ID NO 136
<211> LENGTH: 25
<212> TYPE: PRT
<213> ORGANISM: Homo sapiens
<220> FEATURE:
<223> OTHER INFORMATION: H-FR1 humanized HV11

<400> SEQUENCE: 136

Gln Val Gln Leu Val Gln Ser Gly Pro Glu Val Val Lys Pro Gly Ala
1               5                   10                  15

Ser Val Lys Val Ser Cys Lys Ala Ser
            20                  25

<210> SEQ ID NO 137
<211> LENGTH: 25
<212> TYPE: PRT
```

```
<213> ORGANISM: Homo sapiens
<220> FEATURE:
<223> OTHER INFORMATION: H-FR1 humanized HV18

<400> SEQUENCE: 137

Glu Val Gln Leu Val Gln Ser Gly Pro Glu Val Val Lys Pro Gly Ala
1               5                   10                  15

Ser Val Lys Met Ser Cys Lys Ala Ser
            20                  25

<210> SEQ ID NO 138
<211> LENGTH: 14
<212> TYPE: PRT
<213> ORGANISM: Mouse
<220> FEATURE:
<223> OTHER INFORMATION: H-FR2 mouse R35B9 and 41c

<400> SEQUENCE: 138

Trp Val Lys Gln Ser His Gly Lys Ser Leu Glu Trp Ile Gly
1               5                   10

<210> SEQ ID NO 139
<211> LENGTH: 14
<212> TYPE: PRT
<213> ORGANISM: Homo sapiens
<220> FEATURE:
<223> OTHER INFORMATION: H-FR2 humanized HV5a, HV9a

<400> SEQUENCE: 139

Trp Val Arg Gln Ala Pro Gly Gln Gly Leu Glu Trp Ile Gly
1               5                   10

<210> SEQ ID NO 140
<211> LENGTH: 14
<212> TYPE: PRT
<213> ORGANISM: Homo sapiens
<220> FEATURE:
<223> OTHER INFORMATION: H-FR2 humanized HV5b, HV7b

<400> SEQUENCE: 140

Trp Val Arg Gln Ala His Gly Gln Gly Leu Glu Trp Met Gly
1               5                   10

<210> SEQ ID NO 141
<211> LENGTH: 14
<212> TYPE: PRT
<213> ORGANISM: Homo sapiens
<220> FEATURE:
<223> OTHER INFORMATION: H-FR2 humanized HV6a, HV7a, HV11

<400> SEQUENCE: 141

Trp Val Arg Gln Ala His Gly Gln Ser Leu Glu Trp Met Gly
1               5                   10

<210> SEQ ID NO 142
<211> LENGTH: 14
<212> TYPE: PRT
<213> ORGANISM: Homo sapiens
<220> FEATURE:
<223> OTHER INFORMATION: H-FR2 humanized HV6b, HV6c, HV10

<400> SEQUENCE: 142

Trp Val Arg Gln Ala His Gly Gln Gly Leu Glu Trp Ile Gly
1               5                   10

<210> SEQ ID NO 143
```

```
<211> LENGTH: 14
<212> TYPE: PRT
<213> ORGANISM: Homo sapiens
<220> FEATURE:
<223> OTHER INFORMATION: H-FR2 humanized HV7c

<400> SEQUENCE: 143

Trp Val Lys Gln Ala Pro Gly Gln Gly Leu Glu Trp Ile Gly
1               5                   10

<210> SEQ ID NO 144
<211> LENGTH: 14
<212> TYPE: PRT
<213> ORGANISM: Homo sapiens
<220> FEATURE:
<223> OTHER INFORMATION: H-FR2 humanized HV9b, HV18

<400> SEQUENCE: 144

Trp Val Lys Gln Ala His Gly Gln Ser Leu Glu Trp Ile Gly
1               5                   10

<210> SEQ ID NO 145
<211> LENGTH: 32
<212> TYPE: PRT
<213> ORGANISM: Mouse
<220> FEATURE:
<223> OTHER INFORMATION: H-FR3 mouse R35B9 and 41c

<400> SEQUENCE: 145

Lys Ala Thr Leu Thr Val Asn Lys Ser Ser Arg Ser Ala Tyr Met Glu
1               5                   10                  15

Phe Arg Ser Leu Thr Ser Glu Asp Ser Ala Val Tyr Tyr Cys Ala Ser
            20                  25                  30

<210> SEQ ID NO 146
<211> LENGTH: 32
<212> TYPE: PRT
<213> ORGANISM: Homo sapiens
<220> FEATURE:
<223> OTHER INFORMATION: H-FR3 humanized HV5a, HV6c

<400> SEQUENCE: 146

Arg Ala Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 147
<211> LENGTH: 32
<212> TYPE: PRT
<213> ORGANISM: Homo sapiens
<220> FEATURE:
<223> OTHER INFORMATION: H-FR3 humanized HV5b, HV6a

<400> SEQUENCE: 147

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 148
<211> LENGTH: 32
<212> TYPE: PRT
<213> ORGANISM: Homo sapiens
<220> FEATURE:
<223> OTHER INFORMATION: H-FR3 humanized HV6b
```

<400> SEQUENCE: 148

Arg Ala Thr Ile Thr Ala Asp Lys Ser Thr Thr Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 149
<211> LENGTH: 17
<212> TYPE: PRT
<213> ORGANISM: Mouse
<220> FEATURE:
<223> OTHER INFORMATION: HCDR2 R35B9(Y50)

<400> SEQUENCE: 149

Tyr Ile Asn Pro Arg Asn Gly Trp Thr Asn Tyr Asn Gln Lys Phe Lys
1               5                   10                  15

Gly

<210> SEQ ID NO 150
<211> LENGTH: 32
<212> TYPE: PRT
<213> ORGANISM: Homo sapiens
<220> FEATURE:
<223> OTHER INFORMATION: H-FR3 humanized HV7a

<400> SEQUENCE: 150

Arg Val Thr Ile Thr Ala Asp Thr Ser Thr Arg Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 151
<211> LENGTH: 32
<212> TYPE: PRT
<213> ORGANISM: Homo sapiens
<220> FEATURE:
<223> OTHER INFORMATION: H-FR3 humanized HV7b

<400> SEQUENCE: 151

Arg Val Thr Ile Thr Ala Asp Lys Ser Thr Arg Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 152
<211> LENGTH: 32
<212> TYPE: PRT
<213> ORGANISM: Homo sapiens
<220> FEATURE:
<223> OTHER INFORMATION: H-FR3 humanized HV7c

<400> SEQUENCE: 152

Lys Ala Thr Ile Thr Ala Asp Ser Thr Ser Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 153
<211> LENGTH: 32
<212> TYPE: PRT
<213> ORGANISM: Homo sapiens
<220> FEATURE:
<223> OTHER INFORMATION: H-FR3 humanized HV9a

<400> SEQUENCE: 153

Arg Ala Thr Leu Thr Val Asp Thr Ser Thr Ser Thr Ala Tyr Met Glu
1               5                   10                  15

Phe Ser Ser Leu Arg Ser Glu Asp Thr Ala Val Tyr Tyr Cys Ala Ser
            20                  25                  30

<210> SEQ ID NO 154
<211> LENGTH: 32
<212> TYPE: PRT
<213> ORGANISM: Homo sapiens
<220> FEATURE:
<223> OTHER INFORMATION: H-FR3 humanized HV9b

<400> SEQUENCE: 154

Arg Ala Thr Ile Thr Ala Asp Thr Ser Thr Ser Thr Ala Tyr Met Glu
1               5                   10                  15

Phe Ser Ser Leu Arg Ser Glu Asp Thr Ala Val Tyr Tyr Cys Ala Ser
            20                  25                  30

<210> SEQ ID NO 155
<211> LENGTH: 32
<212> TYPE: PRT
<213> ORGANISM: Homo sapiens
<220> FEATURE:
<223> OTHER INFORMATION: H-FR3 humanized HV10

<400> SEQUENCE: 155

Lys Ala Thr Ile Thr Ala Asp Lys Ser Thr Arg Thr Ala Tyr Met Glu
1               5                   10                  15

Phe Ser Ser Leu Arg Ser Glu Asp Thr Ala Val Tyr Tyr Cys Ala Ser
            20                  25                  30

<210> SEQ ID NO 156
<211> LENGTH: 32
<212> TYPE: PRT
<213> ORGANISM: Homo sapiens
<220> FEATURE:
<223> OTHER INFORMATION: H-FR3 humanized HV11

<400> SEQUENCE: 156

Arg Ala Thr Ile Thr Val Asp Lys Ser Thr Arg Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 157
<211> LENGTH: 32
<212> TYPE: PRT
<213> ORGANISM: Homo sapiens
<220> FEATURE:
<223> OTHER INFORMATION: H-FR3 humanized HV18

<400> SEQUENCE: 157

Lys Ala Thr Leu Thr Val Asp Lys Ser Thr Arg Thr Ala Tyr Met Glu
1               5                   10                  15

Phe Ser Ser Leu Arg Ser Glu Asp Thr Ala Val Tyr Tyr Cys Ala Ser
            20                  25                  30

<210> SEQ ID NO 158
<211> LENGTH: 11
<212> TYPE: PRT
<213> ORGANISM: Mouse
<220> FEATURE:

<223> OTHER INFORMATION: H-FR4 mouse R35B9 and 41c

<400> SEQUENCE: 158

Trp Gly Gln Gly Thr Leu Val Thr Val Ser Ala
1               5                   10

<210> SEQ ID NO 159
<211> LENGTH: 11
<212> TYPE: PRT
<213> ORGANISM: Homo sapiens
<220> FEATURE:
<223> OTHER INFORMATION: H-FR4 humanized (all)

<400> SEQUENCE: 159

Trp Gly Gln Gly Thr Leu Val Thr Val Ser Ser
1               5                   10

<210> SEQ ID NO 160
<211> LENGTH: 23
<212> TYPE: PRT
<213> ORGANISM: Mouse
<220> FEATURE:
<223> OTHER INFORMATION: L-FR1 mouse R35B9 and 41c

<400> SEQUENCE: 160

Asp Val Val Met Thr Gln Thr Pro Leu Thr Leu Ser Val Ala Ile Gly
1               5                   10                  15

Gln Pro Ala Ser Ile Ser Cys
            20

<210> SEQ ID NO 161
<211> LENGTH: 23
<212> TYPE: PRT
<213> ORGANISM: Homo sapiens
<220> FEATURE:
<223> OTHER INFORMATION: L-FR1 human LV0, LV1a, LV1b

<400> SEQUENCE: 161

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 162
<211> LENGTH: 23
<212> TYPE: PRT
<213> ORGANISM: Homo sapiens
<220> FEATURE:
<223> OTHER INFORMATION: L-FR1 humanized LV3a, LV3b, LV4, LV5

<400> SEQUENCE: 162

Asp Val Val Met Thr Gln Ser Pro Leu Ser Leu Pro Val Thr Ile Gly
1               5                   10                  15

Gln Pro Ala Ser Ile Ser Cys
            20

<210> SEQ ID NO 163
<211> LENGTH: 15
<212> TYPE: PRT
<213> ORGANISM: Mouse
<220> FEATURE:
<223> OTHER INFORMATION: L-FR2 mouse R35B9, 41C, LV4, LV5

<400> SEQUENCE: 163

Trp Leu Leu Gln Arg Pro Gly Gln Ser Pro Lys Arg Leu Ile Tyr

```
<210> SEQ ID NO 164
<211> LENGTH: 15
<212> TYPE: PRT
<213> ORGANISM: Homo sapiens
<220> FEATURE:
<223> OTHER INFORMATION: L-FR2 human LV0

<400> SEQUENCE: 164

Trp Phe Gln Gln Arg Pro Gly Gln Ser Pro Arg Arg Leu Ile Tyr
1               5                   10                  15

<210> SEQ ID NO 165
<211> LENGTH: 15
<212> TYPE: PRT
<213> ORGANISM: Homo sapiens
<220> FEATURE:
<223> OTHER INFORMATION: L-FR2 humanized LV1a

<400> SEQUENCE: 165

Trp Leu Gln Gln Arg Pro Gly Gln Ser Pro Arg Arg Leu Ile Tyr
1               5                   10                  15

<210> SEQ ID NO 166
<211> LENGTH: 15
<212> TYPE: PRT
<213> ORGANISM: Homo sapiens
<220> FEATURE:
<223> OTHER INFORMATION: L-FR2 humanized LV1b

<400> SEQUENCE: 166

Trp Phe Leu Gln Arg Pro Gly Gln Ser Pro Arg Arg Leu Ile Tyr
1               5                   10                  15

<210> SEQ ID NO 167
<211> LENGTH: 15
<212> TYPE: PRT
<213> ORGANISM: Homo sapiens
<220> FEATURE:
<223> OTHER INFORMATION: L-FR2 humanized LV3a

<400> SEQUENCE: 167

Trp Phe Leu Gln Arg Pro Gly Gln Ser Pro Lys Arg Leu Ile Tyr
1               5                   10                  15

<210> SEQ ID NO 168
<211> LENGTH: 15
<212> TYPE: PRT
<213> ORGANISM: Homo sapiens
<220> FEATURE:
<223> OTHER INFORMATION: L-FR2 humanized LV3b

<400> SEQUENCE: 168

Trp Leu Leu Gln Arg Pro Gly Gln Ser Pro Arg Arg Leu Ile Tyr
1               5                   10                  15

<210> SEQ ID NO 169
<211> LENGTH: 32
<212> TYPE: PRT
<213> ORGANISM: Mouse
<220> FEATURE:
<223> OTHER INFORMATION: L-FR3 mouse R35B9 and 41c

<400> SEQUENCE: 169

Gly Val Pro Asp Arg Phe Thr Gly Ser Gly Ser Gly Thr Asp Phe Thr
1               5                   10                  15
```

-continued

Leu Lys Ile Ser Arg Val Glu Ala Glu Asp Leu Gly Val Tyr Tyr Cys
            20                  25                  30

<210> SEQ ID NO 170
<211> LENGTH: 32
<212> TYPE: PRT
<213> ORGANISM: Homo sapiens
<220> FEATURE:
<223> OTHER INFORMATION: L-FR3 human LV0, LV1a, LV1b, LV3a, LV3b, LV4, LV5

<400> SEQUENCE: 170

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 171
<211> LENGTH: 10
<212> TYPE: PRT
<213> ORGANISM: Mouse
<220> FEATURE:
<223> OTHER INFORMATION: L-FR4 mouse R35B9, 41c, LV5

<400> SEQUENCE: 171

Phe Gly Gly Gly Thr Lys Leu Glu Ile Lys
1               5                   10

<210> SEQ ID NO 172
<211> LENGTH: 10
<212> TYPE: PRT
<213> ORGANISM: Homo sapiens
<220> FEATURE:
<223> OTHER INFORMATION: L-FR4 human LV0, LV1a, LV1b, LV3a, LV3b, LV4

<400> SEQUENCE: 172

Phe Gly Gly Gly Thr Lys Val Glu Ile Lys
1               5                   10

<210> SEQ ID NO 173
<211> LENGTH: 14
<212> TYPE: PRT
<213> ORGANISM: Homo sapiens
<220> FEATURE:
<223> OTHER INFORMATION: H-FR2 humanized HV0

<400> SEQUENCE: 173

Trp Val Arg Gln Ala Pro Gly Gln Gly Leu Glu Trp Met Gly
1               5                   10

<210> SEQ ID NO 174
<211> LENGTH: 32
<212> TYPE: PRT
<213> ORGANISM: Homo sapiens
<220> FEATURE:
<223> OTHER INFORMATION: H-FR3 humanized HV0

<400> SEQUENCE: 174

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 175
<211> LENGTH: 232

```
<212> TYPE: PRT
<213> ORGANISM: Mouse
<220> FEATURE:
<223> OTHER INFORMATION: 41C mIgG1 heavy chain for crystal

<400> SEQUENCE: 175

Leu Glu Glu Val Gln Leu Gln Gln Ser Gly Pro Glu Leu Val Lys Pro
1               5                   10                  15

Gly Ala Ser Val Lys Met Ser Cys Lys Ala Ser Gly Tyr Thr Phe Thr
            20                  25                  30

Asp Tyr Asn Met His Trp Val Lys Gln Ser His Gly Lys Ser Leu Glu
        35                  40                  45

Trp Ile Gly Tyr Ile Asn Pro Asn Asn Gly Gly Thr Asn Tyr Asn Gln
    50                  55                  60

Lys Phe Lys Gly Lys Ala Thr Leu Thr Val Asn Lys Ser Ser Arg Ser
65                  70                  75                  80

Ala Tyr Met Glu Phe Arg Ser Leu Thr Ser Glu Asp Ser Ala Val Tyr
                85                  90                  95

Tyr Cys Ala Ser Ser Gly Trp Phe Thr Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Thr Ser Gly Gln Ala
    210                 215                 220

Gly Gln His His His His His His
225                 230

<210> SEQ ID NO 176
<211> LENGTH: 221
<212> TYPE: PRT
<213> ORGANISM: Mouse
<220> FEATURE:
<223> OTHER INFORMATION: 41C mK light chain for crystal

<400> SEQUENCE: 176

Ser Arg Asp Val Val Met Thr Gln Thr Pro Leu Thr Leu Ser Val Ala
1               5                   10                  15

Ile Gly Gln Pro Ala Ser Ile Ser Cys Lys Ser Ser Gln Ser Leu Leu
            20                  25                  30

Asn Ser Ala Gly Lys Thr Tyr Leu Asn Trp Leu Leu Gln Arg Pro Gly
        35                  40                  45

Gln Ser Pro Lys Arg Leu Ile Tyr Leu Val Ser Gln Leu Asp Ser Gly
    50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Trp
                85                  90                  95
```

```
Gln Gly Thr His Phe Pro Trp Thr Phe Gly Gly Gly Thr Lys Leu Glu
            100                 105                 110

Ile Lys Arg Ala Asp Ala Ala Pro Thr Val Ser Ile Phe Pro Pro Ser
            115                 120                 125

Ser Glu Gln Leu Thr Ser Gly Gly Ala Ser Val Val Cys Phe Leu Asn
            130                 135                 140

Asn Phe Tyr Pro Lys Asp Ile Asn Val Lys Trp Lys Ile Asp Gly Ser
145                 150                 155                 160

Glu Arg Gln Asn Gly Val Leu Asn Ser Trp Thr Asp Gln Asp Ser Lys
            165                 170                 175

Asp Ser Thr Tyr Ser Met Ser Ser Thr Leu Thr Leu Thr Lys Asp Glu
            180                 185                 190

Tyr Glu Arg His Asn Ser Tyr Thr Cys Glu Ala Thr His Lys Thr Ser
            195                 200                 205

Thr Ser Pro Ile Val Lys Ser Phe Asn Arg Asn Glu Cys
            210                 215                 220

<210> SEQ ID NO 177
<211> LENGTH: 224
<212> TYPE: PRT
<213> ORGANISM: Mouse
<220> FEATURE:
<223> OTHER INFORMATION: R35B9 mIgG1 heavy fab frag for crystal

<400> SEQUENCE: 177

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ser His Gly Lys Ser Leu Glu Trp Ile
            35                  40                  45

Gly Ser Ile Asn Pro Arg Asn Gly Trp Thr Asn Tyr Asn Gln Lys Phe
        50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
            130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Glu Ser Asp Leu
            165                 170                 175

Tyr Thr Leu Ser Ser Ser Val Thr Val Pro Ser Ser Pro Arg Pro Ser
            180                 185                 190

Glu Thr Val Thr Cys Asn Val Ala His Pro Ala Ser Ser Thr Lys Val
            195                 200                 205

Asp Lys Lys Ile Val Pro Arg Asp Cys Gly His His His His His His
            210                 215                 220

<210> SEQ ID NO 178
```

```
<211> LENGTH: 219
<212> TYPE: PRT
<213> ORGANISM: Mouse
<220> FEATURE:
<223> OTHER INFORMATION: R35B9 mK light chain for crystal

<400> SEQUENCE: 178

Asp Val Val Met Thr Gln Thr Pro Leu Thr Leu Ser Val Ala Ile Gly
1               5                   10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Leu Gln Arg Pro Gly Gln Ser
        35                  40                  45

Pro Lys Arg Leu Ile Tyr Leu Val Ser Gln Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr Phe Tyr Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 179
<211> LENGTH: 115
<212> TYPE: PRT
<213> ORGANISM: Homo sapiens
<220> FEATURE:
<223> OTHER INFORMATION: hzR35B9-VH_HV0

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala Pro Gly Gln Gly Leu Glu Trp Met
        35                  40                  45

Gly Ser Ile Asn Pro Arg Asn Gly Trp Thr Asn Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Trp Phe Thr Tyr Trp Gly Gln Gly Thr Leu Val Thr
```

Val Ser Ser
    115

<210> SEQ ID NO 180
<211> LENGTH: 345
<212> TYPE: DNA
<213> ORGANISM: Mouse
<220> FEATURE:
<223> OTHER INFORMATION: R35B9(Y50)-VH

<400> SEQUENCE: 180
gaggtgcagc tgcagcaaag cggcccggag ctggtgaaac cgggtgcgag cgttaaaatg    60
agctgcaagg cgagcggtta cattttcag gattataata tgcattgggt taaacagagc   120
cacggtaaaa gcctggagtg gatcggctat attaatccgc gtaatggttg gaccaactat   180
aaccaaaagt tcaaaggcaa ggcgaccctg accgtgaaca agagcagccg tagcgcgtac   240
atggagtttc gtagcctgac cagcgaagat agcgcggttt actattgcgc gtcttcgggg   300
tggttcacgt attggggtca aggcaccctg gtgaccgtta gcgcg                   345

<210> SEQ ID NO 181
<211> LENGTH: 115
<212> TYPE: PRT
<213> ORGANISM: Mouse
<220> FEATURE:
<223> OTHER INFORMATION: R35B9(Y50)-VH

<400> SEQUENCE: 181

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ser His Gly Lys Ser Leu Glu Trp Ile
        35                  40                  45

Gly Tyr Ile Asn Pro Arg Asn Gly Trp Thr Asn Tyr Asn Gln Lys Phe
    50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
    115

<210> SEQ ID NO 182
<211> LENGTH: 21
<212> TYPE: PRT
<213> ORGANISM: Artificial Sequence
<220> FEATURE:
<223> OTHER INFORMATION: Subdomain 1 (AA30-50)

<400> SEQUENCE: 182

Ala Pro Gly Thr Ala Pro Cys Ser Arg Gly Ser Ser Trp Ser Ala Asp
1               5                   10                  15

Leu Asp Lys Cys Met
            20

<210> SEQ ID NO 183

```
<211> LENGTH: 20
<212> TYPE: PRT
<213> ORGANISM: Artificial Sequence
<220> FEATURE:
<223> OTHER INFORMATION: Subdomain 2 (AA51-70)

<400> SEQUENCE: 183

Asp Cys Ala Ser Cys Arg Ala Arg Pro His Ser Asp Phe Cys Leu Gly
1               5                   10                  15

Cys Ala Ala Ala
            20

<210> SEQ ID NO 184
<211> LENGTH: 10
<212> TYPE: PRT
<213> ORGANISM: Artificial Sequence
<220> FEATURE:
<223> OTHER INFORMATION: Consensus CDR H1
<220> FEATURE:
<221> NAME/KEY: MISC_FEATURE
<222> LOCATION: (3)..(3)
<223> OTHER INFORMATION: X is T, I or R
<220> FEATURE:
<221> NAME/KEY: MISC_FEATURE
<222> LOCATION: (5)..(5)
<223> OTHER INFORMATION: X is T or Q

<400> SEQUENCE: 184

Gly Tyr Xaa Phe Xaa Asp Tyr Asn Met His
1               5                   10

<210> SEQ ID NO 185
<211> LENGTH: 17
<212> TYPE: PRT
<213> ORGANISM: Artificial Sequence
<220> FEATURE:
<223> OTHER INFORMATION: Consensus CDR H2
<220> FEATURE:
<221> NAME/KEY: MISC_FEATURE
<222> LOCATION: (1)..(1)
<223> OTHER INFORMATION: X is Y or S
<220> FEATURE:
<221> NAME/KEY: MISC_FEATURE
<222> LOCATION: (5)..(5)
<223> OTHER INFORMATION: X is N or R
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is G or W

<400> SEQUENCE: 185

Xaa Ile Asn Pro Xaa Asn Xaa Xaa Thr Asn Tyr Asn Gln Lys Phe Lys
1               5                   10                  15

Gly

<210> SEQ ID NO 186
<211> LENGTH: 9
<212> TYPE: PRT
<213> ORGANISM: Artificial Sequence
<220> FEATURE:
<223> OTHER INFORMATION: Consensus CDR L3
<220> FEATURE:
<221> NAME/KEY: MISC_FEATURE
<222> LOCATION: (5)..(5)
<223> OTHER INFORMATION: X is H or F
<220> FEATURE:
<221> NAME/KEY: MISC_FEATURE
```

```
<222> LOCATION: (6)..(6)
<223> OTHER INFORMATION: X is F or Y

<400> SEQUENCE: 186

Trp Gln Gly Thr Xaa Xaa Pro Trp Thr
1               5

<210> SEQ ID NO 187
<211> LENGTH: 17
<212> TYPE: PRT
<213> ORGANISM: Artificial Sequence
<220> FEATURE:
<223> OTHER INFORMATION: Second Consensus CDR H2
<220> FEATURE:
<221> NAME/KEY: MISC_FEATURE
<222> LOCATION: (1)..(1)
<223> OTHER INFORMATION: X is Y or S
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is G or W

<400> SEQUENCE: 187

Xaa Ile Asn Pro Arg Asn Xaa Xaa Thr Asn Tyr Asn Gln Lys Phe Lys
1               5                   10                  15

Gly

<210> SEQ ID NO 188
<211> LENGTH: 9
<212> TYPE: PRT
<213> ORGANISM: Artificial Sequence
<220> FEATURE:
<223> OTHER INFORMATION: Second Consensus CDR L3
<220> FEATURE:
<221> NAME/KEY: MISC_FEATURE
<222> LOCATION: (5)..(5)
<223> OTHER INFORMATION: X is H or F

<400> SEQUENCE: 188

Trp Gln Gly Thr Xaa Tyr Pro Trp Thr
1               5

<210> SEQ ID NO 189
<211> LENGTH: 345
<212> TYPE: DNA
<213> ORGANISM: Artificial Sequence
<220> FEATURE:
<223> OTHER INFORMATION: R35B9(G57)-VH A428 nucleotide

<400> SEQUENCE: 189
gaggtgcagc tgcagcaaag cggcccggag ctggtgaaac cgggtgcgag cgttaaaatg    60
agctgcaagg cgagcggtta cattttttcag gattataata tgcattgggt taaacagagc   120
cacggtaaaa gcctggagtg gatcggctct attaatccgc gtaatggtgg accaactat    180 aaccaaaagt tcaaaggcaa ggcgaccctg accgtgaaca agagcagccg tagcgcgtac   240
atggagtttc gtagcctgac cagcgaagat agcgcggttt actattgcgc gtcttcgggg   300
tggttcacgt attgggtca aggcacccctg gtgaccgtta gcgcg                    345

<210> SEQ ID NO 190
<211> LENGTH: 115
<212> TYPE: PRT
<213> ORGANISM: Artificial Sequence
```

<220> FEATURE:
<223> OTHER INFORMATION: R35B9(G57)-VH A428 amino acid

<400> SEQUENCE: 190

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
                20                  25                  30

Asn Met His Trp Val Lys Gln Ser His Gly Lys Ser Leu Glu Trp Ile
            35                  40                  45

Gly Ser Ile Asn Pro Arg Asn Gly Gly Thr Asn Tyr Asn Gln Lys Phe
        50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
        115

<210> SEQ ID NO 191
<211> LENGTH: 345
<212> TYPE: DNA
<213> ORGANISM: Artificial Sequence
<220> FEATURE:
<223> OTHER INFORMATION: R35B9(T28)-VH A435 nucleotide

<400> SEQUENCE: 191
gaggtgcagc tgcagcaaag cggcccggag ctggtgaaac cgggtgcgag cgttaaaatg      60
agctgcaagg cgagcggtta cacctttcag gattataata tgcattgggt taaacagagc     120
cacggtaaaa gcctggagtg gatcggctct attaatccgc gtaatggttg gaccaactat     180
aaccaaaagt tcaaaggcaa ggcgaccctg accgtgaaca gagcagccg tagcgcgtac      240 atggagtttc gtagcctgac cagcgaagat agcgcggttt actattgcgc gtcttcgggg     300
tggttcacgt attggggtca aggcaccctg gtgaccgtta gcgcg                     345

<210> SEQ ID NO 192
<211> LENGTH: 115
<212> TYPE: PRT
<213> ORGANISM: Artificial Sequence
<220> FEATURE:
<223> OTHER INFORMATION: R35B9(T28)-VH A435 amino acid

<400> SEQUENCE: 192

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Gln Asp Tyr
                20                  25                  30

Asn Met His Trp Val Lys Gln Ser His Gly Lys Ser Leu Glu Trp Ile
            35                  40                  45

Gly Ser Ile Asn Pro Arg Asn Gly Trp Thr Asn Tyr Asn Gln Lys Phe
        50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
        115

<210> SEQ ID NO 193
<211> LENGTH: 345
<212> TYPE: DNA
<213> ORGANISM: Artificial Sequence
<220> FEATURE:
<223> OTHER INFORMATION: R35B9(T30)-VH A436 nucleotide

<400> SEQUENCE: 193
gaggtgcagc tgcagcaaag cggcccggag ctggtgaaac cgggtgcgag cgttaaaatg      60
agctgcaagg cgagcggtta catttttact gattataata tgcattgggt taaacagagc     120
cacggtaaaa gcctggagtg gatcggctct attaatccgc gtaatggttg gaccaactat     180
aaccaaaagt tcaaaggcaa ggcgaccctg accgtgaaca agagcagccg tagcgcgtac     240
atggagtttc gtagcctgac cagcgaagat agcgcggttt actattgcgc gtcttcgggg     300
tggttcacgt attggggtca aggcaccctg gtgaccgtta gcgcg                     345

<210> SEQ ID NO 194
<211> LENGTH: 115
<212> TYPE: PRT
<213> ORGANISM: Artificial Sequence
<220> FEATURE:
<223> OTHER INFORMATION: R35B9(T30)-VH A436 amino acid

<400> SEQUENCE: 194

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Thr Asp Tyr
            20                  25                  30

Asn Met His Trp Val Lys Gln Ser His Gly Lys Ser Leu Glu Trp Ile
        35                  40                  45

Gly Ser Ile Asn Pro Arg Asn Gly Trp Thr Asn Tyr Asn Gln Lys Phe
    50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
        115

<210> SEQ ID NO 195
<211> LENGTH: 345
<212> TYPE: DNA
<213> ORGANISM: Artificial Sequence
<220> FEATURE:
<223> OTHER INFORMATION: R35B9(N54)-VH A438 nucleotide

<400> SEQUENCE: 195
gaggtgcagc tgcagcaaag cggcccggag ctggtgaaac cgggtgcgag cgttaaaatg      60
agctgcaagg cgagcggtta catttttcag gattataata tgcattgggt taaacagagc     120
cacggtaaaa gcctggagtg gatcggctct attaatccga ataatggttg gaccaactat     180
aaccaaaagt tcaaaggcaa ggcgaccctg accgtgaaca agagcagccg tagcgcgtac     240

```
atggagtttc gtagcctgac cagcgaagat agcgcggttt actattgcgc gtcttcgggg      300
tggttcacgt attggggtca aggcaccctg gtgaccgtta gcgcg                      345
```

<210> SEQ ID NO 196
<211> LENGTH: 115
<212> TYPE: PRT
<213> ORGANISM: Artificial Sequence
<220> FEATURE:
<223> OTHER INFORMATION: R35B9(N54)-VH A438 amino acid

<400> SEQUENCE: 196

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Gln Asp Tyr
            20                  25                  30

Asn Met His Trp Val Lys Gln Ser His Gly Lys Ser Leu Glu Trp Ile
        35                  40                  45

Gly Ser Ile Asn Pro Asn Asn Gly Trp Thr Asn Tyr Asn Gln Lys Phe
    50                  55                  60

Lys Gly Lys Ala Thr Leu Thr Val Asn Lys Ser Ser Arg Ser Ala Tyr
65                  70                  75                  80

Met Glu Phe Arg Ser Leu Thr Ser Glu Asp Ser Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ala
        115
```

<210> SEQ ID NO 197
<211> LENGTH: 345
<212> TYPE: DNA
<213> ORGANISM: Artificial Sequence
<220> FEATURE:
<223> OTHER INFORMATION: 41C(R28Q30R54)-VH A450 nucleotide

<400> SEQUENCE: 197

```
gaggtgcagc tgcagcaaag cggcccggag ctggtgaaac cgggtgcgag cgttaaaatg      60
agctgcaagg cgagcggtta caggtttcag gattataata tgcattgggt taaacagagc     120
cacggtaaaa gcctggagtg gatcggctat attaatccgc gtaatggtgg gaccaactat     180
aaccaaaagt tcaaaggcaa ggcgacccta ccgtgaaca agagcagccg tagcgcgtac      240
atggagtttc gtagcctgac cagcgaagat agcgcggttt actattgcgc gtcttcgggg     300
tggttcacgt attggggtca aggcaccctg gtgaccgtta gcgcg                      345
```

<210> SEQ ID NO 198
<211> LENGTH: 115
<212> TYPE: PRT
<213> ORGANISM: Artificial Sequence
<220> FEATURE:
<223> OTHER INFORMATION: 41C(R28Q30R54)-VH A450 amino acid

<400> SEQUENCE: 198

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Arg Phe Gln Asp Tyr
            20                  25                  30

Asn Met His Trp Val Lys Gln Ser His Gly Lys Ser Leu Glu Trp Ile
        35                  40                  45
```

```
Gly Tyr Ile Asn Pro Arg Asn Gly Gly Thr Asn Tyr Asn Gln Lys Phe
     50                  55                  60

Lys Gly Lys Ala Thr Leu Thr Val Asn Lys Ser Ser Arg Ser Ala Tyr
 65                  70                  75                  80

Met Glu Phe Arg Ser Leu Thr Ser Glu Asp Ser Ala Val Tyr Tyr Cys
                 85                  90                  95

Ala Ser Ser Gly Trp Phe Thr Tyr Trp Gly Gln Gly Thr Leu Val Thr
             100                 105                 110

Val Ser Ala
        115

<210> SEQ ID NO 199
<211> LENGTH: 336
<212> TYPE: DNA
<213> ORGANISM: Artificial Sequence
<220> FEATURE:
<223> OTHER INFORMATION: R35B9(F99)-VL A440 nucleotide

<400> SEQUENCE: 199
gacgtggtta tgacccaaac cccgctgacc ctgagcgtgg cgattggtca gccggcgagc    60
attagctgca agagcagcca aagcctgctg aacagcgcgg gtaaaaccta cctgaactgg   120
ctgctgcagc gtccgggtca aagcccgaag cgtctgatct atctggtgag ccagctggac   180
agcggtgtgc cggaccgttt caccggtagc ggtagcggca ccgactttac cctgaaaatt   240
agccgtgtgg aggcggaaga tctgggtgtt tactattgct ggcaaggtac ttttttttccg   300 tggacctttg gtggcggtac caagctggag atcaaa                             336

<210> SEQ ID NO 200
<211> LENGTH: 112
<212> TYPE: PRT
<213> ORGANISM: Artificial Sequence
<220> FEATURE:
<223> OTHER INFORMATION: R35B9(F99)-VL A440 amino acid

<400> SEQUENCE: 200

Asp Val Val Met Thr Gln Thr Pro Leu Thr Leu Ser Val Ala Ile Gly
 1               5                  10                  15

Gln Pro Ala Ser Ile Ser Cys Lys Ser Ser Gln Ser Leu Leu Asn Ser
             20                  25                  30

Ala Gly Lys Thr Tyr Leu Asn Trp Leu Leu Gln Arg Pro Gly Gln Ser
         35                  40                  45

Pro Lys Arg Leu Ile Tyr Leu Val Ser Gln Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr Phe Phe Pro Trp Thr Phe Gly Gly Gly Thr Lys Leu Glu Ile Lys
             100                 105                 110

<210> SEQ ID NO 201
<211> LENGTH: 345
<212> TYPE: DNA
<213> ORGANISM: Artificial Sequence
<220> FEATURE:
<223> OTHER INFORMATION: hzR35B9-VH_HV0 (nucleotide corresponding to
      amino acid SEQ ID NO: 179)

<400> SEQUENCE: 201
```

```
caagtccaac tggtccaaag cggggcagag gtaaagaagc caggtgcatc tgtaaaagtg    60
tcatgcaaag cctctgggta cacttttaca gactacaata tgcactgggt tcgtcaggct   120
cccggccagg gcctggagtg gatggggtcc ataaatccta ggaatggatg gacaaactat   180
aaccaaaaat tcaaaggtcg cgtaacaatt accgccgaca catcaacttc cacagcctat   240
atggaactca gcagtctgcg ctccgaagat actgccgtat attactgtgc ccgatccggc   300
tggttcacat actgggggca aggcacactt gtgactgtct ccagc                   345
```

<210> SEQ ID NO 202
<211> LENGTH: 345
<212> TYPE: DNA
<213> ORGANISM: Homo sapiens
<220> FEATURE:
<223> OTHER INFORMATION: hzR35B9(A56)-HV12a nucleotide

<400> SEQUENCE: 202

```
caagttcaac ttgtccaatc cggtccagaa gtcgtaaaac caggtgctag tgtgaaagtc    60
tcatgcaagg cttcaggcta catatttcaa gactataata tgcattgggt tagacaggca   120
gacggtcagt cactggaatg gatggggtca atcaaccctc gcaacgcctg gacaaattac   180
aaccaaaagt tcaaagggag agctactatc actgtcgata aatctaccag aacagcttac   240
atggagctga gtagtctgag atcagaggac accgccgtct actattgtgc ttcttctggg   300 tggttttacat actgggggca ggggacactg gtgactgtga gttct                  345
```

<210> SEQ ID NO 203
<211> LENGTH: 115
<212> TYPE: PRT
<213> ORGANISM: Homo sapiens
<220> FEATURE:
<223> OTHER INFORMATION: hzR35B9(A56)-HV12a amino acid

<400> SEQUENCE: 203

Gln Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala Asp Gly Gln Ser Leu Glu Trp Met
        35                  40                  45

Gly Ser Ile Asn Pro Arg Asn Ala Trp Thr Asn Tyr Asn Gln Lys Phe
    50                  55                  60

Lys Gly Arg Ala Thr Ile Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 204
<211> LENGTH: 345
<212> TYPE: DNA
<213> ORGANISM: Homo sapiens
<220> FEATURE:
<223> OTHER INFORMATION: hzR35B9(A56)-HV12b nucleotide

<400> SEQUENCE: 204

```
caagttcaac ttgtccaatc cggtccagaa gtcgtaaaac caggtgctag tgtgaaagtc    60
tcatgcaagg cttcaggcta catatttcaa gactataata tgcattgggt tagacaggca   120
cccggtcagt cactggaatg gatggggtca atcaaccctc gcaacgcctg acaaattac    180 aaccaaaagt tcaagggag agctactatc actgtcgata atctaccag aacagcttac    240 atggagctga gtagtctgag atcagaggac accgccgtct actattgtgc ttcttctggg   300
tggtttacat actgggggca ggggacactg gtgactgtga gttct                   345
```

```
<210> SEQ ID NO 205
<211> LENGTH: 115
<212> TYPE: PRT
<213> ORGANISM: Homo sapiens
<220> FEATURE:
<223> OTHER INFORMATION: hzR35B9(A56)-HV12b amino acid

<400> SEQUENCE: 205
```

```
Gln Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Arg Gln Ala Pro Gly Gln Ser Leu Glu Trp Met
        35                  40                  45

Gly Ser Ile Asn Pro Arg Asn Ala Trp Thr Asn Tyr Asn Gln Lys Phe
    50                  55                  60

Lys Gly Arg Ala Thr Ile Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115
```

```
<210> SEQ ID NO 206
<211> LENGTH: 345
<212> TYPE: DNA
<213> ORGANISM: Homo sapiens
<220> FEATURE:
<223> OTHER INFORMATION: hzR35B9(A56)-HV13a nucleotide

<400> SEQUENCE: 206
```

```
caagttcaac ttgtccaatc cggtccagaa gtcgtaaaac caggtgctag tgtgaaagtc    60
tcatgcaagg cttcaggcta catatttcaa gactataata tgcattgggt tagagaagca   120
cacggtcagt cactggaatg gatggggtca atcaaccctc gcaacgcctg acaaattac    180 aaccaaaagt tcaagggag agctactatc actgtcgata atctaccag aacagcttac    240 atggagctga gtagtctgag atcagaggac accgccgtct actattgtgc ttcttctggg   300
tggtttacat actgggggca ggggacactg gtgactgtga gttct                   345
```

```
<210> SEQ ID NO 207
<211> LENGTH: 115
<212> TYPE: PRT
<213> ORGANISM: Homo sapiens
<220> FEATURE:
<223> OTHER INFORMATION: hzR35B9(A56)-HV13a amino acid

<400> SEQUENCE: 207
```

```
Gln Val Gln Leu Val Gln Ser Gly Pro Glu Val Val Lys Pro Gly Ala
```

```
 1               5                  10                  15
Ser Val Lys Val Ser Cys Lys Ala Ser Gly Tyr Ile Phe Gln Asp Tyr
                20                  25                  30

Asn Met His Trp Val Arg Glu Ala His Gly Gln Ser Leu Glu Trp Met
             35                  40                  45

Gly Ser Ile Asn Pro Arg Asn Ala Trp Thr Asn Tyr Asn Gln Lys Phe
          50                  55                  60

Lys Gly Arg Ala Thr Ile Thr Val Asp Lys Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Ser Ser Gly Trp Phe Thr Tyr Trp Gly Gln Gly Thr Leu Val Thr
             100                 105                 110

Val Ser Ser
        115

<210> SEQ ID NO 208
<211> LENGTH: 345
<212> TYPE: DNA
<213> ORGANISM: Homo sapiens
<220> FEATURE:
<223> OTHER INFORMATION: hzR35B9(A56)-HV13b nucleotide

<400> SEQUENCE: 208
caagttcaac ttgtccaatc cggtccagaa gtcgtaaaac caggtgctag tgtgaaagtc    60
tcatgcaagg cttcaggcta catatttcaa gactataata tgcattgggt tagacaggca   120
cacggtcagt cactggaatg gatggggtca atcaaccctc gcaacgcctg acaaattac    180 aaccaaaagt tcggagggag agctactatc actgtcgata atctaccag aacagcttac    240 atggagctga gtagtctgag atcagaggac accgccgtct actattgtgc ttcttctggg   300
tggtttacat actgggggca ggggacactg gtgactgtga gttct                   345

<210> SEQ ID NO 209
<211> LENGTH: 115
<212> TYPE: PRT
<213> ORGANISM: Homo sapiens
<220> FEATURE:
<223> OTHER INFORMATION: hzR35B9(A56)-HV13b amino acid

<400> SEQUENCE: 209

Gln Val Gln Leu Val Gln Ser Gly Pro Glu Val Val Lys Pro Gly Ala
 1               5                  10                  15

Ser Val Lys Val Ser Cys Lys Ala Ser Gly Tyr Ile Phe Gln Asp Tyr
                20                  25                  30

Asn Met His Trp Val Arg Gln Ala His Gly Gln Ser Leu Glu Trp Met
             35                  40                  45

Gly Ser Ile Asn Pro Arg Asn Ala Trp Thr Asn Tyr Asn Gln Lys Phe
          50                  55                  60

Gly Gly Arg Ala Thr Ile Thr Val Asp Lys Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Ser Ser Gly Trp Phe Thr Tyr Trp Gly Gln Gly Thr Leu Val Thr
             100                 105                 110

Val Ser Ser
        115
```

<210> SEQ ID NO 210
<211> LENGTH: 345
<212> TYPE: DNA
<213> ORGANISM: Homo sapiens
<220> FEATURE:
<223> OTHER INFORMATION: hzR35B9(A56)-HV13d nucleotide

<400> SEQUENCE: 210

```
caagttcaac ttgtccaatc cggtccagaa gtcgtaaaac caggtgctag tgtgaaagtc    60
tcatgcaagg cttcaggcta catatttcaa gactataata tgcattgggg cagacaggca   120
cacggtcagt cactggaatg gatggggtca atcaaccctc gcaacgcctg gacaaattac   180
aaccaaaagt tcaaagggag agctactatc actgtcgata atctaccag aacagcttac    240 atggagctga gtagtctgag atcagaggac accgccgtct actattgtgc ttcttctggg   300
tggtttacat actgggggca ggggacactg gtgactgtga gttct                   345
```

<210> SEQ ID NO 211
<211> LENGTH: 115
<212> TYPE: PRT
<213> ORGANISM: Homo sapiens
<220> FEATURE:
<223> OTHER INFORMATION: hzR35B9(A56)-HV13d amino acid

<400> SEQUENCE: 211

```
Gln Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Gly Arg Gln Ala His Gly Gln Ser Leu Glu Trp Met
        35                  40                  45

Gly Ser Ile Asn Pro Arg Asn Ala Trp Thr Asn Tyr Asn Gln Lys Phe
    50                  55                  60

Lys Gly Arg Ala Thr Ile Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115
```

<210> SEQ ID NO 212
<211> LENGTH: 345
<212> TYPE: DNA
<213> ORGANISM: Homo sapiens
<220> FEATURE:
<223> OTHER INFORMATION: hzR35B9(A56)-HV13f nucleotide

<400> SEQUENCE: 212

```
caagttcaac ttgtccaatc cggtccagaa gtcgtaaaac caggtgctag tgtgaaagtc    60
tcatgcaagg cttcaggcta catatttcaa gactataata tgcattgggt tagacaggca   120
cacggtcagt cactggaatg gatggggtca atcaaccctc gcaacgcctg gacaaattac   180
aacgataagt tcaaagggag agctactatc actgtcgata atctaccag aacagcttac    240 atggagctga gtagtctgag atcagaggac accgccgtct actattgtgc ttcttctggg   300
tggtttacat actgggggca ggggacactg gtgactgtga gttct                   345
```

```
<210> SEQ ID NO 213
<211> LENGTH: 115
<212> TYPE: PRT
<213> ORGANISM: Homo sapiens
<220> FEATURE:
<223> OTHER INFORMATION: hzR35B9(A56)-HV13f amino acid

<400> SEQUENCE: 213

Gln Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
                20                  25                  30

Asn Met His Trp Val Arg Gln Ala His Gly Gln Ser Leu Glu Trp Met
            35                  40                  45

Gly Ser Ile Asn Pro Arg Asn Ala Trp Thr Asn Tyr Asn Asp Lys Phe
        50                  55                  60

Lys Gly Arg Ala Thr Ile Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 214
<211> LENGTH: 345
<212> TYPE: DNA
<213> ORGANISM: Homo sapiens
<220> FEATURE:
<223> OTHER INFORMATION: hzR35B9(A56)-HV13g nucleotide

<400> SEQUENCE: 214
caagttcaac ttgtccaatc cggtccagaa gtcgtaaaac caggtgctag tgtgaaagtc        60
tcatgcaagg cttcaggcta catatttcaa gactataata tgcattgggt tagacaggca       120
cacggtgact cactggaatg gatggggtca atcaaccctc gcaacgcctg gacaaattac       180
aaccaaaagt tcaaagggag agctactatc actgtcgata aatctaccag aacagcttac       240
atggagctga gtagtctgag atcagaggac accgccgtct actattgtgc ttcttctggg       300
tggtttacat actgggggca ggggacactg gtgactgtga gttct                      345

<210> SEQ ID NO 215
<211> LENGTH: 115
<212> TYPE: PRT
<213> ORGANISM: Homo sapiens
<220> FEATURE:
<223> OTHER INFORMATION: hzR35B9(A56)-HV13g amino acid

<400> SEQUENCE: 215

Gln Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
                20                  25                  30

Asn Met His Trp Val Arg Gln Ala His Gly Asp Ser Leu Glu Trp Met
            35                  40                  45

Gly Ser Ile Asn Pro Arg Asn Ala Trp Thr Asn Tyr Asn Gln Lys Phe
        50                  55                  60

Lys Gly Arg Ala Thr Ile Thr Val Asp Lys Ser Thr Arg Thr Ala Tyr
65                  70                  75                  80
```

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 216
<211> LENGTH: 345
<212> TYPE: DNA
<213> ORGANISM: Homo sapiens
<220> FEATURE:
<223> OTHER INFORMATION: hzR35B9(A56)-HV16 nucleotide

<400> SEQUENCE: 216
caagttcaac ttcagcaatc cggtccagaa gtcgtaaaac caggtgctag tgtgaaagtc      60
tcatgcaagg cttcaggcta catatttcaa gactataata tgcattgggt taaacaggca     120
cacggtcagt cactggaatg gatggggtca atcaaccctc gcaacgcctg gacaaattac     180
aaccaaaagt tcaaagggaa agctactctg actgtcgata atctaccag aacagcttac      240 atggagctga gtagtctgag atcagaggac accgccgtct actattgtgc ttcttctggg     300
tggtttacat actgggggca ggggacactg gtgactgtga gttct                     345

<210> SEQ ID NO 217
<211> LENGTH: 115
<212> TYPE: PRT
<213> ORGANISM: Homo sapiens
<220> FEATURE:
<223> OTHER INFORMATION: hzR35B9(A56)-HV16 amino acid

<400> SEQUENCE: 217

Gln Val Gln Leu Gln Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Lys Gln Ala His Gly Gln Ser Leu Glu Trp Met
        35                  40                  45

Gly Ser Ile Asn Pro Arg Asn Ala Trp Thr Asn Tyr Asn Gln Lys Phe
    50                  55                  60

Lys Gly Lys Ala Thr Leu Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 218
<211> LENGTH: 345
<212> TYPE: DNA
<213> ORGANISM: Homo sapiens
<220> FEATURE:
<223> OTHER INFORMATION: hzR35B9(A56)-HV17a nucleotide

<400> SEQUENCE: 218
caagttcaac ttcagcaatc cggtccagaa gtcgtaaaac caggtgctag tgtgaaagtc      60
tcatgcaagg cttcaggcta catatttcaa gactataata tgcattgggt taaacaggga     120

```
cacggtcagt cactggaatg gatggggtca atcaaccctc gcaacgcctg gacaaattac    180
aaccaaaagt tcaagggaa agctactctg actgtcgata atctaccag aacagcttac      240 atggagctga gtagtctgag atcagaggac accgccgtct actattgtgc ttcttctggg    300
tggtttacat actggggggca ggggacactg gtgactgtga gttct                    345
```

<210> SEQ ID NO 219
<211> LENGTH: 115
<212> TYPE: PRT
<213> ORGANISM: Homo sapiens
<220> FEATURE:
<223> OTHER INFORMATION: hzR35B9(A56)-HV17a amino acid

<400> SEQUENCE: 219

```
Gln Val Gln Leu Gln Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Lys Gln Gly His Gly Gln Ser Leu Glu Trp Met
        35                  40                  45

Gly Ser Ile Asn Pro Arg Asn Ala Trp Thr Asn Tyr Asn Gln Lys Phe
    50                  55                  60

Lys Gly Lys Ala Thr Leu Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115
```

<210> SEQ ID NO 220
<211> LENGTH: 345
<212> TYPE: DNA
<213> ORGANISM: Homo sapiens
<220> FEATURE:
<223> OTHER INFORMATION: hzR35B9(A56)-HV17b nucleotide

<400> SEQUENCE: 220

```
caagttcaac ttcagcaatc cggtccagaa gtcgtaaaac caggtgctag tgtgaaagtc    60
tcatgcaagg cttcaggcta catatttcaa gactataata tgcattgggt taaacaggca    120
cacggtcagt cactggaatg gatggggtca atcaaccctc gcaacgcctg gacaaattac    180
aaccaaaagt tccacgggaa agctactctg actgtcgata atctaccag aacagcttac     240 atggagctga gtagtctgag atcagaggac accgccgtct actattgtgc ttcttctggg    300
tggtttacat actggggggca ggggacactg gtgactgtga gttct                    345
```

<210> SEQ ID NO 221
<211> LENGTH: 115
<212> TYPE: PRT
<213> ORGANISM: Homo sapiens
<220> FEATURE:
<223> OTHER INFORMATION: hzR35B9(A56)-HV17b amino acid

<400> SEQUENCE: 221

```
Gln Val Gln Leu Gln Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
```

```
                    20                  25                  30
Asn Met His Trp Val Lys Gln Ala His Gly Gln Ser Leu Glu Trp Met
        35                  40                  45

Gly Ser Ile Asn Pro Arg Asn Ala Trp Thr Asn Tyr Asn Gln Lys Phe
    50                  55                  60

His Gly Lys Ala Thr Leu Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 222
<211> LENGTH: 345
<212> TYPE: DNA
<213> ORGANISM: Homo sapiens
<220> FEATURE:
<223> OTHER INFORMATION: hzR35B9(A56)-HV17d nucleotide

<400> SEQUENCE: 222
caagttcaac ttcagcaatc cggtccagaa gtcgtaaaac caggtgctag tgtgaaagtc      60
tcatgcaagg cttcaggcta catatttcaa gactataata tgcattgggt taaacaggca     120
cacggtcagt cactggaatg gatggggtca atcaaccctc gcaacgcctg gacaaaattac    180 aaccaaaagt tcgacgggaa agctactctg actgtcgata atctaccag aacagcttac     240 atggagctga gtagtctgag atcagaggac accgccgtct actattgtgc ttcttctggg     300
tggtttacat actgggggca ggggacactg gtgactgtga gttct                     345

<210> SEQ ID NO 223
<211> LENGTH: 115
<212> TYPE: PRT
<213> ORGANISM: Homo sapiens
<220> FEATURE:
<223> OTHER INFORMATION: hzR35B9(A56)-HV17d amino acid

<400> SEQUENCE: 223

Gln Val Gln Leu Gln Gln Ser Gly Pro Glu Val Val Lys Pro Gly Ala
1               5                   10                  15

Ser Val Lys Val Ser Cys Lys Ala Ser Gly Tyr Ile Phe Gln Asp Tyr
            20                  25                  30

Asn Met His Trp Val Lys Gln Ala His Gly Gln Ser Leu Glu Trp Met
        35                  40                  45

Gly Ser Ile Asn Pro Arg Asn Ala Trp Thr Asn Tyr Asn Gln Lys Phe
    50                  55                  60

Asp Gly Lys Ala Thr Leu Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 224
<211> LENGTH: 345
```

```
<212> TYPE: DNA
<213> ORGANISM: Homo sapiens
<220> FEATURE:
<223> OTHER INFORMATION: hzR35B9(A56)-HV17g nucleotide

<400> SEQUENCE: 224
caagttcaac ttcagcaatc cggtccagaa gtcgtaaaac caggtgctag tgtgaaagtc    60
tcatgcaagg cttcaggcta catatttcaa gactataata tgcattgggt taaacaggca   120
cacggtcagt cactggaatg gatggggtca atcaaccctc gcaacgcctg acaaattac    180 aacgacaagt tcaaagggaa agctactctg actgtcgata atctaccag aacagcttac    240 atggagctga gtagtctgag atcagaggac accgccgtct actattgtgc ttcttctggg   300
tggtttacat actgggggca ggggacactg gtgactgtga gttct                   345

<210> SEQ ID NO 225
<211> LENGTH: 115
<212> TYPE: PRT
<213> ORGANISM: Homo sapiens
<220> FEATURE:
<223> OTHER INFORMATION: hzR35B9(A56)-HV17g amino acid

<400> SEQUENCE: 225

Gln Val Gln Leu Gln Gln Ser Gly Pro Glu Val Val Lys Pro Gly Ala
 1               5                  10                  15

Ser Val Lys Val Ser Cys Lys Ala Ser Gly Tyr Ile Phe Gln Asp Tyr
             20                  25                  30

Asn Met His Trp Val Lys Gln Ala His Gly Gln Ser Leu Glu Trp Met
         35                  40                  45

Gly Ser Ile Asn Pro Arg Asn Ala Trp Thr Asn Tyr Asn Asp Lys Phe
     50                  55                  60

Lys Gly Lys Ala Thr Leu Thr Val Asp Lys Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Ser Ser Gly Trp Phe Thr Tyr Trp Gly Gln Gly Thr Leu Val Thr
            100                 105                 110

Val Ser Ser
        115

<210> SEQ ID NO 226
<211> LENGTH: 345
<212> TYPE: DNA
<213> ORGANISM: Homo sapiens
<220> FEATURE:
<223> OTHER INFORMATION: hzR35B9(A56)-HV17i nucleotide

<400> SEQUENCE: 226
caagttcaac ttcagcaatc cggtccagaa gtcgccaaac caggtgctag tgtgaaagtc    60
tcatgcaagg cttcaggcta catatttcaa gactataata tgcattgggt taaacaggca   120
cacggtcagt cactggaatg gatggggtca atcaaccctc gcaacgcctg acaaattac    180 aaccaaaagt tcaaagggaa agctactctg actgtcgata atctaccag aacagcttac    240 atggagctga gtagtctgag atcagaggac accgccgtct actattgtgc ttcttctggg   300
tggtttacat actgggggca ggggacactg gtgactgtga gttct                   345

<210> SEQ ID NO 227
<211> LENGTH: 115
<212> TYPE: PRT
```

<213> ORGANISM: Homo sapiens
<220> FEATURE:
<223> OTHER INFORMATION: hzR35B9(A56)-HV17i amino acid

<400> SEQUENCE: 227

```
Gln Val Gln Leu Gln Gln Ser Gly Pro Glu Val Ala Lys Pro Gly Ala
1               5                   10                  15
Ser Val Lys Val Ser Cys Lys Ala Ser Gly Tyr Ile Phe Gln Asp Tyr
            20                  25                  30
Asn Met His Trp Val Lys Gln Ala His Gly Gln Ser Leu Glu Trp Met
        35                  40                  45
Gly Ser Ile Asn Pro Arg Asn Ala Trp Thr Asn Tyr Asn Gln Lys Phe
    50                  55                  60
Lys Gly Lys Ala Thr Leu Thr Val Asp Lys Ser Thr Arg Thr Ala Tyr
65                  70                  75                  80
Met Glu Leu Ser Ser Leu Arg Ser Glu Asp Thr Ala Val Tyr Tyr Cys
                85                  90                  95
Ala Ser Ser Gly Trp Phe Thr Tyr Trp Gly Gln Gly Thr Leu Val Thr
            100                 105                 110
Val Ser Ser
        115
```

<210> SEQ ID NO 228
<211> LENGTH: 336
<212> TYPE: DNA
<213> ORGANISM: Homo sapiens
<220> FEATURE:
<223> OTHER INFORMATION: hzR35B9(A56)-LV2a nucleotide

<400> SEQUENCE: 228

```
gatgtagtaa tgacccagtc cccacttagc ttgcccgtta cactcggcca acccgcaagc      60
atatcttgca aatccagtca gagcctcctg aactctgctg gaaagaccta tctgaattgg     120
cttcaacaac gtcccggtca atcccccaga cgaggtatct acttggtaag tcagcttgac     180
tccggggttc cagacaggtt ttccggatct ggaagtggaa ctgatttac actcaaaatt     240
agtcgagtcg aggccgaaga cgtgggtgtc tattattgct ggcaaggcac ctttatcca     300
tggacttttg gtgggggcac caaggttgaa attaag                              336
```

<210> SEQ ID NO 229
<211> LENGTH: 112
<212> TYPE: PRT
<213> ORGANISM: Homo sapiens
<220> FEATURE:
<223> OTHER INFORMATION: hzR35B9(A56)-LV2a amino acid

<400> SEQUENCE: 229

```
Asp Val Val Met Thr Gln Ser Pro Leu Ser Leu Pro Val Thr Leu Gly
1               5                   10                  15
Gln Pro Ala Ser Ile Ser Cys Lys Ser Ser Gln Ser Leu Leu Asn Ser
            20                  25                  30
Ala Gly Lys Thr Tyr Leu Asn Trp Leu Gln Gln Arg Pro Gly Gln Ser
        35                  40                  45
Pro Arg Arg Gly Ile Tyr Leu Val Ser Gln Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
```

Thr Phe Tyr Pro Trp Thr Phe Gly Gly Gly Thr Lys Val Glu Ile Lys
            100                 105                 110

<210> SEQ ID NO 230
<211> LENGTH: 336
<212> TYPE: DNA
<213> ORGANISM: Homo sapiens
<220> FEATURE:
<223> OTHER INFORMATION: hzR35B9(A56)-LV2b nucleotide

<400> SEQUENCE: 230
gatgtagtaa tgacccagtc cccacttagc ttgcccgtta cactcggcca acccgcaagc     60
atatcttgca aatccagtca gagcctcctg aactctgctg gaaagaccta tctgaattgg    120
cttcaacaac gtcccggtca atcccccaga cgacttgcct acttggtaag tcagcttgac    180
tccggggttc cagacaggtt ttccggatct ggaagtggaa ctgattttac actcaaaatt    240
agtcgagtcg aggccgaaga cgtgggtgtc tattattgct ggcaaggcac ctttttatcca   300 tggacttttg gtgggggcac caaggttgaa attaag                              336

<210> SEQ ID NO 231
<211> LENGTH: 112
<212> TYPE: PRT
<213> ORGANISM: Homo sapiens
<220> FEATURE:
<223> OTHER INFORMATION: hzR35B9(A56)-LV2b amino acid

<400> SEQUENCE: 231

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Gln Gln Arg Pro Gly Gln Ser
        35                  40                  45

Pro Arg Arg Leu Ala Tyr Leu Val Ser Gln Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
            100                 105                 110

<210> SEQ ID NO 232
<211> LENGTH: 336
<212> TYPE: DNA
<213> ORGANISM: Homo sapiens
<220> FEATURE:
<223> OTHER INFORMATION: hzR35B9(A56)-LV2c nucleotide

<400> SEQUENCE: 232
gatgtagtaa tgacccagtc cccacttagc ttgcccgtta cactcggcca acccgcaagc     60
atatcttgca aatccagtca gagcctcctg aactctgctg gaaagaccta tctgaattgg    120
cttcaacaac gtcccggtca atcccccaga cgacttatct acttggtaag tgagcttgac    180
tccggggttc cagacaggtt ttccggatct ggaagtggaa ctgattttac actcaaaatt    240
agtcgagtcg aggccgaaga cgtgggtgtc tattattgct ggcaaggcac ctttttatcca   300 tggacttttg gtgggggcac caaggttgaa attaag                              336

<210> SEQ ID NO 233
<211> LENGTH: 112
<212> TYPE: PRT
<213> ORGANISM: Homo sapiens
<220> FEATURE:
<223> OTHER INFORMATION: hzR35B9(A56)-LV2c amino acid

<400> SEQUENCE: 233

```
Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Asn Ser
            20                  25                  30

Ala Gly Lys Thr Tyr Leu Asn Trp Leu Gln Gln Arg Pro Gly Gln Ser
        35                  40                  45

Pro Arg Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
            100                 105                 110
```

<210> SEQ ID NO 234
<211> LENGTH: 336
<212> TYPE: DNA
<213> ORGANISM: Homo sapiens
<220> FEATURE:
<223> OTHER INFORMATION: hzR35B9(A56)-LV2d nucleotide

<400> SEQUENCE: 234

```
gatgtagtaa tgacccagtc cccacttagc ttgcccgtta cactcggcca acccgcaagc      60
atatcttgca aatccagtca gagcctcctg aactctgctg gaaagaccta tctgaattgg     120
cttcaacaac gtcccggtca atcccccaga cgacttatct acttggtaag tcagcttgac     180
gacggggttc cagacaggtt ttccggatct ggaagtggaa ctgattttac actcaaaatt     240
agtcgagtcg aggccgaaga cgtgggtgtc tattattgct ggcaaggcac ctttatcca     300 tggacttttg gtgggggcac caaggttgaa attaag                               336
```

<210> SEQ ID NO 235
<211> LENGTH: 112
<212> TYPE: PRT
<213> ORGANISM: Homo sapiens
<220> FEATURE:
<223> OTHER INFORMATION: hzR35B9(A56)-LV2d amino acid

<400> SEQUENCE: 235

```
Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Asn Ser
            20                  25                  30

Ala Gly Lys Thr Tyr Leu Asn Trp Leu Gln Gln Arg Pro Gly Gln Ser
        35                  40                  45

Pro Arg Arg Leu Ile Tyr Leu Val Ser Gln Leu Asp Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
```

```
                     85                  90                  95

Thr Phe Tyr Pro Trp Thr Phe Gly Gly Gly Thr Lys Val Glu Ile Lys
             100                 105                 110

<210> SEQ ID NO 236
<211> LENGTH: 336
<212> TYPE: DNA
<213> ORGANISM: Homo sapiens
<220> FEATURE:
<223> OTHER INFORMATION: hzR35B9(A56)-LV2f nucleotide

<400> SEQUENCE: 236
gatgtagtaa tgacccagtc cccacttagc ttgcccgtta cactcggcca acccgcaagc        60
atatcttgca aatccagtca gagcctcctg aactctgctg gaaagaccta tctgaattgg       120
cttcaacaac gtcccggtca atcccccaga cgacttatct acttggtagc ccagcttgac       180
tccggggttc cagacaggtt ttccggatct ggaagtggaa ctgattttac actcaaaatt       240
agtcgagtcg aggccgaaga cgtgggtgtc tattattgct ggcaaggcac cttttatcca       300 tggactttg gtgggggcac caaggttgaa attaag                                  336

<210> SEQ ID NO 237
<211> LENGTH: 112
<212> TYPE: PRT
<213> ORGANISM: Homo sapiens
<220> FEATURE:
<223> OTHER INFORMATION: hzR35B9(A56)-LV2f amino acid

<400> SEQUENCE: 237

Asp Val Val Met Thr Gln Ser Pro Leu Ser Leu Pro Val Thr Leu Gly
1               5                  10                  15

Gln Pro Ala Ser Ile Ser Cys Lys Ser Ser Gln Ser Leu Leu Asn Ser
            20                  25                  30

Ala Gly Lys Thr Tyr Leu Asn Trp Leu Gln Gln Arg Pro Gly Gln Ser
        35                  40                  45

Pro Arg Arg Leu Ile Tyr Leu Val Ala Gln Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Phe Tyr Pro Trp Thr Phe Gly Gly Gly Thr Lys Val Glu Ile Lys
            100                 105                 110

<210> SEQ ID NO 238
<211> LENGTH: 25
<212> TYPE: PRT
<213> ORGANISM: Homo sapiens
<220> FEATURE:
<223> OTHER INFORMATION: H-FR1 humanized HV16, HV17a, HV17b, HV17d,
      HV17g,

<400> SEQUENCE: 238

Gln Val Gln Leu Gln Gln Ser Gly Pro Glu Val Val Lys Pro Gly Ala
1               5                  10                  15

Ser Val Lys Val Ser Cys Lys Ala Ser
            20                  25

<210> SEQ ID NO 239
<211> LENGTH: 25
<212> TYPE: PRT
```

```
<213> ORGANISM: Homo sapiens
<220> FEATURE:
<223> OTHER INFORMATION: H-FR1 humanized HV17i

<400> SEQUENCE: 239

Gln Val Gln Leu Gln Gln Ser Gly Pro Glu Val Ala Lys Pro Gly Ala
1               5                   10                  15

Ser Val Lys Val Ser Cys Lys Ala Ser
            20                  25

<210> SEQ ID NO 240
<211> LENGTH: 14
<212> TYPE: PRT
<213> ORGANISM: Homo sapiens
<220> FEATURE:
<223> OTHER INFORMATION: H-FR2 humanized HV12a

<400> SEQUENCE: 240

Trp Val Arg Gln Ala Asp Gly Gln Ser Leu Glu Trp Met Gly
1               5                   10

<210> SEQ ID NO 241
<211> LENGTH: 14
<212> TYPE: PRT
<213> ORGANISM: Homo sapiens
<220> FEATURE:
<223> OTHER INFORMATION: H-FR2 humanized HV12b

<400> SEQUENCE: 241

Trp Val Arg Gln Ala Pro Gly Gln Ser Leu Glu Trp Met Gly
1               5                   10

<210> SEQ ID NO 242
<211> LENGTH: 14
<212> TYPE: PRT
<213> ORGANISM: Homo sapiens
<220> FEATURE:
<223> OTHER INFORMATION: H-FR2 humanized HV13a

<400> SEQUENCE: 242

Trp Val Arg Glu Ala His Gly Gln Ser Leu Glu Trp Met Gly
1               5                   10

<210> SEQ ID NO 243
<211> LENGTH: 14
<212> TYPE: PRT
<213> ORGANISM: Homo sapiens
<220> FEATURE:
<223> OTHER INFORMATION: H-FR2 humanized HV13d

<400> SEQUENCE: 243

Trp Gly Arg Gln Ala His Gly Gln Ser Leu Glu Trp Met Gly
1               5                   10

<210> SEQ ID NO 244
<211> LENGTH: 14
<212> TYPE: PRT
<213> ORGANISM: Homo sapiens
<220> FEATURE:
<223> OTHER INFORMATION: H-FR2 humanized HV13g

<400> SEQUENCE: 244

Trp Val Arg Gln Ala His Gly Asp Ser Leu Glu Trp Met Gly
1               5                   10

<210> SEQ ID NO 245
```

```
<211> LENGTH: 14
<212> TYPE: PRT
<213> ORGANISM: Homo sapiens
<220> FEATURE:
<223> OTHER INFORMATION: H-FR2 humanized HV16, HV17b, HV17d, HV17g,
      HV17i

<400> SEQUENCE: 245

Trp Val Lys Gln Ala His Gly Gln Ser Leu Glu Trp Met Gly
1               5                   10

<210> SEQ ID NO 246
<211> LENGTH: 14
<212> TYPE: PRT
<213> ORGANISM: Homo sapiens
<220> FEATURE:
<223> OTHER INFORMATION: H-FR2 humanized 17a

<400> SEQUENCE: 246

Trp Val Lys Gln Gly His Gly Gln Ser Leu Glu Trp Met Gly
1               5                   10

<210> SEQ ID NO 247
<211> LENGTH: 17
<212> TYPE: PRT
<213> ORGANISM: Homo sapiens
<220> FEATURE:
<223> OTHER INFORMATION: H-CDR2 deimmunized HV13b

<400> SEQUENCE: 247

Ser Ile Asn Pro Arg Asn Ala Trp Thr Asn Tyr Asn Gln Lys Phe Gly
1               5                   10                  15

Gly

<210> SEQ ID NO 248
<211> LENGTH: 17
<212> TYPE: PRT
<213> ORGANISM: Homo sapiens
<220> FEATURE:
<223> OTHER INFORMATION: H-CDR2 deimmunized HV17d

<400> SEQUENCE: 248

Ser Ile Asn Pro Arg Asn Ala Trp Thr Asn Tyr Asn Gln Lys Phe Asp
1               5                   10                  15

Gly

<210> SEQ ID NO 249
<211> LENGTH: 17
<212> TYPE: PRT
<213> ORGANISM: Homo sapiens
<220> FEATURE:
<223> OTHER INFORMATION: H-CDR2 deimmunized HV13f, HV17g

<400> SEQUENCE: 249

Ser Ile Asn Pro Arg Asn Ala Trp Thr Asn Tyr Asn Asp Lys Phe Lys
1               5                   10                  15

Gly

<210> SEQ ID NO 250
<211> LENGTH: 17
<212> TYPE: PRT
<213> ORGANISM: Homo sapiens
<220> FEATURE:
<223> OTHER INFORMATION: H-CDR2 humanized HV17b

<400> SEQUENCE: 250
```

```
Ser Ile Asn Pro Arg Asn Ala Trp Thr Asn Tyr Asn Gln Lys Phe His
1               5                   10                  15

Gly

<210> SEQ ID NO 251
<211> LENGTH: 32
<212> TYPE: PRT
<213> ORGANISM: Homo sapiens
<220> FEATURE:
<223> OTHER INFORMATION: H-FR3 humanized HV16, HV17a, HV17b, HV17d,
      HV17g, HV17i

<400> SEQUENCE: 251

Lys Ala Thr Leu Thr Val Asp Lys Ser Thr Arg Thr Ala Tyr Met Glu
1               5                   10                  15

Leu Ser Ser Leu Arg Ser Glu Asp Thr Ala Val Tyr Tyr Cys Ala Ser
            20                  25                  30

<210> SEQ ID NO 252
<211> LENGTH: 15
<212> TYPE: PRT
<213> ORGANISM: Homo sapiens
<220> FEATURE:
<223> OTHER INFORMATION: L-FR2 humanized LV2a

<400> SEQUENCE: 252

Trp Leu Gln Gln Arg Pro Gly Gln Ser Pro Arg Arg Gly Ile Tyr
1               5                   10                  15

<210> SEQ ID NO 253
<211> LENGTH: 15
<212> TYPE: PRT
<213> ORGANISM: Homo sapiens
<220> FEATURE:
<223> OTHER INFORMATION: L-FR2 humanized LV2b

<400> SEQUENCE: 253

Trp Leu Gln Gln Arg Pro Gly Gln Ser Pro Arg Arg Leu Ala Tyr
1               5                   10                  15

<210> SEQ ID NO 254
<211> LENGTH: 7
<212> TYPE: PRT
<213> ORGANISM: Homo sapiens
<220> FEATURE:
<223> OTHER INFORMATION: L-CDR2 humanized LV2d

<400> SEQUENCE: 254

Leu Val Ser Gln Leu Asp Asp
1               5

<210> SEQ ID NO 255
<211> LENGTH: 7
<212> TYPE: PRT
<213> ORGANISM: Homo sapiens
<220> FEATURE:
<223> OTHER INFORMATION: L-CDR2 humanized LV2c

<400> SEQUENCE: 255

Leu Val Ser Glu Leu Asp Ser
1               5

<210> SEQ ID NO 256
<211> LENGTH: 7
<212> TYPE: PRT
```

```
<213> ORGANISM: Homo sapiens
<220> FEATURE:
<223> OTHER INFORMATION: L-CDR2 humanized LV2f

<400> SEQUENCE: 256

Leu Val Ala Gln Leu Asp Ser
1               5

<210> SEQ ID NO 257
<211> LENGTH: 17
<212> TYPE: PRT
<213> ORGANISM: Artificial Sequence
<220> FEATURE:
<223> OTHER INFORMATION: Third Consensus CDR H2
<220> FEATURE:
<221> NAME/KEY: MISC_FEATURE
<222> LOCATION: (1)..(1)
<223> OTHER INFORMATION: X is Y or S
<220> FEATURE:
<221> NAME/KEY: MISC_FEATURE
<222> LOCATION: (5)..(5)
<223> OTHER INFORMATION: X is N or R
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is G or W
<220> FEATURE:
<221> NAME/KEY: MISC_FEATURE
<222> LOCATION: (13)..(13)
<223> OTHER INFORMATION: X is Q or D
<220> FEATURE:
<221> NAME/KEY: MISC_FEATURE
<222> LOCATION: (16)..(16)
<223> OTHER INFORMATION: X is K, G, H, or D

<400> SEQUENCE: 257

Xaa Ile Asn Pro Xaa Asn Xaa Xaa Thr Asn Tyr Asn Xaa Lys Phe Xaa
1               5                   10                  15

Gly

<210> SEQ ID NO 258
<211> LENGTH: 7
<212> TYPE: PRT
<213> ORGANISM: Artificial Sequence
<220> FEATURE:
<223> OTHER INFORMATION: Consensus CDR L2
<220> FEATURE:
<221> NAME/KEY: MISC_FEATURE
<222> LOCATION: (3)..(3)
<223> OTHER INFORMATION: X is S or A
<220> FEATURE:
<221> NAME/KEY: MISC_FEATURE
<222> LOCATION: (4)..(4)
<223> OTHER INFORMATION: X is Q or E
<220> FEATURE:
<221> NAME/KEY: MISC_FEATURE
<222> LOCATION: (7)..(7)
<223> OTHER INFORMATION: X is S or D

<400> SEQUENCE: 258

Leu Val Xaa Xaa Leu Asp Xaa
1               5

<210> SEQ ID NO 259
<211> LENGTH: 17
<212> TYPE: PRT
<213> ORGANISM: Artificial Sequence
<220> FEATURE:
```

```
<223> OTHER INFORMATION: Fourth Consensus CDR H2
<220> FEATURE:
<221> NAME/KEY: MISC_FEATURE
<222> LOCATION: (1)..(1)
<223> OTHER INFORMATION: X is Y or S
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is G or W
<220> FEATURE:
<221> NAME/KEY: MISC_FEATURE
<222> LOCATION: (13)..(13)
<223> OTHER INFORMATION: X is Q or D
<220> FEATURE:
<221> NAME/KEY: MISC_FEATURE
<222> LOCATION: (16)..(16)
<223> OTHER INFORMATION: X is K, G, H, or D

<400> SEQUENCE: 259

Xaa Ile Asn Pro Arg Asn Xaa Xaa Thr Asn Tyr Asn Xaa Lys Phe Xaa
1               5                   10                  15

Gly
```